US009771345B2

(12) United States Patent
Barany et al.

(10) Patent No.: US 9,771,345 B2
(45) Date of Patent: Sep. 26, 2017

(54) COFERONS AND METHODS OF MAKING AND USING THEM

(75) Inventors: Francis Barany, New York, NY (US); Maneesh Pingle, New York, NY (US); Sarah Filippa Giardina, New York, NY (US); Donald Bergstrom, West Lafayette, IN (US); Lee Daniel Arnold, Mt. Sinai, NY (US)

(73) Assignees: Cornell University, Ithaca, NY (US); Purdue Research Foundation, West Lafayette, IN (US); BlinkBio, Inc., New York, NY (US)

( * ) Notice: Subject to any disclaimer, the term of this patent is extended or adjusted under 35 U.S.C. 154(b) by 735 days.

(21) Appl. No.: 13/500,857

(22) PCT Filed: Oct. 7, 2010

(86) PCT No.: PCT/US2010/002708
§ 371 (c)(1),
(2), (4) Date: Aug. 1, 2012

(87) PCT Pub. No.: WO2011/043817
PCT Pub. Date: Apr. 14, 2011

(65) Prior Publication Data
US 2012/0295874 A1    Nov. 22, 2012

Related U.S. Application Data

(60) Provisional application No. 61/278,523, filed on Oct. 7, 2009.

(51) Int. Cl.
| | | |
|---|---|---|
| *A61K 31/69* | (2006.01) |
| *C07D 319/14* | (2006.01) |
| *C07D 207/12* | (2006.01) |
| *C07D 207/24* | (2006.01) |
| *C07D 209/52* | (2006.01) |
| *C07D 239/42* | (2006.01) |
| *C07D 239/54* | (2006.01) |
| *C07D 241/36* | (2006.01) |
| *C07D 263/20* | (2006.01) |
| *C07D 295/18* | (2006.01) |
| *C07D 307/80* | (2006.01) |
| *C07D 317/10* | (2006.01) |
| *C07D 317/44* | (2006.01) |
| *C07D 319/12* | (2006.01) |
| *C07D 403/06* | (2006.01) |
| *C07D 403/14* | (2006.01) |
| *C07D 405/14* | (2006.01) |
| *C07D 413/06* | (2006.01) |
| *C07D 471/14* | (2006.01) |

(Continued)

(52) U.S. Cl.
CPC ......... *C07D 319/14* (2013.01); *C07D 207/12* (2013.01); *C07D 207/24* (2013.01); *C07D 209/52* (2013.01); *C07D 239/42* (2013.01); *C07D 239/54* (2013.01); *C07D 241/36* (2013.01); *C07D 263/20* (2013.01); *C07D 295/18* (2013.01); *C07D 307/80* (2013.01); *C07D 317/10* (2013.01); *C07D 317/44* (2013.01); *C07D 319/12* (2013.01); *C07D 403/06* (2013.01); *C07D 403/14* (2013.01); *C07D 405/14* (2013.01); *C07D 413/06* (2013.01); *C07D 471/14* (2013.01); *C07D 491/04* (2013.01); *C07D 491/10* (2013.01); *C07D 491/14* (2013.01); *C07F 5/025* (2013.01); *C40B 30/04* (2013.01)

(58) Field of Classification Search
CPC .. C07D 319/14; C07D 207/24; C07D 491/14; C07D 307/80; C07D 491/04; C07D 209/52; C07D 263/20; C07D 319/12; C07D 403/06; C07D 491/10; C07D 317/44; C07D 317/10; C07D 295/18; C07D 471/14; C07D 241/36; C07D 207/12; C07D 413/06; C07D 403/14; C07D 405/14; C07D 239/42; C07D 239/54; C40B 30/04; C07F 5/025
USPC .... 514/64, 210.17, 250, 275, 326, 407, 423, 514/452; 436/501; 435/7.1; 544/229, 544/295; 546/13, 208; 548/371.4, 540, 548/952; 549/379
See application file for complete search history.

(56) References Cited

U.S. PATENT DOCUMENTS 5,643,893 A    7/1997  Benson et al.
6,589,766 B1   7/2003  Barbas et al.
(Continued)

FOREIGN PATENT DOCUMENTS

JP   2002508188 A    3/2002
JP   2004-532203 A   10/2004
(Continued)

OTHER PUBLICATIONS

Connon et al (JOC, 1973, 38(11), 2020-2023).*
(Continued)

*Primary Examiner* — Jason Sims
*Assistant Examiner* — Ibrahim D Bori
(74) *Attorney, Agent, or Firm* — LeClair, a Professional Corporation

(57) ABSTRACT

The present invention is directed to a monomer useful in preparing therapeutic compounds. The monomer includes one or more pharmacophores which potentially binds to a target molecule with a dissociation constant of less than 300 μM and a linker element connected to the pharmacophore. The linker element has a molecular weight less than 500 daltons, is connected, directly or indirectly through a connector, to the pharmacophore.

2 Claims, 32 Drawing Sheets

(51) Int. Cl.

| | | |
|---|---|---|
| C07D 491/04 | (2006.01) | |
| C07D 491/10 | (2006.01) | |
| C07D 491/14 | (2006.01) | |
| C07F 5/02 | (2006.01) | |
| C40B 30/04 | (2006.01) | |

(56) References Cited

U.S. PATENT DOCUMENTS

| | | | |
|---|---|---|---|
| 2005/0153407 A1 | 7/2005 | Greenberg et al. | |
| 2006/0233814 A1 | 10/2006 | Goldmakher et al. | |
| 2007/0010544 A1 | 1/2007 | Abelman et al. | |
| 2008/0234349 A1* | 9/2008 | Lin et al. | 514/406 |
| 2009/0016974 A1* | 1/2009 | Pruche | A61K 8/042 424/59 |
| 2011/0263688 A1 | 10/2011 | Barany et al. | |

FOREIGN PATENT DOCUMENTS

| | | |
|---|---|---|
| WO | 9931263 A1 | 6/1999 |
| WO | 02/076193 A2 | 10/2002 |
| WO | 2005013892 A2 | 2/2005 |
| WO | 2006/050959 A2 | 5/2006 |
| WO | 2006/094813 A2 | 9/2006 |
| WO | 2008124821 A1 | 10/2008 |
| WO | 2009126290 A2 | 10/2009 |
| WO | 2011043817 A1 | 4/2011 |

OTHER PUBLICATIONS

Settepani et al (J. Med. Chem., 1970, 13, 128-131).*
Database Caplus (Online); Chemical Abstracts Service, XP002692232 (as entered on Jun. 28, 2004).
Gareiss et al., "Dynamic Combinatorial Selection of Molecules Capable of Inhibiting the (CUG) Repeat RNA-MBNL1 Interaction in Vitro: Discovery of Lead Compounds Targeting Myotonic Dystrophy (DM1)," J. Am. Chem. Soc. 130:16254-16261 (2008).
Lewis et al., "Click Chemistry in Situ: Acetylcholinesterase as a Reaction Vessel for the Selective Assembly of a Femtomolar Inhibitor From an Array of Building Blocks," Angew. Chem. Int. Ed. 41(6):1053-1057 (2002).
Whiting et al., "Inhibitors of HIV-1 Protease by Using in Situ Click Chemistry," Angew. Chem. Int. Ed. 45:1435-1439 (2006).
Charo et al., "The Many Roles of Chemokines and Chemokine Receptors in Inflammation," N. Engl. J. Med. 354(6): 610-621 (2006).
Dolle et al., "Comprehensive Survey of Combinatorial Library Synthesis: 2005," J. Comb. Chem. 8(5):597-635 (2006).
Eliasson et al., "Differential IgG-Binding Characteristics of Staphylococcal Protein A, Streptococcal Protein G, and a Chimeric Protein AG," J. Immunol. 142(2):575-581 (1989).
Ellman, J.A., "Combinatorial Methods to Engineer Small Molecules for Functional Genomics," Ernst Schering Res. Found. Workshop 32:183-204 (2000).
Freeman et al., "Use of Nanobarcodes Particles in Bioassays," Methods Mol. Biol. 303:73-83 (2005).
Gunneriusson et al., "Surface Display of a Functional Single-Chain Fv Antibody on Staphylococci," J. Bacteriol. 178(5):1341-1346 (1996).
Hanahan et al., "The Hallmarks of Cancer," Cell 100:57-70 (2000).
Melkko et al., "Lead Discovery by DNA-Encoded Chemical Libraries," Drug Discov. Today 12(11/12):465-471 (2007).
Nelson et al., "Convergence of Wnt, Beta-Catenin, and Cadherin Pathways," Science 303(5663):1483-1487 (2004).
Nicewarner-Pena et al., "Submicrometer Metallic Barcodes," Science 294:137-141 (2001).
Nord et al., "Binding Proteins Selected From Combinatorial Libraries of an Alpha-Helical Bacterial Receptor Domain," Nat. Biotechnol. 15:772-777 (1997).
Pawson et al., "Protein-Protein Interactions Define Specificity in Signal Transduction," Genes & Development 14: 1027-1047 (2000).
Penn et al., "Nanoparticles for Bioanalysis," Curr. Opin. Chem. Biol. 7:609-615 (2003).
Polakis, P., "Wnt Signaling and Cancer," Genes Dev. 14:1837-1851 (2000).
Souers et al., "Optimization of a Somatostatin Mimetic Via Constrained Amino Acid and Backbone Incorporation," Bioorg. Med. Chem. Lett. 10:2731-2733 (2000).
Tolmachev et al., "Affibody Molecules: Potential for in Vivo Imaging of Molecular Targets for Cancer Therapy," Expert Opin. Biol. Ther. 7(4):555-568 (2007).
Walton et al., "Particles for Multiplexed Analysis in Solution: Detection and Identification of Striped Metallic Particles Using Optical Microscopy," Anal. Chem. 74:2240-2247 (2002).
Ladame, S., "Dynamic Combinatorial Chemistry: On the Road to Fulfilling the Promise," Org. Biomol. Chem. 6:219-226 (2008).
Muratovska et al., "Targeting Peptide Nucleic Acid (PNA) Oligomers to Mitochondria Within Cells by Conjugation to Lipophilic Cations: Implications for Mitochondrial DNA Replication, Expression and Disease," Nucleic Acids Research 29(9):1852-1863 (2001).
Tokunaga et al., "Formation of Hetero-Boroxines: Dynamic Combinatorial Libraries Generated Through Trimerization of Pairs of Arylboronic Acids," Heterocycles 74:219-223 (2007).
Xing et al., "Self-Assembled Multivalent Vancomycin on Cell Surfaces Against Vancomycin-Resistant Enterococci (VRE)," Chem. Commun. 17:2224-2225 (2003).
Xu, B., "Internal Construction," Nature Chemistry 2:13-14 (2010).
Zhang et al., "Solution and Crystallographic Studies of Branched Multivalent Ligands that Inhibit the Receptor-Binding of Cholera Toxin," J. Am. Chem. Soc. 124(44):12991-12998 (2002).
Zhou et al., "Design at the Atomic Level: Generation of Novel Hybrid Biaryloxazolidinones as Promising New Antibiotics," Bioorg. Med. Chem. Lett. 18:6179-6183 (2008).
Zimmerman et al., "A Rigid Molecular Tweezer with an Active Site Carboxylic Acid: An Exceptionally Efficient Receptor for Adenine in an Organic Solvent," J. Am. Chem. Soc. 111:8054-8055 (1989).
Zimmerman et al., "Chemically Bonded Stationary Phases that Use Synthetic Hosts Containing Aromatic Binding Clefts: HPLC Analysis of Nitro-Substituted Polycyclic Aromatic Hydrocarbons," Proc. Natl. Acad. Sci. 90(4):1190-1193 (1993).
Zimmerman et al., "Complexation of Nucleotide Bases by Molecular Tweezers with Active Site Carboxylic Acids: Effects of Microenvironment," J. Am. Chem. Soc. 113:196-201 (1991).
Zimmerman et al., "Highly Efficient Complexation of a Pi-Acceptor by a Molecular Tweezer Containing Two Pi-Donors: The Role of Preorganization," J. Am. Chem. Soc. 111:8528-8530 (1989).
Zimmerman et al., "Improved Binding of Adenine by a Synthetic Receptor," J. Org. Chem. 55:4789-4791 (1990).
Zimmerman et al., "Rigid Molecular Tweezers: Preorganized Hosts for Electron Donor—Acceptor Complexation in Organic Solvents," J. Am. Chem. Soc. 111:1373-1381 (1989).
Zimmerman et al., "Synthesis and Structure of Molecular Tweezers Containing Active Site Functionality," J. Am. Chem. Soc. 113:183-96 (1991).
International Search Report and Written Opinion for PCT Patent Application No. PCT/US2009/002223 (dated Nov. 4, 2009).
Extended European Search Report for European Patent Application No. 09729677.6 (dated Feb. 25, 2013).
English Translation of Notice of Reasons for Rejection for Japanese Patent Application No. 2011-503998 (dated Aug. 28, 2013).
International Search Report and Written Opinion for Corresponding PCT Patent Application No. PCT/US10/02708 (dated Dec. 10, 2010).
Supplementary European Search Report for Corresponding European Patent Application No. 10822356.1 (dated Mar. 5, 2013).
Duarte et al., "Privileged Structures: A Useful Concept for the Rational Design of New Lead Drug Candidates," Mini. Rev. Med. Chem. 7:1108-1119 (2007).

(56) References Cited

OTHER PUBLICATIONS

Amyes et al., "Rational Design of Transition-State Analogues as Potent Enzyme Inhibitors With Therapeutic Applications," ACS Chem. Biol. 2(11):711-714 (2007).
Sohn et al., "Kinetic and Structural Studies of Specific Protein-Protein Interactions in Substrate Catalysis by Cdc25B Phosphatase," Biochemistry 46:807-818 (2007).
Yadaiah et al., "High Affinity Binding of Bcl-xL to Cytochrome C: Possible Relevance for Interception of Translocated Cytochrome C in Apoptosis," Biochim. Biophys. Acta. 1774:1370-1379 (2007).
Kumar et al., "PINT: Protein-Protein Interactions Thermodynamic Database," Nucleic Acids Research 34:D195-D198 (2006).
Gelinas et al., "Mutational Analysis of the Energetics of the GrpE. DnaK Binding Interface: Equilibrium Association Constants by Sedimentation Velocity Analytical Ultracentrifugation," J. Mol. Biol. 339:447-458 (2004).
Desrosiers et al., "A Binding Free Energy Hot Spot in the Ankyrin Repeat Protein GABPbeta Mediated Protein-Protein Interaction," J. Mol. Biol. 354:375-384 (2005).
Porter et al., "Grb7-SH2 Domain Dimerisation is Affected by a Single Point Mutation," Eur. Biophys. J. 34:454-460 (2005).
Seo et al., "Identification of Erythrocyte p55/MPP1 as a Binding Partner of NF2 Tumor Suppressor Protein/Merlin," Exp. Biol. Med. 234:255-262 (2009).
Schlienger et al., "The Boronic Mannich Reaction in a Solid-Phase Approach," Tertrahedon 56: 10023-10030 (2000).
Carboni et al., "Boronic Ester as a Linker System for Solid Phase Synthesis," Tetrahedron Letters 40: 7979-7983 (1999).
Abed et al., "Preparative Manipulation of Gold Nanoparticles by Reversible Binding to a Polymeric Solid Support," Chem. Eur. J. 11: 2836-2841 (2005).
Priestley et al., "P1 Phenethyl Peptide Bornoic Acid Inhibitors of HCV NS3 Protease," Bioorganic & Medicinal , Chemistry Letters 12: 3199-3202 (2002).
Patent Examination Report in corresponding Australian Application No. 2010303946, 3 pages (dated Sep. 26, 2014).
Office action in corresponding European Application No. 10822356.1, 6 pages (dated Apr. 7, 2016).
Office action in corresponding European Application No. 10822356.1, 4 pages (dated Jul. 17, 2015).
Office action in corresponding European Application No. 10822356.1, 8 pages (dated Nov. 20, 2013).
Office action in European Application No. 09729677.6, 9 pages (dated Nov. 20, 2013).
Office action in European Application No. 09729677.6, 6 pages (dated Jul. 28, 2015).
Office action in U.S. Appl. No. 12/937,053, 21 pages (dated Apr. 3, 2013).
Office action in U.S. Appl. No. 12/937,053, 27 pages (dated Jan. 14, 2014).
Restriction Requirement in U.S. Appl. No. 12/937,053, 9 pages (dated Dec. 10, 2012).
Office action in Canadian Application No. 2,720,587, 7 pages (dated Mar. 3, 2015).
Notice of Reasons for Rejection in Japanese Application No. 2014-226002, 9 pages (dated Sep. 30, 2015).
Notice of Reasons for Rejection in Japanese Application No. 2011-503998, 8 pages (dated Aug. 28, 2013).
Notice of Reasons for Rejection in Japanese Application No. 2011-503998, 6 pages (dated Jul. 7, 2014).
Patent Examination Report in Australian Application No. 2009234373, 6 pages (dated Jun. 12, 2014).
Decision of Rejection in Japanese Application No. 2014-226002, 6 pages (dated May 30, 2016).
Office Action in European National Application No. 09729677.6, dated Oct. 31, 2016, corresponding to PCT/US2009/002223.
Office Action in Canadian National Application No. 2,774,476, dated Nov. 16, 2016, corresponding to PCT/US2010/02708.
Office Action in Canadian National Application No. 2,720,587, dated Mar. 15, 2016, corresponding to PCT/US2009/002223.

Machida et al., "Module Assembly for Protein-Surface Recognition: Geranylgeranyltransferase I Bivalent Inhibitors for Simultaneous Targeting of Interior and Exterior Protein Surfaces," Chem. Eur. J. 14:1392-1401 (2008).
Maly et al., "Combinatorial Target-Guided Ligand Assembly: Identification of Potent Subytpe-Selective c-Src Inhibitors," PNAS 97(6):2419-2424 (2000).
Marks et al., "In Vivo Targeting of Organic Calcium Sensors via Genetically Selected Peptides," Chemistry & Biology 11:347-356 (2004).
McNaughton et al., "Resin-Bound Dynamic Combinatorial Chemistry," Organic Letters 8(9):1803-1806 (2006).
Melkko et al., "Encoded Self-Assembling Chemical Libraries," Nature Biotechnology 22(5):568-574 (2004).
Melkko et al., "Isolation of High-Affinity Trypsin Inhibitors from a DNA-Encoded Chemical Library," Angew. Chem. Int. Ed. 46:4671-4674 (2007).
Melkko et al., "On the Magnitude of the Chelate Effect for the Recognition of Proteins by Pharmacophores Scaffolded by Self-Assembling Oligonucleotides," Chemistry & Biology 13:225-231 (2006).
Monnet et al., "Synthetic Peptides Derived from the Variable Regions of an Anti-CD4 Monoclonal Antibody Bind to CD4 and Inhibit HIV-1 Promoter Activation in Virus-Infected Cells," J. Biol. Chem. 274(6):3789-3796 (1999).
Naresh et al., "Synthesis and Mycobacterial Growth Inhibition Activities of Bivalent and Monovalent Arabinofuranoside Containing Alkyl Glycosides," Org. Biomol. Chem. 6:2388-2393 (2008).
Neri et al., "Encoding Chemistry," Nature Chemical Biology 5(7):452-453 (2009).
Nicolaou et al., "Target-Accelerated Combinatorial Synthesis and Discovery of Highly Potent Antibiotics Effective Against Vancomycin-Resistant Bacteria," Angew. Chem. Int. Ed. 39(21):3823-3828 (2000).
Parang et al., "Designing Bisubstrate Analog Inhibitors for Protein Kinases," Pharmacology & Therapaeutics 93:145-157 (2002).
Passarella et al., "Synthesis and Biological Evaluation of Epothilone a Dimeric Compounds," Bioorganic & Medicinal Chemistry 17:7435-7440 (2009).
Popkov et al., "Multidrug-Resistance Drug-Binding Peptides Generated by Using a Phage Display Library," Eur. J. Biochem. 251:155-163 (1998).
Potashman et al., "Covalent Modifiers: An Orthogonal Approach to Drug Design," J. Med. Chem. 52(5):1231-1246 (2009).
Ramström et al., "Drug Discovery by Dynamic Combinatorial Libraries," Nature Reviews 1:26-36 (2002).
Raynes, K., "Bisquinoline Antimalarials: Their Role in Malaria Chemotherapy," International Journal for Parasitology 29:367-379 (1999).
Rice et al., "Dibasic Inhibitors of Human Mast Cell Tryptase. Part 1: Synthesis and Optimization of a Novel Class of Inhibitors," Bioorg. Med. Chem. Lett. 10:2357-2360 (2000).
Rock et al., "An Antifungal Agent Inhibits an Aminoacyl-tRNA Synthetase by Trapping tRNA in the Editing Site," Science 316:1759-1761 (2007).
Rozenman et al., "Solving Chemical Problems Through the Application of Evolutionary Principles," Curr. Opin. Chem. Biol. 11:259-268 (2007).
Rozinov et al., "Evolution of Peptides that Modulate the Spectral Qualities of Bound, Small-Molecule Fluorophores," Chemistry & Biology 5(12):713-728 (1998).
Saggio et al., "Biotin Binders Selected from a Random Peptide Library Expressed on Phage," Biochem. J. 293:613-616 (1993).
Sakurai et al., "DNA-Templated Functional Group Transformations Enable Sequence-Programmed Synthesis Using Small-Molecule Reagents," J. Am. Chem. Soc. 127:1660-1661 (2005).
Schaller et al., "Structure of Molecular Tweezer Complexes in the Solid State: NMR Experiments, X-ray Investigations, and Quantum Chemical Calculations," J. Am. Chem. Soc. 129:1293-1303 (2007).
Schaschke et al., "Bivalent Inhibition of β-Tryptase: Distance Scan of Neighboring Subunits by Dibasic Inhibitors," Bioorganic & Medicinal Chemistry Letters 12:985-988 (2002).

(56) References Cited

OTHER PUBLICATIONS

Scheuermann et al., "DNA-Encoded Chemical Libraries for the Discovery of MMP-3 Inhibitors," Bioconjugate Chem. 19(3):778-785 (2008).
Schmidt et al., "Sensitized Detection of Inhibitory Fragments and Iterative Development of Non-Peptidic Protease Inhibitors by Dynamic Ligation Screening," Angew. Chem. Int. Ed. 47:3275-3278 (2008).
Schmuck et al., "One-Armed Artificial Receptors for the Binding of Polar Tetrapeptides in Water: Probing the Substrate Selectivity of a Combinatorial Receptor Library," Chem. Eur. J. 12:1339-1348 (2006).
Seiradake et al., "Crystal Structures of the Human and Fungal Cytosolic Leucyl-tRNA Synthetase Editing Domains: A Structural Basis for the Rational Design of Antifungal Benzoxaboroles," J. Mol. Biol. 390:196-207 (2009).
Selwood et al., "The Interaction of Human Tryptase-β with Small Molecule Inhibitors Provides New Insights into the Unusual Functional Instability and Quaternary Structure of the Protease," Biochemistry 44(9):3580-3590 (2005).
Sennhauser et al., "Drug Export Pathway of Multidrug Exporter AcrB Revealed by DARPin Inhibitors," PLOS Biology 5(1e7):106-113 (2007).
Shao et al., "Sequence-Selective Receptors of Peptides. A Simple Molecular Design for Construction of Large Combinatorial Libraries of Receptors," J. Org. Chem. 61:6086-6087 (1996).
Shepherd et al., "Synthesis of Unsymmetrical Tweezer Receptor Libraries and Identification of Receptors for Lys-D-Ala-D-Ala in Aqueous Solution," Chem. Eur. J. 12:713-720 (2006).
Sprinz et al., "Self-Assembly of Bivalent Protein-Binding Agents Based on Oligonucleotide-Linked Organic Fragments," Bioorganic & Medicinal Chemistry Letters 15:3908-3911 (2005).
Sridhar et al., "New Bivalent PKC Ligands Linked by a Carbon Spacer: Enhancement in Binding Affinity," J. Med. Chem. 46(19):4196-4204 (2003).
Sriram et al., "Multivalency-Assisted Control of Intracellular Signaling Pathways: Application for Ubiquitin-Dependent N-End Rule Pathway," Chemistry & Biology 16:121-131 (2009).
Steinfeld et al., "A Novel Multivalent Ligand That Bridges the Allosteric and Orthosteric Binding Sites of the M2 Muscarinic Receptor," Molecular Pharmacology 72(2):291-302 (2007).
Still, C., "Discovery of Sequence-Selective Peptide Binding by Synthetic Receptors Using Encoded Combinatorial Libraries," Acc. Chem. Res. 29:155-163 (1996).
Sun et al., "Design of Small-Molecule Peptidic and Nonpeptidic Smac Mimetics," Accounts of Chemical Research 41 (10):1264-1277 (2008).
Takakusagi et al., "Camptothecin Binds to a Synthetic Peptide Identified by a T7 Phage Display Screen," Bioorganic & Medicinal Chemistry Letters 15:4850-4853 (2005).
Thanos et al., "Potent Small-Molecule Binding to a Dynamic Hot Spot on IL-2," J. Am. Chem. Soc. 125:15280-15281 (2003).
Tian et al., "Bivalent Ligands with Long Nanometer-Scale Flexible Linkers," Biochemistry 48(2):264-275 (2009).
Tian et al., "Potentially Macrocyclic Peptidyl Boronic Acids as Chymotrypsin Inhibitors," J. Org. Chem. 62(3):514-522 (1997).
Vaz et al., "Design of Bivalent Ligands Using Hydrogen Bond Linkers: Synthesis and Evaluation of Inhibitors for Human β-tryptase," Bioorganic & Medicinal Chemistry Letters 14:6053-6056 (2004).
Vogel et al., Designed Ankyrin Repeat Proteins as Anti-Idiotypic-Binding Molecules, Ann. N.Y. Acad. Sci. 1109:9-18 (2007).
Von Mehren et al., "Monoclonal Antibody Therapy for Cancer," Annu. Rev. Med. 54:343-369 (2003).
Wennemers et al., "Diketopiperazine Receptors: A Novel Class of Highly Selective Receptors for Binding Small Peptides," Chem. Eur. J. 7(15):3342-3347 (2001).
Wennemers et al., "Flexible but with a Defined Turn—Influence of the Template on the Binding Properties of Two-Armed Receptors," Chem. Eur. J. 9(2):442-448 (2003).

Wong et al., "Acetylcholinesterase Complexed with Bivalent Ligands Related to Huperzine A: Experimental Evidence for Species-Dependent Protein-Ligand Complementarity," J. Am. Chem. Soc. 125(2):363-373 (2003).
Xing et al., "Multivalent Antibiotics Via Metal Complexes: Potent Divalent Vancomycins Against Vancomycin-Resistant Enterococci," J. Med. Chem. 46(23):4904-4909 (2003).
Agnew et al., "Iterative in Situ Click Chemistry Creates Antibody-Like Protein-Capture Agents," Angew. Chem. Int. Ed. 48:1-5 (2009).
Ayad et al., "Synthesis, Antimalarial Activity and Inhibition of Haem Detoxification of Novel Bisquinolines," Bioorganic & Medicinal Chemistry Letters 11:2075-2077 (2001).
Berg, T., "Modulation of Protein—Protein Interactions with Small Organic Molecules," Angew. Chem. Int. Ed. 42:2462-2481 (2003).
Bonger et al., "Synthesis and Pharmacological Evaluation of Dimeric Follicle-Stimulating Hormone Receptor Antagonists," ChemMedChem 4:2098-2102 (2009).
Bourne et al., "Freeze-Frame Inhibitor Captures Acetylcholinesterase in a Unique Conformation," PNAS 101 (6):1449-1454 (2004).
Brik et al., "Rapid Diversity-Oriented Synthesis in Microtiter Plates for in Situ Screening of HIV Protease Inhibitors," ChemBioChem 4:1246-1248 (2003).
Buck et al., "Disulfide Trapping to Localize Small-Molecule Agonists and Antagonists for a G Protein-Coupled Receptor," PNAS 102(8):2719-2724 (2005).
Bunyapaiboonsri et al., "Generation of Bis-Cationic Heterocyclic Inhibitors of Bacillus subtilis HPr Kinase/Phosphatase from a Ditopic Dynamic Combinatorial Library," J. Med. Chem. 46:5803-5811 (2003).
Calderone et al., "Small-Molecule Diversification from Iterated Branching Reaction Pathways Enabled by DNA-Templated Synthesis," Angew. Chem. Int. Ed. 44:7383-7386 (2005).
Chang et al., "Copper-Free Click Chemistry in Living Animals," PNAS 107(5):1821-1826 (2010) (Epub Dec. 2009).
Chen et al., "Fluorescent, Sequence-Selective Peptide Detection by Synthetic Small Molecules," Science 279:851-853 (1998).
Chène, P., "Drugs Targeting Protein-Protein Interactions," ChemMedChem 1:400-411 (2006).
Cheng et al., "Sequence-Selective Peptide Binding with a Peptido-A,B-trans-steroidal Receptor Selected from an Encoded Combinatorial Receptor Library," J. Am. Chem. Soc. 118:1813-1814 (1996).
Coleska et al., "Interaction of a Cyclic, Bivalent Smac Mimetic with the X-Linked Inhibitor of Apoptosis Protein," Biochemistry 47:9811-9824 (2008).
Conza et al., "Selective Binding of Two-Armed Diketopiperazine Receptors to Side-Chain-Protected Peptides," J. Org. Chem. 67:2696-2698 (2002).
Corson et al., "Design and Applications of Bifunctional Small Molecules: Why Two Heads are Better Than One," ACS Chemical Biology 3(11):677-692 (2008).
De Vega et al., "Modulation of Protein-Protein Interactions by Stabilizing/Mimicking Protein Secondary Structure Elements." Current Topics in Medicinal Chemistry 7:33-62 (2007).
Dumelin et al., "Selection of Streptavidin Binders from a DNA-Encoded Chemical Library," Bioconjugate Chem. 17:366-370 (2006).
Edwards et al., "A Crystal Structure of the Bifunctional Antibiotic Simocyclinone D8, Bound to DNA Gyrase," Science 326:1415-1418 (2009).
Erlanson et al., "In Situ Assembly of Enzyme Inhibitors Using Extended Tethering," Nature Biotechnology 21:308-314 (2003).
Erlanson et al., "Site-Directed Ligand Discovery," PNAS 97(17):9367-9372 (2000).
Franceschi et al., "Structure-Based Drug Design Meets the Ribosome," Biochemical Pharmacology 71:1016-1025 (2006).
Gao et al., "A Dimeric Smac/Diablo Peptide Directly Relieves Caspase-3 Inhibition by XIAP," Journal of Biological Chemistry 282(42):30718-30727 (2007).

(56) References Cited

OTHER PUBLICATIONS

Gestwicki et al., "Chemical Control Over Protein-Protein Interactions: Beyond Inhibitors," Combinatorial Chemistry & High Throughput Screening 10(8):667-675 (2007).

Ghosh et al., "From Orbital Hybridization to Chemotherapeutics Neutralization," Blood 113(24):6262 (2009).

Goldberg et al., "Erythropoietin Mimetics Derived from Solution Phase Combinatorial Libraries," J. Am. Chem. Soc. 124(4):544-555 (2002) (Epub Dec. 29, 2001).

Golden et al, "Green Tea Polyphenols Block the Anticancer Effects of Bortezomib and Other Boronic Acid-Based Proteasome Inhibitors," Blood 113(23):5927-5937 (2009).

Goral et al., "Double-Level "Orthogonal" Dynamic Combinatorial Libraries on Transition Metal Template," PNAS 98 (4):1347-1352 (2001).

Halpin et al., "DNA Display I. Sequence-Encoded Routing of DNA Populations," PLOS Biology 2(7):1015-1021 (2004).

Halpin et al., "DNA Display II. Genetic Manipulation of Combinatorial Chemistry Libraries for Small-Molecule Evolution,"PLOS Biology 2(7):1022-1030 (2004).

Halpin et al., "DNA Display III. Solid-Phase Organic Synthesis on Unprotected DNA," PLOS Biology 2(7):1031-1038 (2004).

Heinis et al., "Phage-Encoded Combinatorial Chemical Libraries Based on Bicyclic Peptides," Nature Chemical Biology 5(7):502-507 (2009).

Hunter, T., "Signaling—2000 and Beyond," Cell 100:113-127 (2000).

Iorio et al., "Sequence-Selective Peptide Detection by Small Synthetic Chemosensors Selected from an Encoded Combinatorial Chemosensor Library," Bioorganic & Medicinal Chemistry Letters 11:1635-1638 (2001).

Ishi-I et al., "Self-Assembled Receptors that Stereoselectively Recognize a Saccharide," Angew. Chem. Int. Ed. 42:2300-2305 (2003).

Jensen et al., Synthesis of Guanidinium-Derived Receptor Libraries and Screening for Selective Peptide Receptors in Water, Chem. Eur. J. 8(6):1300-1309 (2002).

Kawe et al., "Isolation of Intracellular Proteinase Inhibitors Derived from Designed Ankyrin Repeat Proteins by Genetic Screening," Journal of Biological Chemistry 281(52):40252-40263 (2006).

Kehoe et al., "Tyrosylprotein Sulfotransferase Inhibitors Generated by Combinatorial Target-Guided Ligand Assembly," Bioorganic & Medicinal Chemistry Letters 12:329-332 (2002).

Kerckhoffs et al., "Dynamic Combinatorial Libraries Based on Hydrogen-Bonded Molecular Boxes," Chem. Eur. J. 13:2377-2385 (2007).

Kodadek, T., "Antibody Surrogates Click Into Place," Nature Chemistry 1:183-185 (2009).

Kolb et al., "The Growing Impact of Click Chemistry on Drug Discovery," Drug Discovery Today 8(24):1128-1137 (2003).

Laune et al., Systematic Exploration of the Antigen Binding Activity of Synthetic Peptides Isolated from the Variable Regions of Immunoglobulins, J. Biol. Chem. 272(49):30937-30944 (1997).

Lehn et al., "Dynamic Combinatorial Chemistry," Science 291(5512):2331-2332 (2001).

Li et al., "Multivalent Vancomycins and Related Antibiotics Against Infectious Diseases," Current Pharmaceutical Design 11:3111-3124 (2005).

Liang et al., "A Biocompatible Condensation Reaction for Controlled Assembly of Nanostructures in Living Cells," Nature Chemistry 2:54-60 (2010) (Epub Dec. 17, 2009).

Liang et al., "Structure-Activity Relationships of Bivalent Aminoglycosides and Evaluation of Their Microbiological Activities," Bioorganic & Medicinal Chemistry Letters 15:2123-2128 (2005).

Liu et al., "Multivalent Drug Design and Inhibition of Cholera Toxin by Specific and Transient Protein-Ligand Interactions," Chem. Biol. Drug Des. 71:408-419 (2008).

Loll et al., "Vancomycin Forms Ligand-Mediated Supramolecular Complexes," J. Mol. Biol. 385:200-211 (2009).

Long et al., "A Multivalent Approach to Drug Discovery for Novel Antibiotics," J. Antibiot. 61(10):595-602 (2008).

Lu et al., "SM-164: A Novel, Bivalent Smac Mimetic That Induces Apoptosis and Tumor Regression by Concurrent Removal of the Blockade of cIAP-1/2 and XIAP," Cancer Res. 68(22):9384-9393 (2008).

Yu et al., "Formation of the Intermediate Nitronyl Nitroxide-Anthracene Dyad Sensing Saccharides," Biorg. Med. Chem. Lett. 17:94-96 (2007).

Takeuchi et al., "Dopamine Selective Molecularly Imprinted Polymers via Post-Imprinting Modification," Org. Biomol. Chem. 4:565-568 (2006).

Office action in U.S. Appl. No. 14/445,887, 11 pages (dated May 4, 2017).

* cited by examiner

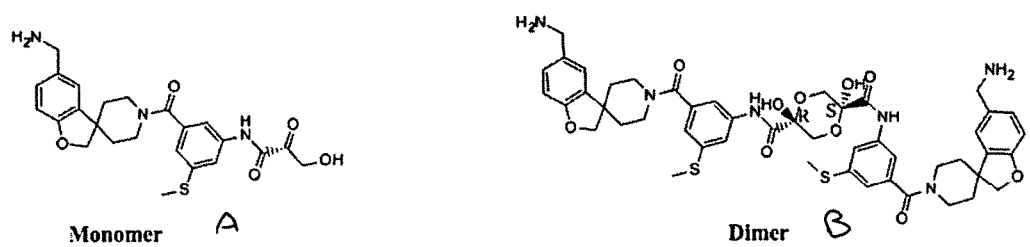
Figure 4

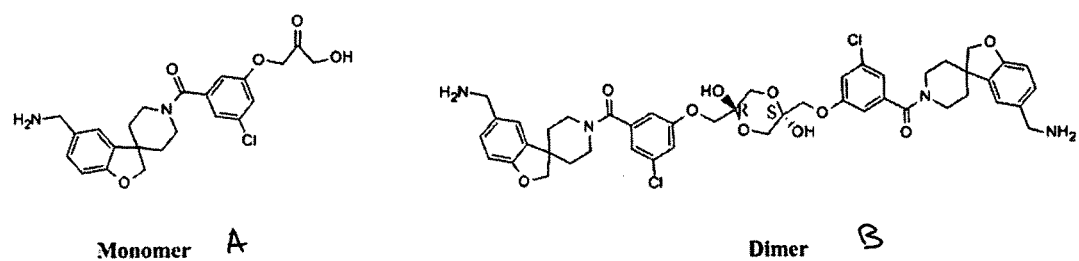
Monomer A          Dimer B
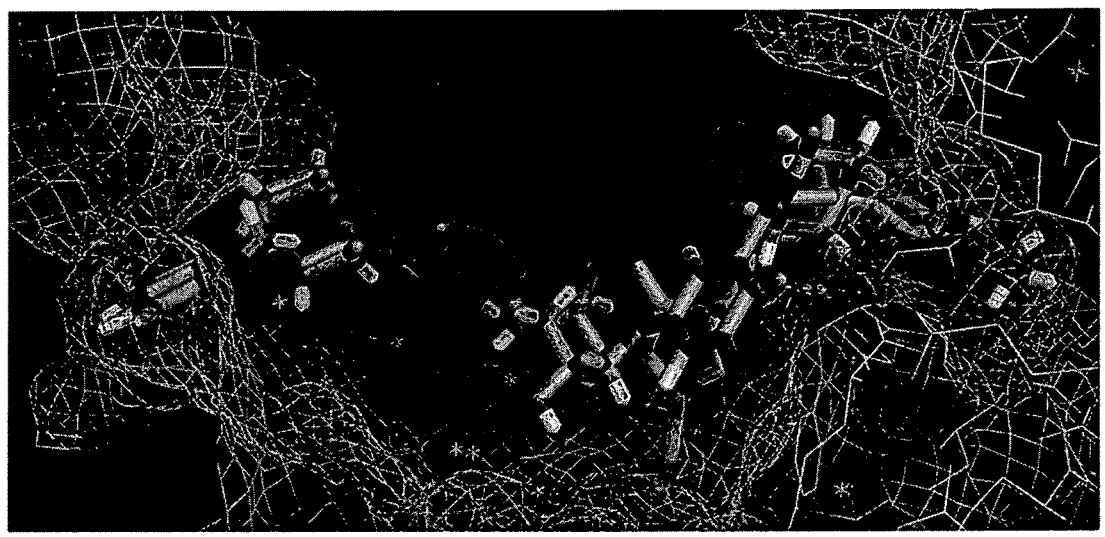
Figure 5  C

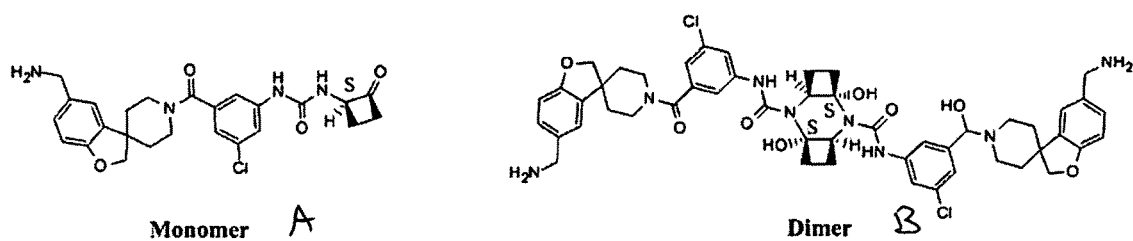
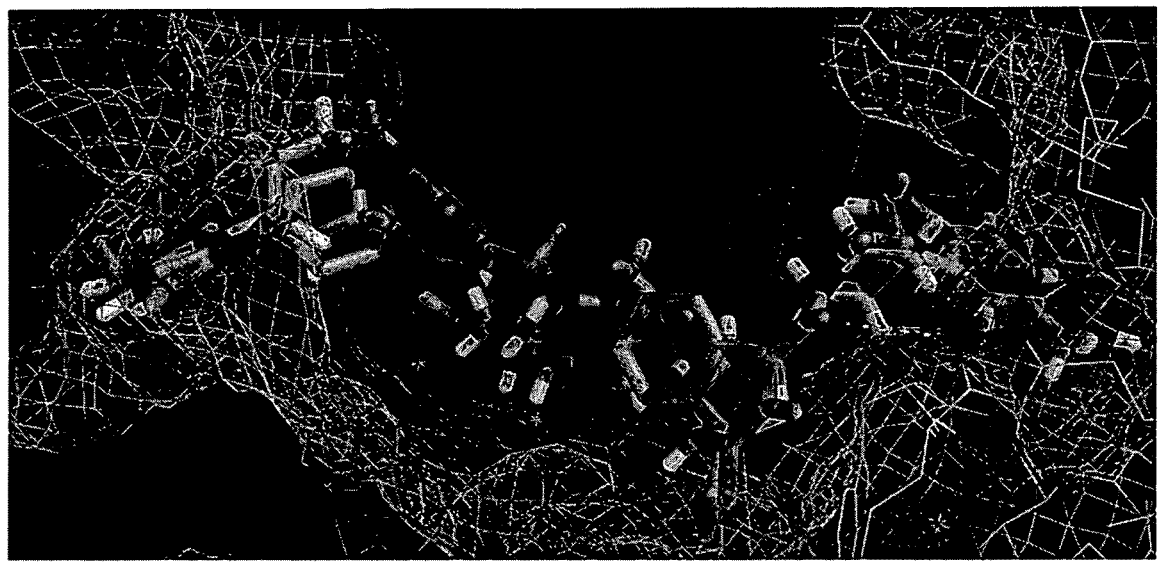
Figure 6

Coferon Ligand (Diversity Element) Library Synthesis:
Bead-encoded libraries.
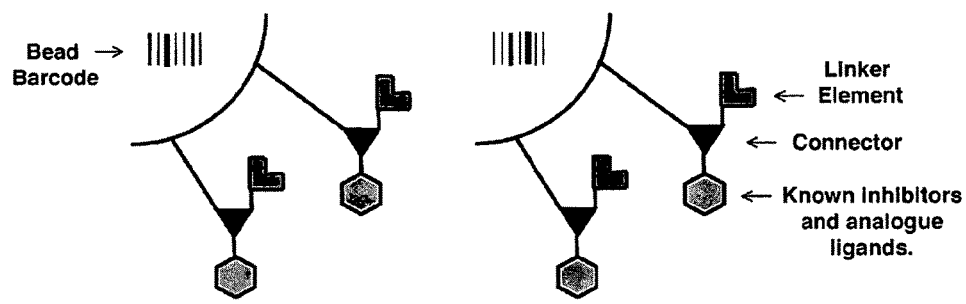
A. Small molecule inhibitors and analogues
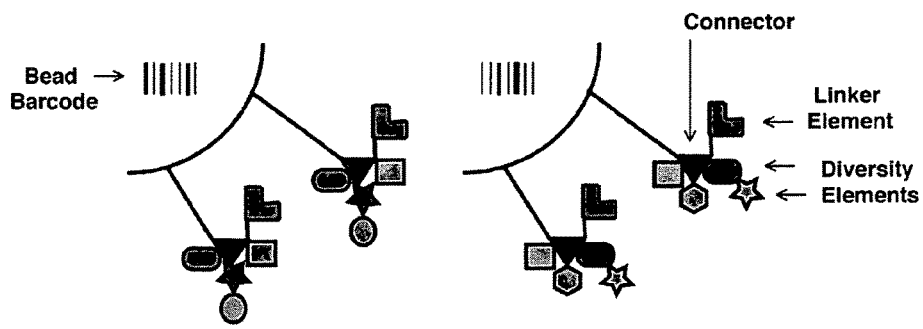
B. Combinatorial chemistry on common platform, version 1.
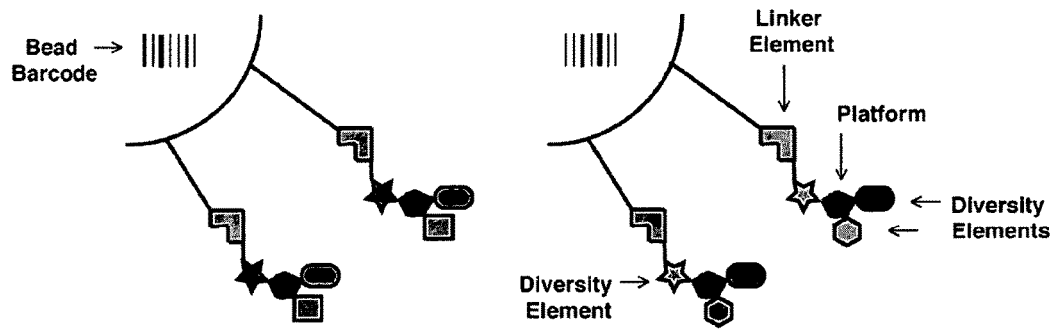
C. Combinatorial chemistry on common platform, version 2.
Figure 8

Directed evolution of Coferons: Bead encoding of diversity elements.

1. A first set of coferon monomers consists of a binding ligand (diversity element) covalently linked to a bead containing a unique barcode as well as a low MW linker element (dynamic combinatorial chemistry element), while a second set is free in solution. The linker elements allow different combinations of ligands to reversably associate with each other. When the combination of solid-phase and solution coferons are brought in contact with a labeled protein target, some combinations will bind tighter than others, and consequently are enriched. The winning pair will cause that bead to be highly labeled, and this may be isolated by flow cytometry or other methods, and the barcode identified.

2. In a companion selection, the second set of coferon monomers is linked to unique encoded beads, while the first set is free in solution. The linker elements allow different combinations of ligands to reversably associate with each other. When the combination of solid-phase and solution coferons are brought in contact with a labeled protein target, some combinations will bind tighter than others, and consequently are enriched. The winning pair will cause that bead to be highly labeled, and this may be isolated by flow cytometry or other methods, and the barcode identified. The diversity elements for both sides of the coferon may be decoded, and then resynthesized with additional variation. Repeating this process of synthesis -selection-amplification mimics Darwinian evolution.

3. The best coferon monomers are resynthesized without the encoded beads for use as orally active drugs. Once ingested coferons are in a dynamic equilibrium between the monomer form (which can traverse the cell membrane), and the dimer form (which binds to and inhibits the protein target).

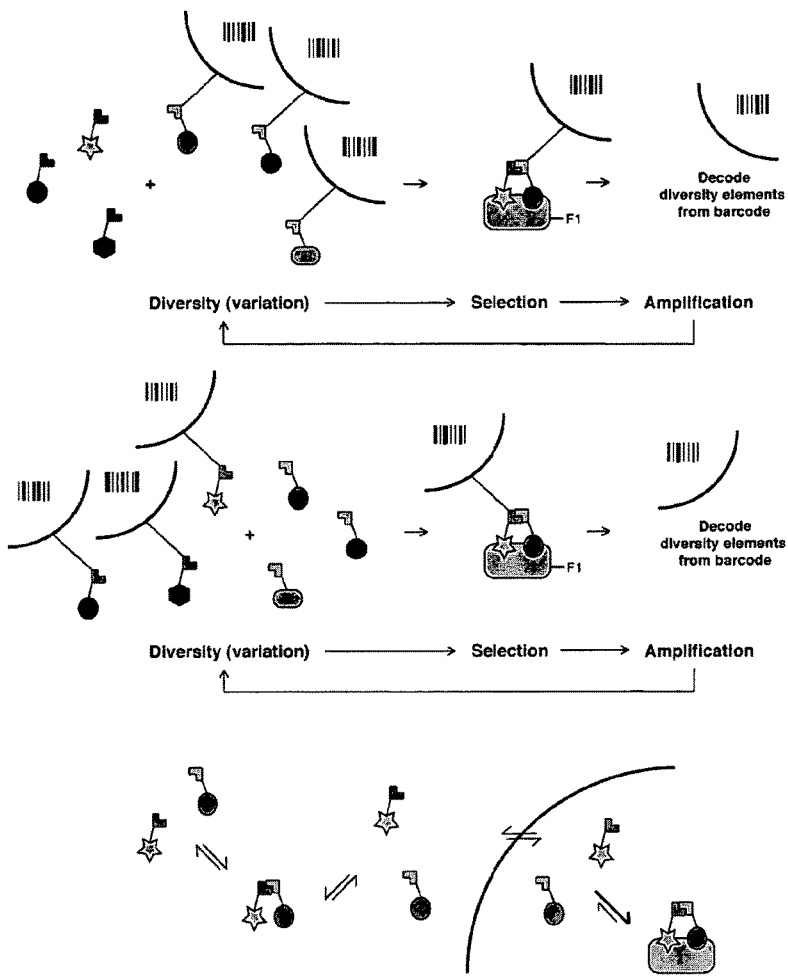

Figure 9

Directed evolution of Coferons:

1. Each coferon monomer consists of a binding ligand (diversity element, identified by a DNA, bead, or positional barcode) and a low MW "summa linker" (dynamic combinatorial chemistry element), which allow different combinations of ligands to reversably associate with each other. When coferons are brought in contact with the protein target, some combinations will bind tighter than others, and consequently are enriched. The winning pair may be identified through the barcodes and re-amplified. Repeating this process of synthesis-selection-amplification mimics Darwinian evolution.

2. The best coferon monomers are resynthesized without barcodes (if needed) for use as orally active drugs. Once ingested coferons are in a dynamic equilibrium between the monomer form (which can traverse the cell membrane), and the dimer form (which binds to and inhibits the protein target).

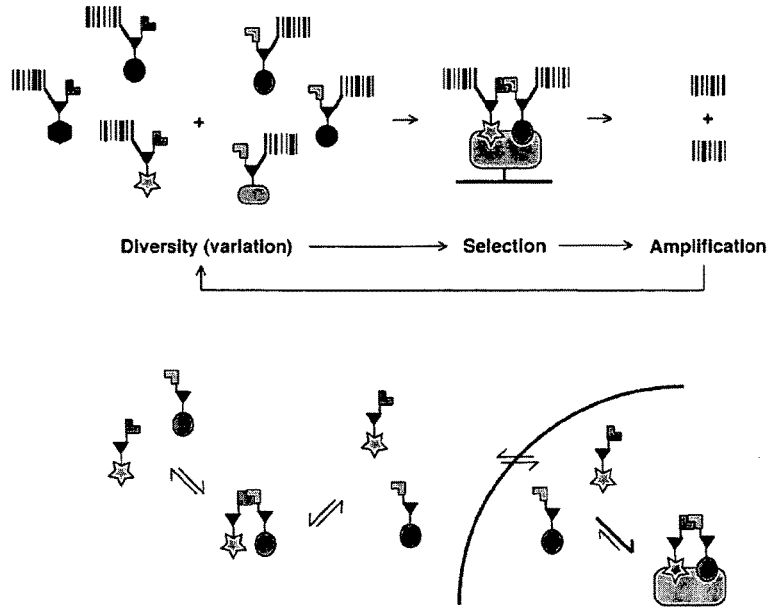

Figure 10

Coferon drug interactions with target, Part 1:
A. Substrate binding to target.
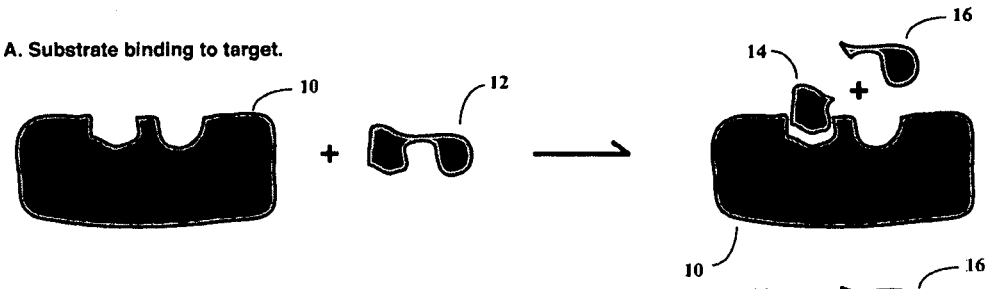
B. Heterodimer coferon binding to target.
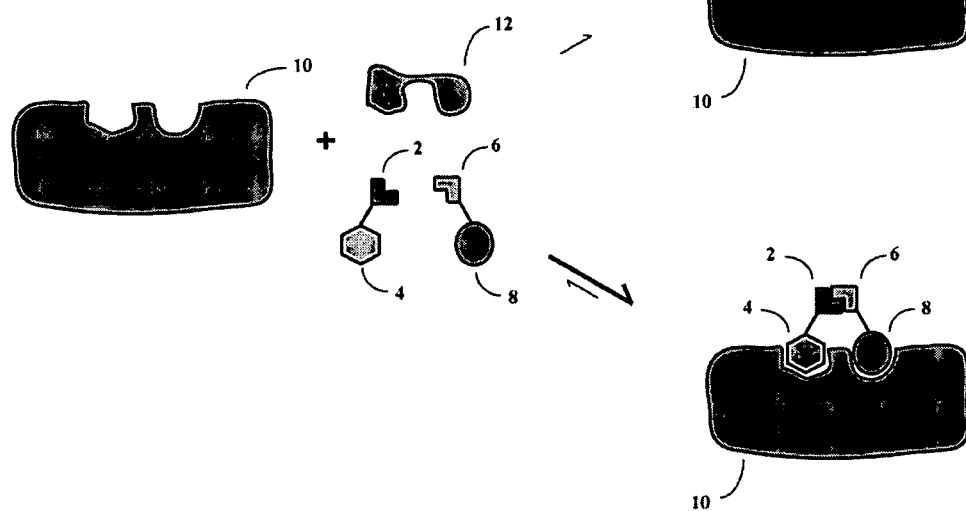
C. Heterodimer coferon displacing protein from target.
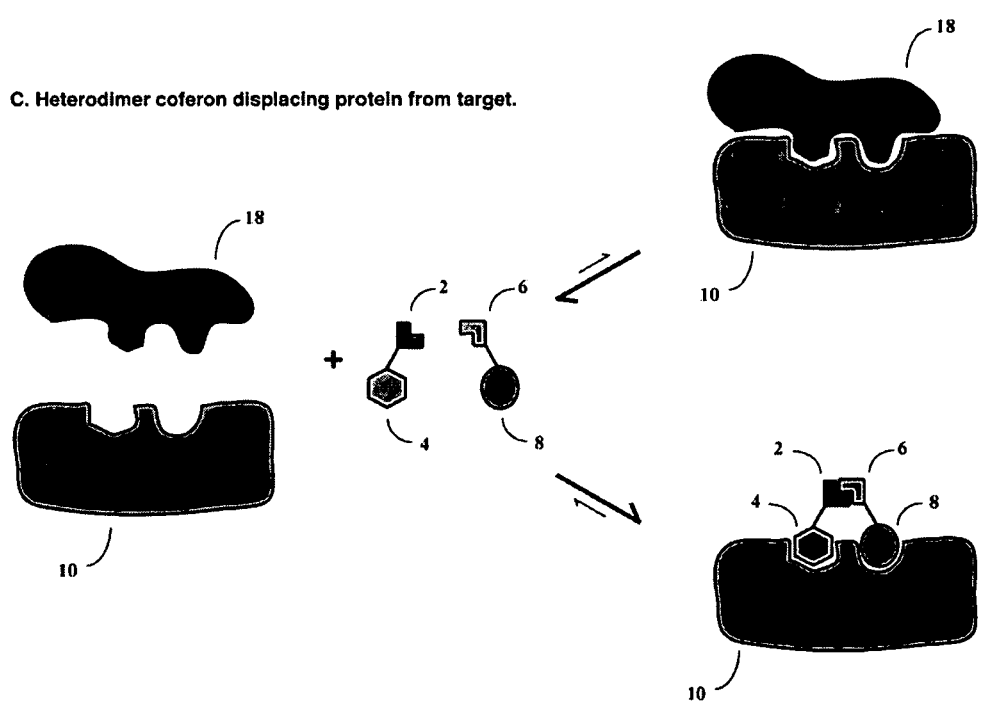
Figure 13

Coferon drug interactions with target, Part 2:
A. Protein activating target.
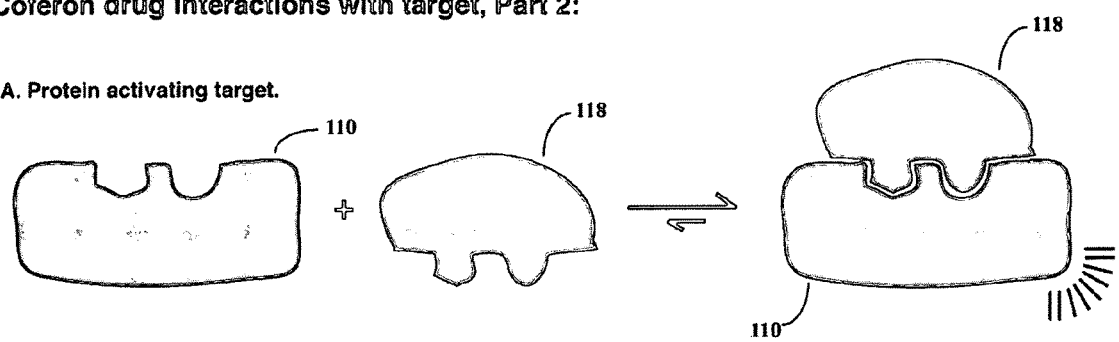
B. Heterodimer coferon activating target.
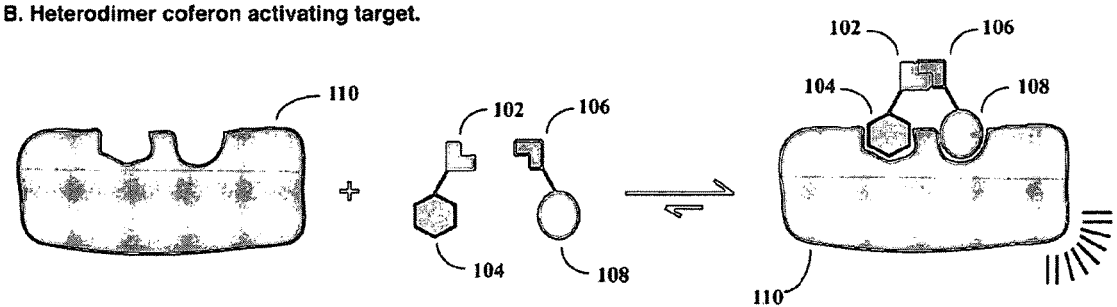
C. Protein inactivating target.
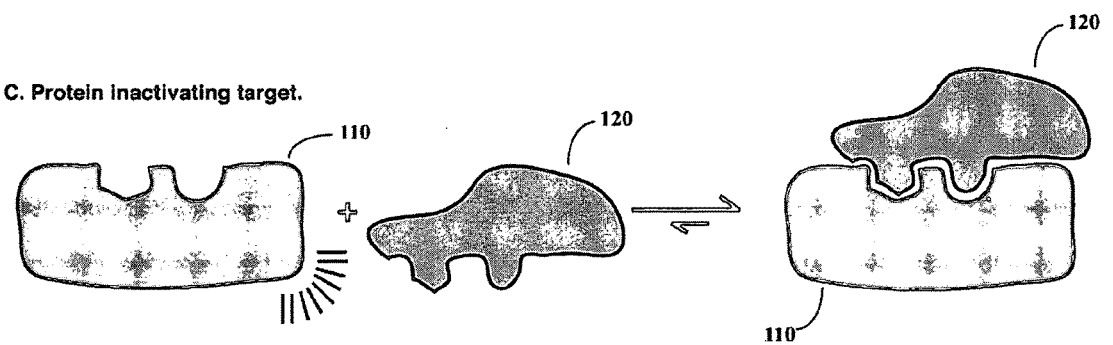
D. Heterodimer coferon inactivating target.
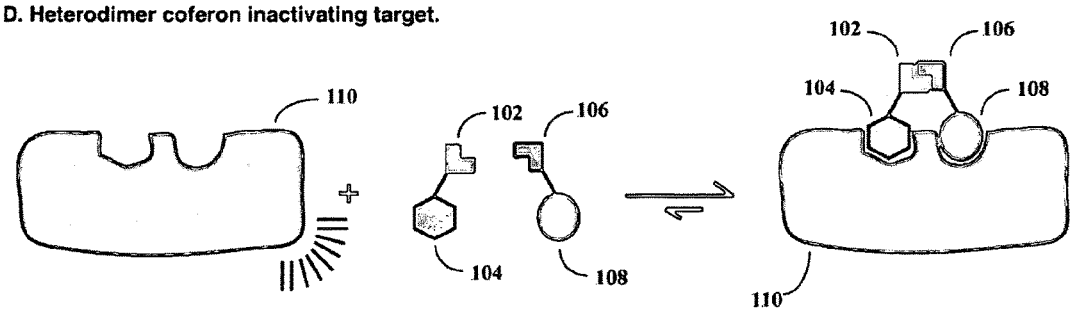
Figure 14

Coferon drug interactions with target, Part 3:
A. Heterodimer coferon enhancing protein activation of target.
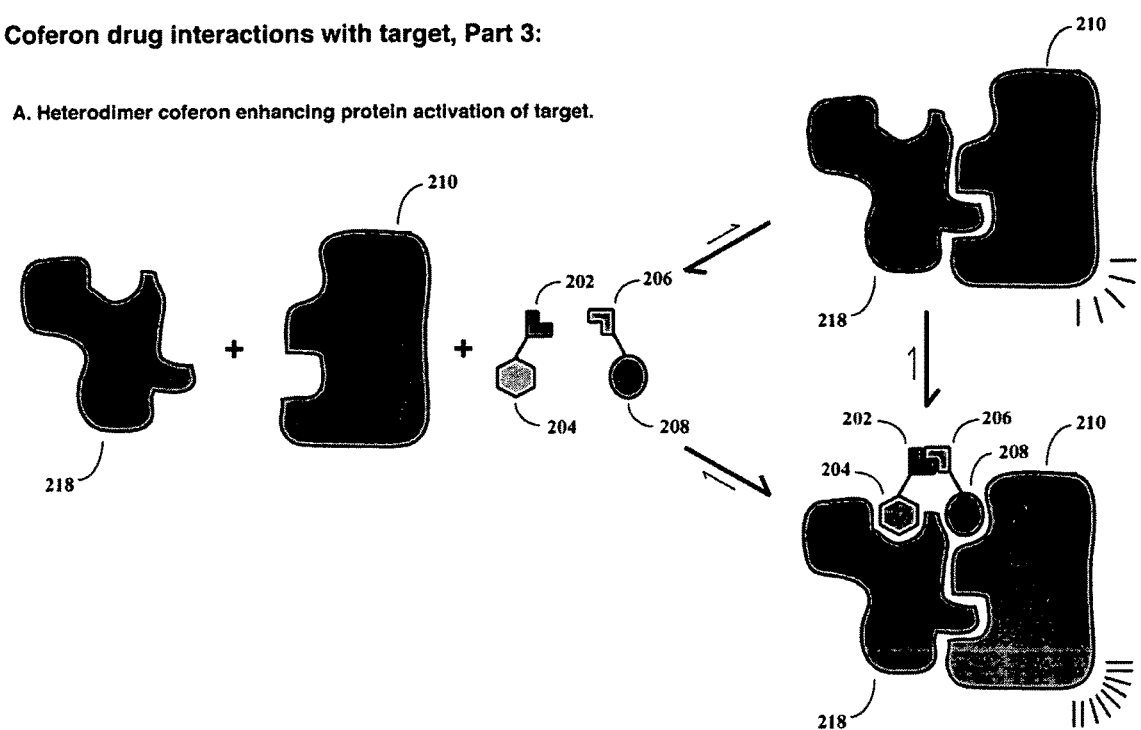
B. Heterodimer coferon enhancing protein inactivation of target.
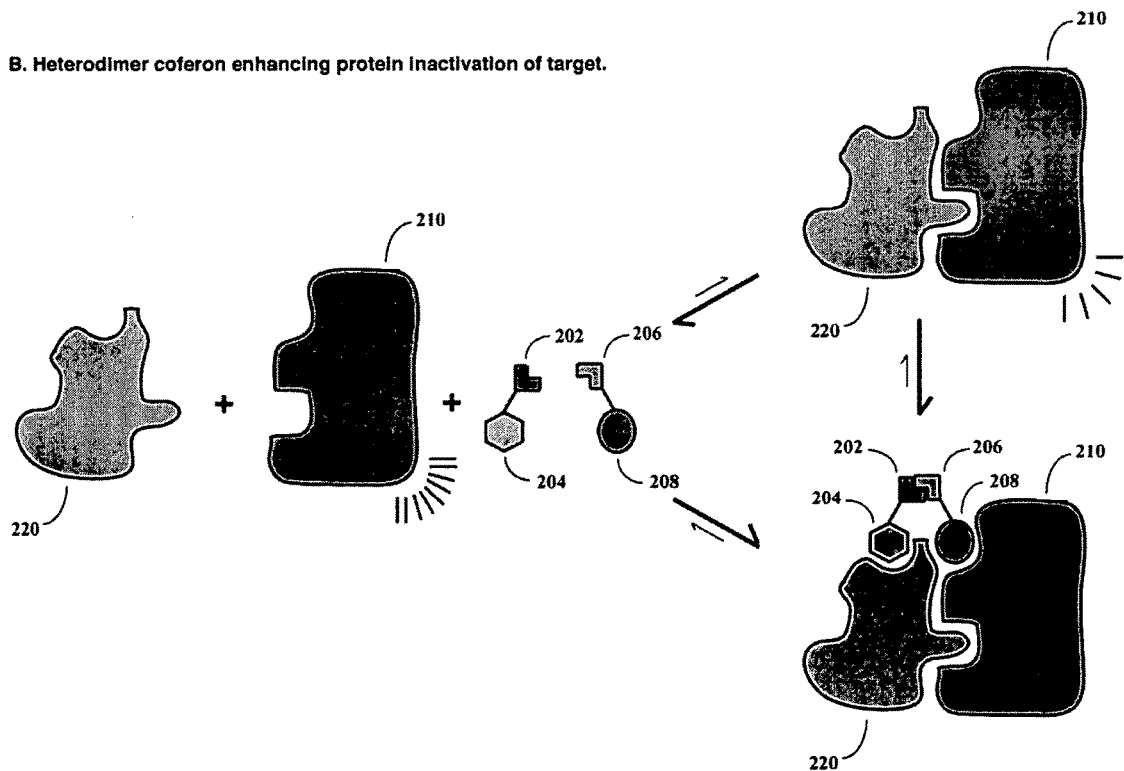
Figure 15

Coferon drug interactions with target, Part 4:
A. Protein activating target.
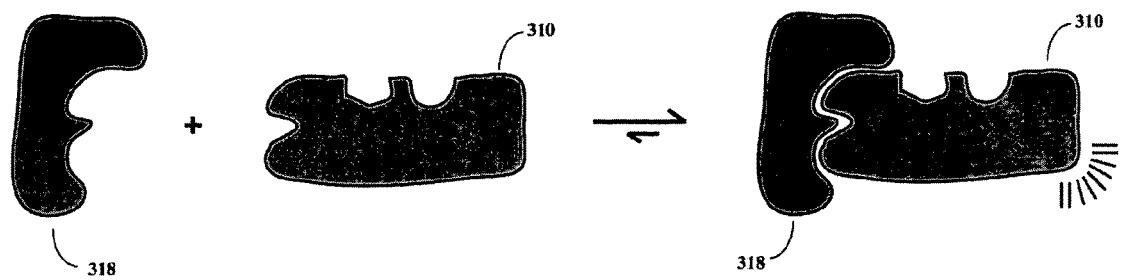
B. Heterodimer coferon enhancing protein activation of mutant target.
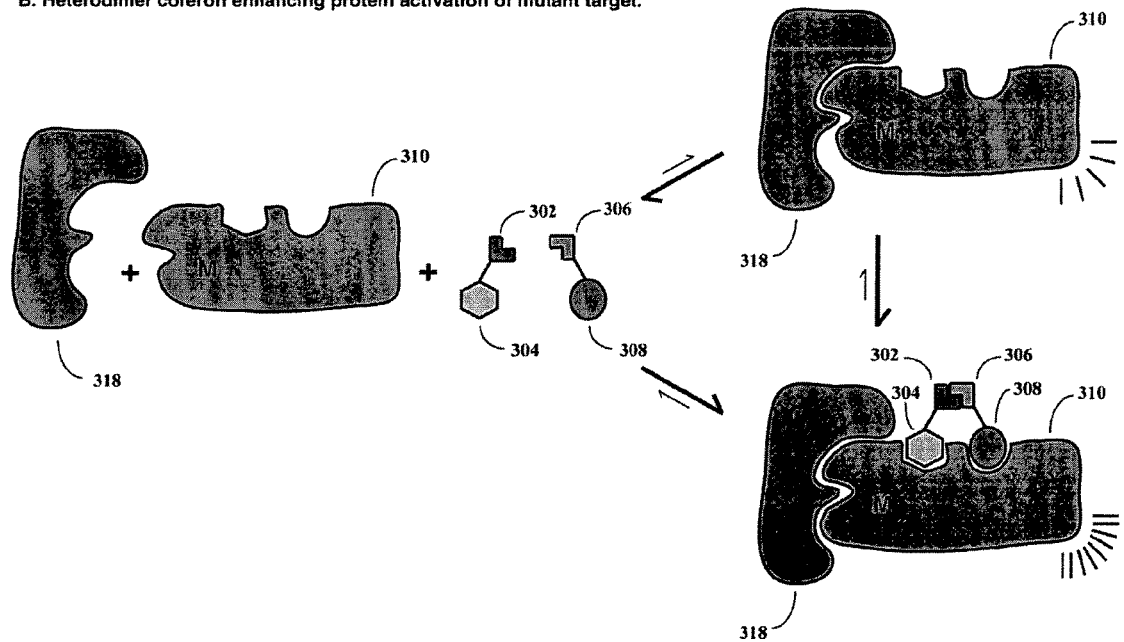
Figure 16

Coferon drug interactions with target, Part 5:
A. Protein inactivating target.
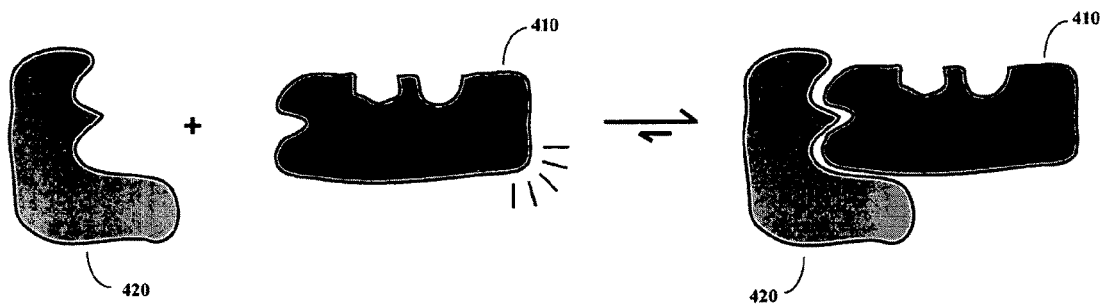
B. Heterodimer coferon enhancing protein inactivation of mutant target.
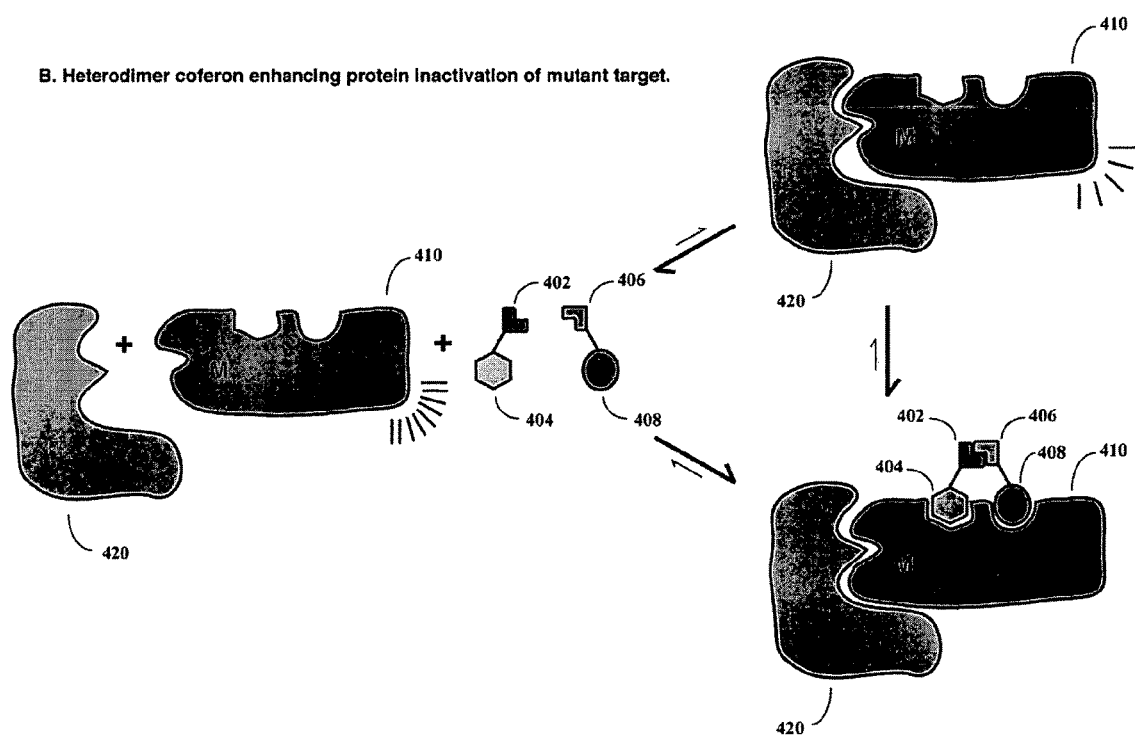
Figure 17

Coferon drug interactions with target, Part 6:
A. Protein binding weakly to target.
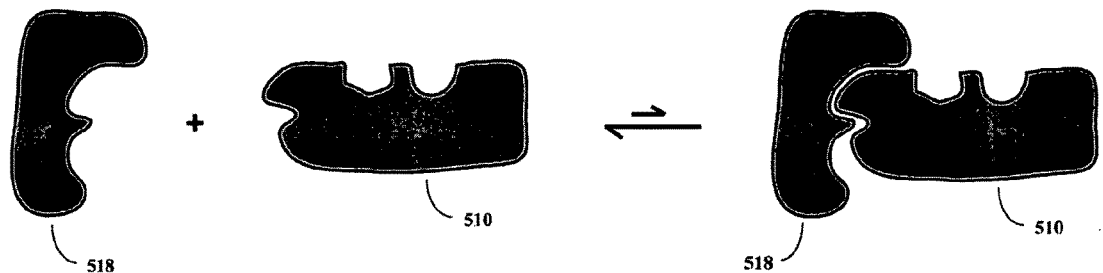
B. Heterodimer coferon and additional protein(s) enhancing protein binding to target.
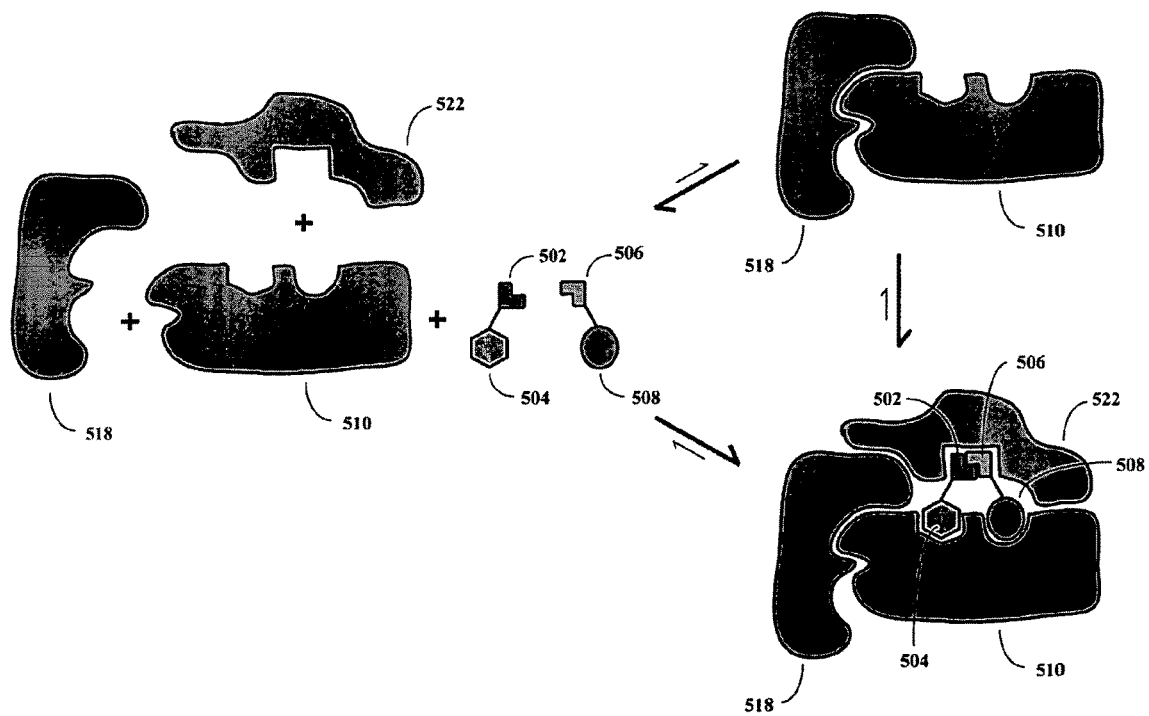
Figure 18

Coferon drug interactions with target, Part 7:
A. Protein binding strongly to target.
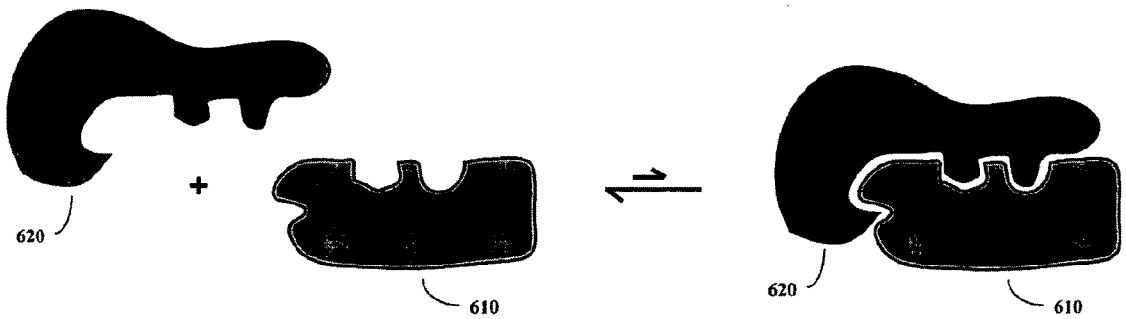
B. Heterodimer coferon and additional protein(s) inhibiting protein binding to target.
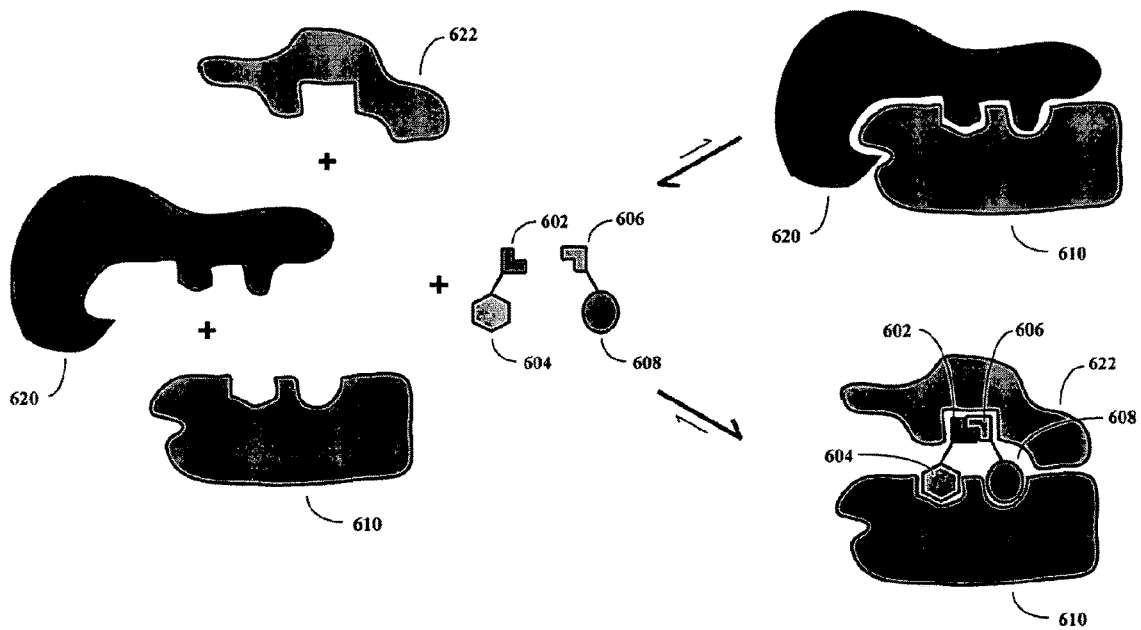
Figure 19

Coferon drug interactions with target, Part 8:
A. Heterodimer coferon and additional protein(s) recruiting protein to target.
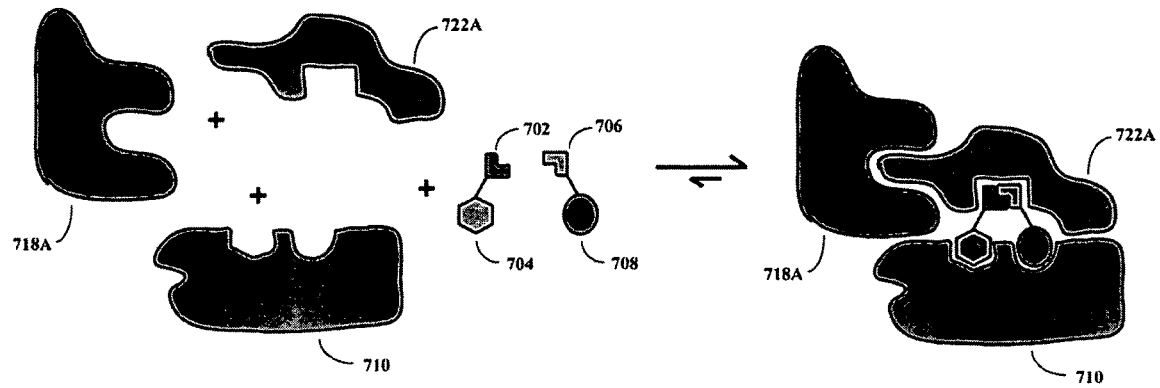
B. Heterodimer coferon and additional protein(s) recruiting protein to target.
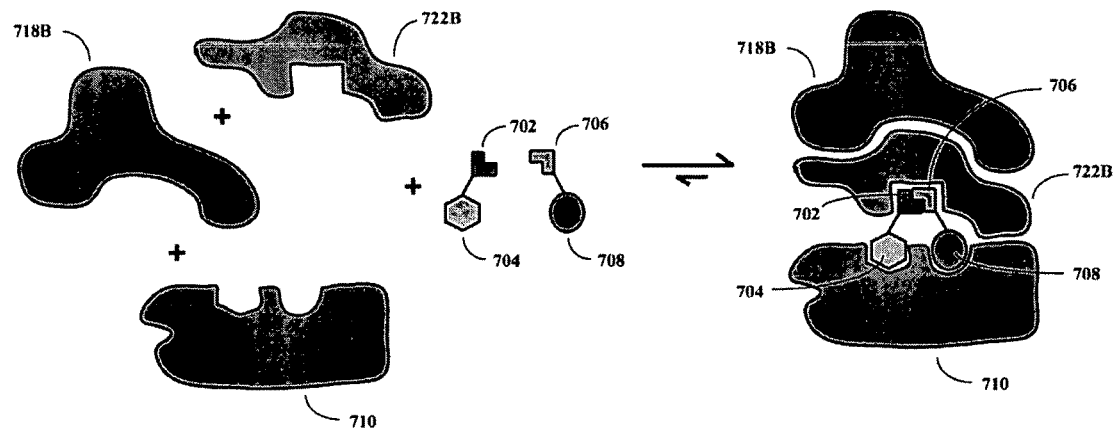
C. Heterodimer coferon and additional protein(s) recruiting protein to target.
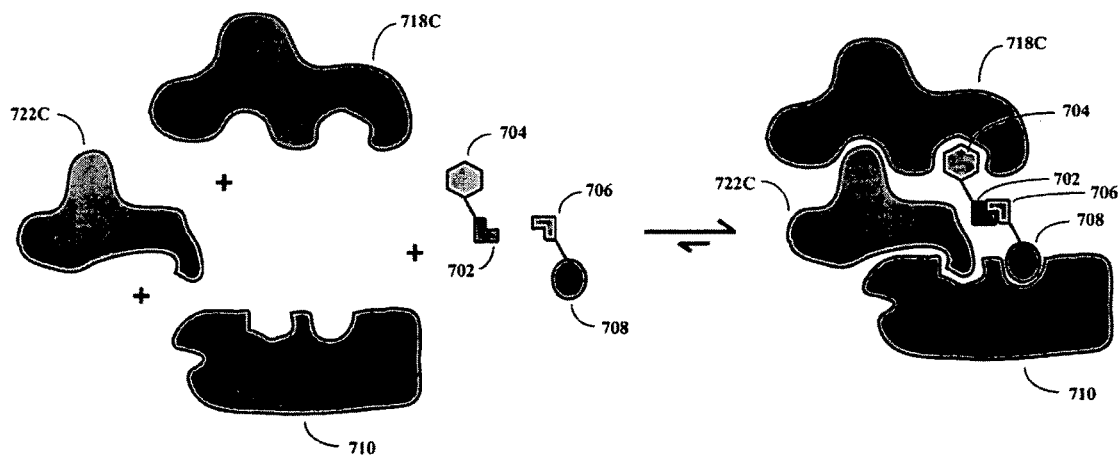
Figure 20

Coferon drug interactions with target, Part 9:
A. Ligand binding to, and activating target receptor.
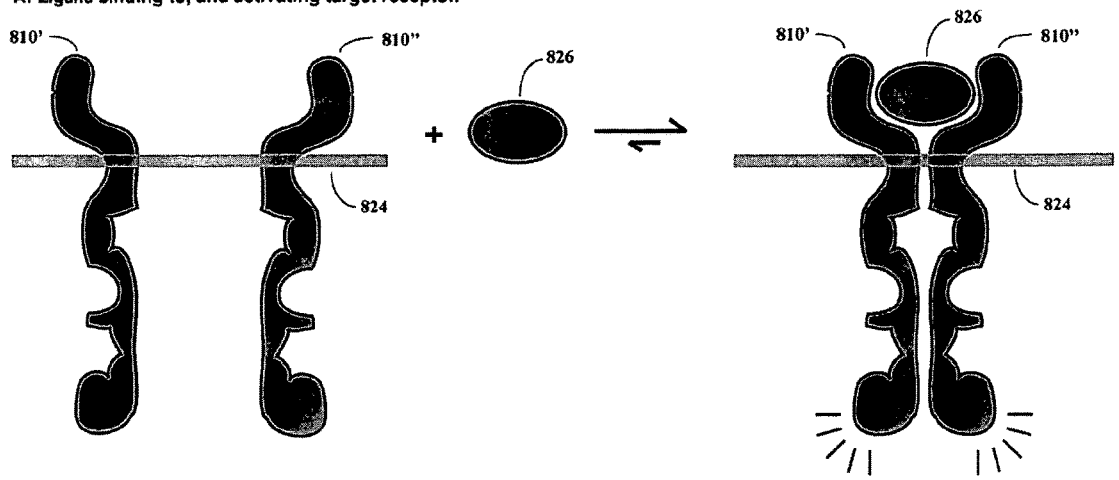
B. Homodimer coferon activating target receptor.
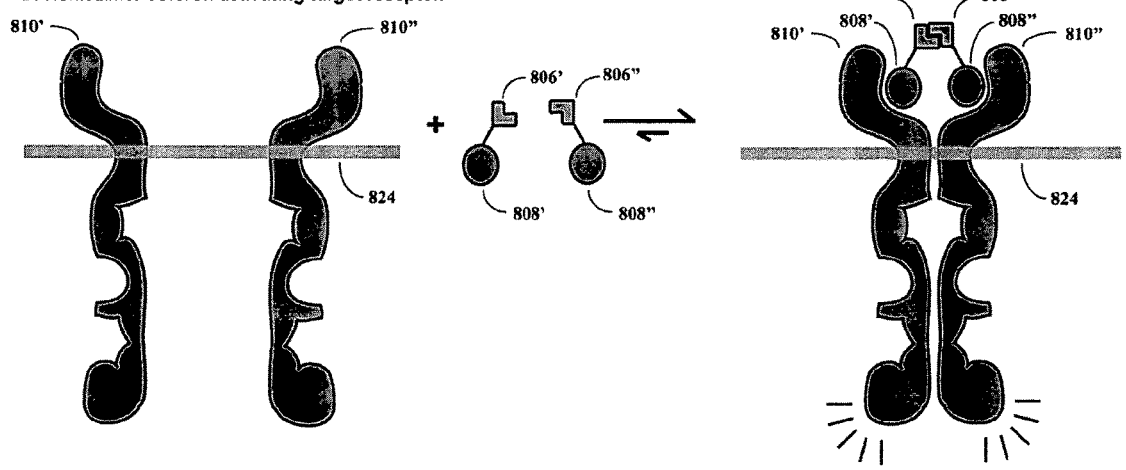
Figure 21

Coferon drug interactions with target, Part 10:
A. Homodimer coferon interfering with activation of target receptor.
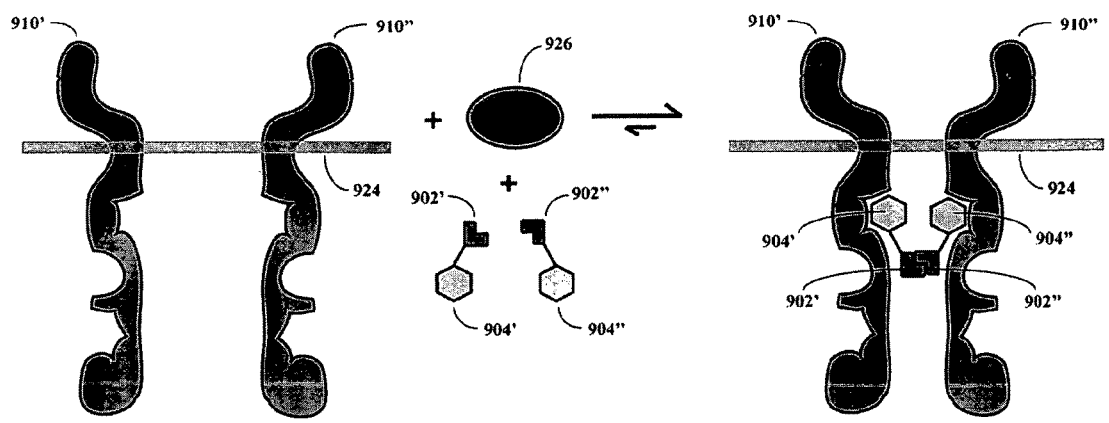
B. Heterodimer coferon inactivating target receptor.
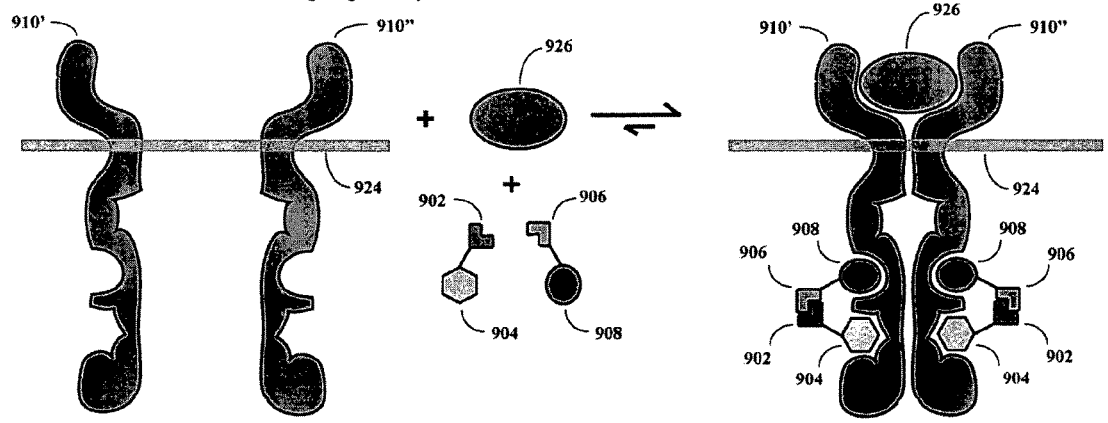
Figure 22

Coferon drug interactions with target, Part 12:
A. Ligand binding to target receptor, recruiting and activating second protein.
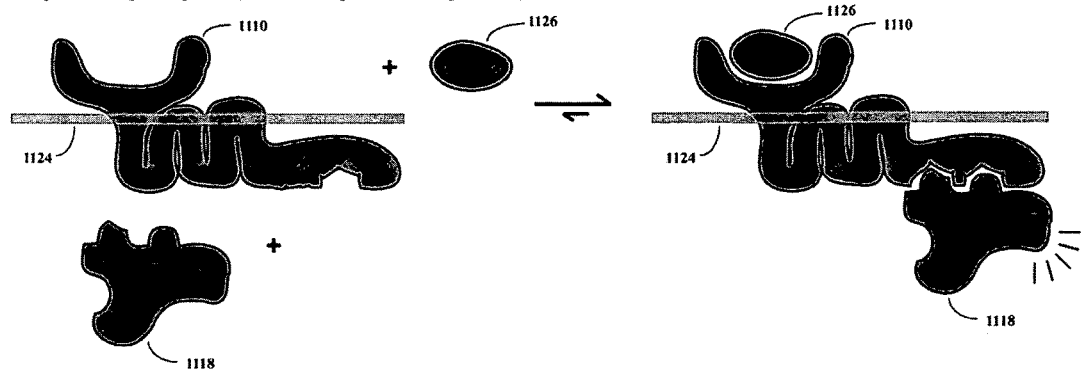
B. Homodimer coferon binding to target receptor, recruiting and activating second protein.
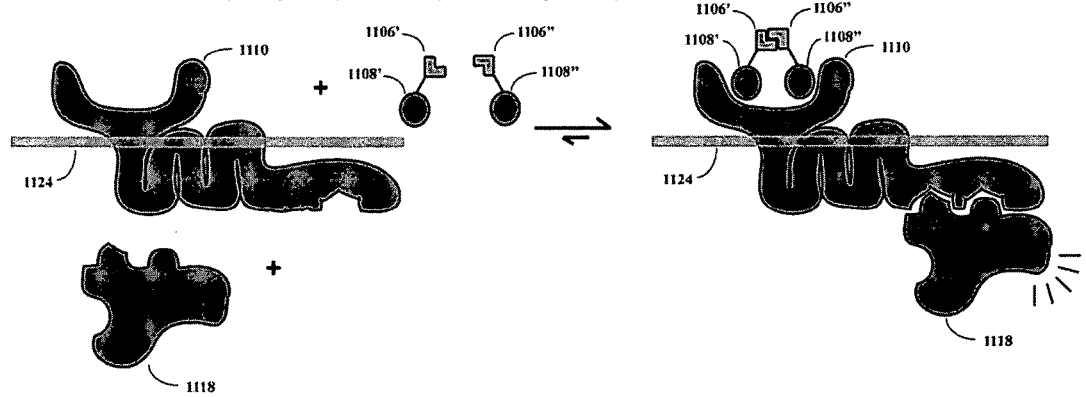
C. Homodimer coferon binding to target receptor, inhibiting recruitment of second protein.
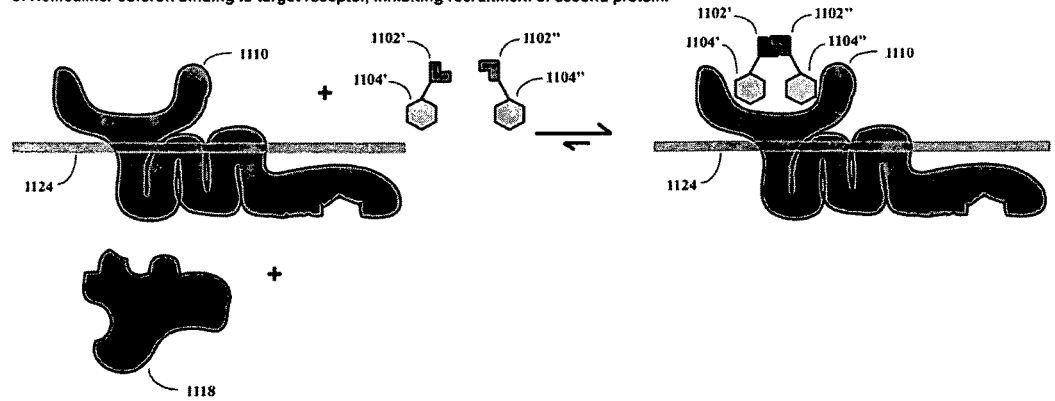
Figure 24

Coferon drug interactions with target, Part 13:

A. Homodimer coferon binding to target receptor, inhibiting recruitment of second protein.

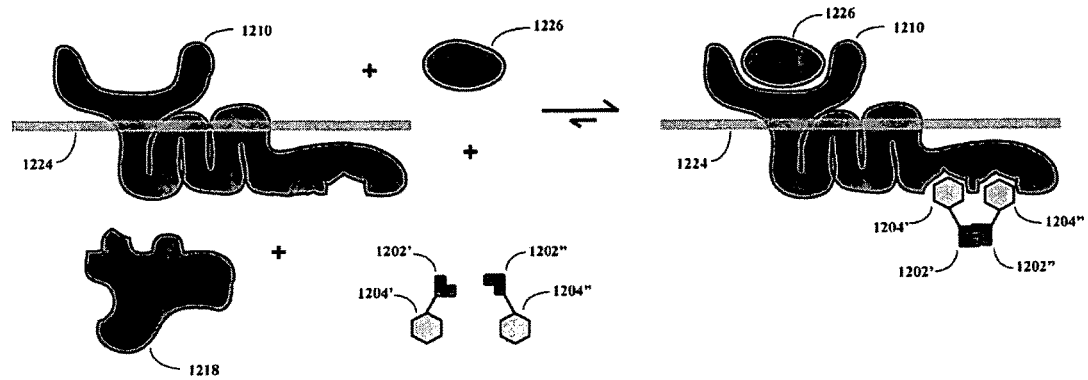

B. Heterodimer coferon binding to target receptor, enhancing recruitment and activation of second protein.

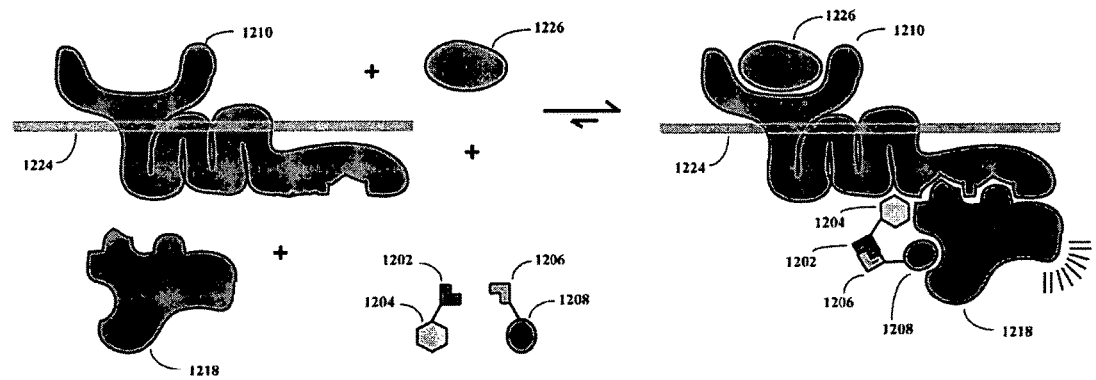

C. Heterodimer coferon binding to ligand and target receptor, enhancing recruitment and activation of second protein.

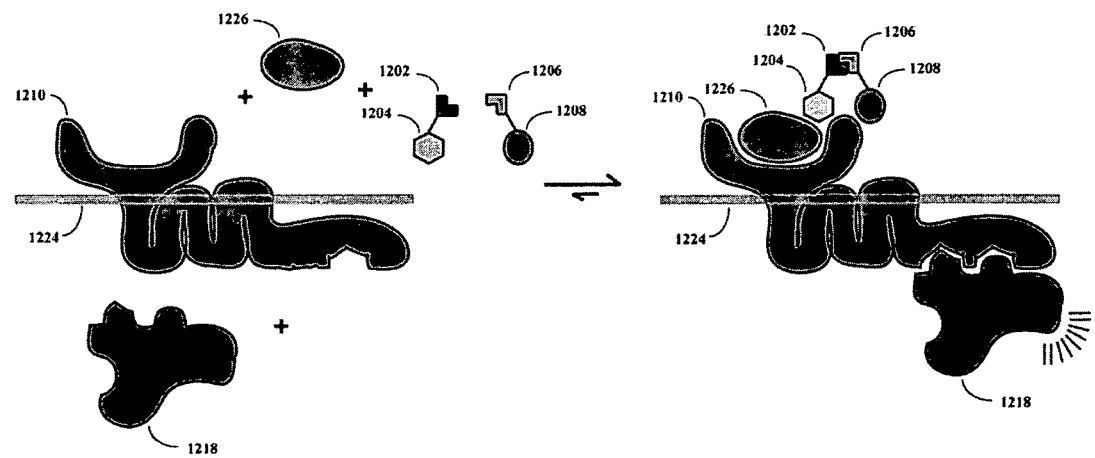

Figure 25

Coferon drug interactions with target, Part 14:
A. Homodimer coferon binding to dimer target.
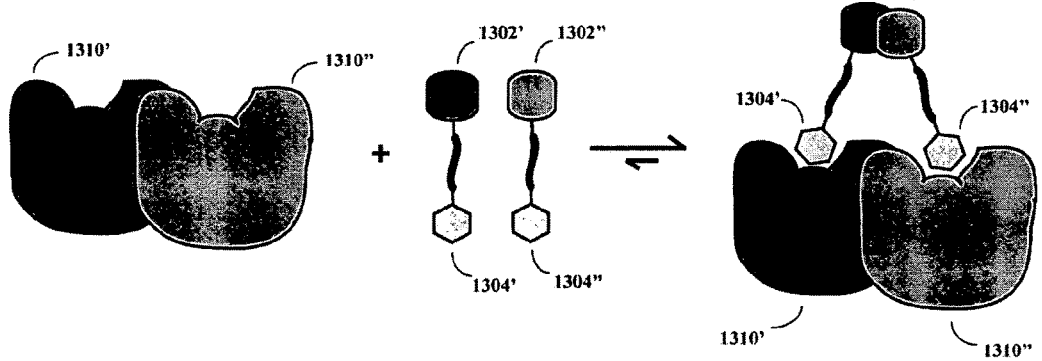
B. Homotetramer coferon binding to dimer target.
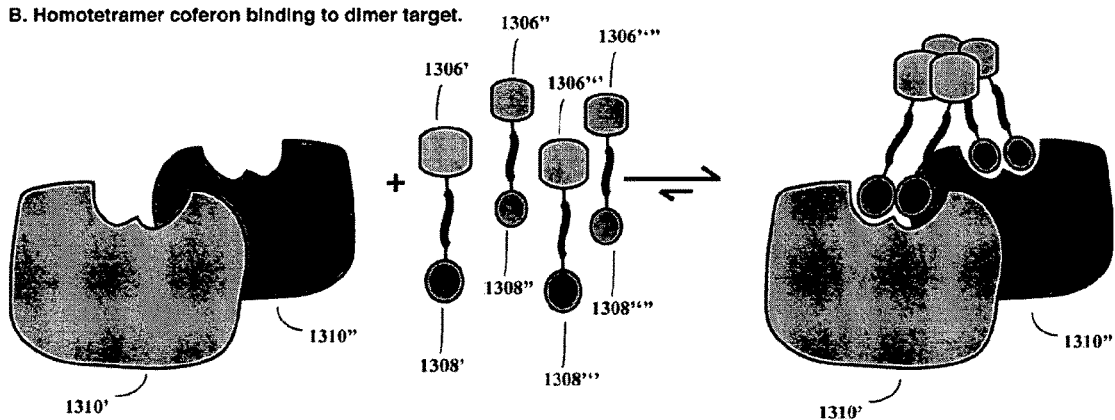
C. Tetramer coferon binding to dimer target.
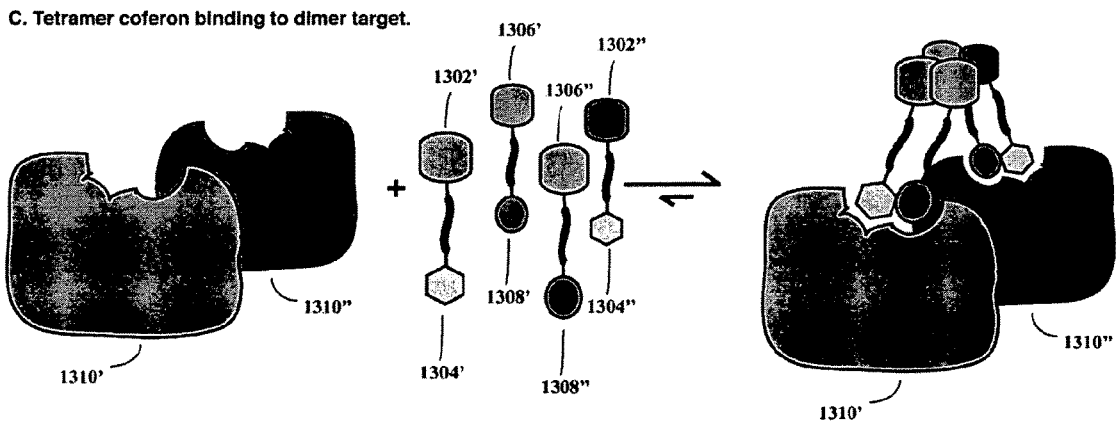
Figure 26

Coferon drug interactions with target, Part 15:
A. Tetramer coferon binding to multimer target.
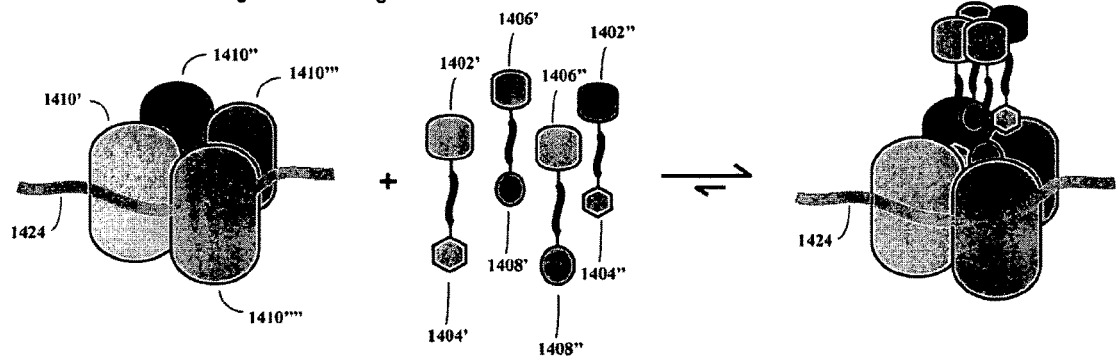
B. Mixed tetramer coferon binding to multimer target.
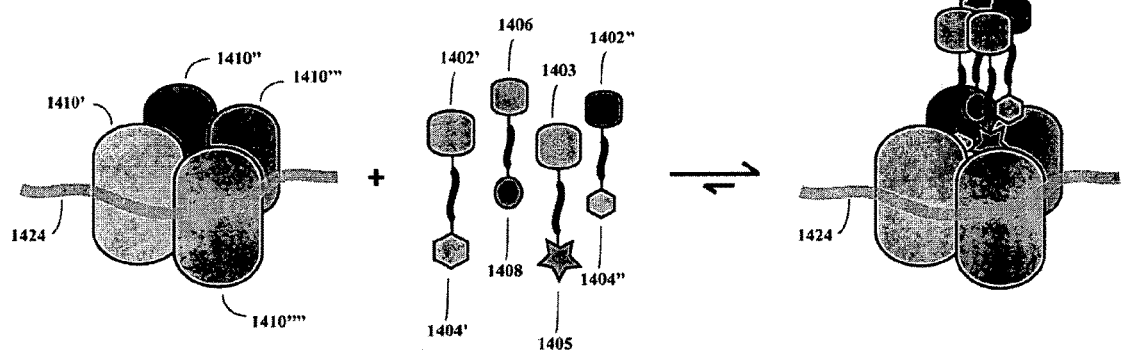
C. Hexamer coferon binding to multimer target.
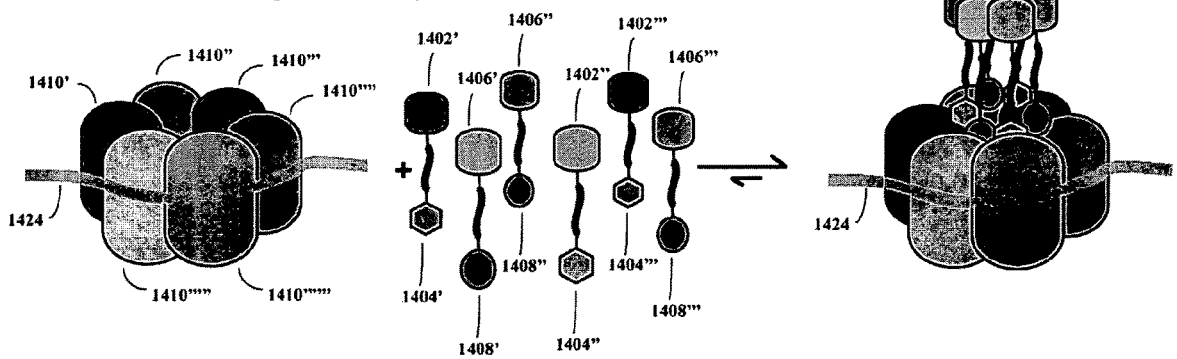
Figure 27

Coferon drug interactions with target, Part 16:

A. Alpha/beta tubulin heterodimer and filament formation.

B. Heterodimer coferon binding beta tubulin may destabilize filament formation.

Coferon drug interactions with target, Part 17:
A. Amyloid beta peptide forms amyloid fibrils.
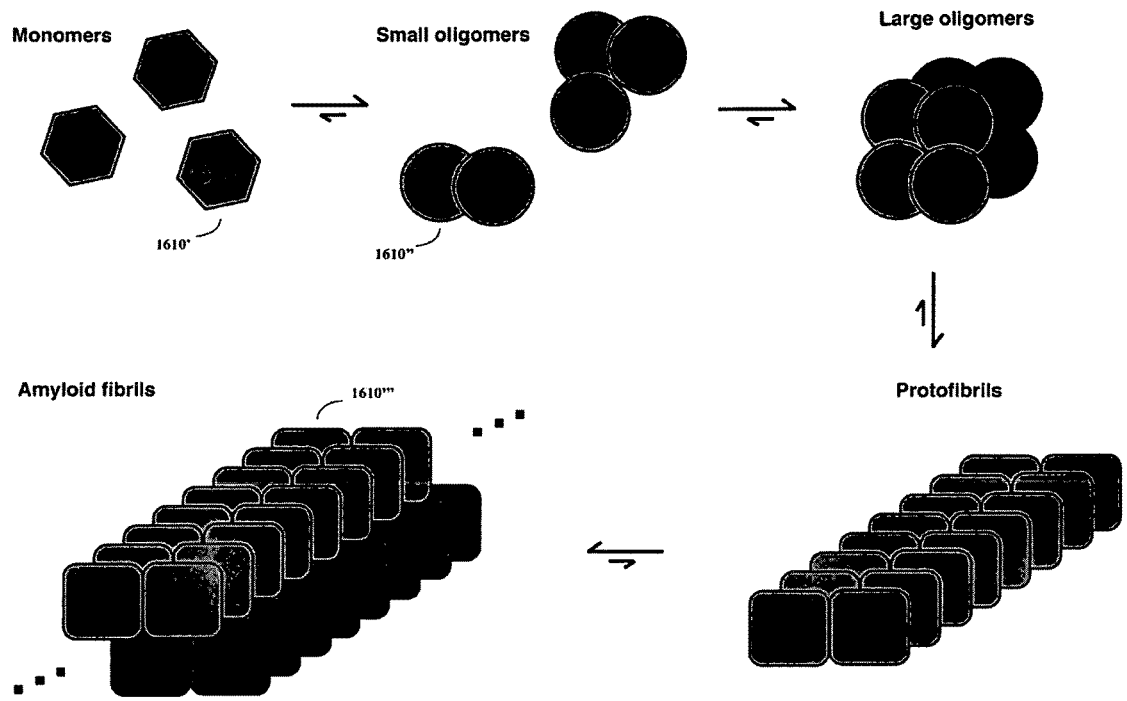
B. Heterodimer coferon inhibiting amyloid beta peptide from forming small oligomers and ultimately fibrils.
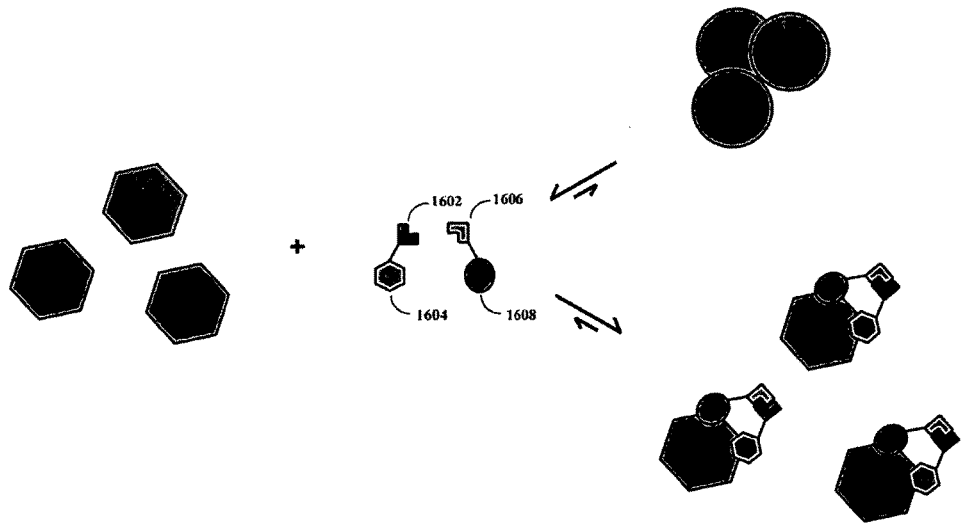
Figure 29

COFERONS AND METHODS OF MAKING AND USING THEM

This application is a national stage application under 35 U.S.C. §371 of PCT Application No. PCT/US2010/002708, filed Oct. 7, 2010, which claims the benefit of priority of U.S. Provisional Patent Application Ser. No. 61/278,523, filed Oct. 7, 2009, both of which are hereby incorporated by reference in their entirety.

This invention was made with government support under Public Health Service grant AI062579-03 from the National Institute of Allergy and Infectious Diseases and Grant No. CA65930-08 from the National Cancer Institute. The government has certain rights in this invention.

FIELD OF THE INVENTION

The present invention is directed to coferons and methods of making and using them.

BACKGROUND OF THE INVENTION

Cancers arise due to mutations or dysregulation of genes involved in DNA replication and repair, cell cycle control, anchorage independent growth, angiogenesis, apoptosis, tissue invasion, and metastasis (Hanahan, D. et al., Cell 100(1): 57-70 (2000)). These processes are controlled by networks of genes in the p53, cell cycle, apoptosis, Wnt signaling, RPTK signaling, and TGF-beta signaling pathways. Such genes and their protein products are the targets of many current and developing therapies.

Signaling pathways are used by cells to generate biological responses to external or internal stimuli. A few thousand gene products control both ontogeny/development of higher organisms and sophisticated behavior by their many different cell types. These gene products work in different combinations to achieve their goals, and do so through protein-protein interactions. The evolutionary architecture of such proteins is through modular protein domains that recognize and/or modify certain motifs. For example, different tyrosine kinases (such as Abl) will add phosphate groups to specific tyrosines embedded in particular peptide sequences, while other enzymes (such as PTEN) act as phosphatases to remove certain signals. Proteins and other macromolecules may also be modified through methylation, acetylation, sumolation, ubiquitination, and these signals in turn are recognized by specific domains that activate the next step in the pathway. Such pathways usually are initiated through signals to receptors on the surface, which move to intracellular protein interactions and often lead to signaling through transcription factor interactions that regulate gene transcription. For example, in the Wnt pathway, Wnt interacts with the Frizzled receptor, signaling through Disheveled, which inhibits the Axin-APC-GSK3 complex, which binds to beta-catenin to inhibit the combination of beta-catenin with TCF4, translocation of this complex into the nucleus, and activation of Myc, Cyclin D, and other oncogenic protein transcription (Polakis, P. et al., Genes Dev 14(15):1837-1851 (2000); Nelson, W. J. et al., Science 303(5663): 1483-1487 (2004)). Signaling may also proceed from the nucleus to secreted factors such as chemokines and cytokines (Charo, I. F. et al., N Engl J Med 354(6):610-621 (2006)). Protein-protein and protein-nucleic acid recognition often work through protein interactions domains, such as the SH2, SH3, and PDZ domains. Currently, there are over 75 such motifs reported in the literature (Hunter, et. al., Cell 100:113-127 (2000); Pawson et. al., Genes & Development 14:1027-1047 (2000)). These protein-interaction domains comprise a rich opportunity for developing targeted therapies.

Other macromolecular interactions that can serve as potential targets include protein-nucleic acid interactions, protein-carbohydrate interactions and protein-lipid interactions. Protein-nucleic acid interactions of interest are the interactions between ribosomal proteins and nucleic acids involved in protein synthesis, especially protein synthesis in bacterial pathogens (Franceschi F et al, Biochem Pharmacol, 71 (7): 1016-1025 (2006)). Interactions between transcription factors and nucleic acids sequences, such as those in promoter regions may also be targets for therapies (Gniazdowski M, et al., Curr Med. Chem., 10(11):909-24 (2003)).

Lectins and other carbohydrate binding proteins are involved in many cellular processes, including trafficking and clearing of glycoproteins, cell adhesion, glycosylation, immune response, apoptosis and tumor genesis. Sugars generally bind to proteins weakly in shallow grooves close to the surface of the protein, with binding affinities in the mM to μM range. The sugar binding sites on proteins that are essential for microorganism pathogenesis may serve as targets for therapy (Ziolkowska N et al, Structure 14:1127-1135 (2006)).

Protein-lipid interactions are most common in membrane proteins where the protein function is directly shaped by interactions with membrane lipids. These interaction are key components in sensory and signaling pathways (Phillips R et al, Nature 459:379-385 (2009)) and may serve as therapeutic targets.

Cancer therapies may be divided into two classical groups: (i) small molecule drugs such as Gleevec that bind into a compact pocket, and (ii) antibody therapeutics such as herceptin which binds and inhibits the HER-2/neu member of the epidermal growth factor receptor (EGFR) family. Antibody and protein therapeutics work by binding over an extended area of the target protein. Antibodies fight cancers by inducing apoptosis, interfering with ligand-receptor interactions, or preventing expression of proteins required for tumor growth (Mehren et al., Ann Rev. Med. 54:343-69 (2003)). Additional successful cancer antibody therapeutics include Rituximab, an anti CD20 antibody, Erbitux (cetuximab) targeted to EGFR, and Avastin (bevacizumab) which interferes with vascular endothelial growth factor (VEGF) binding to its receptor (Mehren et al., Ann Rev. Med. 54:343-69 (2003)). Except for the skin rash associated with EGFR receptor antibodies (which ironically correlates with efficacy), antibody therapies are generally well tolerated and do not have the side-effects associated with traditional chemotherapy.

Antibodies achieve their extraordinary specificity through the diversity generated in their complementarity-determining regions ("CDR's"). An IgG antibody binding surface consists of three CDRs from the variable heavy chain paired with three CDRs from the variable light chain domain. Each CDR consists of a loop of around a dozen amino acid residues, whose structure binds to the target surface with nanomolar affinity (Laune, et. al., J. Biol. Chem. 272:30937-30944 (1997); Monnet, et al., J. Biol. Chem. 274:3789-3796 (1999)). Thus, antibodies achieve their specificity by combining multiple weak interactions across a generally flat surface of approximately 1200-3000 Å$^2$. Monoclonal antibodies may be readily generated to most proteins, and artificial antibodies screened for using in vitro phage or bacterial systems (Mehren et al., Ann Rev. Med. 54:343-69 (2003)). Mouse monoclonal antibodies may be "humanized" to reduce development of undesired human antimouse antibodies. Limitations of using monoclonal antibodies include production of anti-idiotypic antibodies, disordered tumor vasculature, increased hydrostatic pressure within tumor, and heterogeneity of surface antigen within tumors. Due to these barriers, it takes 2 days for an IgG antibody to travel 1 mm and 7-8 months to travel 1 cm into a tumor (Mehren et al., *Ann Rev. Med.* 54:343-69 (2003)). Smaller variations of the IgG motifs have been engineered, including scFv and Affibodies (Eliasson, M. et al., *J Immunol* 142(2):575-581 (1989); Gunneriusson, E. et al., *J Bacteriol* 178(5): 1341-1346 (1996); Nord, K. et al., *Nat Biotechnol* 15(8):772-777 (1997)), and these have improved tumor penetration by cutting down penetration time in about half.

Antibodies can achieve tighter binding and higher specificity than any artificially synthesized therapy. Nevertheless, antibody therapies are limited to interfering with protein-protein interactions or protein receptor activity that are on the surface of tumors or circulating targets, cannot be ingested orally, and are not able to use their extraordinary specificity to inhibit intracellular protein signaling.

On the other end of the spectrum are small molecule drugs. These have the advantages of being orally active, being sufficiently small enough (usually with a molecular weight<750) to diffuse across cell membranes, and binding tightly into compact binding pockets used by all enzymes to bind their substrates (or interfering with macromolecular machinery used in cellular processes) (Landry, Y., et al., *Fundam Clin Pharmacol* 22(1):1-18 (2008); Duarte, C. D., et al., *Mini Rev Med Chem* 7(11):1108-1119 (2007); Amyes, T. L., et al., *ACS Chem Biol* 2(11):711-714 (2007)). Recently, the field of combinatorial chemistry has greatly improved the ability of chemists to identify lead molecules that bind and inhibit specific protein targets (Dolle, et al., *J. Combinatorial Chem.* 6(5):597-635 (2005)).

Thus, current drug design and drug therapy approaches do not address the urgent need to find drugs which interfere with intracellular protein-protein interactions, or protein signaling. Antibodies have the required specificity to distinguish among closely related protein surfaces, yet are too large to be taken orally or enter cells. Orally active pharmaceuticals are too small (i.e. have a molecular weight less than 750) to disrupt protein-protein surface interactions (generally flat, and over 1200-3000 $\text{Å}^2$).

Attempts to identify small molecule drugs that bind over an extended area have mostly been limited to traditional targets containing at least one compact binding site. One approach is based on: (i) preparing a set of potential binding elements where each molecule has a common chemical linkage group; (ii) identifying all binding elements that inhibit even weakly the target enzyme; (iii) preparing a combinatorial library of all the winning binding elements connected by a common chemical linkage group and a series of flexible linkers; and (iv) screening the combinatorial library to identify the tightest binding compound drugs. This approach was used to identify a small molecule inhibitor of the c-Src tyrosine kinase (Maly, et. al., *Proc. Nat't Acad. Sci. USA* 97: 2419-2424 (2000)) as well as the tyrosylprotein sulfotransferase (Kehoe, et al., *BioOrg & Medicinal Chem. Lett.* 12:329-332 (2002)). One flaw in this approach is that the initial screen finds mostly molecules that bind within the initial pocket, but the final product needs to have both binding elements bind with high affinity. Thus, the success of the above approach was the result of a fortuitous alternative binding of one of the elements identified in the initial screen. A second disadvantage is the need to screen each of the potential combinatorial library elements individually.

To overcome the limitation of testing various combinations of ligands and connectors individually, Lehn and coworkers developed dynamic combinatorial chemistry ("DCC") as a new means for drug discovery (Lehn, et. al., *Science* 291:2331-2332 (2001); Ramstrom, et. al., *Nat. Rev. Drug Discovery* 1:26-36 (2002)). In this approach, potential ligand molecules form reversible adducts to different bifunctional connector molecules, and these interconnections are in continuous exchange with each other. When the enzyme target is added, the best bound library constituent is selected from all the possible combinations, allowing for identification of the active species. Using 16 hydrazides, 2 monoaldehydes, and 3 dialdehydes, 440 different combinations were formed and selected against the bifunctional *B. subtilis* HPr. kinase/phosphatase (Bunyapaiboonsri, et. al., *J. Med. Chem.* 46:5803-5811 (2003)). Improvement in synthesis and spatial identification of specific library members is achieved by using resin-bound DCC approaches (McNaughton, et. al., *Organic Letters* 8:1803-1806 (2006)).

The use of DNA to encode self-assembling chemical (ESAC) libraries has extended the potential for dynamic combinatorial chemistry drug discovery (Melkko et al., *Nature Biotech*, 22:568-574 (2004)). The DNA strands are partially complementary to allow for reversible binding to each other under standard incubation conditions and also contain bar codes to identify the ligand element. After using DCC to select for the tightest binding combinations, and identification of ligands based on their DNA code, the ligands are resynthesized with a variety of spacers to identify the tightest binding tethered combinations. This approach was used to find binding molecules with nanomolar affinities to serum albumin, carbonic anhydrase, streptavidin, and trypsin, respectively (Melkko et al., *Nature Biotech*, 22:568-574 (2004); Dumelin et al., *Bioconjugate Chem.* 17:366-370 (2006); Melkko et al., *Angew. Chem.* 46:4671-4674 (2007)). One disadvantage of this approach is the wide footprint of about 15.4 Angstroms introduced by using double-stranded DNA as the dynamic combinatorial chemistry element, separating the ligands by a considerable distance, and requiring a higher MW tether to reestablish tight binding affinities.

In an inversion of the standard small-molecule drug binding within a compact binding pocket in the target enzyme, the macrocycle vancomycin binds to its L-Lys-D-Ala-D-Ala tripeptide target by forming a dimer that surrounds the tripeptide. By using the actual target to accelerate combinatorial synthesis of vancomycin and vancomycin analogue dimers, tethered dimers were isolated with tighter affinities and in vitro activity against some vancomycin resistant bacterial strains (Nicolaou et al., *Angew. Chem.* 39:3823-3828 (2000)). It is unlikely that these derivatives would be orally active due to their high molecular weight and potential for disulfide dimers to be reduced to monomers within the bloodstream.

Many receptors (for example, the erythropoietin receptor) are activated by ligand-induced homodimerization, which leads to internal cellular signals. By using bi- or multifunctional connectors to link ligand molecules to form dimers, trimers, and tetramer libraries, a number of small molecule agonists could be isolated that assisted in erythropoietin receptor homodimerization (Goldberg et. al., *J. Am. Chem. Sec.* 124:544-555 (2002)). These molecules demonstrate the ability of multi-ligand drugs to influence protein-protein interactions, in a manner that mimics the natural activity of cytokines and chemokines.

Sharpless and coworkers have identified reactions that occur readily when the constituent chemical linkage groups are brought in close proximity with each other, termed "click chemistry" (Kolb, et. al., *Drug Discovery Today* 8:1128-

1137 (2003)). By adding various ligands connected to these reactive groups (such as an azide on one set of ligands and acetylene on the other ligands) and combining these library compounds in solution in the presence of enzyme targets, highly potent inhibitors form, for example for the acetylcholine esterase or the HIV protease (Kolb et. al., *Drug Discovery Today,* 8:1128-1137 (2003); Brik et. al., *Chem. BioChem* 4:1246-1248 (2003); Whiting, et. al., *Angew. Chem. Int. Ed.* 45:1435-1439 (2006); Lewis et. al., *Angew Chem* 41:1053-1057 (1002); Bourne et. al., *Proc. Nat'l Acad. Sci. USA* 101:1449-1454 (2004)). In short, the target enzyme acts as a catalyst for the proximal ligation of its own inhibitor. The advantage of this approach is the enrichment of the best binding compound in a single step.

An elegant approach to finding low molecular weight ligands that bind weakly to targeted sites on proteins was developed by Wells and coworkers (Erlanson et. al., *Proc. Nat'l Acad. Sci. USA* 97:9367-9372 (2000); Thanos, et. al., *J. Am. Chem. Sco.* 125:15280-15281 (2003); Erlanson et. al., *Nature Biotechnology* 21:308-314 (2003); Buck et. al., *Proc. Nat'l Acad. Sci. USA* 102:2719-2724 (2005)). A native or engineered cysteine in a protein is allowed to react reversibly with a small library of disulfide-containing molecules. The process of dynamic combinatorial chemistry takes place as the most stable molecules are enriched on the surface of the protein target. These are then readily identified by mass spectroscopy, and serve as lead compounds for further modification.

Dynamic combinatorial or "click" chemistry increases yields of appropriate binding ligand combinations, but still requires enzymatic assays. The disadvantages of these approaches are that they are limited to enzymes with one or more deep binding pockets, where knowledge of at least one potential ligand is often needed. Further, the starting blocks are not readily available and require independent synthesis for each pharmacophore or ligand to be tested. The chemical linkage groups used for click chemistry are not suitable for use in vivo as they would react readily and irreversibly with cellular components. The reactions need to take place with sufficient efficiency and at a large enough scale such that the enzyme selected inhibitor is synthesized in sufficient amounts to allow for purification and identification of the correct product. This last constraint limits the number of ligands that may be screened in a single assay, and limits the throughput of these approaches.

Several groups have recognized that macrocycles provide an opportunity for recognition of extended binding motifs within targets. Several of these are orally active, despite having molecular weight beyond the traditional 750 cutoff. These include cyclosporin (molecular weight 1202.64), rapamycin (molecular weight 914.2), tacrolimus (molecular weight 822.03), erythromycin (molecular weight 733.94), azithromycin (molecular weight 748.88), and clarithromycin (molecular weight 747.9). Note that although vancomycin (molecular weight 1485.74) is used orally for treatment of gastrointestinal infections, it is not absorbed into the body. Cyclosporin is the largest of the groups listed above and illustrates a few features common to these drugs. Their cyclic nature reduces entropic loss upon binding and the extended structure allows for enhanced binding. Cyclosporin has torroidal flexibility, allowing it to bring its polar side-chains into the interior so the outside is nonpolar and this allows for transfer across membranes. Likewise, the drug is in structural equilibrium with its polar conformer, allowing for binding to its target.

As promising as macrocycle and synthetic peptide mimetics are for lead drug candidates, it is not trivial to use synthetic chemistry to generate sufficient diversity required for high affinity binding to extended binding sites in target proteins. Two groups have sought to address this issue using DNA encoded approaches with evolutionary selection. In the first approach, a functional group is attached to a long DNA barcode sequence containing multiple zip-codes (Halpin, D. R. et al., *PLoS Biol* 2(7):E173 (2004); Halpin, D. R. et al., *PLoS Biol* 2(7):E174 (2004); Halpin, D. R. et al., *PLoSBiol* 2(7):E175 (2004)). The molecules are equilibrated with a set of columns (e.g., 10 columns), containing beads with complementary zip-code sequences. DNA hybridization captures library members containing the complementary zip-code sequence on their DNA tag. The library members are eluted into separate new chambers and reacted with a bifunctional moiety (for example, a protected amino acid residue) that corresponds to the given zip-code. The library members are then re-pooled, and then rerouted to the next series of columns. This process was repeated through several rounds to generate $10^6$ pentapeptides. After only two rounds of translation, selection with an antibody to the pentapeptide enkephalin, and amplification, the library converged on enkephalin and slight variants. Potential disadvantages of this approach are the need for DNA encryption strands of 200 or more bases. In the second approach, a bifunctional group is attached to a DNA template sequence containing adjacent zipcode sequences (Calderone, C. T. et al., *Angew Chem Int Ed Engl* 44(45):7383-7386 (2005); Sakurai, K. et al., *J Am Chem Soc* 127(6):1660-1661 (2005)). The DNA sequence serves as a template for adding bifunctional moieties to one end of the bifunctional group on the DNA tag. Each bifunctional moiety (for example, a protected amino acid residue) is attached to a complementary zip-code DNA molecule, which hybridizes on the DNA template containing the original bifunctional group. This hybridization increases the local concentration of the reactant to such an extent that it can drive synthesis to very high yields. This method does not require split-pooling techniques. If 4 sets of 10 each bifunctional moieties are added, this will result in 10,000 pharmacophores in the library. At the end of the synthesis, the last amino acid residue may be reacted with the other end of the original bifunctional group to create a circular pharmacophore. In this version, the identity of the pharmacophore is defined by the zipcode sequences in the DNA template. It may be identified by PCR amplification and sequencing. Further, the PCR amplicons may serve as starting templates for a new round of translation, selection, and amplification, allowing for application of evolutionary principles to synthesize high affinity binding elements. However, the extent of pharmacophores synthesized by the above two approaches are still several orders of magnitude lower than the diversity and affinity achieved by just a single CDR loop from an antibody molecule.

Several groups have investigated the ability of small molecules to interact with each other or encircle other small molecule targets; these are known as "guest-host" interactions or artificial receptors. However, these compounds are not suitable, because they are not of low enough molecular weight or interact under non-physiological conditions or would be too reactive with other intracellular molecules.

A common approach to designing artificial receptors is to construct a "molecular tweezer", consisting of a two armed structure joined by a conformationally restricted linker, such that the two arms point in the same direction (analogous to a tweezer). These "host" structures are often designed with a dye or on a bead, and then screened for binding of the "guest", most often a tri-peptide, again with either a dye or on a bead. (Shao et. al., *J Org. Chem.* 61:6086-6087 (1996);

Still et. al., *Acc. Chem. Res.* 29:155-163 (1996); Cheng, et. al., *J. Am. Chem. Soc.* 118:1813-1814 (1996); Jensen et. al., *Chem. Eur. J.* 8:1300-1309 (2002)). In a variation of this theme, binding of the peptide displaces a quenched fluorescent group from the host pocket, thus creating a fluorescent signal upon binding (Chen, et. al., *Science* 279:851-853 (1998); Iorio et. al., *Bioorganic & Medicinal Chem. Lett.* 11:1635:1638 (2001)). Rigid diketopiperazine backbone receptors with tri-peptide arms have demonstrated both tight binding, as well as how small structural changes in the backbone significantly reduce that binding (Wennemers et al., *Chem. Eur. J.* 7:3342-3347 (2001); Conza et. al., *J. Org. Chem.* 67:2696-2698 (2002); Wennemers et al., *Chem. Eur. J.* 9:442-448 (2003)). Unsymmetrical tweezer and one-armed receptor hosts have been designed to mimic vancomycin binding of an L-Lys-D-Ala-D-Ala tripeptide guest (Shepard et al., *Chem. Eur. J.* 12:713-720 (2006); Schmuck et al., *Chem. Eur. J.* 12:1339-1348 (2006)). Other host-guest systems include napthalene-spaced tweezers and cyanobenzene derivatives (Schaller et al., *J. Am. Chem. Soc.* 129: 1293-1303 (2007)). In some of the examples above, the selection was performed in organic solvents, and, in all cases, at least one of the entities had a molecular weight in excess of 400 and often in excess of 800. Thus, these examples would not be suitable for lead molecules.

Another approach to designing low molecular weight affinity binders is to use phage display. This approach was used to find peptides from 9-13 mers that bind fluorescent dyes; however, only one of these retained sufficient affinity to bind a dye when resynthesized outside the context of the phage protein (Rozinov et. al., *Chemistry & Biology* 5:713-728 (1998), Marks, et. al., *Chemistry & Biology* 11:347-356 (2004)). Other groups have used phage display to design synthetic peptides 8-12 mers that bind biotin (Saggio et. al., *Biochem. J.* 293:613-616 (1993)), camptothecin (Takakusagi et al., *Bioorganic & Medicinal Chem. Lett.* 15:4850-4853 (2005)), as well as doxorubicin and other hydrophobic cancer drugs (Popkov et al, *Eur. J. Biochem.* 251:155-163 (1998)). In all these cases, the fluorescent dye or similarly hydrophobic guest moiety is held in place by a pocket comprised from hydrophobic amino acids, and then additional residues may provide further stability. Since the peptides have molecular weights ranging from about 900 to about 1500, they are too large and not suitable for lead molecules.

Thus, there is a need to design new small molecules that associate with good affinities for one another under physiological conditions. Further there is a need to design such small molecules to bind to biological macromolecules with improved affinity and specificity and influence their structure, function, processing, degradation and role in signal transduction and cellular responses. The present invention is directed to overcoming this deficiency in the art.

SUMMARY OF THE INVENTION

One aspect of the present invention is directed to a monomer useful in preparing therapeutic compounds. The monomer includes one or more pharmacophores or diversity element which potentially binds to a target molecule with a dissociation constant of less than 300 μM and a linker element, each connected, directly or indirectly through a connector, to said pharmacophore. The linker element has a molecular weight less than 500 daltons and has a dissociation constant of less than 300 mM, with or without a co-factor, under physiological conditions. The linker element is selected from the group consisting of 1)

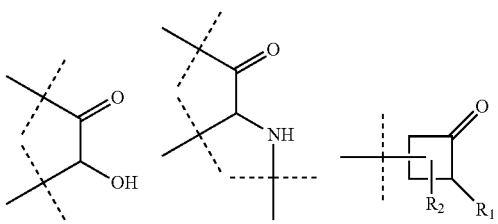

$R_1 = $ ——OH, SH, ——$NH_2$, ——$NHCH_3$, ——$NHR_3$
where $R_3 = $ ——C(═O)$R_4$, ——$SO_2R_4$, ——C(═O)O$R_4$
where $R_4$ is composed of aliphatic, alicyclic, aromatic or heteroaromatic group where $R_3$ may also connect to the pharmacophore and is composed of aliphatic, alicyclic, aromatic or heteroaromatic group
$R_2 = $ ——H, ——$CH_3$, ——Ph or other aliphatic, aromatic or heteroaromatic group

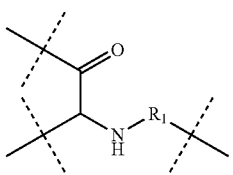

where $R_1 = $ ——CHO, ——C(O)$CH_3$, ——C(O)$R_2$, ——S(O)$_2CH_3$, ——S(O)$_2R_2$
where $R_2$ may also connect to the pharmacophore and is composed of aliphatic, aromatic or heteroaromatic group.

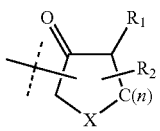

n = 1-4
X = C, N, S, O
$R_1 = $ ——OH, ——SH, $NH_2$, $NHCH_3$, $NHR_3$
where $R_3$ may also connect to the pharmacophore and is composed of aliphatic, aromatic or heteroaromatic group
$R_2 = $ ——H, ——$CH_3$, ——Ph or other aliphatic, aromatic or heteroaromatic group where the lines crossed with a dashed line illustrate the one or more bonds formed joining the one or more pharmacophores, directly or through a connector; 2)

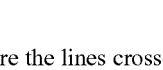

where the lines crossed with a dashed line illustrate the one or more bonds formed joining the one or more pharmacophores, directly or through a connector; 3)

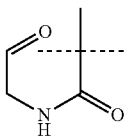

where the lines crossed with a dashed line illustrate the one or more bonds formed joining the one or more pharmacophores, directly or through a connector; 4)

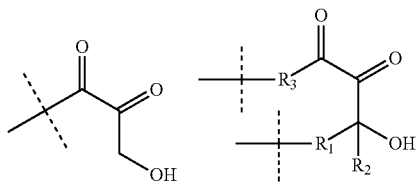

$R_1, R_2 =$ —H, —CH$_3$, —Ph, —C$_6$H$_{11}$, —C$_5$H$_9$,
aromatic or heteroaromatic or connected to each other through a 3, 4, 5 or 6 membered ring.
$R_3 =$ —NH$_2$, —OH, —CH$_3$, —Ph, —NHR$_4$, —CH$_2$R$_4$, —OR$_4$
where R$_4$ may be connected to the pharmacophore and is composed of aliphatic, aromatic or heteroaromatic group, and R$_3$ and R$_4$ may connect to R$_1$ and R$_2$ through a 5, 6, 7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

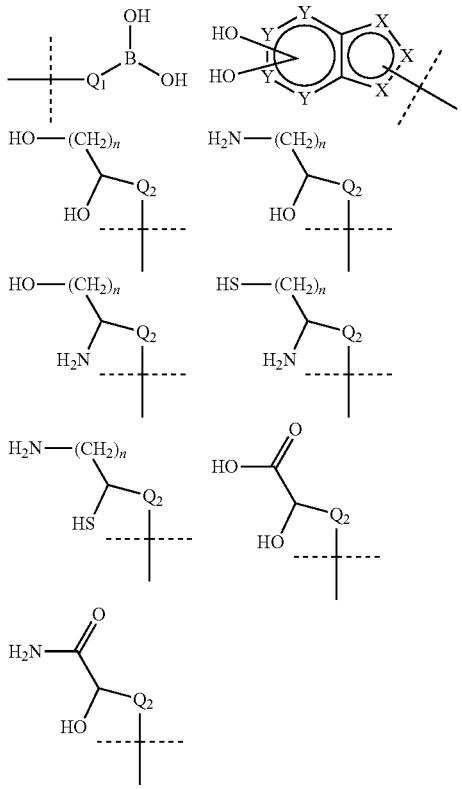

where Q$_1$ and Q$_2$ are aliphatic, alicyclic, or hetero or non-hetero aromatic moieties
where n=1 or 2
where X and Y=C, N, O, or S
where the hydroxy groups emanating from the aromatic ring are ortho to each other

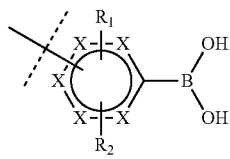

X = C, N
$R_1, R_2 =$ —H, —F, —Cl, —Br, —I, —CF$_3$,
—CN, —OCH$_3$, —NO$_2$
When R$_1$ & R$_2$ are adjacent, may also include fused 5 or 6 membered aromatic or heteroaromatic ring

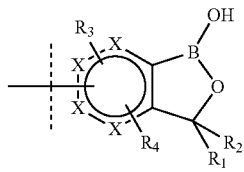

X = C, N
$R_1, R_2 =$ —H, —CH$_3$, —Ph, or connected to each other through a spiro 3, 4, 5 or 6 membered ring
$R_3, R_4 =$ —H, —F, —Cl, —Br, —I, —CF$_3$,
—CN, —OCH$_3$, —NO$_2$
When R$_3$ & R$_4$ are adjacent, may also include fused 5 or 6 membered aromatic or heteroaromatic ring

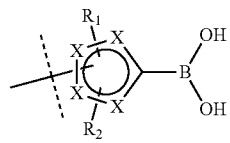

X = C, N, O, S
$R_1, R_2 =$ —H, —F, —Cl, —Br, —I, —CF$_3$,
—CN, —OCH$_3$, —NO$_2$
When R$_1$ & R$_2$ are adjacent, may also include fused 5 or 6 membered aromatic or heteroaromatic ring

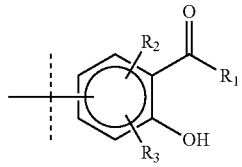

$R_1 =$ —OH, —NH$_2$, —SH, —NHR$_4$
Where R$_4$ = alkyl, hydroxyalkyl
$R_2, R_3 =$ —H, —CH$_3$, —OCH$_3$,
—OH, —COOH, CONH$_2$
When R$_2$ & R$_3$ are adjacent, may also include fused 5 or 6 membered aromatic or heteroaromatic ring

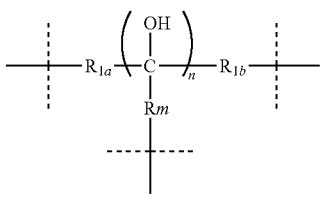

n = 2-6
$R_1, R_{1b} =$ —H, —CH$_3$, —CH$_2$NH$_2$, —CH$_2$NHCH$_3$,
aromatic or heteroaromatic ring, or connected to each other through a 4,5,6,7 or 8-membered ring
$R_m =$ —H, —CH$_3$, —CH$_3$NH$_2$, —CH$_3$OH, —CH$_2$CH$_2$OH and
m = 2-6

-continued

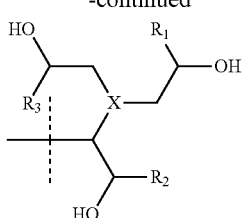

X = C, N
R$_1$, R$_2$, R$_3$ = —H, —CH$_3$, or two R groups connected to each other through a 5 or 6 membered alicyclic ring

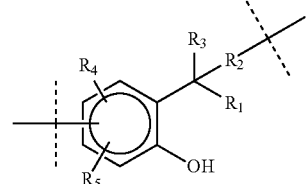

R$_1$ = —OH, —NH$_2$, —SH
R$_2$, R$_3$ = —H, —CH$_3$, —Ph,
or connected to each other through a spiro 3, 4 5 or 6 membered ring
R$_4$, R$_5$ = —H, —CH$_3$, —CH$_2$OH, —C(R$_2$, R$_3$)OH, —OCH$_3$, —OH, —COOH, —CONH$_2$
When R$_4$ & R$_5$ are adjacent, may also include fused 5 or 6 membered aromatic or heteroaromatic ring

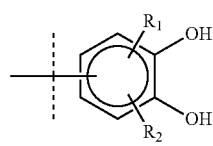

R$_1$, R$_2$ = —H, —CH$_3$, —OCH$_3$, —OH, —COOH, —CONH$_2$, —F, —Cl, —Br, —I, —CF$_3$, —CN, —NO$_2$
When R$_1$ & R$_2$ are adjacent, may also include fused 5 or 6 membered aromatic or heteroaromatic ring

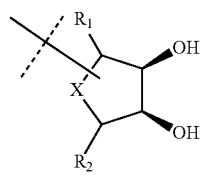

X = C, N, O, S
R$_1$, R$_2$ = —H, —CH$_3$, ----OH, —CH$_2$OH, -Adenyl

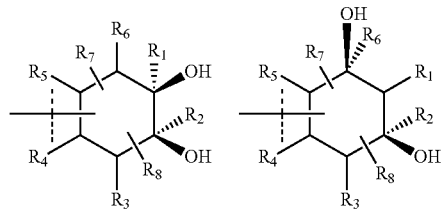

R$_1$, R$_2$, R$_3$, R$_4$, R$_5$, R$_6$ = —H, —CH$_3$
R$_7$, R$_8$ are connected to each other to form 3.1.1, 2.2.1 and 2.2.2 bicyclic ring systems such that the hydroxyls are cis to each other -continued

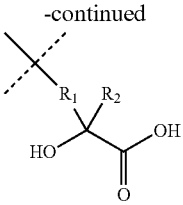

R$_1$, R$_2$ = —H, —CH$_3$, —Ph, —C$_6$H$_{11}$, —C$_5$H$_9$, aromatic or heteroaromatic ring, C$_1$—C$_6$-alkyl or C$_3$—C$_8$ cycloalkyl.

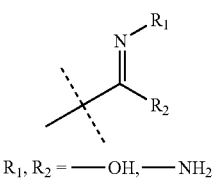

R$_1$, R$_2$ = —OH, —NH$_2$

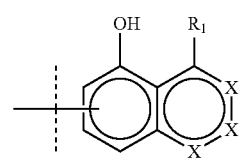

X = C, N
R$_1$ = —OH, —NH$_2$, —NHR$_2$, —NHC(=O)R$_2$, —NHSO$_2$R$_2$

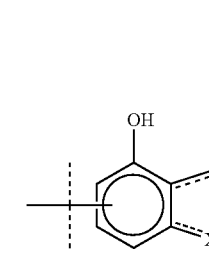

X = C, N, O, S
R$_1$, R$_2$ = —NH$_2$, =O, —OH where the lines crossed with a dashed line illustrate the one or more bonds formed joining the one or more pharmacophores, directly or through a connector. The linker elements may be homodimeric (i.e. dimerizing with same functionality), or heterodimeric (dimerizing with a complementary linker element) through the formation of new chemical bonds. Examples of homodimerizing or homo-oligomerizing linker elements may be selected from the groups 1)-4) above, while heterodimerizing linkers are comprised of linker combinations such as those in group 5) above.

Another aspect of the present invention relates to a therapeutic multimer precursor. The therapeutic multimer precursor includes a plurality of covalently or non-covalently linked monomers. Each monomer comprises one or more pharmacophore which potentially binds to a target molecule with a dissociation constant less than 300 μM, a linker element, and an optional encoding element. The linker element has a molecular weight less than 500 daltons and is selected from the group consisting of 1)

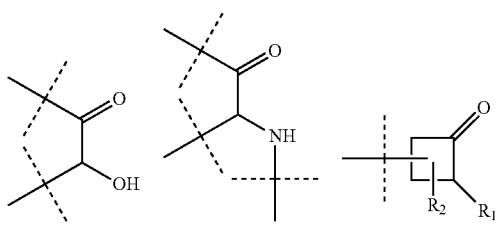

$R_1 = $ —OH, SH, —$NH_2$, —$NHCH_3$, —$NHR_3$
where $R_3 = $ —C(=O)$R_4$, —$SO_2R_4$, —C(=O)$OR_4$
where $R_4$ is composed of aliphatic, alicyclic, aromatic or heteroaromatic group where $R_3$ may also connect to the pharmacophore and is composed of aliphatic, alicyclic, aromatic or heteroaromatic group
$R_2 = $ —H, —$CH_3$, —Ph or other aliphatic, aromatic or heteroaromatic group

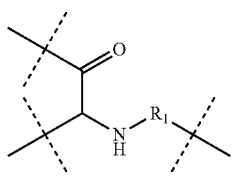

where $R_1 = $ —CHO, —C(O)$CH_3$, —C(O)$R_2$, —S(O)$_2CH_3$, —S(O)$_2R_2$
where $R_2$ may also connect to the pharmacophore and is composed of aliphatic, aromatic or heteroaromatic group.

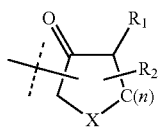

n = 1-4
X = C, N, S, O
$R_1 = $ —OH, —SH, $NH_2$, $NHCH_2$, $NHR_3$
where $R_3$ may also connect to the pharmacophore and is composed of aliphatic, aromatic or heteroaromatic group
$R_2 = $ —H, —$CH_3$, —Ph or other aliphatic, aromatic or heteroaromatic group where the lines crossed with a dashed line illustrate the one or more bonds formed joining the one or more pharmacophores, directly or through a connector; 2)

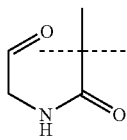

where the lines crossed with a dashed line illustrate the one or more bonds formed joining the one or more pharmacophores, directly or through a connector; 3)

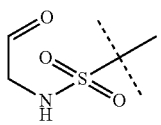

where the lines crossed with a dashed line illustrate the one or more bonds formed joining the one or more pharmacophores, directly or through a connector; 4)

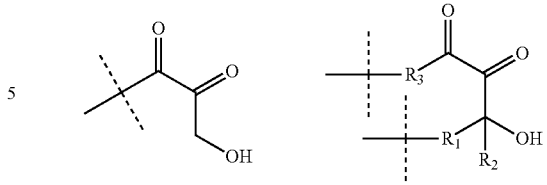

$R_1, R_2 = $ —H, —$CH_3$, —Ph, —$C_6H_{11}$, —$C_5H_9$, aromatic or heteroaromatic or connected to each other through a 3,4,5 or 6 membered ring.
$R_3 = $ —$NH_2$, —OH, —$CH_3$, —Ph, —$NHR_4$, —$CH_2R_4$, —$OR_4$
where $R_4$ may be connected to the pharmacophore and is composed of aliphatic, aromatic or heteroaromatic group, and $R_3$ and $R_4$ may connect to $R_1$ and $R_2$ through a 5,6,7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

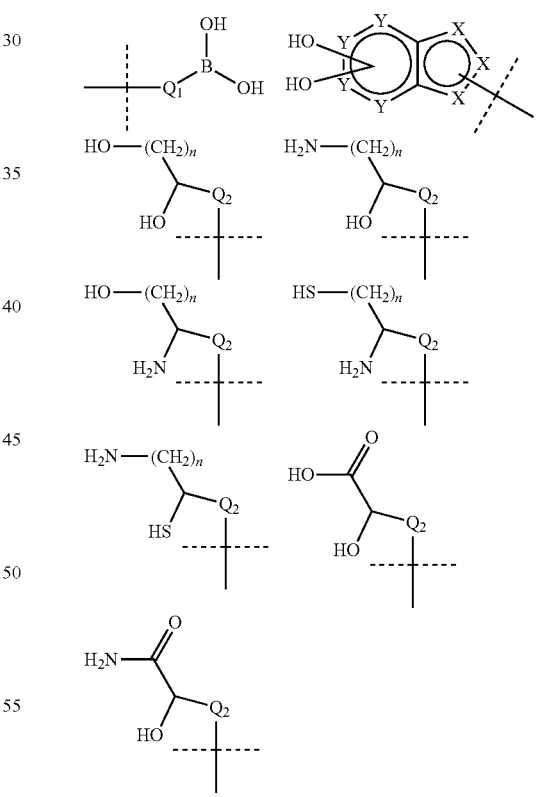

where $Q_1$ and $Q_2$ are aliphatic, alicyclic, or hetero or non-hetero aromatic moieties
where n=1 or 2
where X and Y=C, N, O, or S
where the hydroxy groups emanating from the aromatic ring are ortho to each other

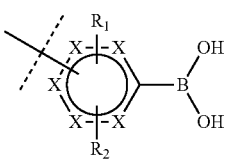

X = C, N
R$_1$, R$_2$ = ——H, ——F, ——Cl, ——Br, ——I, ——CF$_3$,
——CN, ——OCH$_3$, ——NO$_2$
When R$_1$ & R$_2$ are adjacent, may also include
fused 5 or 6 membered aromatic or heteroaromatic ring

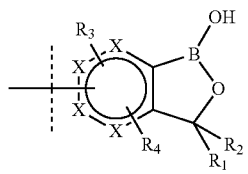

X = C, N
R$_1$, R$_2$ = ——H, ——CH$_3$, ——Ph, or connected to each other
through a spiro 3, 4, 5 or 6 membered ring
R$_3$, R$_4$ = ——H, ——F, ——Cl, ——Br, ——I, ——CF$_3$,
——CN, ——OCH$_3$, ——NO$_2$
When R$_3$ & R$_4$ are adjacent, may also include
fused 5 or 6 membered aromatic or heteroaromatic ring

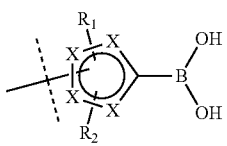

X = C, N, O, S
R$_1$, R$_2$ = ——H, ——F, ——Cl, ——Br, ——I, ——CF$_3$,
——CN, ——OCH$_3$, ——NO$_2$
When R$_1$ & R$_2$ are adjacent, may also include
fused 5 or 6 membered aromatic or heteroaromatic ring

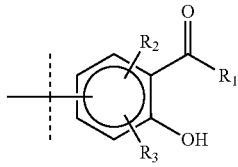

R$_1$ = ——OH, ——NH$_2$, ——SH, ——NHR$_4$
Where R$_4$ = alkyl, hydroxyalkyl
R$_2$, R$_3$ = ——H, ——CH$_3$, ——OCH$_3$,
——OH, ——COOH, CONH$_2$
When R$_2$ & R$_3$ are adjacent, may also include
fused 5 or 6 membered aromatic or
heteroaromatic ring

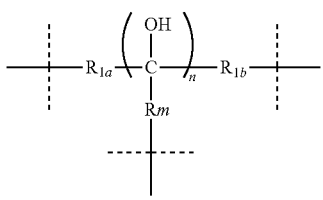

n = 2-6
R$_1$, R$_{1b}$ = ——H, ——CH$_3$, ——CH$_2$NH$_2$, ——CH$_2$NHCH$_3$,
aromatic or heteroaromatic ring, or connected
to each other through a 4.5.6.7 or 8-membered ring
Rm = ——H, ——CH$_3$, ——CH$_3$NH$_2$, ——CH$_3$OH, ——CH$_2$CH$_2$OH and
m = 2-6

-continued

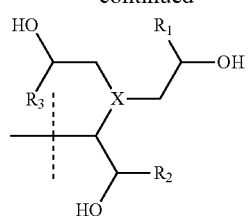

X = C, N
R$_1$, R$_2$, R$_3$ = ——H, ——CH$_3$, or two R groups connected
to each other through a 5 or 6 membered alicyclic ring

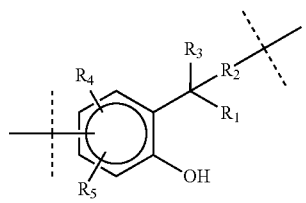

R$_1$ = ——OH, ——NH$_2$, ——SH
R$_2$, R$_3$ = ——H, ——CH$_3$, ——Ph,
or connected to each other through a spiro 3, 4 5 or
6 membered ring
R$_4$, R$_5$ = ——H, ——CH$_3$, ——CH$_2$OH, ——C(R$_2$, R$_3$)OH,
——OCH$_3$, ——OH, ——COOH, ——CONH$_2$
When R$_4$ & R$_5$ are adjacent, may also include
fused 5 or 6 membered aromatic or heteroaromatic ring

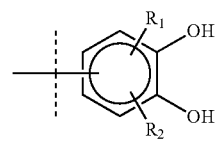

R$_1$, R$_2$ = ——H, ——CH$_3$, ——OCH$_3$, ——OH, ——COOH, ——CONH$_2$,
——F, ——Cl, ——Br, ——I, ——CF$_3$, ——CN, ——NO$_2$
When R$_1$ & R$_2$ are adjacent, may also include
fused 5 or 6 membered aromatic or heteroaromatic ring

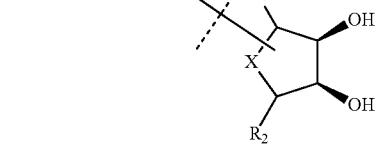

X = C, N, O, S
R$_1$, R$_2$ = ——H, ——CH$_3$, ----OH, ——CH$_2$OH, -Adenyl

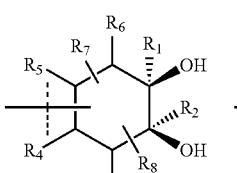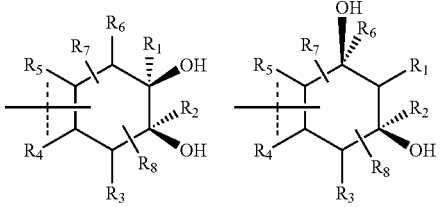

R$_1$, R$_2$, R$_3$, R$_4$, R$_5$, R$_6$ = ——H, ——CH$_3$
R$_7$, R$_8$ are connected to each other to form 3.1.1, 2.2.1 and 2.2.2 bicyclic
ring systems such that the hydroxyls are cis to each other -continued

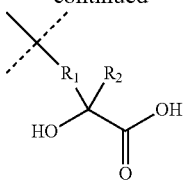

R₁, R₂ = —H, —CH₃, —Ph, —C₆H₁₁, —C₅H₉,
aromatic or heteroaromatic ring, C₁—C₆-alkyl or C₃—C₈ cycloalkyl.

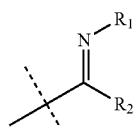

R₁, R₂ = —OH, —NH₂

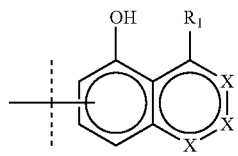

X = C, N
R₁ = —OH, —NH₂, —NHR₂, —NHC(═O)R₂, —NHSO₂R₂

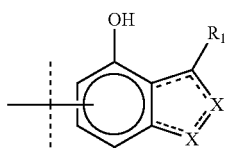

X = C, N, O, S
R₁, R₂ = —NH₂, ═O, —OH where the lines crossed with a dashed line illustrate the one or more bonds formed joining the one or more pharmacophores, directly or through a connector. The pharmacophore and the linker element for each monomer are connected together, directly or indirectly through a connector, and the plurality of monomers are covalently bonded together or non-covalently linked together through their linker elements. The pharmacophores for the plurality of monomers bind to proximate locations of the target molecule.

Yet a further embodiment of the present invention is directed to a method of screening for therapeutic compound precursors which bind to a target molecule associated with a condition. This method includes providing a plurality of monomers. Each monomer comprises one or more pharmacophores which potentially binds to a target molecule with a dissociation constant less than 300 μM and a linker element having a molecular weight of less than 500 daltons. This linker is selected from the group consisting of 1)

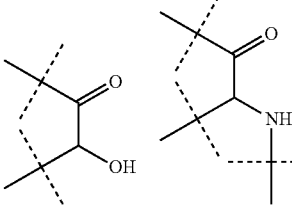

R₁ = —OH, SH, —NH₂, —NHCH₃, —NHR₃
where R₃ = —C(═O)R₄, —SO₂R₄, —C(═O)OR₄
where R₄ is composed of aliphatic, alicyclic, aromatic or heteroaromatic group where R₃ may also connect to the pharmacophore and is composed of aliphatic, alicyclic, aromatic or heteroaromatic group
R₂ = —H, —CH₃, —Ph or other aliphatic, aromatic or heteroaromatic group

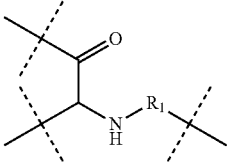

where R₁ = —CHO, —C(O)CH₃, —C(O)R₂, —S(O)₂CH₃, —S(O)₂R₂
where R₂ may also connect to the pharmacophore and is composed of aliphatic, aromatic or heteroaromatic group.

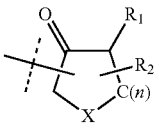

n = 1-4
X = C, N, S, O
R₁ = —OH, —SH, NH₂, NHCH₂, NHR₃
where R₃ may also connect to the pharmacophore and is composed of aliphatic, aromatic or heteroaromatic group
R₂ = —H, —CH₃, —Ph or other aliphatic, aromatic or heteroaromatic group where the lines crossed with a dashed line illustrate the one or more bonds formed joining the one or more pharmacophores, directly or through a connector; 2)

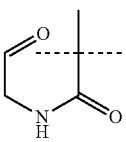

where the lines crossed with a dashed line illustrate the one or more bonds formed joining the one or more pharmacophores, directly or through a connector; 3)

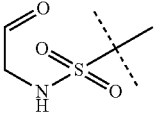

where the lines crossed with a dashed line illustrate the one or more bonds formed joining the one or more pharmacophores, directly or through a connector; 4)

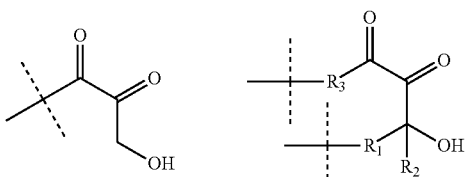

$R_1, R_2 =$ —H, —$CH_3$, —Ph, —$C_6H_{11}$, —$C_5H_9$, aromatic or heteroaromatic or connected to each other through a 3,4,5 or 6 membered ring.
$R_3 =$ —$NH_2$, —OH, —$CH_3$, —Ph, —$NHR_4$, —$CH_2R_4$, —$OR_4$
where $R_4$ may be connected to the pharmacophore and is composed of aliphatic, aromatic or heteroaromatic group, and $R_3$ and $R_4$ may connect to $R_1$ and $R_2$ through a 5,6,7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

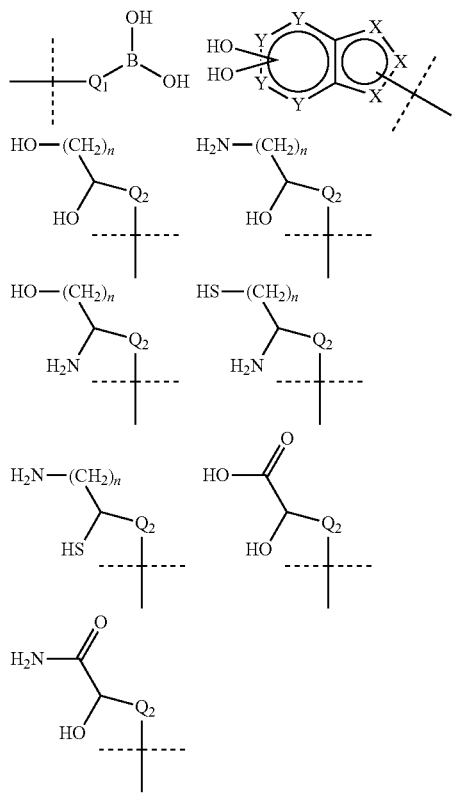

where $Q_1$ and $Q_2$ are aliphatic, alicyclic, or hetero or non-hetero aromatic moieties
where n=1 or 2
where X and Y=C, N, O, or S
where the hydroxy groups emanating from the aromatic ring are ortho to each other

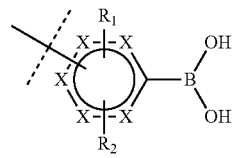

X = C, N
$R_1, R_2 =$ —H, —F, —Cl, —Br, —I, —$CF_3$, —CN, —$OCH_3$, —$NO_2$
When $R_1$ & $R_2$ are adjacent, may also include fused 5 or 6 membered aromatic or heteroaromatic ring

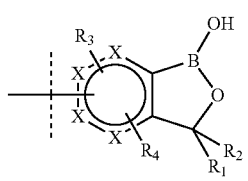

X = C, N
$R_1, R_2 =$ —H, —$CH_3$, —Ph, or connected to each other through a spiro 3, 4, 5 or 6 membered ring
$R_3, R_4 =$ —H, —F, —Cl, —Br, —I, —$CF_3$, —CN, —$OCH_3$, —$NO_2$
When $R_3$ & $R_4$ are adjacent, may also include fused 5 or 6 membered aromatic or heteroaromatic ring

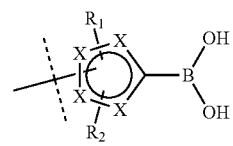

X = C, N, O, S
$R_1, R_2 =$ —H, —F, —Cl, —Br, —I, —$CF_3$, —CN, —$OCH_3$, —$NO_2$
When $R_1$ & $R_2$ are adjacent, may also include fused 5 or 6 membered aromatic or heteroaromatic ring

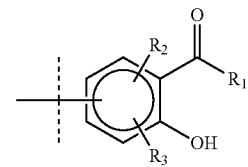

$R_1 =$ —OH, —$NH_2$, —SH, —$NHR_4$
Where $R_4$ = alkyl, hydroxyalkyl
$R_2, R_3 =$ —H, —$CH_3$, —$OCH_3$, —OH, —COOH, $CONH_2$
When $R_2$ & $R_3$ are adjacent, may also include fused 5 or 6 membered aromatic or heteroaromatic ring

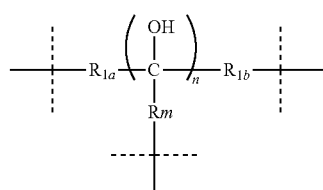

n = 2-6
$R_1, R_{1b} =$ —H, —$CH_3$, —$CH_2NH_2$, —$CH_2NHCH_3$, aromatic or heteroaromatic ring, or connected to each other through a 4,5,6,7 or 8-membered ring
$Rm =$ —H, —$CH_3$, —$CH_3NH_2$, —$CH_3OH$, —$CH_2CH_2OH$ and
m = 2-6

-continued

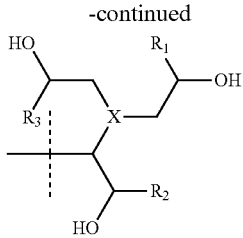

X = C, N
R₁, R₂, R₃ = ——H, ——CH₃, or two R groups connected
to each other through a 5 or 6 membered alicyclic ring

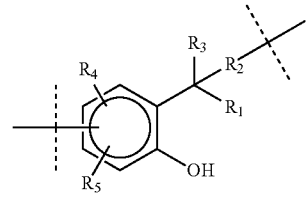

R₁ = ——OH, ——NH₂, ——SH
R₂, R₃ = ——H, ——CH₃, ——Ph,
or connected to each other through a spiro 3, 4 5 or
6 membered ring
R₄, R₅ = ——H, ——CH₃, ——CH₂OH, ——C(R₂, R₃)OH,
——OCH₃, ——OH, ——COOH, ——CONH₂
When R₄ & R₅ are adjacent, may also include
fused 5 or 6 membered aromatic or heteroaromatic ring

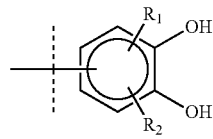

R₁, R₂ = ——H, ——CH₃, ——OCH₃, ——OH, ——COOH, ——CONH₂,
——F, ——Cl, ——Br, ——I, ——CF₃, ——CN, ——NO₂
When R₁ & R₂ are adjacent, may also include
fused 5 or 6 membered aromatic or heteroaromatic ring

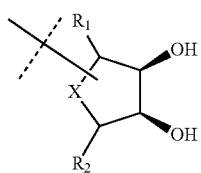

X = C, N, O, S
R₁, R₂ = ——H, ——CH₃, ----OH, ——CH₂OH, -Adenyl

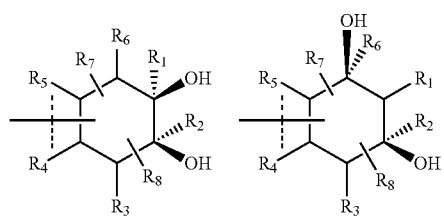

R₁, R₂, R₃, R₄, R₅, R₆ = ——H, ——CH₃
R₇, R₈ are connected to each other to form 3.1.1, 2.2.1 and 2.2.2 bicyclic
ring systems such that the hydroxyls are cis to each other -continued

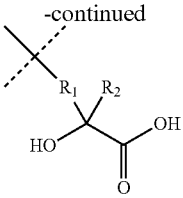

R₁, R₂ = ——H, ——CH₃, ——Ph, ——C₆H₁₁, ——C₅H₉,
aromatic or heteroaromatic ring, C₁——C₆-alkyl or C₃——C₈ cycloalkyl.

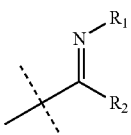

R₁, R₂ = ——OH, ——NH₂

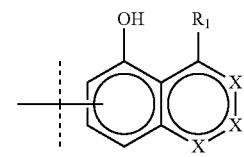

X = C, N
R₁ = ——OH, ——NH₂, ——NHR₂, ——NHC(═O)R₂,
——NHSO₂R₂

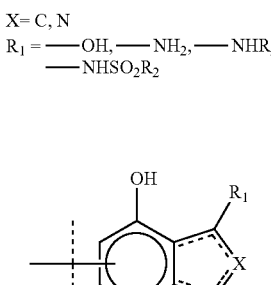

X = C, N, O, S
R₁, R₂ = ——NH₂, ═O, ——OH where the lines crossed with a dashed line illustrate the one or more bonds formed joining the one or more pharmacophores, directly or through a connector. The pharmacophore and said linker element of each monomer are joined together directly or indirectly through a connector. The plurality of monomers are contacted with the target molecule under conditions effective to permit pharmacophores able to bind to the target molecule to undergo such binding. The monomers are then subjected to reaction conditions effective for the linker elements of different monomers to undergo covalent bonding or non-covalent interactions to form therapeutic multimer precursors, either before, after, or during the contacting step. The monomers forming each therapeutic multimer precursor are then identified.

An additional embodiment of the present invention relates to a therapeutic multimer which includes a plurality of covalently or non-covalently linked monomers. Each monomer comprises one or more pharmacophores which potentially bind to a target molecule with a dissociation constant of less than 300 μM and a linker element having a molecular weight less than 500 dalton. The linker is selected from the group consisting of 1)

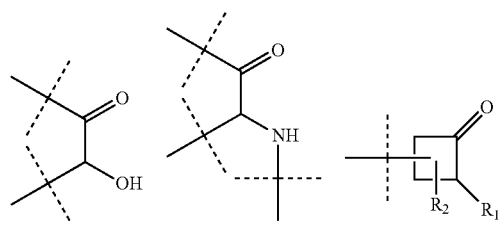

R$_1$ = —OH, SH, —NH$_2$, —NHCH$_3$, —NHR$_3$
where R$_3$ = —C(═O)R$_4$, —SO$_2$R$_4$, —C(═O)OR$_4$
where R$_4$ is composed of aliphatic, alicyclic, aromatic or heteroaromatic group where R$_3$ may also connect to the pharmacophore and is composed of aliphatic, alicyclic, aromatic or heteroaromatic group
R$_2$ = —H, —CH$_3$, —Ph or other aliphatic, aromatic or heteroaromatic group

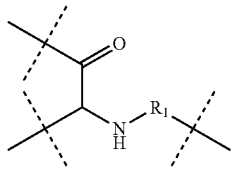

where R$_1$ = —CHO, —C(O)CH$_3$, —C(O)R$_2$, —S(O)$_2$CH$_3$, —S(O)$_2$R$_2$
where R$_2$ may also connect to the pharmacophore and is composed of aliphatic, aromatic or heteroaromatic group.

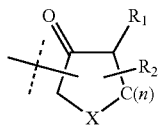

n = 1-4
X = C, N, S, O
R$_1$ = —OH, —SH, NH$_2$, NHCH$_2$, NHR$_3$
where R$_3$ may also connect to the pharmacophore and is composed of aliphatic, aromatic or heteroaromatic group
R$_2$ = —H, —CH$_3$, —Ph or other aliphatic, aromatic or heteroaromatic group where the lines crossed with a dashed line illustrate the one or more bonds formed joining the one or more pharmacophores, directly or through a connector; 2)

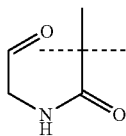

where the lines crossed with a dashed line illustrate the one or more bonds formed joining the one or more pharmacophores, directly or through a connector; 3)

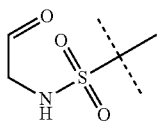

where the lines crossed with a dashed line illustrate the one or more bonds formed joining the one or more pharmacophores, directly or through a connector; 4)

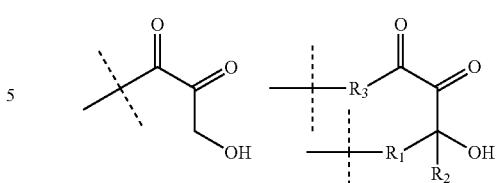

R$_1$, R$_2$ = —H, —CH$_3$, -Ph, —C$_6$H$_{11}$, —C$_5$H$_9$, aromatic or heteroaromatic or connected to each other through a 3, 4, 5 or 6 membered ring.
R$_3$ = —NH$_2$, —OH, —CH$_3$, -Ph, —NHR$_4$, —CH$_2$R$_4$, —OR$_4$
where R$_4$ may be connected to the pharmacophore and is composed of aliphatic, aromatic or heteroaromatic group, and R$_3$ and R$_4$ may connect to R$_1$ and R$_2$ through a 5, 6, 7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

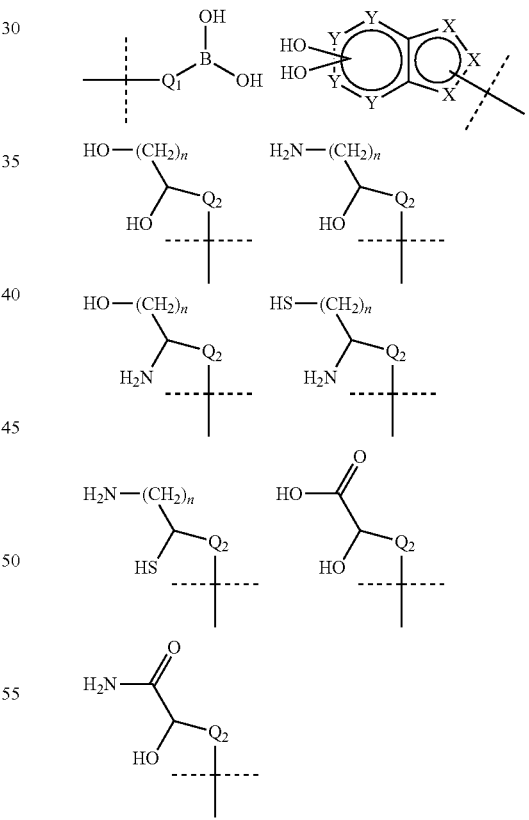

where Q$_1$ and Q$_2$ are aliphatic, alicyclic, or hetero or non-hetero aromatic moieties
where n=1 or 2
where X and Y=C, N, O, or S where the hydroxy groups emanating from the aromatic ring are ortho to each other

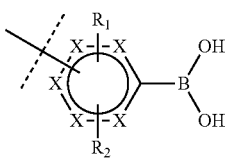

X = C, N
R$_1$, R$_2$ = ——H, ——F, ——Cl, ——Br, ——I, ——CF$_3$,
——CN, ——OCH$_3$, ——NO$_2$
When R$_1$ & R$_2$ are adjacent, may also include
fused 5 or 6 membered aromatic or heteroaromatic ring

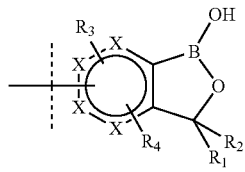

X = C, N
R$_1$, R$_2$ = ——H, ——CH$_3$, ——Ph, or connected to each other
through a spiro 3, 4, 5 or 6 membered ring
R$_3$, R$_4$ = ——H, ——F, ——Cl, ——Br, ——I, ——CF$_3$,
——CN, ——OCH$_3$, ——NO$_2$
When R$_3$ & R$_4$ are adjacent, may also include
fused 5 or 6 membered aromatic or heteroaromatic ring

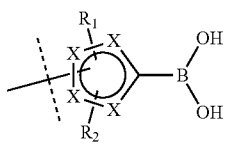

X = C, N, O, S
R$_1$, R$_2$ = ——H, ——F, ——Cl, ——Br, ——I, ——CF$_3$,
——CN, ——OCH$_3$, ——NO$_2$
When R$_1$ & R$_2$ are adjacent, may also include
fused 5 or 6 membered aromatic or heteroaromatic ring

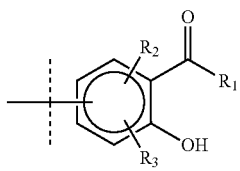

R$_1$ = ——OH, ——NH$_2$, ——SH, ——NHR$_4$
Where R$_4$ = alkyl, hydroxyalkyl
R$_2$, R$_3$ = ——H, ——CH$_3$, ——OCH$_3$,
——OH, ——COOH, CONH$_2$
When R$_2$ & R$_3$ are adjacent, may also include
fused 5 or 6 membered aromatic or
heteroaromatic ring

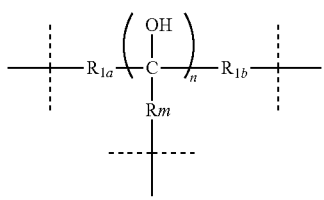

n = 2-6
R$_1$, R$_{1b}$ = ——H, ——CH$_3$, ——CH$_2$NH$_2$, ——CH$_2$NHCH$_3$,
aromatic or heteroaromatic ring, or connected
to each other through a 4.5.6.7 or 8-membered ring
R$_m$ = ——H, ——CH$_3$, ——CH$_3$NH$_2$, ——CH$_3$OH, ——CH$_2$CH$_2$OH and
m = 2-6

-continued

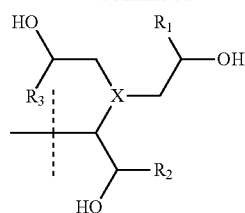

X = C, N
R$_1$, R$_2$, R$_3$ = ——H, ——CH$_3$, or two R groups connected
to each other through a 5 or 6 membered alicyclic ring

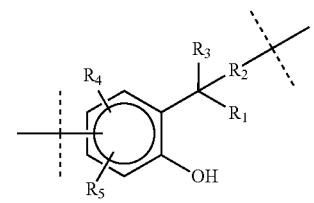

R$_1$ = ——OH, ——NH$_2$, ——SH
R$_2$, R$_3$ = ——H, ——CH$_3$, ——Ph,
or connected to each other through a spiro 3, 4 5 or
6 membered ring
R$_4$, R$_5$ = ——H, ——CH$_3$, ——CH$_2$OH, ——C(R$_2$, R$_3$)OH,
——OCH$_3$, ——OH, ——COOH, ——CONH$_2$
When R$_4$ & R$_5$ are adjacent, may also include
fused 5 or 6 membered aromatic or heteroaromatic ring

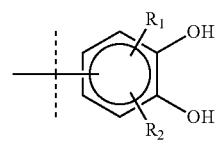

R$_1$, R$_2$ = ——H, ——CH$_3$, ——OCH$_3$, ——OH, ——COOH, ——CONH$_2$,
——F, ——Cl, ——Br, ——I, ——CF$_3$, ——CN, ——NO$_2$
When R$_1$ & R$_2$ are adjacent, may also include
fused 5 or 6 membered aromatic or heteroaromatic ring

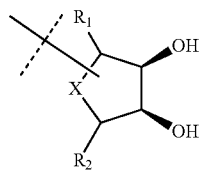

X = C, N, O, S
R$_1$, R$_2$ = ——H, ——CH$_3$, ----OH, ——CH$_2$OH, -Adenyl

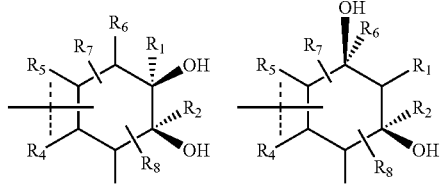

R$_1$, R$_2$, R$_3$, R$_4$, R$_5$, R$_6$ = ——H, ——CH$_3$
R$_7$, R$_8$ are connected to each other to form 3.1.1, 2.2.1 and 2.2.2 bicyclic
ring systems such that the hydroxyls are cis to each other

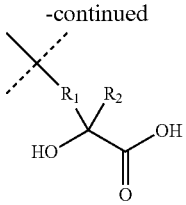

R$_1$, R$_2$ = ––H, ––CH$_3$, ––Ph, ––C$_6$H$_{11}$, ––C$_5$H$_9$,
aromatic or heteroaromatic ring, C$_1$––C$_6$-alkyl or C$_3$––C$_8$ cycloalkyl.

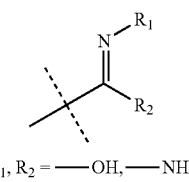

R$_1$, R$_2$ = ––OH, ––NH$_2$

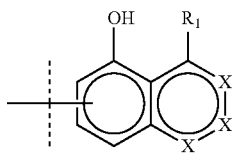

X = C, N
R$_1$ = ––OH, ––NH$_2$, ––NHR$_2$, ––NHC(═O)R$_2$,
––NHSO$_2$R$_2$

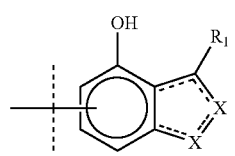

X = C, N, O, S
R$_1$, R$_2$ = ––NH$_2$, ═O, ––OH where the lines crossed with a dashed line illustrate the one or more bonds formed joining the one or more pharmacophores, directly or through a connector. The pharmacophore and the linker element are connected together directly or indirectly through a connector for each monomer. A plurality of monomers are capable of being linked together through their linker elements, and the pharmacophores for the plurality of monomers bind to proximate locations of the target molecule.

The present invention also relates to a plurality of therapeutic monomers capable of combining to form a therapeutic multimer. Each monomer includes one or more pharmacophores which potentially bind to a target molecule with a dissociation constant of less than 300 µM and a linker element. Each linker element has a molecular weight less than 500 daltons and is selected from the group consisting of
1)

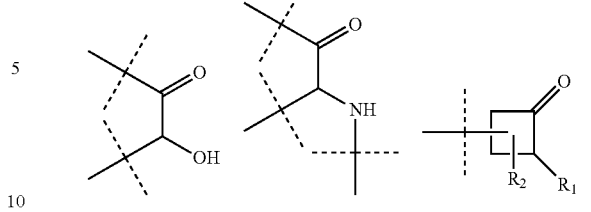

R$_1$ = ––OH, SH, ––NH$_2$, ––NHCH$_3$, ––NHR$_3$
where R$_3$ = ––C(═O)R$_4$, ––SO$_2$R$_4$, ––C(═O)OR$_4$
where R$_4$ is composed of aliphatic, alicyclic, aromatic or heteroaromatic group where R$_3$ may also connect to the pharmacophore and is composed of aliphatic, alicyclic, aromatic or heteroaromatic group
R$_2$ = ––H, ––CH$_3$, ––Ph or other aliphatic, aromatic or heteroaromatic group

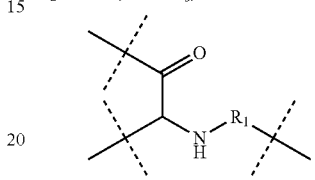

where R$_1$ = ––CHO, ––C(O)CH$_3$, ––C(O)R$_2$, ––S(O)$_2$CH$_3$, ––S(O)$_2$R$_2$
where R$_2$ may also connect to the pharmacophore and is composed of aliphatic, aromatic or heteroaromatic group.

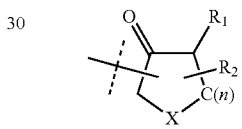

n = 1-4
X = C, N, S, O
R$_1$ = ––OH, ––SH, NH$_2$, NHCH$_2$, NHR$_3$
where R$_3$ may also connect to the pharmacophore and is composed of aliphatic, aromatic or heteroaromatic group
R$_2$ = ––H, ––CH$_3$, ––Ph or other aliphatic, aromatic or heteroaromatic group where the lines crossed with a dashed line illustrate the one or more bonds formed joining the one or more pharmacophores, directly or though a connector; 2)

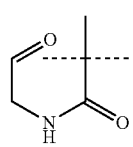

where the lines crossed with a dashed line illustrate the one or more bonds formed joining the one or more pharmacophores, directly or through a connector; 3)

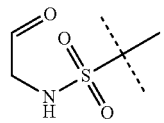

where the lines crossed with a dashed line illustrate the one or more bonds formed joining the one or more pharmacophores, directly or through a connector; 4)

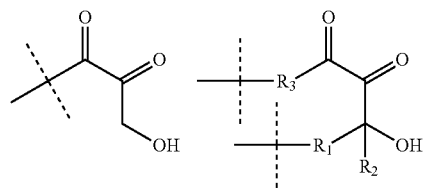

$R_1, R_2 =$ ——H, ——$CH_3$, -Ph, ——$C_6H_{11}$, ——$C_5H_9$, aromatic or heteroaromatic or connected to each other through a 3, 4, 5 or 6 membered ring.

$R_3 =$ ——$NH_2$, ——OH, ——$CH_3$, -Ph, ——$NHR_4$, ——$CH_2R_4$, ——$OR_4$ where $R_4$ may be connected to the pharmacophore and is composed of aliphatic, aromatic or heteroaromatic group, and $R_3$ and $R_4$ may connect to $R_1$ and $R_2$ through a 5, 6, 7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

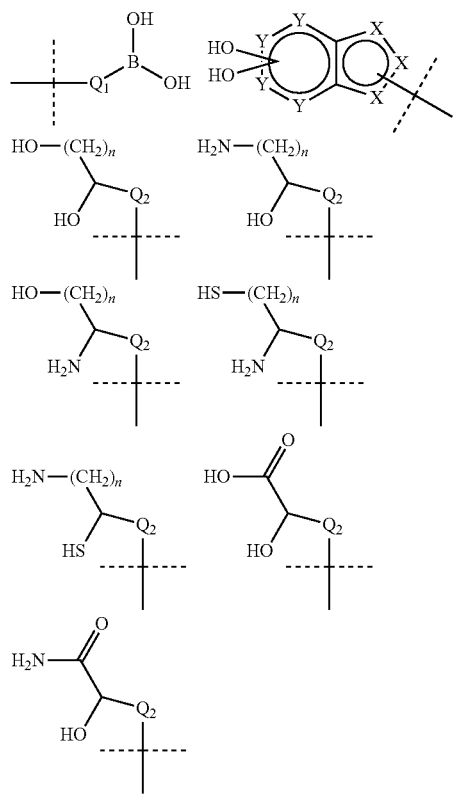

where $Q_1$ and $Q_2$ are aliphatic, alicyclic, or hetero or non-hetero aromatic moieties where n=1 or 2 where X and Y=C, N, O, or S where the hydroxy groups emanating from the aromatic ring are ortho to each other

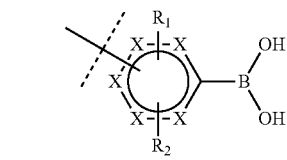

X = C, N $R_1, R_2 =$ ——H, ——F, ——Cl, ——Br, ——I, ——$CF_3$, ——CN, ——$OCH_3$, ——$NO_2$

When $R_1$ & $R_2$ are adjacent, may also include fused 5 or 6 membered aromatic or heteroaromatic ring

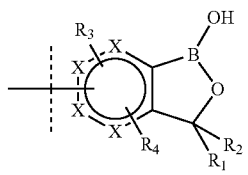

X = C, N $R_1, R_2 =$ ——H, ——$CH_3$, ——Ph, or connected to each other through a spiro 3, 4, 5 or 6 membered ring $R_3, R_4 =$ ——H, ——F, ——Cl, ——Br, ——I, ——$CF_3$, ——CN, ——$OCH_3$, ——$NO_2$ When $R_3$ & $R_4$ are adjacent, may also include fused 5 or 6 membered aromatic or heteroaromatic ring

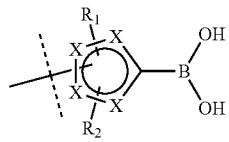

X = C, N, O, S $R_1, R_2 =$ ——H, ——F, ——Cl, ——Br, ——I, ——$CF_3$, ——CN, ——$OCH_3$, ——$NO_2$

When $R_1$ & $R_2$ are adjacent, may also include fused 5 or 6 membered aromatic or heteroaromatic ring

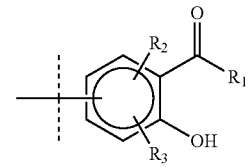

$R_1 =$ ——OH, ——$NH_2$, ——SH, ——$NHR_4$

Where $R_4 =$ alkyl, hydroxyalkyl $R_2, R_3 =$ ——H, ——$CH_3$, ——$OCH_3$, ——OH, ——COOH, $CONH_2$ When $R_2$ & $R_3$ are adjacent, may also include fused 5 or 6 membered aromatic or heteroaromatic ring

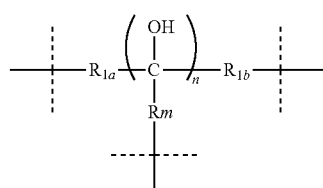

n = 2-6

$R_1, R_{1b} =$ ——H, ——$CH_3$, ——$CH_2NH_2$, ——$CH_2NHCH_3$, aromatic or heteroaromatic ring, or connected to each other through a 4.5.6.7 or 8-membered ring $Rm =$ ——H, ——$CH_3$, ——$CH_3NH_2$, ——$CH_3OH$, ——$CH_2CH_2OH$ and m = 2-6

-continued

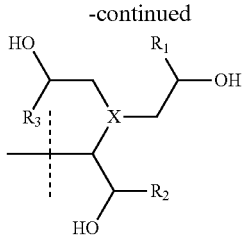

X = C, N
$R_1, R_2, R_3$ = ──H, ──CH$_3$, or two R groups connected
to each other through a 5 or 6 membered alicyclic ring

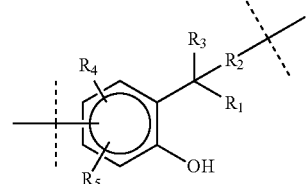

$R_1$ = ──OH, ──NH$_2$, ──SH
$R_2, R_3$ = ──H, ──CH$_3$, ──Ph,
or connected to each other through a spiro 3, 4 5 or
6 membered ring
$R_4, R_5$ = ──H, ──CH$_3$, ──CH$_2$OH, ──C(R$_2$, R$_3$)OH,
──OCH$_3$, ──OH, ──COOH, ──CONH$_2$
When $R_4$ & $R_5$ are adjacent, may also include
fused 5 or 6 membered aromatic or heteroaromatic ring

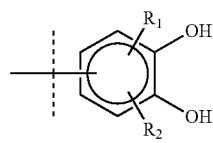

$R_1, R_2$ = ──H, ──CH$_3$, ──OCH$_3$, ──OH, ──COOH, ──CONH$_2$,
──F, ──Cl, ──Br, ──I, ──CF$_3$, ──CN, ──NO$_2$
When $R_1$ & $R_2$ are adjacent, may also include
fused 5 or 6 membered aromatic or heteroaromatic ring

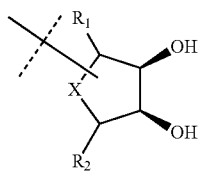

X = C, N, O, S
$R_1, R_2$ = ──H, ──CH$_3$, ----OH, ──CH$_2$OH, -Adenyl

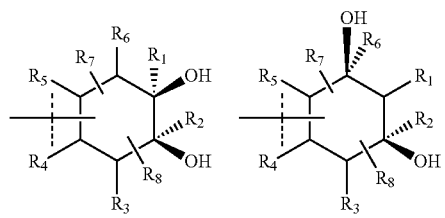

$R_1, R_2, R_3, R_4, R_5, R_6$ = ──H, ──CH$_3$
$R_7, R_8$ are connected to each other to form 3.1.1, 2.2.1 and 2.2.2 bicyclic
ring systems such that the hydroxyls are cis to each other -continued

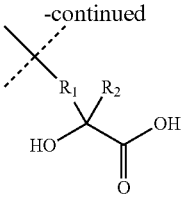

$R_1, R_2$ = ──H, ──CH$_3$, ──Ph, ──C$_6$H$_{11}$, ──C$_5$H$_9$,
aromatic or heteroaromatic ring, C$_1$──C$_6$-alkyl or C$_3$──C$_8$ cycloalkyl.

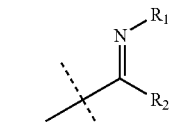

$R_1, R_2$ = ──OH, ──NH$_2$

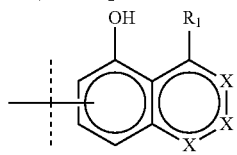

X = C, N
$R_1$ = ──OH, ──NH$_2$, ──NHR$_2$, ──NHC(═O)R$_2$,
──NHSO$_2$R$_2$

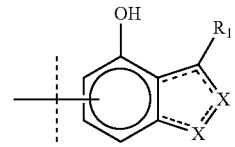

X = C, N, O, S
$R_1, R_2$ = ──NH$_2$, ═O, ──OH where the lines crossed with a dashed line illustrate the one or more bonds formed joining the one or more pharmacophores, directly or through a connector. The one or more, where the lines crossed with a dashed line illustrate the one or more bonds formed joining the one or more pharmacophores directly or through a connector. The pharmacophores and the linker element are connected together directly or indirectly through a connector, for each monomer, a plurality of monomers being linked together through their linker elements, and the pharmacophores for the plurality of monomers bind to proximate locations of the target molecule.

The linker elements of the present invention are low molecular weight moieties that associate with each other in vivo and may or may not react with cellular components. Each linker element has attachment points for introducing diverse ligands. They are compatible with "click chemistry". In a preferred embodiment of this invention, the association between the linker elements is reversible, allowing for dynamic combinatorial chemistry selection of the best ligands. The linker elements allow in vivo assembly of multiple small ligands to produce structures having a molecular weight up to about 4800 and potentially modulate protein-protein interactions.

The linker elements of the present invention have the potential to modulate or inhibit protein-protein signaling, and other macromolecular interactions including protein-carbohydrate, protein-nucleic acid and protein-lipid interactions. The combined size of the linker element-ligand dimers and multimers provides sufficient surface area to interact with protein and macromolecular surfaces with increased selectivity and reduced toxicity. Approaches such as directed evolution may select for tightest binding lead compounds, with the potential to drive affinities to sub-nmol range.

The present invention is directed to a novel class of drug molecules (referred to here as coferons) that can assemble in vivo to provide a multimeric presentation of pharmacophores. A coferon monomer is composed of a pharmacophore or ligand that binds to the target and a dynamic combinatorial chemistry element herein termed a linker element. The linker element of one coferon monomer may reversibly combine with the linker element of another coferon monomer in vivo to form a coferon dimer. In some cases, the linker element binding to each other may be essentially irreversible. In other cases, the linker elements are in a precursor form, and are activated upon entering the body or cells. The linker elements bind to each other through hydrophobic, polar, ionic, hydrogen bonding, and/or reversible covalent interactions. In the presence of the target, the combinations of multiple (weak) interactions between the pharmacophore of one coferon monomer and a target macromolecule, the pharmacophore of a second coferon monomer and the target macromolecule, as well as the two coferons with each other combine to produce a tight binding coferon dimer with highly specific binding to its target. The concept may be extended to include multimer coferons and multimer targets.

Since coferon monomers associate in a reversible manner, the principals of dynamic combinatorial chemistry selection may be used to identify the best ligands for each target in vitro. Combining two coferon libraries, for example with $10^4$ pharmacophores provides the opportunity to screen $10^8$ combinations simultaneously. Use of repeated synthesis, selection, and amplification strategies will allow for evolutionary selection of coferon dimers with nanomolar and even subnanomolar binding affinities. The combined size of linker element dimers and multimers provides sufficient surface area to interact with extended binding protein and macromolecular surfaces. Nevertheless, since coferon assembly on the target is dependent on multiple synergistic interactions, false binding to incorrect proteins and macromolecules will be rare (and can be selected against), and, thus, such drugs should have minimal to no off-target toxicity. Use of circular peptide and peptide analogue containing pharmacophores will also allow for switching between polar and non-polar conformers for easier transport across membranes. Coferon monomers may be designed to have a molecular weight of less than 1000, allowing them to be orally active, penetrate deeply into tumors, and cross membrane barriers to enter inside cells—significant advantages over antibodies—while providing equal specificity.

The key to the linker elements is identifying low molecular weight moieties (with molecular weights preferably within the range of 45 to 450 daltons) that associate with good affinities for one another in vivo. The more sophisticated linker elements described below help catalyze formation of reversible covalent bonds when binding to each other under physiological conditions. The variety of coferon designs may be expanded by uncoupling the screening process for pharmacophore ligands from the final coferon structure used in the drug. This allows the use of linker elements in the final drug whose binding is essentially irreversible. Essentially irreversible linker elements are generally, but not limited to, linker elements that may associate slowly or even very slowly, either in the absence or presence of the target. However, once formed, such linker elements essentially do not dissociate.

Some linkers form cyclic dimeric assemblies through the formation of two covalent bonds. Even though each individual bond between two linker elements may be reversible, once both bonds are established, reversal of one bond still keeps the two molecules tethered together in such close proximity that they will de facto reform the bond again or may isomerize (e.g. with inversion of stereochemistry at the site of bond formation) to produce a different isomeric dimer. Upon dimerization of the linker moieties, a number of isomeric dimeric forms have been observed, and these have been observed to interconvert with their stability and equilibrium affected by numerous variables such as concentration, hydration, pH, metal ions, and the presence of proteins, including the molecular target. Consistent with the observation of numerous isomeric dimeric states for some of the linkers, quantum mechanical calculations indicate that multiple states with similar stabilities are possible, from which the molecular target can preferentially bind those with the highest affinities. Thus the molecular target may be presented with an ensemble of interconvertible dimeric forms from which it will select those with the best "fit", or can promote the formation of the highest affinity dimeric state from monomers or through isomerization of dimers. The binding of the highest affinity dimeric state to the target will shift the equilibrium in favor of this dimeric state leading to higher levels of occupancy of the target by this dimer. The accessibility of coferons to multiple dimeric isomeric states of similar energies thus further increases the combinatorial permutations of pharmacophoric presentations.

Certain linker elements may be reversible under some conditions (used during screening), yet essentially irreversible under other conditions, for example when formulated in the final drug. For those linker elements that have the potential to combine irreversibly during formulation, or, alternatively, in the body prior to entering the target cells, the reactive groups may be protected and rendered unreactive. Upon entering the target cells, the protecting group may be removed by cellular processes, such as disulfide reduction to the thiol by intracellular glutathione, enzymatic cleavage (i.e. esterase), or pH change (if entry is via endosomes or linker elements enter lysosomal compartments) or simply by reversible dissociation upon dilution into the blood stream (i.e. reversible alcohol protection of a reactive boronate group). Linker elements that are essentially irreversible under dynamic combinatorial chemistry (DCC) screening conditions may be rendered reversible using a new approach described herein, which we term "cyclic combinatorial chemistry" (C3) screening.

BRIEF DESCRIPTION OF THE DRAWINGS

FIG. 2A is a schematic drawing of coferon monomers in accordance with the present invention attached to encoded beads via connectors. FIG. 2B is a schematic drawing of a coferon monomer with connector in accordance with the present invention. FIG. 2C is a schematic drawing of a coferon dimer attached to an encoded bead via a connector to one monomer. FIG. 2D is a schematic drawing of a coferon heterodimer with connectors, suitable for therapeutic use. FIG. 2E is a schematic drawing of a coferon homodimer with connectors, suitable for therapeutic use. FIG. 2F is a schematic drawing of coferon monomers in accordance with the present invention attached to encoded beads. FIG. 2G is a schematic drawing of a coferon monomer in accordance with the present invention. FIG. 2H is a schematic drawing of a coferon dimer attached to an encoded bead via one monomer. FIG. 2I is a schematic drawing of a coferon heterodimer, suitable for therapeutic use. FIG. 2J is a schematic drawing of a coferon homodimer, suitable for therapeutic use.

FIGS. 4A-C show the (2R,5S)-2-N,5-N-bis(3-{[5-(aminomethyl)-2H-spiro[1-benzofuran-3,4'-piperidine]-1'-yl]carbonyl}-5-(methylsulfanyl)phenyl)-2,5-dihydroxy-1,4-dioxane-2,5-dicarboxamide coferon dimer docked to the tetrameric human β-tryptase-II. For comparison, in FIG. 4C, the coferon dimer is overlaid with the inhibitor present in the 2ZEB structure of tryptase from the Protein Data Bank. Virtual screening, docking, and scoring of coferon monomers (using Tripos FlexX) containing a pyruvylamide linker elements suggest that tryptase will have a high affinity for this homodimer derivative as its R,S-diastereomer.

FIGS. 5A-C show the (2R,5S)-2,5-bis(3-{[5-(aminomethyl)-2H-spiro[1-benzofuran-3,4'-piperidine]-1'-yl]carbonyl}-5-chlorophenoxymethyl)-1,4-dioxane-2,5-diol coferon dimer docked to the tetrameric human β-tryptase-II. For comparison, in FIG. 5C the coferon dimer is overlaid with the inhibitor present in the 2ZEB structure of tryptase from the Protein Data Bank. Virtual screening, docking and scoring (using Schroedinger's GLIDE) of coferon monomers containing hydroxyacetone linker elements suggest that tryptase will have a high affinity for this homodimer derivative as its R,S-diastereomer.

FIGS. 6A-C show the (1S,3S,6S,8S)-2-N,7-N-bis(3-{[5-(aminomethyl)-2H-spiro[1-benzofuran-3,4'-piperidine]-1'-yl]carbonyl}-5-chlorophenyl)-1,6-dihydroxy-2,7-diazatricyclo[6.2.0.0$^{3,6}$]decane-2,7-dicarboxamide coferon dimer docked to the tetrameric human β-tryptase-II. For comparison, in FIG. 6C the coferon dimer is overlaid with the inhibitor present in the 2ZEB structure of tryptase from the Protein Data Bank. Virtual screening, docking and scoring (using Schroedinger's GLIDE) of coferon monomers containing amido-cyclobutanone linker elements suggest that tryptase will have a high affinity for this homodimer derivative as its S,S,S,S-diastereomer.

FIGS. 8A-C are schematic drawings of components used in pharmacophore library synthesis for bead encoded libraries. FIG. 8A shows small molecule inhibitors and analogues. FIGS. 8B-8C show combinatorial chemistry on a common platform.

FIG. 9 is a schematic drawing of directed evolution of coferons.

FIG. 10 is a schematic drawing of directed evolution of coferons.

FIGS. 13A-C show variations of coferon drug interactions with a target. A first coferon is illustrated as linker element 2 tethered to a hexagon ligand 4, a second coferon as linker element 6 tethered to oval ligand 8, and the target protein 10. Substrate 12 can be cleaved into two halves 14 and 15. Also shown is binding partner 18 of target 10. FIG. 13A is a schematic drawing of a substrate binding to and being cleaved by the target. FIG. 13B is a schematic drawing of two coferon monomers binding to and forming a coferon dimer on the target whose dissociation constant is less than or equal to the dissociation constant of the substrate, thus inhibiting the substrate from binding to and being cleaved by the target. FIG. 13C is a schematic drawing of two coferon monomers binding to and forming a coferon dimer on the target whose dissociation constant is less than or equal to the dissociation constant of a binding protein, thus displacing the binding protein from binding to the target.

FIGS. 14A-D show variations of coferon drug interactions with target 110. The first coferon formed from linker element 102 and ligand 104, the second coferon formed from linker element 106 and ligand 108, and target protein 110 are described above. Activation of target protein 110, for example, by turning on a kinase activity, is illustrated by an arc of lines. Binding partner 120 activates target 110. Binding partner 118 inhibits target 110. FIG. 14A is a schematic drawing of activating binding partner binding 120 to and activating the target 110. FIG. 14B is a schematic drawing of two coferon monomers binding to and forming a coferon dimer on the target, mimicking the activating binding partner by activating the target. FIG. 14C is a schematic drawing of an inactivating binding partner binding to and inactivating the target. FIG. 14D is a schematic drawing of two coferon monomers binding to and forming a coferon dimer on the target, mimicking the inactivating binding partner by inactivating the target.

FIGS. 15A-B show the variations of coferon drug interactions with a target. The first coferon formed from linker element 202 and ligand 204, the second coferon formed from linker element 206 and ligand 208, and target protein 210 are described above. Activation of the target protein, for example, by turning on a kinase activity, is illustrated by an arc of lines, with intensity of activation suggested by the number of lines in the arc. Binding partner 218 activates target 210. Binding partner 220 inhibits target 210. FIG. 15A is a schematic drawing of an activating binding partner binding to and mildly activating the target (upper pathway). Addition of two coferon monomers allows binding to and forming a coferon dimer on the activating binding partner-target complex, thus enhancing activation of the target (lower pathway). FIG. 15B is a schematic drawing of an inactivating binding partner binding to and mildly inactivating the target (upper pathway). Addition of two coferon monomers allows binding to and forming a coferon dimer on the activating binding partner-target complex, thus enhancing inactivation of the target (lower pathway).

FIGS. 16A-B show variations of coferon drug interactions with a target. The first coferon formed from linker element 302 and ligand 304, second coferon formed from linker element 306 and ligand 308, and target protein 310 are described above. A mutant target protein 310 is illustrated with an M. Activation of target protein 310, for example, by turning on a kinase activity, is illustrated by an arc of lines, with intensity of activation suggested by the number of lines in the arc. Binding partner 318 activates target 310. FIG. 16A is a schematic drawing of an activating binding partner 318 binding to and activating the wild-type target 310. FIG. 16B is a schematic drawing of an activating binding partner 318 binding to and mildly activating the mutant target 310 (upper pathway). Addition of two coferon monomers allows binding to and forming a coferon dimer on the mutant target 310 with an M, thus enhancing activation of the mutant target (lower pathway).

FIGS. 17A-B show variations of coferon drug interactions with a target. The first coferon formed from linker element 402 and ligand 404, second coferon formed from linker element 404 and ligand 406, and target protein 410 are described above. Mutant target protein 410 has an M. Inactivation of the target protein 410, is illustrated by (loss of) an arc of lines, with intensity of activation suggested by the number of lines in the arc. Binding partner 420 inactivates target 410. FIG. 17A is a schematic drawing of inactivating binding partner 420 binding to and inactivating the wild-type target 410. FIG. 17B is a schematic drawing of an inactivating binding partner 420 binding to and mildly inactivating the (overactivated) mutant target 410 (upper pathway). Addition of two coferon monomers allows binding to and forming a coferon dimer on the mutant target, thus enhancing inactivation of the mutant target (lower pathway).

FIGS. 18A-B show variations of coferon drug interactions with a target. The first coferon formed from linker element 502 and ligand 504, second coferon formed from linker element 506 and ligand 508, and target protein 510 are described above. First binding partner 518 binds with weak affinity to target 510. Second binding partner 522 binds with affinity to target 510 coferons. FIG. 18A is a schematic drawing of first binding partner 518 binding weakly to target 510. FIG. 18B is a schematic drawing of the first binding partner 510 binding weakly to target 510 (upper pathway). Addition of two coferon monomers allows binding to and forming a coferon dimer on target 510, recruiting second binding partner 522 to bind to target 510, coferons, and first binding partner 518, forming a coferon dimer-target-second binding protein complex, and thus enhancing binding of first binding partner 518 to target 510 (lower pathway).

FIGS. 19A-B show variations of coferon drug interactions with a target. The first coferon with linker element 602 and ligand 604, second coferon with linker element 606 and ligand 608, and target protein 610 are described above. First binding partner 620 binds with strong affinity to target 610. Second binding partner 622 binds with affinity to target 610 and coferons. FIG. 19A is a schematic drawing of first binding partner 618 binding strongly to target 610. FIG. 19B is a schematic drawing of first binding partner 618 binding strongly to target 610 (upper pathway). Addition of two coferon monomers allows binding to and forming a coferon dimer on target 610, recruiting second binding partner 622 to bind to target 610 and the coferons forming a coferon dimer-target-second binding protein complex, whose dissociation constant is less than or equal to the dissociation constant of first binding protein 618, thus displacing the first binding protein 618 from binding to target 610 (lower pathway).

FIGS. 20A-C show the variations of coferon drug interactions with a target. The first coferon with linker element 702 and ligand 704, second coferon with linker element 706 and ligand 708, and target protein 710 are described above. First binding partner 718A-C binds with weak or no affinity to target 710. Second binding partner 722A-C binds with affinity to target 710, coferons, and/or first binding partner 718. FIG. 20A is a schematic drawing of two coferon monomers binding to and forming a coferon dimer on the target 710, recruiting second binding partner 722A to bind to target 710, coferons, and first binding partner 718A, forming a coferon dimer-target-second binding protein complex, and thus recruiting first binding partner 718A to target 710. FIG. 20B is a schematic drawing of two coferon monomers binding to and forming a coferon dimer on target 710, recruiting second binding partner 722B to bind to target 710, coferons, and first binding partner 718B, forming a coferon dimer-target-second binding protein complex, and thus recruiting first binding partner 718B to target 710. FIG. 20C is a schematic drawing of two coferon monomers binding to and forming a coferon dimer on target 710 and first binding protein 718C, recruiting second binding partner 722C to bind to target 710 and first binding partner 718C, forming a coferon dimer-target-first binding protein-second binding protein complex, and thus recruiting first binding partner 718C to target 710.

FIGS. 21A-B show variations of coferon drug interactions with a target. The first coferon with linker element 806' and ligand 808', second coferon with linker element 806" and ligand 808", and target protein 810' and 810" are described above. The receptor dimer 810'-810" has a natural ligand 826 and is positioned on membrane 824. Activation of target protein 810' and 810", for example, by turning on a kinase activity, is illustrated by an arc of lines, with intensity of activation suggested by the number of lines in the arc. FIG. 21A is a schematic drawing of activating ligand 826 binding to the receptor target, 810'-810", facilitating receptor dimerization, and activating the receptor targets 810' and 810". FIG. 21B is a schematic drawing of two coferon monomers binding to and forming a coferon dimer on the target 810'-810", mimicking activating ligand 826, facilitating receptor dimerization, and activating the receptor targets 810' and 810".

FIGS. 22A-B show variations of coferon drug interactions with target 910'-910". The first coferon with linker element 902' or 902 and ligand 904' or 904, second coferon with linker element 902" or 906 and ligand 906" or 908, and target proteins 910' and 910" are described above. Natural ligand 926 is positioned in membrane 924. FIG. 22A is a schematic drawing of two coferon monomers binding to and forming a coferon dimer on target 910'-910", interfering with proper receptor dimerization, and inhibiting activation of the receptor target. FIG. 22B is a schematic drawing of two coferon monomers binding to and forming a coferon dimer on each target 910'-910", inhibiting activation at an allosteric site, even in the presence of activating ligand that facilitates receptor dimerization.

FIG. 23A is a schematic drawing of two coferon monomers binding to and forming a coferon dimer on each target 1010' and 1010", enhancing activation at an allosteric site, which is enhanced in the presence of activating ligand that facilitates receptor dimerization.

FIGS. 24A-C show variations of coferon drug interactions with a target. The first coferon with linker element 1106' or 1102' and ligand 1108' or 1104', second coferon with linker element 1106" or 1102" and ligand 1108" or 1104", and target protein 1110 are described above. The receptor dimer 1110 has natural ligand 1126 and membrane 1124. The target protein 1100 has binding partner 1118 with affinity to the target upon binding its ligand. Upon binding target protein 1110, binding partner 1118 may be activated, for example, by turning on a kinase activity, and is illustrated by an arc of lines, with intensity of activation suggested by the number of lines in the arc. FIG. 24A is a schematic drawing of natural ligand 1118 binding to receptor target 1110, which recruits and activates the binding partner. FIG. 24B is a schematic drawing of two coferon monomers binding to and forming a coferon dimer on receptor target 1110 at the ligand binding site to act as an agonist, mimicking natural ligand, which recruits and activates the binding partner 1118. FIG. 24C is a schematic drawing of two coferon monomers binding to and forming a coferon dimer on the receptor target at the ligand binding site to act as an antagonist, and thus inhibits recruitment and activation of binding partner 1118.

FIGS. 25A-C show variations of coferon drug interactions with a target. The first coferon with linker element 1202 or 1202' and ligand 1204 or 1204', second coferon with linker element 1206 or 1202" and ligand 1208 or 1204", and target protein 1210 are described above. Receptor dimer 1210, which has natural ligand 1226 and is positioned on the membrane 1224, binds to the target 1210 binding partner 1218. Upon binding target protein 1210, binding partner 1218 may be activated, for example, by turning on a kinase activity, and is illustrated by an arc of lines, with intensity of activation suggested by the number of lines in the arc. FIG. 25A is a schematic drawing of two coferon monomers binding to and forming a coferon dimer on the receptor target 1210 at binding partner 1218 binding site to act as an antagonist, and thus inhibit recruitment and activation of the binding partner 1218. FIG. 25B is a schematic drawing of the natural ligand binding to the receptor target 1210, which recruits and activates the binding partner 1218, with two coferon monomers binding to and forming a coferon dimer on the receptor target 1210 and the binding partner 1218 to enhance activation of the binding partner. FIG. 25C is a schematic drawing of the natural ligand binding to the receptor target 1210, which recruits and activates binding partner 1218, with two coferon monomers binding to and forming a coferon dimer on the receptor target 1210 and natural ligand 1226, to enhance activation of the binding partner 1218.

FIGS. 26A-C show the variations of coferon drug interactions with a target. The first coferon has cylindrical linker element 1302', 1306', or 1302" tethered to hexameric ligand 1304' or 1304". The second coferon has cylindrical linker element 1306', 1306", 1306''', or 1306'''' tethered to oval ligand 1308', 1308", 1308''', or 1308'''', target proteins 1310' and 1310" can form dimer 1310'-1310". FIG. 26A is a schematic drawing of two coferon monomers binding to form a coferon homodimer on the dimer target. FIG. 26B is a schematic drawing of a coferon tetramer comprised of four coferon monomers binding to form a coferon homotetramer on the dimer target. FIG. 26C is a schematic drawing of a coferon tetramer comprised of two coferon monomers with one ligand and two coferon monomers with a second ligand binding to form a coferon heterotetramer on the dimer target.

FIGS. 27A-C show variations of coferon drug interactions with a target. The first coferon had cylindrical linker element 1402', 1402', or 1402''' tethered to a hexameric ligand 1404', 1404", or 1404''', the second coferon had cylindrical linker element 1406', 1406", 1406, or 1406''' tethered to oval ligand 1408', 1408", 1408, or 1408''' the third coferon has cylindrical linker element 1403 tethered to a star ligand 1405 and the multimeric target proteins 1410', 1410", 1410''', 1410'''', and 1410''''' are comprised of the larger cylinders with cell membrane 1424. FIG. 27A is a schematic drawing of a coferon tetramer comprised of two coferon monomers with one ligand and two coferon monomers with a second ligand, binding to form a coferon heterotetramer on a multimeric target. FIG. 27B is a schematic drawing of a coferon tetramer comprised of two coferon monomers with one ligand and two different coferon monomers with a second and third ligand, binding to form a coferon heterotetramer on a multimeric target. FIG. 27C is a schematic drawing of a coferon hexamer comprised of three coferon monomers with one ligand and three coferon monomers with a second ligand, binding to form a coferon heterohexamer on a multimeric target.

FIG. 28A is a schematic drawing of alpha and beta tubulin heterodimers combining to form polymerized tubulin filaments. FIG. 28B is a schematic drawing of two coferon monomers binding to form a coferon dimer on the tubulin dimer target, thus destabilizing filament formation.

FIGS. 29A-B show variations of coferon drug interactions with a target. The first coferon has linker element 1602 tethered to hexameric ligand 1604, second coferon has a linker element 1606 tethered to oval ligand 1608, the target amyloid beta peptide as hexamers, circles, and rounded squares 1610', 1610", and 1610'", respectively. FIG. 29A is a schematic drawing of amyloid beta peptide monomers aggregating to form small oligomers, large oligomers, protofibriles, and amyloid fibrils that cause Alzheimer's Disease. FIG. 29B is a schematic drawing of two coferon monomers binding to form a coferon dimer on the amyloid beta peptide monomers, thus inhibiting aggregation and disease.

DETAILED DESCRIPTION OF THE INVENTION

Basic Principles of Coferon Drugs

Coferons are orally active drugs that can enter cells and, once inside, combine with their partner to interfere with or modulate target protein activity. A coferon monomer is composed of a pharmacophore and a linker element.

In general, coferon drugs contain two ligands (termed as pharmacophores or diversity elements) that bind to the target, and are held together through their respective linker element interactions. In order to assure that the coferon drugs bind to a given target, the design of coferon usually incorporates selecting from a known set of pharmacophores and/or synthesizing a wide range of pharmacophores for one or both of the coferon drug dimer.

Once a coferon dimer has been selected for, or screened by various assays, it is important to be able to identify the structure of the pharmacophore. This is especially true under conditions of dynamic combinatorial chemistry, where dozens to hundreds to thousands or even more different pharmacophores are being interrogated simultaneously in the same well or when binding to a target on a solid surface (i.e. affinity column).

The basic coferon design contains the linker element, which is responsible for interacting with its partner linker element, and the pharmacophore, which is responsible for binding to the target. The linker element and the pharmacophore may be directly attached to each other, or linked together by a connector moiety. The linker element and/or connector portion may assist in positioning the pharmacophore in the ideal conformation or orientation for proper binding to the target. In addition, these elements in and of themselves may also interact with the target. When the linker element or connector makes favorable interactions with the target, the portions of the connector or linker element that interact with the target function as secondary pharmacophoric elements. The encryption element, if used, may be attached to the linker element or the connector portion of the molecule. Ideally, it should be linked to the linker element or connector portion in a manner allowing for easy release or cleavage to remove the DNA portion.

Coferon Monomers

Figure 1:
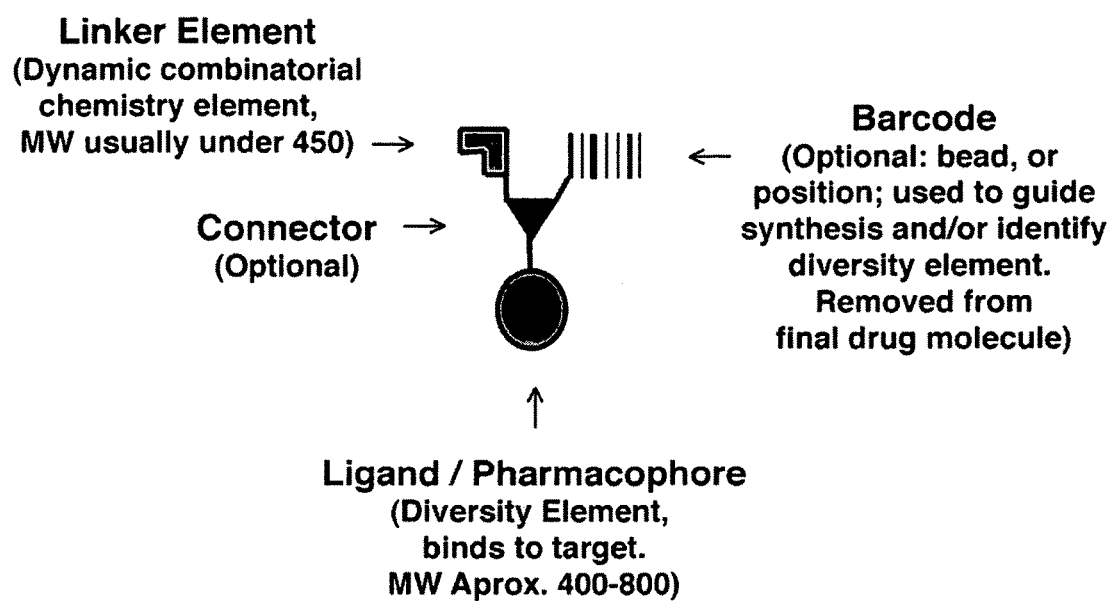
FIG. 1 is a schematic drawing of the components used in a coferon monomer.
Figure 2:
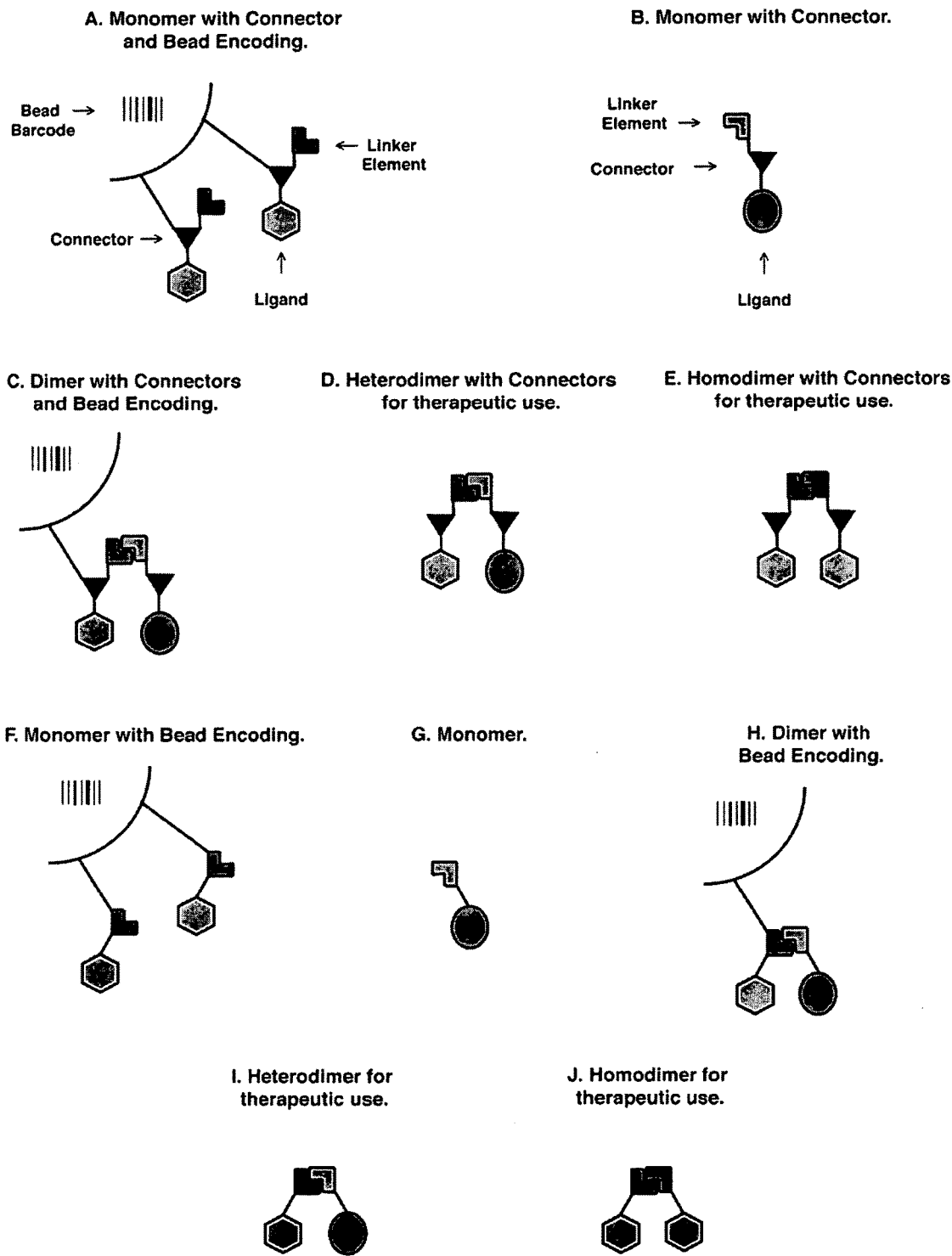
FIGS. 2A to 2J show the variations of the components of coferon drug design.

As shown in FIG. 1, the coferon monomers may includes a linker element, a ligand or pharmacophore, an optional connector, and an optional bar code (i.e. encryption element). The linker element is a dynamic combinatorial chemistry element which may have a molecular weight under 500 daltons, preferably 45-450 daltons; it is responsible for combining with its partner linker element and presenting its attached pharmacophore. The linker element pairings can have a dissociation constants of 100 nM to 300 μM with respect to the molecular target. The ligand or pharmacophore is provided to bind to a target molecule and has a molecular weight of about 400 to 800 with a dissociation constant of 1 nM to 300 μM with respect to the molecular target. The linker element and the pharmacophore may be directly attached to each other or linked together by a connector moiety. An optional connector binds the linker element and the ligand or pharmacophore, assists in synthesis of the coferon monomer, and may assist in positioning the pharmacophore in the ideal conformation or orientation for proper binding to the target. An encryption element or "bar code" moiety can be attached to the linker element or connector for easy release or cleavage. The encryption element is included to guide synthesis and to identify coferon monomers; it is removed from final drug products. FIG. 2A is a schematic drawing of coferon monomers in accordance with the present invention attached to encoded beads via connectors. FIG. 2B is a schematic drawing of a coferon monomer in accordance with the present invention. FIG. 2C is a schematic drawing of a coferon dimer attached to an encoded bead via a connector to one monomer. FIG. 2D is a schematic drawing of a coferon heterodimer with connectors, suitable for therapeutic use. FIG. 2E is a schematic drawing of a of a coferon homodimer with connectors, suitable for therapeutic use. FIG. 2F is a schematic drawing of coferon monomers in accordance with the present invention attached to an encoded bead via the linker element. FIG. 2G is a schematic drawing of a coferon monomer in accordance with the present invention. FIG. 2H is a schematic drawing of a coferon dimer attached to an encoded bead via the linker element. FIG. 2I is a schematic drawing of a coferon heterodimer suitable for therapeutic use. FIG. 2J is a schematic drawing of a of a coferon homodimer suitable for therapeutic use.

One aspect of the present invention is directed to a monomer useful in preparing therapeutic compounds. The monomer includes a pharmacophore, which potentially binds to a macromolecular target molecule with a dissociation constant of less than 300 μM and a linker element connected directly or indirectly through a connector, to said pharmacophore. The linker element has a molecular weight less than 500 daltons and has a dissociation constant of less than 300 mM, with or without a co-factor, under physiological conditions. Linker elements may have dissociation constants up to 1 M in aqueous solutions. The linker is selected from the group consisting of 1)

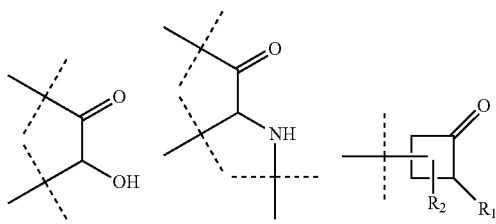

R$_1$ = —OH, SH, —NH$_2$, —NHCH$_3$, —NHR$_3$
where R$_3$ = —C(═O)R$_4$, —SO$_2$R$_4$, —C(═O)OR$_4$
where R$_4$ is composed of aliphatic, alicyclic, aromatic or heteroaromatic group where R$_3$ may also connect to the pharmacophore and is composed of aliphatic, alicyclic, aromatic or heteroaromatic group
R$_2$ = —H, —CH$_3$, —Ph or other aliphatic, aromatic or heteroaromatic group

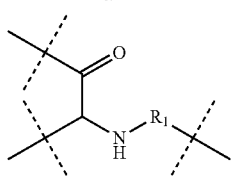

where R$_1$ = —CHO, —C(O)CH$_3$, —C(O)R$_2$, —S(O)$_2$CH$_3$, —S(O)$_2$R$_2$
where R$_2$ may also connect to the pharmacophore and is composed of aliphatic, aromatic or heteroaromatic group.

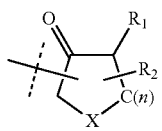

n = 1-4
X = C, N, S, O
R$_1$ = —OH, —SH, NH$_2$, NHCH$_2$, NHR$_3$
where R$_3$ may also connect to the pharmacophore and is composed of aliphatic, aromatic or heteroaromatic group
R$_2$ = —H, —CH$_3$, —Ph or other aliphatic, aromatic or heteroaromatic group where the lines crossed with a dashed line illustrate the one or more bonds formed joining the one or more pharmacophores, directly or through a connector; 2)

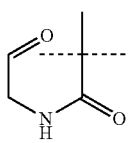

where the lines crossed with a dashed line illustrate the one or more bonds formed joining the one or more pharmacophores, directly or through a connector; 3)

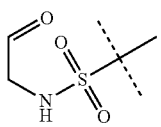

where the lines crossed with a dashed line illustrate the one or more bonds formed joining the one or more pharmacophores, directly or through a connector; 4)

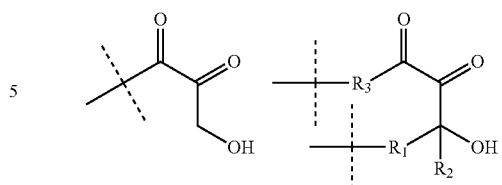

R$_1$, R$_2$ = —H, —CH$_3$, -Ph, —C$_6$H$_{11}$, —C$_5$H$_9$, aromatic or heteroaromatic or connected to each other through a 3, 4, 5 or 6 membered ring.

R$_3$ = —NH$_2$, —OH, —CH$_3$, -Ph, —NHR$_4$, —CH$_2$R$_4$, —OR$_4$
where R$_4$ may be connected to the pharmacophore and is composed of aliphatic, aromatic or heteroaromatic group, and R$_3$ and R$_4$ may connect to R$_1$ and R$_2$ through a 5, 6, 7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

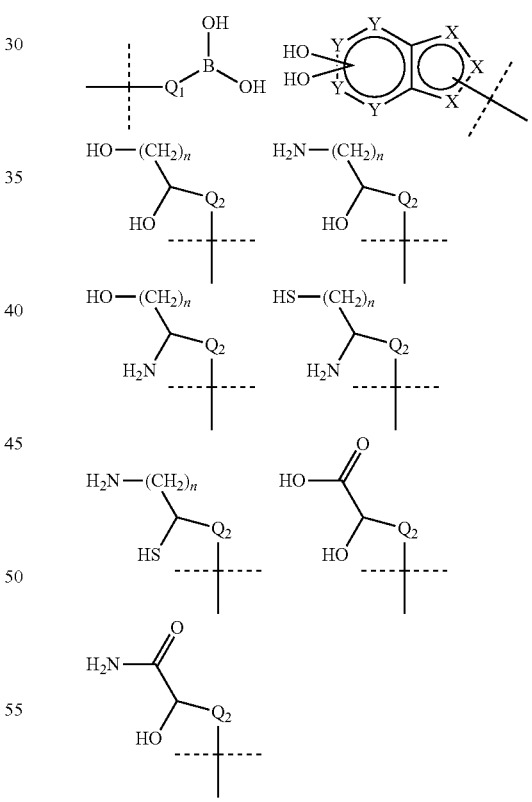

where Q$_1$ and Q$_2$ are aliphatic, alicyclic, or hetero or non-hetero aromatic moieties
where n=1 or 2
where X and Y=C, N, O, or S
where the hydroxy groups emanating from the aromatic ring are ortho to each other X = C, N
R₁, R₂ = —H, —F, —Cl, —Br, —I, —CF₃,
—CN, —OCH₃, —NO₂
When R₁ & R₂ are adjacent, may also include
fused 5 or 6 membered aromatic or heteroaromatic ring X = C, N
R₁, R₂ = —H, —CH₃, —Ph, or connected to each other
through a spiro 3, 4, 5 or 6 membered ring
R₃, R₄ = —H, —F, —Cl, —Br, —I, —CF₃,
—CN, —OCH₃, —NO₂
When R₃ & R₄ are adjacent, may also include
fused 5 or 6 membered aromatic or heteroaromatic ring X = C, N, O, S
R₁, R₂ = —H, —F, —Cl, —Br, —I, —CF₃,
—CN, —OCH₃, —NO₂
When R₁ & R₂ are adjacent, may also include
fused 5 or 6 membered aromatic or heteroaromatic ring R₁ = —OH, —NH₂, —SH, —NHR₄
Where R₄ = alkyl, hydroxyalkyl
R₂, R₃ = —H, —CH₃, —OCH₃,
—OH, —COOH, CONH₂
When R₂ & R₃ are adjacent, may also include
fused 5 or 6 membered aromatic or
heteroaromatic ring n = 2-6
R₁, R₁ₐ = —H, —CH₃, —CH₂NH₂, —CH₂NHCH₃,
aromatic or heteroaromatic ring, or connected
to each other through a 4.5.6.7 or 8-membered ring
Rₘ = —H, —CH₃, —CH₃NH₂, —CH₃OH, —CH₂CH₂OH and
m = 2-6

-continued

X = C, N
R₁, R₂, R₃ = —H, —CH₃, or two R groups connected
to each other through a 5 or 6 membered alicyclic ring R₁ = —OH, —NH₂, —SH
R₂, R₃ = —H, —CH₃, —Ph,
or connected to each other through a spiro 3, 4 5 or
6 membered ring
R₄, R₅ = —H, —CH₃, —CH₂OH, —C(R₂, R₃)OH,
—OCH₃, —OH, —COOH, —CONH₂
When R₄ & R₅ are adjacent, may also include
fused 5 or 6 membered aromatic or heteroaromatic ring R₁, R₂ = —H, —CH₃, —OCH₃, —OH, —COOH, —CONH₂,
—F, —Cl, —Br, —I, —CF₃, —CN, —NO₂
When R₁ & R₂ are adjacent, may also include
fused 5 or 6 membered aromatic or heteroaromatic ring X = C, N, O, S
R₁, R₂ = —H, —CH₃, ----OH, —CH₂OH, -Adenyl R₁, R₂, R₃, R₄, R₅, R₆ = —H, —CH₃
R₇, R₈ are connected to each other to form 3.1.1, 2.2.1 and 2.2.2 bicyclic
ring systems such that the hydroxyls are cis to each other -continued

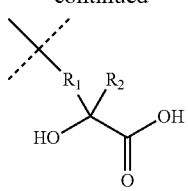

R₁, R₂ = —H, —CH₃, —Ph, —C₆H₁₁, —C₅H₉, aromatic or heteroaromatic ring, C₁—C₆-alkyl or C₃—C₈ cycloalkyl.

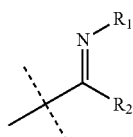

R₁, R₂ = —OH, —NH₂

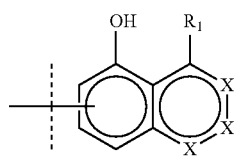

X = C, N
R₁ = —OH, —NH₂, —NHR₂, —NHC(=O)R₂, —NHSO₂R₂

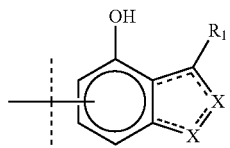

X = C, N, O, S
R₁, R₂ = —NH₂, =O, —OH where the lines crossed with a dashed line illustrate the one or more bonds formed joining the one or more pharmacophores, directly or through a connector.

The monomer can additionally include an encoding element or "bar code", where the pharmacophore, the linker element, and the encoding element are coupled together. The encoding element can be an oligonucleotide or a labeled bead.

Linker Elements

Linker Elements Based on Forming Reversible Imine and Iminium Bonds

The concept of the linker element is to coax two small molecules to bind to one another, taking advantage of hydrophobic, polar, ionic, hydrogen bonding, and/or reversible covalent interactions. The challenge is for that interaction to be sufficiently strong between the two linker elements, while simultaneously not so strong between a linker element and a cellular molecule as to effectively bind and remove the linker elements from solution.

The substituents on the linker elements can be varied to tune the equilibrium of the reversible association of the linker elements in aqueous solution. For reversible covalent bond formation, linker elements may be derived from carbonyl groups or boronates.

These linker elements have the advantage of well-documented literature precedence for use in dynamic combinatorial chemistry selection.

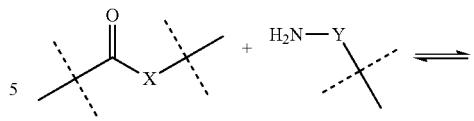

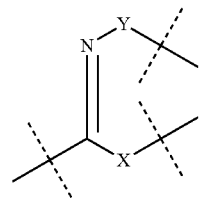

where X and Y may be varied to tune the equilibrium in aqueous solution and the lines crossed with a dashed line illustrate the one or more bonds formed joining the one or more pharmacophores, directly or through a connector, to the molecule. Examples of amines for reversible amine-carbonyl condensations

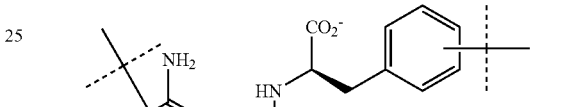
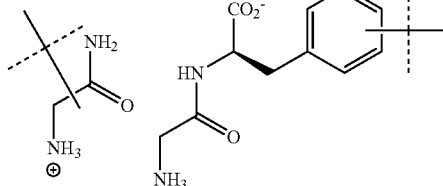
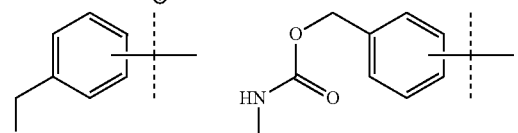
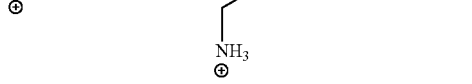

Examples of carbonyl containing molecules for reversible amine-carbonyl condensations

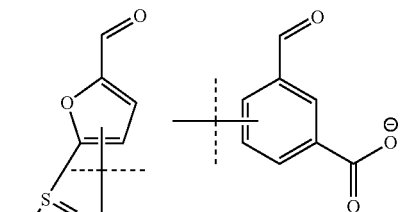

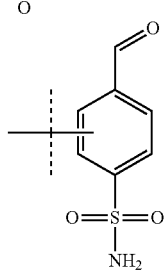

Example of amine-carbonyl condensation

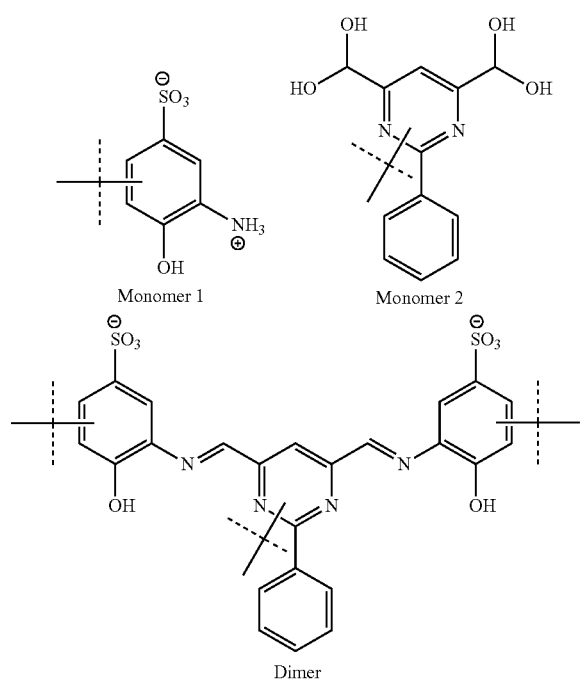

Monomer 1   Monomer 2

Dimer

There is a high concentration of primary amines free in solution (lysine) and in proteins. Thus, when using a coferon containing a primary amine, it is important for the companion aldehyde or ketone containing coferon to find its partner on the surface of the target. However, if the primary amine is beta to a thiol group (which may be in the protected disulfide form outside the cell), then it has the potential to form an irreversible thiazolidine linker in the final coferon dimer.

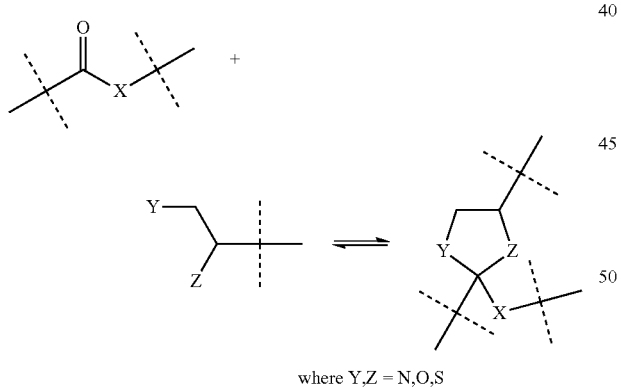

where Y,Z = N,O,S where X, Y, and Z may be varied to tune the equilibrium in aqueous solution and the lines crossed with a dashed line illustrate the one or more bonds formed joining the one or more pharmacophores, directly or through a connector, to the molecule. Similarly, if the amino moiety is beta to an hydroxyl, it may form an oxazolidinyl ring in the assembly of the dimer.

Linker Elements Derived from a Carbonyl Group

Linker elements derived from carbonyl groups may participate in reversible hemiacetal and hemiketal formation with alcohols.

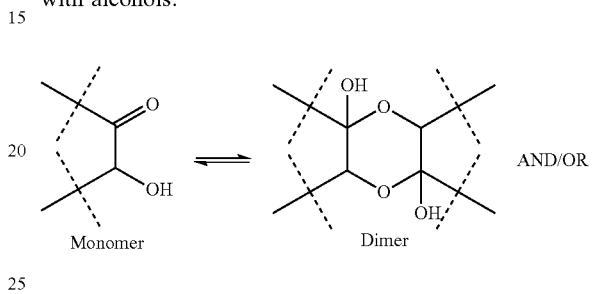

Monomer   Dimer   AND/OR

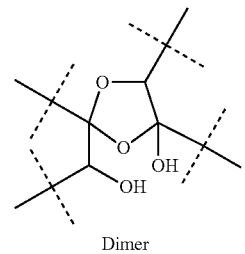

Dimer where X, may be varied to tune the equilibrium in aqueous solution and the lines crossed with a dashed line illustrate the one or more bonds formed joining the one or more pharmacophores, directly or through a connector, to the molecule.

Linker Elements Based on Forming Reversible Boronate Esters

These compounds may be ideal for screening purposes, as well as may work in vivo. One potential caveat is that many sugars have diols that may react with the boronic acid containing linker element. Boronates can also complex with amino alcohols and may also complex with amido acids.

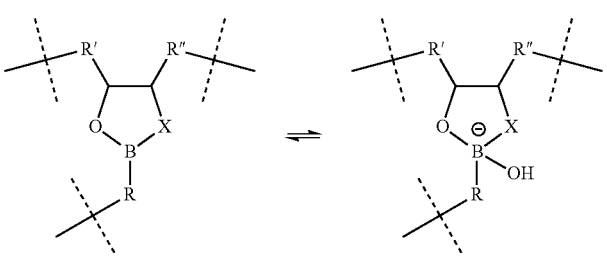

where X, R, R' and R" may be varied to tune the equilibrium in aqueous solution, where the equilibrium species with the tetrahedral boron may include one or both stereoisomers and the lines crossed with a dashed line illustrate the one or more bonds formed joining the one or more pharmacophores, directly or through a connector, to the molecule.

When different pharmacophores are to be presented, heterodimeric linker elements may be preferred, while if identical pharmacophores are to be presented (e.g. to a multimeric target), homodimeric linkers may be desirable. Nevertheless, a successful linker element design that binds tightly to an identical linker element with a different ligand may also be used. If the ligands do not influence self-binding, then using two different ligands with identical linker elements should generate the A-B heterodimer approximately half of the time in the absence of the target.

One class of linker elements involve covalent interactions that occur and are reversible under physiological conditions. These are S—S disulfide bonds, alcohol to ketone to form hemi-ketals, and thiol to ketone to form hemi-thioketals.

An important variation in the linker element design is to have the linker element come together through two covalent bonds. The advantage of such an approach is that even though the individual reaction may be unfavored, once a single bond is made, the local concentration of the other two groups favors formation of the second covalent bond and helps drive the equilibrium towards linker element formation.

A second and related concept is to prevent or minimize side reactions between the individual linker element and active groups on proteins, amino acids, or other molecules in the cell. Such side reactions may be reduced by designing linker element structures that may be sterically hindered when reacting with a large macromolecule, but more amenable to reacting when aligned with a partner linker element especially when bound to the macromolecular target which can serve as a template to position linkers proximally and promote the reaction.

Further, the architecture of the linker element covalent interactions should favor intermolecular bond formation over intramolecular bond formation.

An additional concept is that a linker element in a monomer may react with and form a covalent adduct with the target thus modifying the linker element and allowing it to interact with a different linker element. Further, the dimer or multimer may also form a covalent adduct with the target.

Finally, when the linker elements are in use, they will each have an affinity to their target, and this too will help assemble the dimeric linker element structure. In other words, the intended macromolecular target helps assemble its own inhibitor.

Figure 3:
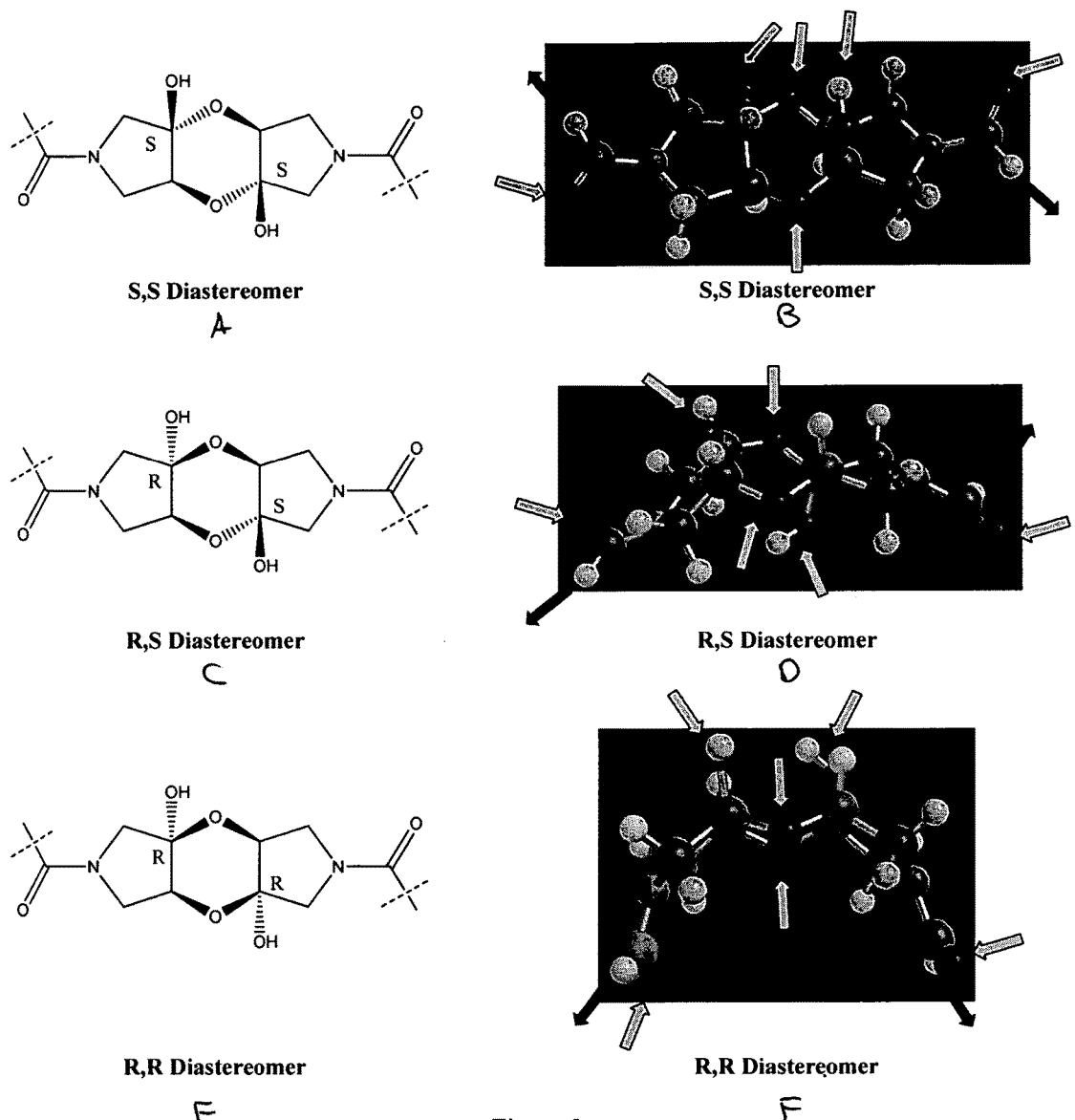
FIGS. 3A-F show the differences in presentation of pharmacophores and hydrogen bonding groups by diastereomers of (4S)-4-hydroxy-3-pyrrolidone based linker element dimers. Only the stereochemistry of the stereochemical centers formed on dimerization are indicated in the figure. (4R)-4-hydroxy-3-pyrrolidone will form a similar, but different set of stereoisomers on dimerization (not shown). While certain diastereomers may be more stable in solution, the macromolecular target may have preference for a different diastereomer that provides more favorable interactions between the pharmacophores, connectors and linker elements. In these figures, the lines crossed with a dashed line represent the bonds formed between the linker elements and the pharmacophores directly or through a connector. The black arrows describe the vector along which the connector and pharmacophore emanate from the linker element dimer and the grey arrows indicate the potential hydrogen bond donors and acceptors that may bind either directly with the macromolecular target or indirectly through bridging water molecules.
Figure 7:
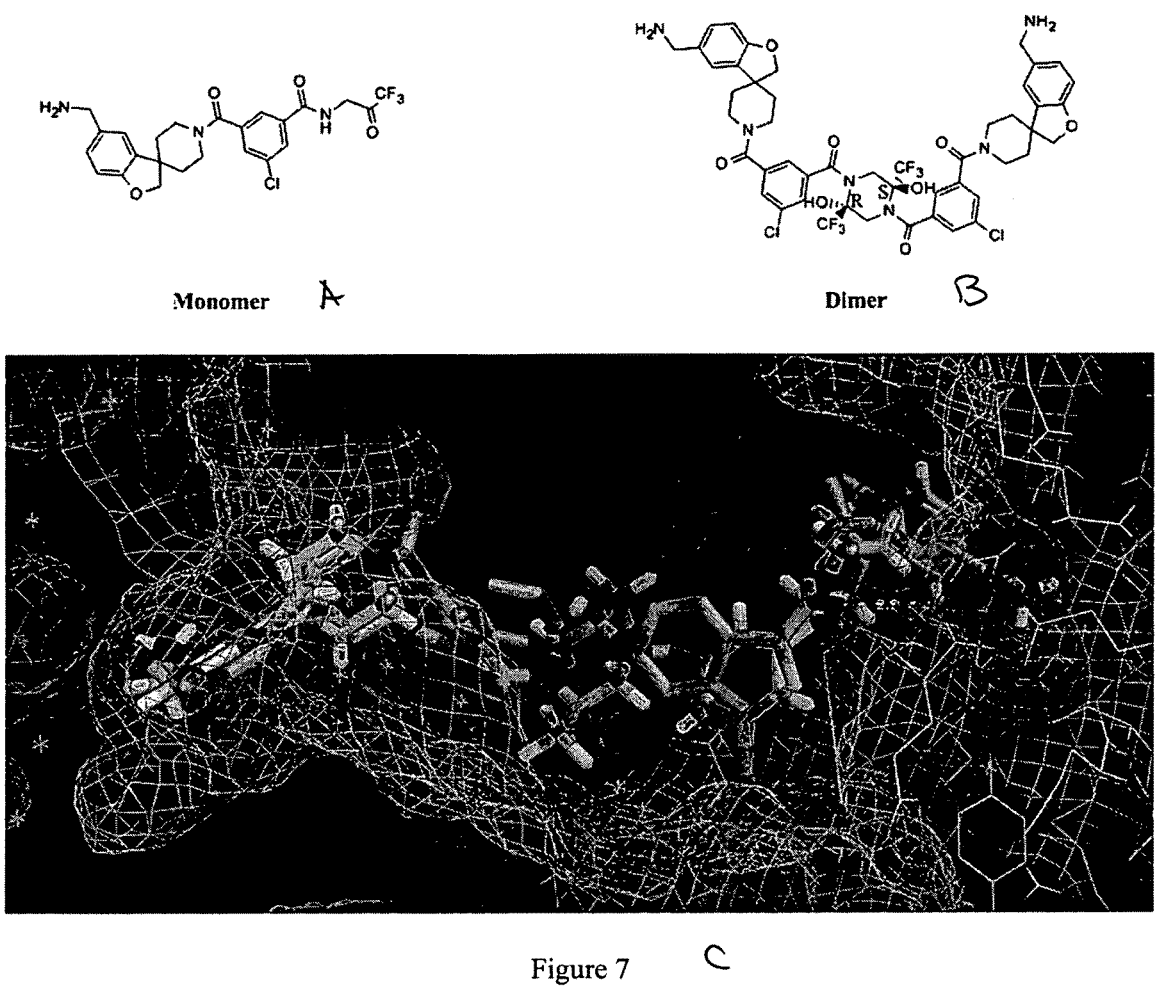
FIGS. 7A-C show the ((2S,5R)-1,4-bis[(3-{[5-(aminomethyl)-2H-spiro[1-benzofuran-3,4'-piperidine]-1'-yl]carbonyl}-5-chlorophenyl)carbonyl]-2,5-bis(trifluoromethyl)piperazine-2,5-diol coferon dimer docked to the tetrameric human (3-tryptase-II. For comparison, in FIG. 7C the coferon dimer is overlaid with the inhibitor present in the 2ZEB structure of tryptase from the Protein Data Bank. Virtual screening, docking, and scoring of coferon monomers (using Tripos FlexX) containing a trifluoromethyl ketone linker element suggest that tryptase will have a high affinity for this homodimeric derivative as its S,R-diastereomer.

Often coferons dynamically and reversibly come together to form multimers with new stereocenters or alternative geometries. For example, boronic acid diesters may be planar ($sp^2$ hybridized) at the boron, or may have tetrahedral geometry ($sp^3$ hybridized) in which the $sp^3$ boron is chiral due to an additional donor ligand or hydroxyl group. In the absence of a target, coferon dimer or multimer stereoisomers may have similar stability or probability of formation. In the presence of target, certain stereoisomers of coferon dimers or multimers will be selectively bound by the macromolecular target, which significantly favors their association and potential formation on the target. If coferons form less preferred stereoisomers, geometries or conformers, they will not be as avidly bound by the target, and hence will be liberated to isomerize to the more preferred isomer that will bind to the target. In another example, the condensation of hydroxyketo linker elements to form bis(hemiketal) dimers results in the formation of two new stereocenters (See FIG. 3). While in solution, diastereomers may have similar stabilities and energies, it is anticipated that each stereoisomer will exhibit differential binding to the target, resulting in the target selecting for the highest affinity diastereomer (See FIGS. 4-7). Less preferred coferon isomers can equilibrate through ring opening or epimerization or dissociation to monomers until the more preferred isomer is produced and bound to the target. Such examples illustrate a key advantage of this technology over existing technologies involving the covalent synthesis, separation of stereoisomers, determination of chirality and testing of fragment assemblies.

Derivatives Based on 1,3-Dihydroxyacetone

Derivatives based on 1,3-dihydroxyacetone (Linker Element 1) would most likely require bulky blocking groups to reduce the natural reactivity of the keto group. Nevertheless, this is the minimal linker element design.

One embodiment of the linker element is an aliphatic compound with a hydroxy group alpha, beta, or gamma to a carbonyl group, where the linker element and its binding partner, when bound together, form a 6 or 8 member di-hemiacetal or di-hemiketal rings, the linker element is

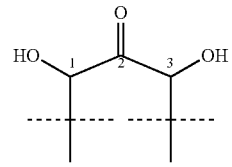

General Structure where
the lines crossed with a dashed line illustrate the one or more bonds formed joining the one or more pharmacophores, directly or through a connector, to the molecule of Formula (I). If there is no pharmacophore at that position, the group may be chosen from the following: —H, —OH or —CH$_3$.

One example of this embodiment is 1,3-dihydroxyacetone (MW: 90) which naturally dimerizes under physiologic conditions.

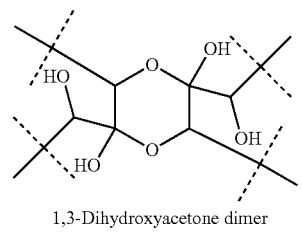

1,3-Dihydroxyacetone dimer

Derivatives Based on α-Hydroxyketones and α-Hydroxyaldehydes

Linker elements that possess a hydroxyl group alpha to a carbonyl group can dimerize through the formation of a 6-membered diketal ring or 5-membered spiroketal ring. When the linker element is chiral in nature the resulting dimers are diastereomers. Certain diastereomers may be favored thermodynamically while others may be favored kinetically. Additionally, the macromolecular target may favor and selectively direct the formation of a specific diastereomer. Electron withdrawing groups adjacent to the carbonyl such as —OH, —C═O and —CF₃ may modify the equilibrium in favor of the dimer.

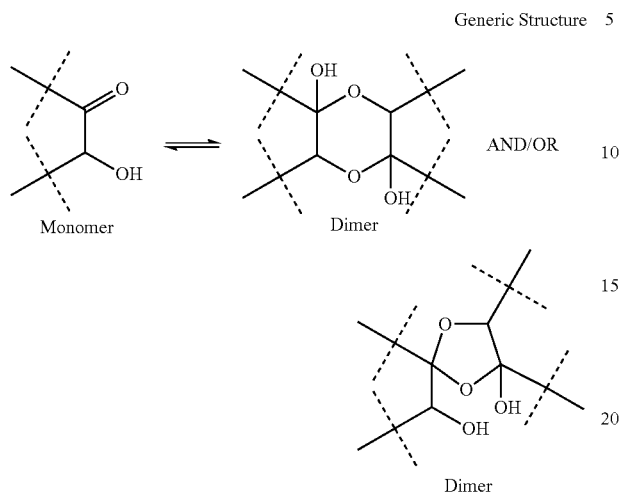

Generic Structure 5 where the lines crossed with a dashed line illustrate the one or more bonds formed joining the one or more pharmacophores, directly or through a connector and where the dimers formed may comprise one or more stereoisomers.

In the embodiments shown below, the lines crossed with a dashed line illustrate the one or more bonds formed joining the one or more pharmacophores, directly or through a connector, to the linker element. The stereoisomers of the dimers in the embodiments shown below are representative of and not limited to the different stereoisomers that can form.

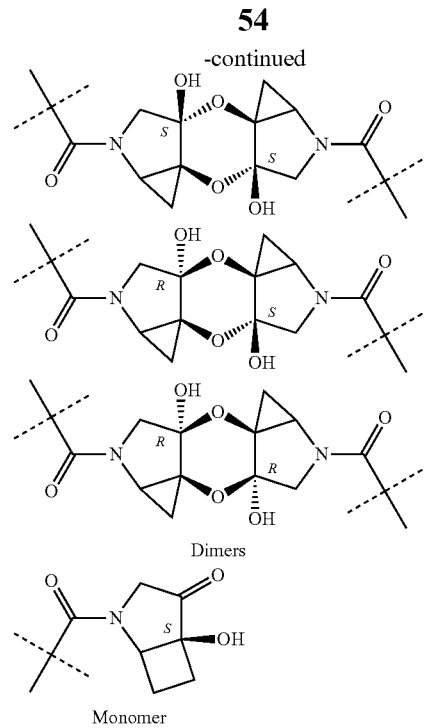

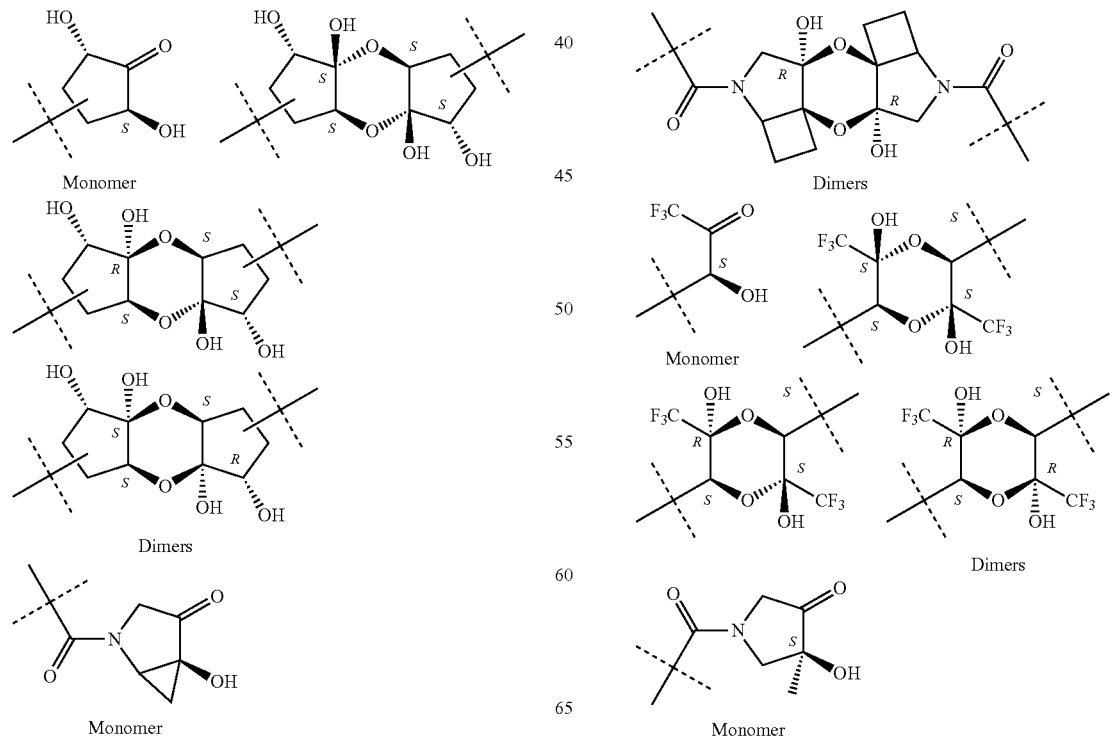

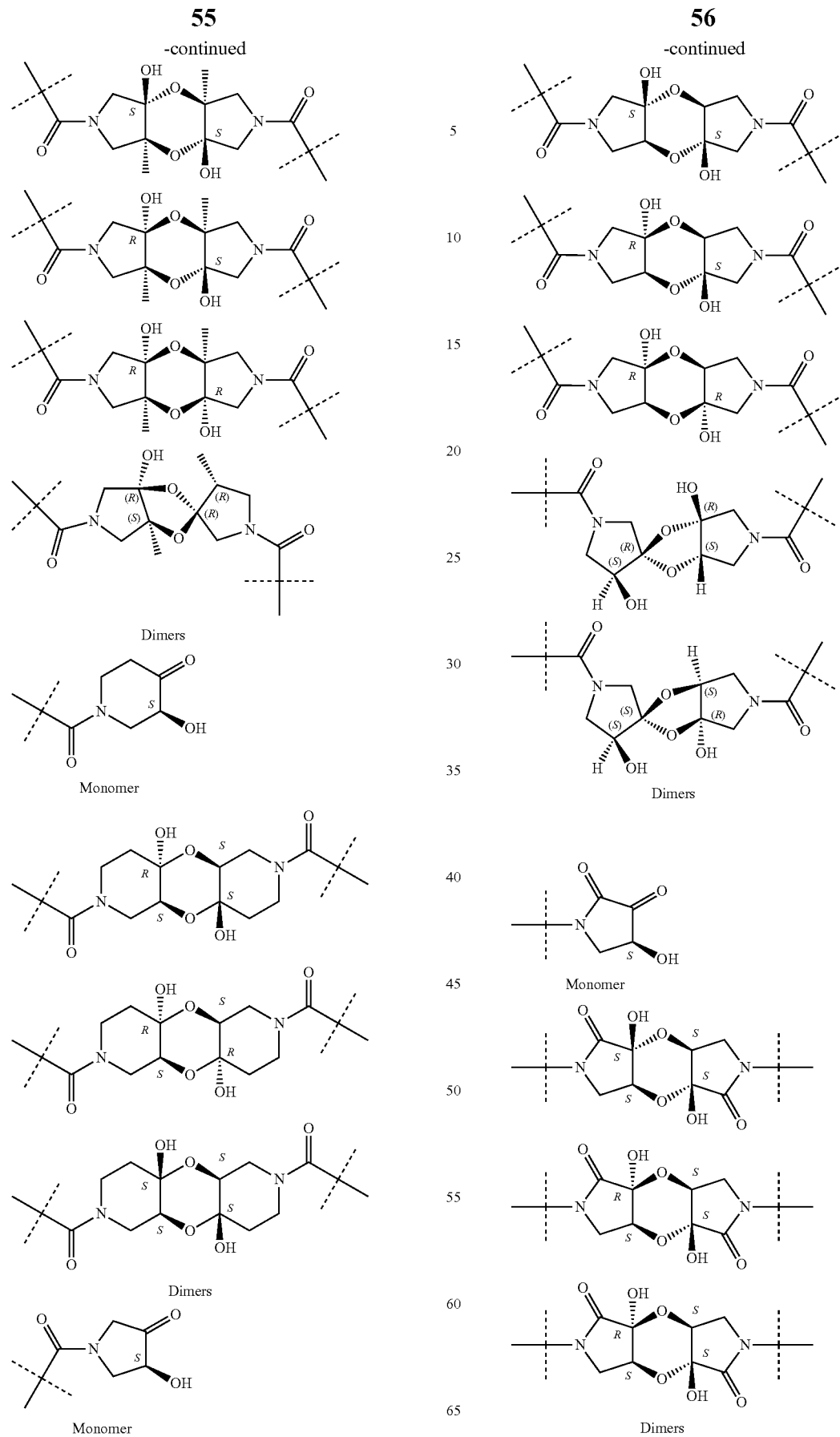

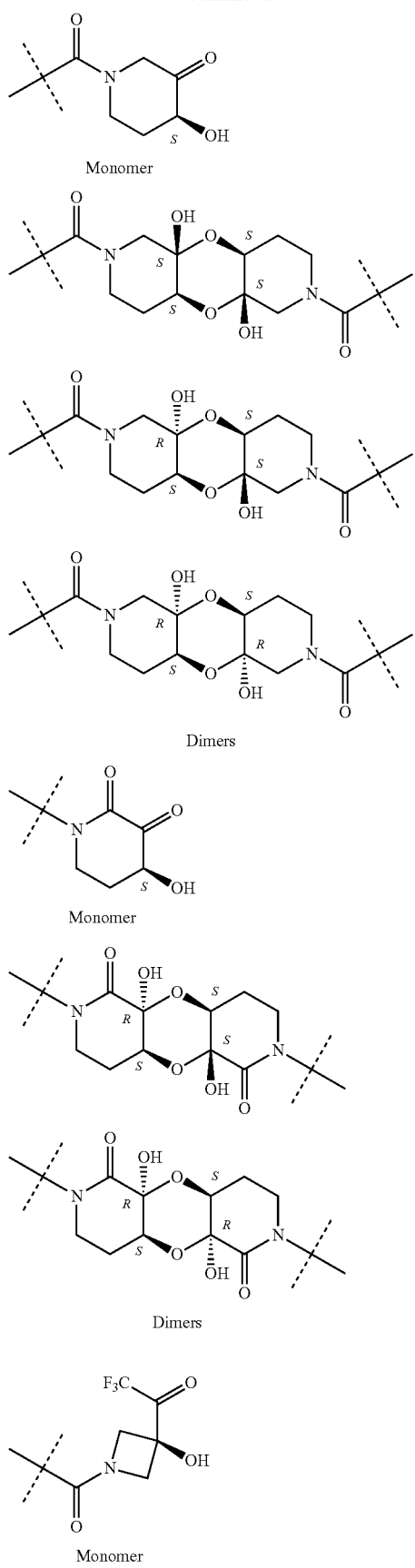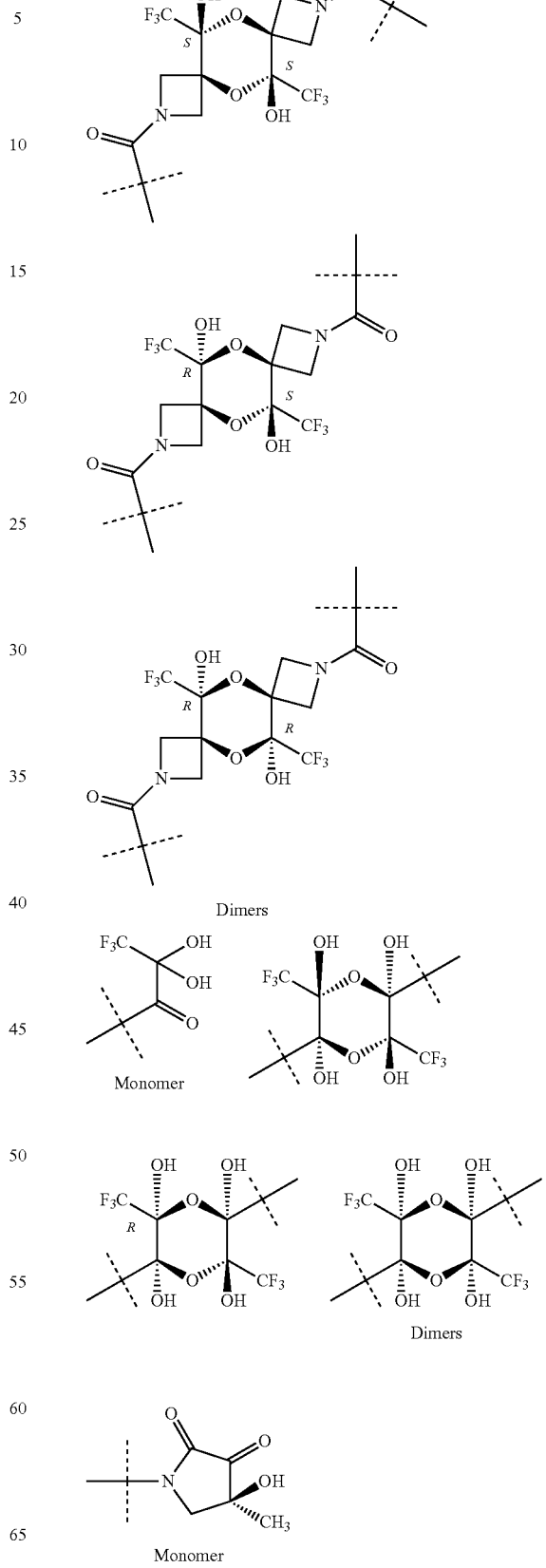

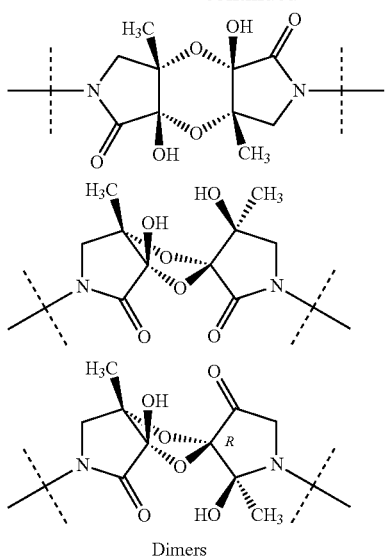

Dimers

Derivatives Based on Pyruvic Acid and Pyruvic Amides

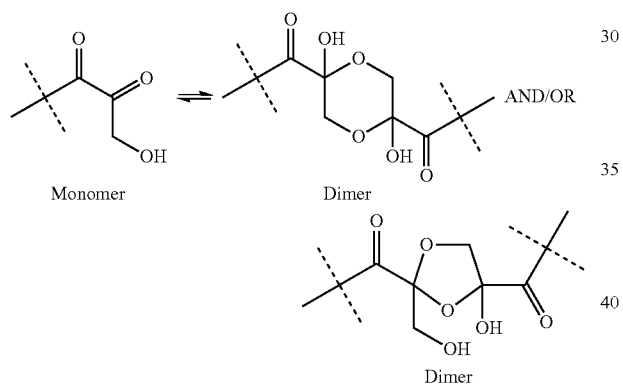

Generic Structure

Monomer    Dimer    AND/OR

Dimer where the lines crossed with a dashed line illustrate the one or more bonds formed joining the one or more pharmacophores, directly or through a connector and where the dimers formed may comprise one or more stereoisomers.

In the embodiments shown below, the lines crossed with a dashed line illustrate the one or more bonds formed joining the one or more pharmacophores, directly or through a connector, to the linker element. The stereoisomers of the dimers in the embodiments shown below are representative of and not limited to the different stereoisomers that can form.

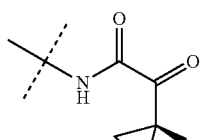

Monomer

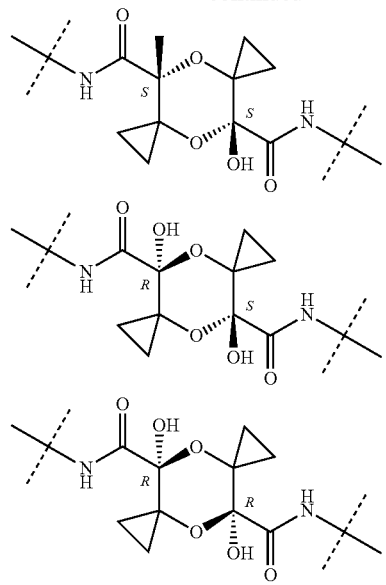

Dimers

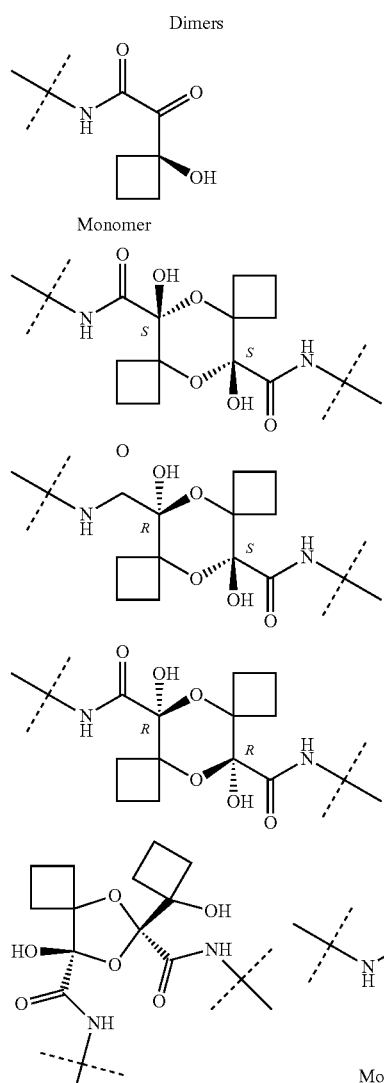

Monomer

Dimers

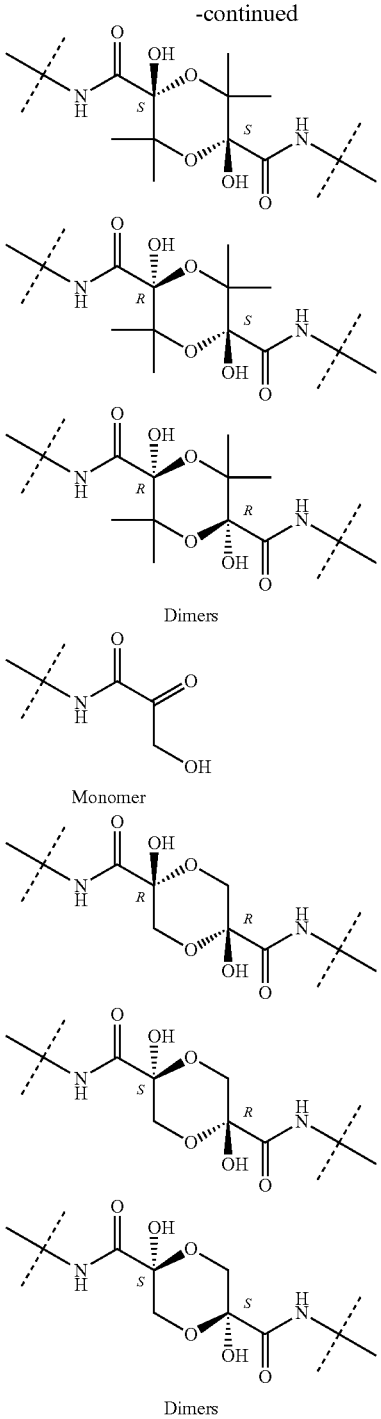

Dimers

Monomer

Dimers

Derivatives Based on α-Aminoketones

Linker elements that possess an amino group alpha to a carbonyl group can dimerize through the formation of a piperazine or oxazolidinyl ring. The amine may serve as a convenient point for the attachment of a pharmacophore directly or through a connector. When the linker element is chiral in nature the resulting dimers are diastereomers. Certain diastereomers may be favored thermodynamically while others may be favored kinetically. Additionally, the macromolecular target may favor and selectively direct the formation of a specific diastereomer. Electron withdrawing groups adjacent to the carbonyl such as —OH, —C=O, and —CF$_3$ may modify the equilibrium in favor of the dimer.

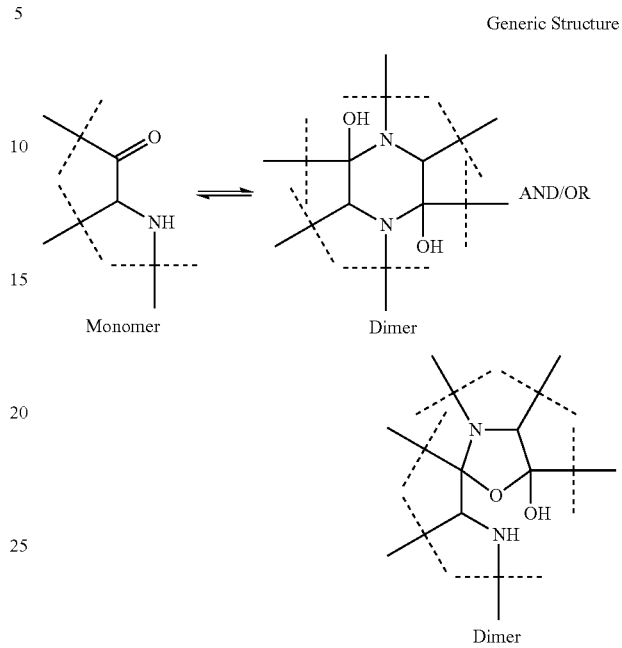

Generic Structure

Monomer    Dimer

AND/OR

Dimer where the lines crossed with a dashed line illustrate the one or more bonds formed joining the one or more pharmacophores, directly or through a connector and where the dimers formed may comprise one or more stereoisomers.

In the examples shown below, the lines crossed with a dashed line illustrate the one or more bonds formed joining the one or more pharmacophores, directly or through a connector, to the linker element. The stereoisomers of the dimers in the embodiments shown below are representative of and not limited to the different stereoisomers that can form.

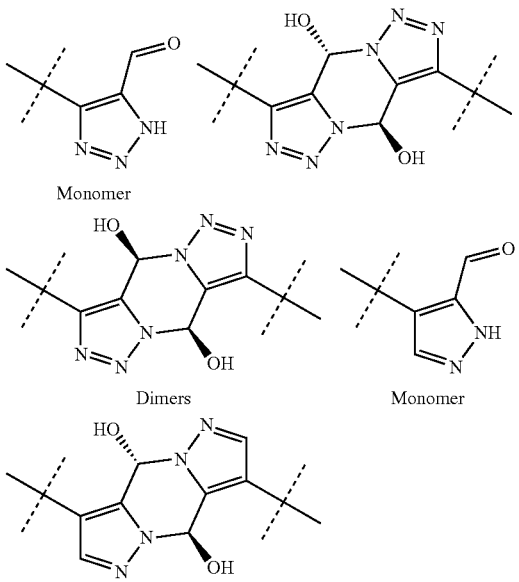

Monomer

Dimers         Monomer

-continued

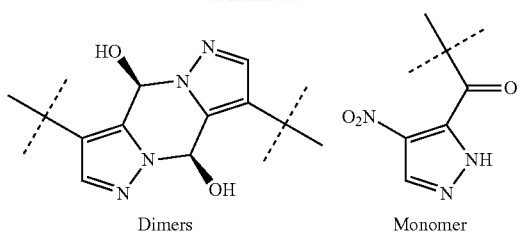
Dimers   Monomer

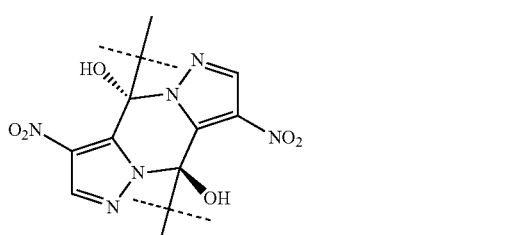
Dimers

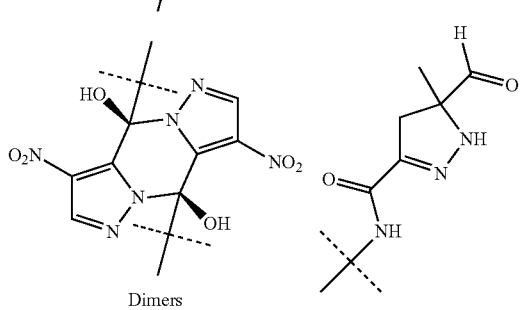
Dimers   Monomer

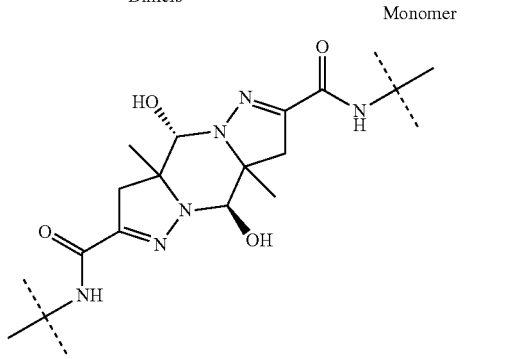
Dimers

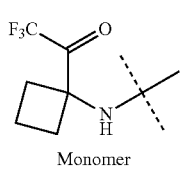
Monomer

-continued

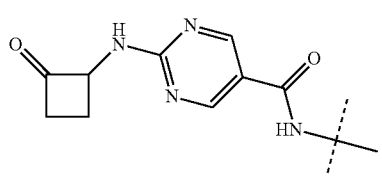
Dimers

Additional examples of linker elements include the following

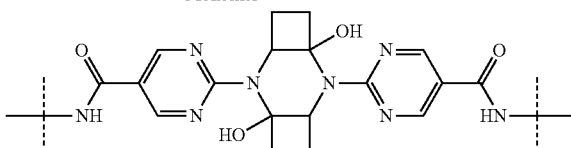
Monomer

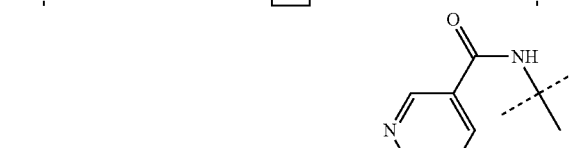

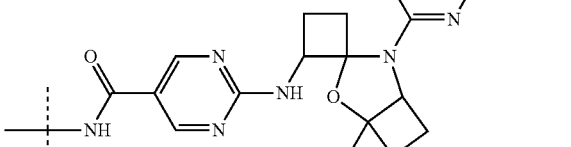
Dimers

Derivatives Based on α-Amidoketones

Linker elements based on α-amidoketones can dimerize through the formation of a piperazine piperazine or oxazolidine ring. The amide can serve as a convenient point for the attachment of a pharmacophore directly or through a connector. When the linker element is chiral in nature, the resulting dimers are diastereomers. Certain diastereomers may be favored thermodynamically while others may be favored kinetically. Additionally, the macromolecular target may favor and selectively direct the formation of a specific diastereomer. Electron withdrawing groups adjacent to the carbonyl such as —OH, —C=O, and —CF₃ may modify the equilibrium in favor of the dimer.

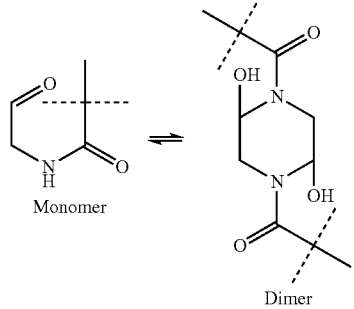
Monomer

Generic Structure

AND/OR

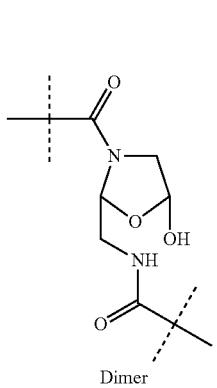
Dimer

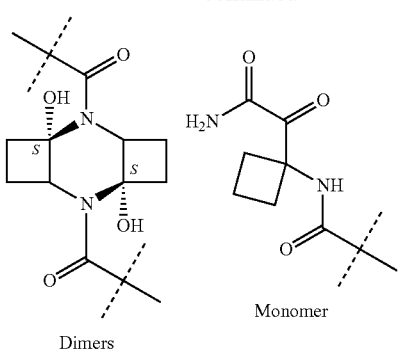
Dimers

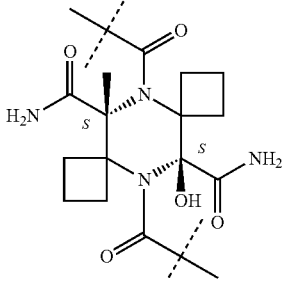
Monomer where the lines crossed with a dashed line illustrate the one or more bonds formed joining the one or more pharmacophores, directly or through a connector and where the dimers formed may comprise one or more stereoisomers.

In the examples shown below, the lines crossed with a dashed line illustrate the one or more bonds formed joining the one or more pharmacophores, directly or through a connector, to the linker element. The stereoisomers of the dimers in the embodiments shown below are representative of and not limited to the different stereoisomers that can form.

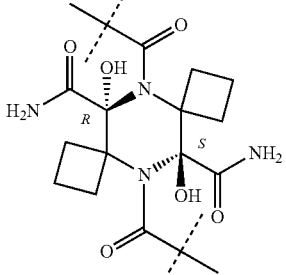

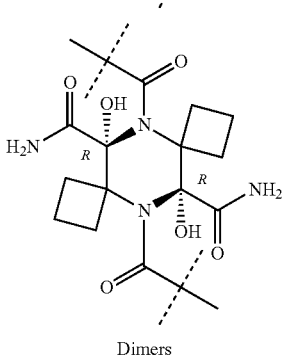
Dimers

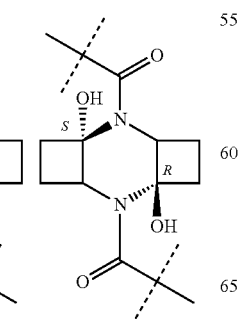
Monomer

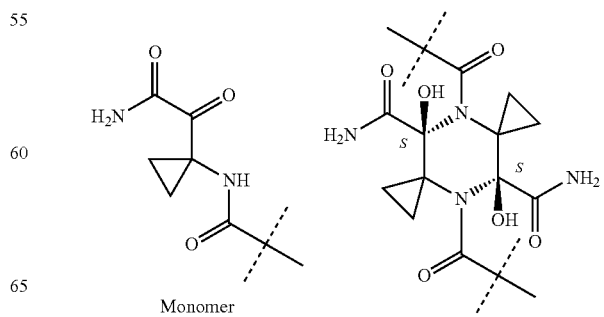
Monomer

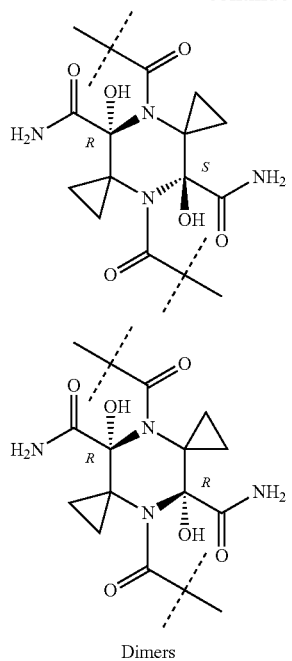
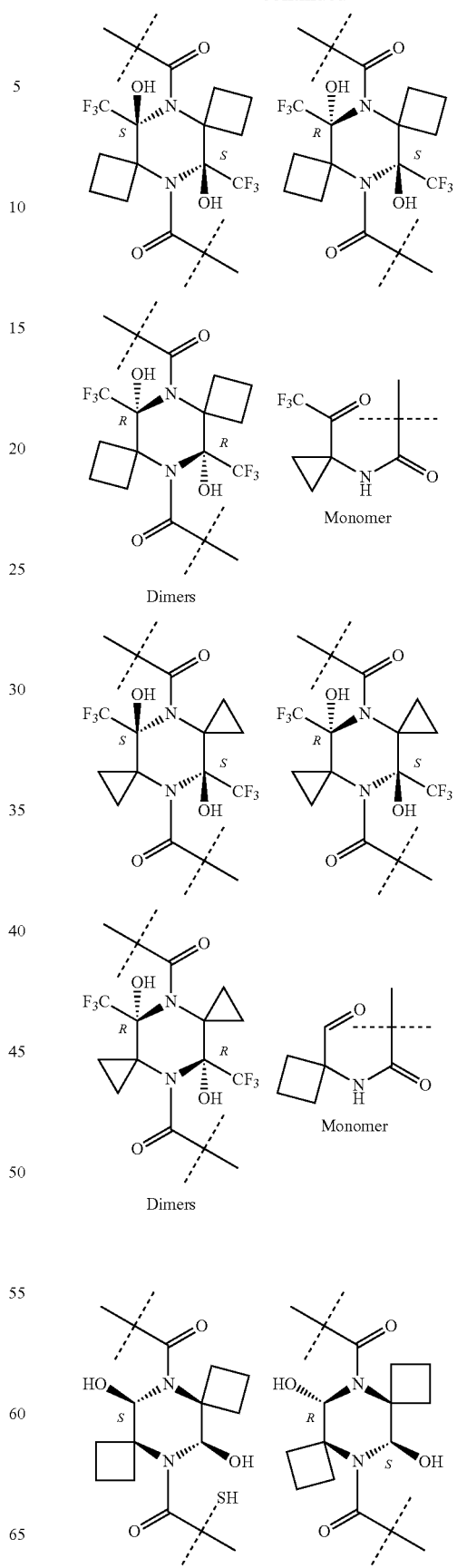

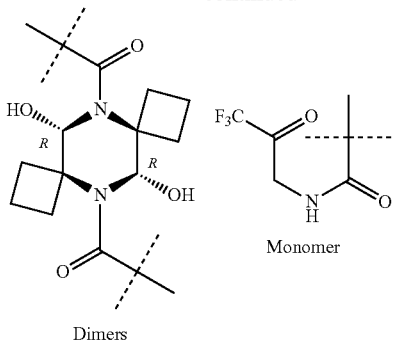

Monomer

Dimers

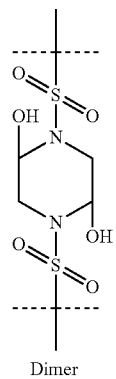

Monomer

Dimer

AND/OR

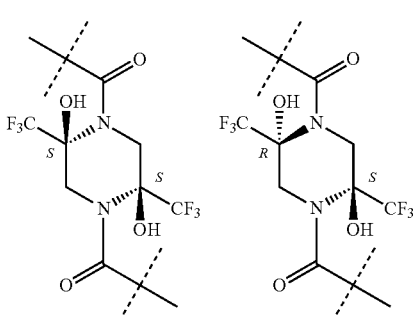

Dimers

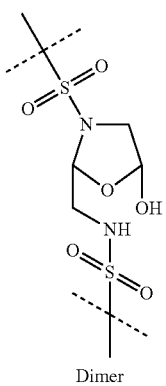

Dimer

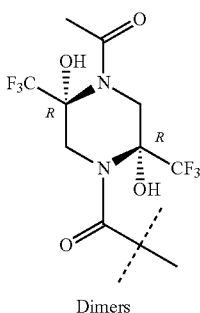

Dimers where the lines crossed with a dashed line illustrate the one or more bonds formed joining the one or more pharmacophores, directly or through a connector and where the dimers formed may comprise one or more stereoisomers.

In the examples shown below, the lines crossed with a dashed line illustrate the one or more bonds formed joining the one or more pharmacophores, directly or through a connector, to the linker element. The stereoisomers of the dimers in the embodiments shown below are representative of and not limited to the different stereoisomers that can form.

Derivatives Based on α-Sulfonamidoketones

Linker elements based on α-sulfonamidoketones can dimerize through the formation of a piperazine or oxazolidine ring. The amide can serve as a convenient point for the attachment of a pharmacophore directly or through a connector. When the linker element is chiral in nature the resulting dimers are diastereomers. Certain diastereomers may be favored thermodynamically while others may be favored kinetically. Additionally, the macromolecular target may favor and selectively direct the formation of a specific diastereomer. Electron withdrawing groups adjacent to the carbonyl such as —OH, —C═O, and —CF₃ may modify the equilibrium in favor of the dimer.

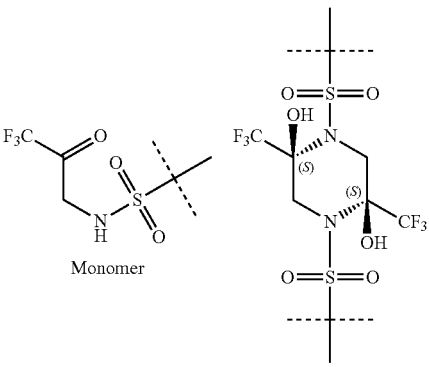

Monomer

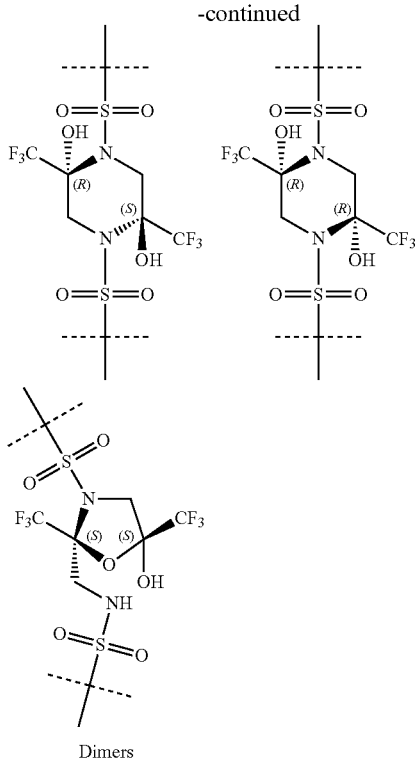

Dimers

Evidence for the Stability of Linker Element Monomers and Dimers

Some of the linker elements described above (based on α-hydroxyketones, α-aminoketones and α-amidoketones) are available commercially, or have been reported in the literature as forming dimers, which indicates that these dimers are thermodynamically stable.

Some examples of commercially available molecules as well as molecules cited in the literature that possess features of the described linker elements.

Commercially Available Dimers

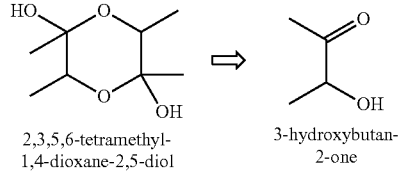

2,3,5,6-tetramethyl-1,4-dioxane-2,5-diol ⇒ 3-hydroxybutan-2-one

The compound 2,3,5,6-tetramethyl-1,4-dioxane-2,5-diol is available commercially and is a dimer of 3-hydroxybutan-2-one.

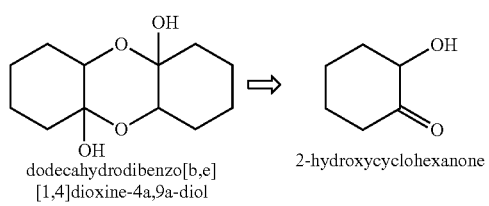 [SMILES: OC12CCCCC1OC1(O)CCCCC1O2 ; O=C1CCCCC1O]

dodecahydrodibenzo[b,e][1,4]dioxine-4a,9a-diol ⇒ 2-hydroxycyclohexanone

The compound dodecahydrodibenzo[b,e][1,4]dioxine-4-a,9a-diol is commercially available and is a dimer of 2-hydroxycyclohexanone.

The compound 2,5-dimethyl-2,5-bis((3-morpholinoprop-1-ynyloxy)methyl)-1,4-dioxane is a derivative of (2,5-dimethyl-1,4-dioxane-2,5-diyl)dimethanol which can be derived from the dimerization of 1-hydroxy-propan-2-one.

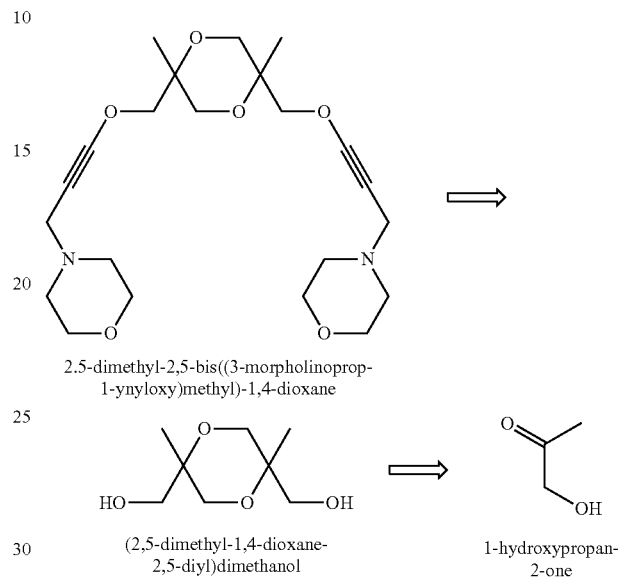

2,5-dimethyl-2,5-bis((3-morpholinoprop-1-ynyloxy)methyl)-1,4-dioxane (2,5-dimethyl-1,4-dioxane-2,5-diyl)dimethanol ⇒ 1-hydroxypropan-2-one Dihydroxyacetone dimers are well precedented in the literature and can be readily functionalized.

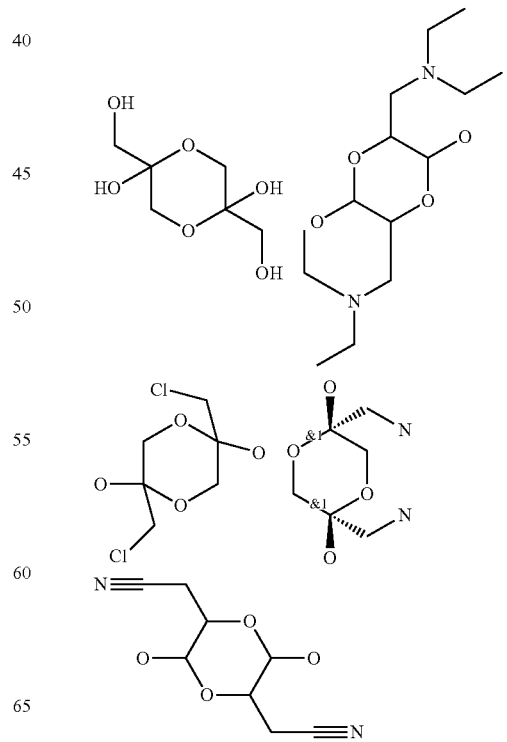

-continued
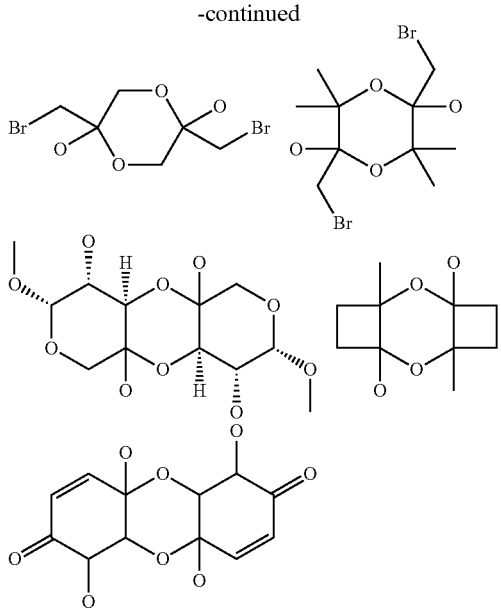
Hydroxyketone Dimers Reported in the Literature
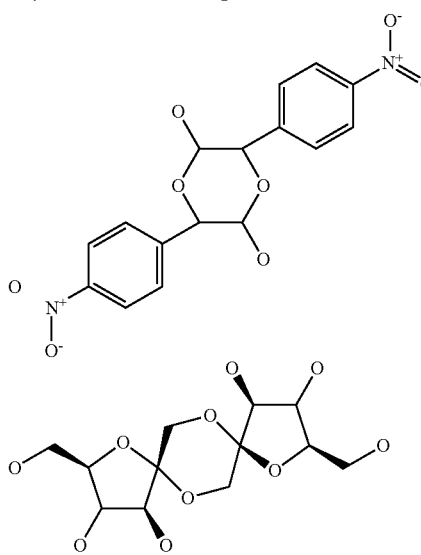
β-Hydroxy-α-Ketoamide Linker Element Precedents
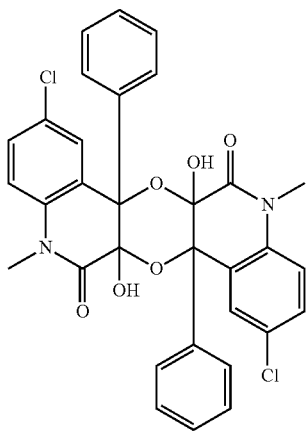 [SMILES: CN1C(=O)C2(O)OC3(c4ccccc4)c4cc(Cl)ccc4N(C)C(=O)C3(O)OC2(c2ccccc2)c2cc(Cl)ccc21]
*Canadian Journal of Chemistry* 46(13):2263-9 (1968), which is hereby incorporated by reference in its entirety.
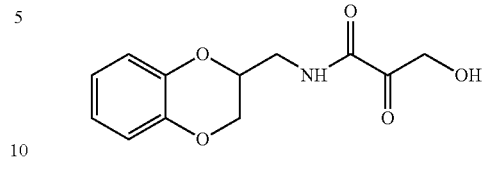
Commercially Available Monomer
Dimers of α-Aminoketones
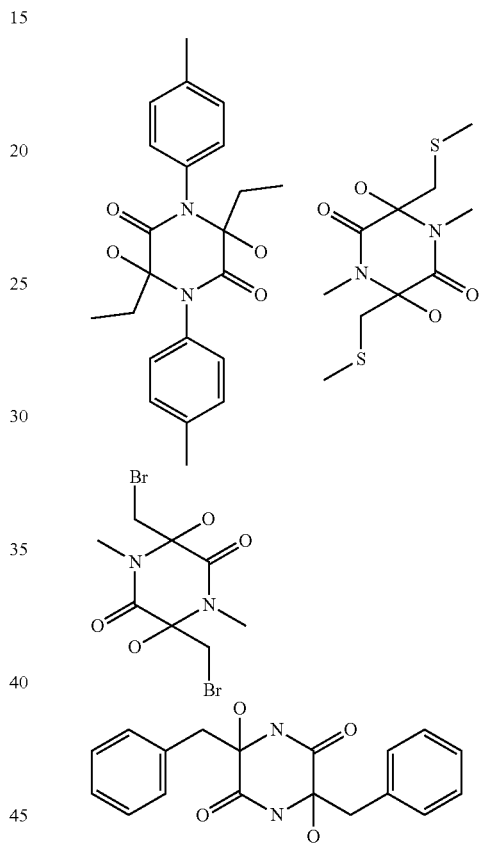
Dimer of α-Aminoketones
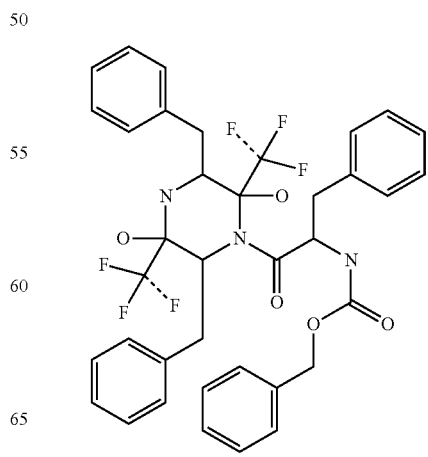

75
-continued
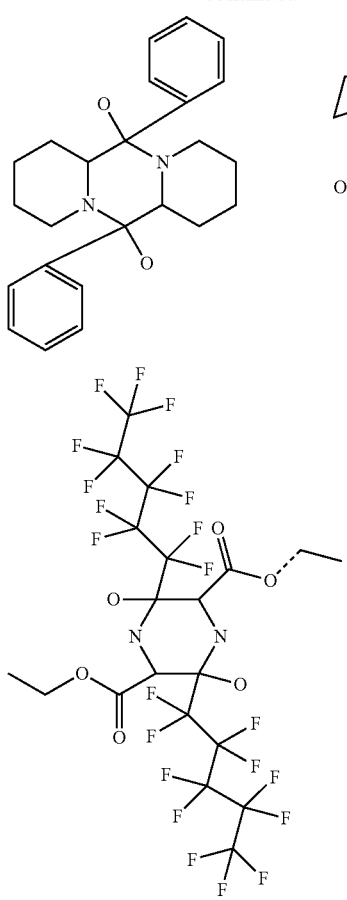
Heterodimers of α-Ketoamides
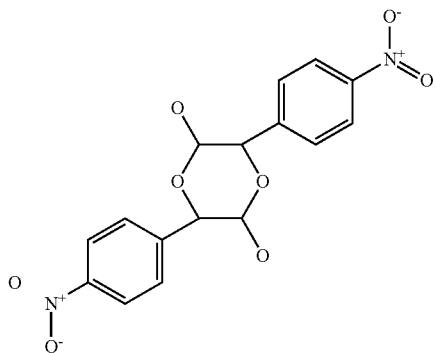
Literature precedent for dimers of α-Hydroxyaldehydes
76
-continued
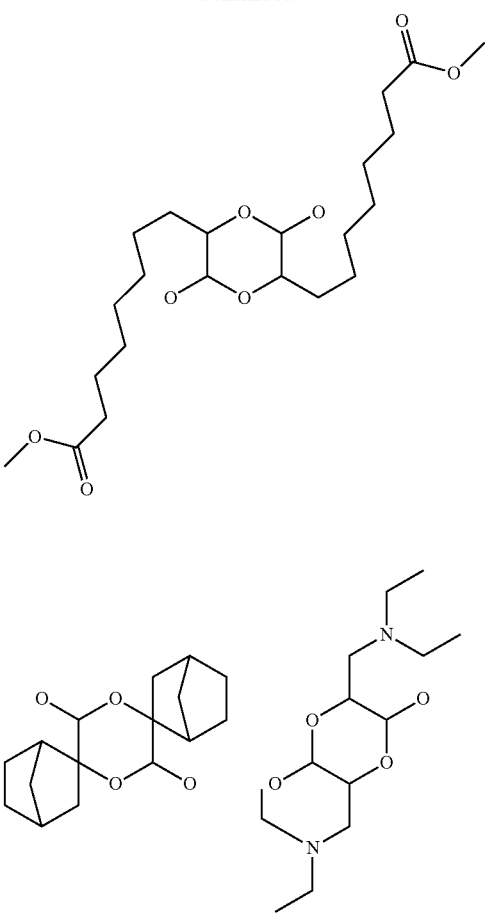
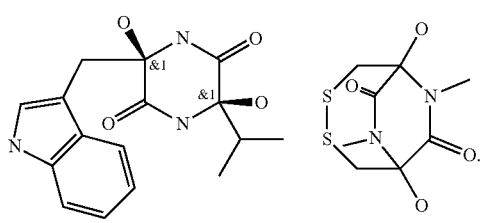
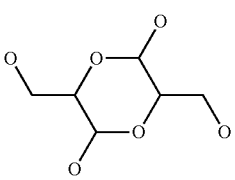
Carboxyketo dimer precedent
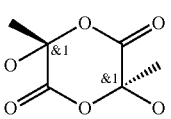
Amido-Trifluoromethyl-ketone Linker element precedent
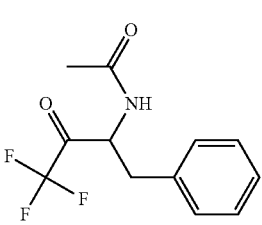

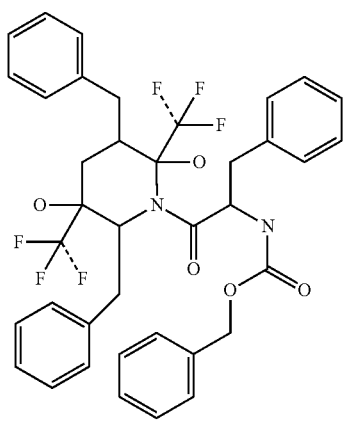

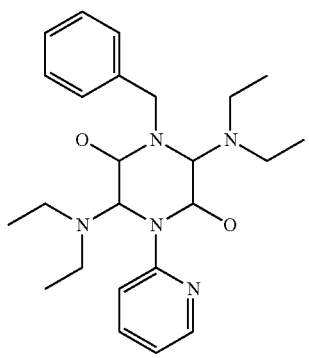

Heteroaromatic-Ketone Linker element precedent

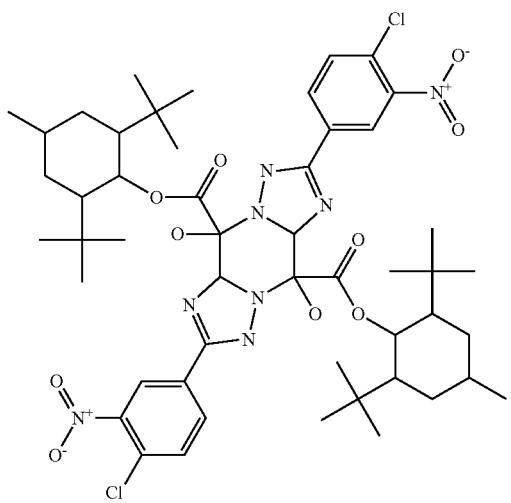

Heteroaromatic-Aldehyde Linker element precedent

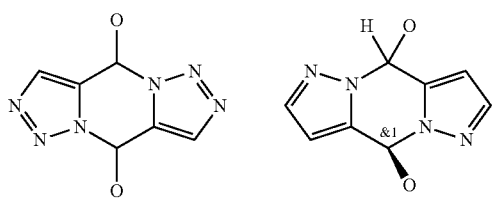

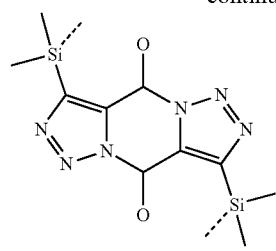

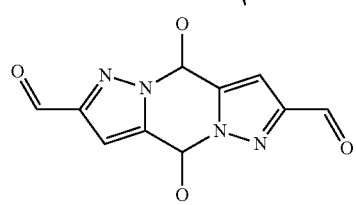

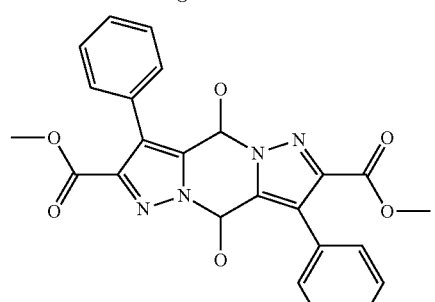

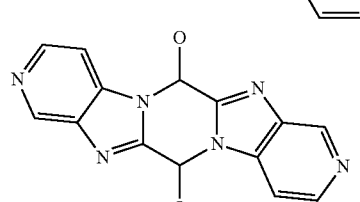

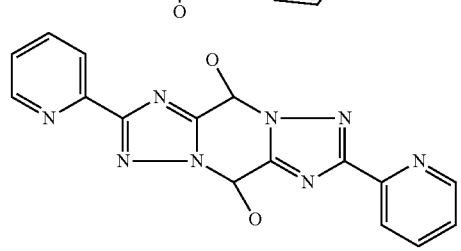

Derivatives Based on Boronic Acid that Form Covalent Interactions with Diols, Catechols, Amino Alcohols, Amino Thiols, α-Hydroxy Acids, α-Hydroxyamides, and Ortho-Hydroxy-Aryl Carboxamides Aliphatic, alicyclic, and aromatic boronic acids can react with 1,2-, 1,3-, 1,4-diols to form boronate esters comprising 5, 6, or 7 membered rings, respectively. An example is shown below for the reaction of a boronic acid with a 1,2-diol.

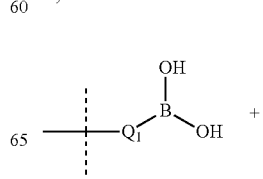

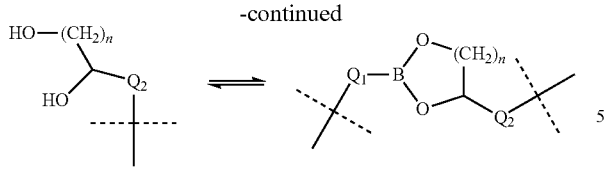

where $Q_1$ and $Q_2$ are aliphatic, alicyclic, or hetero or non-hetero aromatic moieties
where n=1, 2 or 3
where the lines crossed with a dashed line illustrate the one or more bonds formed joining the one or more pharmacophores, directly or through a connector.
An example of a dimer formed from a boronic acid and an aromatic 1,2-diol is shown below:

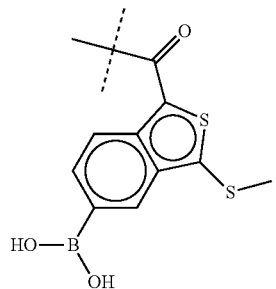

Monomer 1

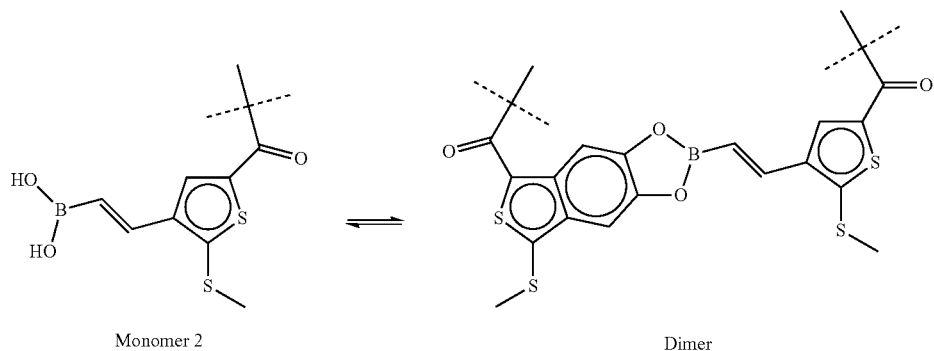

Monomer 2        Dimer

Although only a boronic acid diester with an sp² hybridized boron is shown, boronic acids may also form enantiomeric tetrahedral sp³ boronate ester complexes.
Examples of boronic acid linker element monomers are:

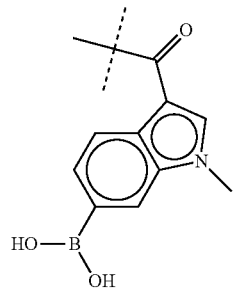

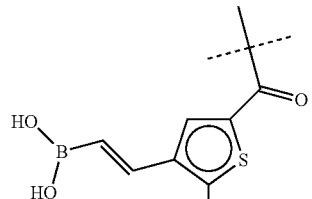

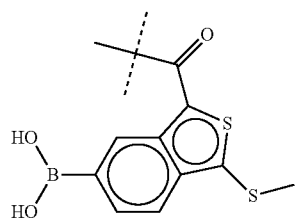

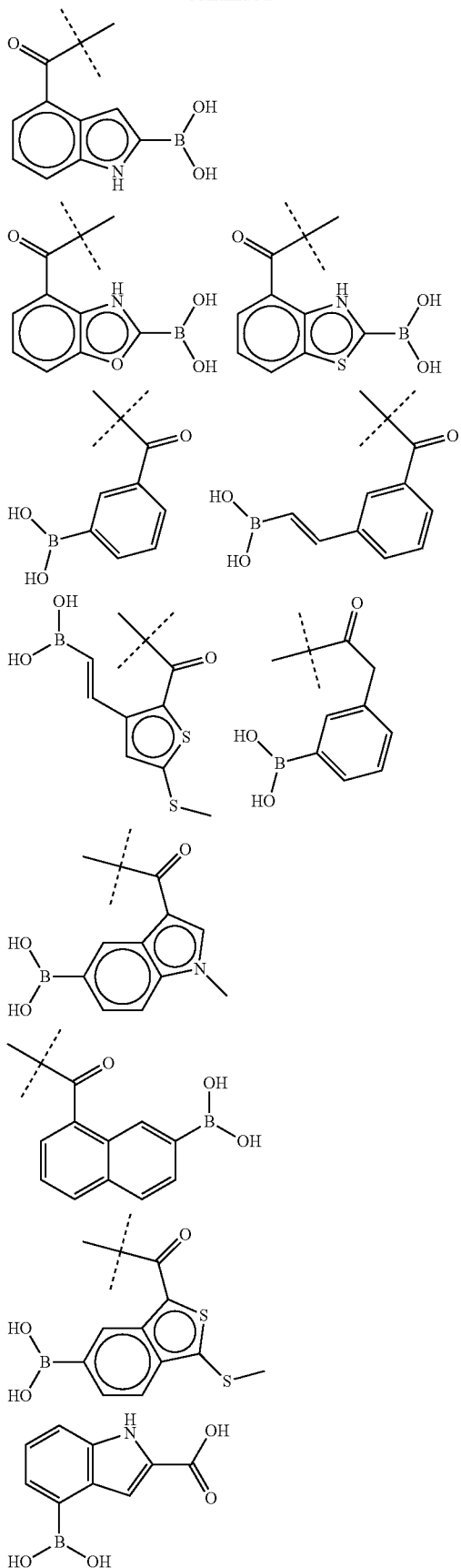

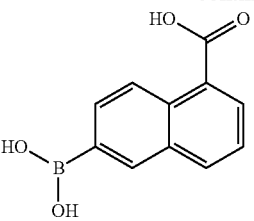

Additional examples of boronic acid linker moieties when appropriately bearing pharmacophoric elements for a macromolecular target elements include but are not limited to those listed below:

| | |
|---|---|
| (5-Amino-2-hydroxymethyl-phenyl)boronic acid | 2-(Hydroxymethyl)phenylboronic acid |
| 2-(N,N-Dimethylamino)-pyridine-5-boronic acid hydrate | 2-(Trifluoromethyl)pyridine-5-boronic acid |
| 2-Chloroquinoline-3-boronic acid | 2-Fluorophenylboronic acid |
| 2-fluoropyridine-3-boronic acid | 2-fluoropyridine-5-boronic acid |
| 2-Methoxypyridine-5-boronic acid | 2-Methoxypyrimidine-5-boronic acid |
| 2,3-Difluorophenylboronic acid | 2,4-Bis(trifluoromethyl)phenylboronic acid |
| 2,4-Bis(trifluoromethyl)phenyl-boronic acid | 2,4-Difluorophenylboronic acid |
| 2,5-Difluorophenylboronic acid | 2,6-Difluorophenylboronic acid |
| 2,6-Difluorophenylboronic acid | 2,6-Difluoropyridine-3-boronic acid hydrate |
| 3-(trifluoromethyl)phenylboronic acid | 3-Fluorophenylboronic acid |
| 3-Nitrophenylboronic acid | 3,4-Difluorophenylboronic acid |
| 3,5-Bis(trifluoromethyl)phenyl-boronic acid | 3,5-Difluorophenylboronic acid |
| 4-Fluorophenylboronic acid | 4-Nitrophenylboronic acid |
| 5-Quinolinylboronic acid | Benzofuran-2-boronic acid |
| Benzothiophene-2-boronic acid | Furan-2-boronic acid |
| Phenylboronic acid | Pyridine-3-boronic acid |
| Pyrimidine-5-boronic acid | Thiophene-2-boronic acid |
| 2-Hydroxymethyl-5-nitrophenyl-boronic acid | 2-Hydroxyphenylboronic acid |
| 2,4-Dimethoxyphenylboronic acid | 2,6-Dimethoxypyridine-3-boronic acid |
| 4-(N,N-Dimethylamino)phenyl-boronic acid | 6-Indolylboronic acid |
| trans-2-Phenylvinylboronic acid | |

Examples of linker elements containing diols that form covalent interactions with boronic

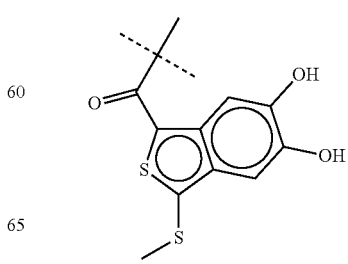

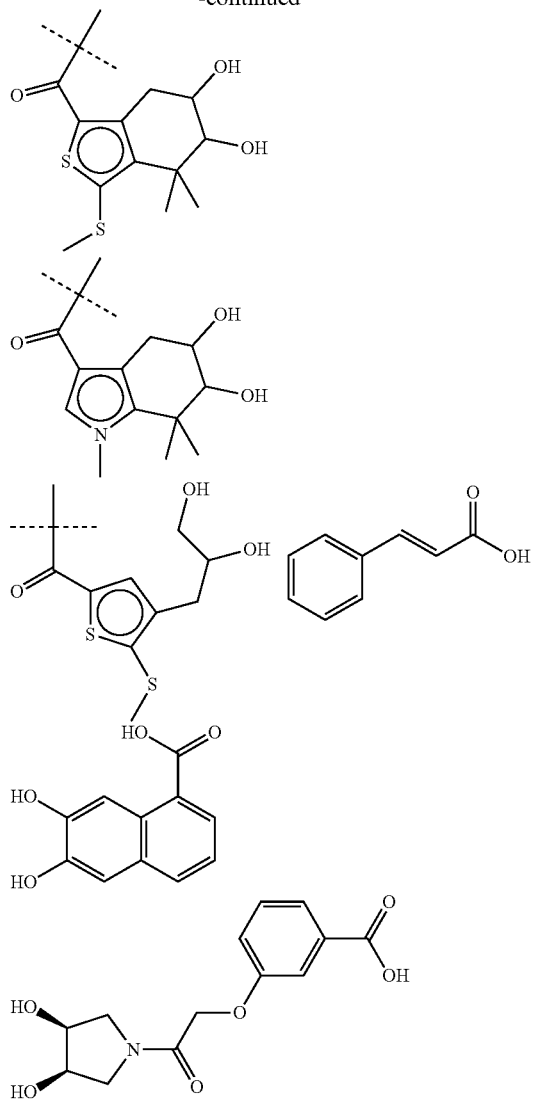

Additional examples of diol linker moieties when appropriately bearing pharmacophoric elements for a macromolecular target include but are not limited to those listed below:

| | |
|---|---|
| (±)-exo,exo-2,3-Camphanediol | (−)-Epigallocatechin gallate |
| (1R,2R,3S,5R)-(−)-Pinanediol | (3S,4R)-pyrrolidine-3,4-diol |
| 2-Hydroxybenzyl alcohol | 2,2,6,6-Tetrakis(hydroxymethyl)cyclohexanol |
| 2,3,4-Trihydroxybenzophenone | 2,6-Bis(hydroxymethyl)-p-cresol |
| 3-Methyl-1,3,5-pentanetriol | 3,4-Dihydroxybenzonitrile |
| 3,4,5-Trihydroxybenzamide | 4-Methylcatechol |
| 6,7-Dihydroxy-4-methylcoumarin | 7,8-Dihydroxy-4-methylcoumarin |
| Adenosine | Alizarin Red S |
| cis-1,2-Cyclooctanediol | cis-1,2-Cyclopentanediol |
| D-(−)-Fructose | D-Sorbitol |
| Gallic acid | Gallic Acid Ethanolamide |
| Labetalol hydrochloride | meso-Erythritol |
| Methyl 3,4,5-trihydroxybenzoate | Propyl gallate |
| Pyrocatechol | Pyrogallol |
| Tricine | Triisopropanolamine |
| 1,1,1-Tris(hydroxymethyl)ethane | 1,3-Dihydroxyacetone |
| 2-(Methylamino)phenol | 2-Acetamidophenol |
| 2-Amino-2-methyl-1,3-propanediol | 2-Amino-4-methylphenol |
| 2-Hydroxy-3-methoxybenzyl alcohol | 3-Methylamino-1,2-propanediol |
| cis-1,2-Cyclohexanediol | D-(+)-Glucose |
| Hydroxypyruvic acid, Lithium salt | Pentaerythritol |
| Phenylpyruvic acid | Pinacol |
| trans-1,2-Cyclohexanediol | Tris Base (TRIZMA Base) |
| 3-Fluorocatechol | |

The example below shows the reaction of a boronic acid with a 1, 2 or 1,3-amino alcohol.

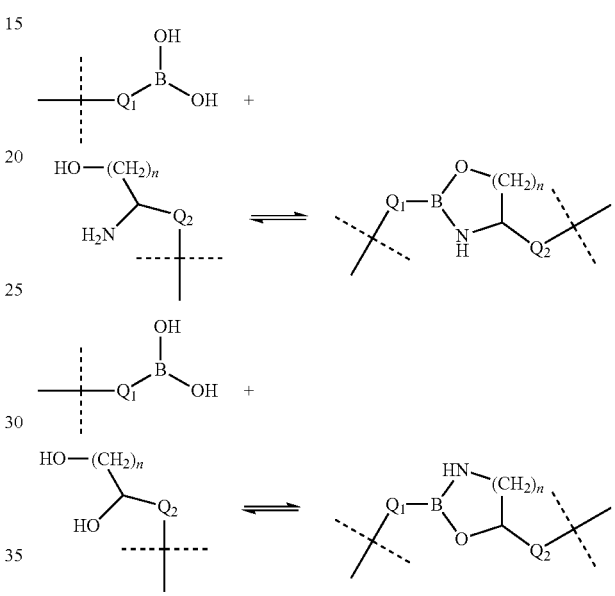

where $Q_1$ and $Q_2$ are aliphatic, alicyclic, or hetero or non-hetero aromatic moieties where n=1 or 2 where the lines crossed with a dashed line illustrate the one or more bonds formed joining the one or more pharmacophores, directly or through a connector.

The example below shows the reaction of a boronic acid with a 1, 2 or 1,3-amino thiol.

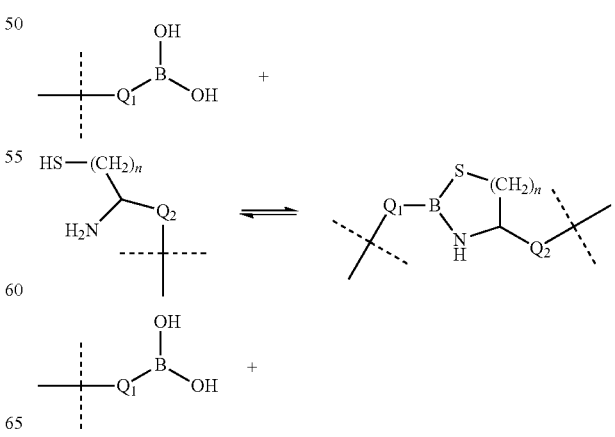

-continued

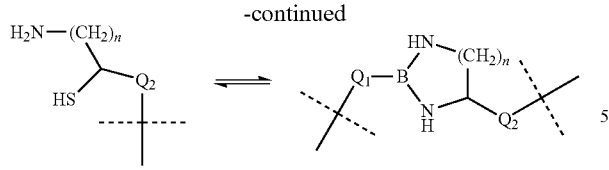

where $Q_1$ and $Q_2$ are aliphatic, alicyclic, or hetero or non-hetero aromatic moieties
where n=1 or 2
where the lines crossed with a dashed line illustrate the one or more bonds formed joining the one or more pharmacophores, directly or through a connector.
The example below shows the reaction of a boronic acid with an ortho-dihydroxy aromatic diol

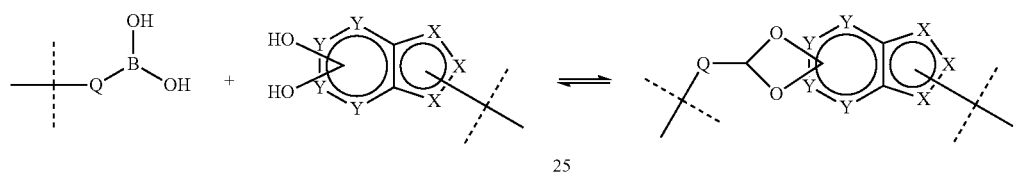

where Q is an aliphatic, alicyclic, or hetero or non-hetero aromatic moiety
where X and Y=C, N, O, or S
where the hydroxy groups emanating from the aromatic ring are ortho to each other where the lines crossed with a dashed line illustrate the one or more bonds formed joining the one or more pharmacophores, directly or through a connector.
The example below shows the reaction of a boronic acid with an α-hydroxy acid.

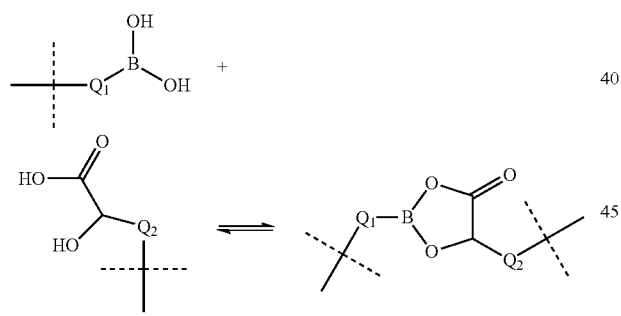

where $Q_1$ and $Q_2$ are aliphatic, alicyclic, or hetero or non-hetero aromatic moieties
where the lines crossed with a dashed line illustrate the one or more bonds formed joining the one or more pharmacophores, directly or through a connector.
Examples of linker elements containing α-hydroxy acids that form covalent interactions with boronic acid linker elements:

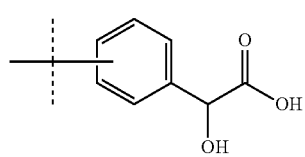

-continued

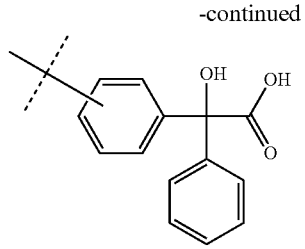

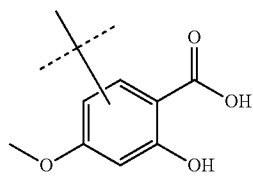

-continued

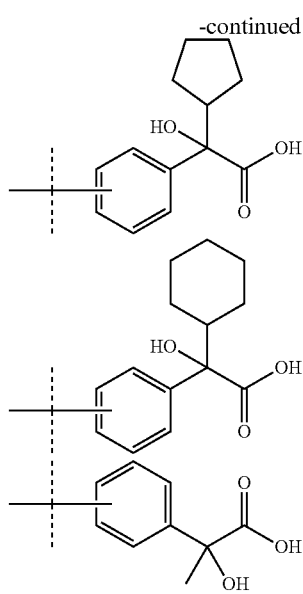

Additional examples of α-hydroxy acid linker elements include but are not limited to those listed below:

| | |
|---|---|
| Lactic acid | 2,2-Bis(hydroxymethyl)propionic acid |
| Salicylic acid | DL-Mandelic acid |
| 3,3,3-Trifluoro-2-hydroxy-2-(trifluoromethyl)propionic acid | 3,3,3-Trifluoro-2-hydroxy-2-methylpropionic Acid |
| 3,5-Difluoromandelic acid | 2,6-Difluoromandelic acid |
| 2,6-Dihydroxybenzoic acid | 2,3-Difluoromandelic acid |
| 2,4-Difluoromandelic acid | 2,5-Difluoromandelic acid |
| 4-(Trifluoromethyl)mandelic acid | D-(−)-Quinic acid |
| Benzilic acid | 2-Fluoromandelic acid |
| DL-Atrolactic acid hemihydrate | α-Cyclohexylmandelic acid |
| α-Cyclopentylmandelic acid | α-Hydroxyisobutyric acid |
| 3-hydroxyazetidine-3-carboxylic acid | 2-Hydroxy-4-methoxybenzoic acid |

The example below shows the reaction of a boronic acid with an α-hydroxyamide.

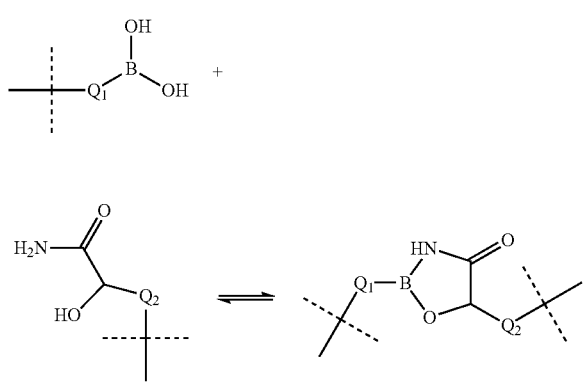

where $Q_1$ and $Q_2$ are aliphatic, alicyclic, or hetero or non-hetero aromatic moieties where the lines crossed with a dashed line illustrate the one or more bonds formed joining the one or more pharmacophores, directly or through a connector.

Examples of linker elements containing α-hydroxyamides or o-hydroxyarylcarboxamides that form covalent interactions with boronic acid linker elements:

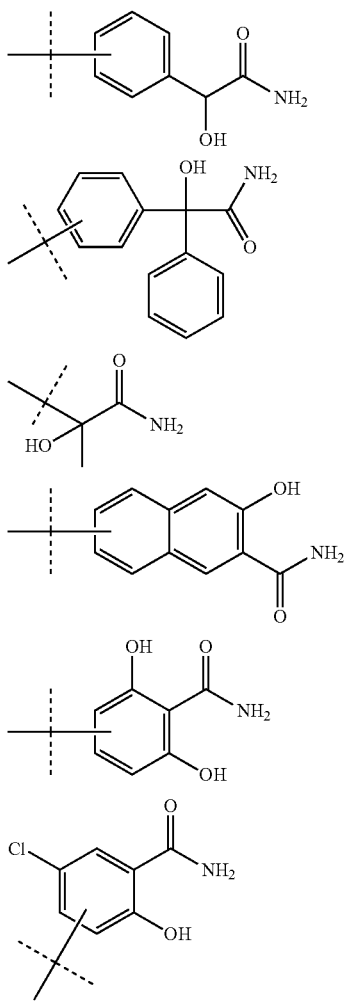

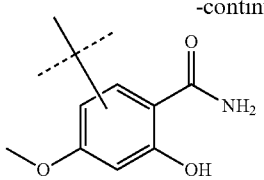

Additional examples of α-hydroxyamides or o-hydroxyarylcarboxamide linker elements include but are not limited to those listed below:

Pharmacophores

| | |
|---|---|
| 2-Hydroxy-3-naphthalenecarboxamide | N-(2-Hydroxyethyl)salicylamide |
| 4-Methoxysalicylamide | Salicylamide |
| 2,6-Dihydroxybenzamide | |

Most drugs work by blocking protein activity, clogging an enzymatic pocket, and thus inhibiting activity. In order for a drug to bind, there needs to be sufficient complementarity and surface area of contact such that van der Waals, hydrogen bonding, and ionic interactions provide the requisite binding energy. The field of combinatorial chemistry is based on the principle of creating ligands or pharmacophores of different shapes and sizes, some of which can bind to the desired surface of the target, and thus serve as lead molecules for subsequent medicinal chemistry.

Coferons have the advantage of being able to bind the target through two or more ligands or pharmacophores. These pharmacophores combine to give the coferon a tighter binding than would be achieved through a single pharmacophore. In addition, coferons provide a linker element (and an optional connector), which may provide additional opportunities to maximize the surface area of interaction between the coferon and protein target.

Combinatorial chemistry approaches seek to maximize pharmacophores, and such molecules are often synthesized using split and recombine or bead-based approaches. There are two general approaches used to generate a diversity library: (i) a single platform with multiple functional groups, each of which is reacted with a family of diversity reagents to create a library of surfaces and (ii) the diversity is generated using bifunctional reagents to create short linear or circular chains, such as peptides and peptide analogues.

In some of the examples below, the order of synthesis is a linker element is attached to a tri-functional connector, with one of the functionalities used to attach the connector-linker element to a bead or "barcode" element. This is followed by attaching or combinatorial synthesis of the diversity library of ligands. The order of these steps and the geometry of the components may be altered. For example, the linker element may also double as the connector, being attached to the pharmacophore on one end and the bead on the other end. Also, the linker element may be added last, after synthesis of the pharmacophore. The examples below are by no means exhaustive of methods for synthesizing linker elements with pharmacophores.

Pharmacophores may be moieties derived from molecules previously known to bind to target proteins, fragments identified through NMR or crystallographic screening efforts, molecules that have been discovered to bind to target proteins after performing high-throughput screening of previously synthesized commercial or non-commercial combinatorial compound libraries or molecules that are discovered to bind to target proteins by screening of newly synthesized combinatorial libraries. Since most pre-existing combinatorial libraries are limited in the structural space and diversity that they encompass, newly synthesized combinatorial libraries will include molecules that are based on a variety of scaffolds.

Monocyclic Scaffolds

These scaffolds may be used to generate the simplest types of combinatorial libraries.

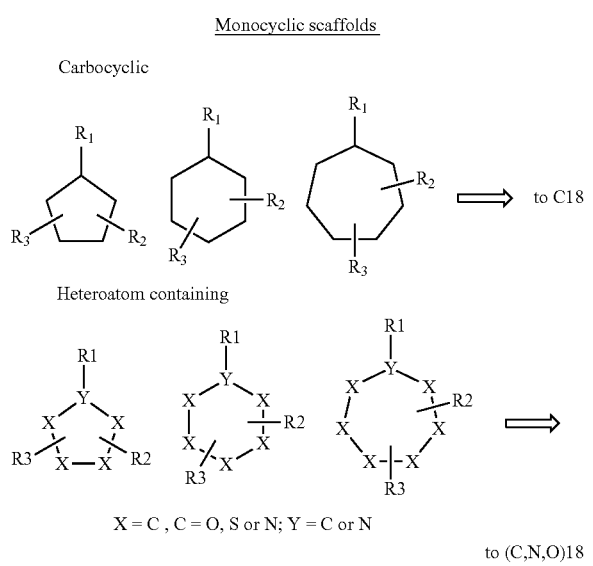

In addition to those nitrogen and carbon atoms that are substituted by $R_2$ and $R_3$, other positions may contain additional substituents including H. Multiple bonds may also be incorporated between ring atoms.

Bicyclic Scaffolds

Each bicyclic scaffold may be substituted at different positions and contain heteroatoms and multiple bonds as illustrated for monocyclic scaffolds above.

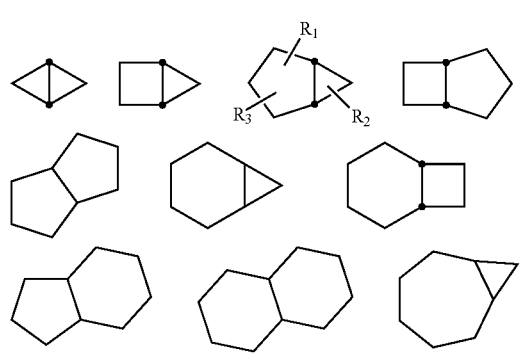

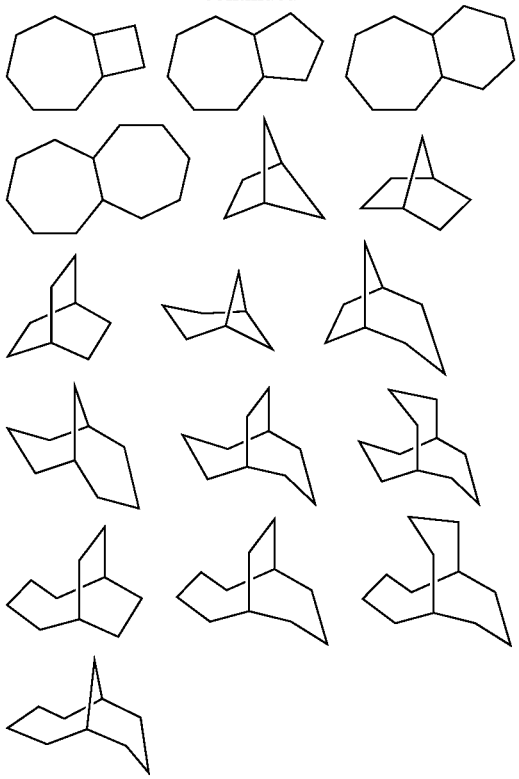

Tricyclic Scaffolds

Tricyclic scaffolds containing 3 rings fused to each other and may contain heteroatoms and multiple bonds as illustrated for monocyclic scaffolds above.

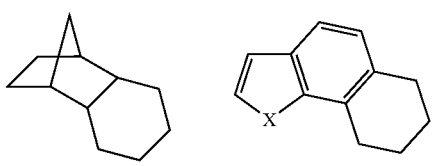

Tetracyclic Scaffolds

Tetracyclic scaffolds containing 4 rings fused to each other and may contain heteroatoms and multiple bonds as illustrated for monocyclic scaffolds above.

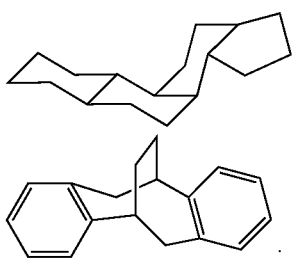

Spiro Scaffolds

Spiro scaffolds where two rings are fused to each other through a single common atom

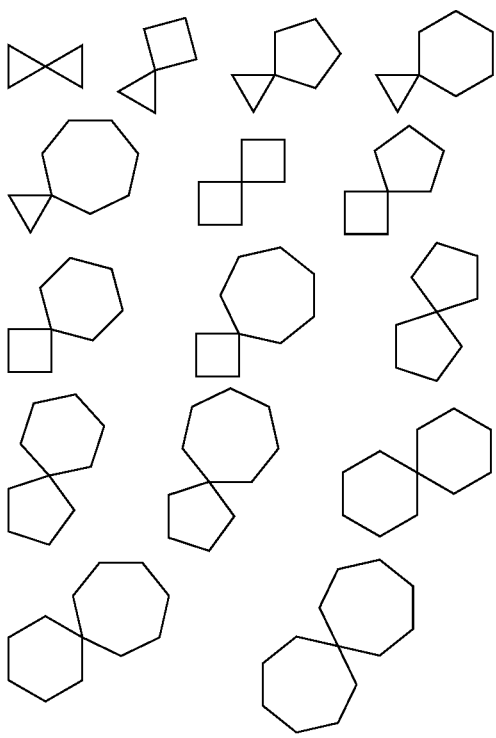

Multicore Scaffolds

Multicore scaffolds where each of the above scaffold core elements are linked by a covalent bond.

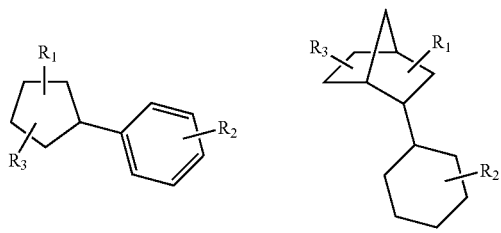

Additionally pharmacophores may be derived from traditional approaches such as fragment based drug design and structure based drug design. Those skilled in the art will recognize that any pharmacophore including pre-existing pharmacophores such as approved drugs are amenable to be designed as coferons through the incorporation of the appropriate linker elements and connectors. Previously approved drugs that have poor efficacy due to a low affinity for the macromolecular target may be utilized as a pharmacophore component of a coferon monomer which when combined with a new pharmacophore that binds the same macromolecular target or a macromolecular target that interacts with the first macromolecular target on a second coferon monomer results in enhanced binding and therefore higher efficacy. Likewise, previously approved drugs that have low efficacy as a result of size, molecular weight or other physicochemical attributes that reduce the cellular uptake of the drug may be amenable to being converted into one or more coferon monomers that bear the appropriate pharmacophoric elements, such that each coferon monomer has physicochemical attributes that allow for increased cellular uptake and the formation of the coferon dimer or multimer regenerates a molecule with the appropriate pharmacophores in the correct geometry and orientation to interact with the macromolecular target.

Connectors

Connectors are used to connect the linker element to the pharmacophore. The connector enables the correct spacing and geometry between the linker element and the pharmacophore such that the coferon dimer or multimer formed from the monomers orients the pharmacophores to allow high affinity binding of the pharmacophores to the macromolecular target. The connector itself may function as a secondary pharmacophore by forming favorable interactions with the macromolecular target. The ideal connectors allow for modular assembly of coferon monomers through facile chemical reactions between reactive groups on the connector and complementary reactive groups on the linker elements and pharmacophores. Additionally, connectors may be tri-functional and allow for the addition of encryption elements to allow for deconvolution of coferon monomers that are synthesized in a combinatorial fashion.

In one embodiment, a linker element is attached to a tri-functional connector, with one of the functionalities used to attach the connector-linker elements to a bead. Beads are distributed to unique wells, and a set of pharmacophores react with the third functional group on the connector (for example 500 different aldehyde containing moieties reacted with an amino group). In this embodiment, the well the synthesis took place in identifies the pharmacophore.

In a second embodiment (FIG. 2A), a linker element is attached to a tri-functional connector, with one of the functionalities used to attach the connector-linker element to an encoded bead. For example, Veracode™ beads (Illumina, San Diego, Calif.) or silicon particles may be used, where each bead has a unique Veracode™ or barcode pattern. The beads or particles are distributed into a set of reaction chambers (for example 10 chambers), identified in each chamber, and then reacted with a bifunctional moiety (for example, a protected amino acid). The beads are mixed, split again into the reaction chambers, and the process is repeated (split-pool synthesis). In this embodiment, repeating the process a total of 4 times will result in 10,000 pharmacophores in the library. In a variation of this approach, at the end of the synthesis, the last amino acid residue is reacted with the connector to create a circular pharmacophore. In this version, the pharmacophore is identified by the code on the bead or particle.

In a third embodiment, a linker element is attached to a tri-functional connector, with one of the functionalities used to attach the connector-linker element to either a Veracode™ bead or a bar code particle. The remaining functionality is connected to a "platform" containing additional functionalities. For example, the platform may be a cyclopentane derivatized on three carbons all in the syn orientation. In this version, one of the encoding processes described in embodiments 2-5 above is used to add mono-functional moieties to the appropriate functional groups on the platform. For example, if there are 20 moieties added in each step, the resultant library will contain 8,000 pharmacophores. The advantage of this approach is to guide all the diversity components in a single orientation for maximum diversity in binding surfaces.

Target Screening

Yet a further embodiment of the present invention is directed to a method of screening for therapeutic compound precursors which bind to a target molecule associated with a condition. This method includes providing a plurality of monomers. Each monomer comprises one or more pharmacophores which potentially binds to a target molecule with a dissociation constant less than 300 μM and a linker element having a molecular weight of less than 500 daltons. Each linker element is selected from the group consisting of 1)

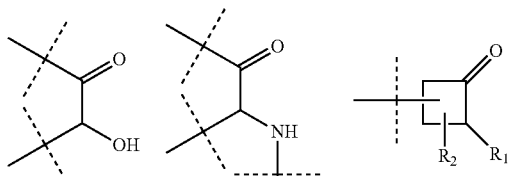

$R_1 = $ —OH, SH, —NH$_2$, —NHCH$_3$, —NHR$_3$
where $R_3 = $ —C(=O)R$_4$, —SO$_2$R$_4$, —C(=O)OR$_4$ where R$_4$ is composed of aliphatic, alicyclic, aromatic or heteroaromatic group
where R$_3$ may also connnect to the pharmacophore and
is composed of aliphatic, alicyclic, aromatic or heteroaromatic group
$R_2 = $ —H, —CH$_3$, —Ph or other aliphatic, aromatic or heteroaromatic group

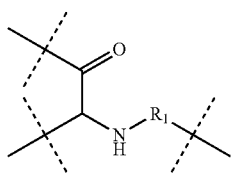

where $R_1 = $ —CHO, —C(O)CH$_3$, —C(O)R$_2$, S(O)$_2$CH$_3$, —S(O)$_2$R$_2$
where R$_2$ may also connect to the pharmacophore and is composed of aliphatic, aromatic or heteroaromatic group.

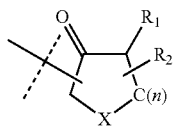

n = 1-4
X = C, N, S, O
$R_1 = $ —OH, —SH, NH$_2$, NHCH$_3$, NHR$_3$
where R$_3$ may also connect to the pharmacophore and
is composed of aliphatic, alicyclic, aromatic or heteroaromatic group
$R_2 = $ —H, —CH$_3$, —Ph or other aliphatic, aromatic or heteroaromatic group where the lines crossed with a dashed line illustrate the one or more bonds formed joining the one or more pharmacophores, directly or through a connector; 2)

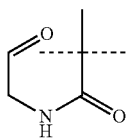

where the lines crossed with a dashed line illustrate the one or more bonds formed joining the one or more pharmacophores, directly or through a connector; 3)

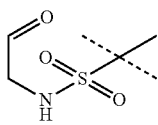

where the lines crossed with a dashed line illustrate the one or more bonds formed joining the one or more pharmacophores, directly or through a connector; 4)

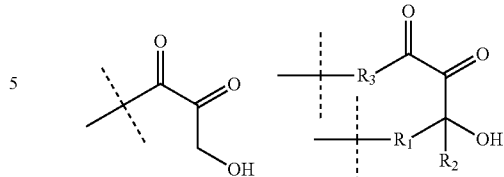

$R_1, R_2 = $ —H, —CH$_3$, —Ph, —C$_6$H$_{11}$, —C$_5$H$_9$, aromatic or heteroaromatic or connected to each other through a 3, 4, 5 or 6 membered ring.
$R_3 = $ —NH$_2$, —OH, —CH$_3$, —Ph, —NHR$_4$, —CH$_2$R$_4$, —OR$_4$
where R$_4$ may be connected to the pharmacophore and is composed of aliphatic, aromatic or heteroaromatic group, and R$_3$ and R$_4$ may connect to R$_1$ and R$_2$ through a 5, 6, 7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

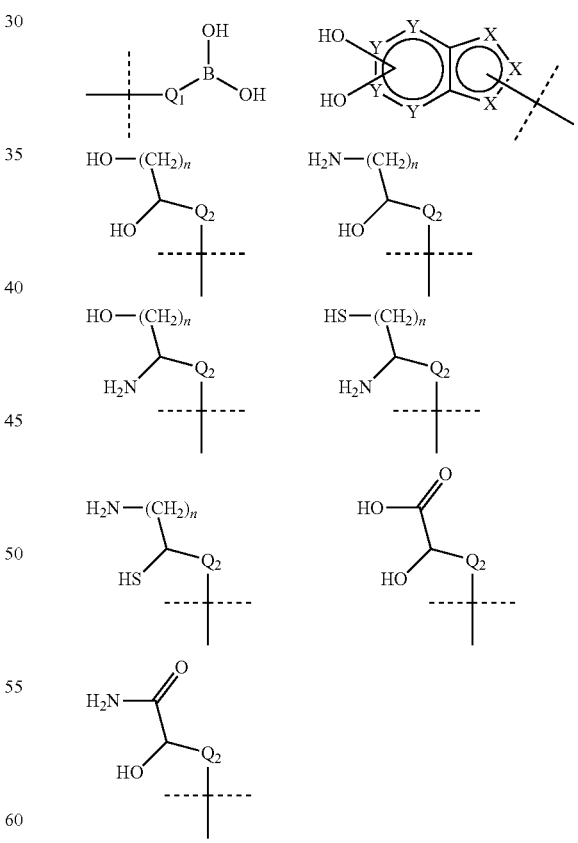

where n=1 or 2
where X and Y=C, N, O, or S
where the hydroxy groups emanating from the aromatic ring are ortho to each other

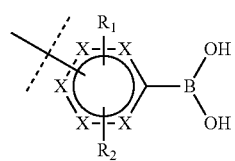

X = C, N
R₁, R₂ = —H, —F, —Cl, —Br, —I, —CF₃, —CN, —OCH₃, —NO₂
Where R₁ & R₂ are adjacent, may also include
fused 5 or 6 membered aromatic or heteroaromatic ring

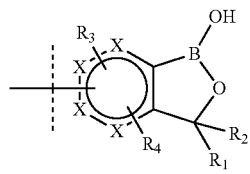

X = C, N
R₁, R₂ = —H, —CH₃, —Ph, or connected to each other through a spiro
3, 4, 5 or 6 membered ring
R₃, R₄ = —H, —F, —Cl, —Br, —I, —CF₃, —CN, —OCH₃, —NO₂
When R₃ & R₄ are adjacent, may also include
fused 5 or 6 membered aromatic or heteroaromatic ring

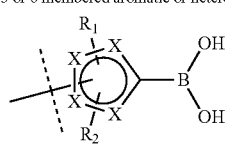

X = C, N, O, S
R₁, R₂ = —H, —F, —Cl, —Br, —I, —CF₃, —CN, —OCH₃, —NO₂
When R₁ & R₂ are adjacent, may also include
fused 5 or 6 membered aromatic or heteroaromatic ring

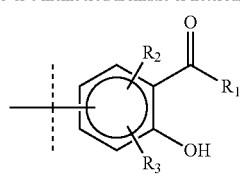

R₁ = —OH, —NH₂, —SH, —NHR₄
where R₄ = alkyl, hydroxyalkyl
R₂, R₃ = —H, —CH₃, —OCH₃, —OH, —COOH, CONH₂
When R₂ & R₃ are adjacent, may also include
fused 5 or 6 membered aromatic or heteroaromatic ring

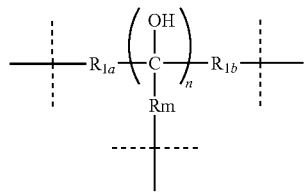

n = 2-6
R₁, R₁b = —H, —CH₃, —CH₂NH₂, —CH₂NHCH₃, aromatic or
heteroaromatic ring, or connected to each other through a
4,5,6,7 or 8-membered ring
Rm = —H, —CH₃, —CH₃NH₂, —CH₃OH, —CH₂CH₂OH and m = 2-6

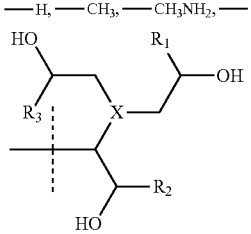

X = C, N
R₁, R₂, R₃ = —H, —CH₃, or two R groups connected
to each other through a 5 or 6 membered alicyclic ring -continued

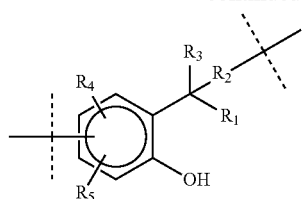

R₁ = —OH, —NH₂, —SH
R₂, R₃ = —H, —CH₃, —Ph, or connected to each other
through a spiro 3, 4 5 or 6 membered ring
R₄, R₅ = —H, —CH₃, —CH₂OH, —C(R₂,R₃)OH, —OCH₃, —OH, —COOH, —CONH₂
When R₄ & R₅ are adjacent, may also include
fused 5 or 6 membered aromatic or heteroaromatic ring

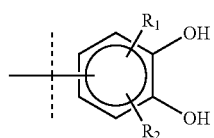

R₁ R₂ = —H, —CH₃, —OCH₃, —OH, —COOH, —CONH₂, —F, —Cl, —Br, —I, —CF₃, —CN, —NO₂
When R₁ & R₂ are adjacent, may also include
fused 5 or 6 membered aromatic or heteroaromatic ring

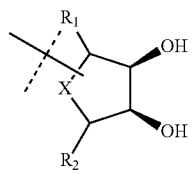

X = C, N, O, S
R₁, R₂ = —H, —CH₃, ----OH, —CH₂OH, -Adenyl

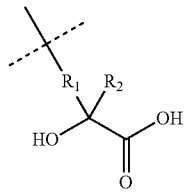

R₁, R₂, R₃, R₄, R₅, R₆ = —H, —CH₃
R₇, R₈ are connected to each other to form 3.1.1, 2.2.1 and 2.2.2 bicyclic ring
systems such that the hydroxyls are cis to each other

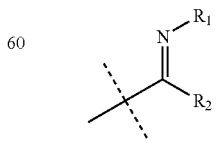

R₁, R₂ = —H, —CH₃, —Ph, —C₆H₁₁, —C₅H₉,
aromatic or heteroaromatic ring, C₁-C₆-alkyl
or C₃-C₈ cycloalkyl.

R₁, R₂ = —OH, —NH₂

-continued

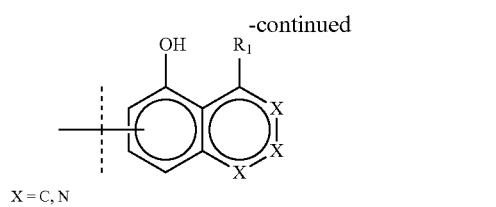

X = C, N
R₁ = —OH, —NH₂, —NHR₂, —NHC(═O)R₂, —NHSO₂R₂

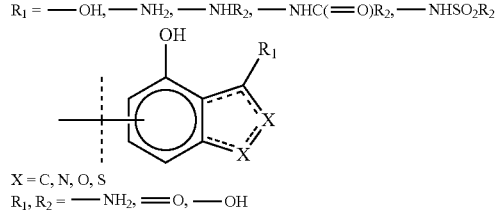

X = C, N, O, S
R₁, R₂ = —NH₂, ═O, —OH where the lines crossed with a dashed line illustrate the one or more bonds formed joining the one or more pharmacophores, directly or through a connector. The pharmacophore and said linker element of each monomer are joined together directly or indirectly through a connector. The plurality of monomers are contacted with the target molecule under conditions effective to permit pharmacophores able to bind to the target molecule to undergo such binding. The monomers are then subjected to reaction conditions effective for the linker elements of different monomers to undergo covalent bonding or non-covalent interactions to form therapeutic multimer precursors, either before, after, or during the contacting step. The monomers forming each therapeutic multimer precursor are then identified.

The pharmacophore and said linker element of each monomer are joined together directly or indirectly through a connector. The plurality of monomers are contacted with the target molecule under conditions effective to permit pharmacophores able to bind to the target molecule to undergo such binding. The monomers are then subjected to reaction conditions effective for the linker elements of different monomers to undergo covalent bonding to form therapeutic multimer precursors, either before, after, or during the contacting step. The monomers forming each therapeutic multimer precursor are then identified.

The step of identifying the monomers can be carried out by determining which therapeutic dimer precursors are more tightly bound to the target molecule. This may be determined by identifying bead barcodes. When each monomer includes an encoding element coupled to the pharmacophore and the linker element for each monomer, the identifying step is carried out by detecting the encoding element in the therapeutic dimer precursor.

When the encoding element is a labeled bead, the steps of providing a plurality of monomers, contacting, subjecting, and identifying the monomers can be repeated to determine which of the therapeutic dimer precursors have a suitable binding affinity to the target molecule.

Alternatively, mass spectrometric methods may be employed to determine the molecular weight of the high affinity dimers and the identities of the monomeric constituents. For example, the use of size-exclusion chromatographic methods may separate unbound monomeric coferons from dimeric coferons bound to the macromolecular target, followed by dissociation and detection of the coferons by mass spectrometry.

The therapeutic dimer resulting from the above method can be prepared by coupling the monomers resulting from the identifying step. Subjects with the condition are identified and the therapeutic dimer is administered to the selected subjects under conditions effective to treat the condition.

Therapeutic monomers resulting from the above method can be prepared by providing the monomers resulting from the identifying step. Subjects with the condition are selected and the therapeutic monomers are administered to the selected subjects under conditions effective to treat the condition.

An additional embodiment of the present invention relates to a therapeutic multimer which includes a plurality of covalently or non-covalently linked monomers. Each monomer comprises one or more pharmacophores which potentially bind to a target molecule with a dissociation constant of less than 300 μM and one or more linker elements having a molecular weight less than 500 dalton. Each linker is selected from the group consisting of 1)

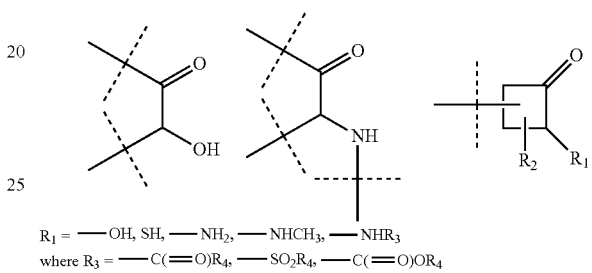

R₁ = —OH, SH, —NH₂, —NHCH₃, —NHR₃
where R₃ = —C(═O)R₄, —SO₂R₄, —C(═O)OR₄ where R₄ is composed of aliphatic, alicyclic, aromatic or heteroaromatic group
where R₃ may also connnect to the pharmacophore and
is composed of aliphatic, alicyclic, aromatic or heteroaromatic group
R₂ = —H, —CH₃, —Ph or other aliphatic, aromatic or heteroaromatic group

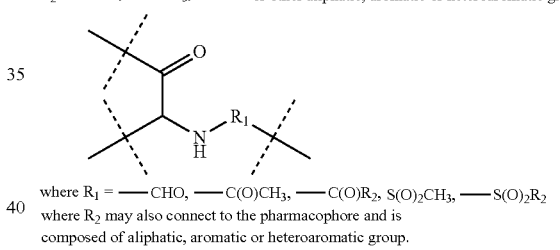

where R₁ = —CHO, —C(O)CH₃, —C(O)R₂, S(O)₂CH₃, —S(O)₂R₂
where R₂ may also connect to the pharmacophore and is
composed of aliphatic, aromatic or heteroaromatic group.

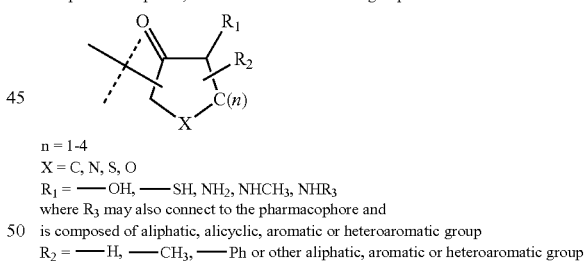

n = 1-4
X = C, N, S, O
R₁ = —OH, —SH, NH₂, NHCH₃, NHR₃
where R₃ may also connect to the pharmacophore and
is composed of aliphatic, alicyclic, aromatic or heteroaromatic group
R₂ = —H, —CH₃, —Ph or other aliphatic, aromatic or heteroaromatic group where the lines crossed with a dashed line illustrate the one or more bonds formed joining the one or more pharmacophores, directly or through a connector; 2)

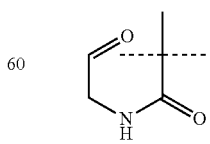

where the lines crossed with a dashed line illustrate the one or more bonds formed joining the one or more pharmacophores, directly or through a connector; 3)

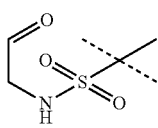

where the lines crossed with a dashed line illustrate the one or more bonds formed joining the one or more pharmacophores, directly or through a connector; 4)

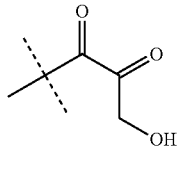 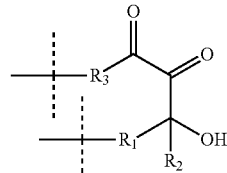

$R_1, R_2 =$ —H, —CH$_3$, —Ph, —C$_6$H$_{11}$, —C$_5$H$_9$, aromatic or heteroaromatic or connected to each other through a 3,4,5 or 6 membered ring.

$R_3 =$ —NH$_2$, —OH, —CH$_3$, —Ph, —NHR$_4$, —CH$_2$R$_4$, —OR$_4$ where R$_4$ may be connected to the pharmacophore and is composed of aliphatic, aromatic or heteroaromatic group, and R$_3$ and R$_4$ may connect to R$_1$ and R$_2$ through a 5,6,7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

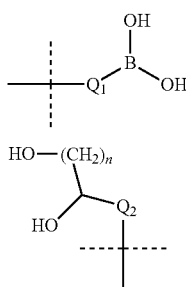

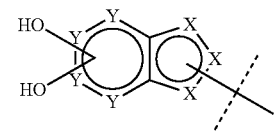

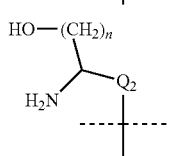 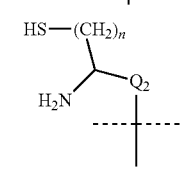

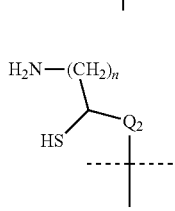 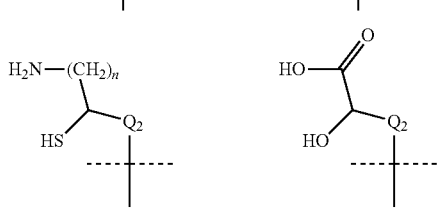

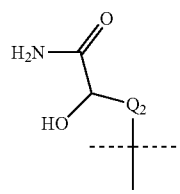

where $Q_1$ and $Q_2$ are aliphatic, alicyclic, or hetero or non-hetero aromatic moieties where n=1 or 2 where X and Y=C, N, O, or S where the hydroxy groups emanating from the aromatic ring are ortho to each other

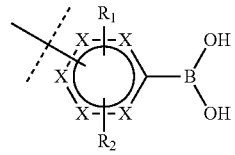

X = C, N
$R_1, R_2 =$ —H, —F, —Cl, —Br, —I, —CF$_3$, —CN, —OCH$_3$, —NO$_2$

Where R$_1$ & R$_2$ are adjacent, may also include fused 5 or 6 membered aromatic or heteroaromatic ring

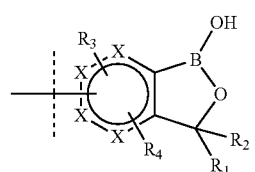

X = C, N
$R_1, R_2 =$ —H, —CH$_3$, —Ph, or connected to each other through a spiro 3, 4, 5 or 6 membered ring
$R_3, R_4 =$ —H, —F, —Cl, —Br, —I, —CF$_3$, —CN, —OCH$_3$, —NO$_2$ When R$_3$ & R$_4$ are adjacent, may also include fused 5 or 6 membered aromatic or heteroaromatic ring

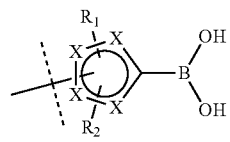

X = C, N, O, S
$R_1, R_2 =$ —H, —F, —Cl, —Br, —I, —CF$_3$, —CN, —OCH$_3$, —NO$_2$

When R$_1$ & R$_2$ are adjacent, may also include fused 5 or 6 membered aromatic or heteroaromatic ring

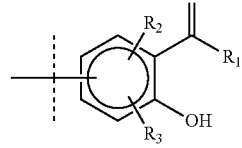

$R_1 =$ —OH, —NH$_2$, —SH, —NHR$_4$
where R$_4$ = alkyl, hydroxyalkyl
$R_2, R_3 =$ —H, —CH$_3$, —OCH$_3$, —OH, —COOH, CONH$_2$
When R$_2$ & R$_3$ are adjacent, may also include fused 5 or 6 membered aromatic or heteroaromatic ring -continued

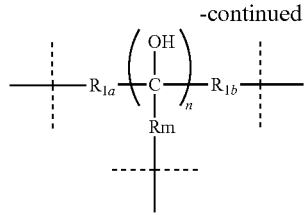

n = 2-6
$R_1, R_{1b}$ = ——H, ——$CH_3$, ——$CH_2NH_2$, ——$CH_2NHCH_3$, aromatic or heteroaromatic ring, or connected to each other through a 4.5.6.7 or 8-membered ring
Rm = ——H, ——$CH_3$, ——$CH_2NH_2$, ——$CH_3OH$, ——$CH_2CH_2OH$ and m = 2-6

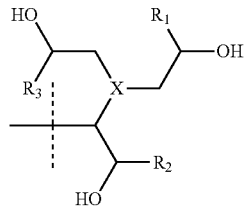

X = C, N
$R_1, R_2, R_3$ = ——H, ——$CH_3$, or two R groups connected to each other through a 5 or 6 membered alicyclic ring

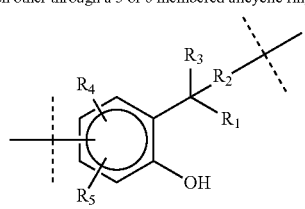

$R_1$ = ——OH, ——$NH_2$, ——SH
$R_2, R_3$ = ——H, ——$CH_3$, ——Ph, or connected to each other through a spiro 3, 4 5 or 6 membered ring
$R_4, R_5$ = ——H, ——$CH_3$, ——$CH_2OH$, ——$C(R_2,R_3)OH$, ——$OCH_3$, ——OH, ——COOH, ——$CONH_2$
When $R_4$ & $R_5$ are adjacent, may also include fused 5 or 6 membered aromatic or heteroaromatic ring

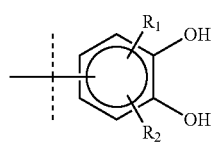

$R_1, R_2$ = ——H, ——$CH_3$, ——$OCH_3$, ——OH, ——COOH, ——$CONH_2$, ——F, ——Cl, ——Br, ——I, ——$CF_3$, ——CN, ——$NO_2$
When $R_1$ & $R_2$ are adjacent, may also include fused 5 or 6 membered aromatic or heteroaromatic ring

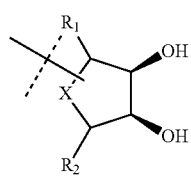

X = C, N, O, S
$R_1, R_2$ = ——H, ——$CH_3$, ----OH, ——$CH_2OH$, -Adenyl

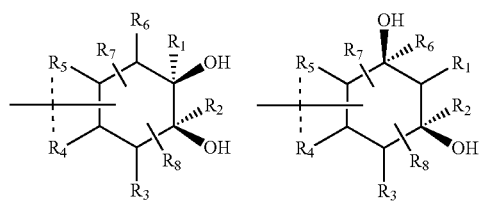

$R_1, R_2, R_3, R_4, R_5, R_6$ = ——H, ——$CH_3$
$R_7, R_8$ are connected to each other to form 3.1.1, 2.2.1 and 2.2.2 bicyclic ring systems such that the hydroxyls are cis to each other -continued

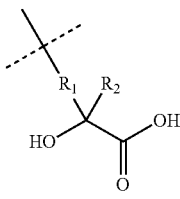

$R_1, R_2$ = ——H, ——$CH_3$, ——Ph, ——$C_6H_{11}$, ——$C_5H_9$, aromatic or heteroaromatic ring, $C_1$-$C_6$-alkyl or $C_3$-$C_8$ cycloalkyl.

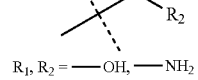

$R_1, R_2$ = ——OH, ——$NH_2$

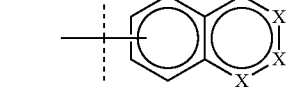

X = C, N
$R_1$ = ——OH, ——$NH_2$, ——$NHR_2$, ——$NHC(=O)R_2$, ——$NHSO_2R_2$

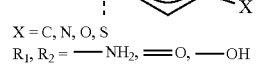

X = C, N, O, S
$R_1, R_2$ = ——$NH_2$, =O, ——OH where the lines crossed with a dashed line illustrate the one or more bonds formed joining the one or more pharmacophores, directly or through a connector. The pharmacophore and the linker element are connected together directly or indirectly through a connector for each monomer. A plurality of monomers are capable of being linked together through their linker elements, and the pharmacophores for the plurality of monomers bind to proximate locations of the target molecule.

The libraries described above are in the format of a bead or solid support with pharmacophore defined by position or Veracode™ encryption of particle. The advantage of working with coferon libraries attached to beads is that each bead contains multiple copies of the identical ligand. This property helps identify the strongest affinity ligand combinations by the intensity of fluorescently labeled entity captured (i.e. protein or other ligand). See FIGS. 9 and 10. Likewise, use of individually encoded beads also allows for directed evolutionary principles to be used in selecting the best coferons. After the winning combinations are identified through the bead barcode, they can be resynthesized with slight variation in a new round of synthesis—followed by a second round of selection. Here, one needs to identify the chemical structure of both coferon monomers which form a dimer. In FIG. 9, schematic diagrams are presented where the experiment is repeated so that the pharmacophores from each half of the coferon may be identified.

FIG. 9 is a schematic overview of directed evolution selection of coferons using only bead encryption. As shown in step 1, a first set of coferon monomers comprises a binding ligand (pharmacophore) covalently linked to a bead containing a unique barcode as well as a low MW linker element (dynamic combinatorial chemistry element), while a second set is free in solution. The linker elements allow different combinations of ligands to reversibly associate with each other. When the combination of solid-phase and solution coferon monomers are brought in contact with a labeled protein target, some combinations will bind tighter than others and, consequently, are enriched. The winning pair will cause that bead to be highly labeled, and this may be isolated by flow cytometry or other methods, and the barcode identified. In a companion selection, as shown in step 2, the second set of coferon monomers is linked to unique encoded beads, while the first set is free in solution. The linker elements allow different combinations of ligands to reversibly associate with each other. When the combination of solid-phase and solution coferons are brought in contact with a labeled protein target, some combinations will bind tighter than others, and consequently are enriched. The winning pair will cause that bead to be highly labeled, and this may be isolated by flow cytometry or other methods, and the barcode identified. The pharmacophores for both sides of the coferon may be decoded, and then resynthesized with additional variation. Repeating this process of synthesis-selection-amplification mimics Darwinian evolution. The best coferon monomers are resynthesized without the encoded beads for use as orally active drugs, as shown in step 3. Once ingested coferons are in a dynamic equilibrium between the monomer form (which can traverse the cell membrane), and the dimer form (which binds to and inhibits the protein target).

FIG. 10 is a generic summation of screening for the tightest binding coferons using directed evolutionary principles. Individual coferons, or multiple copies of the identical coferon on individual beads or particles, or multiple copies of identical coferons within encoded droplets may be screened by a number of different assays that identify binding pharmacophores. The nature of these pharmacophores is determined by identifying the code that corresponds to the pharmacophore, which is then resynthesized, including minor variations. The process may be repeated until further iterations afford minimal improvements or until coferon dimers with binding affinities sufficient for potent pharmacologic effects in vivo are identified.

The best coferon monomers are resynthesized without encoded beads for use as orally active drugs. The coferons may be provided as (i) therapeutic dimers or multimers that dissociate/re-associate in the body, cell, or cellular compartment, (ii) therapeutic monomers in the same or different pills, or administered by different routes of administration; (iii) therapeutic monomer precursors where one or more active moieties is in a protected state, suitable for deprotection once inside the body, cell, or cellular compartment. Once ingested, coferons are in a dynamic equilibrium between the monomer form (which can more readily be absorbed orally, distribute to tissues, and traverse the cell membranes), and the dimer or multimer form (which more potently binds to and inhibits the protein target).

FIG. 2C shows dimers resulting from screening coferon monomers with connectors, while FIG. 2F shows dimers derived from a screen with coferon monomers which are not provided with connectors.

Under physiological conditions, different combinations of ligands are forming and reassociating with each other. The term "physiological conditions" is hereby defined as aqueous conditions inside the body or the cell, comprising a temperature range of about 35-40° C., a pH range of about 5.5-8, a glucose concentration range of about 1-20 mM, and an ionic strength range of about 110 mM to about 260 mM.

The recent work of the Whitesides (Krishnamurthy, et al., *J. Am. Chem. Soc.* 129:1312-1320 (2007), which is hereby incorporated by reference in its entirety) and Neri laboratories (Melkko, et al., *Nat. Biotechnol.* 22(5):568-574 (2004), which is hereby incorporated by reference in its entirety) suggest that pharmacophores will bind to a target with almost as high binding affinity when attached through a flexible ethylene glycol linker as when attached by a rigid linker of the precisely correct geometry. This finding allows one to liberate the process of screening for the best pharmacophores of a given target from the exact linker element (and/or connector) design used in the final coferon drug. Thus, pharmacophores may be optimized for a given target using a set of linker elements which have a favorable equilibrium between the monomer and dimer state; i.e. one that favors the dynamic combinatorial chemistry selection process. Subsequently, these same or different linker elements may be optimized using either flexible or more rigid connectors between the pharmacophores (ligands) and the linker elements to optimally bind the target.

For example, when performing in vitro screening of pharmacophores binding to a target protein, it would be advantageous to use a first linker element containing an aldehyde or ketone, and a second linker element containing a primary or secondary amine. These two linker elements readily form the highly reversible Schiff base in the absence of target at the concentrations of pharmacophores used for screening. There is a high concentration of primary amines free in solution (lysine) and in proteins. Thus, when using a coferon monomer containing a primary amine, it is important for the companion aldehyde or ketone containing coferon monomer to find its partner on the surface of the target molecule. If the primary amine is two carbons away from a thiol group (which may be in the protected disulfide form outside the cell), then it has the potential to form an essentially irreversible thiazolidine linker in the final coferon dimer. The thiazolidine linker is an excellent example of a linker element that may be activated upon entering a cancer cell and then form an essentially irreversible bond with its partner coferon.

In-silico screening can be performed as an aid in selecting from amongst a vast number of pharmacophore-connector-linker arrangements to be synthesized for testing to assist in achieving the optimal presentation of the pharmacophores. In-silico screening may be performed with either a known diversity library, or with an in-silico library, where the potential structures are all known or may be calculated. More typically, a virtual library of coferons comprised of numerous pharmacophores, connectors, and linker moieties in different configurations is enumerated, appropriate homo- or heterodimeric assemblies of the coferons are then produced, and low energy conformers of each are docked to the 3-dimensional structure of the macromolecular target; often the docking exercise affords docking scores for each coferon dimer pose, and these scores can be used to prioritize molecules for synthesis, etc. In-silico screening would allow the testing of huge virtual libraries of different pharmacophores on different scaffolds, with the aim of eliminating the vast majority of potential diversity structures and focusing on a reasonable number of promising leads. This will be especially useful for screening pharmacophores in multimeric coferons.

Identification of a first pharmacophore may assist in identifying a second pharmacophore that binds the target adjacent to the first pharmacophore. Likewise, use of a known ligand as the first pharmacophore will assist in identifying a second pharmacophore that binds the target adjacent to the first pharmacophore. This approach may improve an existing drug by taking advantage of the larger surface area that a coferon pair can use to bind onto the target, thus imbuing the coferon with higher affinity or better specificity, or both.

The coferon concept takes advantage of having three weaker interactions combine to produce a significantly stronger interaction as follows: (i) coferon 1 to coferon 2; (ii) coferon 1 to protein; and (iii) coferon 2 to protein, which results in a very strong interaction between the protein and the two coferon partners. The coferon interaction may be strengthened by covalent bonds between the coferons. The linker moieties of the coferons are designed or chosen such that they are minimally reactive with cellular molecules or off-target proteins, and preferentially react with the linker of their partner coferon. The reactive groups on the coferons are chosen such that they are mostly unreactive with cellular molecules or off target proteins. If they do react with cellular components, such reactions should be reversible and non-toxic.

Just as the interactions between the coferons may be strengthened by covalent bonds, so too, the interactions between the coferons and the protein partners may also be strengthened by incorporating reactive groups within the pharmacophores that bind the protein target. For example, a ketone or aldehyde in the correct orientation may form a Schiff base with a lysine on the protein target. Another example would be reaction of a coferon boronic acid group with a tyrosine or serine residue on the protein target or with a ribose of an adenosine or NAD(p)M cofactor or carbohydrate hydroxyl groups on glycoprotein targets. Coferons containing boronic esters could link with each other as well as with multiple sites on the carbohydrate portion of glycoproteins. Either one or both of these events would significantly shift the equilibrium towards coferon dimer binding to its target. Such designs are dependent on judiciously placed amino acid residues on the target protein. Although there is a risk of non-specific reaction between a reactive group on the coferon drug and an incorrect target, since the rest of the pharmacophore would not provide any additional binding energy, such an off-target effect would be quickly reversible.

The above principle extends even further when applied to coferon multimers, and especially to coferon multimers that bind multimeric protein targets. Multiple weak interactions add to the binding affinity of the overall coferon complex to the correct target.

When screening for the best coferons, either one of the coferons or the protein target is on a solid support (bead), with coferons binding to each other and/or the protein target. The bound coferons are in equilibrium with the coferons in solution, both binding and coming apart through their linker element moieties. Meanwhile, the protein targets are binding and dissociating with coferons in solution and on the solid supports. The most stable complexes of bead coferon to solution coferon to target protein are removed from this equilibrium. The concentration of these components in solution has now decreased, so they dissociate from less stable complexes. This now drives the equilibrium towards forming even more of the most stable complexes, so that the tightest binding combinations are enriched.

For this screening process to work most effectively, the coferon monomers need to efficiently cycle between the monomeric and dimeric (or multimeric) state. This will allow for the greatest number of combinations to be tested, and also for enriching the best binding combinations onto the solid support.

However, as mentioned above, some linker elements may associate slowly until brought in close proximity by the target, but once they associate and form one or more covalent (i.e. hemiacetal) or ionic bond (i.e. through two coferons chelating the same zinc ion), they may not dissociate easily. If off-rates of such multimeric coferon assemblies are slow, these types of reactions are essentially irreversible. While such a property of a coferon may be desirable for linker elements in the final drug molecule, they would inhibit the screening process.

In order to use such linker elements during the dynamic combinatorial chemistry screening process, it is preferable for the dissociation process to occur as rapidly as the association process. One approach is to change the assay conditions, for example, low pH will favor dissociation of hemi-acetals. Another approach is to use linker elements with the same geometry, but now unable to form all the potential covalent bonds.

A new approach is to cycle between conditions that favor formation of dimers and multimers, and conditions that favor dissociation to monomers. Herein, this approach is termed cyclic combinatorial chemistry, or C3 screening.

Consider a coferon pair that associates quickly at pH 9, and dissociates quickly at pH 5. The coferon association is initiated by combining a bead-library and a solution library of coferons with the protein target, for example in a phosphate buffer at pH 9. As library members come together, some pairs will favor binding to the protein target. Other non-productive pairs will also come together. The pH may now be titrated down to pH of 5 by addition of acid. Under these conditions, coferons that are not bound to the target will dissociate, but coferons bound to the target are held in place, and do not dissociate. Subsequently the pH is shifted back to pH 9. Now fresh combinations of coferon pairs form, and again, the pairs that favor binding of the protein will accumulate more protein on the beads or particle. This process may be repeated until sufficient (fluorescently) labeled protein accumulates on the beads containing the best coferon pairs. One caveat with this approach is that the ion concentration in the solution keeps increasing (for example, if HCl and NaOH are used to decrease and increase the pH, respectively, then NaCl will accumulate with each cycle). On the positive side, higher salt concentrations will select for more specific binding. Further, this process is easy and amenable to automation.

As another example, consider coferons that pair through a $Zn^{2+}$ cofactor. Addition of 1 mM $ZnCl_2$ will allow the coferons to dimerize, with the more favorable pairs binding to the target. Addition of a suitable zinc chelating agent (such as 1 mM EDTA) will be able to displace coferons from the zinc so the coferons dissociate into monomers. The chelating agent should not be strong enough to dissociate the zinc when the two coferons are held in place by binding a target. Alternating addition of 1 mM $ZnCl_2$ and 1 mM EDTA will cycle the "free" $Zn^{2+}$ cofactor in solution between approximately 1 mM and 0 mM, cycling the coferons between the dimer (or multimer) and the monomer states. As noted previously with pH cycling, this will eventually accumulate Zn-EDTA (in the process, forming NaCl if the original EDTA was in the disodium salt). This process is also amenable to automation.

To avoid accumulating salt, alternative approaches may be used to modulate pH or divalent metal concentration. For example, the chelating moiety may be attached to a solid support and brought in contact with the coferon screening solution by circulating the screening solution past the solid support. Coferon on beads or particles may be separated from chelator beads or particles by using different size beads or particles, or using paramagnetic beads or particles. To modulate pH, organic molecules that act as buffers may be attached to a solid support. Among these are "Good's buffers", which can stabilize pH values over very precise ranges. The coferon screening solution may be circulated between two chambers, each containing the solid support with the organic molecule that will buffer the screening solution to the right pH. In both of these examples, the solid support may eventually become saturated (with divalent cation, or exceed its buffering capacity), and thus may need to be replaced after a certain number of cycles. As before, this process is also amenable to automation.

In the above examples, the binding of coferons to each other is controlled by the concentration of a positively charged ion or cation: $H^+$ or $Zn^{2+}$. Certain membranes are permeable to small molecules and ions. The Nafion-117 membrane is permeable to $H^+$, and cations such as $Li^+$, $Mg^{2+}$, $Zn^{2+}$, $Na^+$, and $K^+$; but impermeable to coferons, anions, buffers, large cations, nucleic acids, peptides, and proteins. This membrane may be used in a device that allows for cyclic combinatorial chemistry.

Figure 11:
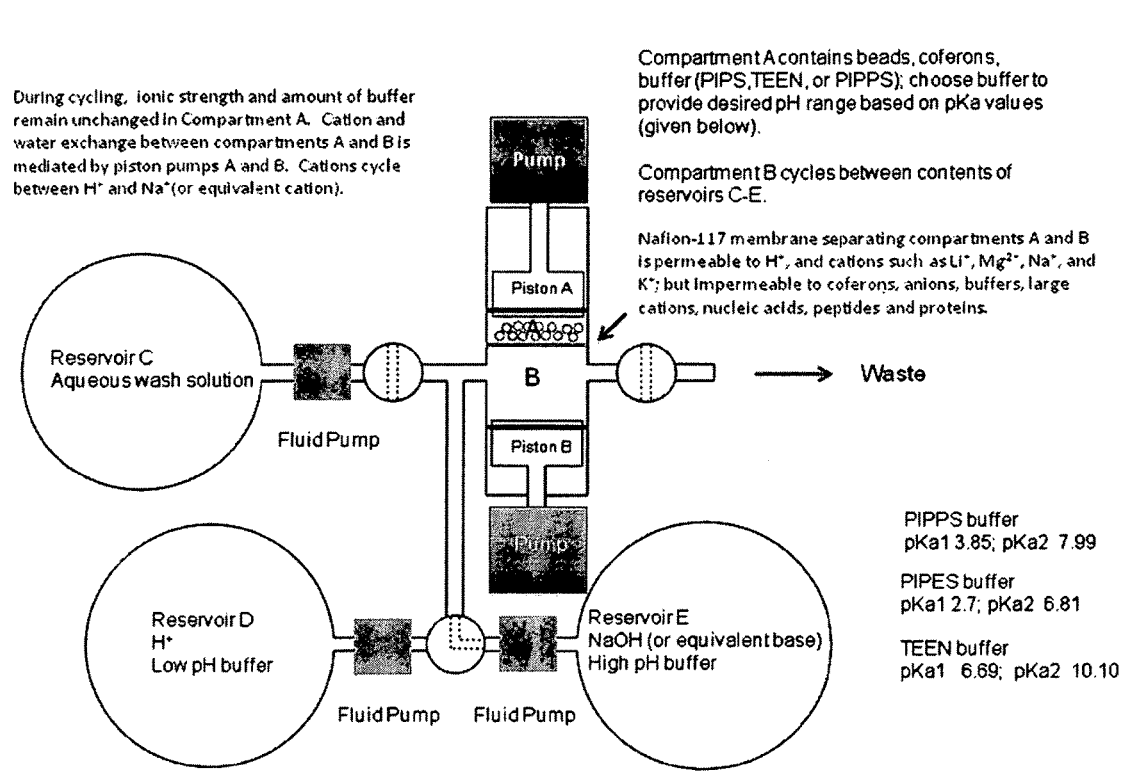
FIG. 11 is a schematic representation of a system for cycling pH for selection of coferons using cyclic combinatorial chemistry. A Nafion-117 membrane separates an upper compartment A from a lower compartment B. Compartment A contains beads, coferons, buffer (such as PIPS, TEEN, or PIPPS), and target protein. The buffer is chosen to provide the desired pH range based on pKa values for the buffer. Cation and water exchange between compartments A and B is mediated by piston pumps A and B. Cations cycle between $H^+$ and $Na^+$ or other equivalent cation. Compartment B is used to wash in and out different buffers in reservoirs C-E. Reservoir C contains an aqueous wash solution. Reservoir D contains $H^+$ or a low pH buffer. Reservoir E contains NaOH (or equivalent base), or a high pH buffer. During cycling, ionic strength and amount of buffer remain unchanged in Compartment A.
Figure 12:
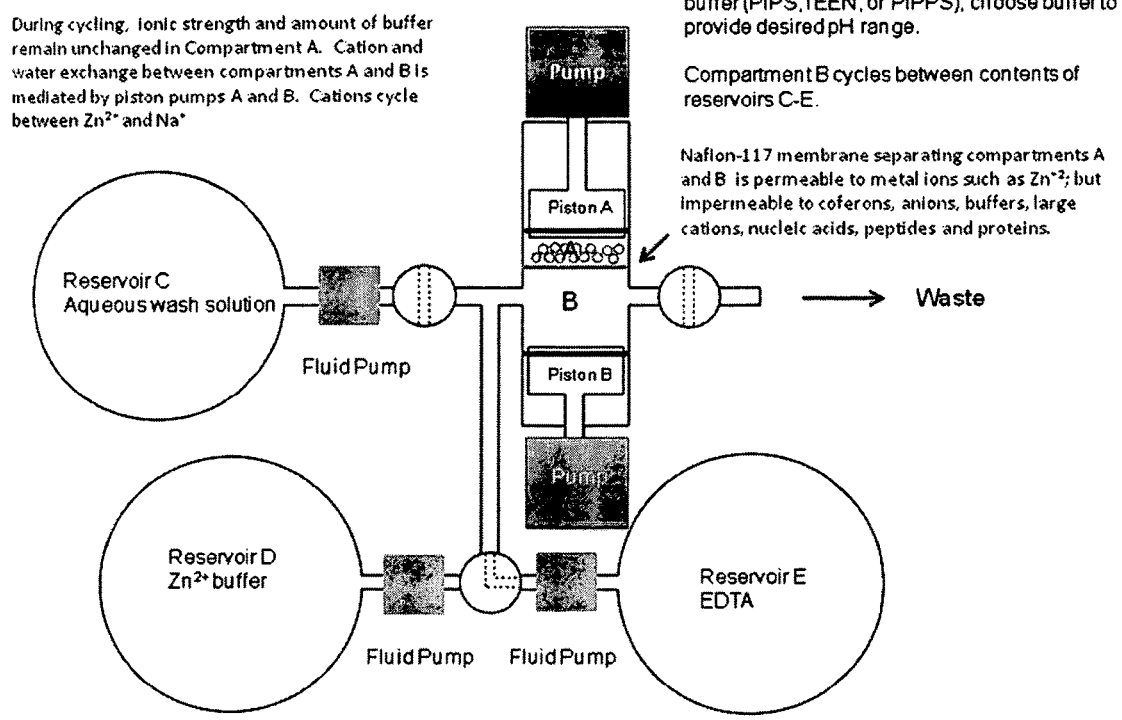
FIG. 12 is a schematic representation of a system for cycling metal ions for selection of metal co-factor coferons using cyclic combinatorial chemistry. A Nafion-117 membrane separates an upper compartment A from a lower compartment B. Compartment A contains beads, coferons, buffer (such as PIPS, TEEN, or PIPPS), and target protein. The buffer is chosen to provide the desired pH range based on pKa values for the buffer. Cation and water exchange between compartments A and B is mediated by piston pumps A and B. Cations cycle between $Zn^{2+}$ and $Na^+$. Compartment B is used to wash in and out different buffers in reservoirs C-E. Reservoir C contains an aqueous wash solution. Reservoir D contains $H^+$ or a low pH buffer. Reservoir E contains NaOH (or equivalent base), or a high pH buffer. During cycling, ionic strength and amount of buffer remain unchanged in Compartment A.

In one embodiment (See FIGS. 11 and 12), the membrane separates an upper compartment A from a lower compartment B. Compartment A contains beads, coferons, buffer (such as PIPS, TEEN, or PIPPS), and target protein. The buffer is chosen to provide the desired pH range based on pKa values (PIPPS buffer has a pKa1 3.85; pKa2 7.99; PIPES buffer has a pKa1 2.7; pKa2 6.81; and TEEN buffer has a pKa1 6.69; pKa2 10.10). At the higher pH, the coferons are more stable in the multimer form, while at the lower pH, the coferons dissociate to form monomers—unless they are bound to the protein target, where they remain as multimers.

Compartment B is used to wash in and out different buffers in reservoirs C-E. Reservoir C contains an aqueous wash solution. Reservoir D contains $H^+$ or a low pH buffer. Reservoir E contains NaOH (or equivalent base), or a high pH buffer. During cycling, ionic strength and amount of buffer remain unchanged in Compartment A. Cation and water exchange across the Nafion-117 membrane between compartments A and B is mediated by piston pumps, stirring liquid in either compartments, applying pressure, or combinations thereof. Cations cycle between H+ and Na+ (or equivalent cation).

If the coferons bind through a $Zn^{2+}$ cofactor, then reservoir D contains the $Zn^{2+}$ and reservoir E contains a chelator, such as EDTA. During cycling, ionic strength and amount of buffer remain unchanged in Compartment A. The $Zn^{2+}$ and $Na^+$ cations (and water) exchange across the Nafion-117 membrane between compartments A and B is mediated by piston pumps, stirring liquid in either compartments, applying pressure, or combinations thereof. Cations cycle between $Zn^{2+}$ and $Na^+$.

The above design is amenable to a multiple well format and automation. A 24 well microtiter plate may be constructed from 2 parts: The top part has cylindrical openings in 24 well format. The bottom part has shallow wells and grooves from a single entry port on the front splitting into 24 lines going into each well, and 24 lines (grooves) out of each well coming together at a single exit port in the back. Such a design can be manufactured very quickly in a simple stamping process. The top and bottom part are welded together with the Nafion-117 membrane in between them. The entry and exit ports both have valves and are attached to piston pumps.

Since the 24 top wells are open, they can be filled with coferons, beads, fluorescent target protein, etc. using a multi-channel pipette or a robotic platform.

The bottom of the wells can be filled with the appropriate reagents by opening the entry and exit valves, and moving the two piston pumps in the same direction. The simplest way to accelerate the exchange is to have the entire device on a rotating platform (microtiter plate shaker). Alternatively, magnetic agitation (stirring) may be used. If it is necessary to speed up the process, the exit pump can be closed, and the volume of all 24 top wells will increase when the entry pump keeps pumping. To decrease the volume of the 24 top wells, the entry valve is closed, and the exit valve is opened and the pump withdraws fluid. This design also makes it easy to transfer a number of reactions into a second microtiter plate for bulk washing away unbound coferons etc.

A fluorescent chelator or dye may be used to monitor the zinc concentration or pH. Examples of fluorescent zinc chelator and some fluorescent pH dyes are: TFLZn, 4-(6-Methoxy-8-quinaldinyl-aminosulfonyl)benzoic acid potassium salt; HPTS, 8-hydroxypyrene-1,3,6-trisulfonic acid trisodium salt; umbelliferone-3-carboxylic acid, 7-hydroxycoumarin-3-carboxylic acid; and 5(6)-carboxynaphthofluorescein.

After the selection is complete, the dye or fluorescent group may be washed away so that it does not interfere with scoring of the beads for those that bound labeled target protein.

The dyes can also be linked to a solid support to make it easy to read and separate from coferon beads (although a separation step may not be needed).

It may be useful to verify the rate and efficiency of exchange using a model system. One such model system would use iminobiotin as the ligand, and fluorescently labeled streptavidin as the target protein. A functional coferon would be synthesized containing the linker element connected to the iminobiotin via a flexible linker, i.e. ethylene glycol chain. When synthesizing this functional coferon on a solid support, spacing would be sufficiently distant to minimize two coferons in close enough proximity to bind to the same streptavidin target. A non-functional coferon would be synthesized containing the linker element connected to another unrelated small molecule or just an amine group via an ethylene glycol chain. The functional coferon containing bead would be mixed in with a 1,000-fold excess of beads containing non-functional coferon. Likewise, the functional coferon in solution would be mixed in with a 1,000-fold excess of non-functional coferon in solution. In the example here, the solution coferon can only make dimers or multimers with the bead-bound coferon.

In the presence of fluorescently labeled streptavidin, two functional coferons, one on the bead, the other in solution bind to the target and provide a small amount of fluorescent label to the single bead. With repeated cycling (100 to 1,000 cycles), the amount of fluorescent signal on the functional coferon bead should steadily increase. Comparing different cycling conditions will help determine the optimal cycling times and pH or cation concentrations.

Considerations for Screening Coferons Binding to Targets

In consideration of the screening process, the following encryption formats—illustrated below using the simplest case of forming dimers between "A" and "B" coferons—may be considered:

Single A Coferon with Single B Coferon.

1. Single A coferon with single B coferon, with coferon biological activity determined using whole-cell assays.

Examples of biological readout are provided below. In these schemes, both coferons are in solution. The identity of the coferon is given by the location of the well where the ligand was synthesized, for example by split synthesis protocols, without re-pooling. Such assays may be compatible with the pooling strategies described above. Alternatively, where assays are not compatible with pooling, ultra high-throughput assays may be developed using nano-droplet (Raindance) technology. Such technology can generate 3,000 droplets per second. Consider the example above of 96 A coferons to be tested in combination with 9,600 B coferons, where the whole-cell assay generates a fluorescent signal. The A coferons are in 1×96 well plate, each well containing a 100,000 beads with a unique barcode and the A coferon attached to the bead. The B coferons are in 25×384 well plates, each well containing a 1,000 beads with a unique barcode and the B coferon attached to the bead. In practice, either the A or B coferon plate may pool the coferons by using split synthesis protocols, with re-pooling, provided the barcodes are attached to the beads. All the A coferons are pooled together and emulsified in oil such that each bead is in its own nanodrop. Likewise, all the B coferons are pooled together and emulsified in oil such that each bead is in its own nanodrop. The A coferon droplets and B coferon droplets are fused, each fused droplet containing one bead each for a total of 9,600,000 droplets. This process (not including setup) takes 3,200 seconds, or just under an hour. These droplets are then exposed to light (or heat, or reagent that may be subsequently neutralized if needed to be biologically compatible) to release the coferons from the beads. Subsequently, the droplets are fused with new droplets containing the cells with the biological target whose inhibition/activation will result in a change in fluorescent signal. This second droplet fusion will also take just under an hour, and this may be followed by a period of incubation to allow the coferons to enter the cells and bind the intended target, resulting in the biological readout. The droplets are placed in a flow sorter, such that the fluorescently altered droplets are separated. Dilution into 384 or 1536 well plates, such that a given well has one or less nanodroplets containing the original bead pair, to identify the winning coferon ligands. If the bar-codes are mass tags attached to the beads, they may be identified by mass spectroscopy.

2. Single A coferon with single B coferon, with coferon binding determined using in vitro readout. Examples of in vitro readout are provided below. In these schemes, both coferons are in solution. The identity of the coferon is given by the location of the well where the ligand was synthesized, for example by split synthesis protocols, without re-pooling.

Coferon Binding Determined Using In Vitro Readout.

Two screens, termed "AlphaScreen" and "AlphaLISA" have been developed (sold by Perkin-Elmer) to measure cell signaling, including protein:protein, protein:peptide, protein:small molecule or peptide:peptide interactions. The assays are based on detecting the close proximity of donor beads containing a first molecule or protein that binds to a second molecule or protein on the acceptor beads. Singlet oxygen molecules, generated by high energy irradiation of donor beads, travel over a constrained distance (approx. 200 nm) to acceptor beads. This results in excitation of a cascading series of chemical reactions, ultimately generating a chemiluminescent signal. (Eglen, et. al., *Curr. Chem. Genomics* 1:1-19 (2008), which is hereby incorporated by reference in its entirety).

The donor bead contains phthalocyanine. Excitation of the donor bead by a laser beam at a wavelength of 680 nm allows ambient oxygen to be converted to singlet oxygen. This is a highly amplified reaction since approx. 60,000 singlet oxygen molecules can be generated and travel at least 200 nm in aqueous solution before decay. Consequently, if the donor and acceptor beads are brought within that proximity as a consequence of protein:protein, protein:peptide, or protein:small molecule interactions, energy transfer occurs. Singlet oxygen molecules react with chemicals in the acceptor beads to produce a luminescent response. If the acceptor bead contains Europium, as in the AlphaLISA assay, an intense luminescence is emitted at a wavelength of 615 nm. (Eglen, et. al., *Curr. Chem. Genomics* 1:1-19 (2008), which is hereby incorporated by reference in its entirety).

For the purposes of the discussion below, this system will be referred to as linking various proteins, fragments or molecules on donor and acceptor beads. Such linking may be chemical in nature, or may be due to tight binding of a tethered ligand, such as if the donor bead is coated with strepavidin and the donor molecule or protein has a biotin attached to it. There are many systems for binding recombinant proteins to beads, including His-Tag, Myc-Tag, GST fusions, Maltose binding protein (MBP) fusions.

A. Identifying Initial Sets of Coferon A Ligands that (Weakly) Bind to the Target Protein Target protein is linked or bound to the donor bead. A generic coferon B, containing a linker element that binds the linker element of coferon A is attached to the acceptor bead. A generic ligand may contain the scaffold and then the simplest pharmacophore in all the diversity positions, for example, alanine if the diversity positions are filled with amino acid moieties. An HTS assay is setup containing acceptor and donor beads in each well, with from 1 to 100 or even 1,000 or more coferon A variants added to each well. The number of variants will depend on the background level and hit level, determined experimentally. Likewise, the number of "generic" variants that can be tested within the same well may range from 1 to 100 or more. Since dynamic combinatorial chemistry takes place, the acceptor bead will bind those variants that bind the donor bead the tightest, as more than one protein will interact with more than one coferon pair to form more than one bridge to the acceptor bead. By using different sets of pools (i.e. rows vs. columns) a large number of potential binders may be rapidly tested.

B. Identifying Optimized Coferon B Ligands that Pair with the Initial Sets of Coferon A Ligands to Tightly Bind to the Target Protein Target protein is linked or bound to the donor bead. The initials sets of coferon A ligands, (containing a linker element that binds the linker element of the test coferon B ligands) are attached to the acceptor beads. An HTS assay is set up containing acceptor and donor beads in each well, with from 1 to 100 or even 1,000 or more coferon B variants added to each well. The number of variants will depend on the background level and hit level, determined experimentally. The strongest binding coferon B ligands will give the brightest signals. As above, when testing more than one coferon B ligand per well, use of different sets of pools (i.e. rows vs. columns) allow a large number of potential binders to be rapidly tested.

C. Identifying Coferon Dimers that Enhance Binding of Two Proteins with Weak or No Binding Affinity to Each Other Target protein 1 is linked or bound to the donor bead. Target protein 2 is linked or bound to the acceptor bead. To identify a new weak binding partner to a given target protein, a yeast two-hybrid or other fish-bait protein complementation assay is set up, with both weak and strong hits identified. An HTS assay is set up containing acceptor and donor beads in each well, with from 1 to 10 or even 100 or more coferon A & B dimer variants added to each well. The number of variants will depend on the background level and hit level, determined experimentally. The coferon dimers that best enhance binding of the two proteins to each other will give the brightest signals. If necessary, candidate coferon A and B monomers that bind either or both protein targets may be identified as in procedure A.

D. Identifying Coferon Dimers that Further Enhance Binding of Two Proteins with Medium to Strong Binding Affinity to Each Other Target protein 1 or a mutant variant with weaker binding is linked or bound to the donor bead. Target protein 2 or a mutant variant with weaker binding is linked or bound to the acceptor bead. If the original proteins are used, they are linked to the beads at low concentration. Often some structural or sequence information is available to guide alanine scanning or targeted mutagenesis to generate variants with the potential to bind weakly. To identify mutations that convert a strong binding partner into a weak binding partner to a given target protein, a yeast two-hybrid or other fish-bait protein complementation assay is set up to test mutant variants, with both weak and strong hits identified. An HTS assay is set up containing acceptor and donor beads in each well, with from 1 to 10 or even 100 or more coferon A & B dimer variants added to each well. The number of variants will depend on the background level and hit level, determined experimentally. The coferon dimers that best enhance binding of the two proteins to each other will give the brightest signals. The winning coferon dimer sets are then retested to determine which set enhances binding of the wild-type proteins to each other.

E. Identifying Coferon Dimers that Inhibit Binding of Two Proteins to Each Other Target protein 1 is linked or bound to the donor bead. Target protein 2 is linked or bound to the acceptor bead. An HTS assay is set up containing acceptor and donor beads in each well, with from 1 to 10 or more coferon A & B dimer variants added to each well. The number of variants will depend on the background level and hit level, determined experimentally. The coferon dimers that best inhibit binding of the two proteins to each other will give the weakest signals. If necessary, candidate coferon A and B monomers that bind either protein targets in the absence of the other protein may be identified as in procedure A.

F. Identifying Coferon Dimers that Inhibit Binding of Two Proteins to Each Other Target protein 1 is linked or bound to the donor bead. Target protein 2 is either added in solution, or linked or bound to neutral beads. A weak or medium binding partner of target protein 1, or an antibody that binds to target protein 1 is linked or bound to the acceptor bead. An HTS assay is set up containing acceptor and donor beads, as well as sufficient target protein 2 in each well, such that target protein 2 interferes with binding of the proteins on the acceptor and donor beads resulting in low or background level signal. Addition of from 1 to 10 or more coferon A & B dimer variants that bind to target protein 2 in such a way as to disrupt binding to target protein 1, allowing for binding of the protein on the acceptor bead to the donor bead, and thus generating positive signal. The number of variants will depend on the background level and hit level, determined experimentally. The coferon dimers that best inhibit binding of the two proteins to each other will give the strongest signals. If necessary, candidate coferon A and B monomers that bind target protein 2 in the absence of the other protein may be identified as in procedure A.

G. Identifying Coferon Dimers that Inhibit Binding of Two Proteins to Each Other The inverse of the above procedure may be performed using target protein 2 linked or bound to the donor bead, and target protein 1 either added in solution, or linked or bound to neutral beads. In this procedure, a weak or medium binding partner of target protein 2, or an antibody that binds to target protein 2 is linked or bound to the acceptor bead. Again, if necessary, candidate coferon A and B monomers that bind target protein 1 in the absence of the other protein may be identified as in procedure A.

H. Identifying Coferon Dimers that Inhibit Binding of Two Proteins to Each Other, Using a Helper Protein Target protein 1 is linked or bound to the donor bead. Target protein 2 is linked or bound to the acceptor bead. A helper protein may have weak or no affinity to target protein 1. An HTS assay is set up containing helper protein, acceptor and donor beads in each well, with from 1 to 10 or more coferon A & B dimer variants added to each well. The number of variants will depend on the background level and hit level, determined experimentally. The coferon dimer that enhances binding of the helper protein to target protein 1, and thus best inhibits binding of the two target proteins to each other will give the weakest signals. If necessary, candidate coferon A and B monomers that enhance binding of the helper protein to target protein 1 in the absence of the other protein may be identified as in procedure C.

I. Identifying Coferon Dimers that Inhibit Binding of Two Proteins to Each Other, Using a Helper Protein Target protein 1 is linked or bound to the donor bead. Target protein 2 is either added in solution, or linked or bound to neutral beads. A weak or medium binding partner of target protein 1, or an antibody that binds to Target protein 1 is linked or bound to the acceptor bead. A helper protein may have weak or no affinity to Target protein 2. An HTS assay is set up containing acceptor and donor beads, as well as sufficient target protein 2 and helper protein in each well, such that target protein 2 interferes with binding of the proteins on the acceptor and donor beads resulting in low or background level signal. Addition of from 1 to 10 or more coferon A & B dimer variants that enhance binding of the helper protein to target protein 2 in such a way as to disrupt binding to target protein 1, allowing for binding of the protein on the acceptor bead to the donor bead, and thus generating positive signal. The number of variants will depend on the background level and hit level, determined experimentally. The coferon dimer that enhances binding of the helper protein to target protein 2, and thus best inhibit binding of the two target proteins to each other will give the strongest signals. If necessary, candidate coferon A and B monomers that enhance binding of the helper protein to target protein 2 in the absence of the other protein may be identified as in procedure C.

J. Identifying Coferon Dimers that Inhibit Binding of Two Proteins to Each Other, Using a Helper Protein The inverse of the above procedure may be performed using target protein 2 linked or bound to the donor bead, and target protein 1 either added in solution, or linked or bound to neutral beads. In this procedure, a weak or medium binding partner of target protein 2, or an antibody that binds to target protein 2 is linked or bound to the acceptor bead. A helper protein may have weak or no affinity to target protein 1. Again, if necessary, candidate coferon A and B monomers that enhance binding of the helper protein to target protein 1 in the absence of the other protein may be identified as in procedure C.

Coferon Biological Activity Determined Using Whole-Cell Assays.

The last few years has seen an explosion of biological assays designed to study protein signaling and protein-protein interactions in whole cells. Many of these are based on protein complementation assays (PCA's) that reconstitute activity of two peptide chains to form a functional reporter protein, which generates either a fluorescent or chemiluminescent signal. Proteins have evolved to code for all the information needed to fold into stable 3-dimensional structures. In some cases, the complementary N-terminal and C-terminal peptide chains can fold independently, and find each other to form a functional (reporter) protein. However, kinetically this process competes with non-specific aggregation, so in many cases expression of complementary N-terminal and C-terminal peptide chains in a cell does not lead to reconstruction of activity. PCA works by fusing interacting proteins to the fragments, which increase the effective concentration of the two fragments, thus favoring the correct folding over any non-productive process. Addition of coferon drugs that would interfere with the two proteins from interacting with each other would lower the effective concentration of the two fragments with each other, and thus cause a disruption or loss of signal from the complementing reporter protein fragments.

One of the oldest forms of protein complementation in based on the alpha-peptide complementation of the enzyme beta-galactosidase. DiscoveRx has developed this enzyme fragment complementation (EFC) technology into a cell-based luminescent platform. Beta-galactosidase is active as a tetramer, but when missing the N-terminal 60 amino acid peptide forms only dimers, which are inactive. By reintroducing the alpha-peptide into the protein, it forms the tetramer and revives activity. Two forms of the alpha-peptide are commercially available, ProLabel™ (DiscoveRx Corp., Fremont, Calif.) with higher affinity to the C-terminal enzyme acceptor protein, and ProLink™ (DiscoveRx Corp., Fremont, Calif.), with lower affinity, and thus optimized to detect protein-protein interactions. By engineering G-Protein Coupled Receptors (GPCRs) to contain the ProLink peptide on one of their termini, and using an engineered beta-arrestin to contain the C-terminal enzyme acceptor protein, DiscoveRx has developed an assay for drug-activation of GPCR with EFC readout in the form of a chemiluminescent signal. Similarly, the ProLabel tag has been used to measure protein expression, degradation, secretion and translocation for a variety of drug discovery target classes.

An alternative approach is marketed by Invitrogen (Carlsbad, Calif.) and termed "GeneBLAzer Technology". GeneBLAzer Technology uses a mammalian-optimized beta-lactamase gene combined with a FRET-enabled substrate. Cells are loaded with an engineered fluorescent substrate containing two fluoroprobes, coumarin and fluorescein. In the absence of beta-lactamase gene expression, the substrate molecule remains intact. In this state, excitation of the coumarin results in fluorescence resonance energy transfer to the fluorescein moiety and emission of green light. However, in the presence of beta-lactamase gene expression, the substrate is cleaved, separating the fluorophores, and disrupting energy transfer. Excitation of the coumarin in the presence of enzyme beta-lactamase activity results in a blue fluorescence signal. The resulting blue:green ratio provides a normalized reporter response.

Invitrogen (Carlsbad, Calif.) has exploited GeneBLAzer to build "Tango" assays that report drug binding to GPCRs. The Tango assay platform is based upon ligand binding to GPCRs that triggers desensitization, a process mediated by the recruitment of intracellular arrestin proteins to the activated receptor. As a result, the ligand-induced activation of GPCRs may be assayed by monitoring the interaction of arrestin with the test GPCR. A major advantage of this approach is that it does not depend on knowledge of the G-protein signaling specificity of the target receptor.

The target GPCR is fused at its intracellular C-terminus to an exogenous transcription factor. Interposed between the receptor and the transcription factor is a specific cleavage sequence for a non-native protease. This chimeric receptor protein is expressed in a cell line containing the beta-lactamase reporter gene responsive to the transcription factor. The cell line also expresses an arrestin-protease fusion protein that recognizes and cleaves the site between the receptor and transcription factor. The assay is performed by adding a ligand to the growing cells for a defined period and measuring the activity of the reporter gene. Activation of the reporter gene provides a quantifiable measurement of the degree of interaction between the target receptor and the protease-tagged arrestin partner. Additionally, the Invitrogen Tango assay is unaffected by other signaling pathways in the cell, thus providing a highly selective readout of target receptor activation.

Protein complementation assays have been developed using (a) dihydrofolate reductase, (b) green fluorescent protein and variants, (c) beta-lactamase, (d) luciferases, (e) aminogycosidephosphotransferase, and (f) CRE-recombinase to screen for drugs that modulate protein-protein interactions, protein subcellular location, protein complex localization, and the association/dissociation of protein complexes Michnick, et. al., *Drug Discov.* 6:569-82 (2007), which is hereby incorporated by reference in its entirety.

For the whole-cell assays described below, in some cases a preliminary in vitro screen using purified proteins as described in the next section, or a preliminary whole-cell assay at higher drug concentrations may be used to identify initial coferon ligands. In some of the descriptions below, a beta-galactosidase system developed by DiscoveRx Corp. (Fremont, Calif.) is used, where the alpha-peptide with independent affinity to the C-terminal enzyme acceptor protein (EA) is referred to as ProLabel, and the alpha-peptide with weak to no affinity to EA is referred to as ProLink. Chemiluminescent or fluorescent signal generated by the reconstructed beta-galactosidase is determined as described (Eglen review). Whole cell assays may not be as amenable to using pooling techniques to screen for coferon pairs, thus the nanodrop technology developed by Raindance Technologies (Lexington, Mass.) may be more appropriate, (Leaman et. al, *Nat. Methods* 3(7): 541-43 (2006), which is hereby incorporated by reference in its entirety). The advantage of using whole cell assays is their immediate screen for coferons that enter cells when targeting intracellular components. The potential disadvantage to whole-cell screens include identifying coferons that elicit the desired phenotype, but not through the intended target. Carefully designed controls can reduce such false positives, and occasionally, these "off-target" results will lead to drugs that influence the process through alternative pathways.

K. Identifying Initial Sets of Coferon A Ligands that (Weakly) Bind to the Target Protein The gene for the target protein is linked to the coding sequence for the ProLink alpha-complementing peptide. Upon activation, target protein recruits a second protein (i.e., GPCR recruits arrestin). The gene for the second protein is linked to the gene for the EA acceptor protein. Linking of two proteins to each other may be accomplished by fusing the C terminus of one protein to the N-terminus of the second protein, with or without a flexible linker peptide, or alternatively using an intein to splice the two proteins together, such that both proteins retain biological function. Both of the above constructs are introduced into the target cell. An HTS assay containing the target cells in each well or nanodrop is set up, with from 1 to 10 or more coferon A variant ligands and 1 or more coferon B generic ligands added to each well or nanodrop. A generic ligand may contain the scaffold and then the simplest pharmacophore in all the diversity positions, for example, alanine if the diversity positions are filled with amino acid moieties. The number of variants will depend on the background level and hit level, determined experimentally. Likewise, the number of "generic" variants that can be tested within the same well or nanodrop may range from 1 to 10 or more. The coferon dimer that best activates the target protein to recruit the second protein will best reconstruct the beta-galactosidase ProLink and EA domains and give the strongest signals. By using different sets of pools (i.e. rows vs. columns) a large number of potential binders may be rapidly tested.

L. Identifying Optimized Coferon B Ligands that Pair with the Initial Sets of Coferon A Ligands to Tightly Bind to the Target Protein The gene for the target protein is linked to the coding sequence for the ProLink alpha-complementing peptide. Upon activation, target protein recruits a second protein (e.g., GPCR recruits arrestin). The gene for the second protein is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. Both of the above constructs are introduced into the target cell. An HTS assay containing the target cells in each well or nanodrop is set up, with from 1 or more coferon A initially selected ligands and 1 to 10 or more coferon B ligands added to each well or nanodrop. The number of variants will depend on the background level and hit level, determined experimentally. The coferon dimer that best activates the target protein to recruit the second protein will best reconstruct the beta-galactosidase ProLink and EA domains and give the strongest signals. As above, when testing more than one coferon B ligand per well, use of different sets of pools (i.e. rows vs. columns) allow a large number of potential binders to be rapidly tested.

In the procedures K and L above, the ProLink alpha-complementing peptide was linked to a membrane bound receptor protein, which upon activation recruits arrestin protein linked to the EA acceptor protein. Under these conditions, agonist coferons may be identified by increased beta-galactosidase signal. Alternatively, the system may be turned on by addition of a known agonist, and then antagonist coferons may be identified by decreased beta-galactosidase signal. The above concept may be expanded to include linking the target protein to the ProLabel alpha-complementing peptide. Upon activation, the target protein moves from the cellular membrane to the nucleus, where it can complement an EA acceptor protein that is localized to the nucleus. In the generalized version of this assay, binding of coferon to the target protein results in either an increase or decrease of reporter signal, cell growth or viability.

M. Identifying Coferon Dimers that Enhance Binding of Two Proteins with Weak or No Binding Affinity to Each Other The gene for target protein 1 is linked to the coding sequence for the ProLink alpha-complementing peptide. The gene for target protein 2 is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. To identify a new weak binding partner to a given target protein, a yeast two-hybrid or other fish-bait protein complementation assay is set up, with both weak and strong hits identified. Both of the above constructs are introduced into the target cell. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that best enhance binding of the two proteins to each other will best reconstruct the beta-galactosidase ProLink and EA domains and give the strongest signals. If necessary, candidate coferon A and B monomers that bind either or both protein targets may be identified by a preliminary in vitro screen (as in procedure A) or whole cell screen (as in procedure K).

N. Identifying Coferon Dimers that Further Enhance Binding of Two Proteins With Medium to Strong Binding Affinity to Each Other The gene for target protein 1 or a mutant variant with weaker binding is linked to the coding sequence for the ProLink alpha-complementing peptide. The gene for target protein 2 or a mutant variant with weaker binding is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. If one or both of the original proteins are used, they may be expressed at a lower level. Often, some structural or sequence information is available to guide alanine scanning or targeted mutagenesis to generate variants with the potential to bind weakly. To identify mutations that convert a strong binding partner into a weak binding partner to a given target protein, a yeast two-hybrid or other fish-bait protein complementation assay is set up to test mutant variants, with both weak and strong hits identified. Both of the above constructs are introduced into the target cell. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that best enhance binding of the two proteins to each other will best reconstruct the beta-galactosidase ProLink and EA domains and give the strongest signals. The winning coferon dimer sets are then retested to determine which set enhances binding of the wild-type proteins to each other.

O. Identifying Coferon Dimers that Inhibit Binding of Two Proteins to Each Other The gene for target protein 1 is linked to the coding sequence for the ProLink alpha-complementing peptide. The gene for target protein 2 is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. Both of the above constructs are introduced into the target cell. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that best inhibit binding of the two proteins to each other will interfere with reconstructing the beta-galactosidase ProLink and EA domains and give the weakest signals. If necessary, candidate coferon A and B monomers that bind either protein targets in the absence of the other protein may be identified by a preliminary in vitro screen (as in procedure A) or whole cell screen (as in procedure K).

P. Identifying Coferon Dimers that Inhibit Binding of Two Proteins to Each Other The gene for target protein 1 is linked to the coding sequence for the ProLabel alpha-complementing peptide. The ProLabel peptide sequence may be modified to include a nuclear localization signal. The gene for target protein 2 is either currently or is modified to prefer localization in the cytoplasm or at the cellular membrane. The gene for the EA acceptor protein is modified to include a nuclear localization signal. These constructs are introduced into the target cell, and if needed, expression is adjusted such that under normal conditions binding of target protein 1 (containing the ProLabel peptide) to target protein 2 localizes the two proteins in the cytoplasm or at the cell membrane, thus preventing the ProLabel portion from entering the nucleus and complementing the EA acceptor protein, resulting in low or no background level signal. Addition of from 1 to 10 or more coferon A and B dimer variants (in wells or nanodrops) that bind to target protein 2 in such a way as to disrupt binding to target protein 1, allowing for transport of the ProLabel peptide (linked to target protein 1) to enter the nucleus and combine with the EA acceptor protein, and thus generating positive signal. The number of variants will depend on the background level and hit level, determined experimentally. The coferon dimers that best inhibit binding of the two proteins to each other will give the strongest signals. If necessary, candidate coferon A and B monomers that bind target protein 2 in the absence of the other protein may be identified by a preliminary in vitro screen (as in procedure A) or whole cell screen (as in procedure K).

In this example, the ProLabel alpha-complementing peptide was localized to the cytoplasm or cellular membrane by the two target proteins binding each other, while the EA acceptor protein was localized to the nucleus. The above concept may be expanded to include localization of these proteins to the reverse or other compartments. In addition, in some cases binding of the two target proteins to each other will create a bulky complex that would inhibit binding of the ProLabel alpha-complementing peptide to the EA acceptor protein, even if they are in the same compartment. The generalized version of this assay is one where binding of the two target proteins to each other squelches, inhibits, or occludes binding of the ProLabel alpha-complementing peptide to the EA acceptor protein.

Q. Identifying Coferon Dimers that Inhibit Binding of Two Proteins to Each Other The inverse of the above procedure may be performed using Target protein 2 linked to the coding sequence for the ProLabel alpha-complementing peptide, and Target protein 1 localized to the cytoplasm or at the cellular membrane. The gene for the EA acceptor protein is modified to include a nuclear localization signal. Addition of from 1 to 10 or more coferon A and B dimer variants that bind to target protein 1 in such a way as to disrupt binding to target protein 2, allowing for transport of the ProLabel peptide (linked to target protein 2) to enter the nucleus and combine with the EA acceptor protein, and thus generating positive signal. Again, if necessary, candidate coferon A and B monomers that bind target protein 1 in the absence of the other protein may be identified by a preliminary in vitro screen (as in procedure A) or whole cell screen (as in procedure K).

R. Identifying Coferon Dimers that Inhibit Binding of Two Proteins to Each Other, Using a Helper Protein The gene for target protein 1 is linked to the coding sequence for the ProLink alpha-complementing peptide. The gene for target protein 2 is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. Both of the above constructs are introduced into the target cell, which also produces a helper protein that may have weak or no affinity to target protein 1. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that enhances binding of the helper protein to target protein 1, and thus best inhibits binding of the two target proteins to each other will give the weakest signals. If necessary, candidate coferon A and B monomers that enhance binding of the helper protein to target protein 1 in the absence of the other protein may be identified by a preliminary in vitro screen (as in procedure C) or whole cell screen (as in procedure M).

S. Identifying Coferon Dimers that Inhibit Binding of Two Proteins to Each Other, Using a Helper Protein The gene for target protein 1 is linked to the coding sequence for the ProLabel alpha-complementing peptide. The ProLabel peptide sequence may be modified to include a nuclear localization signal. The gene for target protein 2 is either currently or is modified to prefer localization in the cytoplasm or at the cellular membrane. The gene for the EA acceptor protein is modified to include a nuclear localization signal. These constructs are introduced into the target cell, which also produces a helper protein that may have weak or no affinity to target protein 2. If needed, expression is adjusted such that under normal conditions binding of target protein 1 (containing the ProLabel peptide) to target protein 2 localizes the two proteins in the cytoplasm or at the cell membrane, thus preventing the ProLabel portion from entering the nucleus and complementing the EA acceptor protein, resulting in low or no background level signal. Addition of from 1 to or more coferon A and B dimer variants (in wells or nanodrops) that enhance binding of the helper protein to target protein 2 in such a way as to disrupt binding to target protein 1, allowing for transport of the ProLabel peptide (linked to target protein 1) to enter the nucleus and combine with the EA acceptor protein, and thus generating positive signal. The number of variants will depend on the background level and hit level, determined experimentally. The coferon dimers that enhances binding of the helper protein to target protein 2, and thus best inhibit binding of the two target proteins to each other will give the strongest signals. If necessary, candidate coferon A and B monomers that enhance binding of the helper protein to target protein 2 in the absence of the other protein may be identified by a preliminary in vitro screen (as in procedure C) or whole cell screen (as in procedure M).

T. Identifying Coferon Dimers that Inhibit Binding of Two Proteins to Each Other, Using a Helper Protein The inverse of the above procedure may be performed using target protein 2 linked to the coding sequence for the ProLabel alpha-complementing peptide, and target protein 1 localized to the cytoplasm or at the cellular membrane. The gene for the EA acceptor protein is modified to include a nuclear localization signal. Both of the above constructs are introduced into the target cell, which also produces a helper protein that may have weak or no affinity to target protein 1. Addition of from 1 to 10 or more coferon A and B dimer variants (in wells or nanodrops) that enhance binding of the helper protein to target protein 1 in such a way as to disrupt binding to target protein 2, allowing for transport of the ProLabel peptide (linked to target protein 2) to enter the nucleus and combine with the EA acceptor protein, will generate a positive signal. Again, if necessary, candidate Coferon A and B monomers that enhance binding of the helper protein to target protein 1 in the absence of the other protein may be identified by a preliminary in vitro screen (as in procedure C) or whole cell screen (as in procedure M).

Screening of Multimer Coferons

There are many proteins that function only when they assemble into multimeric structures. The coferon design allows for expanding on the multivalency concept. One example is for inhibition of the heptameric protective antigen which is responsible for anthrax toxicity. See FIG. 30.

When considering coferon multimers, it should be recognized that this creates both unique opportunities in drug design, as well as unique challenges in screening for the best multimers. Multimeric coferons may be used to bind to monomeric protein targets, targets comprised of multiple protein monomers or dimer subunits, or targets comprised of multiple different subunits. For example, consider a transporter composed of 3 identical membrane subunits. A coferon drug could be designed wherein the linker element allows for self-assembly of 3 molecules, each with the same pharmacophore “A”.

In the absence of assembled protein target the coferons bind reversibly and weakly to each other. In addition, each individual coferon may have weak binding to the transporter, but when combining four such interactions together, the tetrameric coferon structure may bind essentially irreversibly. See FIG. 31.

Alternatively, the coferon drug could be composed of two subunits (“A” and “B”), that assemble to form A-B heterodimers, and then continue to assemble to form a 6-membered circular structure of alternating A-B coferons. Each individual coferon may have weak binding to the transporter, but when combining 6 such interactions together, the hexameric coferon structure may bind with the same avidity as full-sized antibodies.

Assembly of linker elements into multimeric structures is discussed in greater detail below (above), but there are some general concepts. It may be very difficult to identify the best binding coferon multimers if more than 3 of the ligands arise from pharmacophores. Thus, one theme is to screen for the best coferons under conditions where the same pharmacophore is connected two or more times to the dynamic combinatorial chemistry element. Here, the linker element will be connected to two or more of the same drug molecule and may be in the same geometry to cover two or more linker elements that would be present in the final monomeric form of the coferon drug molecule.

The connection between the linker element and the pharmacophore may also vary. For example, when the same ligand binds to the same active site in a dimer or tetrameric multimer of the same protein target subunit, the connector would most likely be a flexible (such as an ethylene glycol) chain, to allow for each ligand to bind to an active site, even though the active sites are on different faces of the multimeric protein. Alternatively, if the coferon is binding in a large groove, then the linker element geometry may be critical, both in generating the overall shape of the multimeric scaffold, and in positioning the pharmacophores in the proper orientation.

Coferons, by virtue of their ability to bind to an extended surface area of one or more macromolecules provide the opportunity to develop enhanced versions of existing drugs, as well as entirely new classes of inhibitors (See Table 1).

TABLE 1

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| G-PROTEIN COUPLED RECEPTORS | $\beta_2$ adrenergic receptors | epinephrine, norepinephrine | albuterol, salbutamol, terbutaline, salmeterol | propranolol, butoxamine | HitHunter, PathHunter (DiscoverX), cAMP assay, Intracellular calcium flux, TANGO, GeneBlazer, ELISA, binding assays |
| G-PROTEIN COUPLED RECEPTORS | Muscarinic receptors | Acetylcholine | Acetylcholine, Pilocarpine | Scopolamine, atropine, ipratropium, caproctamine | HitHunter, PathHunter (DiscoverX), cAMP assay, Intracellular calcium flux, TANGO, GeneBlazer, ELISA, binding assays |

TABLE 1-continued Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| G-PROTEIN COUPLED RECEPTORS | H1 histamine receptor | histamine | Histamine | diphenhydramine, doxylamine, pyrilamine, brompheniramine, chlorpheniramine, Loratadine, Fexofenadine, Cetrizine, Desoratadine | HitHunter, PathHunter (DiscoverX), cAMP assay, Intracellular calcium flux, TANGO, GeneBlazer, ELISA, binding assays |
| NUCLEAR RECEPTORS | Estrogen receptor[1-3] | Estriol, estrone, estradiol | 17-beta-estradiol, Chlorotrianisene, Dienestrol, Fosfestrol, Diethylstilbestrol, Zeranol | Tamoxifen, ICI 164,384, Keoxifene, Mepitiostane | Hit-hunter (Discoverx), reporter assays, TANGO, GeneBlazer, ELISA, ligand binding assays, |
| VOLTAGE GATED ION CHANNELS | voltage-gated sodium channels[4-6] | | veratridine, aconitine | tetrodotoxin, saxitoxin, | Intracellular ion flux assays |
| VOLTAGE GATED ION CHANNELS | voltage-gated calcium channels[7-9] | | BAY K 8644, CGP 28392 | ω-conotoxin, ω-agatoxins, dihydropyridine, nifedipine | Intracellular ion flux assays |
| LIGAND GATED ION CHANNELS | kainate receptor[10] | glutamate | kainic acid, domoic acid, LY339434, ATPA, iodowillardiine, (2S,4R)-4-methylglutamic acid | CNQX, LY293558, LY294486 | HitHunter, PathHunter (DiscoverX), cAMP assay, Intracellular ion flux, TANGO, GeneBlazer, ELISA, ligand binding assays, |
| RECEPTOR TYROSINE KINASES | epidermal growth factor receptor (EGFR)[11, 12] | epidermal growth factor | EGF, TGFa, amphiregulin, betacellulin, epiregulin, neuregulins | PD153035, anti-EGFR antibody C225, aeroplysinin-1, AG18 AG82, AG99, AG112, AG213, AG490, AG494, AG527, AG555, AG556 | reporter assays, kinase assays, CO-IP, BRET, FRET, TANGO, GeneBlazer, HitHunter, PathHunter (DiscoverX), ELISA |
| GROWTH FACTORS | Vascular endothelial growth factor[13-16] | VEGFR | | Ranibizumab, bevacizumab, sunitinib, sorafenib, axitinib, pazopanib, Naphthamides | Hit-hunter (Discoverx), reporter assays, TANGO, GeneBlazer, ELISA, ligand binding assays, |
| PROTEASES | Caspase[17] | granzyme B; caspase | Granzyme B, caspase | Z-VAD(OMe)-FMK, Z-VAD-CHO | caspase assays, apoptosis assays, mitochondrial Dy, CO-IP, BRET, FRET, TANGO, GeneBlazer, HitHunter, PathHunter (DiscoverX), ELISA |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| PHOSPHATASES | PP1[18, 19] | phosphoserine/threonine residues | | calyculin A, nodularin, tautomycin | protein tyrosine phosphatase assay, CO-IP, BRET, FRET, TANGO, GeneBlazer, HitHunter, PathHunter (DiscoverX), ELISA |
| PROTEIN KINASES | ERK[20-22] | MEK | | AG126, apigenin, Ste-MPKKKPTPIQLNP-NH2, H-GYGRKKRRQRRR-G-MPKKKPTPIQLNP-NH2, PD98059, U0126, | kinase assay, CO-IP, BRET, FRET, reporter assays, TANGO, GeneBlazer, HitHunter, PathHunter (DiscoverX) |
| MISC ENZYMES | Adenylate cyclase[23, 24] | G proteins, calcium | bordetella pertussis, cholera toxin, forskolin | NKY80, 2',3'-Dideoxyadenosine, 2',5'-Dideoxyadenosine, SQ22536, MDL-12330A | BRET, FRET, calcium flux assays, cAMP assays, TANGO, GeneBlazer, HitHunter, PathHunter (DiscoverX) |
| MISC ENZYMES | Acetylcholinesterase[25-27] | | | Caproctamine, Metrifonate, Physostigmine, Galantamine, Dyflos, Neostigmine | Acetylcholinesterase Assay, Amplex Red, Ellman method, HPLC |
| BIOACTIVE LIPIDS | Ceramide[28-30] | sphingomyelin | TNFα, Fas ligand, 1,25 dihydroxy vitamin D, γ-interferon | fumonisin B | TLC lipid charring, diacylglycerol kinase labeling in vitro |
| CYTOKINES | IL2[31-37] | IL2R | BAY 50-4798, P1-30, SP4206 | daclizumab, basiliximab, SP4206 | TANGO, GeneBlazer, HitHunter, PathHunter (DiscoverX), IL2 dependent mouse CTLL cell line, ELISA |
| MISC PROTEINS | BCLXL[38-40] | BAD | | BH3I-1, A-371191, ABT-737 | TANGO, GeneBlazer, HitHunter, PathHunter (DiscoverX), CO-IP, BRET, FRET, ELISA |
| MISC PROTEINS | p53[41-44] | MDM2, JNK1-3, ERK1-2, p38 MAPK, ATR, ATM, Chk1, Chk2, DNA-PK, CAK | PRIMA-1, MIRA-1, RITA, | Pifithrin-α | caspase assays, apoptosis assays, mitochondrial Dy, CO-IP, BRET, FRET, TANGO, GeneBlazer, HitHunter, PathHunter (DiscoverX), ELISA |
| MISC PROTEINS | Tubulin[27, 45, 46] | tubulin | | ALB109564, ABT-751, D24851, D64131, benomyl, estramustine, LY290181 | kinase assay, CO-IP, BRET, FRET, reporter assays, TANGO, GeneBlazer, β-arrestin(DiscoverX |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| MISC PROTEINS | β-amyloid[47-51] | | | L 1,10-phenanthroline derivatives, KLVFF, LVFFA, Memoquin, SLF-CR | Stagnant Amyloid Fibril Formation Assay, amyloid fibrillization assay |
| MISC PROTEINS | thymidylate synthase[52-56] | | | raltitrexed, pemetrexed, nolatrexed, ZD9331, GS7904L, fluorouracil | caspase assays, apoptosis assays, mitochondrial Dy, CO-IP, BRET, FRET, TANGO, GeneBlazer, HitHunter, PathHunter (DiscoverX), ELISA |
| UBIQUITIN LIGASES | MDM2[57-59] | p53 | | trans-4-Iodo, 4'-boranyl-chalcone, Nutlins, MI-219, MI-63, RITA, HLI98 | TANGO, GeneBlazer, HitHunter, PathHunter (DiscoverX), CO-IP, BRET, FRET, ELISA, reporter assay |
| VIRAL REGULATORS | HPV E2[60, 61] | HPV E1 | | indandiones, podophyllotoxin | E2 displacement assay, TANGO, GeneBlazer, HitHunter, PathHunter (DiscoverX), CO-IP, BRET, FRET, ELISA, reporter assay |
| BACTERIAL CELL DIVISION PROTEINS | ZipA[62] | FtsZ | | substituted 3-(2-indolyl)piperidines, 2-phenyl indoles | TANGO, GeneBlazer, HitHunter, PathHunter (DiscoverX), CO-IP, BRET, FRET, ELISA, reporter assay, polarization competition assay, |
| CYTOKINES | TNF[63] | TNFR | | infliximab, adalimumab, etanercept | TANGO, GeneBlazer, HitHunter, PathHunter (DiscoverX), CO-IP, BRET, FRET, ELISA, |
| SCAFFOLD PROTEINS | JIP1[64, 65] | JNK | | BI-78D3, TIJIP | TANGO, GeneBlazer, HitHunter, PathHunter (DiscoverX), CO-IP, BRET, FRET, ELISA, kinase assay |
| DNA REPAIR | PARP[66-69] | | | INO-1001, AG014699, BS-201, AZD2281, BS-401 | TANGO, GeneBlazer, HitHunter, PathHunter (DiscoverX), CO-IP, BRET, FRET, ELISA, |
| RIBOSOMES | Antibiotics[70] | ribosomes | | tetracyclins, macrolides, lincosamides, streptogramins | cell death assay, |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| HISTONE DEACETYLASES | HDAC1[71-73] | | | suberoylanilide hydroxamic acid, trichostatin A, LBH589 | TANGO, GeneBlazer, HitHunter, PathHunter (DiscoverX), CO-IP, BRET, FRET, ELISA, |
| APOPTOSIS REGULATORS | XIAP[74,75] | SMAC/DIABLO, caspase 3, caspase 7, caspase 9 | | SM102-SM130 | CO-IP, BRET, FRET, reporter assays, TANGO, GeneBlazer, HitHunter, PathHunter (DiscoverX), cell death assays |
| CHAPERONE PROTEINS | Hsp90[76,77] | Cdc37, survivin | | Celastrol, shepherdin | CO-IP, BRET, FRET, reporter assays, TANGO, GeneBlazer, HitHunter, PathHunter (DiscoverX), |
| SERINE/THREONINE PROTEIN KINASES | mTOR[78,79] | Raptor, mLST8/GβL | | Rapamycin, caffeine, farnesylthiosalicylic acid, curcumin, temsirolimus, everolimus | kinase assay, CO-IP, BRET, FRET, reporter assays, TANGO, GeneBlazer, HitHunter, PathHunter (DiscoverX) |
| SERINE/THREONINE-PROTEIN KINASES | B-raf & B-raf V600E[80] | K-ras | | PLX4720 | kinase assay, CO-IP, BRET, FRET, reporter assays, TANGO, GeneBlazer, HitHunter, PathHunter (DiscoverX), |
| CYCLIN DEPENDENT KINASES | CDK2[81,82] | Cyclin A, cyclin E | | Variolin, Meriolin | kinase assay, CO-IP, BRET, FRET, reporter assays, TANGO, GeneBlazer, HitHunter, PathHunter (DiscoverX), |
| GROWTH FACTOR RECEPTORS | IGF-1R[83] | IGFII | | PQIP | CO-IP, BRET, FRET, reporter assays, TANGO, GeneBlazer, HitHunter, PathHunter (DiscoverX), |
| PROTEASOME | 20S[84,85] | 19S | | Bortezomib, salinosporamide A, | CO-IP, BRET, FRET, cell viability |

All of the following citations are hereby incorporated by reference in their entirety.
1. Jordan, V. C., et al., *J Clin Oncol*, 25: 5815-24 (2007).
2. Jordan, V. C., et al., *Steroids*, 72: 7-25 (2007).
3. Dahlman-Wright, K., et al., *Pharmacological Rev*, 58: 773-81 (2006).
4. Johannessen Landmark, C., *CNS Drugs*, 22: 27-47 (2008).
5. Roselli, F., et al., *Recent Patents on CNS Drug Discovery*, 1: 83-91 (2006).
6. Heinemann, S. H., et al., *Cell Mol Life Sci*, 64: 1329-40 (2007).
7. Hidalgo, P., et al., *Cell Calcium*, 42: 389-96 (2007).
8. Gribkoff, V. K., *Semin Cell Dev Biol*, 17: 555-64 (2006).
9. Le Guennec, J. Y., et al., *Recent Patents on Anti-Cancer Drug Discovery*, 2: 189-202 (2007).
10. Lees, G. J., *Drugs*, 59: 33-78 (2000).
11. Voelzke, W. R., et al., *Curr Treat Options Oncol*, 9: 23-31, (2008).
12. Ng, K., et al., *Critical Rev Oncol Hematol*, 65: 8-20 (2008).
13. Harmange, J. C., et al., *J Med Chem*, 51: 1649-67 (2008).
14. Borzilleri, R. M., et al., *J Med Chem*, 48: 3991-4008 (2005).

15. Ignoffo, R. J., *Am J Health-Syst Ph*, 61: S21-6 (2004).
16. Bates, D. O., et al., *Microcirculation*, 6: 83-96 (1999).
17. Denault, J. B., et al., *Meth Mol Biol*, 414: 191-220 (2008).
18. Ishida, A., et al., *Pharmacol Therap*, 100: 291-305 (2003).
19. Vogt, A., et al., *Pharmacol Therap*, 107: 212-21 (2005).
20. Ohori, M., *Drug News Perspect*, 21: 245-50 (2008).
21. Kelemen, B. R., et al., *J Biol Chem*, 277: 8741-8 (2002).
22. Favata, M. F., et al., *J Biol Chem*, 273: 18623-32 (1998).
23. Onda, T., et al., *J Biol Chem*, 276: 47785-93 (2001).
24. Iwatsubo, K., et al., *Endocr Metab Immune Disord Drug Targets*, 6: 239-47 (2006).
25. Rosini, M., et al., *J Med Chem*, 51: 4381-4 (2008).
26. Tumiatti, V., et al., *J Med Chem*, 46: 954-66 (2003).
27. Singh, P., et al., *IUBMB Life*, 60: 368-75 (2008).
28. Marasas, W. F., et al., *J Nutrition*, 134: 711-6 (2004).
29. Soriano, J. M., et al., *Prog Lipid Res*, 44: 345-56 (2005).
30. Menaldino, D. S., et al., *Pharmacol Res*, 47: 373-81 (2003).
31. Mottershead, M., et al., *Expert Opin Biol Th*, 7: 1583-96 (2007).
32. Kapic, E., et al., *Medicinski Arhiv*, 58: 373-6 (2004).
33. Thanos, C. D., et al., *Proc Natl Acad Sci USA*, 103: 15422-7 (2006).
34. Hartmann, G., *Curr Opin Mol Ther*, 6: 221-7 (2004).
35. Eckenberg, R., et al., *Cell Mol Biol*, 47: 703-7 (2001).
36. Arkin, M. R., et al., *Proc Natl Acad Sci USA*, 100: 1603-8 (2003).
37. Braisted, A. C., et al., *J Am Chem Soc*, 125: 3714-5 (2003).
38. Hetschko, H., et al., *J Neuro-Oncol*, 86: 265-72 (2008).
39. Schwartz, P. S., et al., *Mol Cancer Ther*, 6: 2073-80 (2007).
40. Wang, L., et al., *Bioorg Med Chem Lett*, 18: 236-40 (2008).
41. Bykov, V. J., et al., *Nature Med*, 8: 282-8 (2002).
42. Bykov, V. J., et al., *J Biol Chem*, 280: 30384-91 (2005).
43. Issaeva, N., et al., *Nature Med*, 10: 1321-8 (2004).
44. Komarov, P. G., et al., *Science*, 285: 1733-7 (1999).
45. Kuppens, I. E., *Curr Clin Pharmacol*, 1: 57-70 (2006).
46. Galmarini, C. M., *Curr Opin Investig D*, 6: 623-30 (2005).
47. Barnham, K. J., et al., *Proc Natl Acad Sci USA*, 105: 6813-8 (2008).
48. Kelly, J. W., *New Engl J Med*, 352: 722-3 (2005).
49. Blazer, L. L., et al., *Neuropsychopharmacology*, (2008)
50. Takahashi, T., et al., *Accounts Chemical Res*, 41: 1309-18 (2008).
51. Green, N. S., et al., *J Am Chem Soc*, 125: 13404-14 (2003).
52. Van Cutsem, E., *Expert Opin Inv Drug*, 7: 823-34 (1998).
53. Taylor, E. C., *Adv Exp Med Biol*, 338: 387-408 (1993).
54. Dash, A. K., et al., *J Pharm Sci*, 85: 1123-7 (1996).
55. Jackman, A. L., et al., *Adv Exp Med Biol*, 370: 185-8 (1994).
56. Chu, E., et al., *Cancer Chemo Pharmacol*, 52: S80-9 (2003).
57. Kumar, S. K., et al., *J Med Chem*, 46: 2813-5 (2003).
58. Vassilev, L. T., *Cell Cycle*, 3: 419-21 (2004).
59. Shangary, S., et al., *Proc Natl Acad Sci USA*, 105: 3933-8 (2008).
60. Liu, Y., et al., *Biochemistry*, 42: 8862-9 (2003).
61. Schaack, J., et al., *J Virol*, 64: 78-85 (1990).
62. Jennings, L. D., et al., *Bioorgan Med Chem*, 12: 5115-31 (2004).
63. Hochberg, M. C., et al., *Ann Rheum Dis*, 62: 13-6 (2003).
64. Stebbins, J. L., et al., *Proc Natl Acad Sci USA*, 105: 16809-13 (2008).
65. Arthur, P. G., et al., *J Neurochem*, 102: 65-76 (2007).
66. Woodhouse, B. C., et al., *DNA Repair*, 7: 1077-86 (2008).
67. Ashworth, A., *J Clin Oncol*, 26: 3785-90 (2008).
68. Martin, S. A., et al., *Curr Opin GenDev*, 18: 80-6 (2008).
69. Haince, J. F., et al., *Trends Mol Med*, 11: 456-63 (2005).
70. Tenson, T., et al., *Mol Microbiol*, 59: 1664-77 (2006).
71. Carew, J. S., et al., *Cancer Lett*, 269: 7-17 (2008).
72. Shankar, S., et al., *Adv Exp Med Biol*, 615: 261-98 (2008).
73. Jones, P., et al., *Curr Pharm Design*, 14: 545-61 (2008).
74. Sun, H., et al., *Accounts Chemical Res*, 41: 1264-77 (2008).
75. Nikolovska-Coleska, Z., et al., *Anal Biochem*, 374: 87-98 (2008).
76. Plescia, J., et al., *Cancer Cell*, 7: 457-68 (2005).
77. Zhang, T., et al., *Mol Cancer Ther*, 7: 162-70 (2008).
78. Cruzado, J. M., *Transplantation Rev*, 22: 73-81 (2008).
79. LoPiccolo, J., et al., *Drug Res Update*, 11: 32-50 (2008).
80. Tsai, J., et al., *Proc Natl Acad Sci USA*, 105: 3041-6 (2008).
81. Echalier, A., et al., *J Med Chem*, 51: 737-51 (2008).
82. Bettayeb, K., et al., *Cancer Res*, 67: 8325-34 (2007).
83. Ji, Q. S., et al., *Mol Cancer Ther*, 6: 2158-67 (2007).
84. Guedat, P., et al., *BMC Biochemistry*, 8: S14 (2007).
85. Williamson, M. J., et al., *Mol Cancer Ther*, 5: 3052-6 (2006).

At their most basic level, coferons may interfere or enhance protein activity where the substrate ranges in size from a medium to macromolecule. For example, coferons may be designed to inhibit sequence-specific proteases, such as the caspases, which play a role in the apoptotic pathway (See FIGS. 13A and B).

Coferons may be used to inhibit or facilitate protein-protein interactions, including activating or inactivating a signaling pathway (FIGS. 13C, 15A and 15B). Coferons may activate signaling through more than one mechanism. For example, the coferon may do more than link two proteins together more tightly. It also further affects the conformation of the target protein so that it is more active compared to when the two proteins are bound in the absence of coferon (FIG. 15A). Alternatively, coferons may shift the equilibrium to tighter binding so that the numbers of complexes in the bound state is greater. In some cases, the coferon may act as a mimetic of a protein-protein interaction, either activating or inactivating signaling from that target (FIGS. 14D-G).

To illustrate these concepts, consider the Wnt signaling pathway, which is often disregulated in colon cancer. Wnt proteins bind to and activate the Frizzled receptor, which in turn act via Disheveled to suppress the activity of GSK-3β. Under normal conditions, GSK-3β is part of a complex with axin and APC, which binds β-catenin. However, when Disheveled suppresses the activity of GSK-3β, this prevents GSK-3β from phosphorylating β-catenin, which therefore escapes degradation and accumulates in the cytoplasm and in the nucleus. Once in the nucleus, β-catenin associates with Tcf/Lef transcription factor to drive the expression of a variety of genes, such as Myc, which enable cell proliferation.

In this Wnt signaling pathway, coferons could be designed to: (i) inhibit Wnt binding to Frizzled; (ii) inhibit frizzled activation of Disheveled; (iii) inhibit Disheveled inactivation of GSK-3β; (iv) enhance binding of β-catenin to Axin; and (v) inhibit binding of β-catenin to Tcf/Lef.

In colon tumors, the APC gene is often truncated or reduced in copy number or expression. Thus, it no longer binds β-catenin, liberating β-catenin to migrate into the nucleus. However, coferons designed to enhance binding of β-catenin to Axin, allow active GSK-3beta to phosphorylate β-catenin and send it down a path of degradation, thus avoiding proliferation and inhibiting tumor growth.

Some proteins, such as the tumor suppressor p53, are mutated in cancer cells, causing them to unfold more easily and thus not function properly. Binding of a coferon across the surface of such a protein may act as a molecular staple, keeping the domains or regions in the proper conformation (FIG. 16). Likewise, some proteins undergo conformational changes, which may activate or deactivate enzymatic activity or additional signaling. Coferons may be designed to bind one or the other conformer more tightly, and thus act as an activator or inhibitor of protein function (FIG. 14).

There are examples in nature where a small molecule (FK506, rapamycin) uses a helper protein (FKBP) to create a composite surface that binds the target protein (calcineurin, FRAP) more tightly. This helper protein may be used to either recruit additional protein(s) or inhibit binding of other proteins to the target protein. Coferons may be designed to mimic the role of FK506 to either enhance binding of a new protein to the complex (FIG. 18B, FIGS. 20A-C), or inhibit binding of a new protein to the complex (FIG. 19B). In these examples (FIG. 18B, FIGS. 20A-B), the linker elements were designed to mimic the portion of FK506 that binds tightly to FKBP ("orange" protein), but many other configurations may also be used.

Many proteins use protein interaction domains as modular units within their structure to achieve their desired functions. (See Table 2)

TABLE 2

Examples of Protein Domains

| DOMAIN | PARTNER | EXAMPLE OF PROTEIN CONTAINING DOMAIN | EXAMPLES OF KNOWN INHIBITORS | EXAMPLES OF DETECTION ASSAYS | APPROXIMATE $K_D$ OF BINDING PARTNERS |
|---|---|---|---|---|---|
| SH2 | Phospho-tyrosine residues | Grb2 | Fmoc-Glu-Tyr-Aib-Asn-NH2; Ac-SpYVNVQ-NH2, macrocycles, STATTIC[1-4] | Surface plasmon resonance (SPR) technology, | 0.2-11 μM[5-10] |
| FHA | Phospho-threonine and phospho-tyrosine residues | KIF13B | | | 1-100 μM[11, 12] |
| 14-3-3 | Phospho-serine residues | 14-3-3 | R18[13] | | 7 nM-20 μM[14-16] |
| WW | ligands containing PpxY, Proline-rich sequences | Pin1 | Zn(II) Dipicolylamine-based artificial receptors[17] | | 6 μM-190 μM[18-20] |
| WD40 | | Apaf-1 | | | 1 μM[21] |
| MH2 | phospho-serine residues | SMAD2 | | | 240 nM[22] |
| BROMO | acetylated lysine residues | CBP | | | 1 μM-4 mM[23-25] |
| UBA | mono-, di-, tri-, and tetra-ubiquitin | HHR23A | | | 6 μM-2.35 mM[26-28] |
| PTB | Phospho-tyrosine residues, Asn-Pro-X-Tyr motifs | IRS-1 | LSNPTX-NH2, LYASSNOAX-NH2, LYASSNPAX-NH2[29] | PTB domain binding assays | 160 nM-10 μM[30-33] |
| SH3 | Proline-rich peptides with consensus Pro-X-X-Pro | Grb2 | Peptidimer-c, VPPPVPPRRR, (VPPPVPPRRR)2K)[10, 34] | | 1-500 μM[10, 35-37] |
| EVH1 | FPxΦP motifs, PPxxF motifs | ActA | | | 10-50 μM[38-40] |
| GYF | proline-rich sequences, | CDBP2 | | | 10-160 μM[41] |
| VHS | | TOM1 | | | 11-50 μM[42-44] |
| PDZ | PDZ, Val-COOH | MNT1 | NSC668036, FJ9[45, 46] | | 1-500 μM[47-50] |
| PUF | RNA | PUM1 | | | 10-100 nM[51-53] |
| TUBBY | DNA, phosphotidylinositol | TULP1 | | | |
| SAM | | CNK | | | 71 nM-1 μM[54-56] |
| DD | DD | FADD | | | |
| CARD | CARD | Apaf-1 | | | 1.4 μM[57] |
| PyD | PyD | Pyrin | | | 4 μM[58] |
| PB1 | PB1 | Bem1 | | | 4-500 nM[59-61] |
| BRCT | BRCT | BRCA1 | | | 113 nM-6 μM[62-66] |
| PH | phosphatidylinositol-4,5-bisphosphate, PI-3, 4-P2 or PI-3,4,5-P3 | AKT1 | NSC 348900, perifosine, SH5, SH23, SH24, SH25, ml14, ml15, ml16[67-69] | | 1.76 nM-350 μM[30, 70-75] |
| FYVE | Phosphatidylinositol 3-phosphate, zinc | SARA | | | 50 nM-140 μM |
| C1 | phorbol esters, diacylglycerol | PKC isoforms | | | 0.58-800 nM[76-79] |

TABLE 2-continued

Examples of Protein Domains

| DOMAIN | PARTNER | EXAMPLE OF PROTEIN CONTAINING DOMAIN | EXAMPLES OF KNOWN INHIBITORS | EXAMPLES OF DETECTION ASSAYS | APPROXIMATE $K_D$ OF BINDING PARTNERS |
|---|---|---|---|---|---|
| FERM | PI(3)P, PI(4)P, PI(5)P, IP3, | PTLP1 | | | 200 nM-30 µM[80-82] |
| C2 | Calcium, acidic phospholipids | Nedd4 | | | 250 nM-94 µM[83-85] |
| PX | PI(3,4)P2, PI(3)P, PI(3,5)P2, PI(4)P, PI(5)P, PI(3,4,5)P3, PI(4,5)P2 | CISK | | | 1.8 nM-50 µM[36, 86, 87] |
| ENTH | PtdIns(4,5)P2, PtdIns(1,4,5)P3, PI(3,4)P2; PI(3,5)P2 | Epsin1 | | | 98 nM-1 µM[88-90] |

All of the following citations are hereby incorporated by reference in their entirety.
1. Choi, W. J., et al., *Bioorg Med Chem Lett*, 16: 5265-9 (2006).
2. Lung, F. D., et al., *Biopolymers*, 80: 628-35 (2005).
3. Ogura, K., et al., *J Biomol NMR*, 42: 197-207 (2008).
4. Schust, J., et al., *Chem Biol*, 13: 1235-42 (2006).
5. Domchek, S. M., et al., *Biochemistry*, 31: 9865-70 (1992).
6. Piccione, E., et al., *Biochemistry*, 32: 3197-202 (1993).
7. Case, R. D., et al., *J Biol Chem*, 269: 10467-74 (1994).
8. Ladbury, J. E., et al., *Proc Natl Acad Sci USA*, 92: 3199-203 (1995).
9. Porter, C. J., et al., *Eur Biophys J*, 34: 454-60 (2005).
10. Garbay, C., et al., *Biochem Pharmacol*, 60: 1165-9 (2000).
11. Byeon, I.-J. L., et al., *J Mol Biol*, 314: 577 (2001).
12. Byeon, I. J., et al., *Nat Struct Mol Biol*, 12: 987-93 (2005).
13. Petosa, C., et al., *J Biol Chem*, 273: 16305-10 (1998).
14. Masters, S. C., et al., *Biochemistry*, 38: 5216-21 (1999).
15. Rajagopalan, S., et al., *Nucleic Acids Res*, 36: 5983-91 (2008).
16. Wang, B., et al., *Biochemistry*, 38: 12499-504 (1999).
17. Ojida, A., et al., *J Am Chem Soc*, 128: 2052-8 (2006).
18. Koepf, E. K., et al., *Biochemistry*, 38: 14338-51 (1999).
19. Kanelis, V., et al., *Nat Struct Biol*, 8: 407-12 (2001).
20. Dalby, P. A., et al., *Protein Sci*, 9: 2366-76 (2000).
21. Nash, P., et al., *Nature*, 414: 514 (2001).
22. Chong, P. A., et al., *J Biol Chem*, 279: 40707-14 (2004).
23. Sun, H., et al., *Biochem Biophys Res Comm*, 358: 435 (2007).
24. Dhalluin, C., et al., *Nature*, 399: 491 (1999).
25. Mujtaba, S., et al., *Mol Cell*, 13: 251 (2004).
26. Murphy, J. M., et al., *Proc Natl Acad Sci USA*, 104: 14336-41 (2007).
27. Trempe, J. F., et al., *Embo J*, 24: 3178-89 (2005).
28. Matta-Camacho, E., et al., *J Mol Biol*, 386: 569 (2009).
29. Giorgetti-Peraldi, S., et al., *Mol Cell Biol*, 17: 1180-8 (1997).
30. Zwahlen, C., et al., *Embo J*, 19: 1505-15 (2000).
31. Li, S. C., et al., *Proc Natl Acad Sci USA*, 94: 7204-9 (1997).
32. Takeuchi, H., et al., *Biochem J*, 334: 211-8 (1998).
33. Dhalluin, C., et al., *Mol Cell*, 6: 921 (2000).
34. Ye, Y. B., et al., *Biochem Pharmacol*, 75: 2080-91 (2008).
35. Demers, J.-P., et al., *J Am Chem Soc*, 131: 4355-67 (2009).
36. Hiroaki, H., et al., *Nat Struct Biol*, 8: 526-30 (2001).
37. Donaldson, L. W., et al., *Proc Natl Acad Sci USA*, 99: 14053-8 (2002).
38. Zimmermann, J., et al., *J Biol Chem*, 278: 36810-8 (2003).
39. Ball, L. J., et al., *Embo J*, 19: 4903-14 (2000).
40. Machner, M. P., et al., *J Biol Chem*, 276: 40096-103 (2001).
41. Kofler, M., et al., *J Biol Chem*, 280: 33397-402 (2005).
42. Zhu, G., et al., *FEBS Lett*, 537: 171 (2003).
43. He, X., et al., *Biochemistry*, 42: 12174-80 (2003).
44. Yoon-Hun, H., et al., *FEBS Lett*, 583: 287 (2009).
45. Fujii, N., et al., *Cancer Res*, 67: 573-9 (2007).
46. Shan, J., et al., *Biochemistry*, 44: 15495-503 (2005).
47. Li, X., et al., *Protein Sci*, 15: 2149-58 (2006).
48. Hoffmoller, U., et al., *Angewandte Chemie International Ed*, 38: 2000-4 (1999).
49. Harris, B. Z., et al., *Biochemistry*, 40: 5921-30 (2001).
50. Niethammer, M., et al., *Neuron*, 20: 693 (1998).
51. Hook, B., et al., *Rna*, 11: 227-33 (2005).
52. Miller, M. T., et al., *Nat Struct Mol Biol*, 15: 397 (2008).
53. Stumpf, C. R., et al., *RNA*, 14: 1550-7 (2008).
54. Kim, C. A., et al., *Nat Struct Biol*, 9: 453-7 (2002).
55. Kim, C. A., et al., *J Biol Chem*, 280: 27769-75 (2005).
56. Bhunia, A., et al., *Proteins*, 74: 328-43 (2009).
57. Chen, Y. R., et al., *Protein Sci*, 13: 2196-206 (2004).
58. Srimathi, T., et al., *J Biol Chem*, 283: 15390-8 (2008).
59. Wilson, M. I., et al., *Mol Cell*, 12: 39 (2003).
60. Massenet, C., et al., *J Biol Chem*, 280: 13752-61 (2005).
61. Muller, S., et al., *FEBS Lett*, 580: 341-4 (2006).
62. Manke, I. A., et al., *Science*, 302: 636-9 (2003).
63. Williams, R. S., et al., *Nat Struct Mol Biol*, 11: 519-25 (2004).
64. Yu, X., et al., *Science*, 302: 639-42 (2003).
65. Ekblad, C. M., et al., *Protein Sci*, 13: 617-25 (2004).
66. Shiozaki, E. N., et al., *Mol Cell*, 14: 405 (2004).
67. Mahadevan, D., et al., *Mol Cancer Ther*, 7: 2621-32 (2008).
68. Kondapaka, S. B., et al., *Mol Cancer Ther*, 2: 1093-103 (2003).
69. Caron, R. W., et al., *Mol Cancer Ther*, 4: 257-70 (2005).
70. Chen, R. H., et al., *Embo J*, 16: 1351-9 (1997).
71. Zheng, J., et al., *J Mol Biol*, 255: 14 (1996).
72. Bourguignon, L. Y., et al., *J Biol Chem*, 279: 26991-7007 (2004).
73. Zhu, G., et al., *Embo J*, 26: 3484-93 (2007).
74. Levine, T. P., et al., *Curr Biol*, 8: 729 (1998).
75. Landgraf, K. E., et al., *Biochemistry*, 47: 12260-9 (2008).

76. Harjes, E., et al., *Structure*, 14: 881-8 (2006).
77. Lorenzo, P. S., et al., *Mol Pharmacol*, 57: 840-6 (2000).
78. Eing, A., et al., *Chembiochem*, 3: 190-7 (2002).
79. Aroca, P., et al., *FEBS Lett*, 483: 27-32 (2000).
80. Takai, Y., et al., *Acta Crystallogr F*, 63: 49-51 (2007).
81. Terawaki, S., et al., *Acta Crystallogr F*, 64: 911-3 (2008).
82. Yang, Y., et al., *Proc Natl Acad Sci USA*, 106: 4189-94 (2009).
83. Reddy Nanga, R. P., et al., *Protein Expr Purif* 52: 329-33 (2007).
84. Sanchez-Bautista, S., et al., *J MolBiol*, 362: 901 (2006).
85. Benes, C. H., et al., *Cell*, 121: 271-80 (2005).
86. Karathanassis, D., et al., *Embo J*, 21: 5057-68 (2002).
87. Stahelin, R. V., et al., *J Biol Chem*, 279: 54918-26 (2004).
88. Hom, R. A., et al., *J Mol Biol*, 373: 412-23 (2007).
89. Itoh, T., et al., *Science*, 291: 1047-51 (2001).
90. Hussain, N. K., et al., *J Biol Chem*, 278: 28823-30 (2003).

For example, SH2 domains are miniature receptors for protein regions containing a phosphorylated tyrosine. SH2 domains are found in proteins that act as, or play a role in: adaptors, scaffolds, kinases, phosphatases, ras signalling, transcription, ubiquitination, cytoskeletal regulation, signal regulation, and phospholipid second messenger signaling. As another example, SH3 domains bind peptide loops with the motif RXXK or PXXP. Many proteins have both SH2 and SH3 domains, which act as "receptors" to bind one or more protein partners. Coferons may be designed to inhibit binding of a phosphotyrosine protein to its cognate SH2 domain. Alternatively, coferons may be designed so one ligand binds one motif (i.e. SH2), and a second ligand binds a second motif (i.e. SH3), either on the same or different proteins.

Many large proteins or macromolecular complexes (such as ribosomes—see below, tubulin filaments) have multiple binding sites with known drug inhibitors. Coferons may be used to bring together two previous drugs on the same target to: (i) bind the target with higher affinity; (ii) exhibit a stronger inhibition than either drug alone; (iii) exhibit greater activation than either drug alone; or (iv) create a binding entity covering a larger surface area of the target, making it harder for the organism/cell/virus to develop resistance to the drug via point mutations.

Coferons may be used to create bifunctional drugs that bind to the same target, for example, protein receptor tyrosine kinases. One ligand would bind to the ATP binding site, while the other mimics the auto-inhibiting peptide. These two ligands would be attached to separate coferons, which when brought into the proper proximity by linker element binding, would lock down into both binding pockets and bind the receptor kinase with excellent specificity. This approach would overcome limitations of earlier inhibitor designs that bind only to one pocket and, consequently, lack either proper specificity, or sufficient binding affinity to be effective drugs in vivo.

Combining multiple known drugs using coferons may generate new classes of agonists or antagonists for: protein kinases, calcium channel proteins, muscarinic receptors (antagonists), beta-2 adrenergic receptor (agonist), sodium channel drugs, and H1 histamine receptor (antagonists). See Table 1. Receptor proteins provide multiple opportunities for coferon design to inhibit, activate, dampen, or amplify signals (FIG. 24 and FIG. 25).

Figure 23:
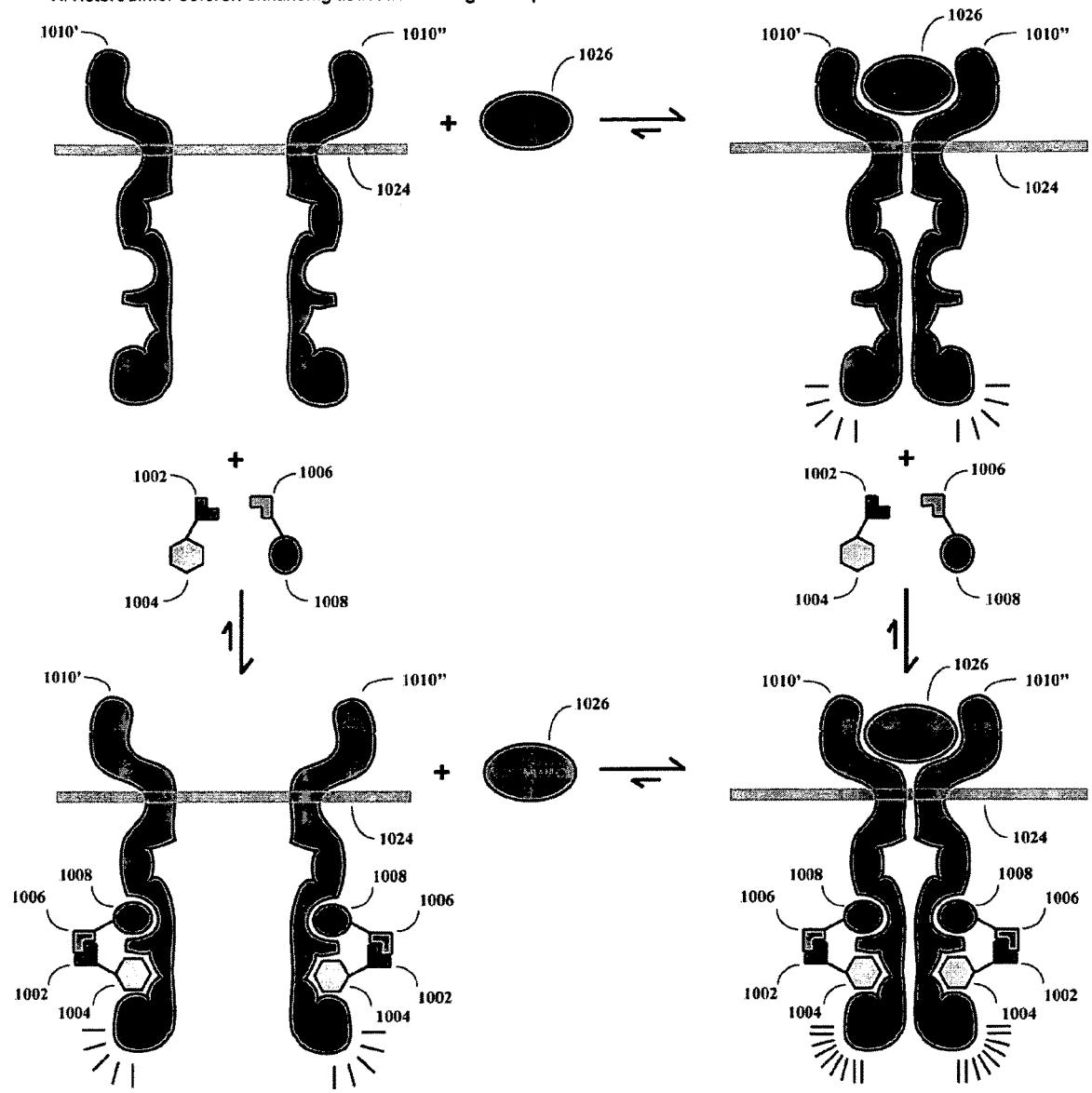
FIG. 23A shows variations of coferon drug interactions with target 1010'-1010". The first coferon with linker element 1002 and ligand 1004, second coferon with linker element 1006 and ligand 1008, and target proteins 1010' and 1010" are described above. Receptor dimer 1010'-1010" has natural ligand 1026 and is positioned on membrane 1024. Activation of target proteins 1010' and 1010", for example, by turning on a kinase activity, is illustrated by an arc of lines, with intensity of activation suggested by the number of lines in the arc.

Many proteins act as dimers. Homodimer coferons could act as agonists to help keep two receptors close enough for auto-phosphorylation and activation (FIG. 21 B2). Homodimers could also act as antagonists, by preventing two receptors from undergoing auto-phosphorylation (FIG. 22A). Coferon heterodimers may also act to dampen (FIG. 22B) or amplify (FIG. 23A) ligand directed signaling.

Use of coferon homodimers may also help inhibit dimer enzymes by blocking both ligand-binding sites simultaneously (FIG. 26A). Such homodimer, homotetramer, heterotetramer, hexamer, and other multimer coferons may have PEG linkers or other spacers to the linker elements, allowing for binding two sites that are several nanometers apart (FIGS. 26B and C, FIGS. 27A-C). They may use linker elements that bind to each other with minimal or no added help from the ligand binding events.

Many proteins have allosteric sites to either activate or inhibit enzymatic activity. Such sites are generally too distant from the active site to allow for a traditional small molecule drug to bind to both sites simultaneously. However, heterodimer coferons composed of ligands that bind into both the allosteric and either adjacent or active site regions would be potent activators or inhibitors.

Figure 28:
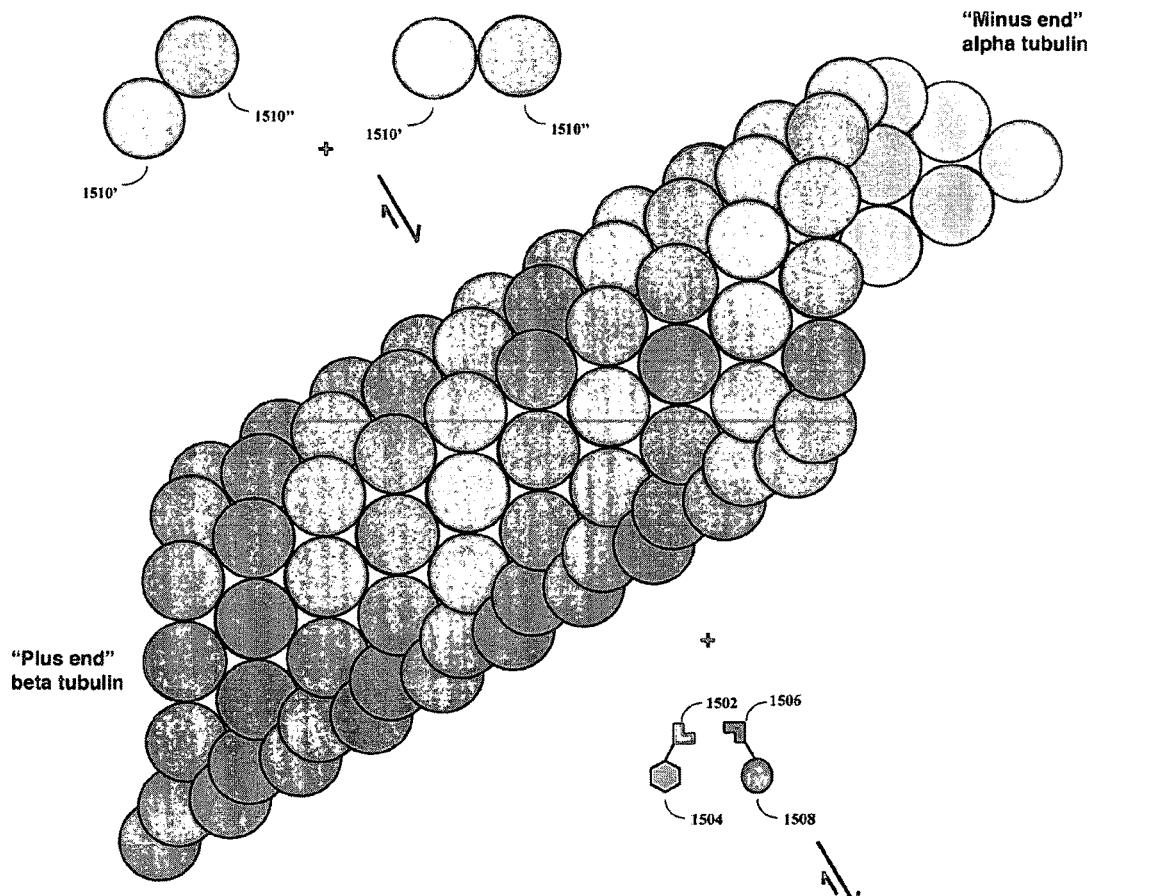
FIGS. 28A-B show the variations of coferon drug interactions with a target. The first coferon has linker element 1502 tethered to a hexameric ligand 1504, the second coferon is illustrated as a linker element 1506 tethered to an oval ligand 1508, and the target tubulin heterodimer as the circles 1510' and 1510".
Figure 30:
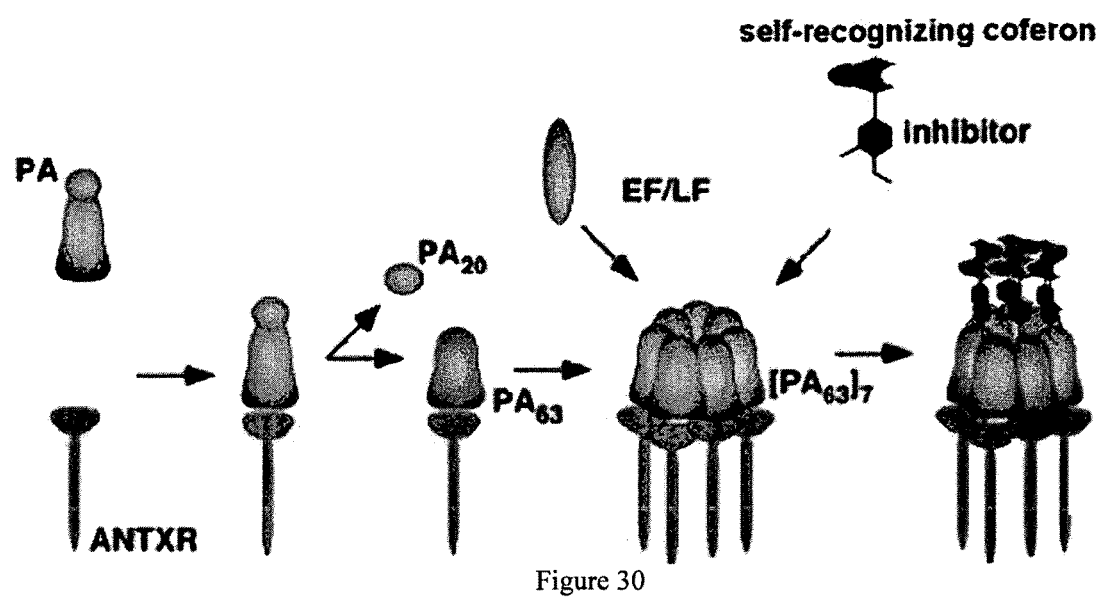
FIG. 30 is a schematic representation of a multimeric protein being inhibited by a coferon monomer that is capable of assembling in to a multimer. Protective antigen (PA) binds to the cellular anthrax receptor (ANTXR). The protective antigen is cleaved by a protease, while a 20 kDa fragment ($PA_{20}$) leaves, a 63 kDa fragment ($PA_{63}$) remains bound to the receptor. $PA_{63}$ self-associates forming a heptamer, $[PA_{63}]_{17}$, to which the edema factor (EF) and lethal factor (LF) bind. A coferon monomer that can self-assemble (self-recognizing coferon) in to a multimeric structure can bind and inhibit translocation of the EF/LF in to the cell.
Figure 31:
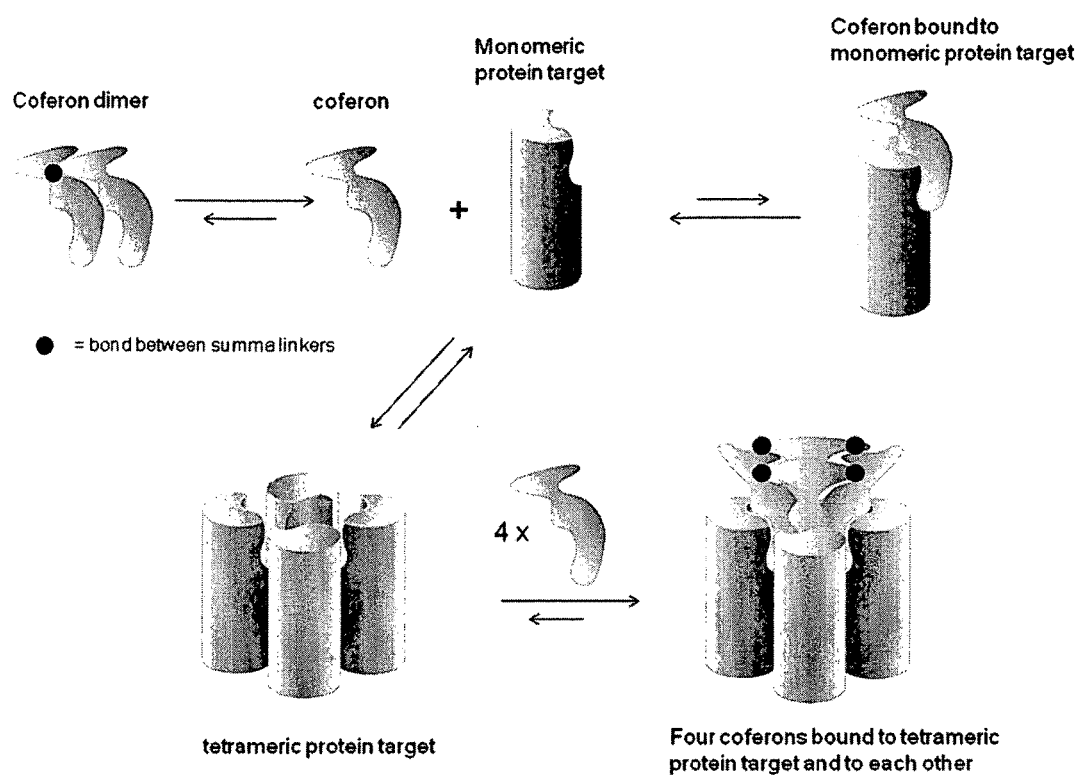
FIG. 31 is a schematic representation of a tetrameric protein being bound by a coferon that can assemble in to tetramers. The coferon dimer is in reversible equilibrium with the monomeric form of the coferon. The monomer can bind and inhibit the protein monomer by itself. If the protein monomers assemble to form a tetrameric protein target, the coferon monomers can bind the individual protein monomers thereby forming a tetrameric coferon.

Microtubulins play a key role during mitosis and differentiation, and thus are targeted in treating tumors. Microtubulins are composed of two subunits, alpha and beta tubulin that are in a dynamic instability either assembling or disassembling during the cell cycle. During mitosis, the rates of both assembly and disassembly are increased so that the chromosomes can capture the microtubules forming the mitotic spindle. During differentiation, microtubule-associated proteins help stabilize the filaments, thus allowing cellular cytoplasm to organize. Vinca alkaloid anticancer agents such as vincristine and vinblastine are cytotoxic by disrupting microtubules, while taxanes such as palitaxel and docetaxel stabilize microtubules, and thus may nudge tumor cells toward differentiation. Coferon pairs composed of one or two tubulin ligands may have enhanced antitumor activity (see FIG. 28).

Many neurodegenerative diseases arise due to misfolding of proteins that aggregate to form plaques. For example, Alzheimer's disease arises due to plaques composed of amyloid beta-peptide. Since coferons assemble at the target site, there is an opportunity to design coferons small enough to traverse the blood-brain barrier, yet large enough to combine on the surface of amyloid beta-peptide monomers and inhibit formation of oligomers and ultimately amyloid fibrils (FIG. 29).

Some linker element designs may allow linker elements to bind to each other with minimal or no added binding help from the pharmacophores. These designs expand the potential uses of coferons.

As another example of irreversible association within a cell, one coferon may have a disulfide group beta to a primary amine, while the other may have a ketone group. In the blood stream or in non-cancerous cells, the two coferons may associate through forming a Schiff base between the amine and the ketone group. However, upon entering cancer cells, the disulfide is reduced to a thiol, which may then act in concert with the primary amine to create a thiazolidine linker. Such dimer coferons may be used to bring two target proteins into close proximity.

Coferons using linker elements that bind to each other with minimal or no added help from the target binding event may be used to generate bifunctional drugs to different targets. Such drugs would concentrate two cancer-fighting ligands into the same cancer cell. This approach is also being used with HIV drugs.

Such coferons may also be used to create trap-door drugs. One coferon would be designed to bind to a target that is found in abundance in the target cancer cell, but not so frequently in normal cells. This coferon would be administered first to the patient. Subsequently, a second coferon with known drug moiety would be administered. The second coferon enters most cells, but then is preferentially trapped in target cancer cells. This approach may need to use coferons with almost irreversible linkages between linker elements.

The trap-door concept may be used in reverse to clog drug export pumps, many of which are responsible for resistance to chemotherapy. Coferons are designed to enter cells as monomers. One of the pharmacophores is a substrate for export. However, when the first coferon covalently attaches to second coferon, this creates a plug to clog the export pump. Such a coferon "plug" would be combined with a traditional cancer drug. This concept is similar to augmentin (amoxicillin clavulanate), where the clavulanic acid inhibits beta-lactamase.

The above examples emphasize the ability of coferons to inhibit, modulate, or activate protein-protein interactions. Coferons may also inhibit, modulate, or activate other major worlds of macromolecule interactions. For example, coferons may be used to tune protein-protein-nucleic acid interactions when transcription factors bind to dsDNA, or proteins that bind to RNA (e.g. ribosome). These could be every bit as significant wherein one targets the protein and the nucleic acid interaction by coferons. Many proteins undergo modifications (i.e. phosphorylation, acetylation, methylation, sumolation, prenylation, and ubiquitination), where these modifications allow for signaling, transport, or degradation through additional protein interactions. All of these processes may be inhibited or activated by judiciously designed coferons. Larger modifications, such as synthesis of glycoproteins provide the potential for coferons blocking interactions when proteins bind to the carbohydrate moieties.

Many proteins have signals to move them to various compartments or macromolecular structures.

Coferons may be used to bring together two proteins to either accelerate or inhibit movement of the two proteins to the: (i) membrane, (ii) cytoplasm, (iii) mitochondria, (iv) lysosome, (v) proteosome, (vi) golgi, (vii) endoplasmic reticulum, (viii) extracellular space, (ix) nucleus, (x) cellular filaments or scaffolding, or (xi) other intracellular or extracellular compartment, cellular structure, or space.

Coferons provide a unique opportunity for targeted entry into cancer cells. In the most direct form, folic acid is used as both the linker element and a means to transport the drug moiety into cancer cells. The folate transporter is found over-expressed in many cancers and especially in metastatic cancer cells. Thus, the folate transporter helps concentrate the drug molecule within cancer cells. Folic acid and derivatives are very "sticky" and tend to associate with each other. This association may be enhanced by addition of appropriate reactive groups (preferably, those forming reversible covalent bonds) to the two folic acid linker elements.

An alternative use of folic acid is as a transporter of a coferon precursor into the cells. Here, the folic acid group is linked to the coferon via a disulfide bond. Glutathione levels are 1,000-fold higher in tumor cells than in the blood. Inactive form of thiol-containing coferon is internalized, then opened by glutathione, brought into proximity with it's coferon pair (also activated by glutathione). The released thiol groups are then available to participate in crosslinking reactions when two coferons come together ultimately leading to cell death. This approach has the advantage that the coferon drug molecules are in an inactive precursor form in the blood stream as well as normal cells, but are activated upon entering cancer cells.

Potential transporters of coferon or coferon-cofactors include: glucose transporter, taurine transporter, cationic amino acids transporter, organic anion transporter, proline transporter, monoamine transporter, Anion exchange transporter, folate transporter, monocarboxylic acid transporter, Zn transporter, amino acid transporter, Na dependent vitamin transporter, fatty acid transporter, nucleoside transporter, and proton-coupled divalent metal ion transporter.

Subunits of the above transporters are overexpressed in both primary and metastatic colon tumors. Use of transporters or receptors may provide a second life for existing drugs. An existing drug is attached to a linker element that binds its pair independent of target to create the first coferon. The second coferon has affinity to transporter specific to the target organ or target tumor, specific to a receptor protein on the cell surface or even to a cytoplasmic protein, any one of which may help pull the drug on the first coferon into the desired cells. Some uptake systems bring the solute into an endosome where it is released from the transporter (for example by a change in pH). In some of these cases, the drug molecule may still need to cross a membrane. One advantage of coferons is that the linker element portion may be modified, for example made more lipophilic, such that the entire coferon is more easily transported into the target cell.

Cancer cells provide multiple opportunities to take advantage of the unique properties of coferons. For example, coferon pairs may be synthesized to contain spatially separated ketone and a disulfide group two carbons from a primary or secondary amine. When screening for suitable pharmacophores in vitro, the disulfide group remains oxidized. Coferon pairs can form via a reversible imine (primary amine) or imminium ion (secondary amine) formation. Dynamic combinatorial chemistry is used to select the best pharmacophores. When the winning pair of coferons is introduced into the patient, the coferons remain as monomers (occasionally associating to form dimers) until they enter the cell. The disulfide bond is reduced by internal glutathione, and then the liberated thiol group on the coferon can now react with the imine or imminium ion to form an irreversible thiazolidine link between the two coferon pairs. Judicious choice of the linker element design can drive the reaction forward only inside cancer cells containing the desired target.

Additional approaches to unmasking reactive groups of coferons upon entering target cells include but are not limited to use of esterases to cleave esters and liberate a reactive alcohol group, and peptidases to liberate a reactive amino group.

Coferons as Multivalent Drugs Against Bacteria.

There are a number of antibiotics that inhibit or interfere with proper ribosome function. Aminoglycosides (gentamicin, tobramycin, amikacin, kanamycin, neomycin, paromomycin) induce formation of aberrant, nonfunctional complexes, as well as causing misreading of the mRNA. In a second mechanism, some aminoglycosides also prevent the transfer of peptidyl tRNA from the A-site to the P-site, thus preventing elongation of the polypeptide chain. Aminoglycosides bind irreversibly to specific ribosomal proteins. Streptomycin binds S12 in 30S subunit, while others bind to the L6 protein of the 50S subunit.

Tetracyclines (tetracycline, minocycline, doxycycline, demeclocycline) binds reversibly to 30S ribosome.

Inhibits binding of aminoacyl tRNA into the A site of the bacterial ribosome. Chloramphenicol inhibits peptide bond formation by binding to a peptidyltransferase enzyme on the 50S ribosome.

Macrolides (erythromycin, azithromycin, clarithromycin, dirithromycin) are large lactone ring compounds that bind reversibly to the 50S ribosomes and impair the peptidyltransferase reaction (i.e. prevent forming a peptide bond between the amino acids), or translocation (i.e. preventing transfer of the peptidyl tRNA from the A-site to the P-site), or both.

Oxazolidinones (Linezolid) bind to the 50S subunit and interfere with formation of the mRNA, f-met-tRNA and 50S subunit complex. Lincosamides (clindamycin) also inhibits protein synthesis by binding to the 50S ribosome.

Coferon dimers containing one each of the above drugs from two different binding regions as the ligands may show greater biological activity than the monomers. This may be especially true if the drugs bind synergistically, and are kept in the approximate proper orientation by the linker element tether. Such drugs may also stay within cells longer, allowing for more intermittent dosing of the drug. Finally, it may be more difficult for the bacteria to mutate both monomeric drug binding sites simultaneously.

Coferons as Drugs Against Rapidly Evolving Viruses.

RNA viruses are a constant public health threat as their rapidly evolving genomes have outwitted repeated attempts to generate neutralizing antibodies or vaccines. The last 20 years has seen enormous strides in the synthesis of inhibitors to various viral proteins, such as proteases and reverse transcriptase. Nevertheless, in time, viruses escape these drugs through mutational selection to resistance. Coferons provide two unique opportunities to inhibit RNA viruses. Resistant variants for many existing drugs are now known, and thus coferons may be screened against both sensitive and resistant variants, allowing for selection of the winning families or clades of coferon monomers. Use of a limited number of each family member (for example 10 each for coferon "A" and coferon "B") allows for addition of a "therapeutic cocktail" where the protein target selects the tightest binding pair (which will be 10% of the total molecules) and thus selects for its own strongest inhibitor. A second opportunity arises from viral protein interactions with a human host protein, and this interaction may be disrupted by identifying coferons that bind to the host protein, or bind and recruit a second protein to the host protein, and thus either directly or indirectly inhibit binding of the viral protein to the host protein. Below are some examples based on HIV.

HIV Protease

From structural work and alanine scanning mutagenesis studies, the contact points for HIV protease and its substrates are determined. Then, families of "A" and "B" coferons are designed, such that the combination of A+B provide enough structural space to allow binding to mutational variations in the target HIV protease, thus achieving desired inhibition of said protease. Since coferons A+B bind reversibly, dynamic combinatorial chemistry will assure that each protease variant binds the tightest inhibitor combination.

HIV Entry

HIV entry into cells depends on binding to the CCR5 receptor. While attempts to make vaccines to the HIV envelope protein have been unsuccessful, coferons could be designed to bind to the CCR5 receptor, either as a dimer, tetramer, or recruiting another protein to CCR5, thus blocking the HIV from binding to the same receptor.

HIV Reverse Transcriptase

Traditional reverse transcriptase inhibitors are based on nucleotide analogues. However, resistant variant reverse transcription easily arises. Coferons could be more effective in inhibiting this enzyme by designing a family of nucleotide analogs "A" which bind both "wild-type" and different drug resistant variations of HIV reverse transcriptase, and a family of second drugs "B" that bind the HIV RT elsewhere. Combining coferons A+B provides enough structural space to allow binding to mutational variations in the target HIV reverse transcriptase, while still inhibiting its activity.

HIV Vif Protein

Human cellular protein A3G sabotages HIV by dramatically mutating its genes. HIV Vif protein interferes with this process. One approach is to use coferons to generate a mimetic decoy of A3G, such that the HIV Vif protein binds the coferons instead of the A3G protein. A second approach is to use coferons to bind to A3G, or bind and recruit another cellular protein to A3G, thus blocking Vif binding to A3G. Since A3G is a human protein, and not undergoing the same mutational drift as the HIV Vif protein, it is easier to design coferons that either mimic, or bind to A3G.

HIV Integrase

HIV integrase, with the help of the human cellular protein LEDGF, integrates the ds DNA copy of the virus into the human genome. Coferons may be selected to interfere with HIV integrase activity, as well as integrase binding to LEDGF. As above, since LEDGF is a human protein, and not undergoing the same mutational drift as the HIV integrase protein, it is easier to design coferons that either mimic, or bind to LEDGF.

Mother-Child Coferons

Figure 32:
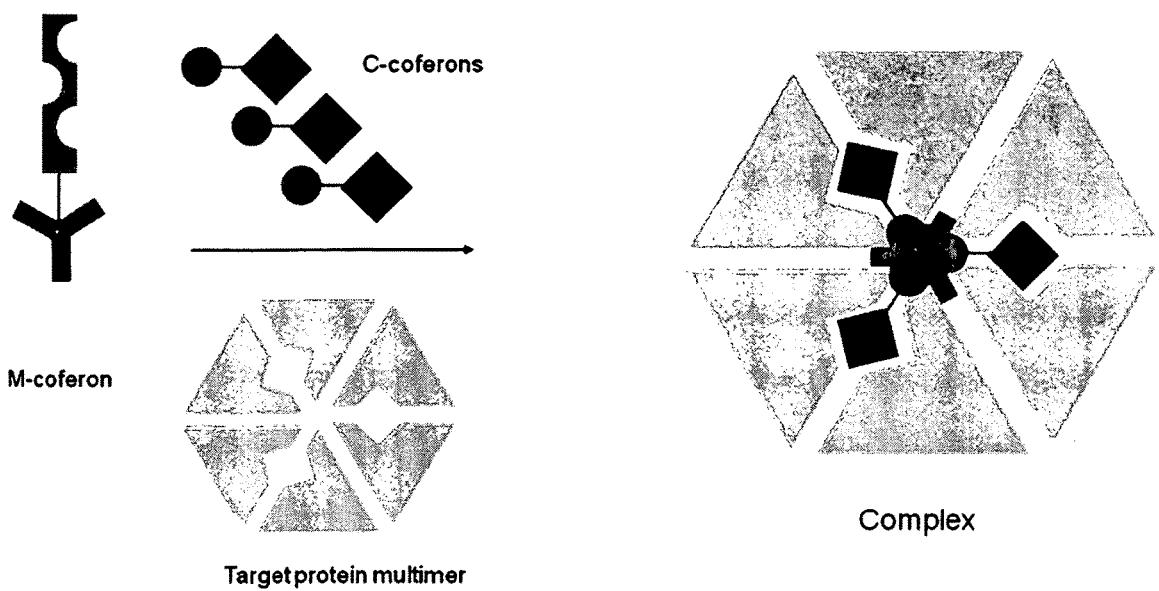
FIG. 32 is a schematic drawing of a coferon drug with mother-child linker elements.

Derivatives based on mother-child linker elements (M-Coferons) M-coferons are coferons that possess a single "mother" linker element capable of linking to multiple "child" linker elements from C-coferons. The M,C coferon system is designed to target protein multimers, especially those that contain a channel or cavity. Examples would include transporters (p-glycoprotein, polyamine transporter), proteasomes, viral protein coats, biomolecular machines. This is illustrated in FIG. 32.

An example of the M,C coferon system which utilizes a disaccharide (lactose in the following example) as the M-coferon and a boronate as the C-coferon. Disaccharides are of particular interest since there are specific transporters for them, e.g. galactose receptors are found on the surface of cancer cells.

Mother coferon

Child coferon

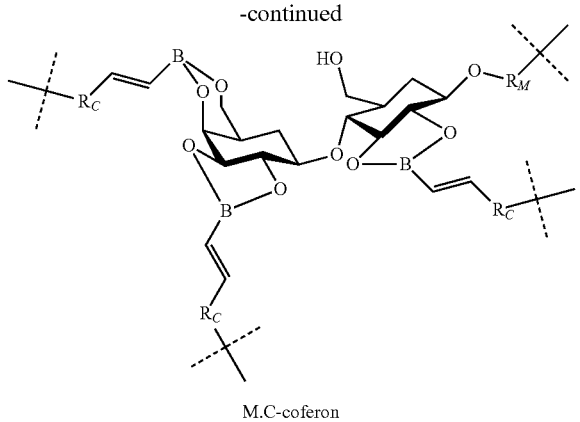

M.C-coferon

Non-saccharide polyols may also serve as M-coferons as shown in the example below.

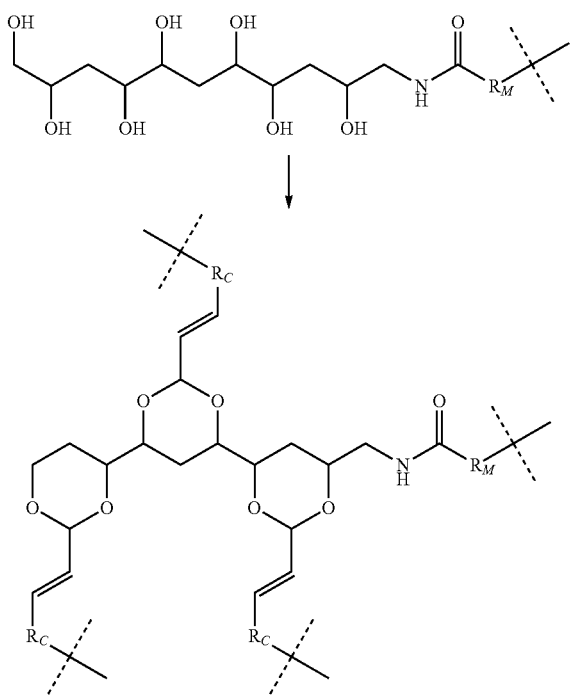

Selection Based on Screening

Coferons may be thought of as miniature antibodies that may disassemble outside a cell and reassemble inside a cell to influence macromolecule interactions. There are two issues at play, how well the coferon can distinguish between the correct target and other closely related targets (i.e. specificity), and how it modulates the biological activity in question.

The evolutionarily driven selections described above are all based on binding to the target, but they do not address binding to a specific surface or face of the target, nor do they address the specificity issue. For example, aptamers can be selected to bind known proteins with very high binding affinities; however, these often turn out to be driven by the negatively charged DNA backbone interacting with positively charged residues on the protein target—and such aptamers often have substantial non-specific binding to incorrect targets.

With current recombinant techniques, it is straightforward to generate purified wild-type and specific mutant variants of virtually any protein, covalently attach protein targets to solid surfaces such as beads, as well as fluorescently label such proteins. In addition, there are several reagents for attaching fluorescent and quenching groups onto small molecules, binding ligands etc. Combinations of such groups may be used to detect close binding of two macromolecules by observing a FRET signal, or conversely, detect two macromolecules no longer binding by separating the fluorescent group from a nearby quenching group. Finally, for many protein targets that require an energy source, such as ATP, to signal or function properly, there are many analogues which may "freeze" the protein in either an "active" or "inactive" conformation.

Selecting coferons to bind to a particular face or substrate-binding pocket of a protein. Under these conditions a non-binding target protein is synthesized or engineered, wherein the protein contains one or more mutations or chemical modifications or inhibitor binding to the face in question, such that the non-binding target protein no longer has the ability to bind its partner protein, or substrate.

When one coferon is attached to a bead, and the binding of protein is detected using a fluorescently labeled protein: Add unlabeled engineered non-binding target protein at a molar excess to the labeled target protein, for example at a 100:1 excess. Beads containing coferon pairs that bind uniquely to the target protein but not the engineered non-binding target protein will bind fluorescently labeled protein and can then be distinguished.

When the protein is attached to beads, and the coferon selected by tighter binding to the protein on beads: target proteins can be attached to magnetic beads, or coded beads that may be separated from the other beads. Engineered non-binding target protein may be attached to other beads, which are present at a greater level, for example at a 100:1 excess. Excess beads containing engineered non-binding target protein will swamp out coferons binding at the wrong surface. However, coferons binding the correct surface of target proteins may be selected by (i) magnetic separation or (ii) FACS sorting of these beads, respectively.

Selecting coferons to bind to a particular conformation of the protein, for example when it is binding ATP. Under these conditions, a non-reversible ATP analogue is used to bind to the protein to "freeze" it in the active conformation. Under these conditions a non-analogue binding target protein is synthesized or engineered, where the protein contains one or more mutations or chemical modifications, such that the non-analogue binding target protein no longer has the ability to "freeze" it in the active conformation.

When one coferon is attached to a bead, and the binding of protein in the active conformation is detected using a fluorescently labeled protein bound to the non-reversible analogue substrate, unlabeled engineered non-analogue binding target protein is added at a molar excess to the labeled target protein, for example at a 100:1 excess. Beads containing coferon pairs that bind uniquely to the target protein but not the engineered non-analogue binding target protein will bind to fluorescently labeled protein and can then be distinguished.

When the protein in the active conformation is attached to beads, and the coferon selected by tighter binding to the protein on beads, target proteins in the active conformation are attached (by using the non-reversible analogue substrate) to magnetic beads, or coded beads that may be separated from the other beads. Engineered non-analogue binding target protein are attached to other beads, which are present at a greater level, for example at a 100:1 excess. Excess beads containing engineered non-analogue binding target protein will inhibit coferons binding the wrong conformation. However, coferons binding the correct conformation of target proteins may be selected by (i) magnetic separation or (ii) FACS sorting of these beads, respectively.

Coferons can be selected to bind to a particular face of a protein to interfere with that protein binding a second protein.

When one coferon is attached to a bead, and the binding of target protein is detected using a fluorescently labeled protein, a target protein with a fluorescent signal, and an excess of secondary protein with quenching group(s) that binds to the target protein are used to quench the fluorescent signal. Beads containing coferon pairs that bind uniquely to the target protein in a way that interferes with binding of the second protein will bind fluorescently labeled protein and can then be distinguished.

Coferons can be selected to bind to enhance a protein-protein binding interaction.

When one coferon is attached to a bead, and the binding of target protein is detected using a fluorescently labeled protein, use a target protein with a fluorescent signal, and a secondary protein with another fluorescent group that will generate a FRET signal when binding to the target protein. Beads containing coferon pairs that bind uniquely to the target protein and second target protein so as to enhance their interaction will generate a FRET signal and can then be distinguished.

Coferons can be selected to inhibit or enhance enzymatic action or protein function.

When one coferon is attached to a bead, and the binding of target protein is detected using a fluorescently labeled protein, those beads which are fluorescently labeled are selected, indicating binding of proteins into microtiter wells, and assay for individual protein activity.

General Method for the Preparation of Coferon Monomers

Coferon monomers are comprised of a pharmacophore, a connector and a linker element. Various linker elements provide different equilibrium properties between the monomer and dimer or multimer form, have different geometries that allow for connectors or pharmacophores to be oriented in appropriate fashion, and span different distances. One approach to making coferon monomers for a specific target involves selecting appropriate pharmacophores identified through literature precedents or crystal structures, determining the geometry and spacing required to span the distance between the pharmacophores and selecting the appropriate linker elements and connectors that provide the optimum spacing and geometry. In silico methods can be employed to aid in the selections of the best permutations of pharmacophore, connector and linker. Virtual screening of the permutations using docking and scoring of coferons to known structures of the macromolecular target (e.g. from NMR or x-ray methods), either directly or in combination with ligand-based pharmacophore models can aid in selecting the most promising Coferon designs. Alternatively, in silico methods may start from a known co-crystal structure of an inhibitor bound to the macromolecular target, and virtually replace regions of the inhibitor scaffold with novel linker elements to produce coferon designs. A series of candidate coferon monomers can then be synthesized by combining the selected pharmacophores, connectors, and linker elements in a combinatorial fashion. The coferon monomers can then be screened against the target to determine the best candidates. An analogous approach is to design pharmacophores from a fragment based drug design screen or a structure based drug design virtual screen, and combine the pharmacophores, connectors, and linker elements in a combinatorial fashion. The coferon monomers can then be screened against the target to determine the best candidates.

A third approach is to prepare a library of coferon monomers by combining various known pharmacophores as well as molecules containing known and unknown pharmacophoric elements with a variety of connectors and linker elements in a combinatorial fashion. The coferon monomers can then be screened in a combinatorial fashion to find the best pairs of monomers for a specific target.

Specific Examples of Coferons

Coferons Targeted Towards Human Mast Cell β-Tryptase-II

The human mast cell β-tryptase-II is a tetrameric serine protease that is concentrated in mast cell secretory granules. The enzyme is involved in IgE-induced mast cell degranulation in an allergic response and is potentially a target for the treatment of allergic asthma, rhinitis, conjunctivitis and dermatitis. Tryptase has also been implicated in the progression of renal, pulmonary, hepatic, testicular fibrosis, and inflammatory conditions such as ulcerative colitis, inflammatory bowel disease, rheumatoid arthritis, and various other mast cell-related diseases. Hence, potent selective inhibitors of this target have significant therapeutic potential.

Coferons Based on Hydroxypyruvylamide Linker Elements

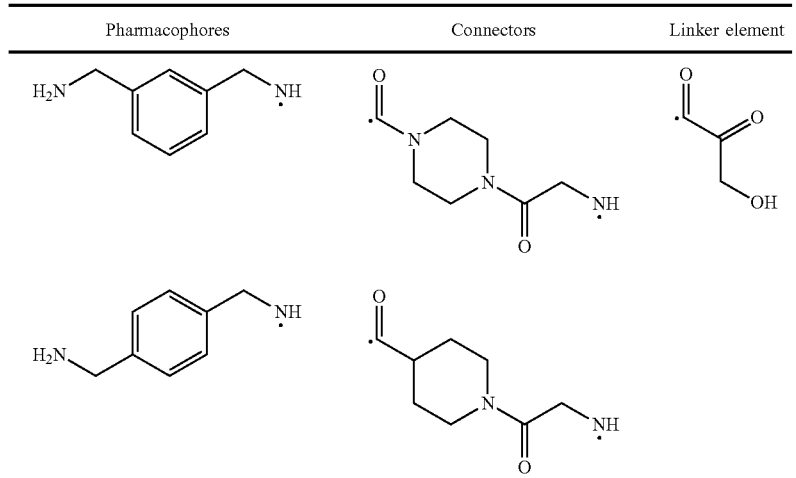

-continued
| Pharmacophores | Connectors | Linker element |
|---|---|---|
| 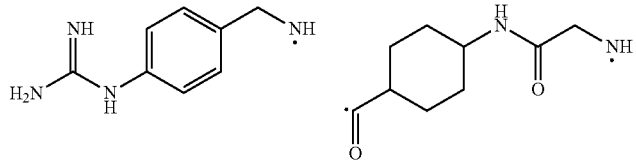 | | |
| 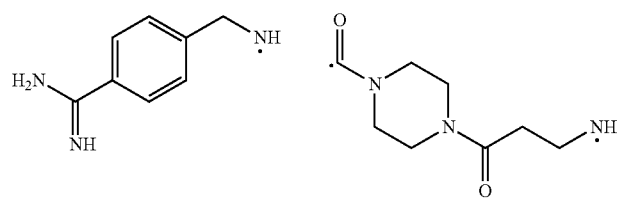 | | |
| 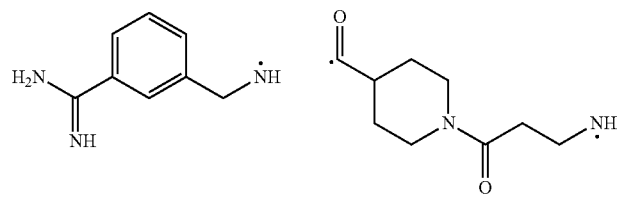 | | |
| 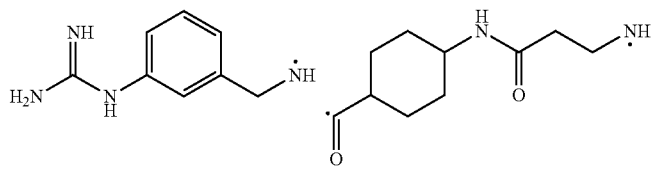 | | |
| 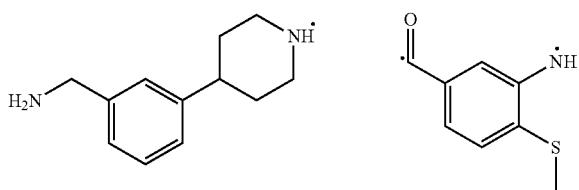 | | |
| 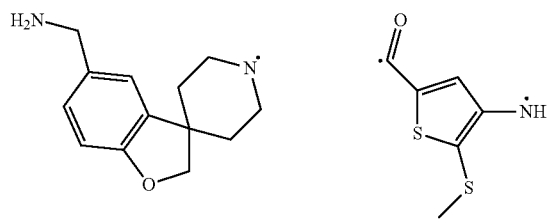 | | |
| | 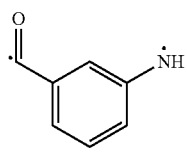 | | where carbonyl groups of the linker elements are covalently linked to the amine groups of the connectors indicated by dots and the carbonyl groups of the connectors are covalently linked to the amine groups of the pharmacophores indicated by dots.

A few examples of coferon monomers containing hydroxypyruvylamide linker elements and the dimers formed from them are shown below. In each case only a single diastereomer of a diketal or dioxanyl dimer is shown although the active species may include one or more diketal or spiroketal (dioxolanyl) diastereomers.

Coferon Monomer

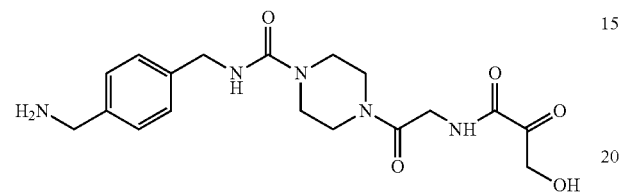

N-(4-(ammnomethyl)benzyl)-4-(2-(3-hydroxy-2-oxopropanamido)acetyl)piperazine-1-carboxamide Coferon Dimer

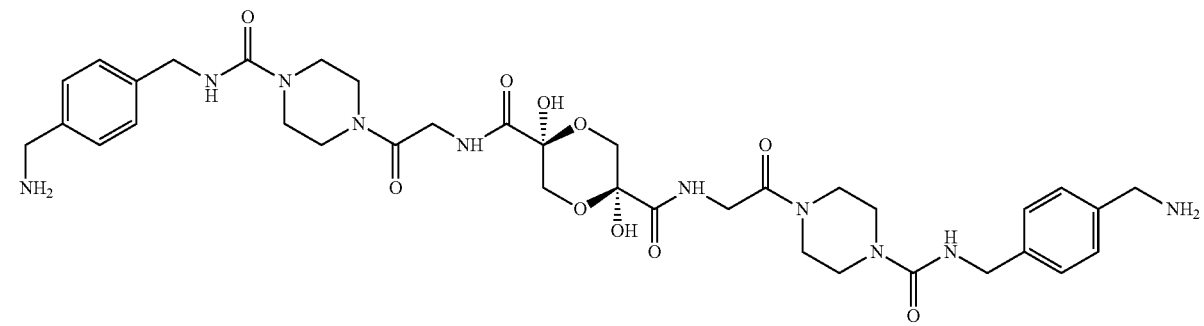 [SMILES: NCc1ccc(CNC(=O)N2CCN(C(=O)CNC(=O)[C@]3(O)CO[C@](O)(C(=O)NCC(=O)N4CCN(C(=O)NCc5ccc(CN)cc5)CC4)CO3)CC2)cc1]

(2S,5S)—N2,N5-bis(2-(4-(4-(aminomethyl)benzylcarbamoyl)piperazin-1-yl)-2-oxoethyl)-2,5-dihydroxy-1,4-dioxane-2,5-dicarboxamide Coferon Monomer

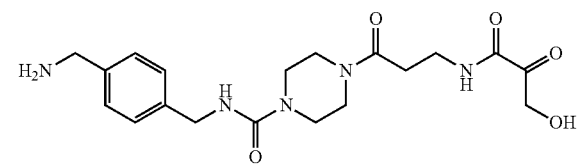 [SMILES: NCc1ccc(CNC(=O)N2CCN(C(=O)CCNC(=O)C(=O)CO)CC2)cc1]

N-(4-(aminomethyl)benzyl)-4-(3-(3-hydroxy-2-oxopropanamido)propanoyl)piperazine-1-carboxamide Coferon dimer

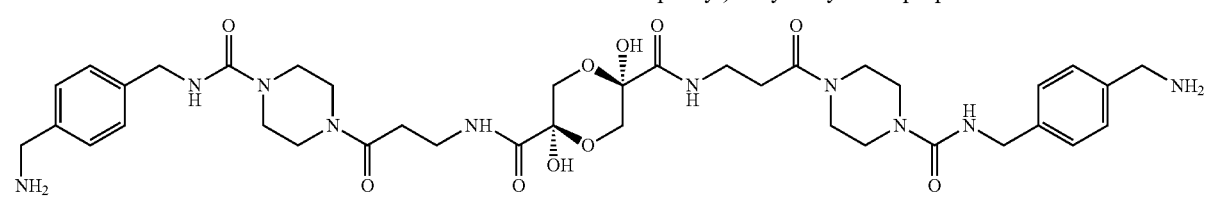

(2R,5R)—N2,N5-bis(3-(4-(4-(aminomethyl)benzylcarbamoyl)piperazin-1-yl)-3-oxopropyl)-2,5-dihydroxy-1,4-dioxane-2,5-dicarboxamide Coferon Monomer

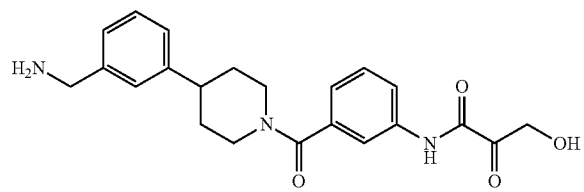 [SMILES: NCc1cccc(C2CCN(C(=O)c3cccc(NC(=O)C(=O)CO)c3)CC2)c1]

N-(3-(4-(3-(aminomethyl)phenyl)piperidine-1-carbonyl)phenyl)-3-hydroxy-2-oxopropanamide Coferon dimer
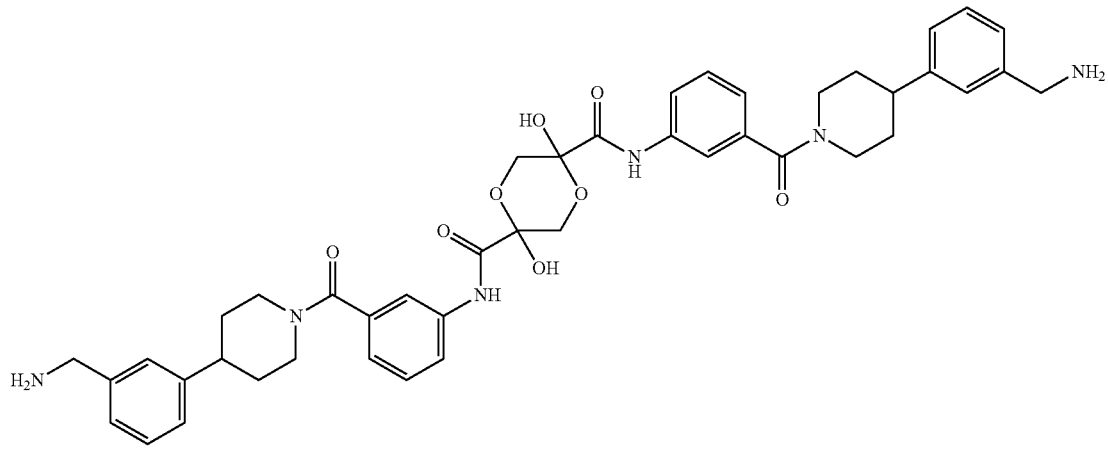 [SMILES: NCc1cccc(C2CCN(C(=O)c3cccc(NC(=O)C4(O)COC(O)(C(=O)Nc5cccc(C(=O)N6CCC(c7cccc(CN)c7)CC6)c5)CO4)c3)CC2)c1]
Coferon Monomer
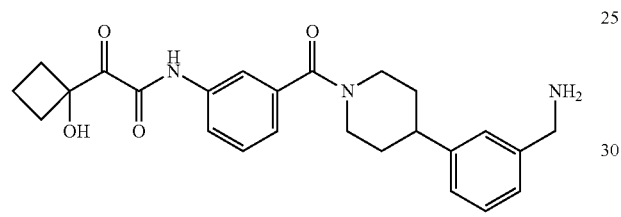
Coferon dimers
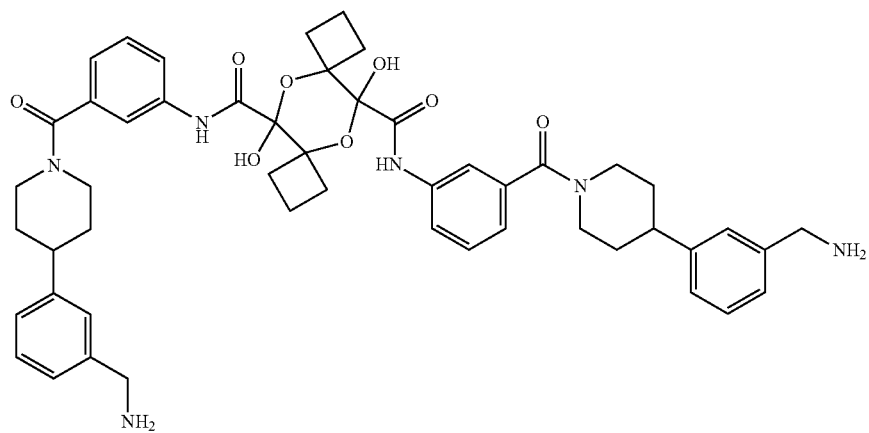
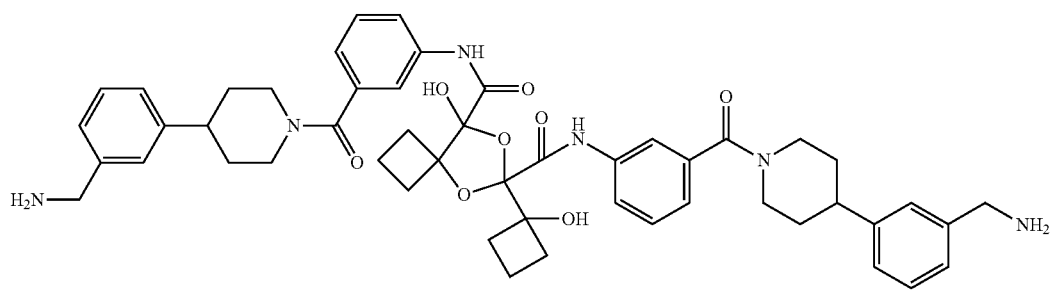

Coferons Based on Hydroxyacetone Linker Elements

| Pharmacophores | Connectors | Linker element |
|---|---|---| where linker elements are covalently linked to the oxygen of the connectors through the atoms indicated by the dots and the carbonyls of the connectors are covalently linked to the amines of the pharmacophores through the atoms indicated by dots.

A few examples of coferon monomers containing hydroxyacetone linker elements and the dimers formed from them are shown below. In each case, only a single diastereomer of a diketal dimer is shown although the active species may include one or more diketal or spiroketal diastereomers.

Coferon Monomer

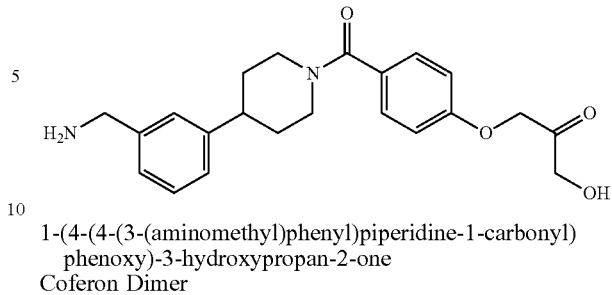

1-(4-(4-(3-(aminomethyl)phenyl)piperidine-1-carbonyl)phenoxy)-3-hydroxypropan-2-one
Coferon Dimer

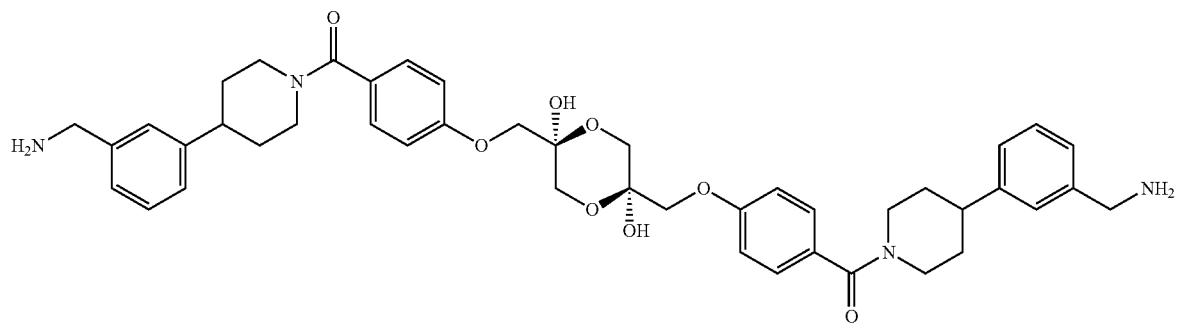 [SMILES: NCc1cccc(C2CCN(C(=O)c3ccc(OC[C@]4(O)CO[C@](O)(COc5ccc(C(=O)N6CCC(c7cccc(CN)c7)CC6)cc5)CO4)cc3)CC2)c1]

(4,4'-((2R,5R)-2,5-dihydroxy-1,4-dioxane-2,5-diyl)bis(methylene)bis(oxy)bis(4,1-phenylene))bis((4-(3-(aminomethyl)phenyl)piperidin-1-yl)methanone)
Coferon Monomer

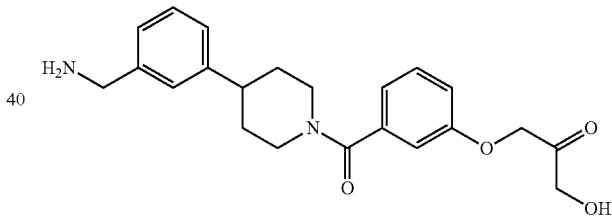

1-(3-(4-(3-(aminomethyl)phenyl)piperidine-1-carbonyl)phenoxy)-3-hydroxypropan-2-one
Coferon Dimer

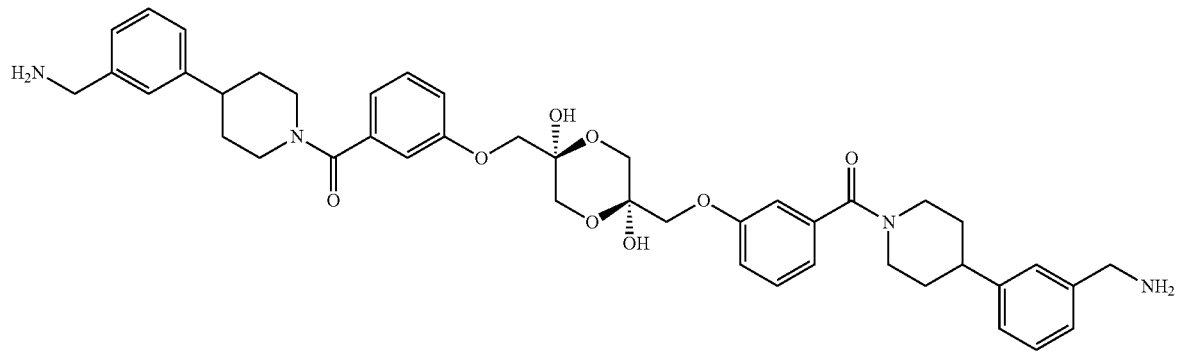 [SMILES: NCc1cccc(C2CCN(C(=O)c3cccc(OC[C@]4(O)CO[C@](O)(COc5cccc(C(=O)N6CCC(c7cccc(CN)c7)CC6)c5)CO4)c3)CC2)c1]

(3,3'-((2R,5R)-2,5-dihydroxy-1,4-dioxane-2,5-diyl)bis (methylene)bis(oxy)bis(3,1-phenylene))bis((4-(3-(aminomethyl)phenyl)piperidin-1-yl)methanone)
Coferon Monomer

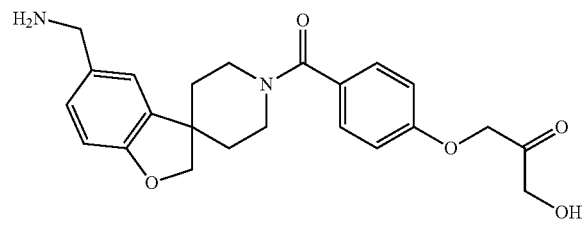 [SMILES: NCc1ccc2c(c1)C1(CCN(C(=O)c3ccc(OCC(=O)CO)cc3)CC1)CO2]

1-(4-(5-(aminomethyl)-2H-spiro[benzofuran-3,4'-piperidine]-1'-ylcarbonyl)phenoxy)-3-hydroxypropan-2-one
Coferon Dimer

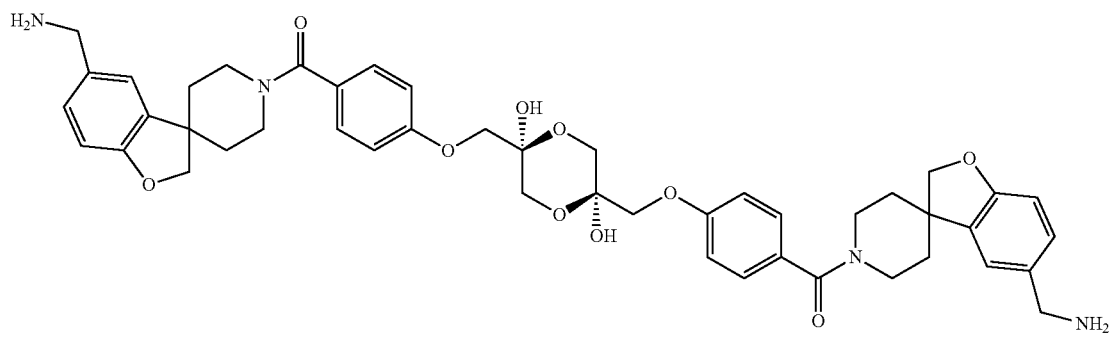 [SMILES: NCc1ccc2c(c1)C1(CCN(C(=O)c3ccc(OC[C@]4(O)CO[C@](O)(COc5ccc(C(=O)N6CCC7(CC6)COc6ccc(CN)cc67)cc5)CO4)cc3)CC1)CO2]

(4,4'-((2R,5R)-2,5-dihydroxy-1,4-dioxane-2,5-diyl)bis (methylene)bis(oxy)bis(4,1-phenylene))bis((5-(aminomethyl)-2H-spiro[benzofuran-3,4'-piperidine]-1'-yl)methanone)
Coferon Monomer

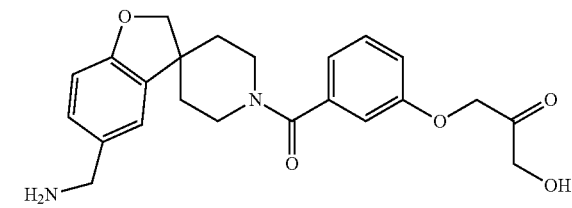 [SMILES: NCc1ccc2c(c1)C1(CCN(C(=O)c3cccc(OCC(=O)CO)c3)CC1)CO2]

1-(3-(5-(aminomethyl)-2H-spiro[benzofuran-3,4'-piperidine]-1'-ylcarbonyl)phenoxy)-3-hydroxypropan-2-one
Coferon Dimer (3,3'-((2R,5R)-2,5-dihydroxy-1,4-dioxane-2,5-diyl)bis (methylene)bis(oxy)bis(3,1-phenylene))bis((5-(aminomethyl)-2H-spiro[benzofuran-3,4'-piperidine]-1'-yl)methanone)
Coferon Monomer

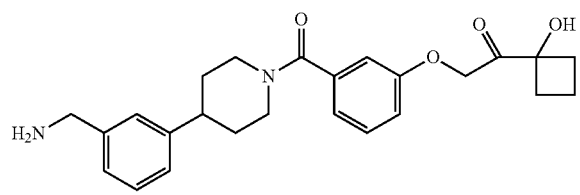

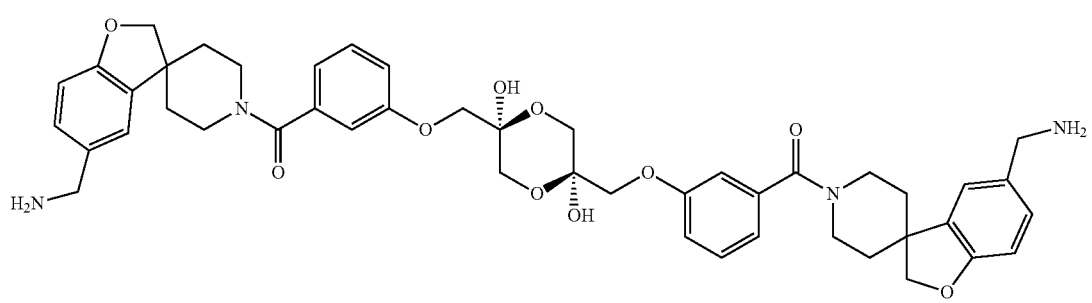 [SMILES: NCc1ccc2c(c1)C1(CCN(C(=O)c3cccc(OC[C@]4(O)CO[C@](O)(COc5cccc(C(=O)N6CCC7(CC6)COc6ccc(CN)cc67)c5)CO4)c3)CC1)CO2]

Coferon Dimer

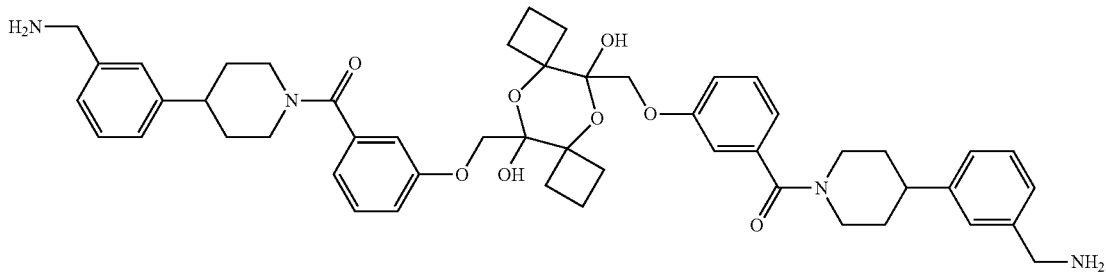 [SMILES: NCc1cccc(C2CCN(C(=O)c3cccc(OCC4(O)OC5(CCC5)C(O)(COc5cccc(C(=O)N6CCC(c7cccc(CN)c7)CC6)c5)OC45CCC5)c3)CC2)c1]

Cl and S-Me substituents on the aryl connector are predicted to enhance the binding affinity.

Coferons based on 2-amidocyclobutanone linker elements

| Pharmacophores | Connectors | Linker element |
|---|---|---|

-continued

| Pharmacophores | Connectors | Linker element |
|---|---|---| where linker elements are covalently linked to amine groups of the connectors through the atoms indicated by dots and carbonyl groups of the connectors are covalently linked to amine groups of the pharmacophores through the atoms indicated by dots.

A few examples of coferon monomers containing 2-aminocyclobutanone linker elements and the dimers formed from them are shown below. In each case only a single diastereomer of a diaminal piperazinyl dimer is shown although the active species may include one or more diaminal or spiroaminal oxazolidinyl diastereomers.

Coferon Monomer

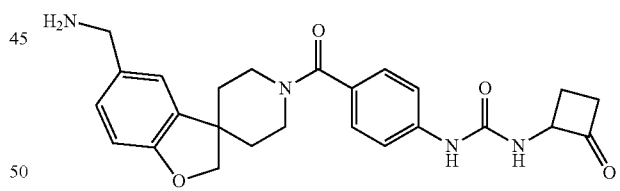

1-(4-(5-(aminomethyl)-2H-spiro[benzofuran-3,4'-piperidine]-1'-ylcarbonyl)phenyl)-3-(2-oxocyclobutyl)urea Coferon Dimer

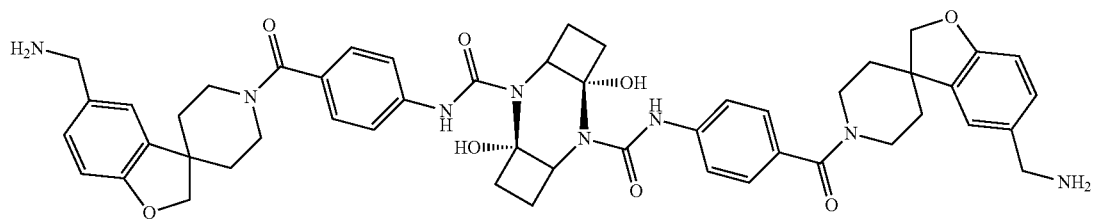

(1S,6S)-2-N,7-N-bis(4-{[5-(aminomethyl)-2H-spiro[1-benzofuran-3,4'-piperidine]-1'-yl]carbonyl}phenyl)-1,6-dihydroxy-2,7-diazatricyclo[6.2.0.03,6]decane-2,7-dicarboxamide Coferon Monomer

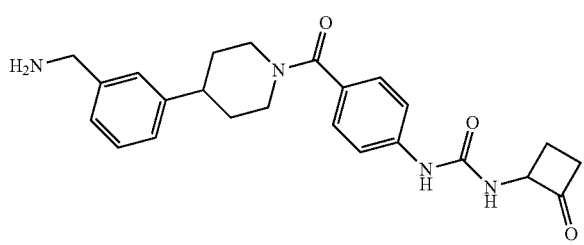 [SMILES: NCc1cccc(C2CCN(C(=O)c3ccc(NC(=O)NC4CCC4=O)cc3)CC2)c1]

1-(4-(4-(3-(aminomethyl)phenyl)piperidine-1-carbonyl)phenyl)-3-(2-oxocyclobutyl)urea Coferon Dimer -continued

| Pharmacophores | Connectors | Linker element |
|---|---|---| where linker elements are covalently linked to carbonyl groups on the right side of the connectors through the atoms indicated by dots and carbonyl groups on the left side of the connectors are covalently linked to amine groups of the pharmacophores through the atoms indicated by dots.

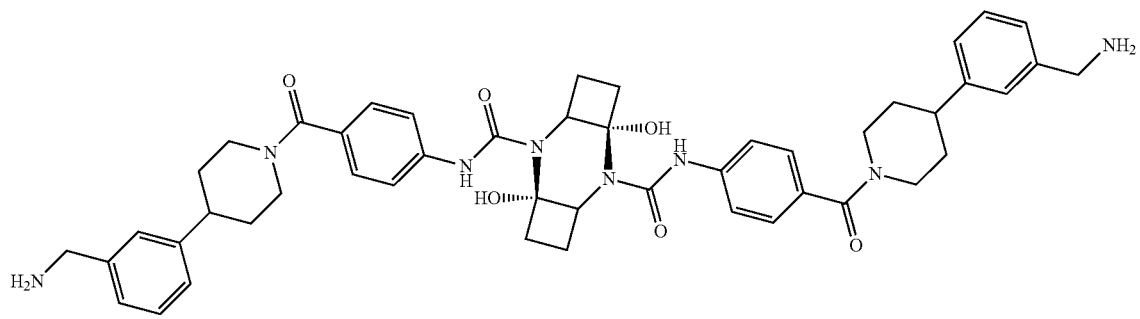

(1S,6S)-2-N,7-N-bis[4-({4-[3-(aminomethyl)phenyl]piperidin-1-yl}carbonyl)phenyl]-1,6-dihydroxy-2,7-diazatricyclo[6.2.0.03,6]decane-2,7-dicarboxamide Coferons based on hydroxytrifluoromethyl ketone linker elements

| Pharmacophores | Connectors | Linker element |
|---|---|---|

A few examples of coferon monomers containing hydroxytrifluoromethyl ketone linker elements and the dimers formed from them are shown below. In each case only a single diastereomer of a dioxanyl diketal dimer is shown although the active species may include one or more diketal or dioxolanyl spiroketal diastereomers.

Coferon Monomer

N-(4-(aminomethyl)benzyl)-4-(3-hydroxy-3-(2,2,2-trifluoroacetyl)azetidine-1-carbonyl)piperazine-1-carboxamide Coferon Dimer

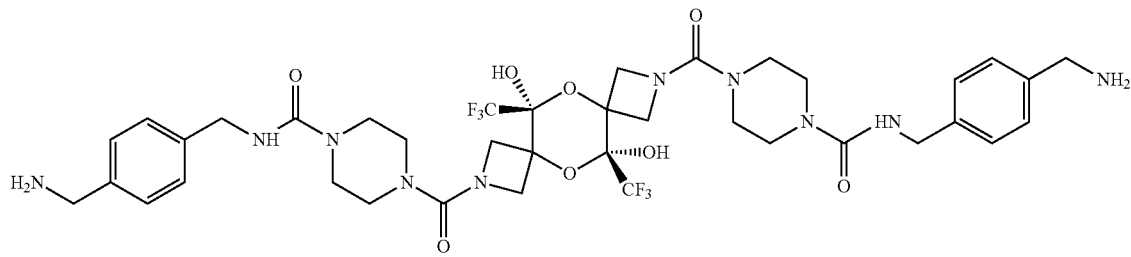 [SMILES: NCc1ccc(CNC(=O)N2CCN(C(=O)N3CC4(C3)O[C@](O)(C(F)(F)F)C3(CN(C(=O)N5CCN(C(=O)NCc6ccc(CN)cc6)CC5)C3)O[C@]4(O)C(F)(F)F)CC2)cc1]

N-{[4-(aminomethyl)phenyl]methyl}-4-{[(6S)-9-{[4-({[4-(aminomethyl)phenyl]methyl}carbamoyl)piperazin-1-yl]carbonyl}-6,12-dihydroxy-6,12-bis(trifluoromethyl)-5,11-dioxa-2,9-diazadispiro[3.2.37.24]dodecan-2-yl]carbonyl}piperazine-1-carboxamide Coferon Monomer

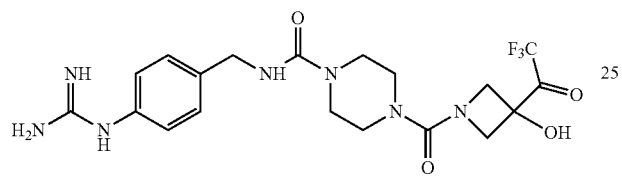

N-(4-guanidinobenzyl)-4-(3-hydroxy-3-(2,2,2-trifluoroacetyl)azetidine-1-carbonyl)piperazine-1-carboxamide

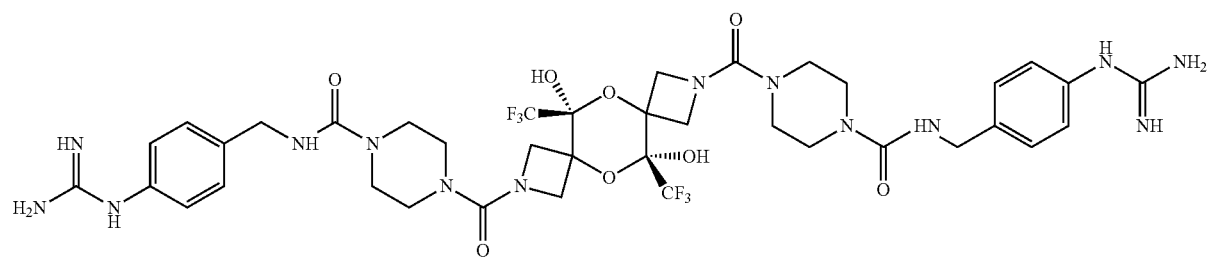 [SMILES: N=C(N)Nc1ccc(CNC(=O)N2CCN(C(=O)N3CC4(C3)O[C@](O)(C(F)(F)F)C3(CN(C(=O)N5CCN(C(=O)NCc6ccc(NC(=N)N)cc6)CC5)C3)O[C@]4(O)C(F)(F)F)CC2)cc1]

N-[(4-carbamimidamidophenyl)methyl]-4-{[(6S)-9-[(4-{[(4-carbamimidamidophenyl)methyl]carbamoyl}piperazin-1-yl)carbonyl]-6,12-dihydroxy-6,12-bis(trifluoromethyl)-5,11-dioxa-2,9-diazadispiro[3.2.37.24]dodecan-2-yl]carbonyl}piperazine-1-carboxamide Coferons based on hydroxylpyrrolidone linker elements

| Pharmacophores | Connectors | Linker element |
|---|---|---|

| Pharmacophores | Connectors | Linker element |
|---|---|---|
| 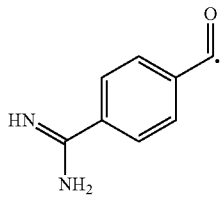 | | |
| 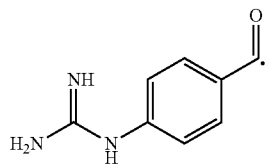 | | | where the amine groups of the linker elements are covalently linked to the connectors through the carbonyl groups indicated by dots and the amine groups of the connectors are covalently linked to the carbonyl groups of the pharmacophores through the atoms indicated by dots.

A few examples of coferon monomers containing hydroxylpyrrolidone linker elements and the dimers formed from them are shown below. In each case only a single diastereomer of a diketal dioxanyl dimer is shown although the active species may include one or more diketal or spiroketal dioxolanyl diastereomers.

Coferon Monomer

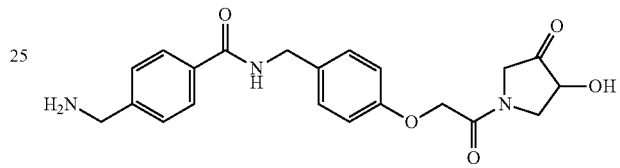

4-(aminomethyl)-N-(4-(2-(3-hydroxy-4-oxopyrrolidin-1-yl)-2-oxoethoxy)benzyl)benzamide Coferon Dimer

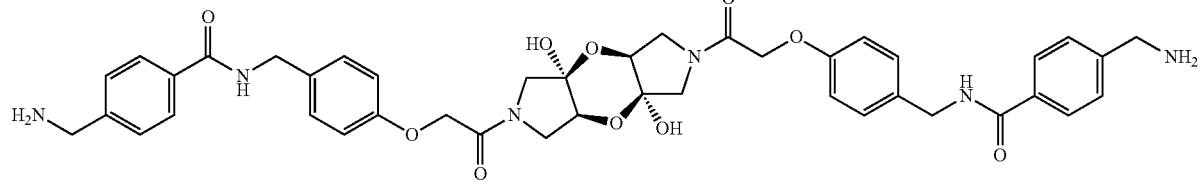

4-(aminomethyl)-N-[(4-{2-[(1R,3S,7R,9S)-11-{2-[4-({[4-(aminomethyl)phenyl]formamido}methyl)phenoxy]acetyl}-1,7-dihydroxy-2,8-dioxa-5,11-diazatricyclo[7.3.0.03,7]dodecan-5-yl]-2-oxoethoxy}phenyl)methyl]benzamide 5,11-diazatricyclo[7.3.0.03,7]dodecan-5-yl]-2-oxoethoxy}phenyl)methyl]benzamide Coferons based on Linker elements containing boronic acids that form covalent interactions with diols

| Pharmacophores | Diol Linker element | Boronic acid Linker element |
|---|---|---|
| 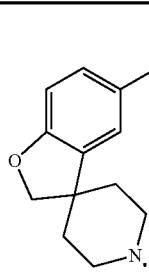 | 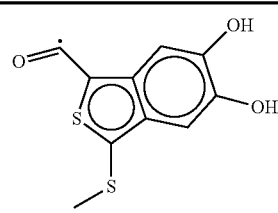 | 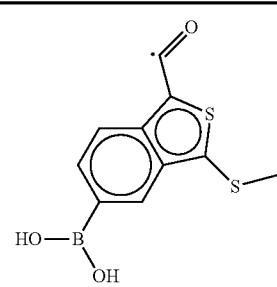 |

| Pharmacophores | Diol Linker element | Boronic acid Linker element |
|---|---|---|
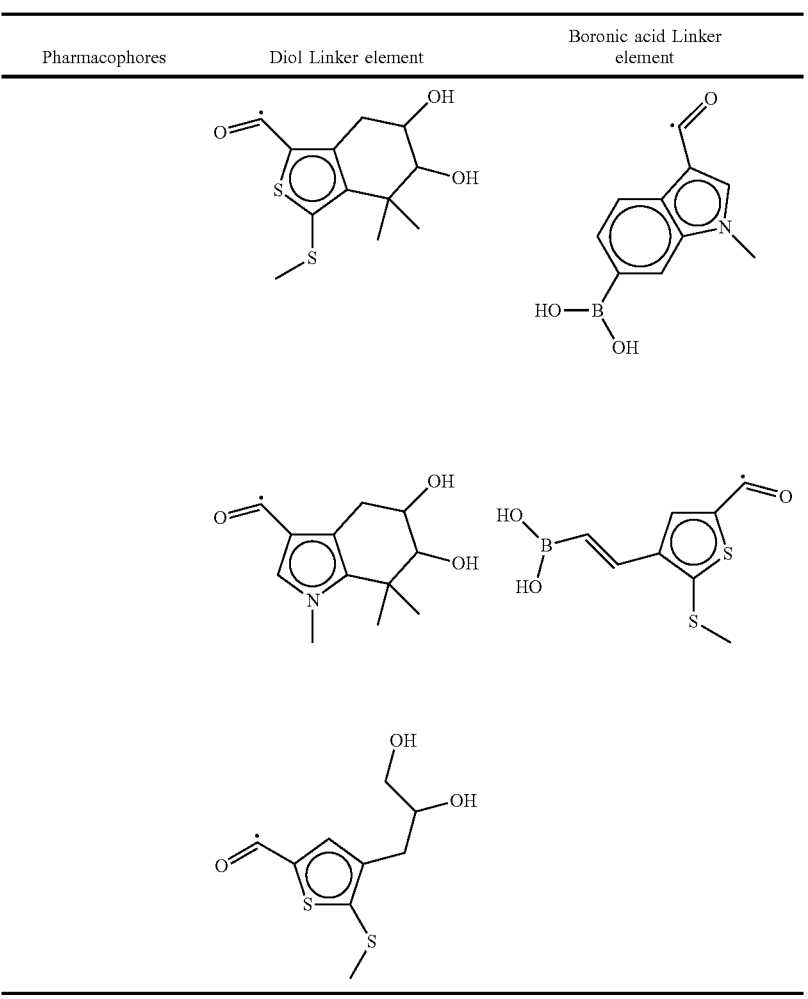
where linker elements are covalently linked to the pharmacophores through the atoms indicated by dots.
An example of coferon monomers containing a diol and boronic acid linker elements and the dimer formed from them is shown below.
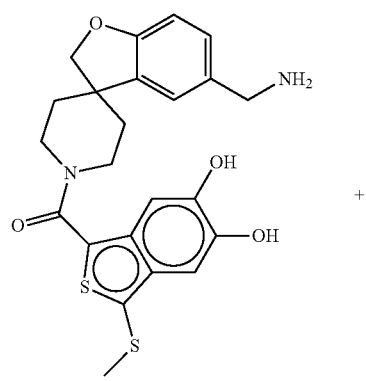
Coferon Monomer 1
+

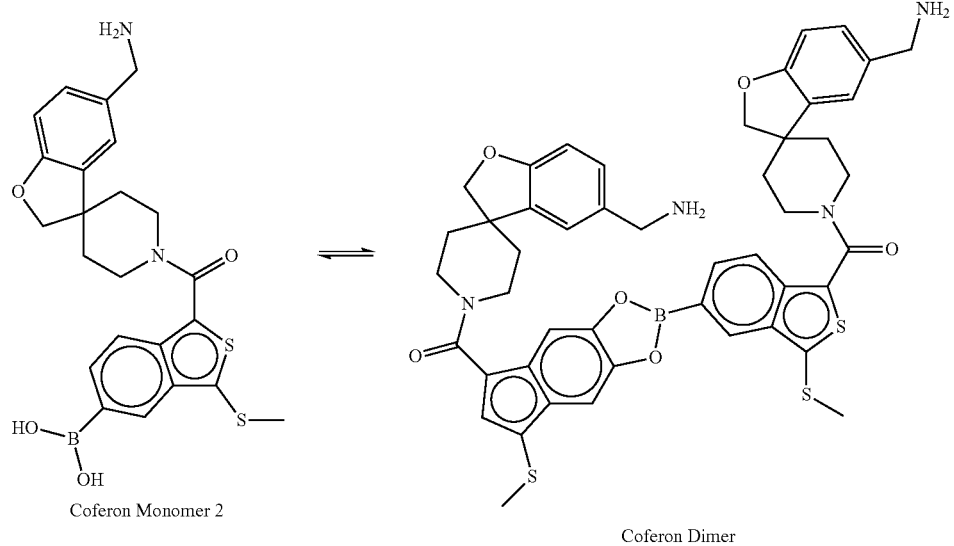

Coferon Monomer 2 ⇌ Coferon Dimer

Boronic acids may form tetrahedral boronate ester complexes as shown below. Only a single stereoisomer is shown although both enantiomers may be formed.

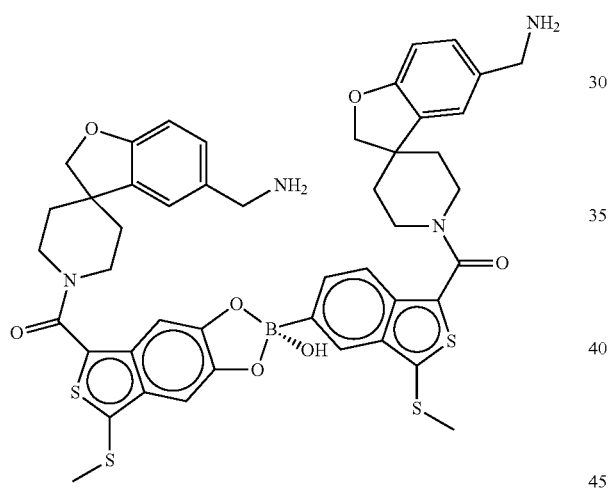

Examples of coferon monomers based on linker elements containing boronic acids that form covalent interactions with diols, α-hydroxyacids, o-hydroxy arylamides are shown below.

| Monomer | IUPAC NAME |
|---|---|
|  | {3-[3-({4-[3-(aminomethyl)phenyl]piperidin-1-yl}carbonyl)phenyl]phenyl}boronic acid |

| Monomer | IUPAC NAME |
|---|---|
| | [2-({4-[3-(aminomethyl)phenyl]piperidin-1-yl}carbonyl)-1H-indol-4-yl]boronic acid |
| | (2-{[5-(aminomethyl)-2H-spiro[1-benzofuran-3,4'-piperidine]-1'-yl]carbonyl}-1H-indol-4-yl)boronic acid |
| | (5-{[5-(aminomethyl)-2H-spiro[1-benzofuran-3,4'-piperidine]-1'-yl]carbonyl}naphthalen-2-yl)boronic acid |
| | [5-({4-[3-(aminomethyl)phenyl]piperidin-1-yl}carbonyl)naphthalen-2-yl]boronic acid |

-continued

| Monomer | IUPAC NAME |
|---|---|
|  | [2-({4-[3-(aminomethyl)phenyl]piperidin-1-yl}carbonyl)-1H-indol-5-yl]boronic acid |
|  | [3-(2-{4-[3-(aminomethyl)phenyl]piperidin-1-yl}-2-oxoethyl)phenyl]boronic acid |
|  | [(E)-2-[3-({4-[3-(aminomethyl)phenyl]piperidin-1-yl}carbonyl)phenyl]ethenyl]boronic acid |
|  | [5-({4-[3-(aminomethyl)phenyl]piperidin-1-yl}carbonyl)-1H-indol-2-yl]boronic acid |

| Monomer | IUPAC NAME |
|---|---|
| 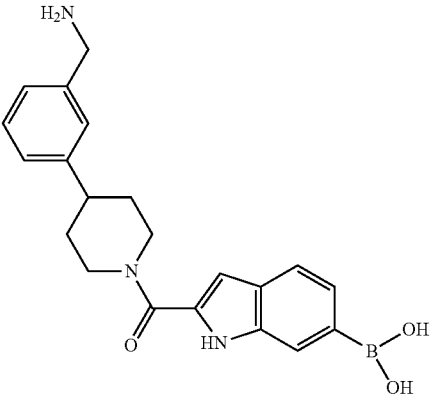 [SMILES: NCc1cccc(C2CCN(C(=O)c3cc4ccc(B(O)O)cc4[nH]3)CC2)c1] | [2-({4-[3-(aminomethyl)phenyl]piperidin-1-yl}carbonyl)-1H-indol-6-yl]boronic acid |
| 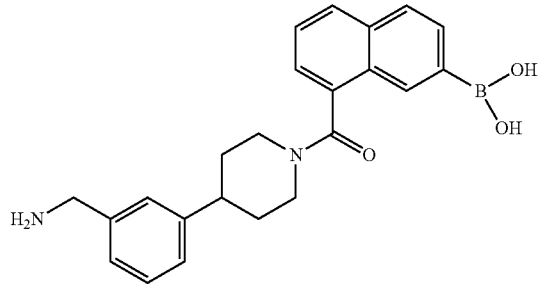 [SMILES: NCc1cccc(C2CCN(C(=O)c3cccc4ccc(B(O)O)cc34)CC2)c1] | [8-({4-[3-(aminomethyl)phenyl]piperidin-1-yl}carbonyl)naphthalen-2-yl]boronic acid |
| 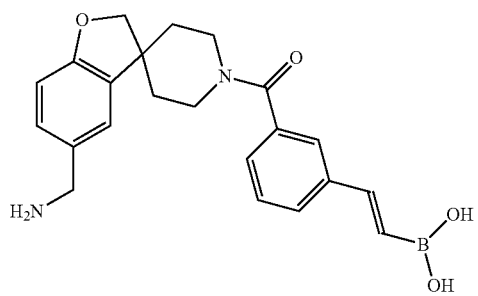 [SMILES: NCc1ccc2c(c1)C1(CCN(C(=O)c3cccc(/C=C/B(O)O)c3)CC1)CO2] | [(E)-2-(3-{[5-(aminomethyl)-2H-spiro[1-benzofuran-3,4'-piperidine]-1'-yl]carbonyl}phenyl)ethenyl]boronic acid |
| 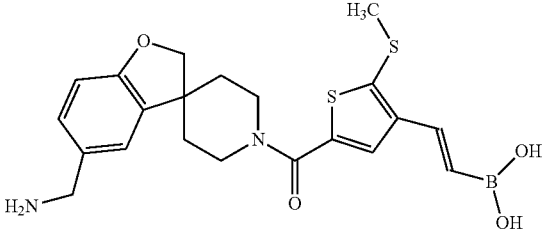 [SMILES: CSc1sc(C(=O)N2CCC3(CC2)COc2ccc(CN)cc23)cc1/C=C/B(O)O] | [(E)-2-(5-{[5-(aminomethyl)-2H-spiro[1-benzofuran-3,4'-piperidine]-1'-yl]carbonyl}-2-(methylsulfanyl)thiophen-3-yl)ethenyl]boronic acid |
| 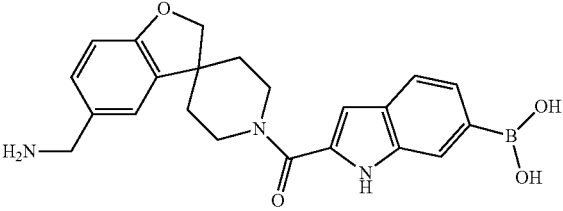 [SMILES: NCc1ccc2c(c1)C1(CCN(C(=O)c3cc4ccc(B(O)O)cc4[nH]3)CC1)CO2] | (2-{[5-(aminomethyl)-2H-spiro[1-benzofuran-3,4'-piperidine]-1'-yl]carbonyl}-1H-indol-6-yl)boronic acid |

| Monomer | IUPAC NAME |
|---|---|
| | (2-{[5-(aminomethyl)-2H-spiro[1-benzofuran-3,4'-piperidine]-1'-yl]carbonyl}-1H-indol-5-yl)boronic acid |
| | {4-[(1E)-3-[5-(aminomethyl)-2H-spiro[1-benzofuran-3,4'-piperidine]-1'-yl]-3-oxoprop-1-en-1-yl]phenyl}boronic acid |
| | (2-{[5-(aminomethyl)-2H-spiro[1-benzofuran-3,4'-piperidine]-1'-yl]carbonyl}-1H-indol-5-yl)boronic acid |
| | (5-{[5-(aminomethyl)-2H-spiro[1-benzofuran-3,4'-piperidine]-1'-yl]carbonyl}-1H-indol-3-yl)boronic acid |

-continued
| Monomer | IUPAC NAME |
|---|---|
| 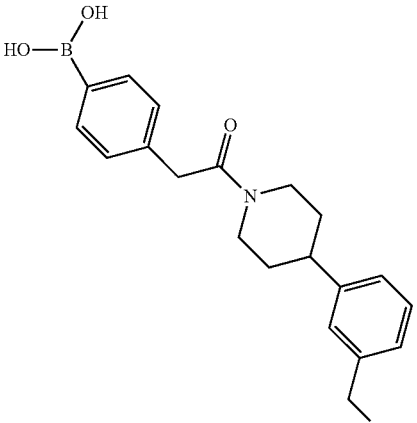 | [4-(2-{4-[3-(aminomethyl)phenyl]piperidin-1-yl}-2-oxoethyl)phenyl]boronic acid |
| 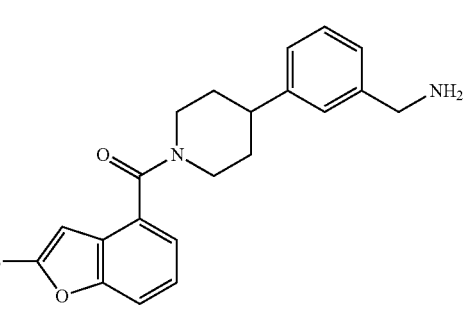 | [4-({4-[3-(aminomethyl)phenyl]piperidin-1-yl}carbonyl)-1-benzofuran-2-yl]boronic acid |
| 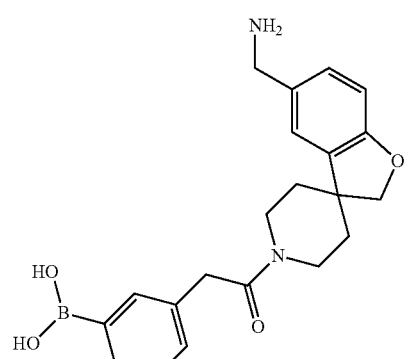 | (3-{2-[5-(aminomethyl)-2H-spiro[1-benzofuran-3,4'-piperidine]-1'-yl]-2-oxoethyl}phenyl)boronic acid |
| 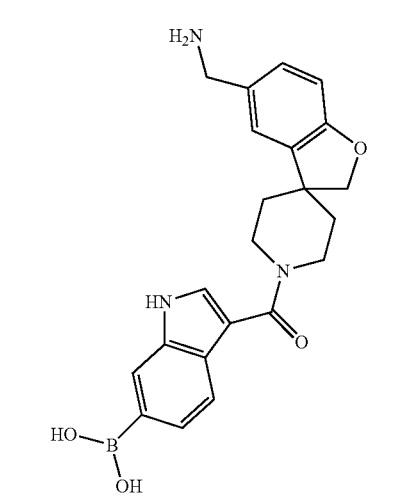 [SMILES: NCc1ccc2c(c1)C1(CCN(C(=O)c3c[nH]c4cc(B(O)O)ccc34)CC1)CO2] | (3-{[5-(aminomethyl)-2H-spiro[1-benzofuran-3,4'-piperidine]-1'-yl]carbonyl}-1H-indol-6-yl)boronic acid |

| Monomer | IUPAC NAME |
|---|---|
| (structure) | {2-[3-({4-[3-(aminomethyl)phenyl]piperidin-1-yl}carbonyl)phenyl]phenyl}boronic acid |

Examples of coferon monomers based on linker elements containing diols, α-hydroxyacids, and o-hydroxy arylamides that form covalent interactions with boronic acids are shown below.

| Monomer | IUPAC Name |
|---|---|
| (structure) | 4-(2-{4-[3-(aminomethyl)phenyl]piperidin-1-yl}-2-oxoethyl)-2-hydroxybenzamide |
| (structure) | 4-[(1E)-3-{4-[3-(aminomethyl)phenyl]piperidin-1-yl}-3-oxoprop-1-en-1-yl]-2-hydroxybenzamide |

| Monomer | IUPAC Name |
|---|---|
| | 5-[(1E)-3-{4-[3-(aminomethyl)phenyl]piperidin-1-yl}-3-oxoprop-1-en-1-yl]-2-hydroxybenzamide |
| | 8-({4-[3-(aminomethyl)phenyl]piperidin-1-yl}carbonyl)-1,3-dihydroxynaphthalene-2-carboxamide |
| | 3-[(1E)-3-{4-[3-(aminomethyl)phenyl]piperidin-1-yl}-3-oxoprop-1-en-1-yl]-2,6-dihydroxybenzamide |
| | (2R)-2-[3-({4-[3-(aminomethyl)phenyl]piperidin-1-yl}carbonyl)phenyl]-2-hydroxy-2-phenylacetic acid |

| Monomer | IUPAC Name |
|---|---|
| 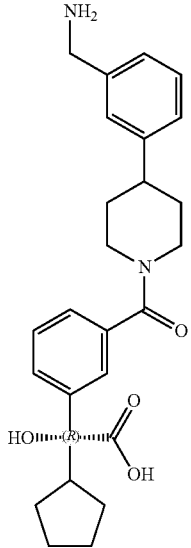 | (2R)-2-[3-({4-[3-(aminomethyl)phenyl]piperidin-1-yl}carbonyl)phenyl]-2-cyclopentyl-2-hydroxyacetic acid |
| 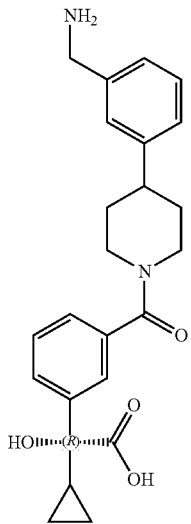 | (2R)-2-[3-({4-[3-(aminomethyl)phenyl]piperidin-1-yl}carbonyl)phenyl]-2-cyclopropyl-2-hydroxyacetic acid |
| 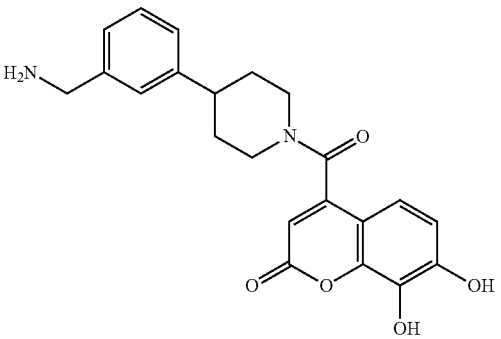 [SMILES: NCc1cccc(C2CCN(C(=O)c3cc(=O)oc4c(O)c(O)ccc34)CC2)c1] | 4-({4-[3-(aminomethyl)phenyl]piperidin-1-yl}carbonyl)-7,8-dihydroxy-2H-chromen-2-one |

-continued

| Monomer | IUPAC Name |
|---|---|
|  | 3-({4-[3-(aminomethyl)phenyl]piperidin-1-yl}carbonyl)-6,7-dihydroxy-2H-chromen-2-one |
|  | 4-(2-{4-[3-(aminomethyl)phenyl]piperidin-1-yl}-2-oxoethyl)-6,7-dihydroxy-2H-chromen-2-one |
|  | 3-({4-[3-(aminomethyl)phenyl]piperidin-1-yl}carbonyl)-7,8-dihydroxy-2H-chromen-2-one |
|  | 3-(2-{4-[3-(aminomethyl)phenyl]piperidin-1-yl}-2-oxoethyl)-6,7-dihydroxy-4-methyl-2H-chromen-2-one |
|  | 3-(2-{4-[3-(aminomethyl)phenyl]piperidin-1-yl}-2-oxoethyl)-7,8-dihydroxy-4-methyl-2H-chromen-2-one |

-continued

| Monomer | IUPAC Name |
|---|---|
| | 4-(2-{4-[3-(aminomethyl)phenyl]piperidin-1-yl}-2-oxoethyl)-7,8-dihydroxy-2H-chromen-2-one |
| | (1S,2S,3R,5S)-2-{2-[4-({4-[3-(aminomethyl)phenyl]piperidin-1-yl}carbonyl)phenoxy]ethyl}-6,6-dimethylbicyclo[3.1.1]heptane-2,3-diol |
| | (1R,2R,4S,5R,6S)-N-[3-({4-[3-(aminomethyl)phenyl]piperidin-1-yl}carbonyl)phenyl]-5,6-dihydroxybicyclo[2.2.2]octane-2-carboxamide |
| | (1R,2R,3R,4R,5S)-4-[3-({4-[3-(aminomethyl)phenyl]piperidin-1-yl}carbonyl)phenoxy]-2,6,6-trimethylbicyclo[3.1.1]heptane-2,3-diol |

-continued

| Monomer | IUPAC Name |
|---|---|
| | (1R,2R,4S,5S,6R)-N-[3-({4-[3-(aminomethyl)phenyl]piperidin-1-yl}carbonyl)phenyl]-5,6-dihydroxybicyclo[2.2.2]octane-2-carboxamide |
| | (1S,2R,3R,4R,5R)-4-[3-({4-[3-(aminomethyl)phenyl]piperidin-1-yl}carbonyl)phenoxy]-2,6,6-trimethylbicyclo[3.1.1]heptane-2,3-diol |
| | (1R,2R,4S,5R,6S)-N-[3-({4-[3-(aminomethyl)phenyl]piperidin-1-yl}carbonyl)phenyl]-5,6-dihydroxybicyclo[2.2.1]heptane-2-carboxamide |
| | (1S,2R,3S,4S,5R)-5-[4-({4-[3-(aminomethyl)phenyl]piperidin-1-yl}carbonyl)phenoxy]-5-methylbicyclo[2.2.1]heptane-2,3-diol |

-continued

| Monomer | IUPAC Name |
|---|---|
| | (1S,2R,4R,5S,6R)-N-[3-({4-[3-(aminomethyl)phenyl]piperidin-1-yl}carbonyl)phenyl]-5,6-dihydroxybicyclo[2.2.2]octane-2-carboxamide |
| | (1R,2R,3S,4R,5S)-5-[3-({4-[3-(aminomethyl)phenyl]piperidin-1-yl}carbonyl)phenoxy]bicyclo[2.2.2]octane-2,3-diol |
| | (1R,2S,3R,4R,5S)-5-[3-({4-[3-(aminomethyl)phenyl]piperidin-1-yl}carbonyl)phenoxy]-5-methylbicyclo[2.2.1]heptane-2,3-diol |
| | (2R)-3-{[3-({4-[3-(aminomethyl)phenyl]piperidin-1-yl}carbonyl)phenyl]carbamoyl}-2-hydroxy-2-phenylpropanoic acid |
| | (2S)-3-{[3-({4-[3-(aminomethyl)phenyl]piperidin-1-yl}carbonyl)phenyl]carbamoyl}-2-hydroxy-2-phenylpropanoic acid |

-continued

| Monomer | IUPAC Name |
|---|---|
| | (2R)-2-[4-({4-[3-(aminomethyl)phenyl]piperidin-1-yl}carbonyl)-1H-indol-2-yl]-2-hydroxypropanoic acid |
| | (2S)-3-{[3-({4-[3-(aminomethyl)phenyl]piperidin-1-yl}carbonyl)phenyl]carbamoyl}-2-hydroxy-2-methylpropanoic acid |
| | (2S)-3-[3-({4-[3-(aminomethyl)phenyl]piperidin-1-yl}carbonyl)phenoxy]-2-hydroxy-2-phenylpropanoic acid |

-continued

| Monomer | IUPAC Name |
|---|---|
|  | (2R)-3-[3-({4-[3-(aminomethyl)phenyl]piperidin-1-yl}carbonyl)phenoxy]-2-hydroxy-2-phenylpropanoic acid |
|  | (2S)-3-[3-({4-[3-(aminomethyl)phenyl]piperidin-1-yl}carbonyl)phenoxy]-2-hydroxy-2-methylpropanoic acid |
|  | (2R)-3-[3-({4-[3-(aminomethyl)phenyl]piperidin-1-yl}carbonyl)phenoxy]-2-hydroxy-2-methylpropanoic acid |
|  | (2S)-2-[2-({4-[3-(aminomethyl)phenyl]piperidin-1-yl}carbonyl)-1H-indol-4-yl]-2-hydroxypropanoic acid |

-continued

| Monomer | IUPAC Name |
|---|---|
| 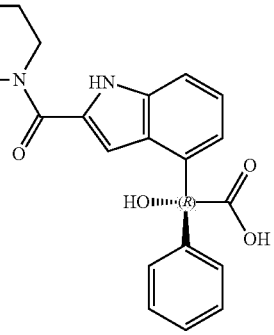 | (2R)-2-[2-({4-[3-(aminomethyl)phenyl]piperidin-1-yl}carbonyl)-1H-indol-4-yl]-2-hydroxy-2-phenylacetic acid |
| 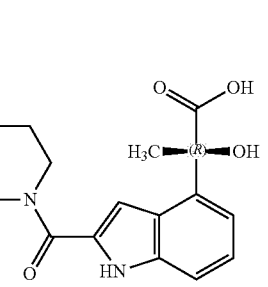 | (2R)-2-[2-({4-[3-(aminomethyl)phenyl]piperidin-1-yl}carbonyl)-1H-indol-4-yl]-2-hydroxypropanoic acid |
| 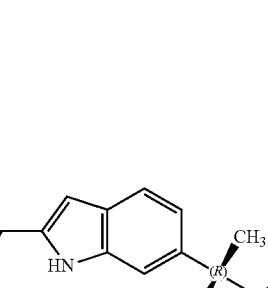 | (2R)-2-[2-({4-[3-(aminomethyl)phenyl]piperidin-1-yl}carbonyl)-1H-indol-6-yl]-2-hydroxypropanoic acid |
| 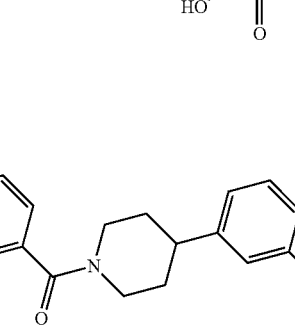 | 2-[3-({4-[3-(aminomethyl)phenyl]piperidin-1-yl}carbonyl)phenoxy]-1-[(3R,4S)-3,4-dihydroxypyrrolidin-1-yl]ethan-1-one |
| 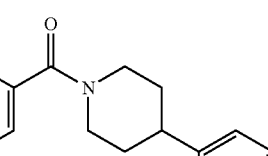 | (2R)-3-[3-({4-[3-(aminomethyl)phenyl]piperidin-1-yl)carbonyl)phenoxy]propane-1,2-diol |

| Monomer | IUPAC Name |
|---|---|
| 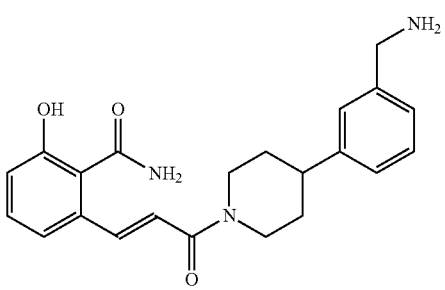 [SMILES: NCc1cccc(C2CCN(C(=O)/C=C/c3cccc(O)c3C(N)=O)CC2)c1] | 2-[(1E)-3-{4-[3-(aminomethyl)phenyl]piperidin-1-yl}-3-oxoprop-1-en-1-yl]-6-hydroxybenzamide |
| 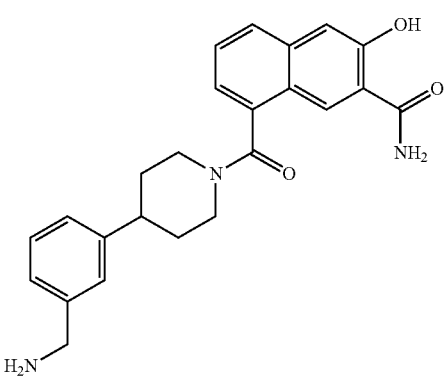 [SMILES: NCc1cccc(C2CCN(C(=O)c3cccc4cc(O)c(C(N)=O)cc34)CC2)c1] | 8-({4-[3-(aminomethyl)phenyl]piperidin-1-yl}carbonyl)-3-hydroxynaphthalene-2-carboxamide |
| 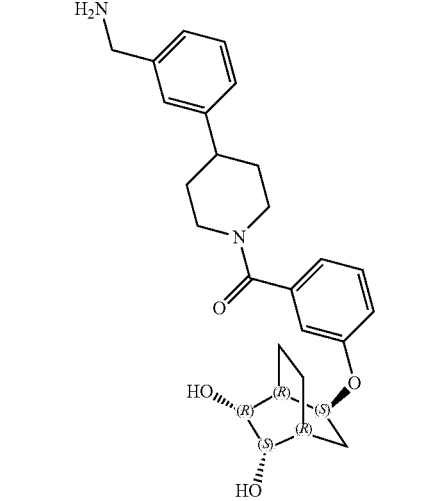 | (1R,2S,3R,4R,5S)-5-[3-({4-[3-(aminomethyl)phenyl]piperidin-1-yl}carbonyl)phenoxy]bicyclo[2.2.2]octane-2,3-diol |
| 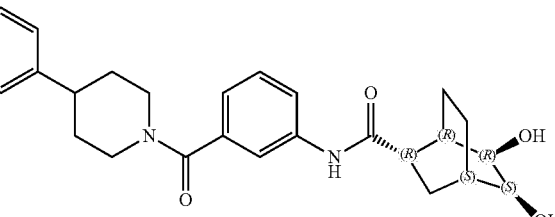 | (1R,2S,4S,5S,6R)-N-[3-({4-[3-(aminomethyl)phenyl]piperidin-1-yl}carbonyl)phenyl]-5,6-dihydroxybicyclo[2.2.2]octane-2-carboxamide |

| Monomer | IUPAC Name |
|---|---|
| | (2S)-3-[3-({4-[3-(aminomethyl)phenyl]piperidin-1-yl}carbonyl)phenoxy]-2-cyclopentyl-2-hydroxypropanoic acid |
| | (2S)-3-{[4-({4-[3-(aminomethyl)phenyl]piperidin-1-yl}carbonyl)phenyl]carbamoyl}-2-hydroxy-2-phenylpropanoic acid |
| | (2R)-2-[2-({4-[3-(aminomethyl)phenyl]piperidin-1-yl}carbonyl)-1H-indol-6-yl]-2-hydroxy-2-phenylacetic acid |

-continued
| Monomer | IUPAC Name |
|---|---|
| 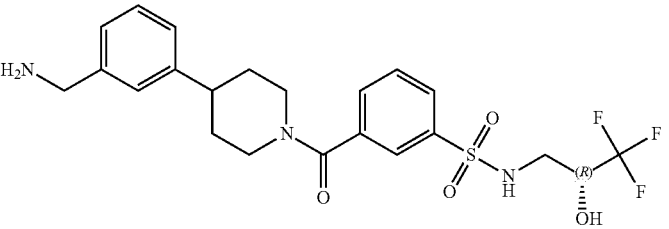 | (2R)-S-[3-({4-[3-(aminomethyl)phenyl]piperidin-1-yl}carbonyl)phenyl]-3,3,3-trifluoro-2-hydroxypropane-1-sulfonamido |
| 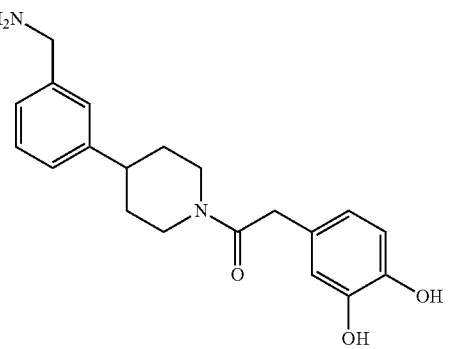 | 1-{4-[3-(aminomethyl)phenyl]piperidin-1-yl}-2-(3,4-dihydroxyphenyl)ethan-1-one |
| 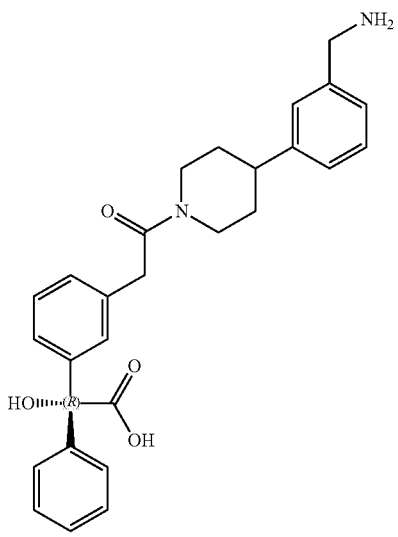 | (2R)-2-[3-(2-{4-[3-(aminomethyl)phenyl]piperidin-1-yl}-2-oxoethyl)phenyl]-2-hydroxy-2-phenylacetic acid |
| 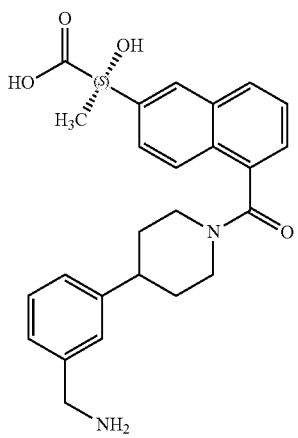 | (2S)-2-[5-({4-[3-(aminomethyl)phenyl]piperidin-1-yl}carbonyl)naphthalen-2-yl]-2-hydroxypropanoic acid |

| Monomer | IUPAC Name |
|---|---|
| | (2S)-2-[2-({4-[3-(aminomethyl)phenyl]piperidin-1-yl}carbonyl)-1H-indol-6-yl]-2-hydroxypropanoic acid |
| | (2S)-2-[2-({4-[3-(aminomethyl)phenyl]piperidin-1-yl}carbonyl)-1H-indol-6-yl]-2-hydroxy-2-phenylacetic acid |

Specific examples of the dimers obtained from these sets of monomers are shown below. Although only the sp² hybridized boron containing diesters, oxazaborolanes, oxazaborinanes, dioxaborininone, and oxazoborininones are shown, both enantiomers of the sp³ hybridized boronate esters, hydroxy dioxaborininones, and hydroxy oxazoborininones can also be formed.

Structure

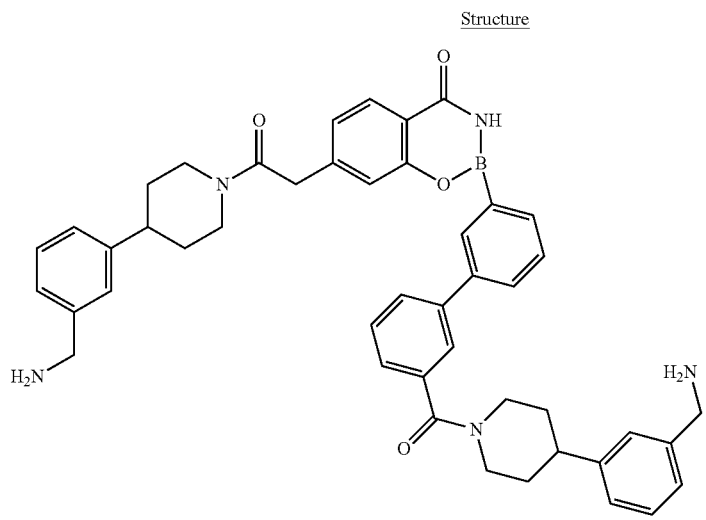

7-(2-{4-[3-(aminomethyl)phenyl]piperidin-1-yl}-2-oxoethyl)-2-{3-[3-({4-[3-(aminomethyl)phenyl]piperidin-1-yl]-carbonyl)phenyl]phenyl)-3,4-dihydro-2H-1,3,2-benzoxazaborinin-4-one

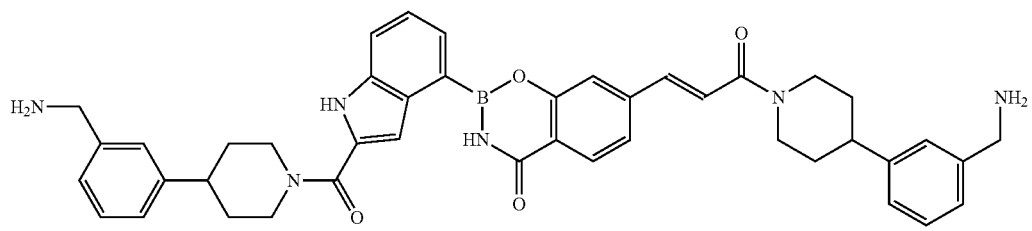

7-[(1E)-3-{4-[3-(aminomethyl)phenyl]piperidin-1-yl}-3-oxoprop-1-en-1-yl]-2-
[2-({4-[3[aminomethyl]phenyl]piperidin-1-yl)carbonyl)-1H-indol-4-yl]-3,4-
dihydro-2H-1,3,2-benzoxazaborinin-4-one

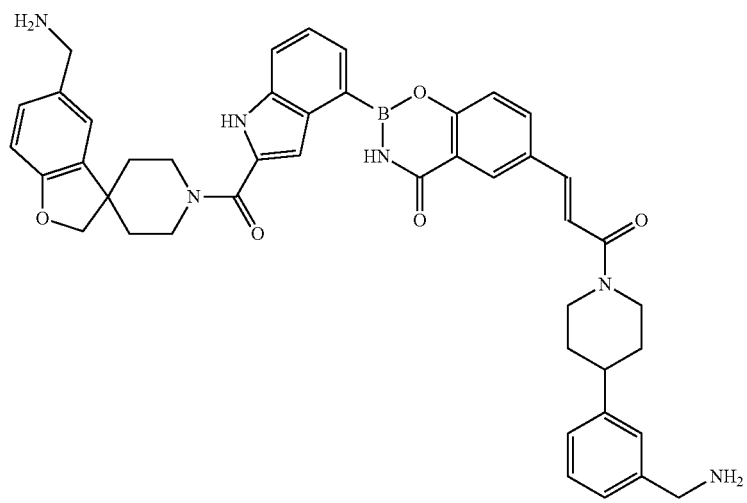

2-(2-{[5-(aminomethyl)-2H-spiro[1-benzofuran-3,4'-piperidine]-1'-yl]carbonyl}-
1H-indol-4-yl)-6-[(1E)-3-{4-[3-(aminomethyl)phenyl]piperidin-1-yl}-3-oxoprob-1-
en-1-yl]-3,4-dihydro-2H-1,3,2-benzoxazaborinin-4-one

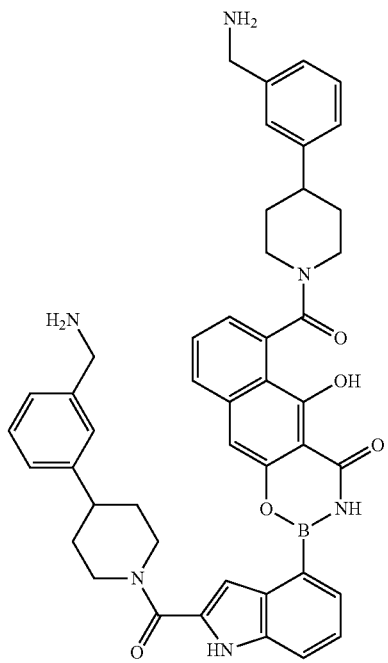

6-({4-[3-(aminomethyl)phenyl]piperidin-1-yl}carbonyl)-2-[2-({4-[3-
(aminomethyl)phenyl]piperidin-1-yl}carbonyl)-1H-indol-4-yl]-5-hydroxy-
2H,3H,4H-naphtho[2,3-e][1,3,2]oxazaborinin-4-one

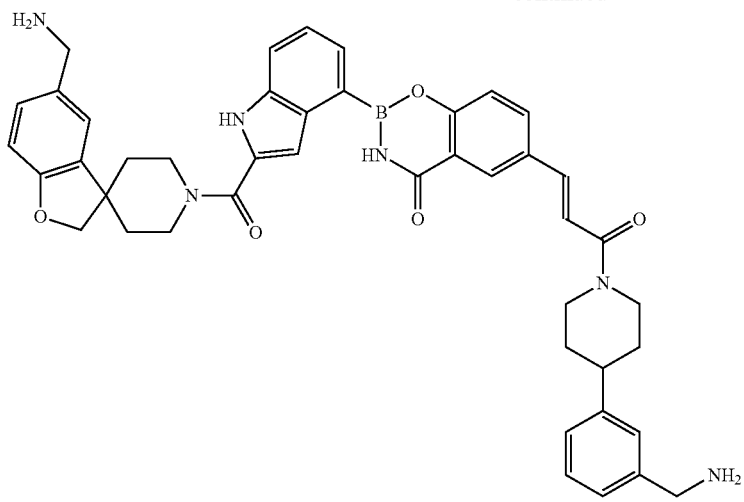
2-(2-{[5-(aminomethyl)-2H-spiro[1-benzofuran-3,4'-piperidine]-1'-yl]carbonyl}-1H-indol-4-yl)-6-[(1E)-3-{4-[3-(aminomethyl)phenyl]piperidin-1-yl}-3-oxoprop-1-en-1-yl]-5-hydroxy-3,4-dihydro-2H-1,3,2-benzoxazaborinin-4-one
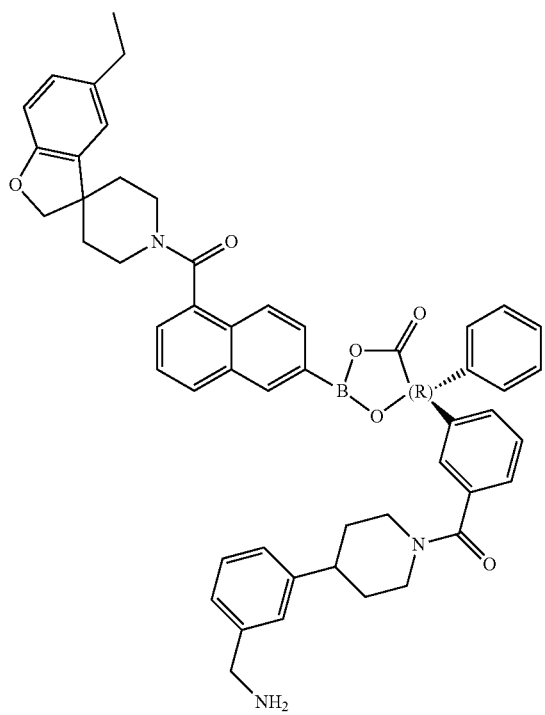
(5R)-2-(5-{[5-(aminomethyl)-2H-spiro[1-benzofuran-3,4'-piperidine]-1'-yl]carbonyl}naphthalen-2-yl)-5-[3-({4-[3-(aminomethyl)phenyl]piperidin-1-yl}carbonyl)phenyl]-5-phenyl-1,3,2-dioxaborolan-4-one

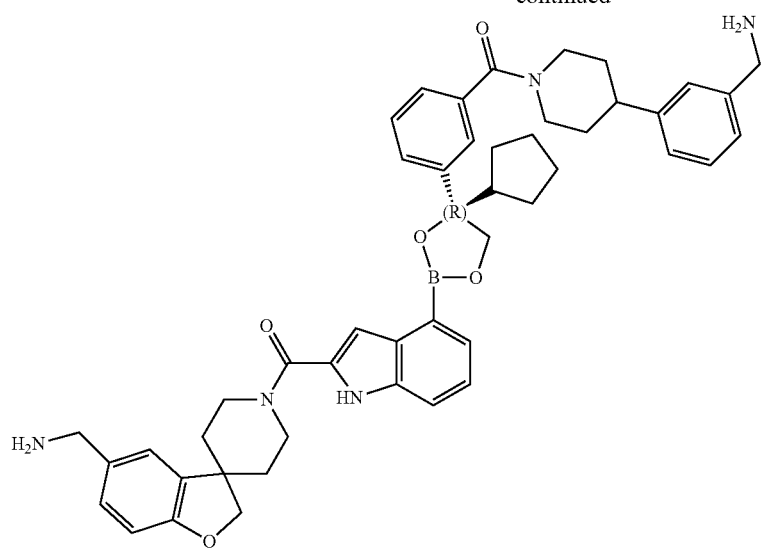
(5R)-2-(2-{[5-(aminomethyl)-2H-spiro[1-benzofuran-3,4'-piperidine]-1'-yl]carbonyl}-1H-indol-4-yl)-5-[3-({4-[3-(aminomethyl)phenyl]piperidin-1-yl}carbonyl)phenyl]-5-cyclopentyl-1,3,2-dioxaborolan-4-one
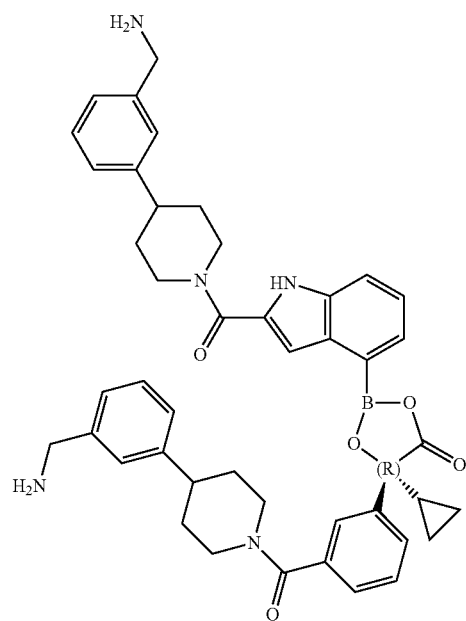
(5R)-2-[2-({4-[3-(aminomethyl)phenyl]piperidin-1-yl}carbonyl)-1H-indol-4-yl]-5-[3-({4-[3-(aminomethyl)phenyl]piperidin-1-yl}carbonyl)phenyl]-5-cyclopropyl-1,3,2-dioxaborolan-4-one

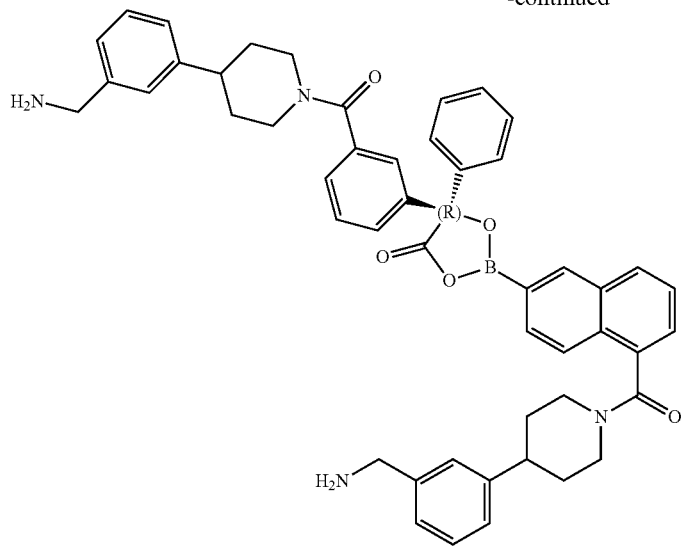

(5R)-2-[5-({4-[3-(aminomethyl)phenyl]piperidin-1-yl}carbonyl)naphthalen-2-yl]-5-[3-({4-[3-(aminomethyl)phenyl]piperidin-1-yl}carbonyl)phenyl]-5-phenyl-1,3,2-dioxaborolan-4-one

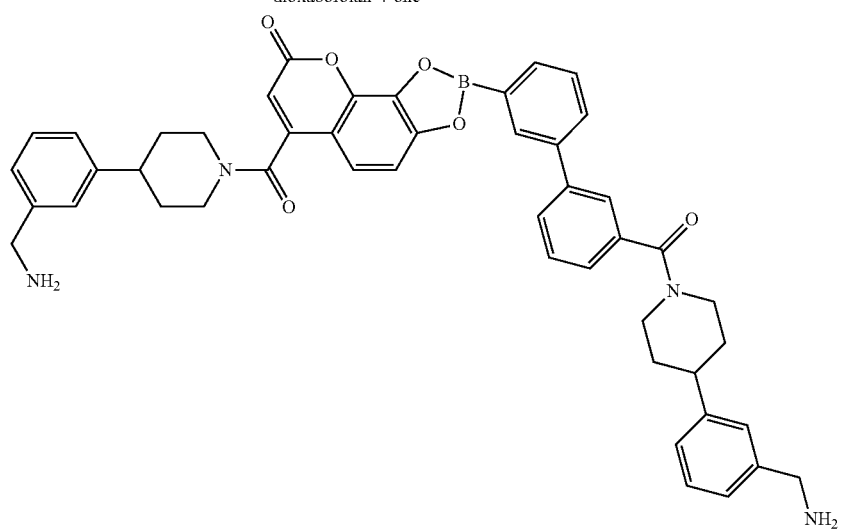

6-({4-[3-(aminomethyl)phenyl]piperidin-1-yl}carbonyl)-2-{3-[3-({4-[3-(aminomethyl)phenyl]piperidin-1-yl}carbonyl)phenyl]phenyl}2H,8H-[1,3,2]dioxaborolo[4,5-h]chromen-8-one

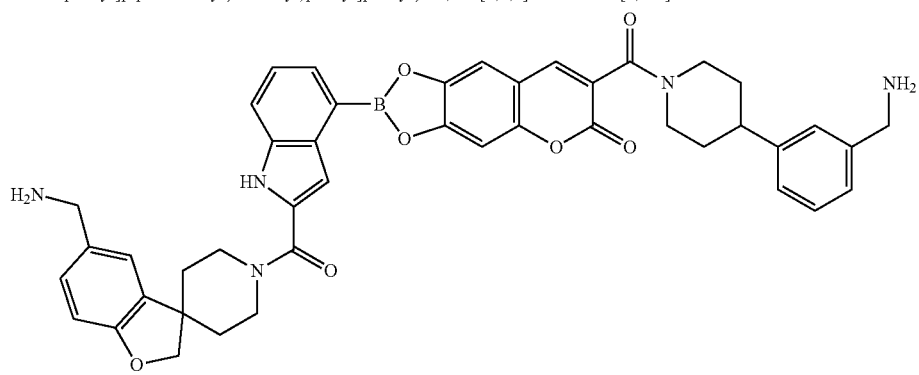

2-(2-{[5-(aminomethyl)-2H-spiro[1-benzofuran-3,4'-piperidine]-1'-yl]carbonyl}-1H-indol-4-yl)-7-({4-[3-(aminomethyl)phenyl]piperidin-1-yl}carbonyl)-2H,6H-[1,3,2]dioxaborolo[4,5-g]chromen-6-one

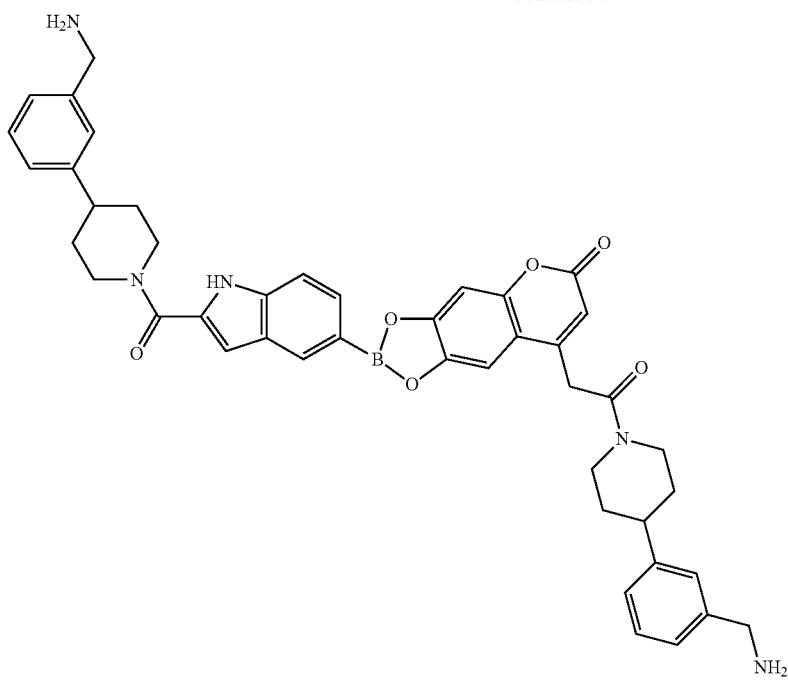
8-(2-{4-[3-(aminomethyl)phenyl]piperidin-1-yl}-2-oxoethyl)-2-[2-({4-[3-(aminomethyl)phenyl]piperidin-1-yl}carbonyl)-1H-indol-5-yl]-2H,6H-[1,3,2]dioxaborolo[4,5-g]chromen-6-one
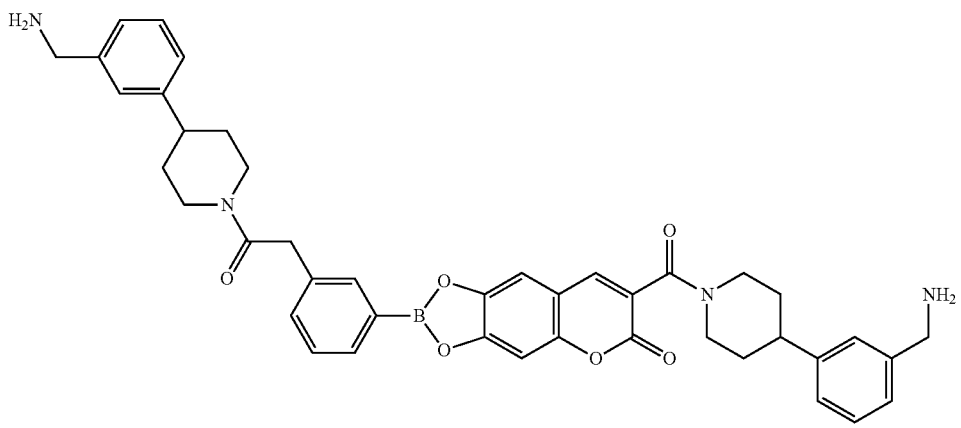
2-[3-(2-{4-[3-(aminomethyl)phenyl]piperidin-1-yl}-2-oxoethyl)phenyl]-7-({4-[3-(aminomethyl)phenyl]piperidin-1-yl}carbonyl)-2H,6H-[1,3,2]dioxaborolo[4,5-g]chromen-6-one -continued
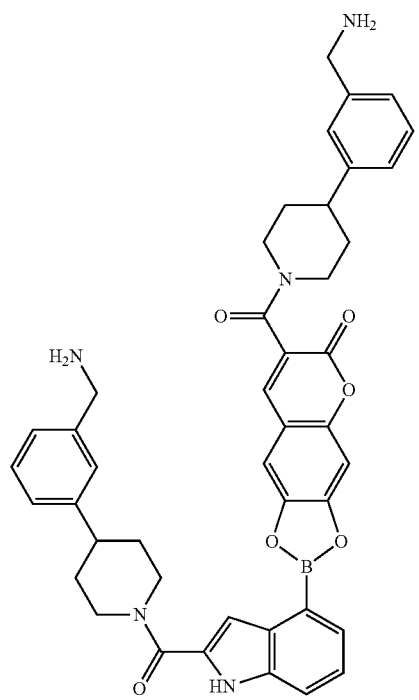
7-({4-[3-(aminomethyl)phenyl]piperridin-1-yl}carbonyl)-2-[2-({4-[3-(aminomethyl)phenyl]piperidin-1-yl}carbonyl)-1H-indol-4-yl]-2H,6H-[1,3,2]dioxaborolo[4,5-g]chromen-6-one
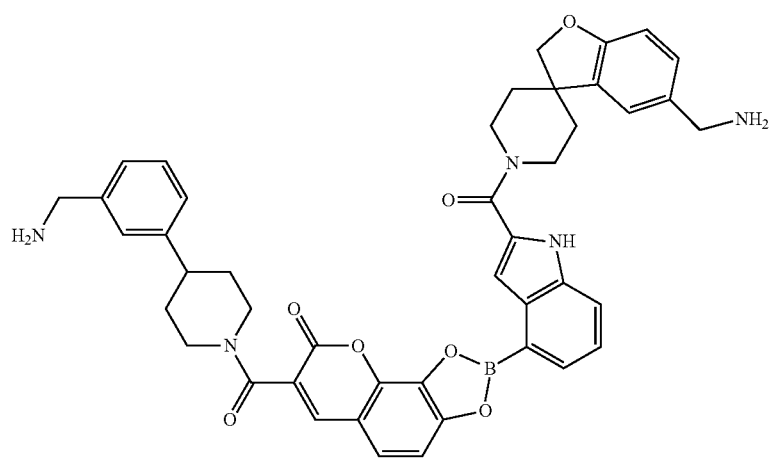
2-(2-{[5-(aminomethyl)-2H-spiro[1-benzofuran-3,4'-piperidine]-1'-yl]carbonyl}-1H-indol-4-yl)-7-({4-[3-(aminomethyl)phenyl]piperidin-1-yl}carbonyl)-2H,8H-[1,3,2]dioxaborolo[4,5-h]chromen-8-one

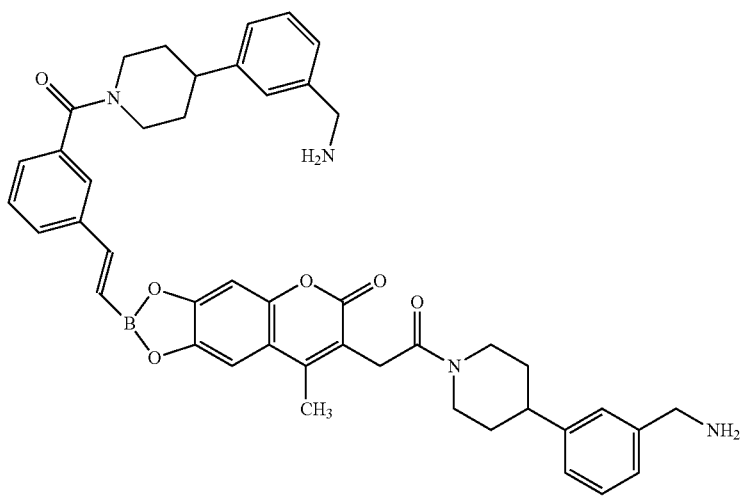
7-(2-{4-[3-(aminomethyl)phenyl]piperidin-1-yl}-2-oxoethyl)-2-[(E)-2-[3-({4-[3-(aminomethyl)phenyl]piperidin-1-yl}carbonyl)phenyl]ethenyl]-8-methyl-2H,6H-[1,3,2]dioxaborolo[4,5-g]chromen-6-one
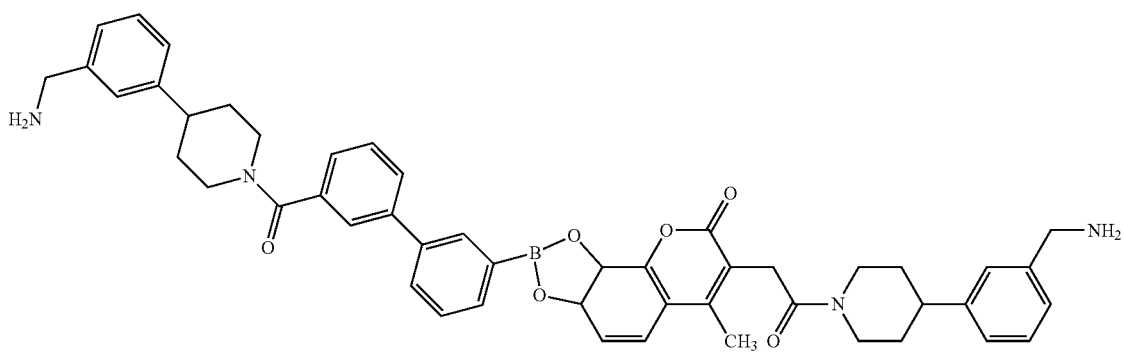
7-(2-{4-[3-(aminomethyl)phenyl]piperidin-1-yl}-2-oxoethyl)-2-{3-[({4-[3-(aminomethyl)phenyl]piperidin-1-yl}carbonyl)phenyl]phenyl}-6-methyl-2H,8H-[1,3,2]dioxaborolo[4,5-h]chromen-8-one
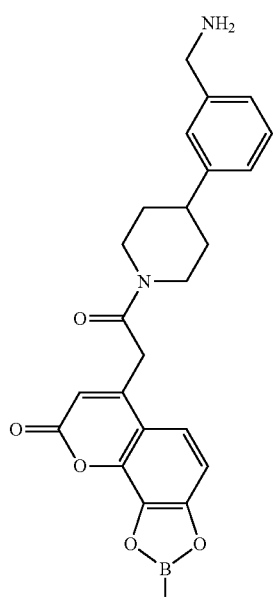

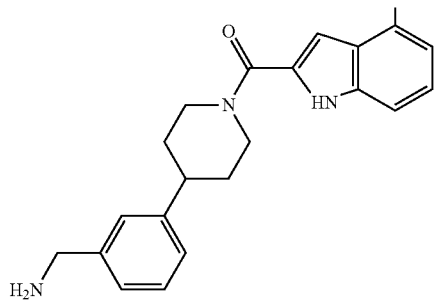
6-(2-{4-[3-(aminomethyl)phenyl]piperidin-1-yl}-2-oxoethyl)-2-[2-({4-[3-(aminomethyl)phenyl] piperidin-1-yl)carbonyl)-1H-indol-4-yl]-2H,8H-[1,3,2]dioxaborolo[4,5-h]chromen-8-one
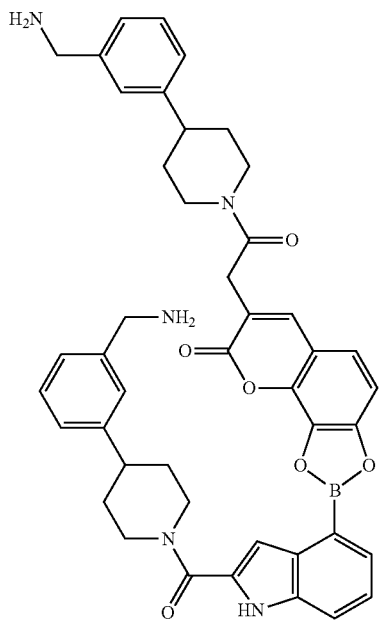
7-(2-{4-[3-(aminomethyl)phenyl]piperidin-1-yl}-2-oxoethyl)-2-[2-({4-[3-(aminomethyl) phenyl]piperidin-1-yl}carbonyl)-1H-indol-4-yl]-6-methyl-2H,8H-[1,3,2]dioxaborolo[4,5-h] chromen-8-one

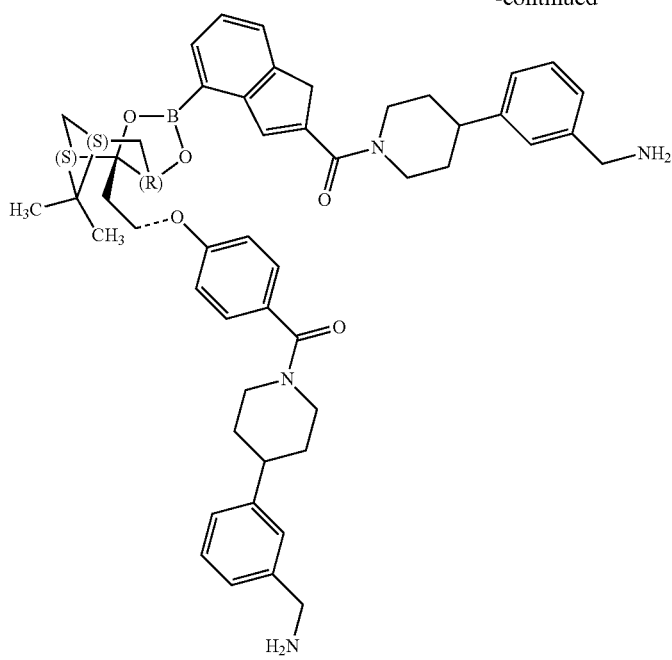
(3-{1-[(4-{2-[(1S,2S,6R,8S)-4-[2-({4-[3-(aminomethyl)phenyl]piperidin-1-yl)carbonyl)-1H-indol-4-yl]-9,9-dimethyl-3,5-dioxa-4-boratricyclo[6.1.1.0$^{2,6}$]decan-2-yl]ethoxy}phenyl)carbonyl]piperidin-4-yl}phenyl)methanamine
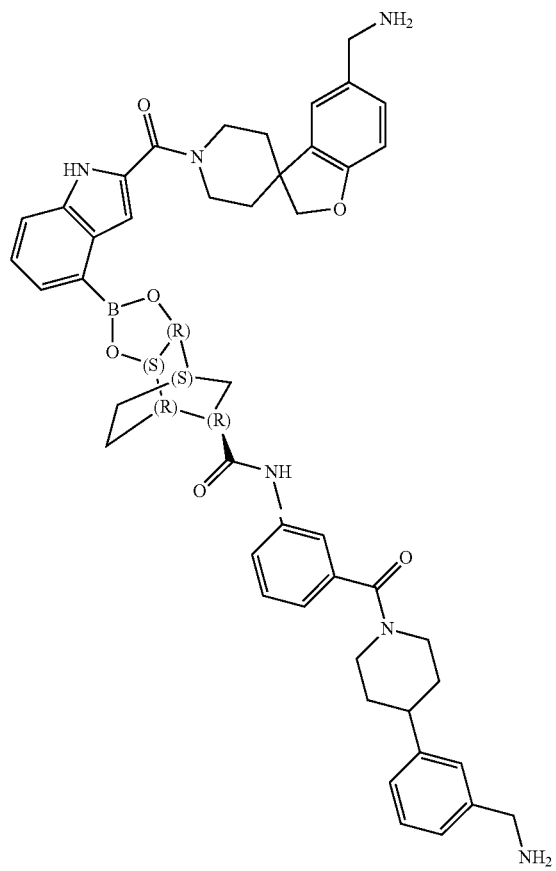
(1S,2R,6S,7R,8R)-4-(2-{[5-(aminomethyl)-2H-spiro[1-benzofuran-3,4'-piperidine]-1'-yl]carbonyl}-1H-indol-4-yl)-N-[3-({4-[3-(aminomethyl)phenyl]piperidin-1-yl}carbonyl)phenyl]-3,5-dioxa-4-boratricyclo[5.2.2.0$^{2,6}$]undecane-8-carboxamide -continued
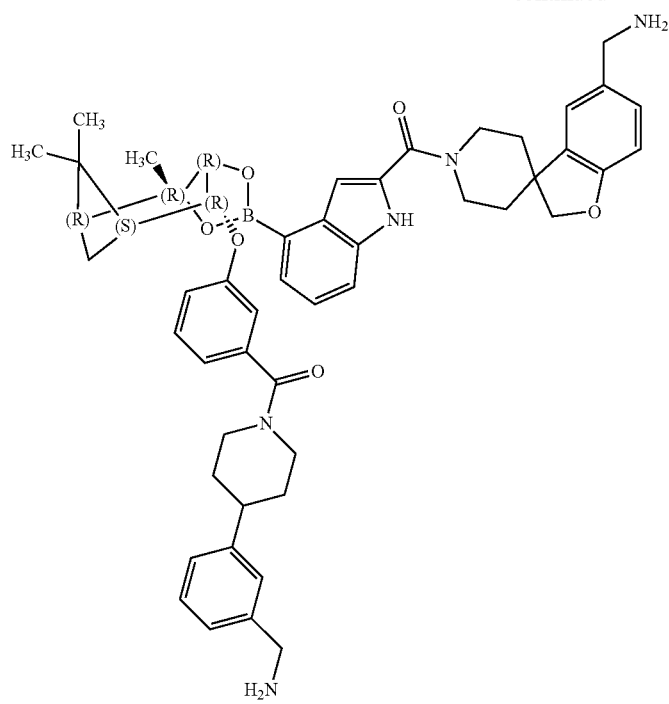
1'-({4-[(1R,2R,6R,7R,8S)-7-[3-({4-[3-(aminomethyl)phenyl]piperidin-1-yl}carbonyl)
phenoxy]-2,9,9-trimethyl-3,5-dioxa-4-boratricyclo[6.1.1.0²,⁶]decan-4-yl]-1H-indol-2-yl}
carbonyl)-2H-spiro[1-benzofuran-3,4'-piperidine]-5-ylmethanamine
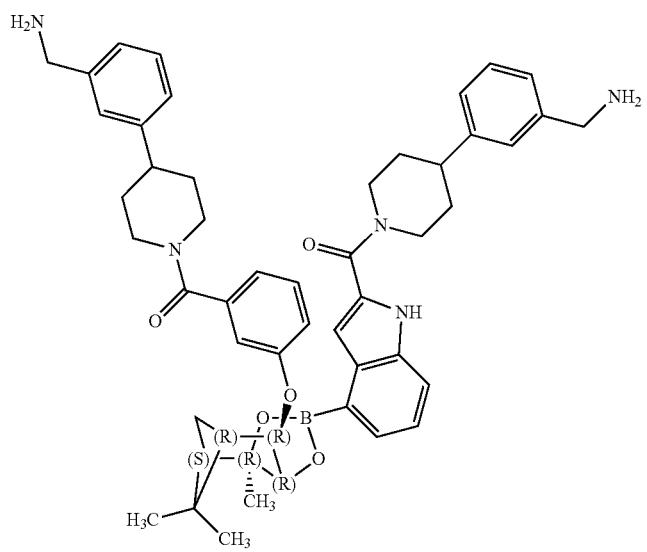
(1S,2S,6R,7R,8R)-4-(2-{[5-(aminomethyl)-2H-spiro[1-benzofuran-3,4'-piperidine]-
1'-yl]carbonyl}-1H-indol-4-yl)-N-[3-({4-[3-(aminomethyl)phenyl]piperidin-1-yl}
carbonyl)phenyl]-3,5-dioxa-4-boratricyclo[5.2.2.0²,⁶]undecane-8-carboxamide

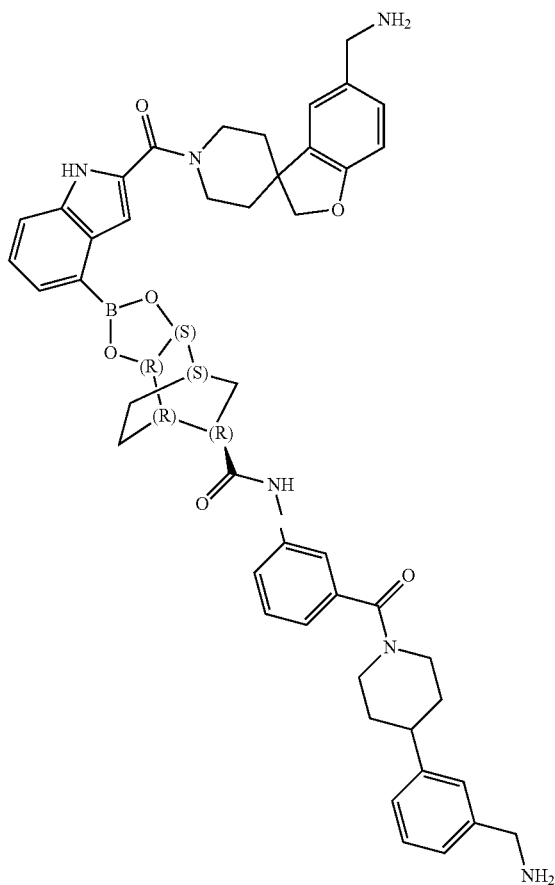
(3-{1-[(3-{[(1S,2R,6R,7R,8R)-4-[2-({4-[3-(aminomethyl)phenyl]piperidin-1-yl}carbonyl)-1H-indol-4-yl]-2,9,9-trimethyl-3,5-dioxa-4-boratricyclo[6.1.1.0$^{2,6}$]decan-7-yl]oxy}phenyl)carbonyl]piperidin-4-yl}phenyl)methanamine

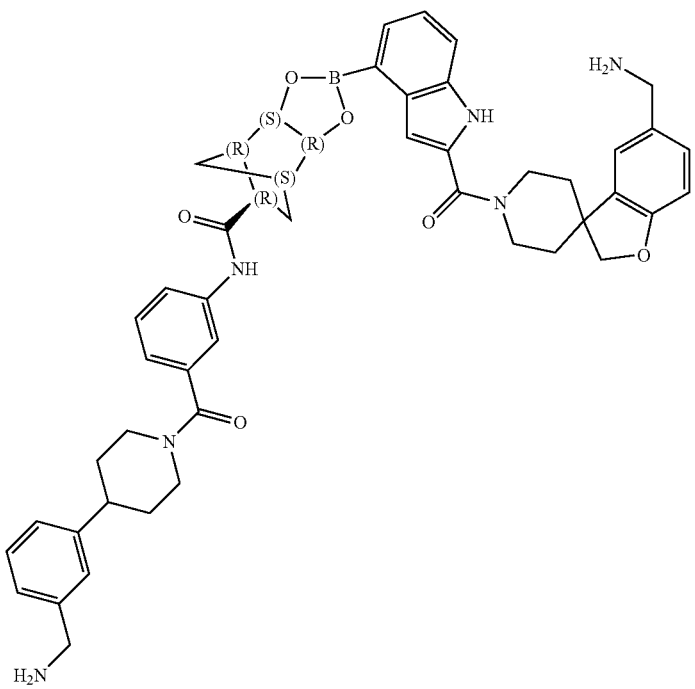
(1S,2R,6S,7R,8R)-4-(2-{[5-(aminomethyl)-2H-spiro[1-benzofuran-3,4′-piperidine]-1′-yl]carbonyl}-1H-indol-4-yl)-N-[3-({4-[3-(aminomethyl)phenyl]piperidin-1-yl}carbonyl)phenyl]-3,5-dioxa-4-boratricyclo[5.2.1.0²,⁶]decane-8-carboxamide
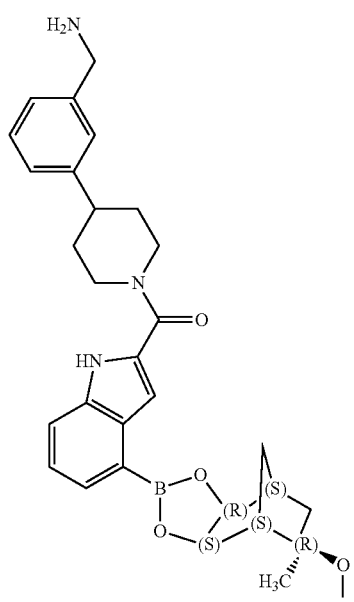

-continued

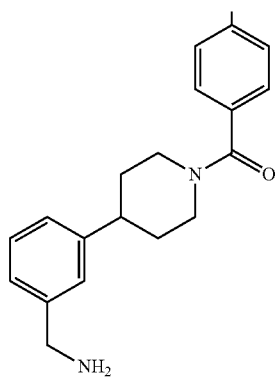

{3-[1-({4-[(1S,2R,6S,7S,8R)-8-[4-({4-[3-(aminomethyl)phenyl]piperidin-1-yl}carbonyl)phenoxy]-8-methyl-3,5-dioxa-4-boratricyclo[5.2.1.0²,⁶]decan-4-yl]-1H-indol-2-yl}carbonyl)piperidin-4-yl]phenyl}methanamine

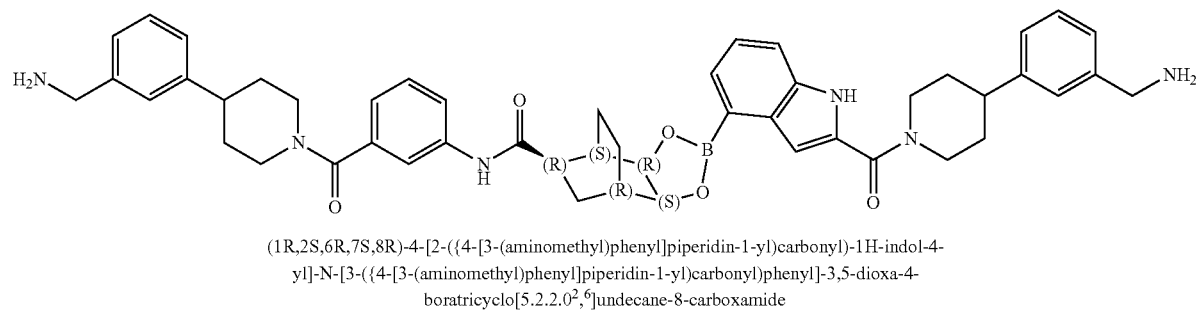

(1R,2S,6R,7S,8R)-4-[2-({4-[3-(aminomethyl)phenyl]piperidin-1-yl}carbonyl)-1H-indol-4-yl]-N-[3-({4-[3-(aminomethyl)phenyl]piperidin-1-yl}carbonyl)phenyl]-3,5-dioxa-4-boratricyclo[5.2.2.0²,⁶]undecane-8-carboxamide

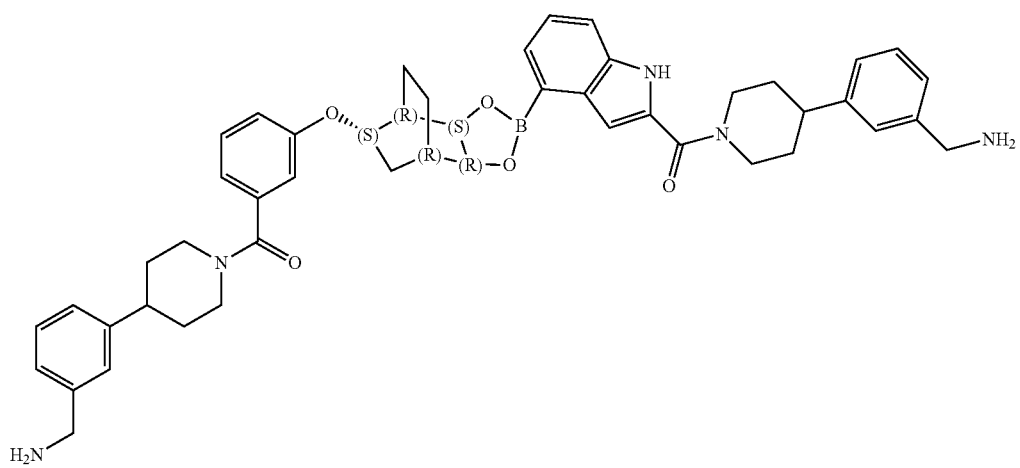

(3-{1-[(3-{[(1R,2R,6S,7R,8S)-4-[2-({4-[3-(aminomethyl)phenyl]piperidin-1-yl}carbonyl)-1H-indol-4-yl]-3,5-dioxa-4-boratricyclo[5.2.2.0²,⁶]undecan-8-yl]oxy}phenyl)carbonyl]piperidin-4-yl}phenyl)methanamine

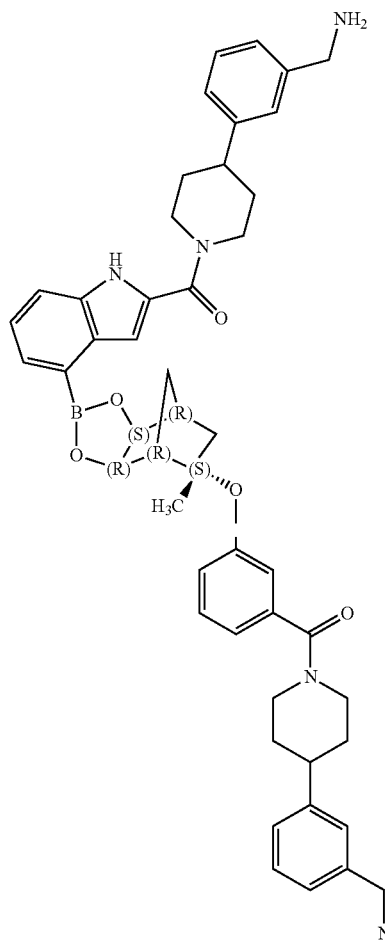
{3-[1-({4-[(1R,2S,6R,7R,8S)-8-[3-({4-[3-(aminomethyl)phenyl]piperidin-1-yl}carbonyl)phenoxy]-8-methyl-3,5-dioxa-4-boratricyclo[5.2.1.0$^{2,6}$]decan-4-yl]-1H-indol-2-yl}carbonyl)piperidin-4-yl]phenyl}methanamine

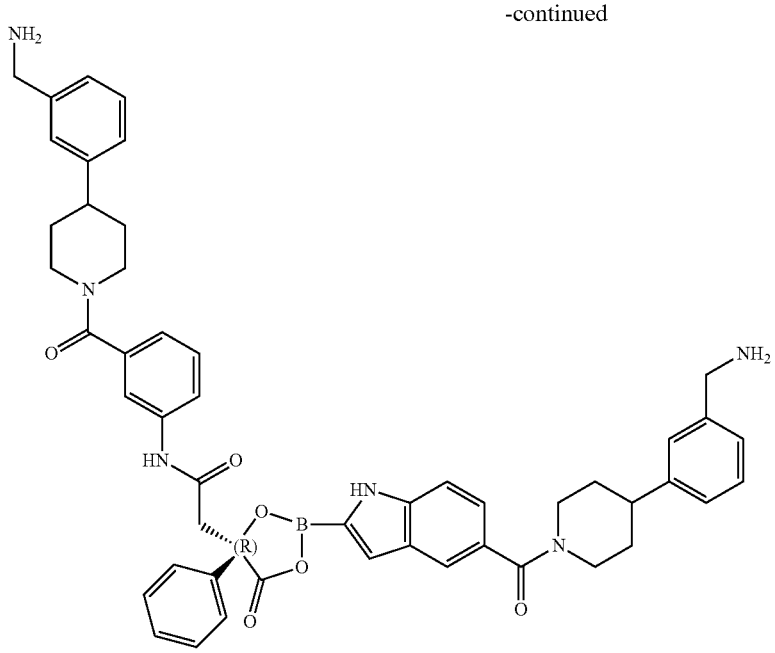
2-[(4R)-2-[5-({4-[3-(aminomethyl)phenyl]piperidin-1-yl}carbonyl-1H-indol-2-yl]
5-oxo-4-phenyl-1,3,2-dioxaborolan-4-yl]-N-[3-({4-[3-(aminomethyl)phenyl]piperidin-1-
yl}carbonyl)phenyl]acetamide
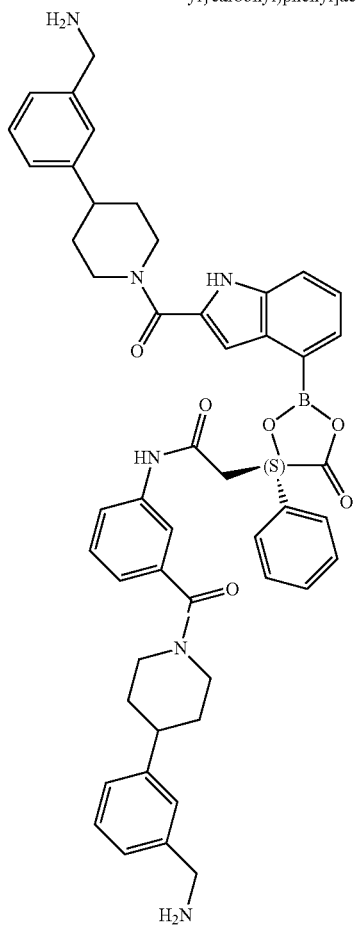
2-[(4S)-2-[2-({4-[3-(aminomethyl)phenyl]piperidin-1-yl}carbonyl)-
1H-indol-4-yl]-5-oxo-4-phenyl-1,3,2-dioxaborolan-4-yl]-N-[3-({4-[3-
(aminomethyl)phenyl]piperidin-1-yl}carbonyl)phenyl]acetamide

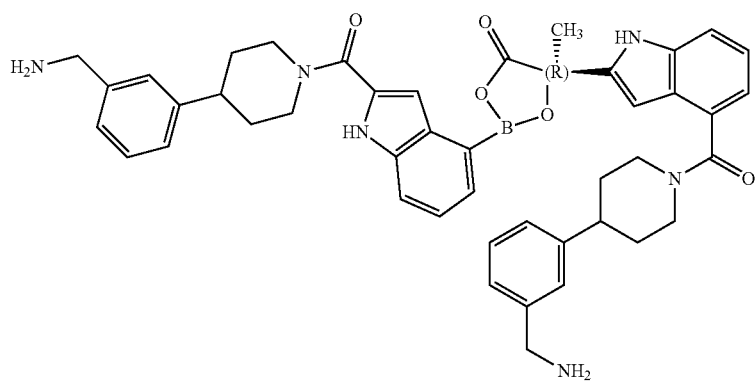
(5R)-5-[4-({4-[3-aminomethyl)phenyl]piperidin-1-yl)carbonyl)-1H-indol-2-yl]-2-[2-({4-[3-(aminomethyl)phenyl]piperidin-1-yl}carbonyl)-1H-indol-4-yl]-5-methyl-1,3,2-dioxaborolan-4-one
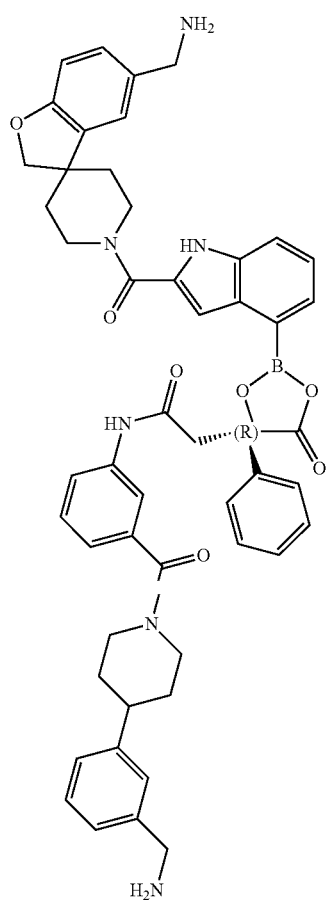
2-[(4R)-2-(2-{[5-(aminomethyl)-2H-spiro[1-benzofuran-3,4'-piperidine]-1'-yl]carbonyl}-1H-indol-4-yl)-5-oxo-4-phenyl-1,3,2-dioxaborolan-4-yl]-N-[3-({4-[3-(aminomethyl)phenyl]piperidin-1-yl)carbonyl)phenyl]acetamide -continued
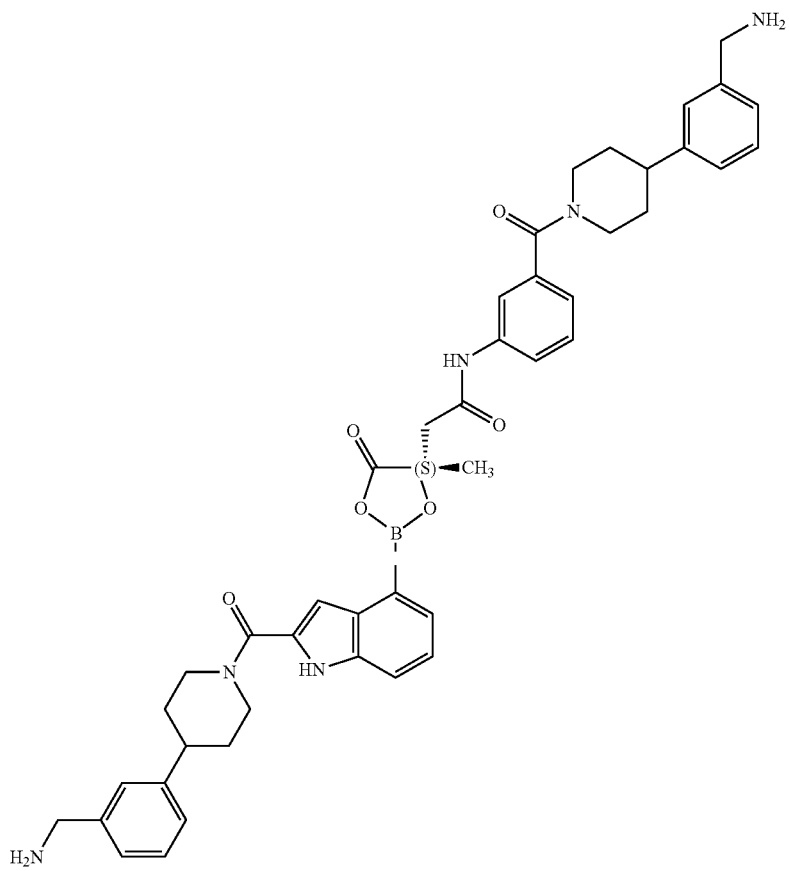
2-[(4S)-2-[2-({4-[3-(aminomethyl)phenyl]piperidin-1-yl}carbonyl)-1H-indol-4-yl]-4-methyl-5-oxo-1,3,2-dioxaborolan-4-yl]-N-[3-({4-[3-(aminomethyl)phenyl]piperidin-1-yl}carbonyl)phenyl]acetamide
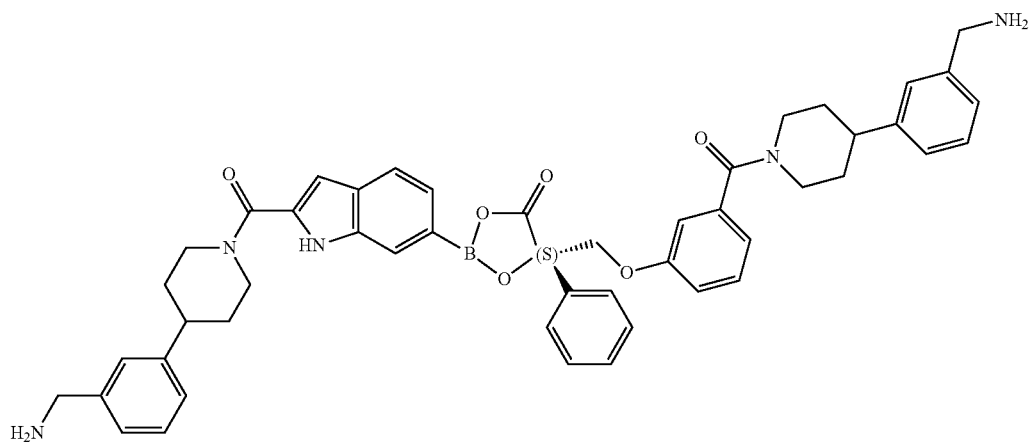
(5S)-2-[2-({4-[3-(aminomethyl)phenyl]piperidin-1-yl}carbonyl)-1H-indol-6-yl]-5-[3-({4-[3-(aminomethyl)phenyl]piperidin-1-yl)carbonyl)phenoxymethyl]-5-phenyl-1,3,2-dioxaborolan-4-one 241 242
-continued
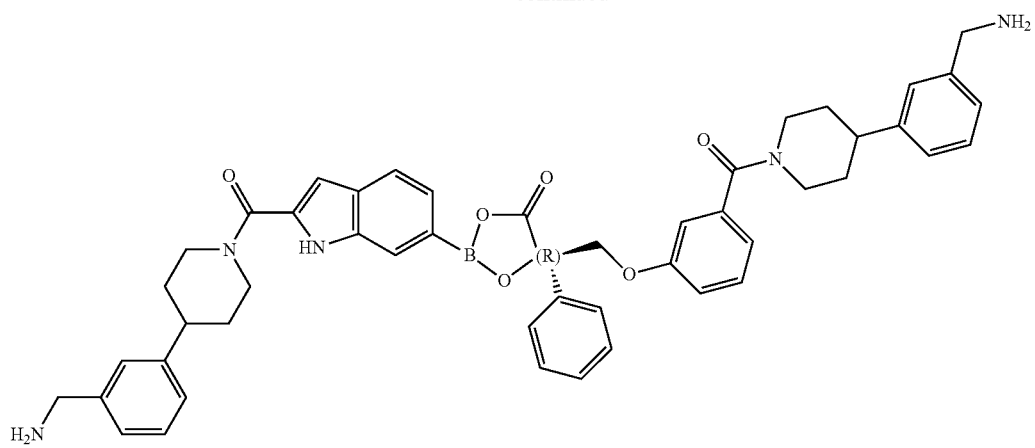
(5R)-2-[2-({4-[3-(aminomethyl)phenyl]piperidin-1-yl}carbonyl)-1H-indol-6-
yl]-5-[3-({4-[3-(aminomethyl)phenyl]piperidin-1-yl}carbonyl)phenoxymethyl]-5-
phenyl-1,3,2-dioxaborolan-4-one
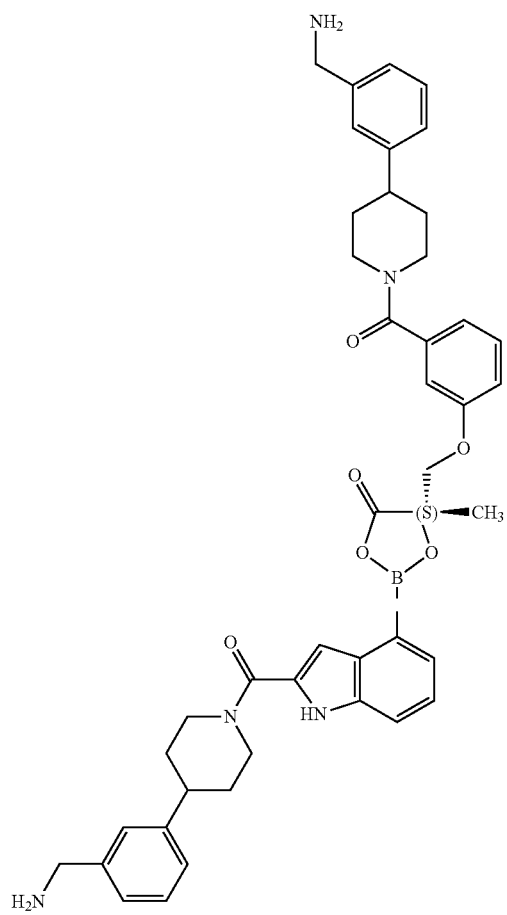
(5S)-2-[2-({4-[3-(aminomethyl)phenyl]piperidin-1-yl}carbonyl)-1H-indol-4-
yl]-5-[3-({4-[3-(aminomethyl)phenyl]piperidin-1-yl}carbonyl)phenoxymethyl]-5-methyl-1,3,2-
dioxaborolan-4-one -continued

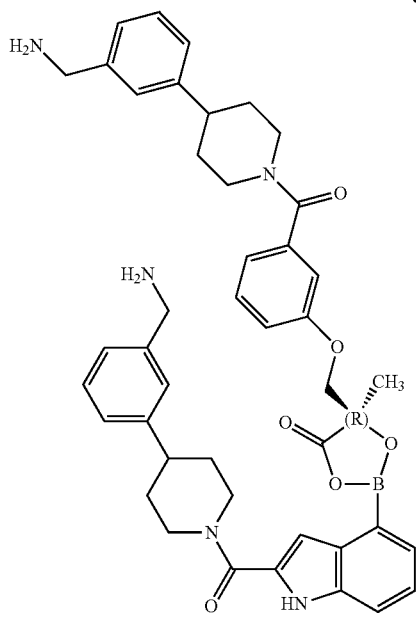

(5R)-2-[2-({4-[3-(aminomethyl)phenyl]piperidin-1-yl}carbonyl)-1H-indol-4-yl]-5-[3-({4-[3-(aminomethyl)phenyl]piperidin-1-yl}carbonyl)phenoxymethyl]-5-methyl-1,3,2-dioxaborolan-4-one

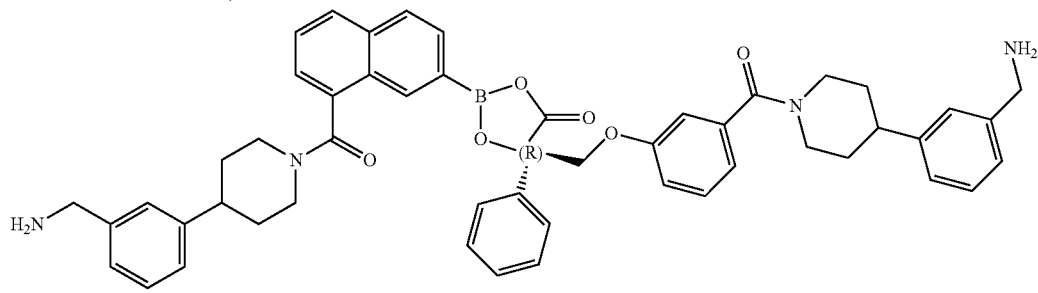

(5R)-2-[8-({4-[3-(aminomethyl)phenyl]piperidin-1-yl}carbonyl)naphthalen-2-yl]-5-[3-({4-[3-(aminomethyl)phenyl]piperidin-1-yl}carbonyl)phenoxymethyl]-5-phenyl-1,3,2-dioxaborolan-4-one

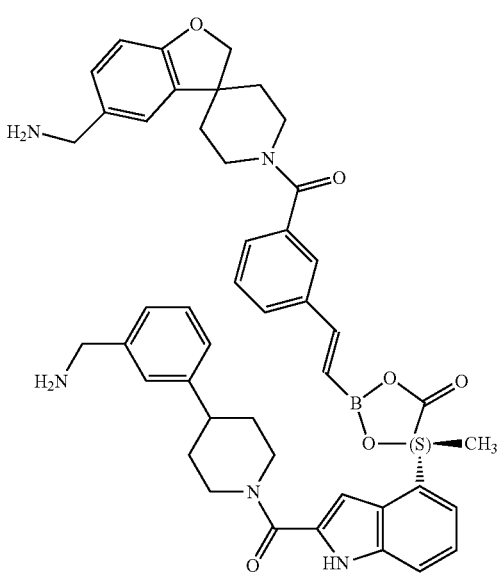

(5S)-2-[(E)-2-(3-{[5-(aminomethyl)-2H-spiro[1-benzofuran-3,4'-piperidine]-1'-yl]carbonyl}phenyl)ethenyl]-5-[2-({4-[3-(aminomethyl)phenyl]piperidin-1-yl}carbonyl)-1H-indol-4-yl]-5-methyl-1,3,2-dioxaborolan-4-one -continued
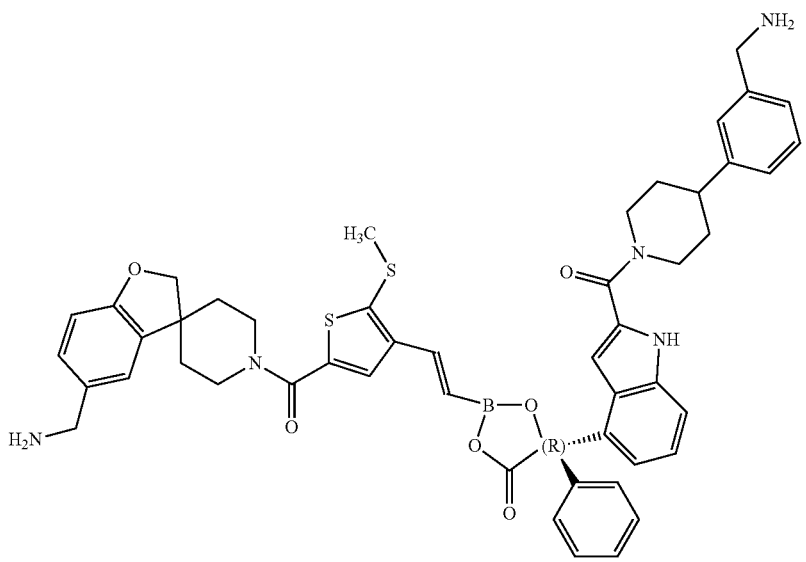
(5R)-2-[(E)-2-(5-{[5-(aminomethyl)-2H-spiro[1-benzofuran-3,4'-piperidine]-1'-yl]carbony}-2-(methylsulfanyl)thiophen-3-yl)ethenyl]-5-[2-({4-[3-(aminomethyl)phenyl]piperidin-1-yl}carbonyl)-1H-indol-4-yl]-5-phenyl-1,3,2-dioxaborolan-4-one
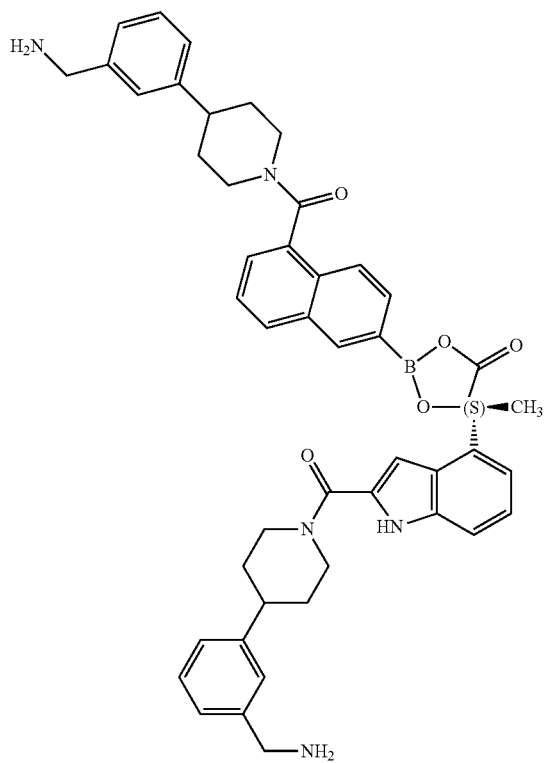
(5S)-5-[2-({4-[3-(aminomethyl)phenyl]piperidin-1-yl}carbonyl)-1H-indol-4-yl]-2-[5-({4-[3-(aminomethyl)phenyl]piperidin-1-yl}carbonyl)naphthalen-2-yl]-5-methyl-1,3,2-dioxaborolan-4-one

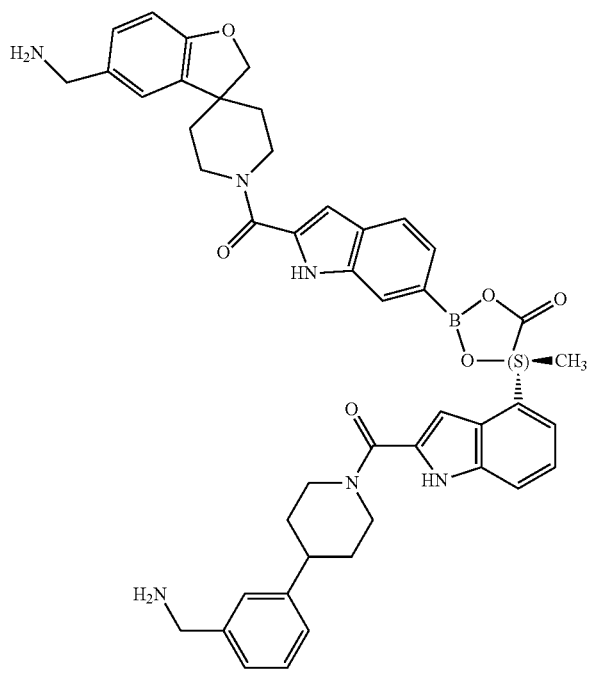
(5S)-2-(2-{[5-(aminomethyl)-2H-spiro[1-benzofuran-3,4'-piperidine]-1'-yl]carbonyl}-1H-indol-6-yl)-5-[2-({4-[3-(aminomethyl)phenyl]piperidin-1-yl}carbonyl)-1H-indol-4-yl]-5-methyl-1,3,2-dioxaborolan-4-one
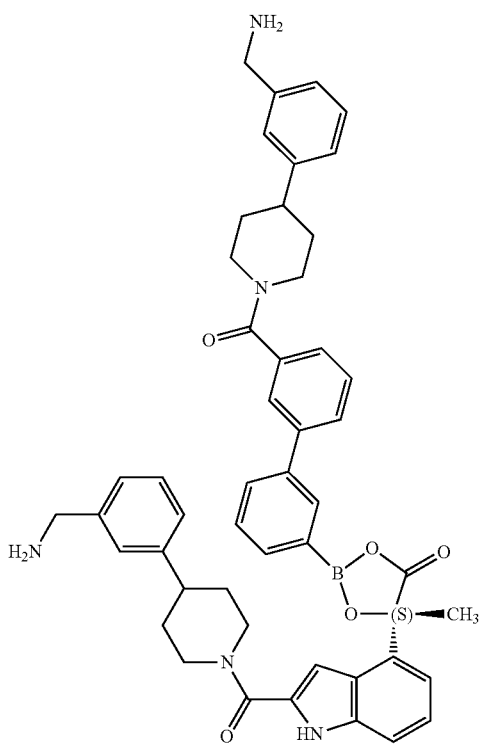
(5S)-5-[2-({4-[3-(aminomethyl)phenyl]piperidin-1-yl}carbonyl)-1H-indol-4-yl]-2-{3-[3-({4-[3-(aminomethyl)phenyl]piperidin-1-yl}carbonyl)phenyl]phenyl}-5-methyl-1,3,2-dioxaborolan-4-one

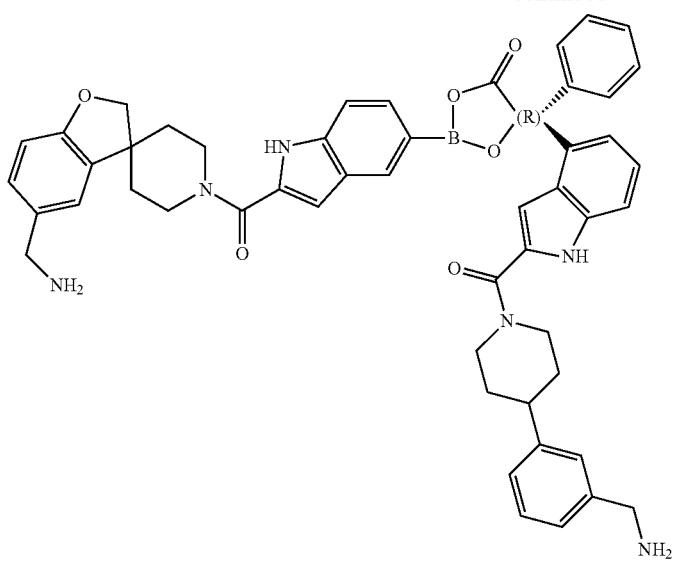
(5R)-2-(2-{[5-(aminomethyl)-2H-spiro[1-benzofuran-3,4'-piperidine]-1'-yl]carbonyl}-1H-indol-5-yl)-5-[2-({4-[3-(aminomethyl)phenyl]piperidin-1-yl}carbonyl)-1H-indol-4-yl]-5-phenyl-1,3,2-dioxaborolan-4-one
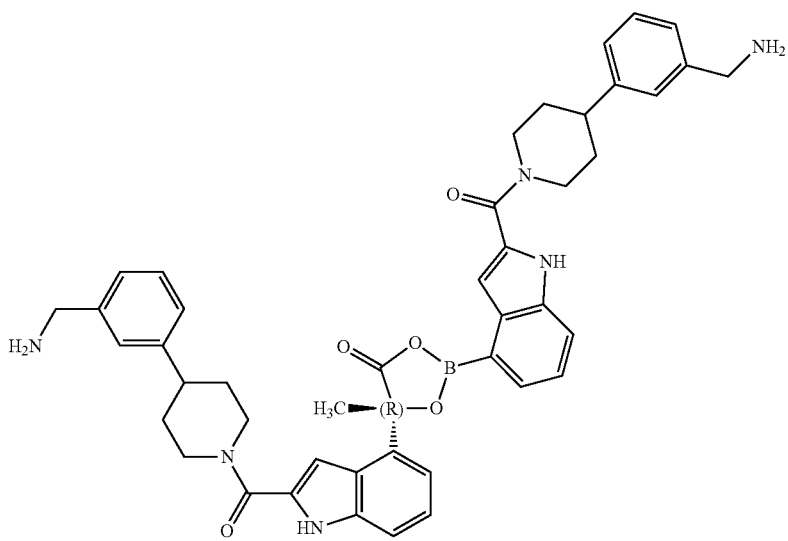
(5R)-2,5-bis[2-({4-[3-(aminomethyl)phenyl]piperidin-1-yl}carbonyl)-1H-indol-4-yl]-5-methyl-1,3,2-dioxaborolan-4-one

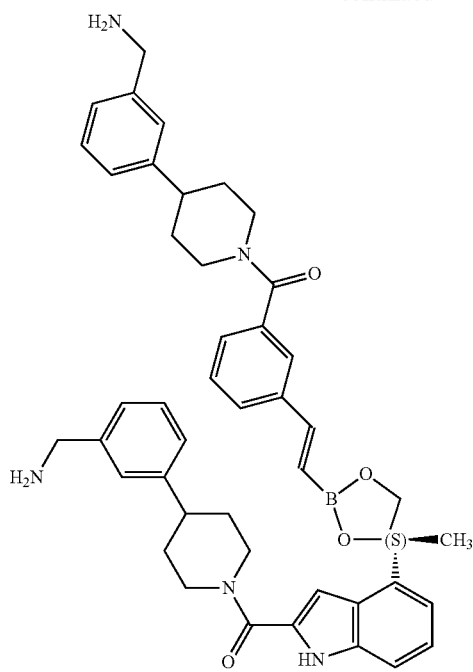
(5S)-5-[2-({4-[3-(aminomethyl)phenyl]piperidin-1-yl}carbonyl)-1H-indol-4-yl]-2-[(E)-2-[3-({4-[3-(aminomethyl)phenyl]piperidin-1-yl}carbonyl)phenyl]ethenyl]-5-methyl-1,3,2-dioxaborolan-4-one
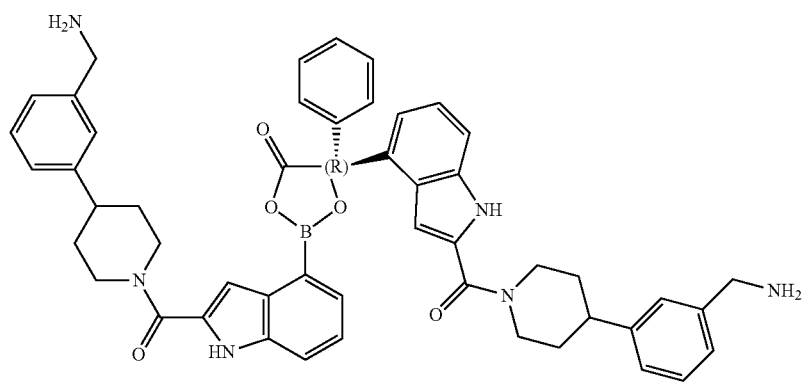
(5R)-2,5-bis[2-({4-[3-(aminomethyl)phenyl]piperidin-1-yl}carbonyl)-1H-indol-4-yl]-5-phenyl-1,3,2-dioxaborolan-4-one

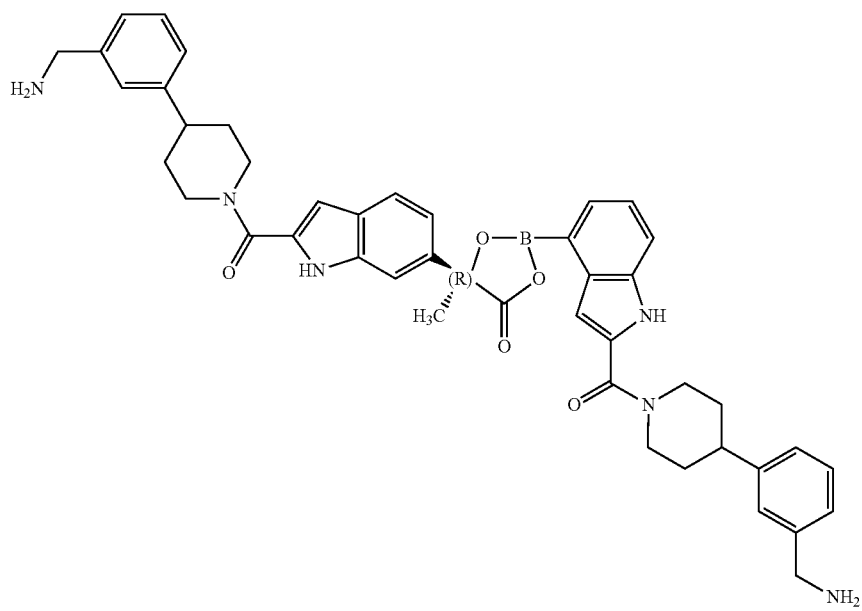
(5R)-2-[2-({4-[3-(aminomethyl)phenyl]piperidin-1-yl}carbonyl)-1H-indol-4-yl]-5-[2-({4-[3-(aminomethyl)phenyl]piperidin-1-yl}carbonyl)1H-indol-6-yl]-5-methyl-1,3,2-dioxaborolan-4-one
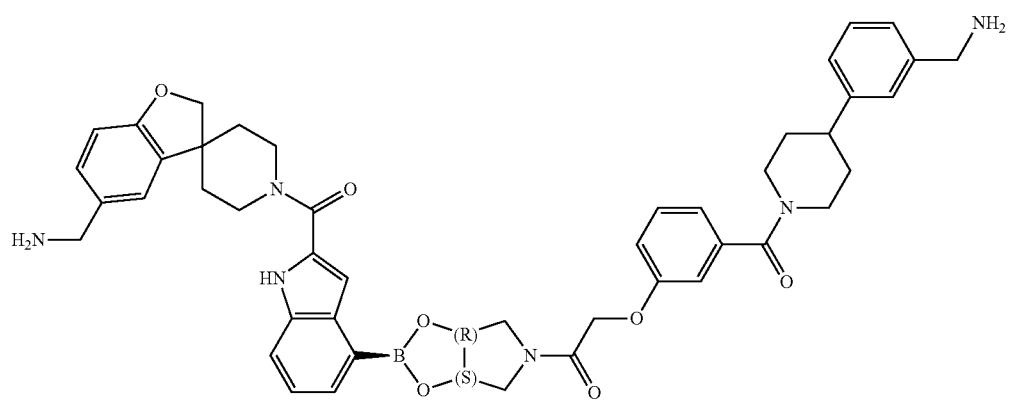
1-[(3aR,6aS)-2-)2-{[5-(aminomethyl)-2H-spiro[1-benzofuran-3,4'-piperidine]-1'-yl]carbonyl}-1H-indol-4-yl)-hexahydro-[1,3,2]dioxaborolo[4,5-c]pyrrol-5-yl]-2-[3-({4-[3-(aminomethyl)phenyl]piperidin-1-yl}carbonyl)phenoxy]ethan-1-one -continued

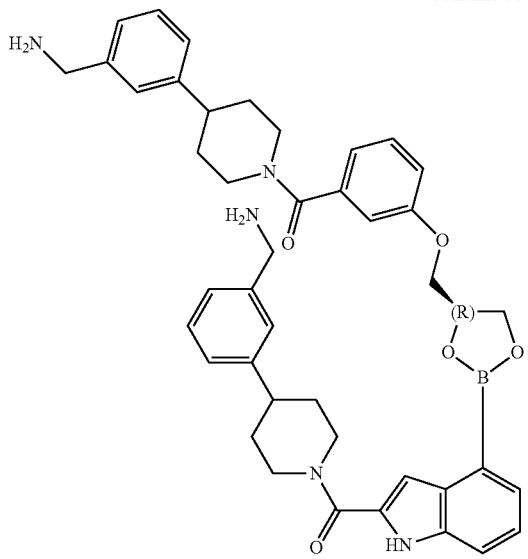

(3-{1-[(3-{[(4R)-2-[2-({4-[3-(aminomethyl)phenyl]piperidin-1-yl}carbonyl)-1H-indol-4-yl]-1,3,2-dioxaborolan-4-yl]methoxy}phenyl)carbonyl]piperidin-4-yl}phenyl)methanamine

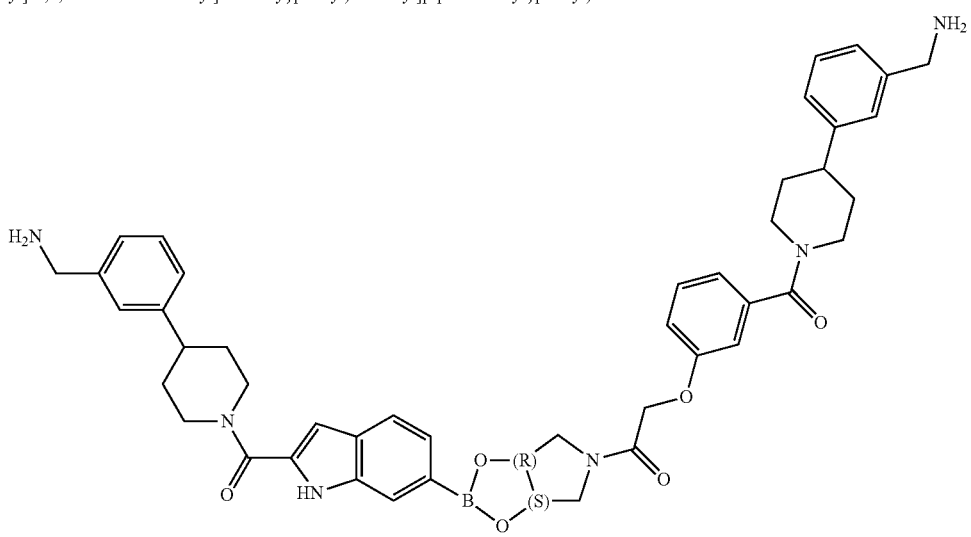

1-[(3aR,6aS)-2-[2-({4-[3-(aminomethyl)phenyl]piperidin-1-yl}carbonyl)-1H-indol-6-yl]hexahydro-[1,3,2]dioxaborolo[4,5-c]pyrrol-5-yl]-2-[3-({4-[3-(aminomethyl)phenyl]piperidin-1-yl}carbonyl)phenoxy]ethan-1-one

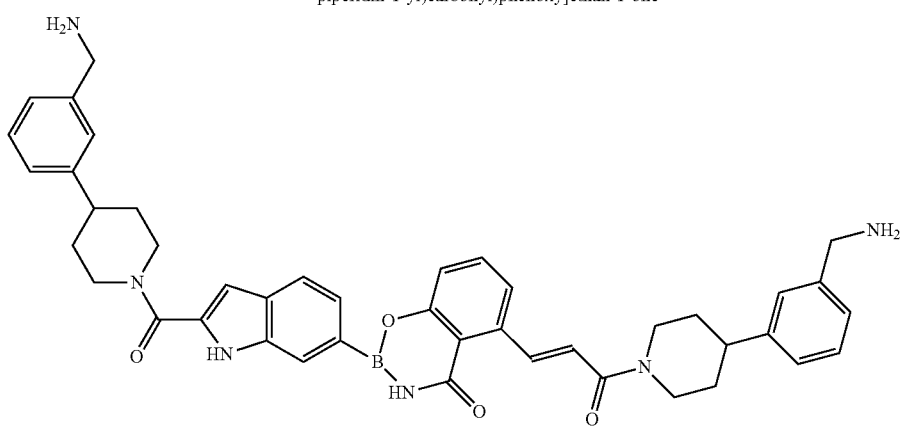

5-[(1E)-3-{4-[3-(aminomethyl)phenyl]piperidin-1-yl}-3-oxoprop-1-en-1-yl]-2-[2-({4-[3-(aminomethyl)phenyl]piperidin-1-yl}carbonyl)-1H-indol-6-yl]-3,4-dihydro-2H-1,3,2-benzoxazaborinin-4-one

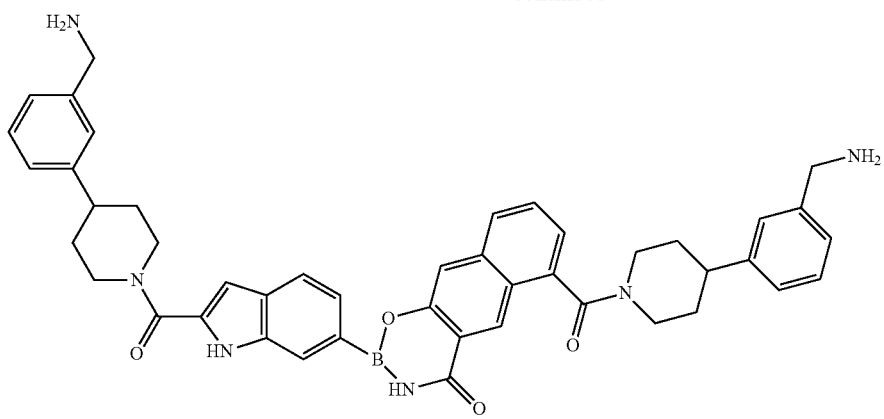
6-({4-[3-(aminomethyl)phenyl]piperidin-1-yl}carbonyl)-2-[2-({4-[3-(aminomethyl)phenyl]piperidin-1-yl)carbonyl)-1H-indol-6-yl]-2H,3H,4H-naphtho[2,3-e][1,3,2]oxazaborinin-4-one
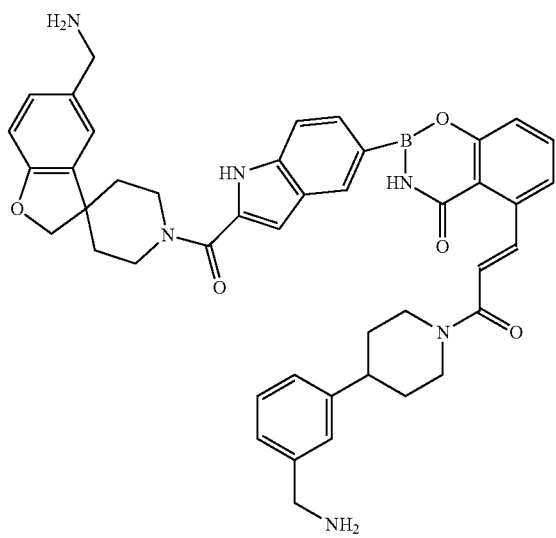
2-(2-{[5-(aminomethyl)-2H-spiro[1-benzofuran-3,4'-piperidine]-1'-yl]carbonyl}-1H-indol-5-yl)-5-[(1E)-3-{4-[3-(aminomethyl)phenyl]piperidin-1-yl}-3-oxoprop-1-en-1-yl]-3,4-dihydro-2H-1,3,2-benzoxazaborinin-4-one -continued

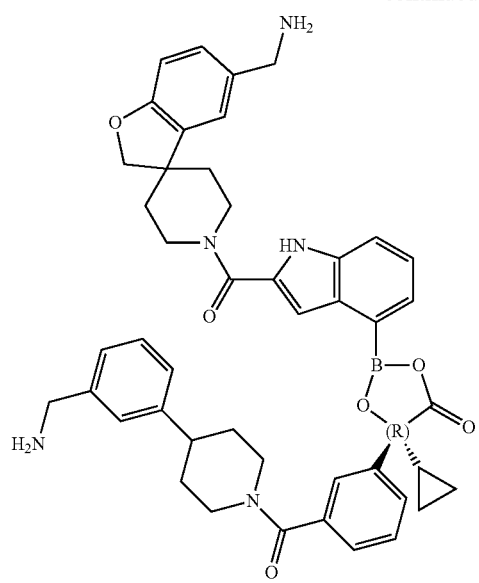

(5R)-2-(2-{[5-(aminomethyl)-2H-spiro[1-benzofuran-3,4'-piperidine]-1'-yl]carbonyl}-
1H-indol-4-yl)-5-[3-({4-[3-(aminomethyl)phenyl]piperidin-1-yl}carbonyl)phenyl]-5-cyclopropyl-
1,3,2-dioxaborolan-4-one

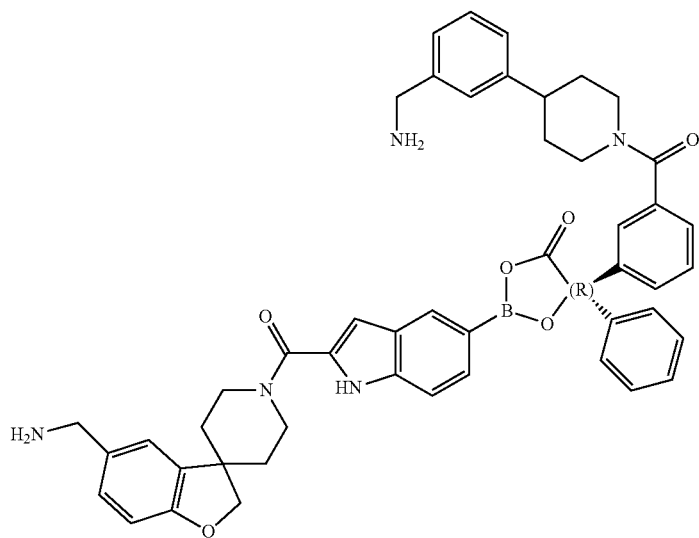

(5R)-2-(2-{[5-(aminomethyl)-2H-spiro[1-benzofuran-3,4'-piperidine]-1'-
yl]carbonyl}-1H-indol-5-yl)-5-[3-({4-[3-(aminomethyl)phenyl]piperidin-1-yl}carbonyl)
phenyl]-5-phenyl-1,3,2-dioxaborolan-4-one

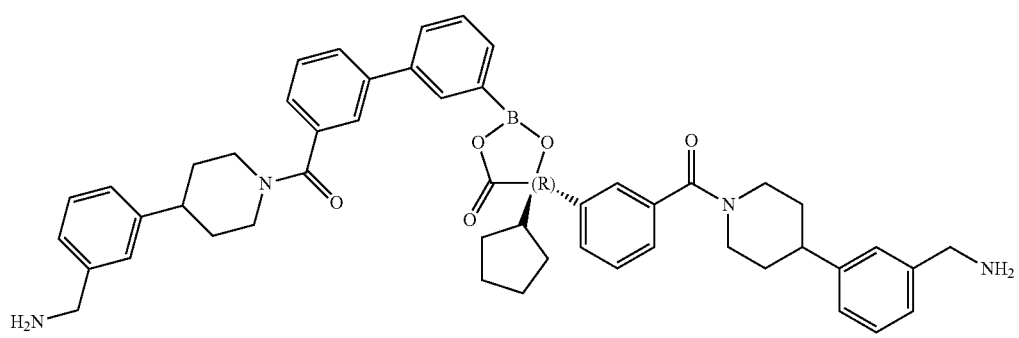

(5R)-5-[3-({4-[3-(aminomethyl)phenyl]piperidin-1-yl}carbonyl)phenyl]-2-{3-[3-({4-[3-
(aminomethyl)phenyl]piperidin-1-yl}carbonyl)phenyl]phenyl}-5-cyclopentyl-
1,3,2-dioxaborolan-4-one -continued

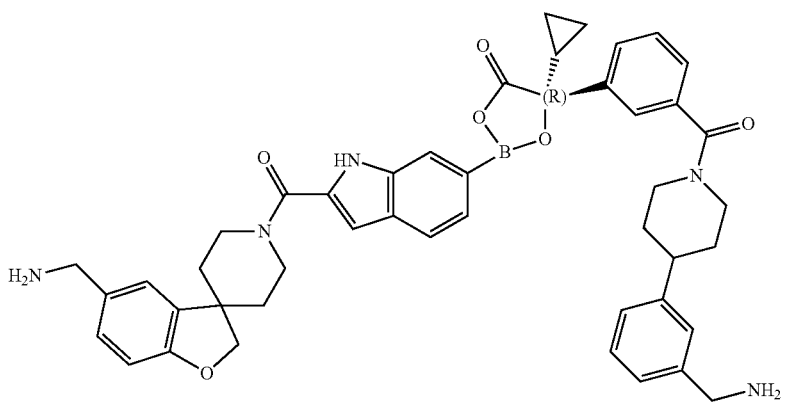

(5R)-2-(2-{[5-(aminomethyl)-2H-spiro[1-benzofuran-3,4′-piperidine]-1′-yl]carbonyl}-1H-indol-6-yl)-5-[3-({4-[3-(aminomethyl)phenyl]piperidin-1-yl}carbonyl)phenyl]-5-cyclopropyl-1,3,2-dioxaborolan-4-one

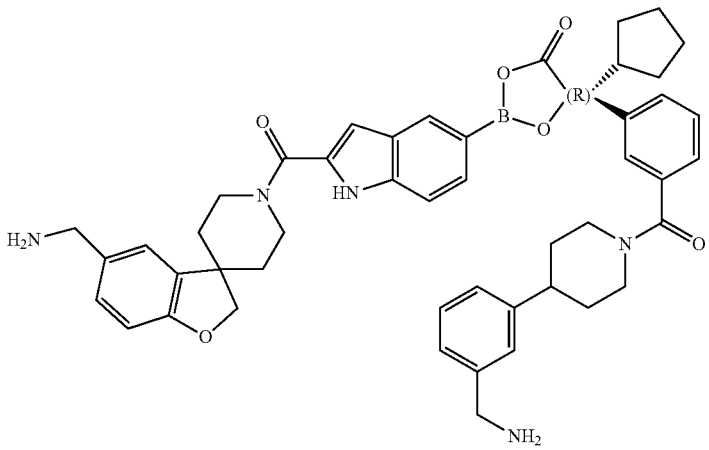

(5R)-2-(2-{[5-(aminomethyl)-2H-spiro[1-benzofuran-3,4′-piperidine]-1′-yl]carbonyl}-1H-indol-5-yl)-5-[3-({4-[3-(aminomethyl)phenyl]piperidin-1-yl}carbonyl)phenyl]-5-cyclopentyl-1,3,2-dioxaborolan-4-one

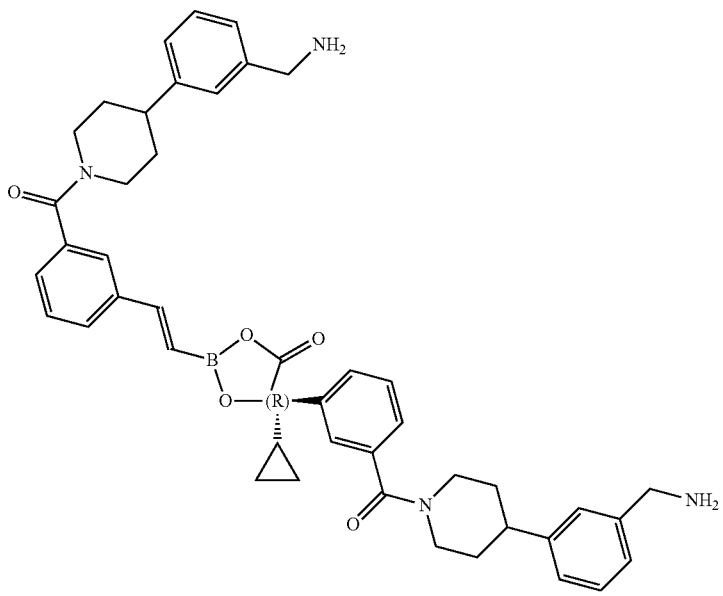

(5R)-5-[3-({4-[3-(aminomethyl)phenyl]piperidin-1-yl}carbonyl)phenyl]-2-[(E)-2-[3-({4-[3-(aminomethyl)phenyl]piperidin-1-yl}carbonyl)phenyl]ethenyl]-5-cyclopropyl-1,3,2-dioxaborolan-4-one

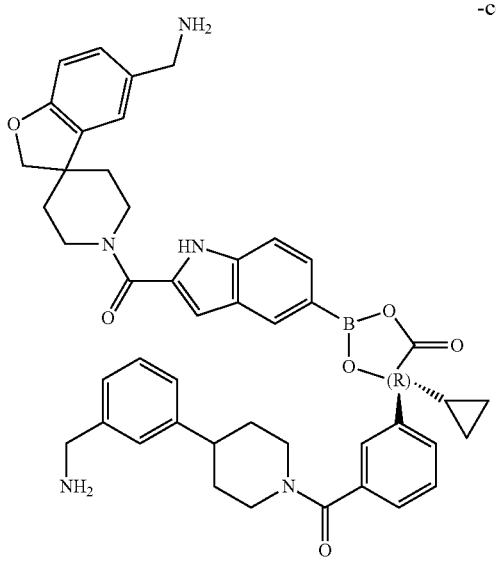
(5R)-2-(2-{[5-(aminomethyl)-2H-spiro[1-benzofuran-3,4'-piperidine]-1'-yl]carbonyl}-1H-indol-5-yl)-5-[3-({4-[3-(aminomethyl)phenyl]piperidin-1-yl}carbonyl)phenyl]-5-cyclopropyl-1,3,2-dioxaborolan-4-one
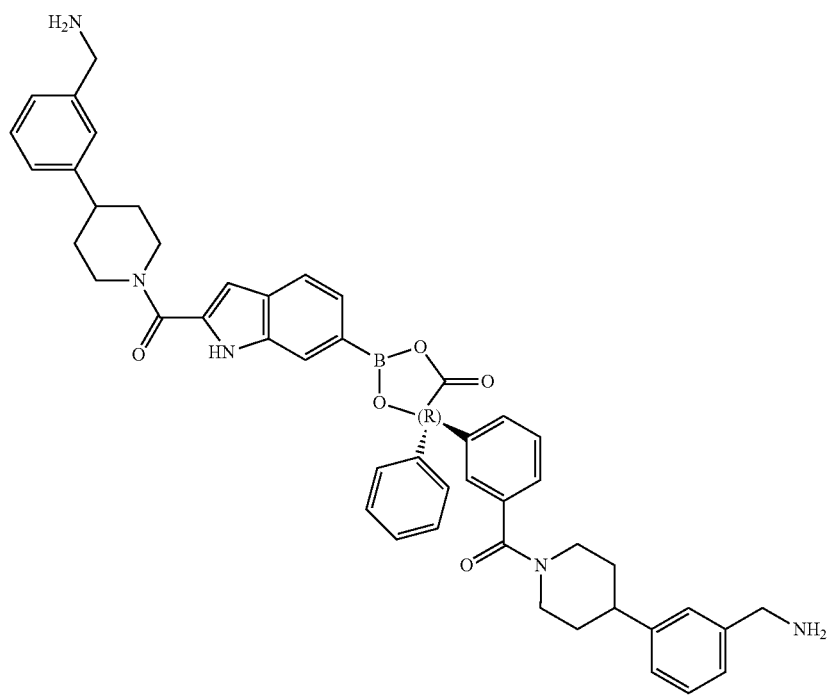
(5R)-2-[2-({4-[3-(aminomethyl)phenyl]piperidin-1-yl}carbonyl)-1H-indol-6-yl]-5-[3-({4-[3-(aminomethyl)phenyl]piperidin-1-yl}carbonyl)phenyl-5-phenyl-1,3,2-dioxaborolan-4-one

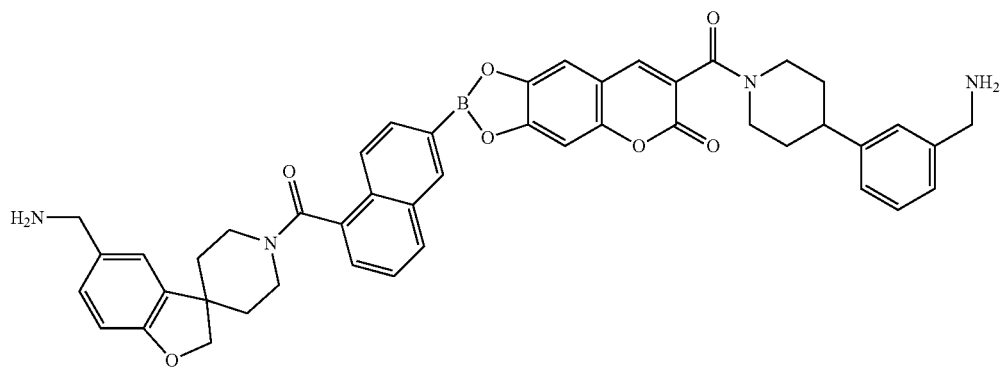
2-(5-{[5-(aminomethyl)-2H-spiro[1-benzofuran-3,4′-piperidine]-1′-yl]carbonyl}naphthalen-2-yl)-7-({4-[3-(aminomethyl)phenyl]piperidin-1-yl}carbonyl)-2H,6H-[1,3,2]dioxaborolo[4,5-g]chromen-6-one
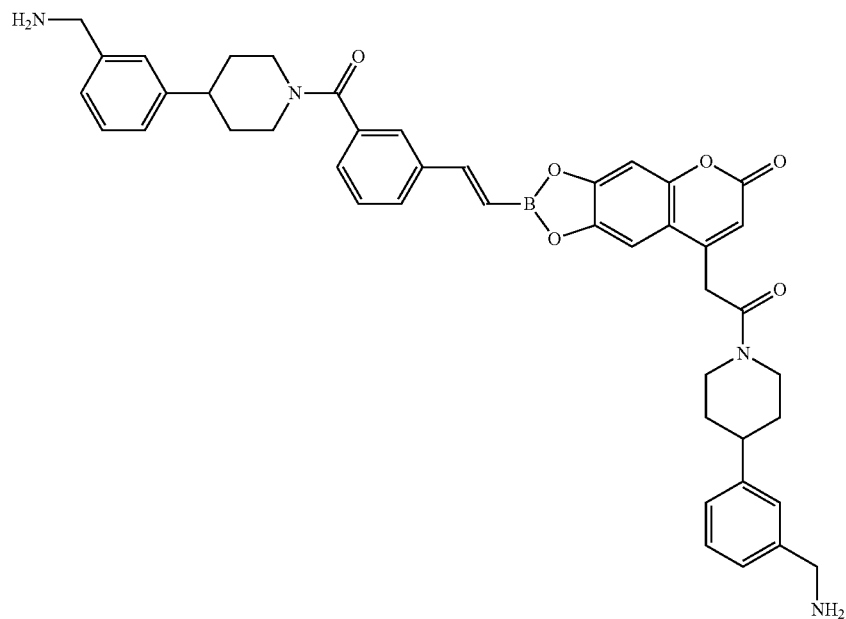
8-(2-{4-[3-(aminomethyl)phenyl]piperidin-1-yl}-2-oxoethyl)-2-[(E)-2-[3-({4-[3-(aminomethyl)phenyl]piperidin-1-yl}carbonyl)phenyl]ethenyl-2H,6H-[1,3,2]dioxaborolo[4,5-g]chromen-6-one

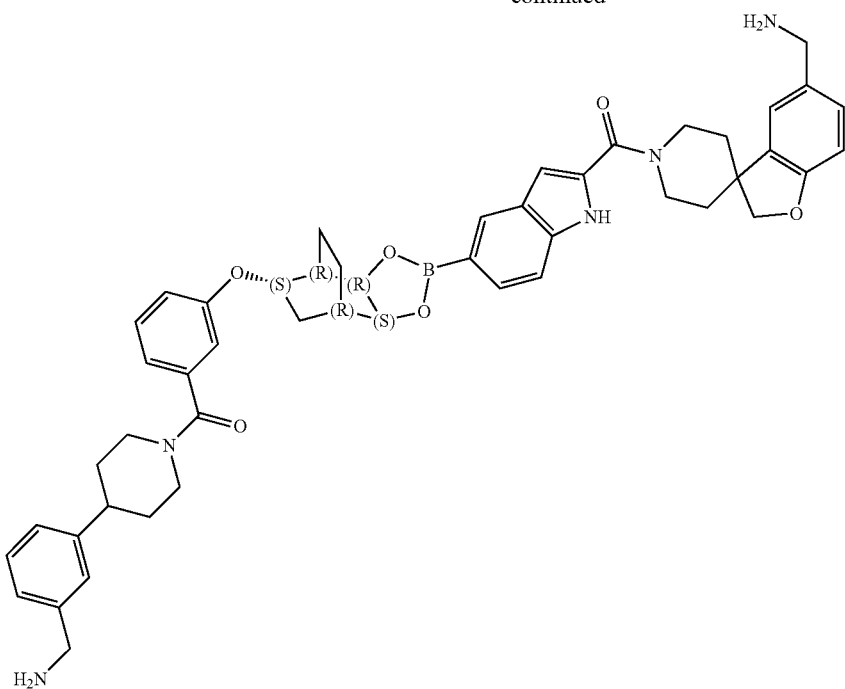
1'-({5-[(1R,2S,6R,7R,8S)-8-[3-({4-[3-(aminomethyl)phenyl]piperidin-1-yl}carbonyl)phenoxy]-3,5-dioxa-4-boratricyclo[5.2.2.0$^{2,6}$]undecan-4-yl]-1H-indol-2-yl}carbonyl)-2H-spiro[1-benzofuran-3,4'-piperidine]-5-ylmethanamine
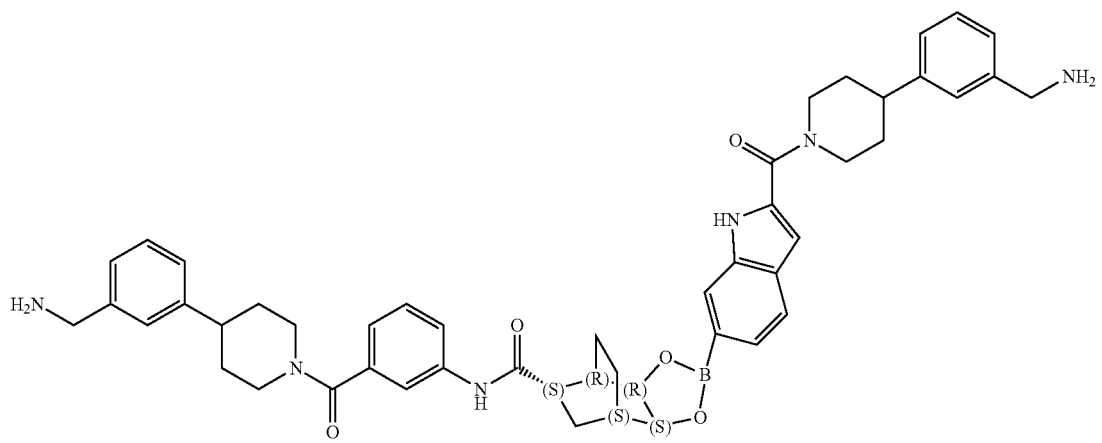
(1S,2S,6R,7R,8S)-4-[2-({4-[3-(aminomethyl)phenyl]piperidin-1-yl}carbonyl)-1H-indol-6-yl]-N-[3-({4-[3-(aminomethyl)phenyl]piperidin-1-yl}carbonyl)phenyl]-3,5-dioxa-4-boratricyclo[5.2.2.0$^{2,6}$]undecane-8-carboxamide -continued
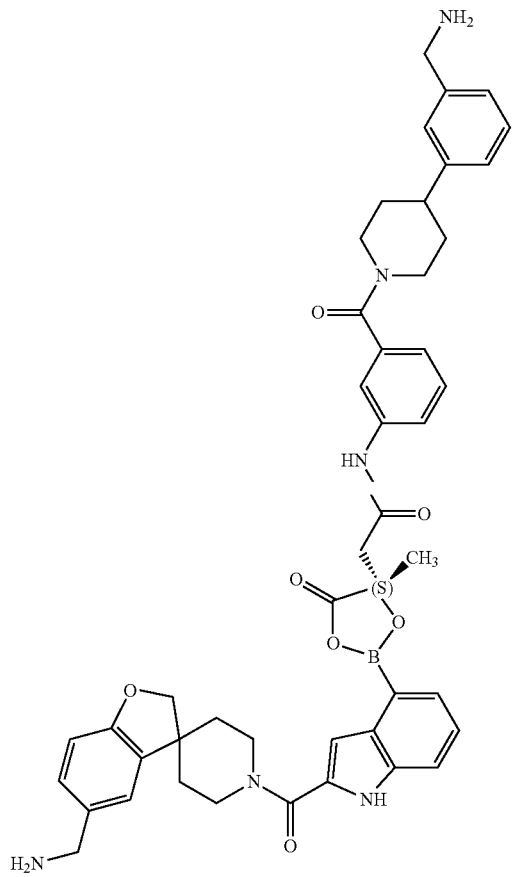
2-[(4S)-2-(2-{[5-(aminomethyl)-2H-spiro[1-benzofuran-3,4'-piperidine]-1'-yl]carbonyl}-1H-indol-4-yl)-4-methyl-5-oxo-1,3,2-dioxaborolan-r-yl]-N-[3-({4-[3-(aminomethyl)phenyl]piperidin-1-yl}carbonyl)phenyl]acetamide

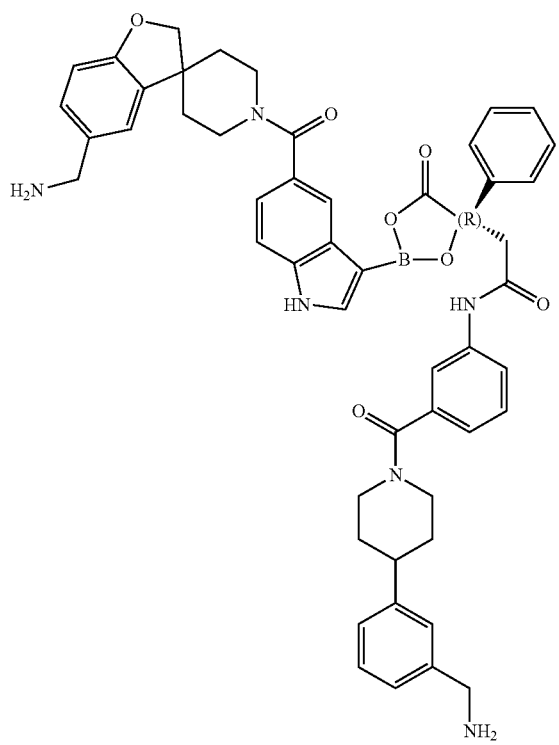
2-[(4R)-2-(5-{[5-(aminomethyl)-2H-spiro[1-benzofuran-3,4'-piperidine]-1'-yl]carbonyl}-1H-indol-3-yl)-5-oxo-4-phenyl-1,3,2-dioxaborolan-4-yl]-N-[3-({4-[3-(aminomethyl)phenyl]piperidin-1-yl}carbonyl)phenyl]acetamide
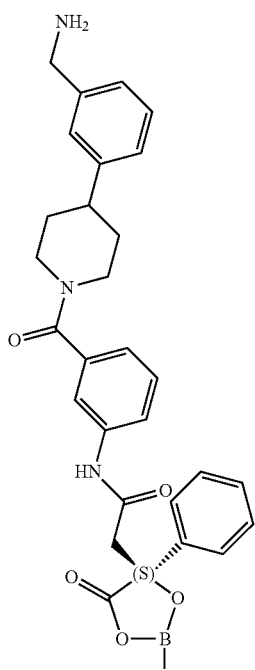

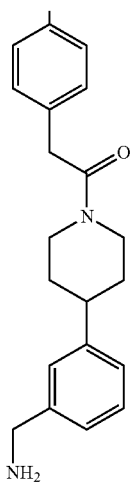
2-[(4S)-2-[4-(2-{4-[3-(aminomethyl)phenyl]piperidin-1-yl}-2-oxoethyl)phenyl]-5-oxo-4-phenyl-1,3,2-dioxaborolan-4-yl]-N-[3,({4-[3-(aminomethyl)phenyl]piperidin-1-yl}carbonyl)phenyl]acetamide
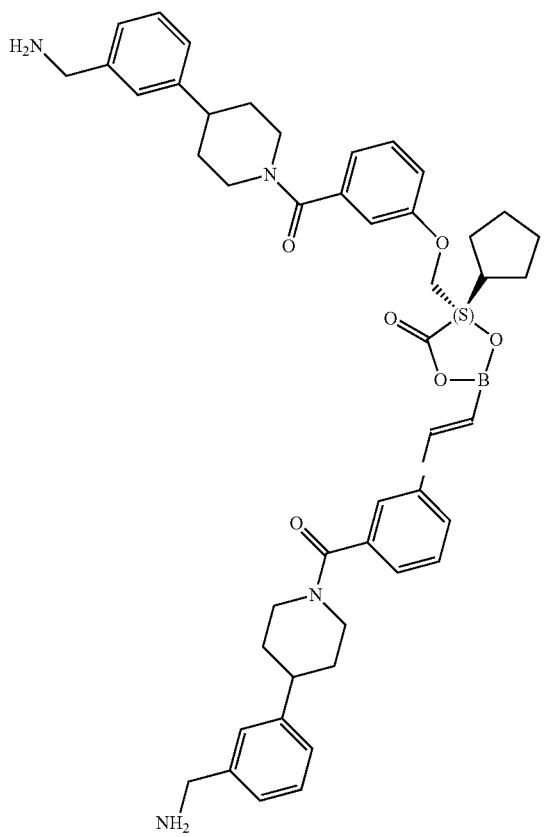
(5S)-5-[3-({4-[3-(aminomethyl)phenyl]piperidin-1-yl}carbonyl)phenoxymethyl]-2-[(E)-2-[3-({4-[3-(aminomethyl)phenyl]piperidin-1-yl}carbonyl)phenyl]ethenyl]-5-cyclopentyl-1,3,2-dioxaborolan-4-one

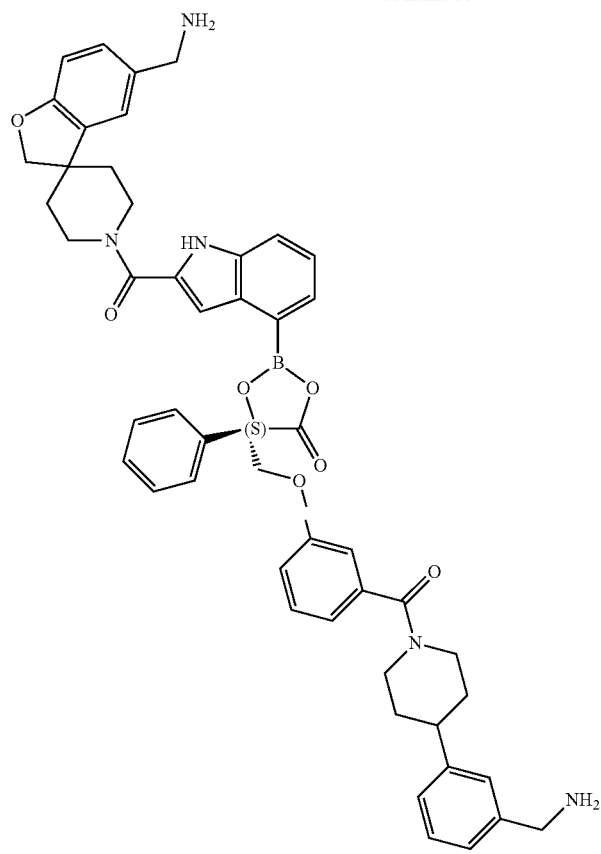
(5S)-2-(2-{[5-(aminomethyl)-2H-spiro[1-benzofuran-3,4'-piperidine]-1'-yl]carbonyl}-1H-indol-4-yl)-5-[3-({4-[3-(aminomethyl)phenyl]piperidin-1-yl}carbonyl)phenoxymethyl]-5-phenyl-1,3,2-dioxaborolan-4-one
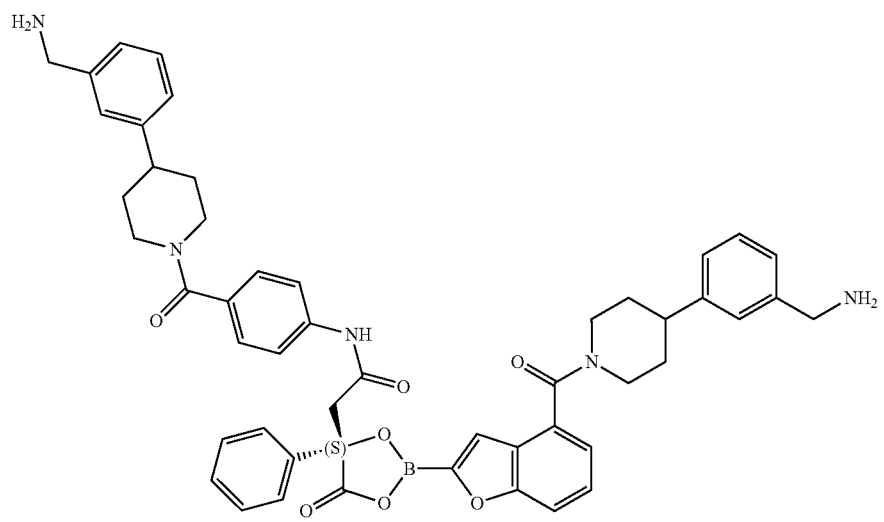
2-[(4S)-2-[4-({4-[3-(aminomethyl)phenyl]piperidin-1-yl}carbonyl)-1-benzofuran-2-yl]-5-oxo-4-phenyl-1,3,2-dioxaborolan-4-yl]-N-[4-({4-[3-(aminomethyl)phenyl]piperidin-1-yl}carbonyl)phenyl]acetamide -continued
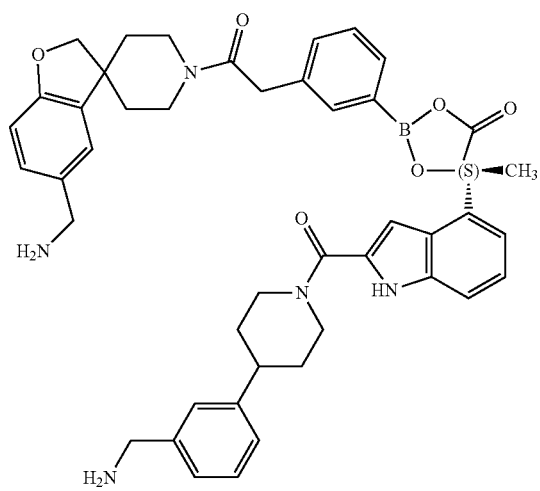
(5S)-2-(3-{2-[5-(aminomethyl)-2H-spiro[1-benzofuran-3,4'-piperidine]-1'-yl]-2-oxoethyl}phenyl)-5-[2-({4-[3-(aminomethyl)phenyl]piperidin-1-yl}carbonyl)-1H-indol-4-yl]-5-methyl-1,3,2-dioxaborlan-4-one
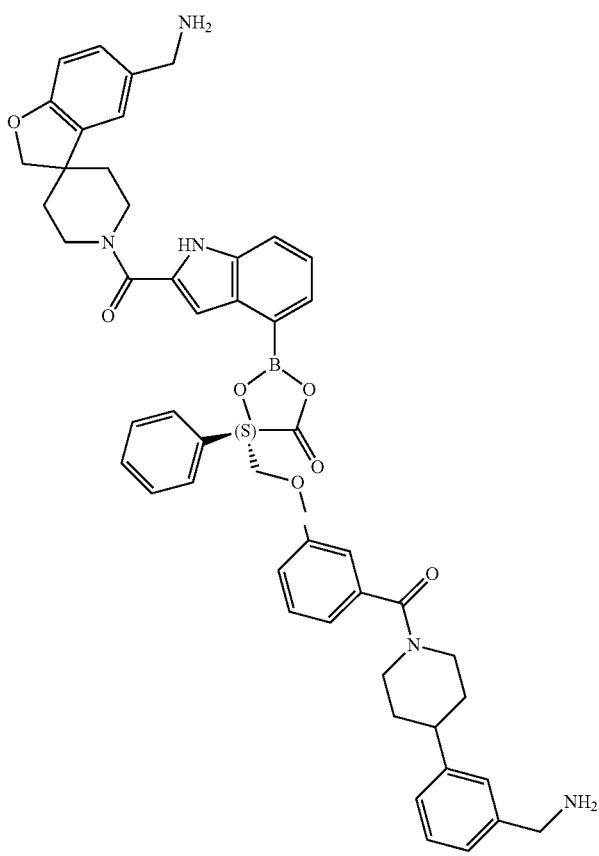
(5S)-2-(2-{[5-(aminomethyl)-2H-spiro[1-benzofuran-3,4'-piperidine]-1'-yl]carbonyl}-1H-indol-4-yl)-5-[3-({4-[3-(aminomethyl)phenyl]piperidin-1-yl}carbonyl)phenoxymethyl-5-phenyl-1,3,2-dioxaborolan-4-one -continued
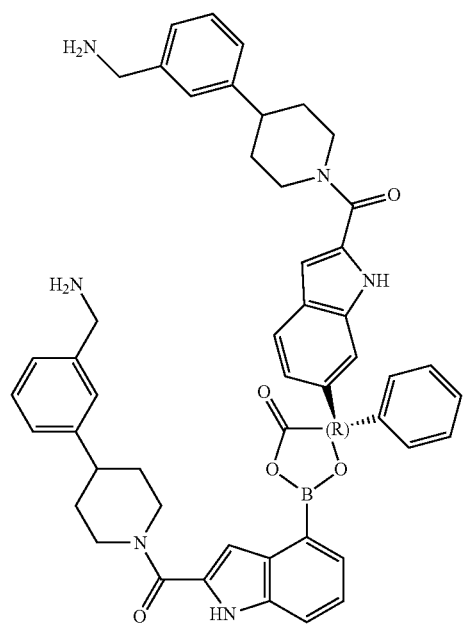
(5R)-2-[2-({4-[3-(aminomethyl)phenyl]piperidin-1-yl}carbonyl)-1H-indol-4-yl]-5-[2-({4-[3-(aminomethyl)phenyl]piperidin-1-yl}carbonyl)-1H-indol-6-yl]-5-phenyl-1,3,2-dioxaborolan-4-one
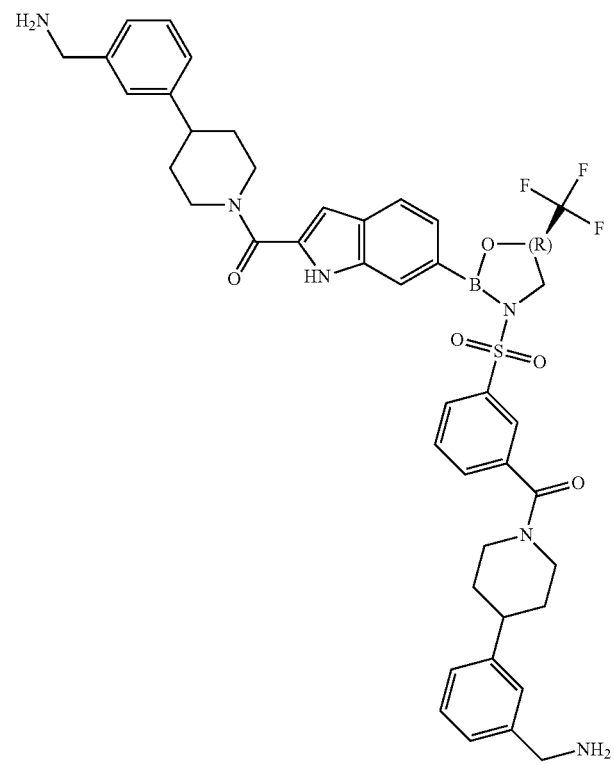
{3-[1-({6-[(5R)-3-{-3-({4-[3-(aminomethyl)phenyl]piperidin-1-yl}carbonyl)benzene]sulfonyl)-5-(trifluoromethyl)-1,3,2-oxazaborolidin-2-yl]-1H-indol-2-yl}carbonyl)piperidin-4-yl]phenyl}methanamine

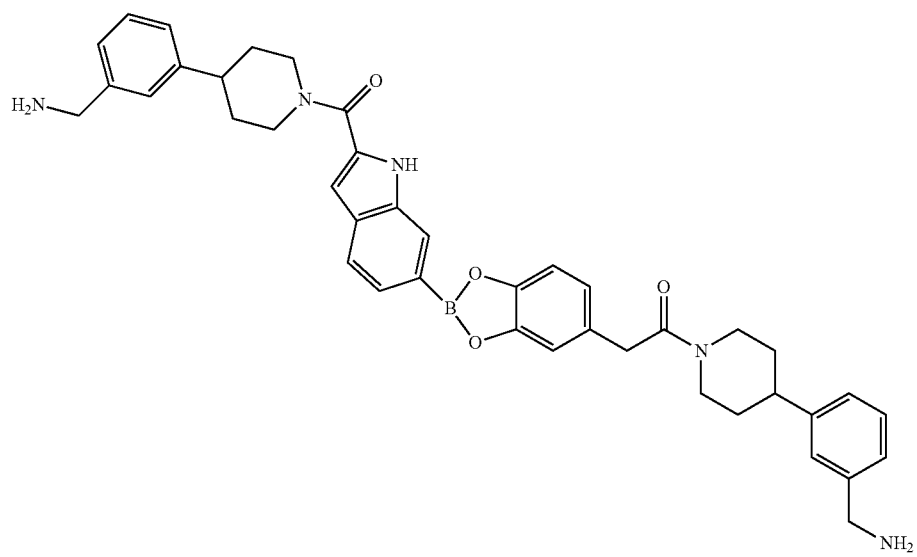
1-{4-[3-(aminomethyl)phenyl]piperidin-1-yl}-2-{2-[2-({4-[3-(aminomethyl)phenyl]piperidin-1-yl}carbonyl)-1H-indol-6-yl]-2H-1,3,2-benzodioxaborol-5-yl}ethan-1-one
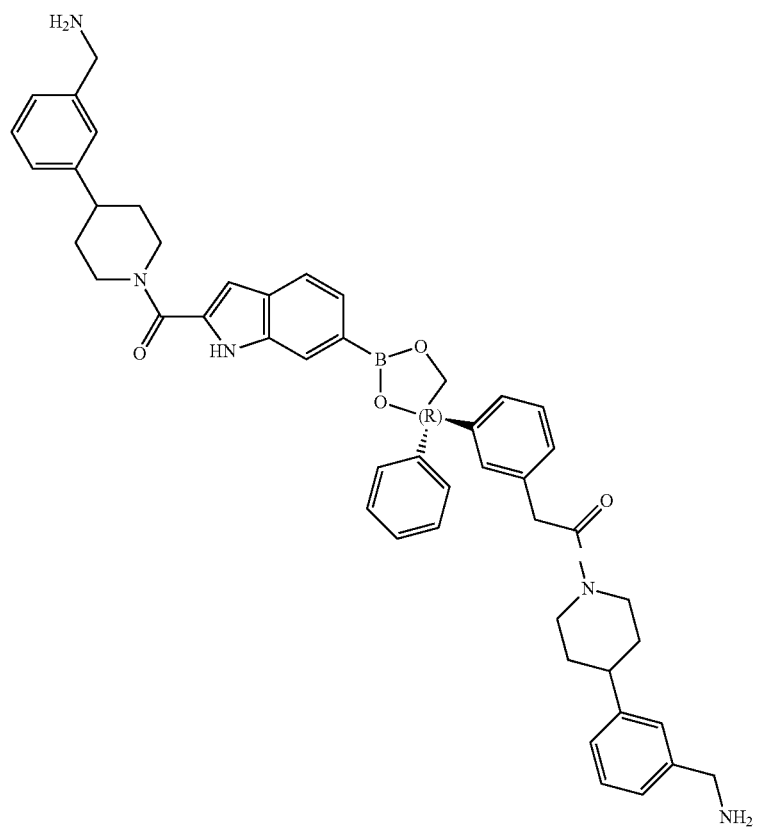
(5R)-5-[3-(2-{4-[3-(aminomethyl)phenyl]piperidin-1-yl}-2-oxoethyl)phenyl]-2-[2-({4-[3-(aminomethyl)phenyl]piperidin-1-yl}carbonyl)-1H-indol-6-yl]-5-phenyl-1,3,2-dioxaborolan-4-one -continued

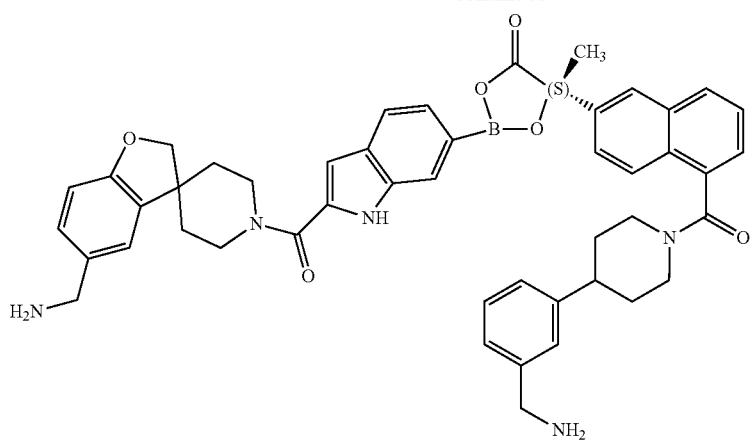

(5S)-2-(2-{[5-(aminomethyl)-2H-spiro[1-benzofuran-3,4'-piperidine]-1'-yl]carbonyl}-1H-indol-6-yl)-5-[5-({4-[3-(aminomethyl)phenyl]piperidin-1-yl}carbonyl)naphthalen-2-yl]-5-methyl-1,3,2-dioxaborolan-4-one

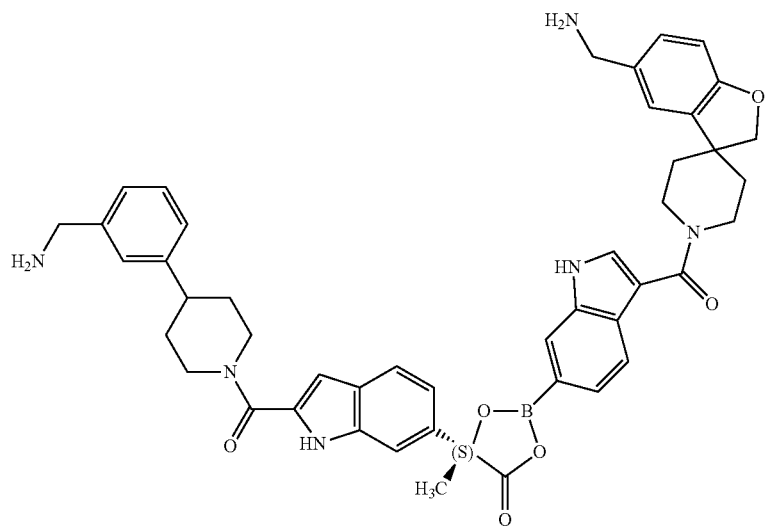

(5S)-2-(3-{[5-(aminomethyl)-2H-spiro[1-benzofuran-3,4'-piperidine]-1'-yl]carbonyl}-1H-indol-6-yl)-5-[2-({4-[3-(aminomethyl)phenyl]piperidin-1-yl}carbonyl)-1H-indol-6-yl]-5-methyl-1,3,2-dioxaborolan-4-one

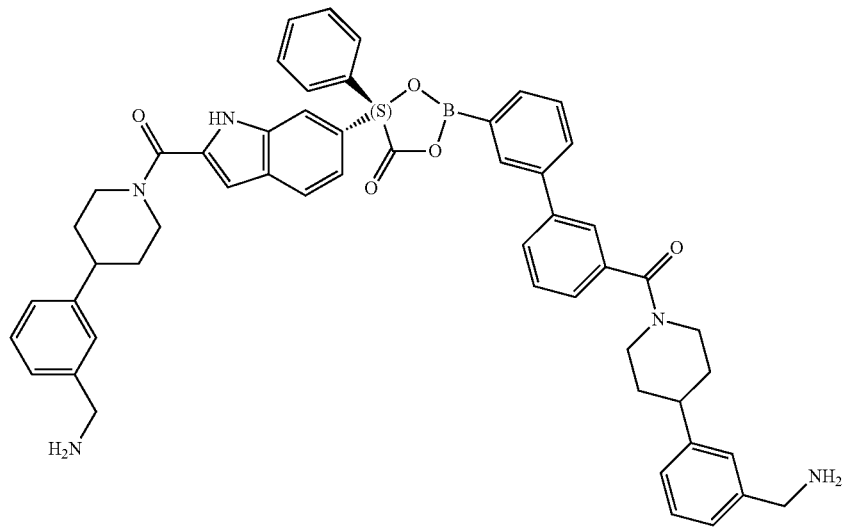

(5S)-5-[2-({4-[3-(aminomethyl)phenyl]piperidin-1-yl}carbonyl)-1H-indol-6-yl]-2-{3-[3-({4-[3-(aminomethyl)phenyl]piperidin-1-yl}carbonyl)phenyl]phenyl}-5-phenyl-1,3,2-dioxaborolan-4-one -continued

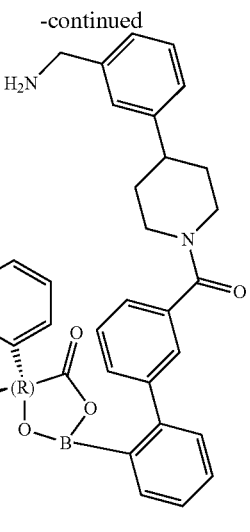

(5R)-5-[2-({4-[3-(aminomethyl)phenyl]piperidin-1-yl}carbonyl)-1H-indol-4-yl]-2-{2-[3-({4-[3-(aminomethyl)phenyl]piperidin-1-yl}carbonyl)phenyl]phenyl}-5-phenyl-1,3,2-dioxaborolan-4-one

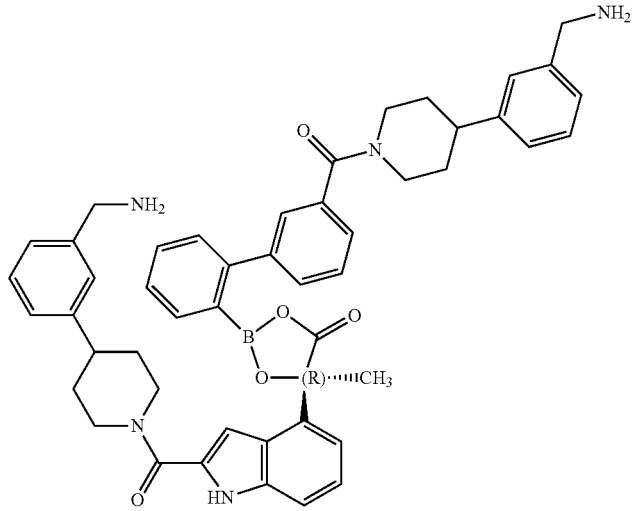

(5R)-5-[2-({4-[3-(aminomethyl)phenyl]piperidin-1-yl}carbonyl)-1H-indol-4-yl]-2-{2-[3-({4-[3-(aminomethyl)phenyl]piperidin-1-yl}carbonyl)phenyl]phenyl}-5-methyl-1,3,2-dioxaborolan-4-one In use, the above-described linker elements can be used in a cofereon multimer as either homodimers or heterodimers. When producing heterodimers, one of the linker elements is {3-[3-({4-[3-(aminomethyl)phenyl]piperidin-1-yl}carbonyl)phenyl]phenyl}boronic acid; [2-({4-[3-(aminomethyl)phenyl]piperidin-1-yl}carbonyl)-1H-indol-4-yl] boronic acid; (2-{[5-(aminomethyl)-2H-spiro[1-benzofuran-3,4'-piperidine]-1'-yl]carbonyl}-1H-indol-4-yl) boronic acid; (5-{[5-(aminomethyl)-2H-spiro[1-benzofuran-3,4'-piperidine]-1-yl}carbonyl)naphthalen-2-yl) boronic acid; [5-({4-[3-(aminomethyl)phenyl]piperidin-1-yl}carbonyl)naphthalen-2-yl]boronic acid; [2-({4-[3-(aminomethyl)phenyl]piperidin-1-yl}carbonyl)-1H-indol-5-yl]boronic acid; [3-(2-{4-[3-(aminomethyl)phenyl]piperidin-1-yl}-2-oxoethyl)phenyl]boronic acid; [(E)-2-[3-({4-[3-(aminomethyl)phenyl]piperidin-1-yl}carbonyl)phenyl]ethenyl]boronic acid; [5-({4-[3-(aminomethyl)phenyl]piperidin-1-yl}carbonyl)-1H-indol-2-yl]boronic acid; [2-({4-[3-(aminomethyl)phenyl]piperidin-1-yl}carbonyl)-1H-indol-6-yl]boronic acid; [8-({4-[3-(aminomethyl)phenyl]piperidin-1-yl}carbonyl)naphthalen-2-yl] boronic acid; [(E)-2-(3-{[5-(aminomethyl)-2H-spiro[1-benzofuran-3,4'-piperidine]-1'-yl]carbonyl}phenyl)ethenyl] boronic acid; [(E)-2-(5-{[5-(aminomethyl)-2H-spiro[1-benzofuran-3,4'-piperidine]-1'-yl]carbonyl}-2-(methylsulfanyl)thiophen-3-yl)ethenyl]boronic acid, (2-{[5-(aminomethyl)-2H-spiro[1-benzofuran-3,4'-piperidine]-1'-yl]carbonyl}-1H-indol-6-yl)boronic acid, (2-{[5-(aminomethyl)-2H-spiro[1-benzofuran-3,4'-piperidine]-1'-yl]carbonyl}-1H-indol-5-yl)boronic acid; {4-[(1E)-3-[5-(aminomethyl)-2H-spiro[1-benzofuran-3,4'-piperidine]-1'-yl]-3-oxoprop-1-en-1-yl]phenyl}boronic acid; (2-{[5-(aminomethyl)-2H-spiro[1-benzofuran-3,4'-piperidine]-1'-yl]carbonyl}-1H-indol-5-yl)boronic acid; (5-{[5-(aminomethyl)-2H-spiro[1-benzofuran-3,4'-piperidine]-1'-yl]carbonyl}-1H-indol-3-yl)boronic acid; [4-(2-{4-[3-(aminomethyl)phenyl]piperidin-1-yl}-2-oxoethyl)phenyl] boronic acid; [4-({4-[3-(aminomethyl)phenyl]piperidin-1- yl}carbonyl)-1-benzofuran-2-yl]boronic acid; (3-{2-[5-(aminomethyl)-2H-spiro[1-benzofuran-3,4'-piperidine]-1'-yl]-2-oxoethyl}phenyl)boronic acid; (3-{[5-(aminomethyl)-2H-spiro[1-benzofuran-3,4'-piperidine]-1'-yl]carbonyl}-1H-indol-6-yl)boronic acid; {2-[3-({4-[3-(aminomethyl)phenyl]piperidin-1-yl}carbonyl)phenyl]phenyl}boronic acid, (5-(4-(3-(amino methyl)phenyl)piperidine-1-carbonyl)napthalen-2-yl)boronic acid; (8-(4-(3-(aminomethyl)phenyl)piperidine-1-carbonyl)naphthalen-2-yl)boronic acid, (3-(2-(4-(3-(aminomethyl)phenyl)piperidin-1-yl)-2-oxoethyl)phenyl)boronic acid; or (4-(2-(4-(3-(aminomethyl)phenyl)piperidin-1-yl)-2-oxoethyl)phenyl)boronic acid.

In such heterodimers, the partner linker element can be 4-(2-{4-[3-(aminomethyl)phenyl]piperidin-1-yl}-2-oxoethyl)-2-hydroxybenzamide; 4-[(1E)-3-{4-[3-(aminomethyl)phenyl]piperidin-1-yl}-3-oxoprop-1-en-1-yl]-2-hydroxybenzamide; 5-[(1E)-3-{4-[3-(aminomethyl)phenyl]piperidin-1-yl}-3-oxoprop-1-en-1-yl]-2-hydroxybenzamide; 8-({4-[3-(aminomethyl)phenyl]piperidin-1-yl}carbonyl)-1,3-dihydroxynaphthalene-2-carboxamide; 3-[(1E)-3-{4-[3-(aminomethyl)phenyl]piperidin-1-yl}-3-oxoprop-1-en-1-yl]-2,6-dihydroxybenzamide; (2R)-2-[3-({4-[3-(aminomethyl)phenyl]piperidin-1-yl}carbonyl)phenyl]-2-hydroxy-2-phenylacetic acid, (2R)-2-[3-({4-[3-(aminomethyl)phenyl]piperidin-1-yl}carbonyl)phenyl]-2-cyclopentyl-2-hydroxyacetic acid; (2R)-2-[3-({4-[3-(aminomethyl)phenyl]piperidin-1-yl}carbonyl)phenyl]-2-cyclopropyl-2-hydroxyacetic acid, 4-({4-[3-(aminomethyl)phenyl]piperidin-1-yl}carbonyl)-7,8-dihydroxy-2H-chromen-2-one; 3-({4-[3-(aminomethyl)phenyl]piperidin-1-yl}carbonyl)-6,7-dihydroxy-2H-chromen-2-one; 4-(2-{4-[3-(aminomethyl)phenyl]piperidin-1-yl}-2-oxoethyl)-6,7-dihydroxy-2H-chromen-2-one; 3-({4-[3-(aminomethyl)phenyl]piperidin-1-yl}carbonyl)-7,8-dihydroxy-2H-chromen-2-one; 3-(2-{4-[3-(aminomethyl)phenyl]piperidin-1-yl}-2-oxoethyl)-6,7-dihydroxy-4-methyl-2H-chromen-2-one; 3-(2-{4-[3-(aminomethyl)phenyl]piperidin-1-yl}-2-oxoethyl)-7,8-dihydroxy-4-methyl-2H-chromen-2-one; 4-(2-{4-[3-(aminomethyl)phenyl]piperidin-1-yl}-2-oxoethyl)-7,8-dihydroxy-2H-chromen-2-one; (1S,2S,3R,5S)-2-{2-[4-({4-[3-(aminomethyl)phenyl]piperidin-1-yl}carbonyl)phenoxy]ethyl}-6,6-dimethylbicyclo[3.1.1]heptane-2,3-diol; (1R,2R,4S,5R,6S)—N-[3-({4-[3-(aminomethyl)phenyl]piperidin-1-yl}carbonyl)phenyl]-5,6-dihydroxybicyclo[2.2.2]octane-2-carboxamide; (1R,2R,3R,4R,5S)-4-[3-({4-[3-(aminomethyl)phenyl]piperidin-1-yl}carbonyl)phenoxy]-2,6,6-trimethylbicyclo[3.1.1]heptane-2,3-diol; (1R,2R,4S,5S,6R)—N-[3-({4-[3-(aminomethyl)phenyl]piperidin-1-yl}carbonyl)phenyl]-5,6-dihydroxybicyclo[2.2.2]octane-2-carboxamide; (1S,2R,3R,4R,5R)-4-[3-({4-[3-(aminomethyl)phenyl]piperidin-1-yl}carbonyl)phenoxy]-2,6,6-trimethylbicyclo[3.1.1]heptane-2,3-diol; (1R,2R,4S,5R,6S)—N-[3-({4-[3-(aminomethyl)phenyl]piperidin-1-yl}carbonyl)phenyl]-5,6-dihydroxybicyclo[2.2.1]heptane-2-carboxamide; (1S,2R,3S,4S,5R)-5-[4-({4-[3-(aminomethyl)phenyl]piperidin-1-yl}carbonyl)phenoxy]-5-methylbicyclo[2.2.1]heptane-2,3-diol; (1S,2R,4R,5S,6R)—N-[3-({4-[3-(aminomethyl)phenyl]piperidin-1-yl}carbonyl)phenyl]-5,6-dihydroxybicyclo[2.2.2]octane-2-carboxamide; (1R,2R,3S,4R,5S)-5-[3-({4-[3-(aminomethyl)phenyl]piperidin-1-yl}carbonyl)phenoxy]bicyclo[2.2.2]octane-2,3-diol; (1R,2S,3R,4R,5S)-5-[3-({4-[3-(aminomethyl)phenyl]piperidin-1-yl}carbonyl)phenoxy]-5-methylbicyclo[2.2.1]heptane-2,3-diol; (2R)-3-{[3-({4-[3-(aminomethyl)phenyl]piperidin-1-yl}carbonyl)phenyl]carbamoyl}-2-hydroxy-2-phenylpropanoic acid; (2S)-3-{[3-({4-[3-(aminomethyl)phenyl]piperidin-1-yl}carbonyl)phenyl]carbamoyl}-2-hydroxy-2-phenylpropanoic acid; (2R)-2-[4-({4-[3-(aminomethyl)phenyl]piperidin-1-yl}carbonyl)-1H-indol-2-yl]-2-hydroxypropanoic acid; (2S)-3-{[3-({4-[3-(aminomethyl)phenyl]piperidin-1-yl}carbonyl)phenyl]carbamoyl}-2-hydroxy-2-methylpropanoic acid; (2S)-3-[3-({4-[3-(aminomethyl)phenyl]piperidin-1-yl}carbonyl)phenoxy]-2-hydroxy-2-phenylpropanoic acid; (2R)-3-[3-({4-[3-(aminomethyl)phenyl]piperidin-1-yl}carbonyl)phenoxy]-2-hydroxy-2-phenylpropanoic acid; (2S)-3-[3-({4-[3-(aminomethyl)phenyl]piperidin-1-yl}carbonyl)phenoxy]-2-hydroxy-2-methylpropanoic acid; (2R)-3-[3-({4-[3-(aminomethyl)phenyl]piperidin-1-yl}carbonyl)phenoxy]-2-hydroxy-2-methylpropanoic acid; (2S)-2-[2-({4-[3-(aminomethyl)phenyl]piperidin-1-yl}carbonyl)-1H-indol-4-yl]-2-hydroxypropanoic acid, (2R)-2-[2-({4-[3-(aminomethyl)phenyl]piperidin-1-yl}carbonyl)-1H-indol-4-yl]-2-hydroxy-2-phenylacetic acid; (2R)-2-[2-({4-[3-(aminomethyl)phenyl]piperidin-1-yl}carbonyl)-1H-indol-4-yl]-2-hydroxypropanoic acid; (2R)-2-[2-({4-[3-(aminomethyl)phenyl]piperidin-1-yl}carbonyl)-1H-indol-6-yl]-2-hydroxypropanoic acid, 2-[3-({4-[3-(aminomethyl)phenyl]piperidin-1-yl}carbonyl)phenoxy]-1-[(3R,4S)-3,4-dihydroxypyrrolidin-1-yl]ethan-1-one; (2R)-3-[3-({4-[3-(aminomethyl)phenyl]piperidin-1-yl}carbonyl)phenoxy]propane-1,2-diol; 2-[(1E)-3-{4-[3-(aminomethyl)phenyl]piperidin-1-yl}-3-oxoprop-1-en-1-yl]-6-hydroxybenzamide; 8-({4-[3-(aminomethyl)phenyl]piperidin-1-yl}carbonyl)-3-hydroxynaphthalene-2-carboxamide; (1R,2S,3R,4R,5S)-5-[3-({4-[3-(aminomethyl)phenyl]piperidin-1-yl}carbonyl)phenoxy]bicyclo[2.2.2]octane-2,3-diol; (1R,2S,4S,5S,6R)—N-[3-({4-[3-(aminomethyl)phenyl]piperidin-1-yl}carbonyl)phenyl]-5,6-dihydroxybicyclo[2.2.2]octane-2-carboxamide; (2S)-3-[3-({4-[3-(aminomethyl)phenyl]piperidin-1-yl}carbonyl)phenoxy]-2-cyclopentyl-2-hydroxypropanoic acid; (2S)-3-{[4-({4-[3-(aminomethyl)phenyl]piperidin-1-yl}carbonyl)phenyl]carbamoyl}-2-hydroxy-2-phenylpropanoic acid; (2R)-2-[2-({4-[3-(aminomethyl)phenyl]piperidin-1-yl}carbonyl)-1H-indol-6-yl]-2-hydroxy-2-phenylacetic acid; (2R)—S-[3-({4-[3-(aminomethyl)phenyl]piperidin-1-yl}carbonyl)phenyl]-3,3,3-trifluoro-2-hydroxypropane-1-sulfonamido; 1-{4-[3-(aminomethyl)phenyl]piperidin-1-yl}-2-(3,4-dihydroxyphenyl)ethan-1-one; (2R)-2-[3-(2-{4-[3-(aminomethyl)phenyl]piperidin-1-yl}-2-oxoethyl)phenyl]-2-hydroxy-2-phenylacetic acid, (2S)-2-[5-({4-[3-(aminomethyl)phenyl]piperidin-1-yl}carbonyl)naphthalen-2-yl]-2-hydroxypropanoic acid; (2S)-2-[2-({4-[3-(aminomethyl)phenyl]piperidin-1-yl}carbonyl)-1H-indol-6-yl]-2-hydroxypropanoic acid; (2S)-2-[2-({4-[3-(aminomethyl)phenyl]piperidin-1-yl}carbonyl)-1H-indol-6-yl]-2-hydroxy-2-phenylacetic acid; (4-(3-(aminomethyl)phenyl)piperidin-1-yl)(3-(2-hydroxy-2-(1-hydroxycyclobutyl)ethoxy)phenyl)methanone; (E)-1-(4-(3-(aminomethyl)phenyl)piperidin-1-yl)-3-(3,4-dihydroxyphenyl)prop-2-en-1-one, (4-(3-(aminomethyl)phenyl)piperidin-1-yl)(6,7-dihydroxynaphthalen-1-yl)methanone; or 4-(aminomethyl)-N-(4-(2-((3R,4S)-3,4-dihydroxypyrrolidin-1-yl)-2-oxoethoxy)benzyl)benzamide. Additional linker elements for coferons targeted to tryptase may be selected from, but are not restricted to the following substructures.

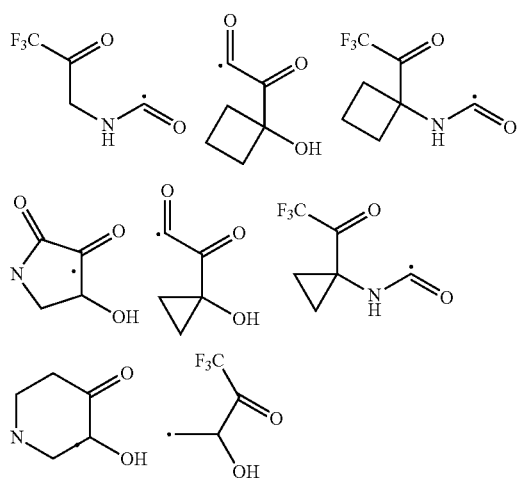

Additional coferon monomers targeted to Tryptase

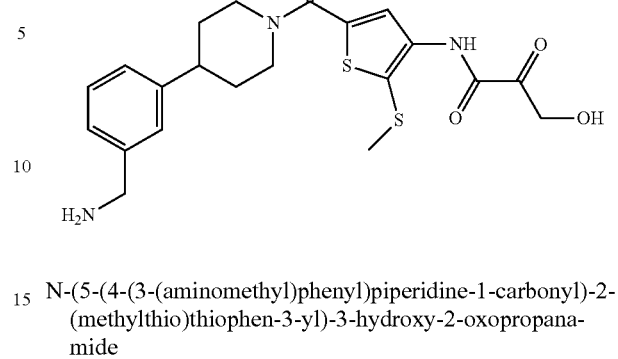

N-(5-(4-(3-(aminomethyl)phenyl)piperidine-1-carbonyl)-2-(methylthio)thiophen-3-yl)-3-hydroxy-2-oxopropanamide

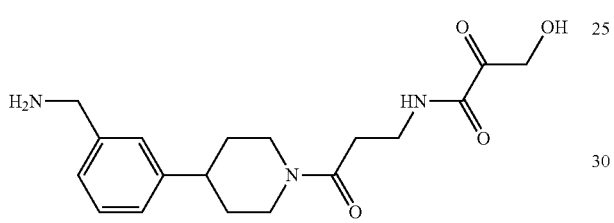

N-(3-(4-(3-(aminomethyl)phenyl)piperidin-1-yl)-3-oxopropyl)-3-hydroxy-2-oxopropanamide

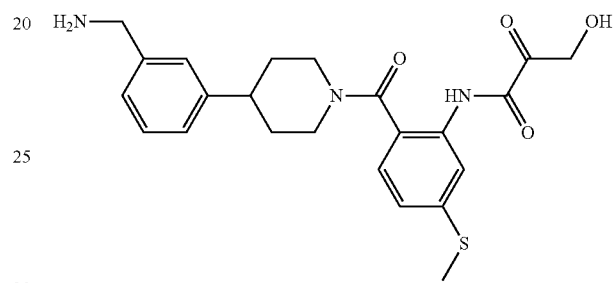

N-(2-(4-(3-(aminomethyl)phenyl)piperidine-1-carbonyl)-5-(methylthio)phenyl)-3-hydroxy-2-oxopropanamide

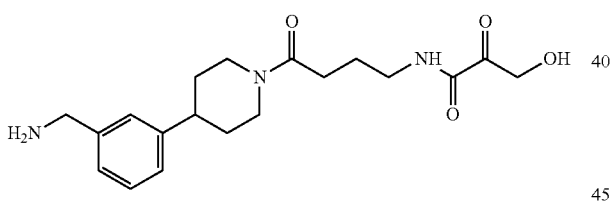

N-(4-(4-(3-(aminomethyl)phenyl)piperidin-1-yl)-4-oxobutyl)-3-hydroxy-2-oxopropanamide

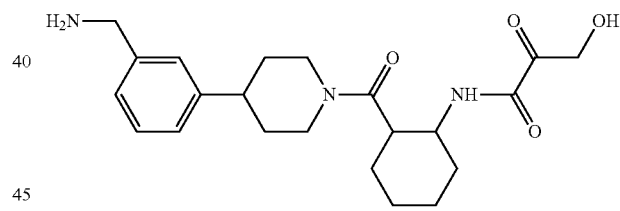

N-(2-(4-(3-(aminomethyl)phenyl)piperidine-1-carbonyl)phenyl)-3-hydroxy-2-oxopropanamide

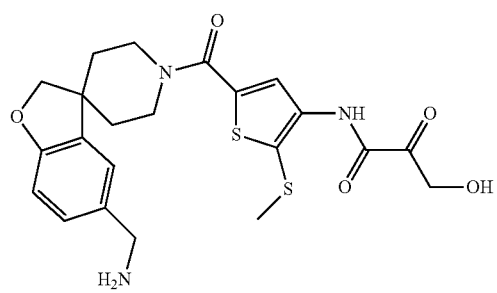 [SMILES: CSc1sc(C(=O)N2CCC3(CC2)COc2ccc(CN)cc23)cc1NC(=O)C(=O)CO]

N-(5-(5-(aminomethyl)-2H-spiro[benzofuran-3,4'-piperidine]-1'-ylcarbonyl)-2-(methylthio)thiophen-3-yl)-3-hydroxy-2-oxopropanamide

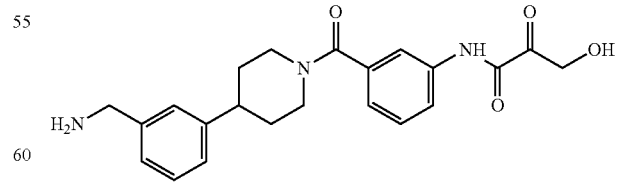

N-(3-(4-(3-(aminomethyl)phenyl)piperidine-1-carbonyl)phenyl)-3-hydroxy-2-oxopropanamide

291

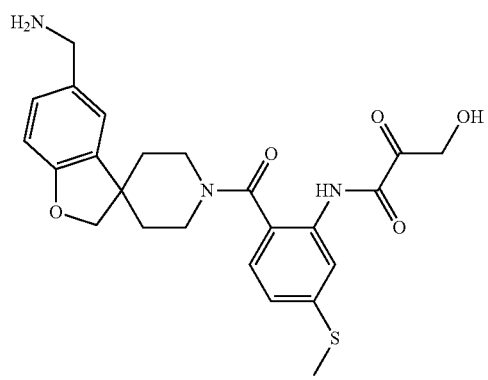 [SMILES: CSc1ccc(C(=O)N2CCC3(CC2)COc2ccc(CN)cc23)c(NC(=O)C(=O)CO)c1]

N-(2-(5-(aminomethyl)-2H-spiro[benzofuran-3,4'-piperidine]-1'-ylcarbonyl)-5-(methylthio)phenyl)-3-hydroxy-2-oxopropanamide

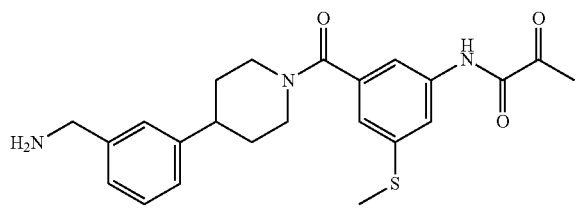 [SMILES: CSc1cc(NC(=O)C(C)=O)cc(C(=O)N2CCC(c3cccc(CN)c3)CC2)c1]

N-(3-(4-(3-(aminomethyl)phenyl)piperidine-1-carbonyl)-5-(methylthio)phenyl)-2-oxopropanamide

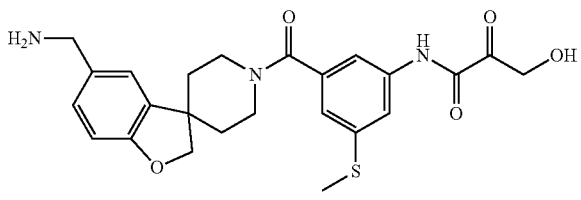 [SMILES: CSc1cc(NC(=O)C(=O)CO)cc(C(=O)N2CCC3(CC2)COc2ccc(CN)cc23)c1]

N-(3-(5-(aminomethyl)-2H-spiro[benzofuran-3,4'-piperidine]-1'-ylcarbonyl)-5-(methylthio)phenyl)-3-hydroxy-2-oxopropanamide

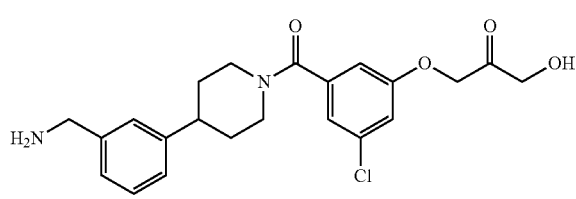 [SMILES: NCc1cccc(C2CCN(C(=O)c3cc(Cl)cc(OCC(=O)CO)c3)CC2)c1]

1-(3-(4-(3-(aminomethyl)phenyl)piperidine-1-carbonyl)-5-chlorophenoxy)-3-hydroxypropan-2-one

292

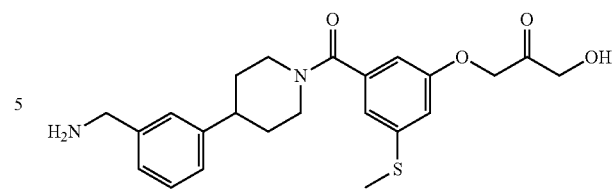

1-(3-(4-(3-(aminomethyl)phenyl)piperidine-1-carbonyl)-5-(methylthio)phenoxy)-3-hydroxypropan-2-one

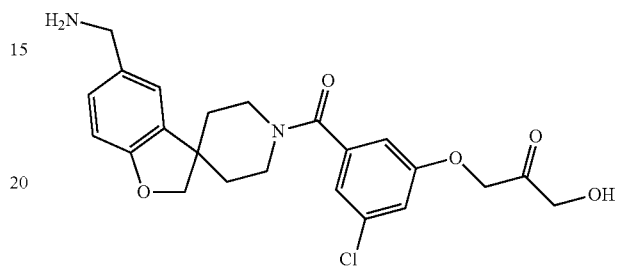

1-(3-(5-(aminomethyl)-2H-spiro[benzofuran-3,4'-piperidine]-1'-ylcarbonyl)-5-chlorophenoxy)-3-hydroxypropan-2-one

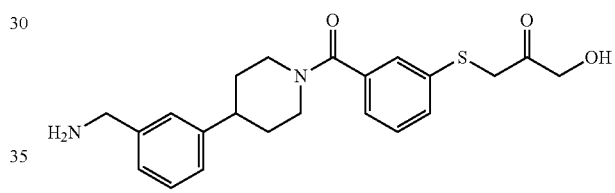

1-(3-(4-(3-(aminomethyl)phenyl)piperidine-1-carbonyl)phenylthio)-3-hydroxypropan-2-one

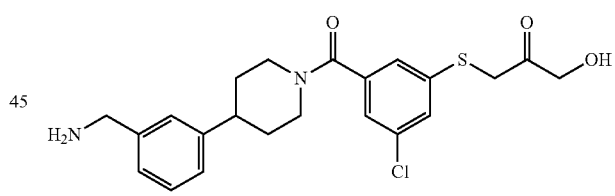

1-(3-(4-(3-(aminomethyl)phenyl)piperidine-1-carbonyl)-5-chlorophenylthio)-3-hydroxypropan-2-one

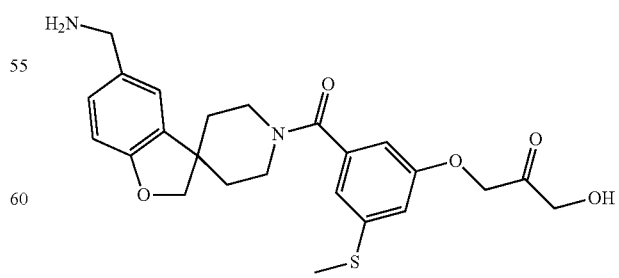

1-(3-(5-(aminomethyl)-2H-spiro[benzofuran-3,4'-piperidine]-1'-ylcarbonyl)-5-(methylthio)phenoxy)-3-hydroxypropan-2-one

293

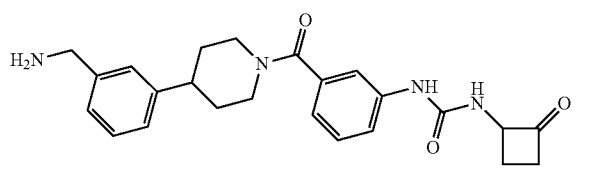 [SMILES: NCc1cccc(C2CCN(C(=O)c3cccc(NC(=O)NC4CCC4=O)c3)CC2)c1]

1-(3-(4-(3-(aminomethyl)phenyl)piperidine-1-carbonyl)phenyl)-3-(2-oxocyclobutyl)urea

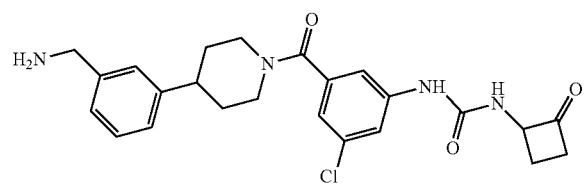 [SMILES: NCc1cccc(C2CCN(C(=O)c3cc(Cl)cc(NC(=O)NC4CCC4=O)c3)CC2)c1]

1-(3-(4-(3-(aminomethyl)phenyl)piperidine-1-carbonyl)-5-chlorophenyl)-3-(2-oxocyclobutyl)urea

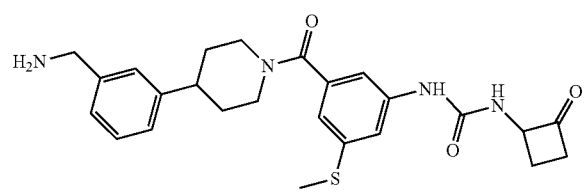 [SMILES: CSc1cc(NC(=O)NC2CCC2=O)cc(C(=O)N2CCC(c3cccc(CN)c3)CC2)c1]

1-(3-(4-(3-(aminomethyl)phenyl)piperidine-1-carbonyl)-5-(methylthio)phenyl)-3-(2-oxocyclobutyl)urea

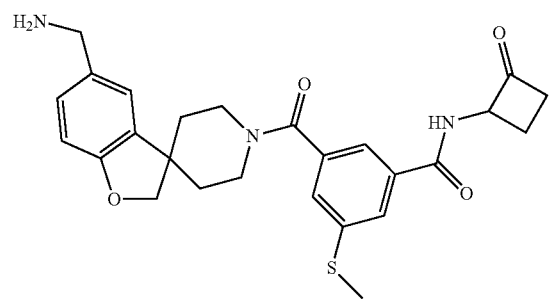 [SMILES: CSc1cc(C(=O)NC2CCC2=O)cc(C(=O)N2CCC3(CC2)COc2ccc(CN)cc23)c1]

3-(5-(aminomethyl)-2H-spiro[benzofuran-3,4'-piperidine]-1'-ylcarbonyl)-5-(methylthio)-N-(2-oxocyclobutyl)benzamide

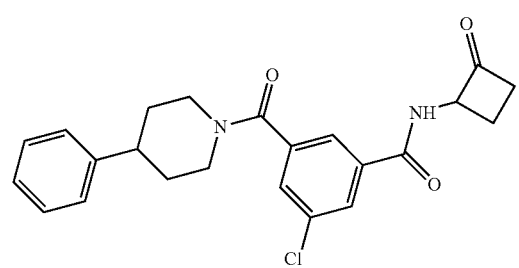 [SMILES: O=C(NC1CCC1=O)c1cc(Cl)cc(C(=O)N2CCC(c3ccccc3)CC2)c1]

3-chloro-N-(2-oxocyclobutyl)-5-(4-phenylpiperidine-1-carbonyl)benzamide

294

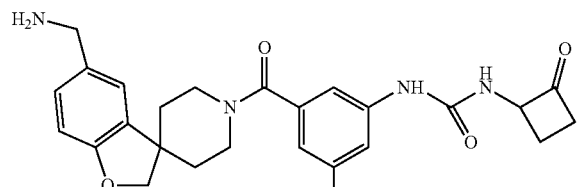

1-(3-(5-(aminomethyl)-2H-spiro[benzofuran-3,4'-piperidine]-1'-ylcarbonyl)-5-chlorophenyl)-3-(2-oxocyclobutyl)urea

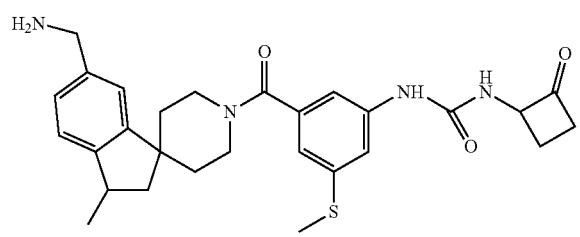 [SMILES: CSc1cc(NC(=O)NC2CCC2=O)cc(C(=O)N2CCC3(CC2)CC(C)c2ccc(CN)cc23)c1]

1-(3-(6-(aminomethyl)-3-methyl-2,3-dihydrospiro[indene-1,4'-piperidine]-1'-ylcarbonyl)-5-(methylthio)phenyl)-3-(2-oxocyclobutyl)urea

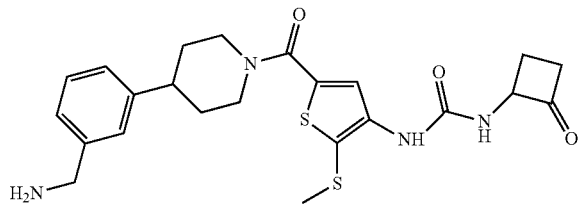 [SMILES: CSc1sc(C(=O)N2CCC(c3cccc(CN)c3)CC2)cc1NC(=O)NC1CCC1=O]

1-(5-(4-(3-(aminomethyl)phenyl)piperidine-1-carbonyl)-2-(methylthio)thiophen-3-yl)-3-(2-oxocyclobutyl)urea

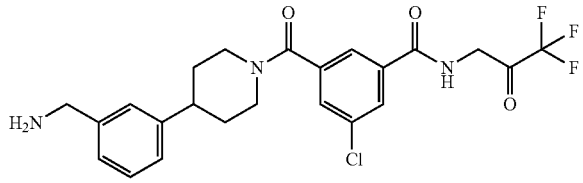 [SMILES: NCc1cccc(C2CCN(C(=O)c3cc(Cl)cc(C(=O)NCC(=O)C(F)(F)F)c3)CC2)c1]

3-(4-(3-(aminomethyl)phenyl)piperidine-1-carbonyl)-5-chloro-N-(3,3,3-trifluoro-2-oxopropyl)benzamide

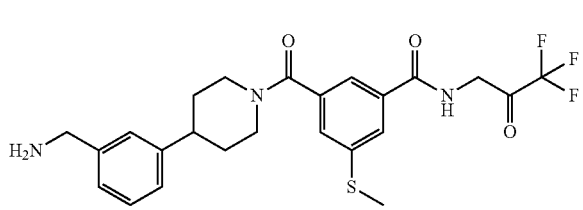 [SMILES: CSc1cc(C(=O)NCC(=O)C(F)(F)F)cc(C(=O)N2CCC(c3cccc(CN)c3)CC2)c1]

3-(4-(3-(aminomethyl)phenyl)piperidine-1-carbonyl)-5-(methylthio)-N-(3,3,3-trifluoro-2-oxopropyl)benzamide

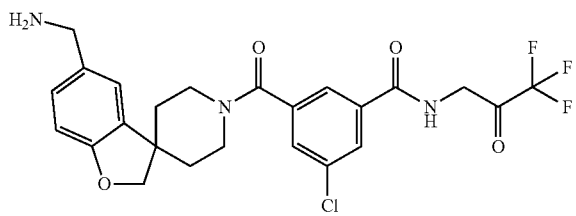 [SMILES: NCc1ccc2c(c1)C1(CCN(C(=O)c3cc(Cl)cc(C(=O)NCC(=O)C(F)(F)F)c3)CC1)CO2]

3-(5-(aminomethyl)-2H-spiro[benzofuran-3,4'-piperidine]-1'-ylcarbonyl)-5-chloro-N-(3,3,3-trifluoro-2-oxopropyl)benzamide

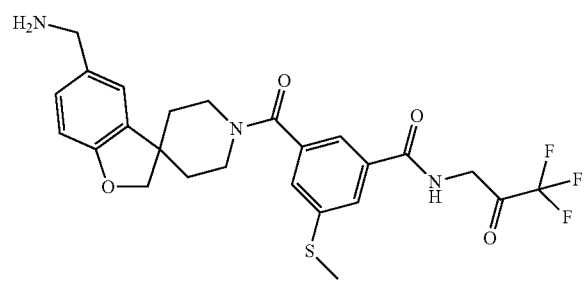 [SMILES: CSc1cc(C(=O)NCC(=O)C(F)(F)F)cc(C(=O)N2CCC3(CC2)COc2ccc(CN)cc23)c1]

3-(5-(aminomethyl)-2H-spiro[benzofuran-3,4'-piperidine]-1'-ylcarbonyl)-5-(methylthio)-N-(3,3,3-trifluoro-2-oxopropyl)benzamide

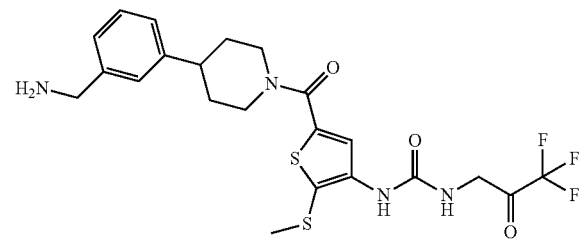 [SMILES: CSc1sc(C(=O)N2CCC(c3cccc(CN)c3)CC2)cc1NC(=O)NCC(=O)C(F)(F)F]

1-(5-(4-(3-(aminomethyl)phenyl)piperidine-1-carbonyl)-2-(methylthio)thiophen-3-yl)-3-(3,3,3-trifluoro-2-oxopropyl)urea

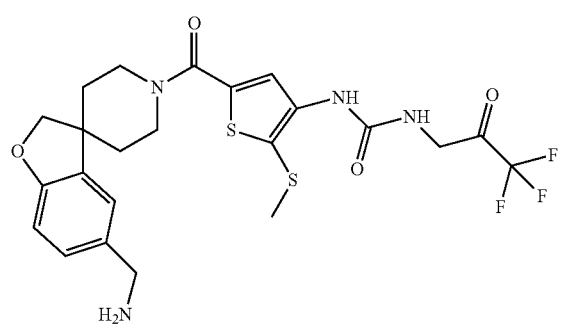 [SMILES: CSc1sc(C(=O)N2CCC3(CC2)COc2ccc(CN)cc23)cc1NC(=O)NCC(=O)C(F)(F)F]

1-(5-(5-(aminomethyl)-2H-spiro[benzofuran-3,4'-piperidine]-1'-ylcarbonyl)-2-(methylthio)thiophen-3-yl)-3-(3,3,3-trifluoro-2-oxopropyl)urea

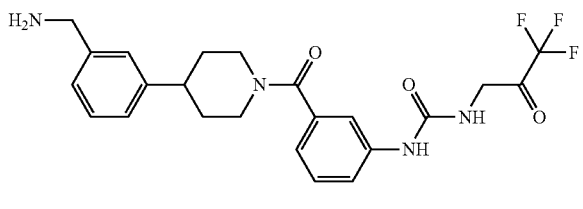 [SMILES: NCc1cccc(C2CCN(C(=O)c3cccc(NC(=O)NCC(=O)C(F)(F)F)c3)CC2)c1]

1-(3-(4-(3-(aminomethyl)phenyl)piperidine-1-carbonyl)phenyl)-3-(3,3,3-trifluoro-2-oxopropyl)urea Coferons Targeted Towards XIAP: Bivalent IAP Inhibitors for Treatment of Human Cancers The IAP family of proteins consists of 8 proteins of which XIAP is the most potent. These proteins block cell death through the inhibition of caspases. These proteins share one or more zinc-binding motifs (BIR domains) that interact with caspases -3, -7, and -9. The IAP proteins affect both the intrinsic and extrinsic apoptotic pathways and function downstream of Bcl2 and Bcl-xL. Smac is a potent endogenous binder of XIAP by competing with caspases to bind XIAP. Smac binds two BIR domains, BIR2 (caspase-3/-7) and BIR3 (caspase-9) and is often upregulated in lung, colorectal, breast, pancreatic, ovarian, and prostate cancer cells to prevent apoptosis. Small molecule Smac mimetics release activated caspases from inhibition by XIAP, thus allowing initiation of the apoptotic cascade. Coferon monomers can combine and function as Smac mimetics. Nikolovska-Coleska et al., *Biochem.* 47:9811-9824 (2008), which is hereby incorporated by reference in its entirety, reported a cyclic octapeptide bivalent Smac mimetic that binds XIAP with an $IC_{50}$ of 0.5 nM. Such cyclic octapeptides are likely to be poorly absorbed and have little to no oral activity and represent an ideal scenario for the use of coferon monomers that are small molecules that can cross the cell membrane and combine on the macromolecular protein target and bind with high affinity. An example of such a coferon monomer is shown below.

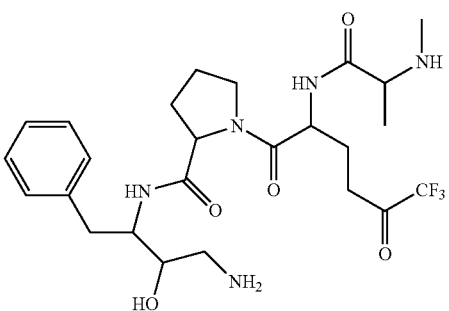

Coferon Monomer

-continued

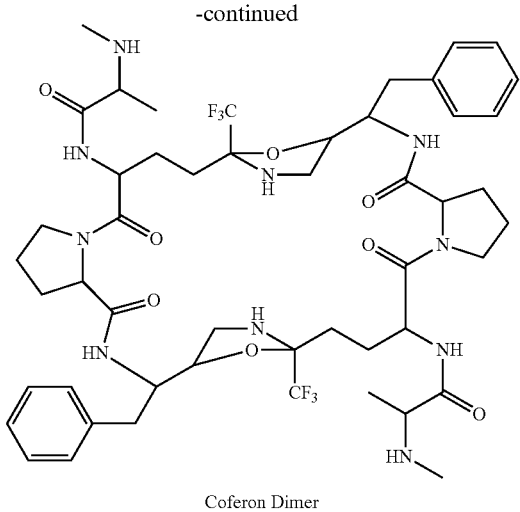

Coferon Dimer

Importantly, alternative homo- and hetero-dimeric linkers such as those described in this disclosure may be used to generate similar bivalent inhibitors. For example, homodimers incorporating appropriate hydroxyketo, or amidoketo linker moieties, or heterodimeric boronic acid-diol linker moieties may also be employed to similarly present the key pharmacophoric elements.

Coferons Targeted Towards Bacterial Ribosomes

A variety of antibiotics elicit their antibacterial activity by binding to the bacterial ribosome and inhibiting protein synthesis. Many of these antibiotics bind the peptidyl transferase center of the ribosome (P site). Linezolid, an oxazolidinone antibiotic does not bind the P site but binds adjacent to the biding site for Sparsomycin, a non-specific P-site binding protein synthesis inhibitor. The close juxtaposition of the linezolid binding site with the sparosmycin binding site presents an ideal scenario for developing coferon monomers based linezolid and sparsomycin that can dimerize on binding to the ribosome, thereby creating a high affinity and high specificity inhibitor of bacterial protein synthesis. While sparsomycin is a non-specific binder, its specificity can be increased by replacing the uridine ring in the molecule with an aromatic moiety such as a pyridine ring (Jhou Z et al, *Biorg & Med Chem. Lett.*, 18: 6179 (2008), which is hereby incorporated by reference in its entirety). An example of coferon monomers, one with a diol containing linker element and the other with a boronic acid containing linker element is shown below.

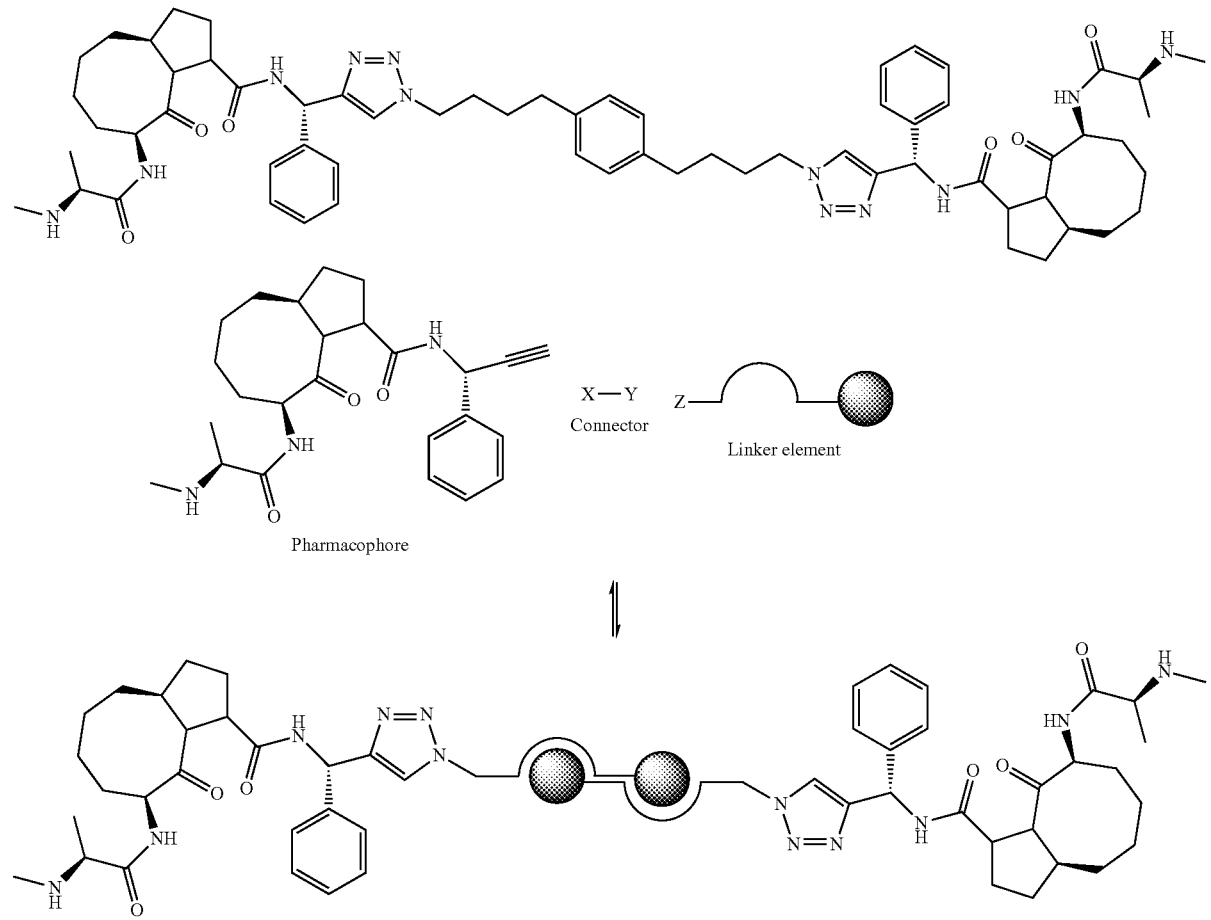

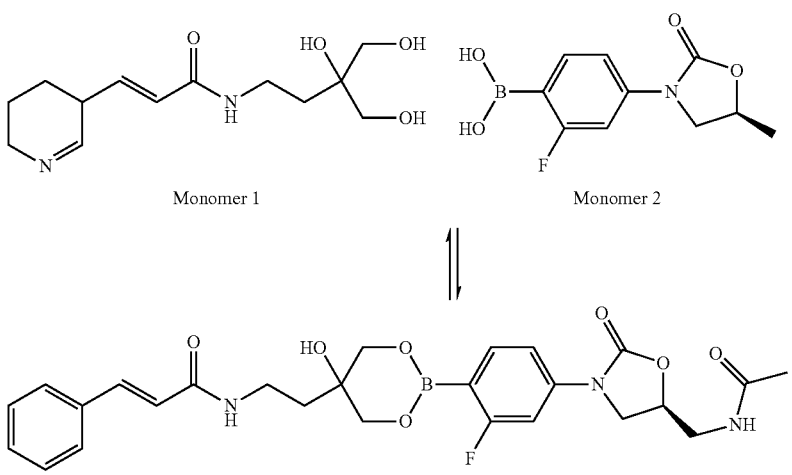

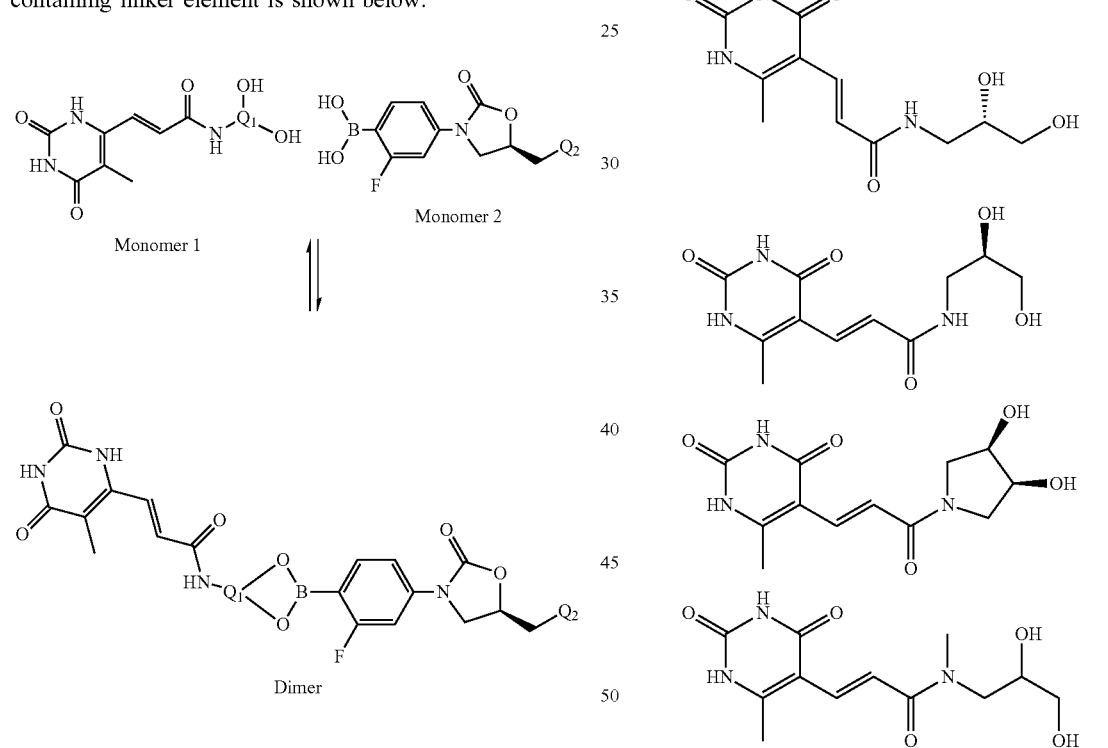

Other examples of coferon monomers, one with a diol containing linker element and the other with a boronic acid containing linker element is shown below:

where $Q_1$ and $Q_2$ are aliphatic, alicyclic, or hetero or non-hetero aromatic moieties.

The dimer may also exist as a tetrahedral boronate ester.

Specific examples of coferon monomers of this type are shown below:

-continued

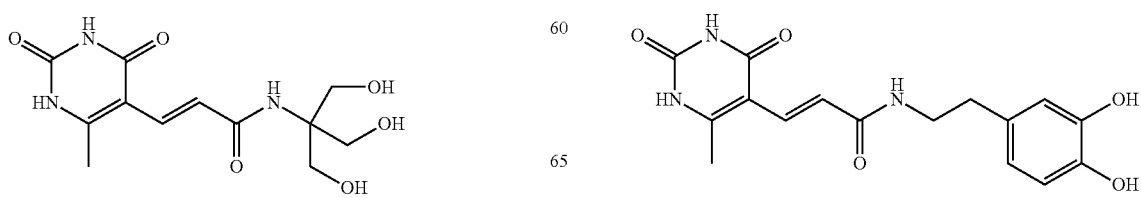

301

-continued

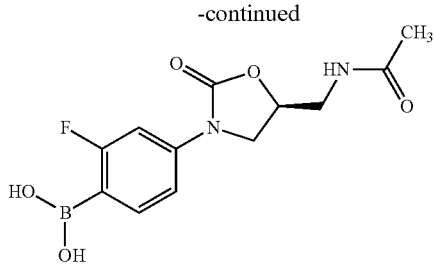

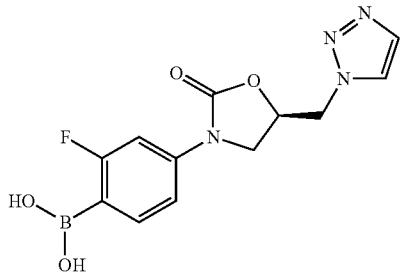

An example of another type of coferon monomers, one with a diol containing linker element and the other with a boronic acid containing linker element is shown below:

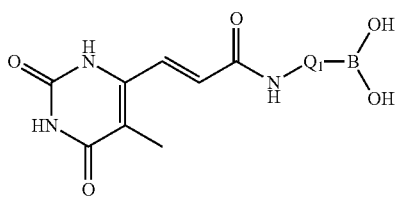 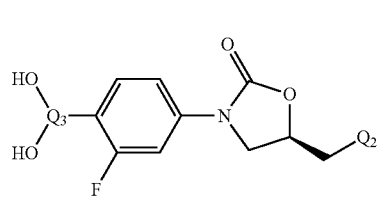

Monomer 1  Monomer 2

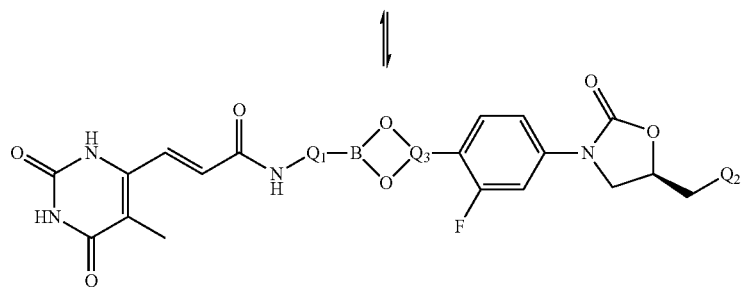

Dimer where $Q_1$, $Q_2$ and $Q_3$ are aliphatic, alicyclic, or hetero or non-hetero aromatic moieties. The dimer may also exist as a tetrahedral boronate ester.

Specific examples of coferon monomers of this type are shown below:

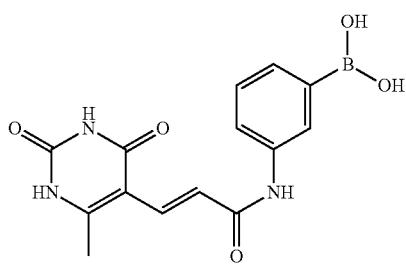

302

-continued

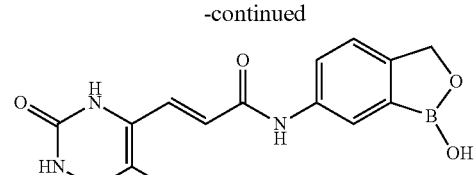

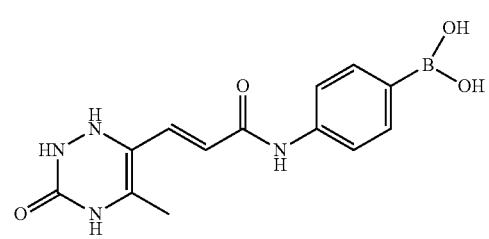

-continued

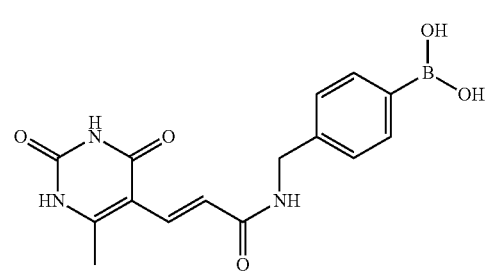

-continued

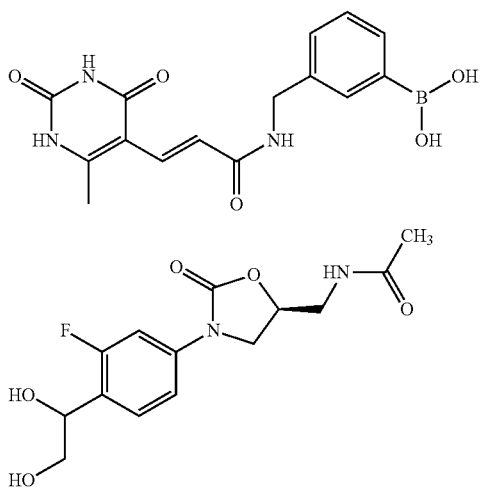

Importantly, alternative homo- and hetero-dimeric linkers such as those described in this disclosure may be employed to achieve the association to produce similar bivalent inhibitors. For example, homodimers incorporating appropriate hydroxyketo, or amidoketo linker moieties, or heterodimeric boronic acid-diol linker moieties may also be employed to similarly present the key pharmacophoric elements.

Therapeutics

An additional embodiment of the present invention relates to a therapeutic multimer which includes a plurality of covalently or non-covalently linked monomers. Each monomer comprises one or more pharmacophores which potentially bind to a target molecule with a dissociation constant of less than 300 μM and a linker element having a molecular weight less than 500 dalton. Each linker is selected from the group consisting of 1)

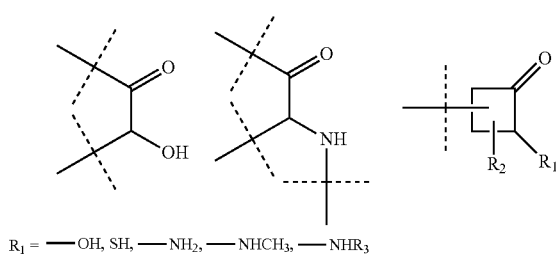

$R_1 =$ —OH, SH, —$NH_2$, —$NHCH_3$, —$NHR_3$
where $R_3 =$ —C(=O)$R_4$, —$SO_2R_4$, —C(=O)$OR_4$
where $R_4$ is composed of aliphatic, alicyclic, aromatic or heteroaromatic group
where $R_3$ may also connnect to the pharmacophore and
is composed of aliphatic, alicyclic, aromatic or heteroaromatic group
$R_2 =$ —H, —$CH_3$, —Ph or other aliphatic, aromatic or heteroaromatic group

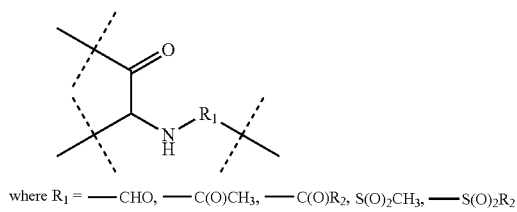

where $R_1 =$ —CHO, —C(O)$CH_3$, —C(O)$R_2$, S(O)$_2CH_3$, —S(O)$_2R_2$
where $R_2$ may also connect to the pharmacophore and is composed of aliphatic, aromatic or heteroaromatic group.

-continued

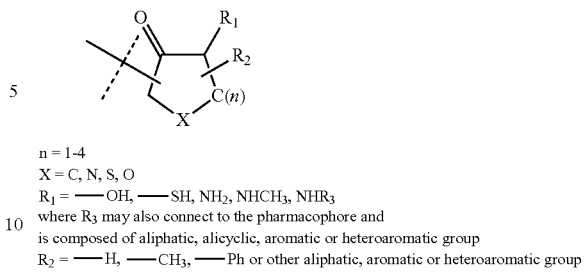

n = 1-4
X = C, N, S, O
$R_1 =$ —OH, —SH, $NH_2$, NHCH$_3$, NHR$_3$
where $R_3$ may also connect to the pharmacophore and
is composed of aliphatic, alicyclic, aromatic or heteroaromatic group
$R_2 =$ —H, —$CH_3$, —Ph or other aliphatic, aromatic or heteroaromatic group where the lines crossed with a dashed line illustrate the one or more bonds formed joining the one or more pharmacophores, directly or through a connector; 2)

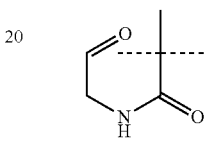

where the lines crossed with a dashed line illustrate the one or more bonds formed joining the one or more pharmacophores, directly or through a connector; 3)

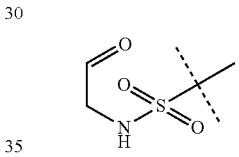

where the lines crossed with a dashed line illustrate the one or more bonds formed joining the one or more pharmacophores, directly or through a connector; 4)

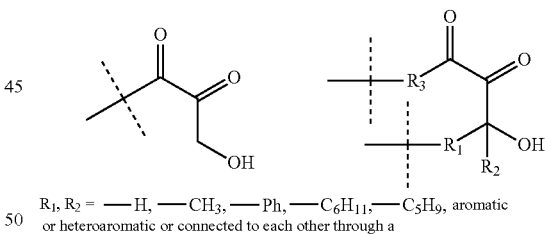

$R_1, R_2 =$ —H, —$CH_3$, —Ph, —$C_6H_{11}$, —$C_5H_9$, aromatic
or heteroaromatic or connected to each other through a
3,4,5 or 6 membered ring.
$R_3 =$ —$NH_2$, —OH, —$CH_3$, —Ph, —$NHR_4$, —$CH_2R_4$, —$OR_4$
where $R_4$ may be connected to the pharmacophore and is composed of
aliphatic, aromatic or heteroaromatic group, and $R_3$ and $R_4$ may
connect to $R_1$ and $R_2$ through a 5,6,7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

305

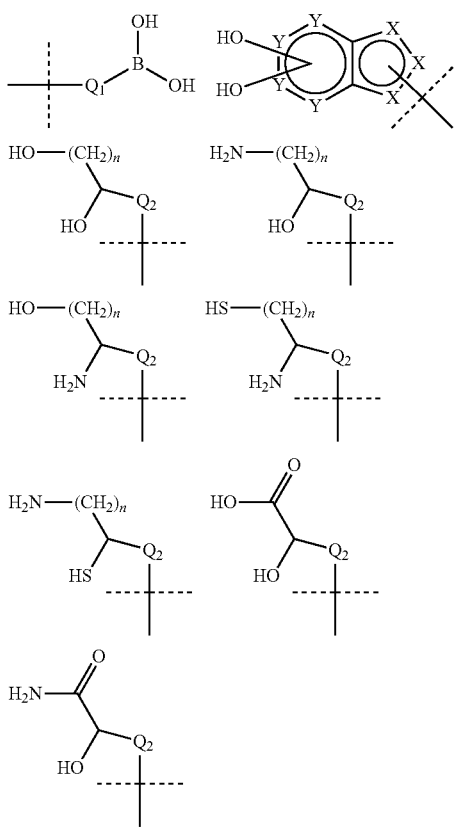

where $Q_1$ and $Q_2$ are aliphatic, alicyclic, or hetero or non-hetero aromatic moieties
where n=1 or 2
where X and Y=C, N, O, or S
where the hydroxy groups emanating from the aromatic ring are ortho to each other

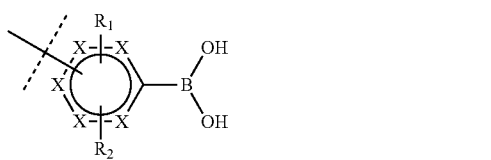

X = C, N
$R_1, R_2$ = —H, —F, —Cl, —Br, —I, —CF$_3$, —CN, —OCH$_3$, —NO$_2$
Where $R_1$ & $R_2$ are adjacent, may also include fused 5 or 6 membered aromatic or heteroaromatic ring

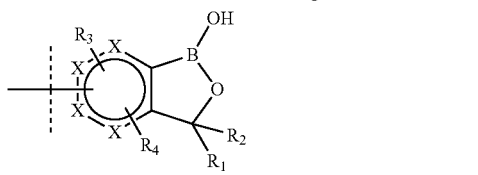

X = C, N
$R_1, R_2$ = —H, —CH$_3$, —Ph, or connected to each other through a spiro 3, 4, 5 or 6 membered ring
$R_3, R_4$ = —H, —F, —Cl, —Br, —I, —CF$_3$, —CN, —OCH$_3$, —NO$_2$
When $R_3$ & $R_4$ are adjacent, may also include fused 5 or 6 membered aromatic or heteroaromatic ring 306
-continued

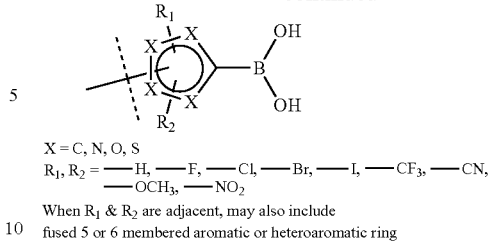

X = C, N, O, S
$R_1, R_2$ = —H, —F, —Cl, —Br, —I, —CF$_3$, —CN, —OCH$_3$, —NO$_2$
When $R_1$ & $R_2$ are adjacent, may also include fused 5 or 6 membered aromatic or heteroaromatic ring

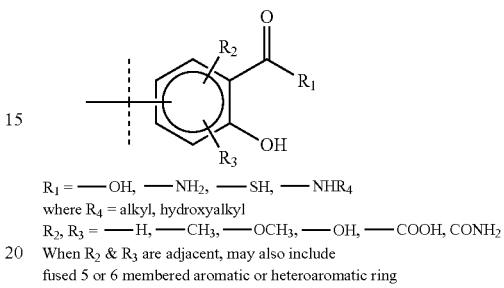

$R_1$ = —OH, —NH$_2$, —SH, —NHR$_4$
where $R_4$ = alkyl, hydroxyalkyl
$R_2, R_3$ = —H, —CH$_3$, —OCH$_3$, —OH, —COOH, CONH$_2$
When $R_2$ & $R_3$ are adjacent, may also include fused 5 or 6 membered aromatic or heteroaromatic ring

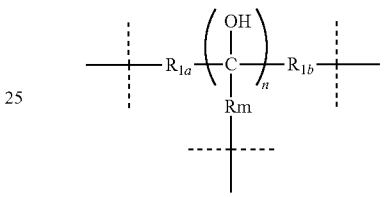

n = 2-6
$R_1, R_{1b}$ = —H, —CH$_3$, —CH$_2$NH$_2$, —CH$_2$NHCH$_3$, aromatic or heteroaromatic ring, or connected to each other through a 4,5,6,7 or 8-membered ring
Rm = —H, —CH$_3$, —CH$_3$NH$_2$, —CH$_3$OH, —CH$_2$CH$_2$OH and m = 2-6

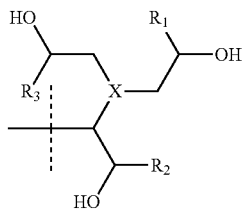

X = C, N
$R_1, R_2, R_3$ = —H, —CH$_3$, or two R groups connected to each other through a 5 or 6 membered alicyclic ring

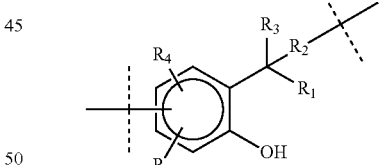

$R_1$ = —OH, —NH$_2$, —SH
$R_2, R_3$ = —H, —CH$_3$, —Ph, or connected to each other through a spiro 3, 4, 5 or 6 membered ring
$R_4, R_5$ = —H, —CH$_3$, —CH$_2$OH, —C(R$_2$,R$_3$)OH, —OCH$_3$, —OH, —COOH, —CONH$_2$
When $R_4$ & $R_5$ are adjacent, may also include fused 5 or 6 membered aromatic or heteroaromatic ring

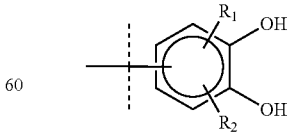

$R_1, R_2$ = —H, —CH$_3$, —OCH$_3$, —OH, —COOH, —CONH$_2$, —F, —Cl, —Br, —I, —CF$_3$, —CN, —NO$_2$
When $R_1$ & $R_2$ are adjacent, may also include fused 5 or 6 membered aromatic or heteroaromatic ring -continued

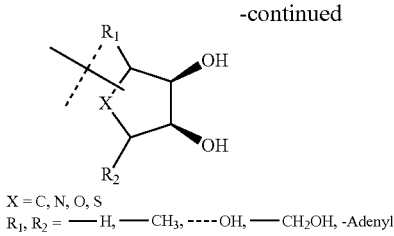

X = C, N, O, S
R₁, R₂ = ——H, ——CH₃, ----OH, ——CH₂OH, -Adenyl

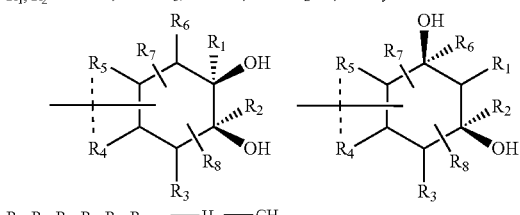

R₁, R₂, R₃, R₄, R₅, R₆ = ——H, ——CH₃
R₇, R₈ are connected to each other to form 3.1.1, 2.2.1 and 2.2.2 bicyclic ring systems such that the hydroxyls are cis to each other

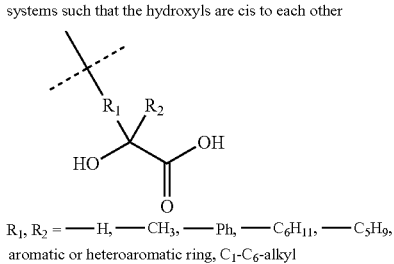

R₁, R₂ = ——H, ——CH₃, ——Ph, ——C₆H₁₁, ——C₅H₉, aromatic or heteroaromatic ring, C₁-C₆-alkyl or C₃-C₈ cycloalkyl.

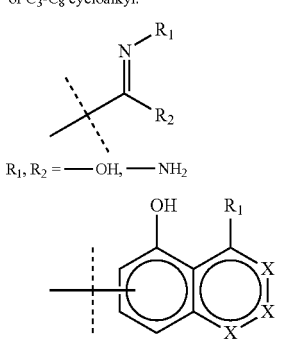

R₁, R₂ = ——OH, ——NH₂

X = C, N
R₁ = ——OH, ——NH₂, ——NHR₂, ——NHC($=$O)R₂, ——NHSO₂R₂

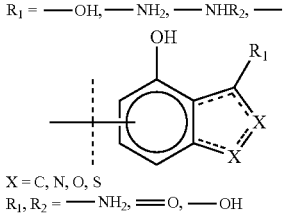

X = C, N, O, S
R₁, R₂ = ——NH₂, $=$O, ——OH where the lines crossed with a dashed line illustrate the one or more bonds formed joining the one or more pharmacophores, directly or through a connector. The pharmacophore and the linker element are connected together directly or indirectly through a connector for each monomer. A plurality of monomers are capable of being linked together through their linker elements, and the pharmacophores for the plurality of monomers bind to proximate locations of the target molecule.

A method of treating a subject for a condition associated with target molecule can be carried out by providing the therapeutic dimer, selecting a subject with the condition, and administering the treatment dimer to the selected subject under conditions effective to treat the condition.

The present invention also relates to a plurality of therapeutic monomers capable of combining to form a therapeutic multimer. Each monomer includes one or more pharmacophores which potentially bind to a target molecule with a dissociation constant of less than 300 μM and a linker element. The linker element has a molecular weight less than 500 daltons and is selected from the group consisting of 1)

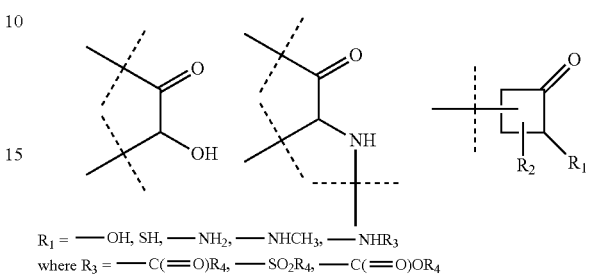

R₁ = ——OH, SH, ——NH₂, ——NHCH₃, ——NHR₃
where R₃ = ——C($=$O)R₄, ——SO₂R₄, ——C($=$O)OR₄ where R₄ is composed of aliphatic, alicyclic, aromatic or heteroaromatic group
where R₃ may also connnect to the pharmacophore and
is composed of aliphatic, alicyclic, aromatic or heteroaromatic group
R₂ = ——H, ——CH₃, ——Ph or other aliphatic, aromatic or heteroaromatic group

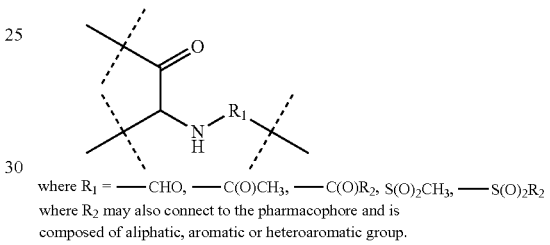

where R₁ = ——CHO, ——C(O)CH₃, ——C(O)R₂, S(O)₂CH₃, ——S(O)₂R₂
where R₂ may also connect to the pharmacophore and is composed of aliphatic, aromatic or heteroaromatic group.

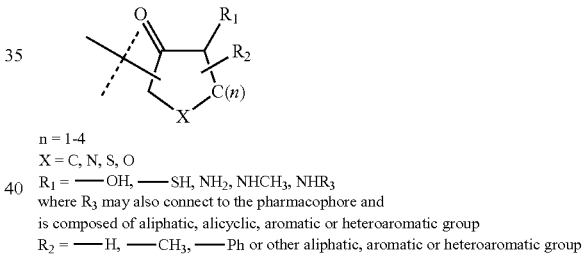

n = 1-4
X = C, N, S, O
R₁ = ——OH, ——SH, NH₂, NHCH₃, NHR₃
where R₃ may also connect to the pharmacophore and
is composed of aliphatic, alicyclic, aromatic or heteroaromatic group
R₂ = ——H, ——CH₃, ——Ph or other aliphatic, aromatic or heteroaromatic group where the lines crossed with a dashed line illustrate the one or more bonds formed joining the one or more pharmacophores, directly or through a connector; 2)

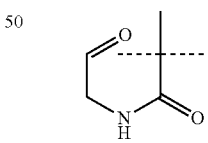

where the lines crossed with a dashed line illustrate the one or more bonds formed joining the one or more pharmacophores, directly or through a connector; 3)

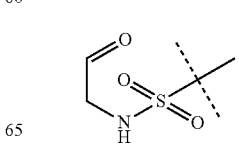

where the lines crossed with a dashed line illustrate the one or more bonds formed joining the one or more pharmacophores, directly or through a connector; 4)

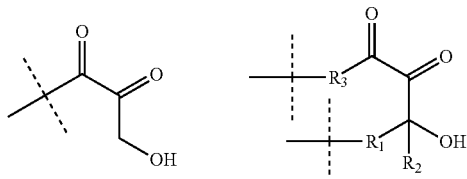

R₁, R₂ = —H, —CH₃, —Ph, —C₆H₁₁, —C₅H₉, aromatic
or heteroaromatic or connected to each other through a
3,4,5 or 6 membered ring.
R₃ = —NH₂, —OH, —CH₃, —Ph, —NHR₄, —CH₂R₄, —OR₄
where R₄ may be connected to the pharmacophore and is composed of aliphatic, aromatic or heteroaromatic group, and R₃ and R₄ may connect to R₁ and R₂ through a 5,6,7 or 8 membered ring where the lines crossed with a dashed line illustrate the one or more bonds formed joining the one or more pharmacophores, directly or through a connector; and 5) aliphatic, alicyclic and aromatic boronic acids capable of reacting with diols, catechols, amino alcohols, amino thiols, α-hydroxy acids, α-hydroxyamides and ortho-hydroxy-arylcarboxamides to form boronate esters comprising 5, 6, or 7 membered rings, oxazaborolanes and oxazaborinanes, thiazaborolanes, thiazaborinanes, dioxaborininone and oxazoborininones as follows:

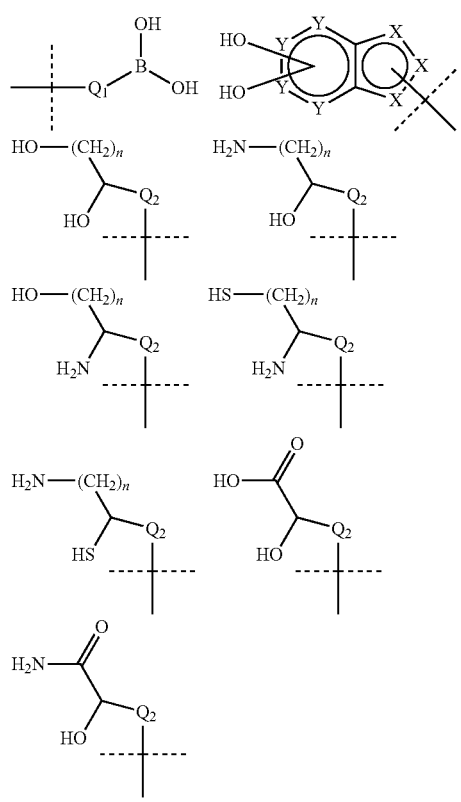

where $Q_1$ and $Q_2$ are aliphatic, alicyclic, or hetero or non-hetero aromatic moieties
where n=1 or 2
where X and Y=C, N, O, or S where the hydroxy groups emanating from the aromatic ring are ortho to each other

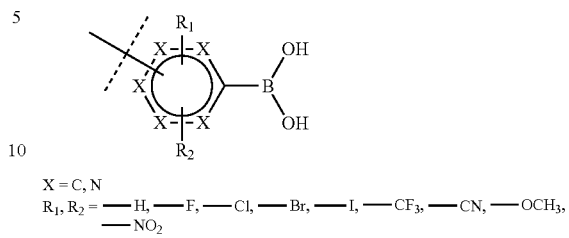

X = C, N
R₁, R₂ = —H, —F, —Cl, —Br, —I, —CF₃, —CN, —OCH₃, —NO₂
Where R₁ & R₂ are adjacent, may also include
fused 5 or 6 membered aromatic or heteroaromatic ring

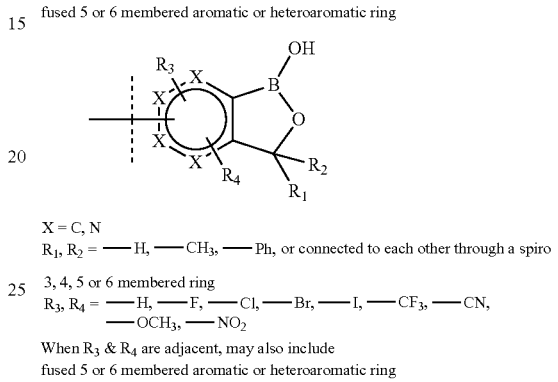

X = C, N
R₁, R₂ = —H, —CH₃, —Ph, or connected to each other through a spiro
3, 4, 5 or 6 membered ring
R₃, R₄ = —H, —F, —Cl, —Br, —I, —CF₃, —CN, —OCH₃, —NO₂
When R₃ & R₄ are adjacent, may also include
fused 5 or 6 membered aromatic or heteroaromatic ring

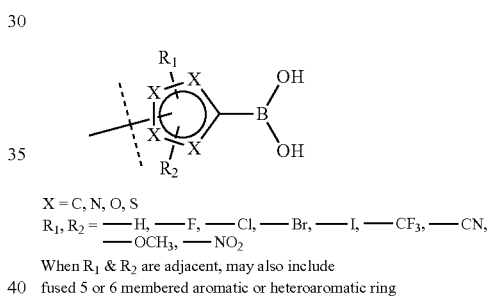

X = C, N, O, S
R₁, R₂ = —H, —F, —Cl, —Br, —I, —CF₃, —CN, —OCH₃, —NO₂
When R₁ & R₂ are adjacent, may also include
fused 5 or 6 membered aromatic or heteroaromatic ring

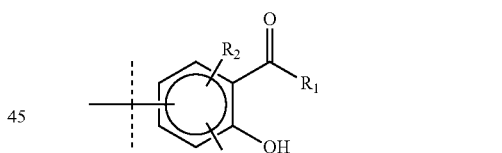

R₁ = —OH, —NH₂, —SH, —NHR₄
where R₄ = alkyl, hydroxyalkyl
R₂, R₃ = —H, —CH₃, —OCH₃, —OH, —COOH, CONH₂
When R₂ & R₃ are adjacent, may also include
fused 5 or 6 membered aromatic or heteroaromatic ring

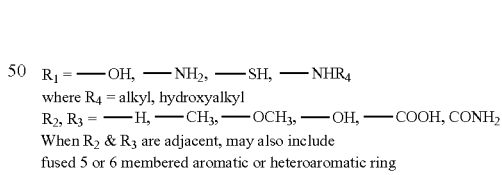

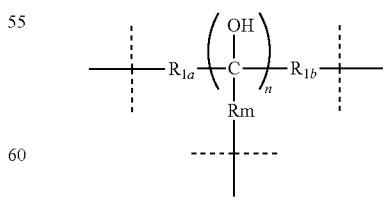

n = 2-6
R₁, R₁ᵦ = —H, —CH₃, —CH₂NH₂, —CH₂NHCH₃, aromatic or
heteroaromatic ring, or connected to each other through a
4,5,6,7 or 8-membered ring
Rm = —H, —CH₃, —CH₃NH₂, —CH₃OH, —CH₂CH₂OH and m = 2-6

-continued

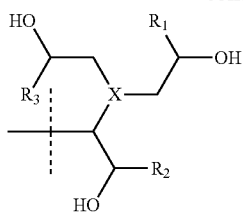

X = C, N
$R_1, R_2, R_3$ = ——H, ——$CH_3$, or two R groups connected to each other through a 5 or 6 membered alicyclic ring

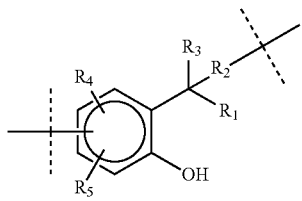

$R_1$ = ——OH, ——$NH_2$, ——SH
$R_2, R_3$ = ——H, ——$CH_3$, ——Ph, or connected to each other through a spiro 3, 4, 5 or 6 membered ring
$R_4, R_5$ = ——H, ——$CH_3$, ——$CH_2OH$, ——$C(R_2,R_3)OH$, ——$OCH_3$, ——OH, ——COOH, ——$CONH_2$
When $R_4$ & $R_5$ are adjacent, may also include fused 5 or 6 membered aromatic or heteroaromatic ring

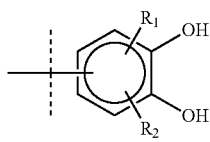

$R_1, R_2$ = ——H, ——$CH_3$, ——$OCH_3$, ——OH, ——COOH, ——$CONH_2$, ——F, ——Cl, ——Br, ——I, ——$CF_3$, ——CN, ——$NO_2$
When $R_1$ & $R_2$ are adjacent, may also include fused 5 or 6 membered aromatic or heteroaromatic ring

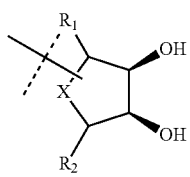

X = C, N, O, S
$R_1, R_2$ = ——H, ——$CH_3$, ----OH, ——$CH_2OH$, -Adenyl

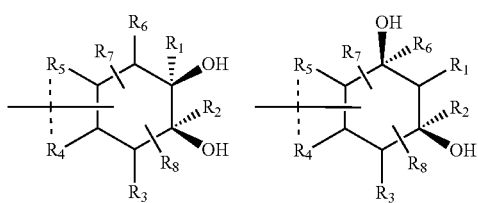

$R_1, R_2, R_3, R_4, R_5, R_6$ = ——H, ——$CH_3$
$R_7, R_8$ are connected to each other to form 3.1.1, 2.2.1 and 2.2.2 bicyclic ring systems such that the hydroxyls are cis to each other

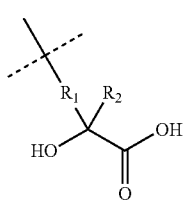

$R_1, R_2$ = ——H, ——$CH_3$, ——Ph, ——$C_6H_{11}$, ——$C_5H_9$, aromatic or heteroaromatic ring, $C_1$-$C_6$-alkyl or $C_3$-$C_8$ cycloalkyl.

-continued

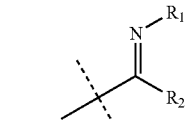

$R_1, R_2$ = ——OH, ——$NH_2$

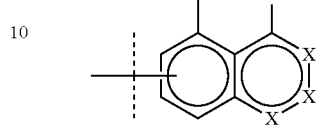

X = C, N
$R_1$ = ——OH, ——$NH_2$, ——$NHR_2$, ——$NHC(=O)R_2$, ——$NHSO_2R_2$

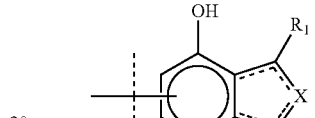

X = C, N, O, S
$R_1, R_2$ = ——$NH_2$, =O, ——OH where the lines crossed with a dashed line illustrate the one or more bonds formed joining the one or more pharmacophores, directly or through a connector. The one or more pharmacophores and the linker element are connected together directly or indirectly through a connector, for each monomer, a plurality of monomers being linked together through their linker elements, and the pharmacophores for the plurality of monomers bind to proximate locations of the target molecule.

A method of treating a subject for a condition associated with target molecule is carried out by providing a plurality of the therapeutic monomers, selecting a subject with the condition, administering the plurality of treatment monomers to the selected subject under conditions effective to treat the condition.

This method can be used to treat conditions activated by trypase. Mast cell mediated inflammatory conditions, in particular asthma, are a growing public health concern. Asthma is frequently characterized by progressive development of hyper-responsiveness of the trachea and bronchi to both immunospecific allergens and generalized chemical or physical stimuli, which lead to the onset of chronic inflammation. Leukocytes containing IgE receptors, notably mast cells and basophils, are present in the epithelium and underlying smooth muscle tissues of bronchi. These leukocytes initially become activated by the binding of specific inhaled antigens to the IgE receptors and then release a number of chemical mediators. For example, degranulation of mast cells leads to the release of proteoglycans, peroxidase, arylsulfatase B, chymase, and tryptase, which results in bronchiole constriction.

Tryptase is stored in the mast cell secretory granules and is the major protease of human mast cells. Tryptase has been implicated in a variety of biological processes, including degradation of vasodilatory and bronchodilatory neuropeptides (Caughey, et al., *J. Pharmacol. Exp. Ther.*, 244: 133-137 (1988); Franconi, et al., *J. Pharmacol. Exp. Ther.*, 248: 947-951 (1988); and Tarn, et al., *Am. J. Respir. Cell Mol. Biol*, 3: 27-32 (1990), which are hereby incorporated by reference in their entirety) and modulation of bronchial responsiveness to histamine (Sekizawa, et al., *J. Clin. Invest.*, 83: 175-179 (1989), which is hereby incorporated by reference in its entirety).

As a result, tryptase inhibitors may be useful as anti-inflammatory agents (K Rice, P. A. Sprengler, Current Opinion in *Drug Discovery and Development*, 2(5): 463-474 (1999), which is hereby incorporated by reference in its entirety) for treatment of inflammatory disease particularly in the treatment of asthma (e.g., chronic asthma) (M. Q. Zhang, H. Timmerman, *Mediators Inflamm.*, 112: 311-317 (1997), which is hereby incorporated by reference in its entirety), and may also be useful in treating or preventing allergic rhinitis (S. J. Wilson et al, *Clin. Exp. Allergy*, 28: 220-227 (1998), which is hereby incorporated by reference in its entirety), inflammatory bowel disease (S. C. Bischoff et al, *Histopathology*, 28: 1-13 (1996), which is hereby incorporated by reference in its entirety), psoriasis (A. Naukkarinen et al, *Arch. Dermatol. Res.*, 285: 341-346 (1993), which is hereby incorporated by reference in its entirety), ocular or vernal or ulcerative conjunctivitis (A. A. Irani et al, *J. Allergy Clin. Immunol.*, 86: 34-40 (1990), which is hereby incorporated by reference in its entirety), dermatological conditions (e.g., psoriasis, eczema, or atopic dermatitis) (A. Jarvikallio et al, *Br. J. Dermatol.*, 136: 871-877 (1997), which is hereby incorporated by reference in its entirety), arthritis (e.g., rheumatoid arthritis (L. C Tetlow et al, *Ann. Rheum. Dis.*, 54: 549-555 (1998), which is hereby incorporated by reference in its entirety), osteoarthritis (M. G. Buckley et al, *J. Pathol*, 186: 67-74 (1998), which is hereby incorporated by reference in its entirety), hematoid arthritis, traumatic arthritis, rubella arthritis, psoriatic arthritis, or gouty arthritis), rheumatoid spondylitis, interstitial lung disease, chronic obstructive pulmonary disease, and diseases of joint cartilage destruction.

In addition, tryptase has been shown to be a potent mitogen for fibroblasts, suggesting its involvement in the pulmonary fibrosis in asthma and interstitial lung diseases (Ruoss et al., *J. Clin. Invest.*, 88: 493-499 (1991), which is hereby incorporated by reference in its entirety). Therefore, tryptase inhibitors may be useful in treating or preventing fibrotic conditions (J. A. Cairns and A. F. Walls, J. Clin. Invest., 99: 1313-1321 (1997), which is hereby incorporated by reference in its entirety) for example, fibrosis, sceleroderma, pulmonary fibrosis, liver cirrhosis, myocardial fibrosis, neurofibromas, hepatic fibrosis, renal fibrosis, testicular, and hypertrophic scars.

Additionally, tryptase inhibitors may be useful in treating or preventing myocardial infarction, stroke, angina and other consequences of atherosclerotic plaque rupture (M. Jeziorska et al, *J. Pathol*, 182: 115-122 (1997), which is hereby incorporated by reference in its entirety).

Tryptase has also been discovered to activate prostromelysin that in turn activates collagenase, thereby initiating the destruction of cartilage and periodontal connective tissue, respectively. Therefore, tryptase inhibitors could be useful in the treatment or prevention of arthritis, periodontal disease, diabetic retinopathy, a condition relating to atherosclerotic plaque rupture, anaphylatis ulcerative colitis, and tumour growth (W J. Beil et al, *Exp. Hematol.*, 26: 158-169 (1998), which is hereby incorporated by reference in its entirety). Also, tryptase inhibitors may be useful in the treatment of anaphylaxis (L. B. Schwarz et al, *J. Clin. Invest.*, 96: 2702-2710 (1995), which is hereby incorporated by reference in its entirety), multiple sclerosis (M. Steinhoff et al, *Nat. Med.* (N.Y.), 6(2): 151-158 (2000), which is hereby incorporated by reference in its entirety), peptic ulcers and syncytial viral infections.

Therapeutic dimers are those dimers from which encryption elements and beads have been removed.

Therapeutically effective doses of compounds of the present invention may be administered orally, topically, parenterally, by inhalation spray, or rectally in dosage unit formulations containing conventional non-toxic pharmaceutically acceptable carriers, adjuvants, and vehicles. The term parenteral, as used herein, includes subcutaneous injections, intravenous, intramuscular, intrasternal injection, or infusion techniques.

The pharmaceutical compositions containing the active ingredient may be in the form suitable for oral use, for example, as tablets, troches, lozenges, aqueous or oily suspensions, dispersible powders or granules, emulsions, hard or soft capsules, or syrups or elixirs. The pharmaceutical compositions of the present invention contain the active ingredient formulated with one or more pharmaceutical excipients. As used herein, the term "pharmaceutical excipient" means a non-toxic, inert solid, semi-solid or liquid filler, diluent, encapsulating material, or formulation auxiliary of any type. Some examples of pharmaceutical excipients are sugars such as lactose, glucose, and sucrose; starches such as corn starch or potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic, compatible lubricants such as sodium lauryl sulfate and magnesium stearate; as well as coloring agents, releasing agents, sweetening, and flavoring and perfuming agents. Preservatives and antioxidants, such as ethyl or n-propyl p-hydroxybenzoate, can also be included in the pharmaceutical compositions.

Dosage forms for topical or transdermal administration of compounds disclosed in the present invention include ointments, pastes, creams, lotions, gels, plasters, cataplasms, powders, solutions, sprays, inhalants, or patches. The active component is admixed under sterile conditions with a pharmaceutically acceptable carrier and any needed preservatives or buffers, as may be required. The ointments, pastes, creams and gels may contain, in addition to an active compound of the present invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

For nasal administration, compounds disclosed in the present invention can be administered, as suitable, in liquid or powdered form from a nasal applicator. Forms suitable for ophthalmic use will include lotions, tinctures, gels, ointment and ophthalmic inserts, as known in the art. For rectal administration (topical therapy of the colon), compounds of the present invention may be administered in suppository or enema form, in solution in particular, for example in vegetable oil or in an oily system for use as a retention enema.

Compounds disclosed in the present invention may be delivered to the lungs by the inhaled route either in nebulizer form or as a dry powder. The advantage of the inhaled route, over the systemic route, in the treatment of asthma and other diseases of airflow obstruction and/or chronic sinusitis, is that patients are exposed to very small quantities of the drug and the compound is delivered directly to the site of action.

Dosages of compounds of the present invention employed will vary depending on the site of treatment, the particular condition to be treated, the severity of the condition, the subject to be treated (who may vary in body weight, age, general health, sex, and other factors) as well as the effect desired.

The amount of active ingredient that may be combined with the pharmaceutical carrier materials to produce a single dosage form will vary depending upon the host treated and the particular mode of administration.

The target molecule can be selected from the group consisting of: (1) G-protein coupled receptors; (2) nuclear receptors; (3) voltage gated ion channels; (4) ligand gated ion channels; (5) receptor tyrosine kinases; (6) growth factors; (7) proteases; (8) sequence specific proteases; (9) phosphatases; (10) protein kinases; (11) bioactive lipids; (12) cytokines; (13) chemokines; (14) ubiquitin ligases; (15) viral regulators; (16) cell division proteins; (17) scaffold proteins; (18) DNA repair proteins; (19) bacterial ribosomes; (20) histone deacetylases; (21) apoptosis regulators; (22) chaperone proteins; (23) serine/threonine protein kinases; (24) cyclin dependent kinases; (25) growth factor receptors; (26) proteasome; (27) signaling protein complexes; (28) protein/nucleic acid transporters; and (29) viral capsids.

The therapeutic multimer, or plurality of therapeutic monomers contains one or more known ligands as pharmacophores and achieves greater efficacy against both wild-type and mutant variants of the target molecule than would be achieved with a single ligand.

The therapeutic multimer or plurality of therapeutic monomers bind to or mimics one or more of the domains selected from the group consisting of SH2, FHA, 14-3-3, WW, WD40, MH2, BROMO, UBA, PTB, SH3, EVH1, GYF, VHS, PDZ, PUF, TUBBY, SAM, DD, CARD, PyD, PB1, BRCT, PH, FYVE, C1, FERM, C2, PX, and ENTH.

The therapeutic multimer or plurality of monomers either interferes with, inhibits binding of, or inhibits activation of the following: (1) target cleavage of a substrate, by binding to the target with a dissociation constant that is less than or equal to the dissociation constant of the substrate from the target; (2) binding of a binding protein to a target, by binding to the target with a dissociation constant that is less than or equal to the dissociation constant of the binding protein; (3) inactivation of a target that by a binding partner, by binding to the target and mimicking the binding partner; (4) inactivation of a target or mutant target by a binding partner, by binding to an inactivating binding partner-target complex or inactivating binding partner-mutant target complex; (5) binding of a first binding partner to a target, by binding to the target and recruiting a second binding partner to bind to the target and the multimer and forming a multimer-target-second binding protein complex, whose dissociation constant is less than or equal to the dissociation constant of the first binding protein; (6) binding to a receptor target, by binding to the receptor target and interfering with receptor dimerization; (7) binding to a binding partner by reducing its recruitment to a receptor target, by binding the receptor target at a ligand binding site to act as an antagonist, or binding the receptor target at the binding partner binding site to act as an antagonist; (8) polymerization of a target into filaments, by binding on a monomer or dimer target; and (13) aggregation of a target, by binding a monomer or dimer target.

The therapeutic multimer or plurality of therapeutic monomers either enhances activation of, enhances binding of, or activates the following: (1) activation of a target by a binding partner, by binding to the target and mimicking the binding partner; (2) activation of a target or mutant target by a binding partner, by binding to an activating binding partner-target complex or activating binding partner-mutant target complex; (3) a first weak binding partner to a target, by binding to the target and recruiting a second binding partner to bind to the target, multimer, and first binding partner and forming a multimer-target-second binding protein complex, or forming a multimer-target-first binding protein-second binding protein complex; (4) a receptor target by binding to the receptor target at the ligand binding site, and facilitating receptor dimerization; (5) a receptor target by binding to an allosteric site on the receptor target and facilitating receptor dimerization in the presence of activating ligand; and (6) a binding partner that is recruited to a receptor target by a ligand binding to the receptor target, by binding to the receptor target at the ligand binding site to act as an agonist, which recruits and activates the binding partner, or binding to the receptor target and the ligand or the receptor target and the binding partner, to accelerate recruitment and activation of the binding partner.

The therapeutic multimer or plurality of therapeutic monomers either enhances or alters protein metabolism by: (1) stabilizing target or mutant target folding; (2) enhancing or interfering with a covalent signaling event; (3) mimicking a covalent signaling event; (4) inhibiting multi-subunit assembly; (5) inhibiting multi-subunit disassembly; or (6) inhibiting degradation by binding the target or target binding partner.

The therapeutic multimer or plurality of therapeutic monomers interferes with, activates, enhances, or mimics covalent modification of the target by phosphorylation, dephosphorylation, acetylation, methylation, sumolation, ubiquitination, farnesylation, and addition of sugar and carbohydrate moieties, by binding to the target or the target-modifying enzyme complex to inhibit, activate, enhance, or modulate protein signaling, transport, or degradation through additional protein interactions.

The therapeutic multimer or plurality of therapeutic monomers interferes with or inhibits either: (1) an essential viral target from a set of targets that includes reverse transcriptase, protease, or viral integration proteins, by providing a plurality of monomers that can bind at a first site, and a plurality of monomers that can bind at an adjacent second site, said plurality of monomers creating a cocktail of therapeutic multimers providing broad inhibition of viral target and mutant variant viral targets; (2) viral entry into cells by binding to and inhibiting the cellular receptor responsible for assisting viral entry; (3) a cellular protein that assists with viral function; or (4) a viral protein such that it no longer inhibits a host defense protein.

The therapeutic multimer has a dissociation constant from the macromolecular target that is from within the range 0.01 pM to 500 nM such that binding of the therapeutic multimer to the target molecule is sufficient to compete with the binding of another protein, protein domain, macromolecule, or substrate to the macromolecular target, or is of sufficiently tight binding to activate, enhance, or inhibit the biological activity of the target molecule or its binding partners to achieve the desired therapeutic effect. This method includes providing a first monomer, wherein the dissociation constant of the constituent pharmacophore from the target molecule is less than 30 pM. A second monomer, wherein the dissociation constant of its constituent pharmacophore from the target molecule is less than 30 μM is also provided. The dissociation constant between the linker element of the first monomer and its binding partner of the second monomer is less than 300 mM. The connector joining the linker element to the pharmacophore for each monomer is in the range of about 2 or less rotatable bonds to about 5 rotatable bonds.

EXAMPLES

Example 1—Synthesis of Pyrrolidone Based Linker Element Monomer

Pyrrolidone based linker element monomers are synthesized according to the following reaction scheme:

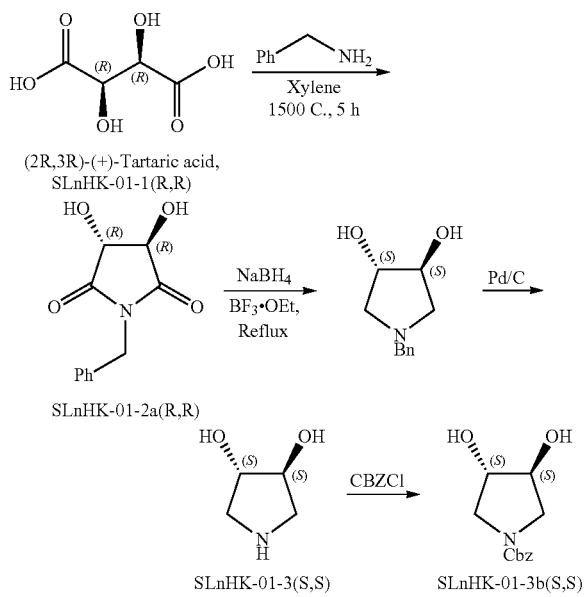

Experimental Procedure

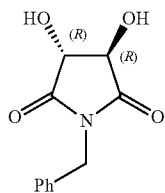

(3R,4R)-1-Benzyl-3,4-dihydroxypyrrolidine-2,5-dione (SLnHK-01-2a (R,R))

To a stirred solution of L-Tartaric acid (50 g, 0.33 mol) in xylene (250 mL) was added benzylamine (36.7 mL, 0.33 mol) and the mixture was heated under reflux at 150° C. for 3 h using a Dean-Stark trap. After the reaction mixture was allowed to cool overnight, crystals were collected by filtration and washed with acetone. The resultant crude product was recrystallized from ethanol to obtain SLnHK-01-2a (R,R) (33.1 g, 45%) as solid.

$^1$H NMR (200 MHz, DMSO-$d_6$): δ 7.35-7.25 (m, 5H), 6.30-6.26 (m, 2H), 4.55 (d, J=15.0 Hz, 2H), 4.40-4.36 (m, 2H).

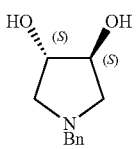

(3S,4S)-1-Benzylpyrrolidine-3,4-diol (SLnHK-01-3a (S,S))

To a stirred solution of boron trifluoride ethyl etherate (23 mL, 0.16 mol) in DME (120 mL) were added SLnHK-01-2a (10 g, 0.04 mol) and sodium borohydride (6.2 g, 0.16 mol) at 0° C. The mixture was stirred at 70° C. for 2 h. Then 6 N HCl (62.5 mL) was added slowly at 70° C., stirred for 15 min. Sodium fluoride (28 g) was added and the mixture was heated at reflux temperature for 30 min. The mixture was cooled to room temperature, 20% aq. NaOH (53 mL) was added and the resulting mixture was filtered. The organic phase was isolated, evaporated to dryness and obtained residue was partitioned between water and diethyl ether. The water phase was extracted with diethyl ether (2×100 mL). The combined organic phases were dried over MgSO$_4$, evaporated to dryness and obtained crude material was recrystallized from ethyl acetate to obtain SLnHK-01-3a (S,S) (7.0 g, 45%) as white crystals.

$^1$H NMR (200 MHz, CDCl$_3$): δ 7.34-7.25 (m, 5H), 4.04 (t, J=4.2 Hz, 2H), 3.58 (d, J=7.8 Hz, 2H), 2.92-2.88 (m, 2H), 2.44-2.40 (m, 2H).

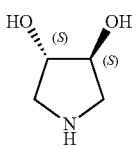

(3S,4S)-Pyrrolidine-3,4-diol (SLnHK-01-3 (S,S))

To a solution of SLnHK-01-3a (S,S) (5.0 g, 0.02 mol) in MeOH (35 mL) was added AcOH (15 mL) followed by addition of Pd/C (1.6 g). The mixture was then exposed to H$_2$ at 50 psi for 24 h. The mixture was filtered through celite pad and filtrate was concentrated under reduced pressure to afford SLnHK-01-3 (S,S) (2.5 g, crude). The crude material was taken up for next step without further purification.

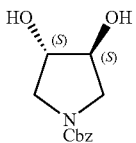

(3S,4S)-Benzyl 3,4-dihydroxypyrrolidine-1-carboxylate (SLnHK-01-3b(S,S))

To a stirred solution of SLnHK-01-3 (S,S) (2.5 g, 0.024 mol) in 1,4-dioxane (70 mL) was added aqueous Na$_2$CO$_3$ (4.1 g, 0.038 mol) was added drop wise at 0° C. to give a solution of pH 10. Then CBZCl (5.5 mL, 0.038 mol) was added portion wise the reaction mixture. More aqueous Na$_2$CO$_3$ (ca.5 mL) was added during the addition of CBZCl to maintain the solution around pH 9. The mixture was stirred for 30 min at 0° C. and then warmed up to room temperature and stirred for another 30 min., removed the dioxane, extracted with EtOAc, dried over MgSO$_4$, filtered, and concentrated under reduced pressure. The crude material was purified over silica gel column chromatography to afford SLnHK-01-3b(S,S) (2.0 g, 32% for two steps) as a colorless syrup.

$^1$H NMR (500 MHz, CDCl$_3$): δ 7.34-7.27 (m, 5H), 5.11 (s, 2H), 4.16-4.07 (m, 2H), 3.68 (dd, J=12, 4.5 Hz, 2H), 3.40 (dd, J=14.0, 12.0 Hz, 2H), 3.06 (brs, 1H), 2.86 (brs, 1H).

Example 2—Synthesis of Pyrrolidone Linker Element Dimer

Pyrrolidone based linker element dimers are synthesized according to the following reaction scheme

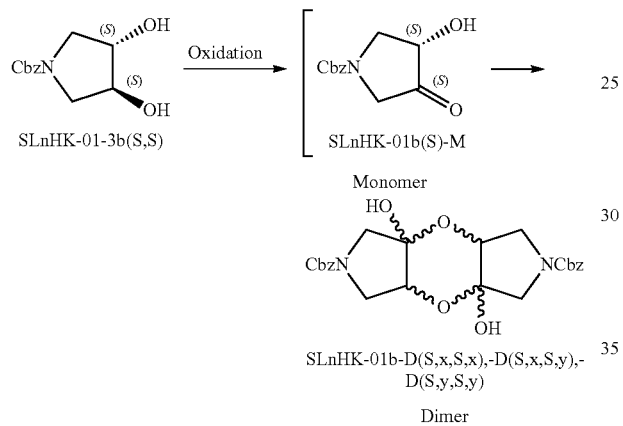

Experimental Procedure

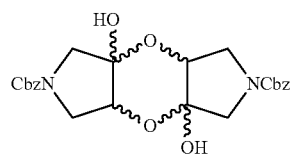

3a,7a-Dihydroxy-octahydro-4,8-dioxa-2,6-diaza-s-indacene-2,6-dicarboxylic acid di-benzyl ester To a stirred solution of oxalyl chloride (0.091 mL, 1.0 mmol) in anhydrous THF (5 mL) was added dimethyl sulfoxide (0.095 mL, 1.3 mmol) at −70° C. under an inert atmosphere. After being stirred for 20 min, SLnHK-01-3b (S,S) (0.2 g, 0.84 mmol) in THF (3 mL) was added at −70° C. and stirred for 1 h. Then triethyl amine (0.58 mL, 4.2 mmol) was added at −70° C., the mixture was stirred for additional 20 min at −70° C. and min at room temperature. The reaction mixture was quenched with water, extracted with ethyl acetate. The organic phase was washed with brine, dried over MgSO$_4$, filtered, and concentrated under reduced pressure. The crude material was purified over silica gel column chromatography to afford Dimer (0.1 g, 25%) as solid. LC-MS/MS indicated that the material consists of 3 major and one minor separable isomers of the dimer, at least one of which is a spiroketal.

$^1$H NMR (500 MHz, DMSO-d$_6$): δ 7.47-7.38 (m, 10H), 6.84 (brs, 2H), 5.07 (s, 4H), 4.08-4.01 (m, 2H), 3.80-3.62 (m, 2H), 3.61 (t, J=8 Hz, 2H), 3.41-4.27 (m, 4H). LCMS=493 (M+Na, 100%); 516 (M+2Na, 40%).

Example 3—Synthesis of Pharmacophore with Connector

Pharmacophores with connectors are synthesized according to the following reaction scheme:

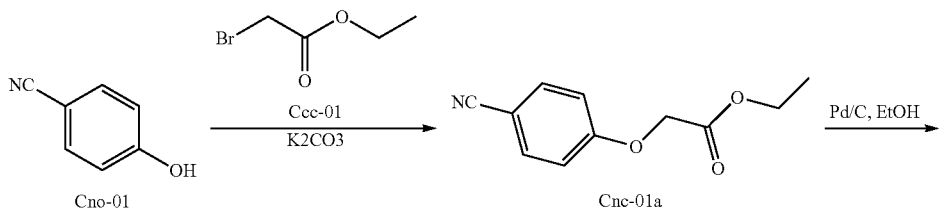

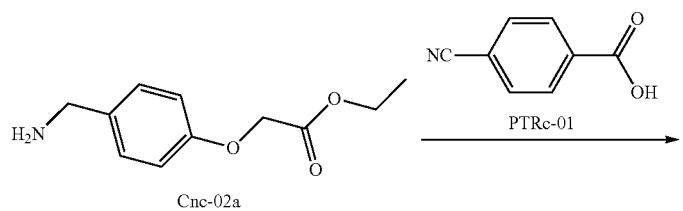

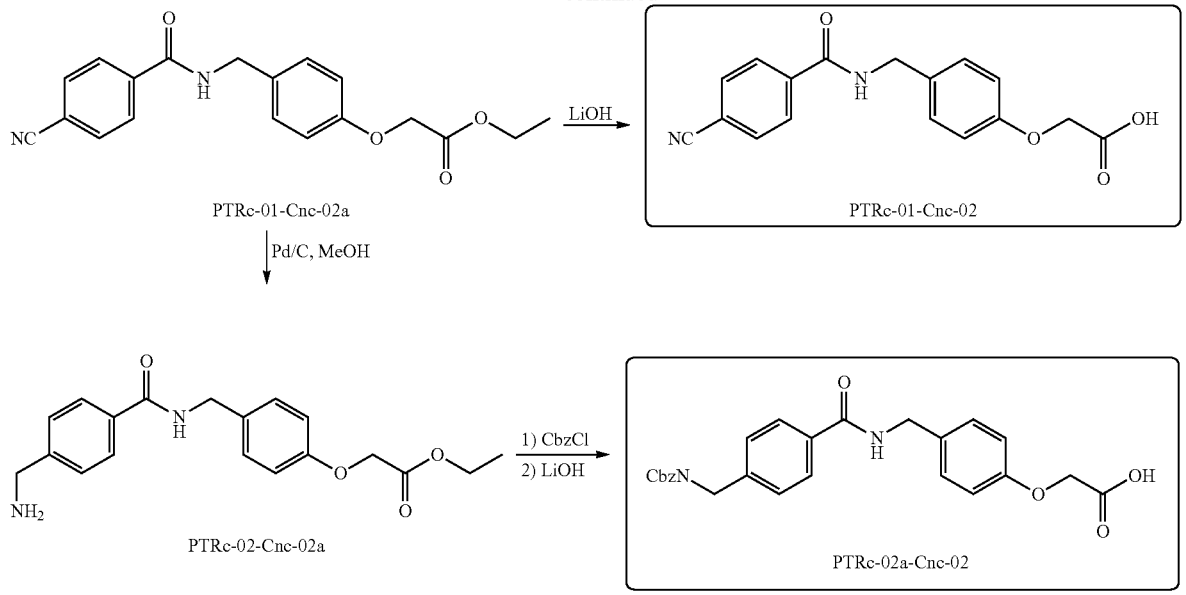

Experimental Procedure

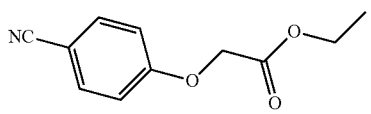

Ethyl 2-(4-cyanophenoxy)acetate (Cnc-01a)

To a stirred solution of 4-cyanophenol (10 g, 84 mmol) in acetone were added K₂CO₃ (34.3 g, 249 mmol) and ethylbromo acetate (11.2 mL, 100 mmol) at room temperature. The mixture was stirred at reflux temperature for 12 h. The mixture was filtered, filtrate was evaporated, and obtained residue was dissolved in water (50 mL). The aqueous layer was extracted with EtOAc (2×100 mL). The combined organic phases were washed with brine, dried over Na₂SO₄, filtered, and concentrated under reduced pressure. The crude material was purified over silica gel column chromatography to afford Cnc-01a (13 g, 75%).

¹H NMR (200 MHz, CDCl₃): δ 7.62-7.58 (d, J=7.5 Hz, 2H), 7.0-6.80 (d, J=7.4 Hz, 2H), 4.65 (s, 2H), 4.25 (q, J=8.0 Hz, 2H), 1.25 (t, J=8.0 Hz, 3H).

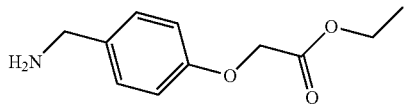

Ethyl 2-(4-(aminomethyl)phenoxy)acetate (Cnc-02a)

To a solution of Cnc-01a (0.5 g, 2.4 mmol) in EtOH (6 mL) was added AcOH (3 mL) followed by addition of Pd/C (0.1 g). The mixture was then exposed to H₂ (100 psi) for 24 h. The mixture was filtered through a celite pad and filtrate was concentrated under reduced pressure. The obtained residue was dissolved in water (10 mL) and washed with EtOAc (25 mL). The aqueous phase was basified to pH ~9 using sat. NaHCO₃ and then extracted with DCM (2×25 mL). The combined organic phases were washed with brine, dried over Na₂SO₄, filtered, and concentrated under reduced pressure to afford Cnc-02a (0.35 g, 70%).

¹H NMR (200 MHz, CDCl₃): δ 7.25-7.20 (m, 2H), 6.90-6.80 (m, 2H), 4.60 (s, 2H), 4.25 (q, J=8.0 Hz, 2H), 3.90 (s, 2H), 1.60 (brs, 2H), 1.25 (t, J=8.0 Hz, 3H).

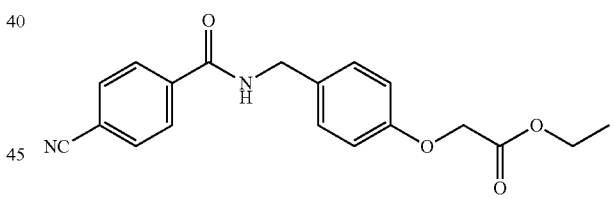

Ethyl 2-(4-((4-cyanobenzamido)methyl)phenoxy) acetate (PTRc-01-Cnc-02a)

To a stirred solution of 4-cyanobenzoic acid (0.19 g, 1.33 mmol) in DMF (10 mL) were added HATU (0.76 g, 2.0 mmol), DIPEA (0.79 mL, 5.0 mmol) and Cnc-02a (0.35 g, 1.67 mmol), reaction mixture was stirred for 4 h at room temperature. The reaction mixture was quenched with water and extracted with EtOAc (2×30 mL)). The combined organic phases were washed with saturated NaHCO₃, water, brine, dried over Na₂SO₄, filtered, and concentrated under reduced pressure. The crude material was purified over silica gel column chromatography to afford PTRc-01-Cnc-02a (0.2 g, 35%).

¹H NMR (200 MHz, CDCl₃): δ 7.85 (d, J=7.5 Hz, 2H), 7.65 (d, J=7.5 Hz, 2H), 7.30 (m, 1H), 6.90 (d, J=7.5 Hz, 2H), 4.60 (s, 2H), 4.58 (d, J=8.0 Hz, 2H), 4.25 (q, J=8.0 Hz, 2H), 1.25 (t, J=8.0 Hz, 3H).

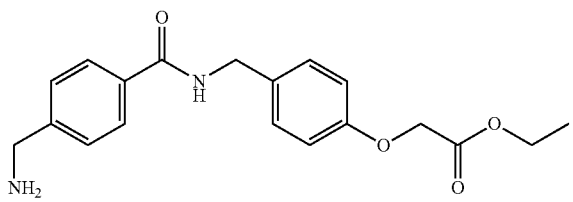 [SMILES: CCOC(=O)COc1ccc(CNC(=O)c2ccc(CN)cc2)cc1]

Ethyl 2-(4-((4-(aminomethyl)benzamido)methyl)phenoxy)acetate (PTRc-02-Cnc-02a)

To a solution of PTRc-01-Cnc-02a (0.5 g, 1.4 mmol) in EtOH (8 mL) was added AcOH (4 mL) followed by addition of Pd/C (0.1 g). The mixture was then exposed to $H_2$ (100 psi) for 24 h. The mixture was filtered through a celite pad and filtrate was concentrated under reduced pressure. The obtained residue was dissolved in water (10 mL) and washed with EtOAc (25 mL). The aqueous phase was basified to pH ~9 using sat. $NaHCO_3$ and then extracted with DCM (2×25 mL). The combined organic phases were washed with brine, dried over $Na_2SO_4$, filtered, and concentrated under reduced to afford PTRc-02-Cnc-02a (0.35 g, 70%).

$^1$H NMR (200 MHz, $CDCl_3$): δ 7.80 (d, J=7.5 Hz, 2H), 7.40-7.25 (m, 2H), 6.90 (d, J=7.5 Hz, 2H), 4.62-4.58 (m, 2H), 4.25 (q, J=8.0 Hz, 2H), 3.90 (s, 2H), 1.25 (t, J=8.0 Hz, 3H).

2-(4-((4-Cyanobenzamido) methyl)phenoxy)acetic acid (PTRc-01-Cnc-02)

To a stirred solution of PTRc-01-Cnc-02a (1.4 g, 4.1 mmol) in THF (10 mL) and water (20 mL) was added lithium hydroxide monohydrate (0.56 g, 13.5 mmol) and the reaction mixture was stirred at room temperature for 16 h. The volatiles were evaporated under vacuum; the residue was diluted with water (30 mL) and extracted with EtOAc (2×50 mL)). The combined organic phases were washed with brine, dried over $Na_2SO_4$, filtered, and concentrated under reduced pressure. The crude material was purified over silica gel column chromatography to afford PTRc-01-Cnc-02 (0.9 g, 70%).

Example 4—Synthesis of (S)-4-(aminomethyl)-N-(4-(2-(3-hydroxy-4-oxopyrrolidin-1-yl)-2-oxoethoxy)benzyl)benzamide (SCN-MA9004-56)

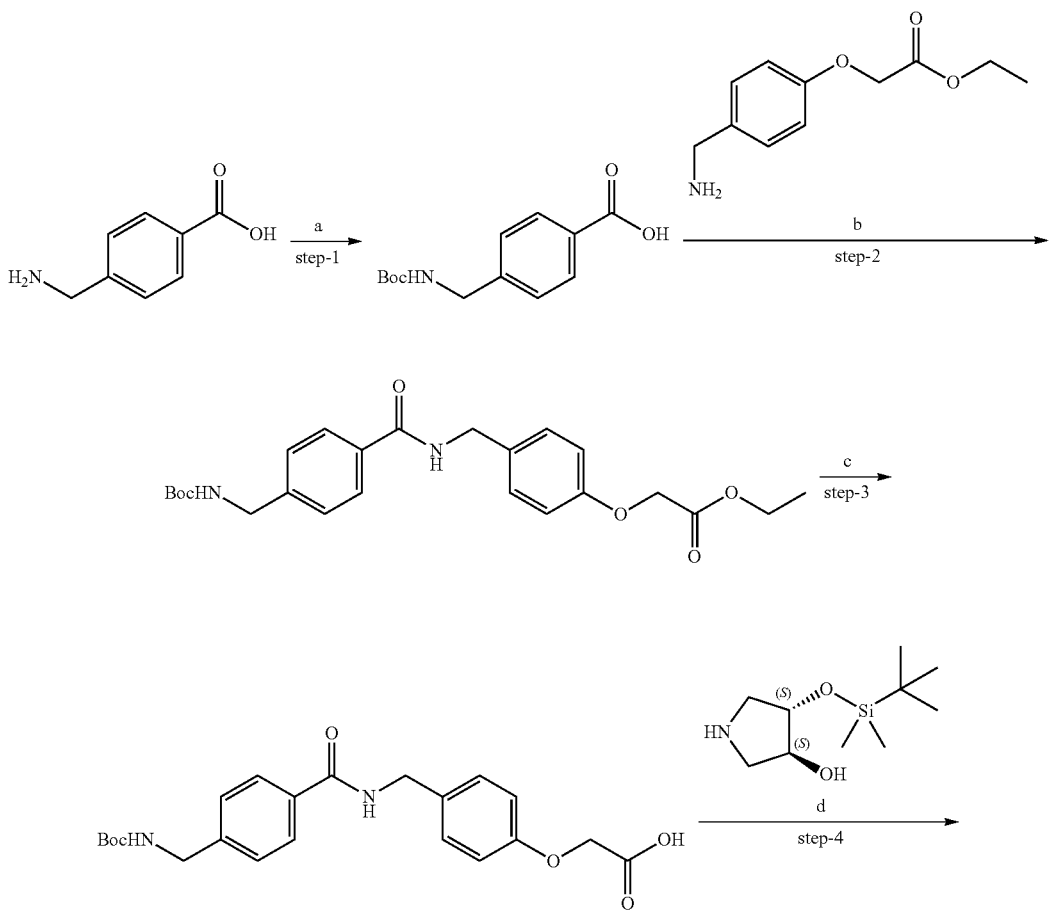

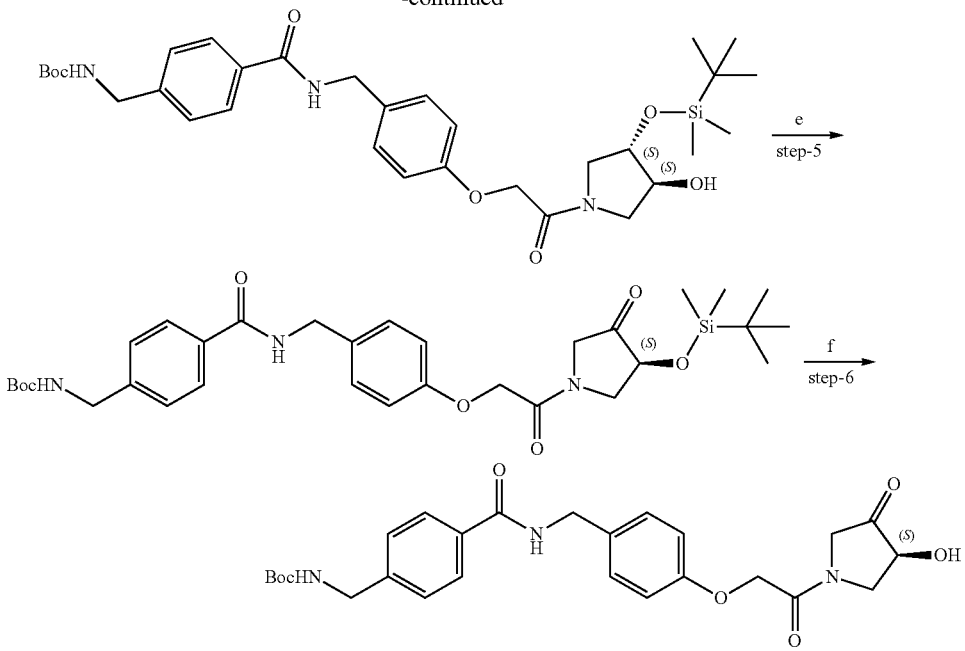

Reagents and Conditions:
a) (Boc)₂O, NaHCO₃,1,4-Dioxane in H₂O, 0° C.-rt, 16 h;
b) HATU, DIPEA, DMF, 0° C.-rt, 45 min; c) LiOH, THF in H₂O, 0° C.-rt, 2 h; d) BOP, Pyridine, DMF, 0° C.-rt, 16 h; e) (COCl)₂, Et₃N, DMSO, THF, −70° C.-rt, 1.5 h; f) HCl in Et₂O, CH₂Cl₂, 0° C.-rt, 4 h.

Experimental Procedure

Step-1: Synthesis of 4-((Tert-butoxycarbonylamino)methyl)benzoic acid (2)

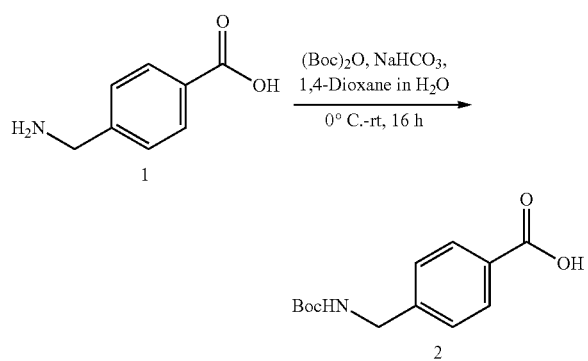

To a stirred solution of 4-(aminomethyl)benzoic acid (5 g, 33 mmol) in 1,4-dioxane (50 mL) and H₂O (25 mL) was added NaHCO₃ (8.3 g, 99.2 mmol) followed by Boc anhydride (10.8 g, 49.6 mmol) at 0° C. The resulting reaction mixture was stirred at room temperature for 16 h. After completion of reaction (by TLC), the volatiles were evaporated under reduced pressure and the residue was neutralized using cold 1N HCl solution. The precipitated solid was filtered and dried under reduced pressure to afford 4-(((tert-butoxycarbonyl)amino)methyl)benzoic acid (5.5 g, 66%) as a white solid.

Step-2: Synthesis of Ethyl 2-(4-((4-(((tert-butoxycarbonyl)amino)methyl)benzamido) methyl)phenoxy)acetate

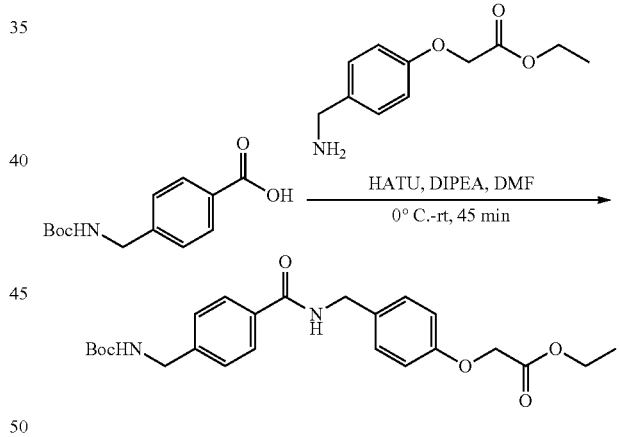

To a stirred solution of 4-(((tert-butoxycarbonyl)amino) methyl)benzoic acid (3.0 g, 11.95 mmol) in DMF (30 mL) were added DIPEA (6.37 mL, 35.8 mmol) and HATU (6.8 g, 17.9 mmol) at room temperature under nitrogen atmosphere. The resulting reaction mixture was cooled to 0° C. and stirred for 15 min. A solution of ethyl 2-(4-(aminomethyl)phenoxy)acetate (3.5 g, 13.1 mmol) in DMF (30 mL) was then added to the reaction mixture at 0° C. and the stirring was continued for another 20 min at room temperature. After completion of reaction (by TLC), the reacting reaction mixture was diluted with cold water and the aqueous layer was extracted with EtOAc (2×100 mL). The combined organic phases were washed with brine and dried over Na₂SO₄. After filtration and evaporation, the crude material was purified by silica gel column chromatography to afford ethyl 2-(4-((4-(((tert-butoxycarbonyl)amino) methyl)benzamido) methyl)phenoxy)acetate (3.3 g, 62.5%) as an off-white solid.

Step-3: Synthesis of 2-(4-((4-(((Tert-butoxycarbonylamino)methyl)benzamido) methyl)phenoxy)acetic acid

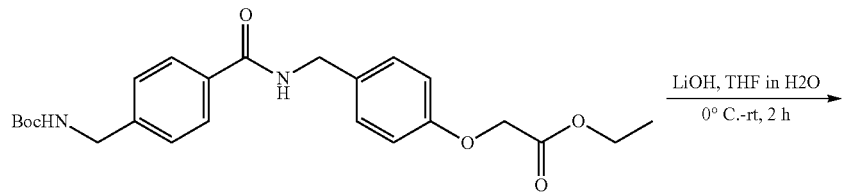

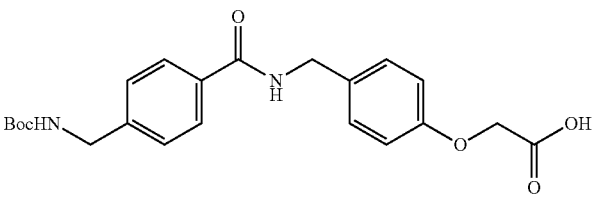

To a stirred solution of ethyl 2-(4-((4-(((tert-butoxycarbonyl)amino)methyl)benzamido) methyl)phenoxy)acetate (1.3 g, 2.94 mmol) in THF (20 mL) and H₂O (10 mL) was added lithium hydroxide monohydrate (0.37 g, 8.81 mmol) at 0° C. The resulting reaction mixture was stirred at room temperature for 2 h. After completion of reaction (by TLC), the volatiles were evaporated under reduced pressure and the residue was neutralized with 1N HCl at 0° C. The precipitated solid was filtered and dried under vacuum to afford 2-(4-((4-(((tert-butoxycarbonyl)amino)methyl)benzamido)methyl)phenoxy)acetic acid (1 g, 82.6%) as an off white solid.

Step-4: Synthesis of Tert-butyl 4-(4-(2-((3R,4R)-3-(tert-butyldimethylsilyloxy)-4-hydroxypyrrolidin-1-yl)-2-oxoethoxy)benzylcarbamoyl)benzylcarbamate

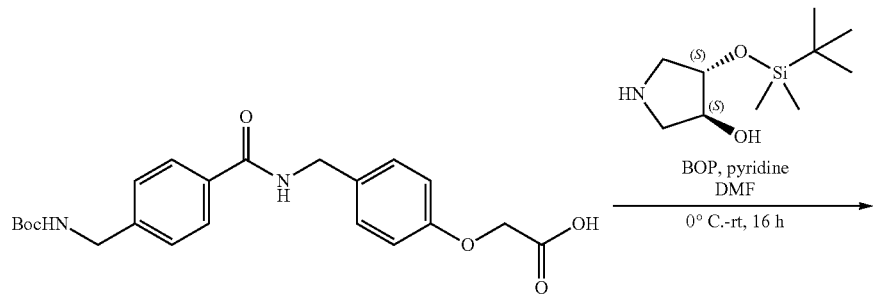

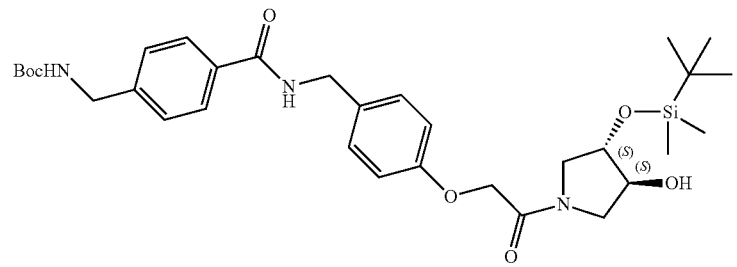

To a stirred solution of 2-(4-((4-((tert-butoxycarbonyl amino)methyl)benzamido) methyl)phenoxy)acetic acid (0.9 g, 2.17 mmol) in DMF (3 mL) was added pyridine (5 mL) and BOP (1.15 g, 2.81 mmol) at room temperature. The reaction mixture was cooled to 0° C. and stirred for 20 min. A solution of (3S,4S)-4-(tert-butyldimethylsilyloxy)pyrrolidin-3-ol (0.61 g, 2.81 mmol) in DMF (5 mL) was added to the reaction mixture slowly at 0° C. Then the reaction mixture was allowed to warm to room temperature and stirred for 16 h. After completion of reaction (by TLC), the reaction mixture was quenched with saturated CuSO₄ solution (2×25 mL) and extracted with EtOAc (2×50 mL). The combined organic phases were dried over Na₂SO₄. After filtration and evaporation of solvent, the crude material was purified by silica gel column chromatography to afford tert-butyl 4-(4-(2-((3R,4R)-3-(tert-butyldimethylsilyloxy)-4-hydroxypyrrolidin-1-yl)-2-oxoethoxy)benzylcarbamoyl) benzylcarbamate (0.65 g, 48.8%) as an off white solid.

Step-5: Synthesis of (S)-tert-butyl 4-(4-(2-(3-(tert-butyldimethylsilyloxy)-4-oxopyrrolidin-1-yl)-2-oxoethoxy)benzylcarbamoyl)benzylcarbamate

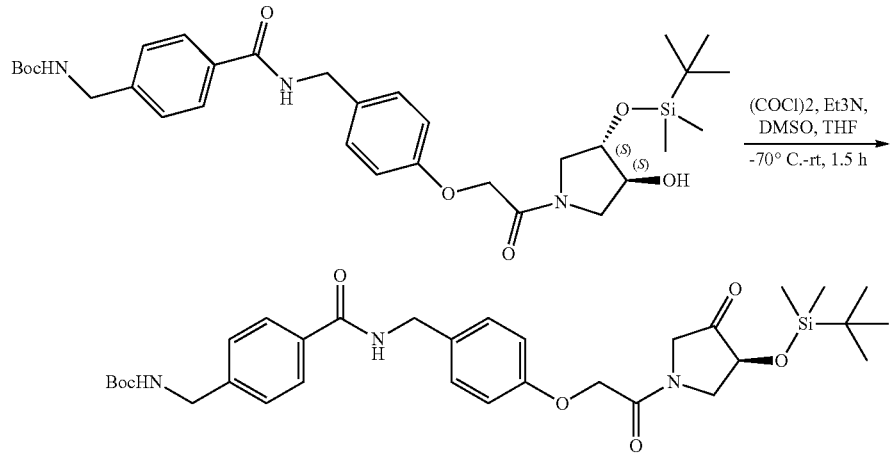

To a stirred solution of oxalyl chloride (0.07 mL, 0.78 mmol) in dry THF (5 mL) was added dimethyl sulfoxide (0.074 mL, 1.04 mmol) drop wise at −70° C. under inert atmosphere. After being stirred for 10 min at same temperature, a solution of tert-butyl 4-(4-(2-((3s,4s)-3-(tert-butyldimethylsilyloxy)-4-hydroxypyrrolidin-1-yl)-2-oxoethoxy)benzylcarbamoyl)benzylcarbamate (0.4 g, 0.65 mmol) in THF (5 mL) was added to the reaction mixture slowly at −70° C. After being stirred for 1 h at −70° C., triethyl amine (0.45 mL, 3.26 mmol) was added to the reaction mixture at −70° C. and stirred for additional 20 min. The reaction mixture was allowed to warm to room temperature and stirred for 15 min. After completion of reaction (by TLC), the reaction mixture was diluted with water and extracted with EtOAc (2×30 mL). The combined organic phases were dried over anhydrous Na₂SO₄, filtered and concentrated under reduced pressure. The crude material was purified by silica gel column chromatography to afford (S)-tert-butyl 4-(4-(2-(3-(tert-butyldimethylsilyloxy)-4-oxopyrrolidin-1-yl)-2-oxoethoxy)benzylcarbamoyl)benzylcarbamate (0.25 g, 62.8%) as an off-white solid.

Step-6: Synthesis of (S)-4-(aminomethyl)-N-(4-(2-(3-hydroxy-4-oxopyrrolidin-1-yl)-2-oxo ethoxy) benzyl)benzamide

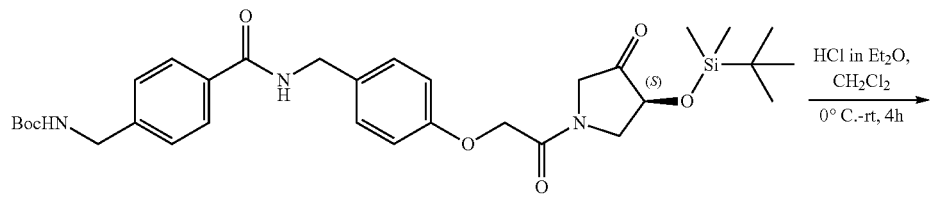

-continued

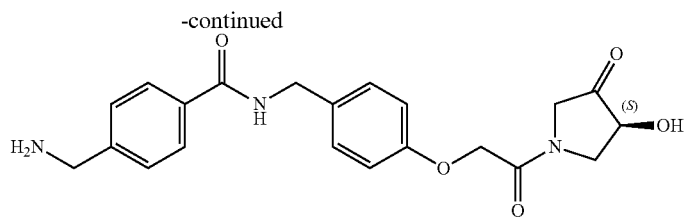

To a stirred solution of (S)-tert-butyl-4-(4-(2-(3-(tert-butyldimethyl silyloxy)-4-oxopyrrolidin-1-yl)-2-oxoethoxy)benzyl carbamoyl)benzylcarbamate (0.14 g, 0.23 mmol) in CH$_2$Cl$_2$ (8 mL) was added 4 N HCl in diethyl ether (2 mL) at 0° C. The resulting reaction mixture was stirred at 0° C. for 3 h and for 1 h at room temperature. After completion of reaction (by TLC), the volatiles were evaporated under reduced pressure and the residue was washed with EtOAc (4 mL) and diethyl ether (4 mL). The crude material was purified by preparative HPLC to afford (S)-4-(aminomethyl)-N-(4-(2-(3-hydroxy-4-oxopyrrolidin-1-yl)-2-oxo ethoxy)benzyl)benzamide (32 mg (10 mg (97% purity) & 22 mg (85% purity)), 35.2% yield) as a white solid.

$^1$H NMR (500 MHz, DMSO-d$_6$): δ 9.01 (bs, NH), 8.28 (bs, 2H), 7.92 (d, J=8.0 Hz, 2H), 7.53 (d, J=8.0 Hz, 2H), 7.23 (d, J=8.0 Hz, 2H), 6.87 (d, J=8.5 Hz, 2H), 6.07-5.92 (m, 1H), 4.41-4.13 (m, 8H), 3.73-3.62 (m, 1H), 3.46-3.23 (m, 2H), 2.73-2.20 (m, 2H).

LCMS: m/z [M+1]=398, 100%; [M+18]=416, 75% (226 nm, RT=8.85; purity 97.4%)
Mobile Phase A: 0.05% TFA in water, Mobile Phase B: Acetonitrile,
Flow rate: 1 ml/min; Temperature: Ambient,
Column: Primesep 200 (150×4.6 mm)
Gradient: Time/% B 0.01/10, 3/10, 15/90, 25/90

Example 5—Synthesis of 4-(aminomethyl)-N-(4-(2-((3S,4S)-3,4-dihydroxypyrrolidin-1-yl)-2-oxoethoxy)benzyl)benzamide.HCl salt (SCN-MA9004-61)

Reagents and Conditions:
a) 4N HCl in Et$_2$O, CH$_2$Cl$_2$, 0° C.-rt, 1 h.

To a stirred solution of tert-butyl 4-((4-(2-((3S,4S)-3-((tert-butyldimethylsilyl)oxy)-4-hydroxypyrrolidin-1-yl)-2-oxoethoxy)benzyl)carbamoyl)benzylcarbamate (0.1 g, 0.163 mmol) in CH$_2$Cl$_2$ (4 mL) was added 4 N HCl in diethyl ether (0.5 mL) at 0° C. The resulting reaction mixture was stirred at room temperature for 1 h. After completion of reaction (by TLC), the volatiles were evaporated under reduced pressure and the residue was triturated with EtOAc (4 mL) and diethyl ether (4 mL) to afford 4-(aminomethyl)-N-(4-(2-((3S,4S)-3,4-dihydroxypyrrolidin-1-yl)-2-oxoethoxy)benzyl)benzamide.HCl salt (50 mg) as a white solid.

$^1$H NMR (500 MHz, DMSO-d$_6$): δ 9.08 (t, J=6.0 Hz, 1H), 8.46 (bs, 2H), 7.95 (d, J=8.0 Hz, 2H), 7.60 (d, J=8.0 Hz, 2H), 7.27 (d, J=8.0 Hz, 2H), 6.91 (d, J=8.0 Hz, 2H), 5.79 (s, 2H), 4.70 (s, 2H), 4.44 (d, J=6.0 Hz, 2H), 4.13-4.10 (m, 2H), 4.03 (s, 1H), 3.94 (s, 1H), 3.70-3.67 (m, 1H), 3.46-3.31 (m, 4H).

LCMS: m/z [M+1]=400, 100%; [M+23]=422, 75% (226 nm, RT=9.47; purity 98.5%)
Mobile Phase A: 0.05% TFA in water, Mobile Phase B: Acetonitrile,
Flow rate: 1 ml/min; Temperature: Ambient,
Column: Primesep 200 (150×4.6 mm)
Gradient: Time/% B 0.01/10, 3/10, 15/90, 25/90

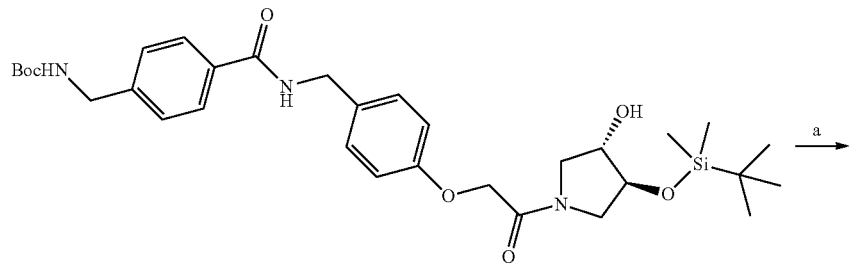

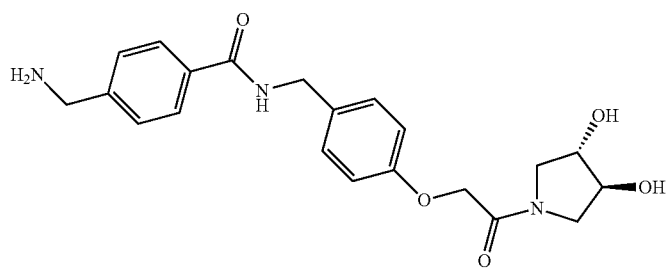

Example 6—Synthesis of (R)-4-(aminomethyl)-N-(4-(2-(3-hydroxy-4-oxopyrrolidin-1-yl)-2-oxoethoxy)benzyl)benzamide (SCN-MA9004-65)

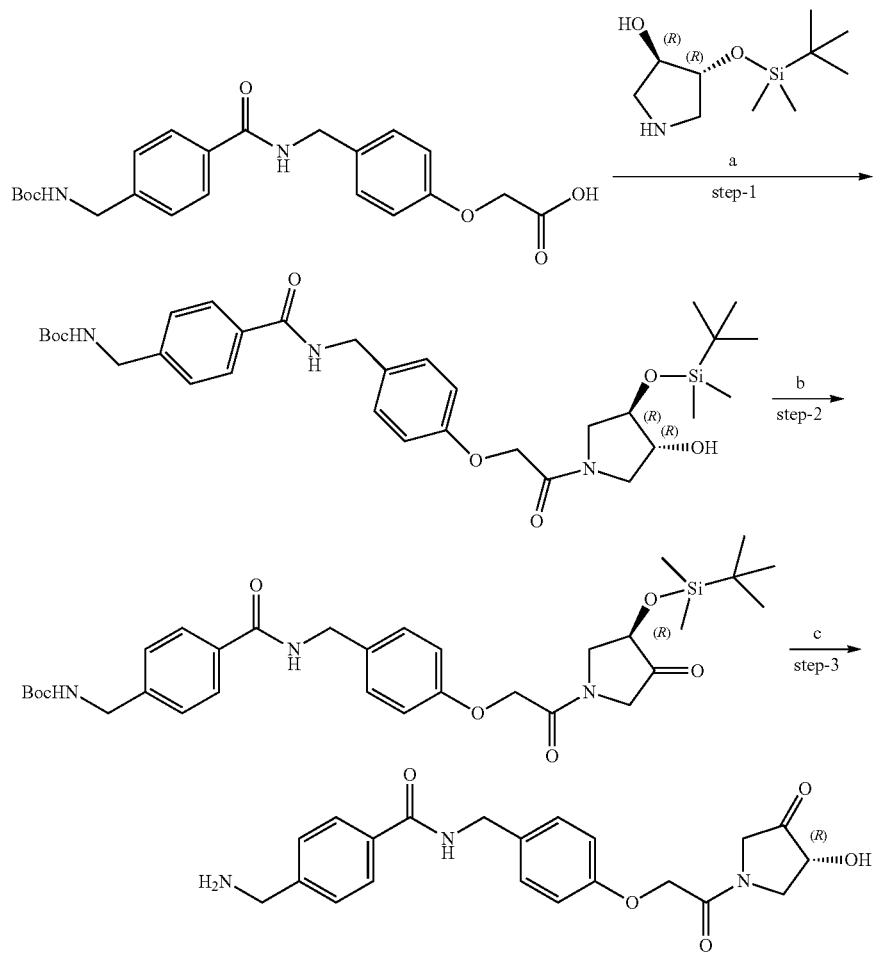

Reagents and Conditions:
a) BOP, Pyridine, DMF, 0° C.-rt, 16 h; b) (COCl)$_2$, Et$_3$N DMSO, THF, −70° C.-rt, 1.5 h; c) HCl in Et$_2$O, CH$_2$Cl$_2$, 0° C.-rt, 4 h.

Experimental Procedure

Step-1: Synthesis of Tert-butyl-4-(4-(2-((3R,4R)-3-(tert-butyldimethylsilyloxy)-4-hydroxy pyrrolidin-1-yl)-2-oxoethoxy)benzylcarbamoyl)benzylcarbamate

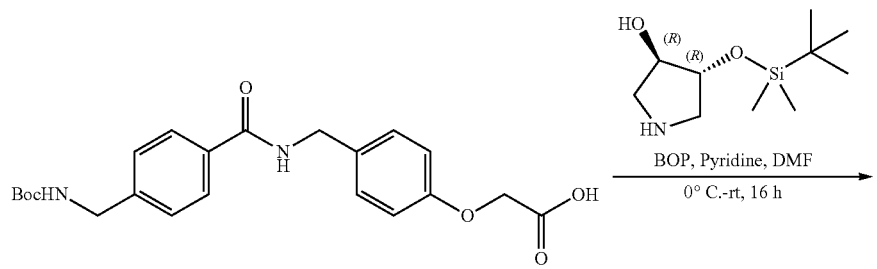

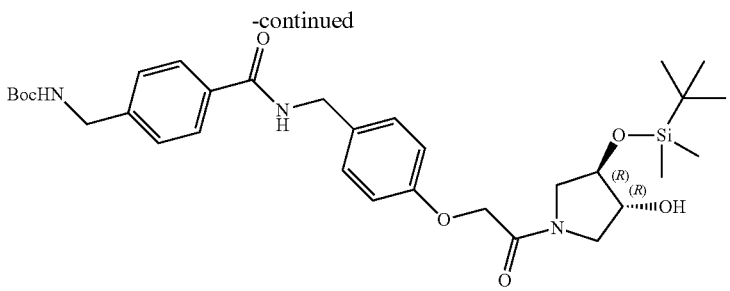

To a stirred solution of 2-(4-((4-(((tert-butoxy carbonyl)amino)methyl)benzamido)methyl)phenoxy)acetic acid (0.7 g, 1.69 mmol) in DMF (3 mL) was added pyridine (4 mL) and BOP (0.897 g, 2.02 mmol) at room temperature. The reaction mixture was cooled to 0° C. and stirred for 15 min. A solution of (3R,4R)-4-((tert-butyldimethylsilyl)oxy)pyrrolidin-3-ol (0.44 g, 2.0 mmol) in DMF (3 mL) was added to the reaction mixture slowly at 0° C. Then, the reaction mixture was allowed to warm to room temperature and stirred for 16 h. After completion of reaction (by TLC), the reaction mixture was diluted with cold water and extracted with EtOAc (2×50 mL). The combined organic phases were washed with saturated CuSO₄ solution (2×25 mL) and dried over Na₂SO₄. After filtration and evaporation of solvent, the crude material was purified by silica gel column chromatography to afford tert-butyl-4-(4-(2-((3R,4R)-3-(tert-butyldimethylsilyloxy)-4-hydroxypyrrolidin-1-yl)-2-oxoethoxy)benzyl carbamoyl)benzyl carbamate (0.45 g, 43.6%) as a white syrup.

Step-2: Synthesis of (R)-Tert-butyl-4-(4-(2-(3-(tert-butyldimethylsilyloxy)-4-oxopyrrolidin-1-yl)-2-oxoethoxy)benzylcarbamoyl)benzylcarbamate To a stirred solution of oxalyl chloride (0.07 mL, 0.78 mmol) in dry THF (5 mL) was added dimethyl sulfoxide (0.074 mL, 1.04 mmol) drop wise at −70° C. under inert atmosphere. After being stirred for 10 min at same temperature, a solution of tert-butyl-4-(4-(2-((3R,4R)-3-(tert-butyldimethylsilyloxy)-4-hydroxypyrrolidin-1-yl)-2-oxoethoxy)benzylcarbamoyl)benzylcarbamate (0.4 g, 0.65 mmol) in THF (5 mL) was added to the reaction mixture slowly at −70° C. After being stirred for 1 h at −70° C., triethyl amine (0.45 mL, 3.26 mmol) was added to the reaction mixture at −70° C. and stirred for additional 20 min. The reaction mixture was allowed to warm to room temperature and stirred for 15 min. After completion of reaction (by TLC), the reaction mixture was diluted with water and extracted with EtOAc (2×30 mL). The combined organic phases were dried over anhydrous Na₂SO₄, filtered, and concentrated under reduced pressure. The crude material was purified by silica gel column chromatography to afford (R)-tert-butyl-4-(4-(2-(3-(tert-butyldimethylsilyloxy)-4-oxopyrrolidin-1-yl)-2-oxoethoxy)benzylcarbamoyl)benzylcarbamate (0.25 g, 62.8%) as an off-white solid.

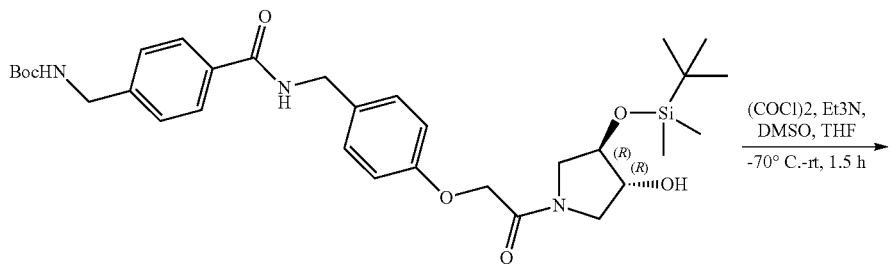

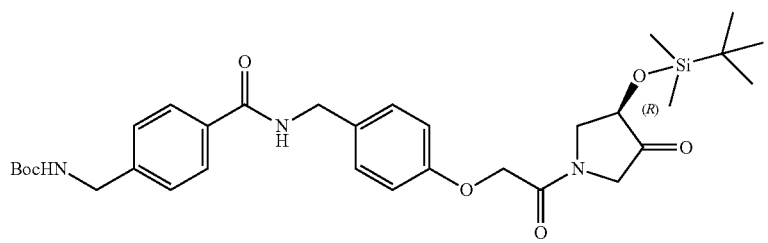

Step-3: Synthesis of (R)-4-(aminomethyl)-N-(4-(2-(3-hydroxy-4-oxopyrrolidin-1-yl)-2-oxo ethoxy)benzyl)benzamide

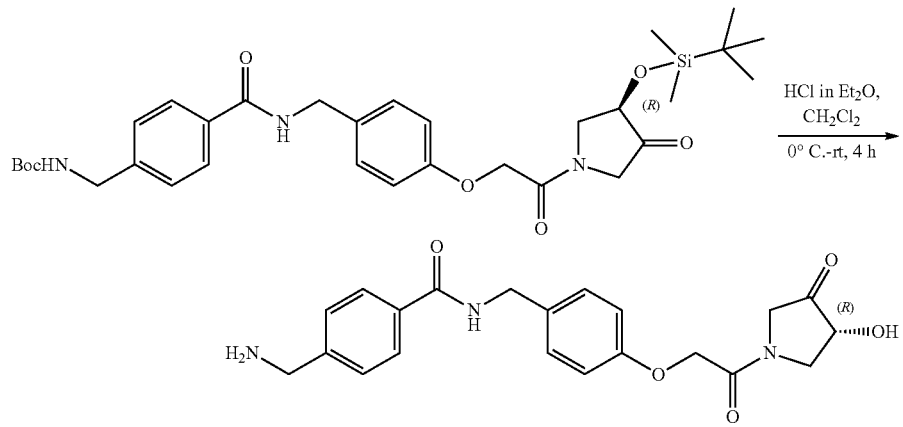

To a stirred solution of (R)-tert-butyl-4-(4-(2-(3-(tert-butyldimethyl silyloxy)-4-oxopyrrolidin-1-yl)-2-oxoethoxy)benzyl carbamoyl)benzylcarbamate (0.14 g, 0.23 mmol) in CH$_2$Cl$_2$ (8 mL) was added 2 N HCl in diethyl ether (2 mL) at 0° C. The resulting reaction mixture was stirred at 0° C. for 3 h and for 1 h at room temperature. After completion of reaction (by TLC), the volatiles were evaporated under reduced pressure and the residue was washed with EtOAc (4 mL) and diethyl ether (4 mL). The crude material was purified by preparative HPLC to afford (R)-4-(aminomethyl)-N-(4-(2-(3-hydroxy-4-oxopyrrolidin-1-yl)-2-oxo ethoxy)benzyl)benzamide (0.32 g, 35.2%) as a white solid.

$^1$H NMR (500 MHz, DMSO-d$_6$): δ 9.01 (bs, NH), 8.28 (bs, 2H), 7.92 (d, J=8.0 Hz, 2H), 7.53 (d, J=8.0 Hz, 2H), 7.23 (d, J=8.0 Hz, 2H), 6.87 (d, J=8.5 Hz, 2H), 6.07-5.92 (m, 1H), 4.41-4.13 (m, 8H), 3.73-3.62 (m, 1H), 3.46-3.23 (m, 2H), 2.73-2.20 (m, 2H).

LCMS: m/z [M+1]=398, 100%; [M+18]=416, 90% (226 nm, RT=9.82; purity 93.0%)
Mobile Phase A: 0.05% TFA in water, Mobile Phase B: Acetonitrile,
Flow rate: 1 ml/min; Temperature: Ambient,
Column: Primesep 200 (150×4.6 mm), 5u
Gradient: Time/% B 0.01/10, 3/10, 15/90, 25/90

Example 7—Synthesis of 4-(aminomethyl)-N-(4-(2-((3R,4R)-3,4-dihydroxypyrrolidin-1-yl)-2-oxoethoxy)benzyl)benzamide.HCl salt (SCN-MA9004-66)

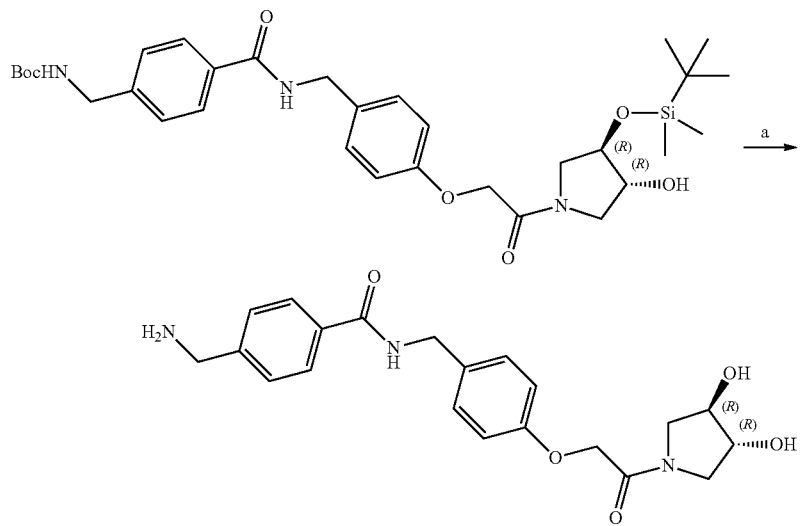

Reagents and Conditions:
a) 4N HCl in Et$_2$O, CH$_2$Cl$_2$, 0° C.-rt, 2 h.

To a stirred solution of tert-butyl 4-((4-(2-((3R,4R)-3-((tert-butyldimethylsilyl)oxy)-4-hydroxypyrrolidin-1-yl)-2-oxoethoxy)benzyl)carbamoyl)benzylcarbamate (80 mg, 0.13 mmol) in CH$_2$Cl$_2$ (2 mL) was added 4 N HCl in diethyl ether (0.4 mL) at 0° C. The resulting reaction mixture was stirred at room temperature for 2 h. After completion of reaction (by TLC), the volatiles were evaporated under reduced pressure and the residue was triturated with EtOAc (4 mL) and diethyl ether (4 mL) to afford 4-(aminomethyl)-N-(4-(2-((3R,4R)-3,4-dihydroxypyrrolidin-1-yl)-2-oxoethoxy)benzyl)benzamide. HCl salt (15 mg) as a white solid.

$^1$H NMR (500 MHz, DMSO-d$_6$): δ 9.08 (t, J=6.0 Hz, 1H), 8.46 (bs, 2H), 7.95 (d, J=8.0 Hz, 2H), 7.60 (d, J=8.0 Hz, 2H), 7.27 (d, J=8.0 Hz, 2H), 6.91 (d, J=8.0 Hz, 2H), 5.79 (s, 2H), 4.70 (s, 2H), 4.44 (d, J=6.0 Hz, 2H), 4.13-4.10 (m, 2H), 4.03 (s, 1H), 3.94 (s, 1H), 3.70-3.67 (m, 1H), 3.46-3.31 (m, 4H).

LCMS: m/z [M+1]=400, 100%; [M+23]=422, 5% (226 nm, RT=9.2 min; purity 96.9%)

Mobile Phase A: 0.05% TFA in water, Mobile Phase B: Acetonitrile,
Flow rate: 1 ml/min; Temperature: Ambient,
Column: Primesep 200 (150×4.6 mm), 5u
Gradient: Time/% B 0.01/10, 3/10, 20/90, 30/90

Example 8—Synthesis of (S)-4-(amino methyl)-N-(4-(3-(3-hydroxy-4-oxopyrrolidin-1-yl)-3-oxopropoxy)benzyl)benzamide hydrochloride (SCN-MA9004-79)

Synthetic Scheme:

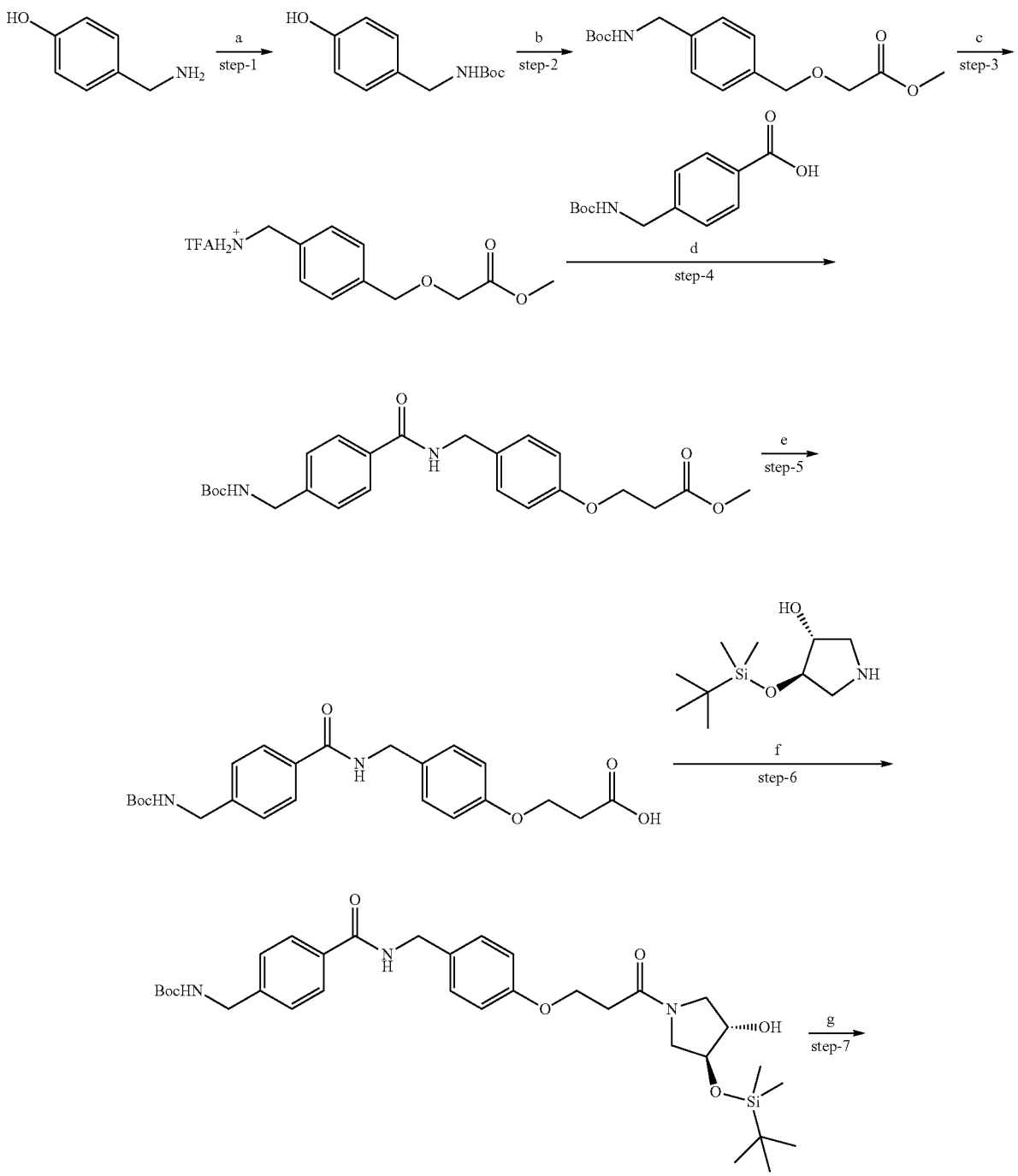

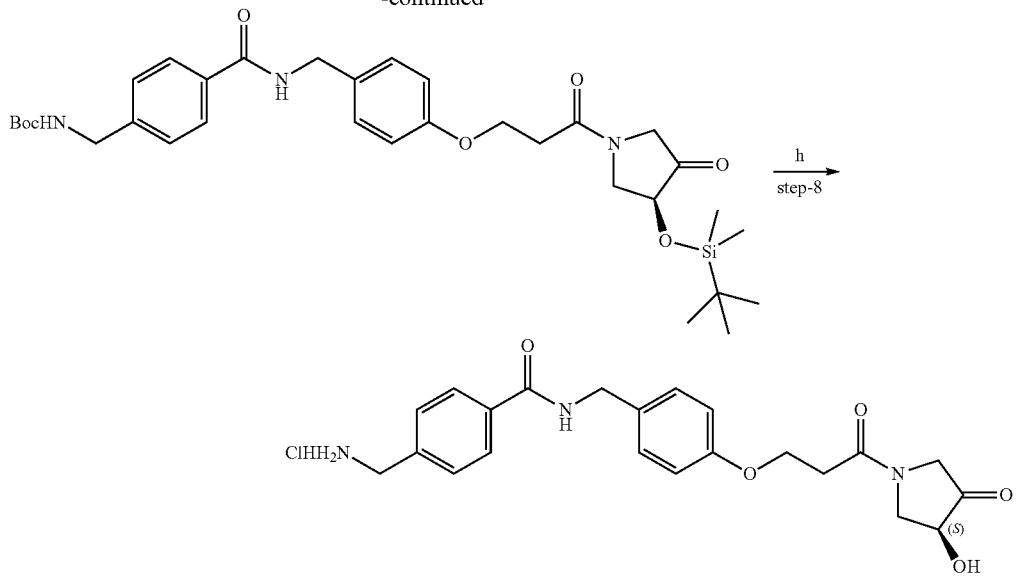

Reagents and Conditions:

a) (Boc)₂O, Et₃N, CH₂Cl₂, 0° C.-rt, 3 h; b) methylacrylate, Na, hydroquinone, reflux, 48 h; c) TFA, CH₂Cl₂, 0° C.-rt, 30 min; d) HATU, DIPEA, DMF, 0° C.-rt, 16 h; e) LiOH, THF, H₂O, 0° C.-rt, 2 h; f) BOP, Pyridine, DMF, 0° C.-rt, 16 h; g)

Oxalyl chloride, Et₃N, DMSO, dry THF, −70° C.-rt, 1.5 h; h) 4 N HCl in Et₂O, CH₂Cl₂, 0° C.-rt, 3 h.

Experimental Procedure

Step-1: Synthesis of Tert-butyl 4-hydroxybenzylcarbamate

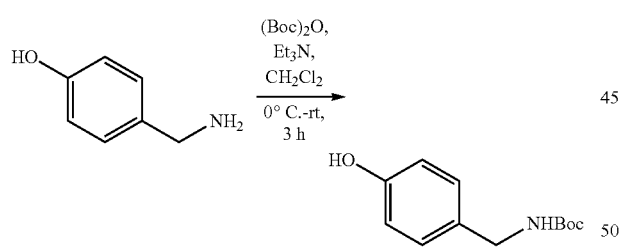

To a stirred solution of 4-(amino methyl)phenol (5 g, 40.60 mmol) in CH₂Cl₂ (100 mL) was added Et₃N (12.13 g, 120.0 mmol) followed by (Boc)₂O (10.58 g, 48.31 mmol) drop wise at 0° C. under inert atmosphere. The resulting reaction mixture was warmed up to room temperature and stirred for 3 h. After the consumption of starting material (by TLC), the reaction mixture was quenched with saturated citric acid solution and separated organic layer. The combined organic extracts were washed with water (2×100 mL) followed by brine solution (2×50 mL). The separated organic layer was dried over anhydrous Na₂SO₄, filtered and concentrated under reduced pressure. The obtained crude material was purified by silica gel column chromatography to afford Tert-butyl 4-hydroxybenzylcarbamate (6 g, 66%). TLC: 30% EtOAc/Hexane (Rf: 0.3)

Step-2: Synthesis of Methyl 3-(4-((tert-butoxycarbonylamino)methyl)phenoxy)propionate

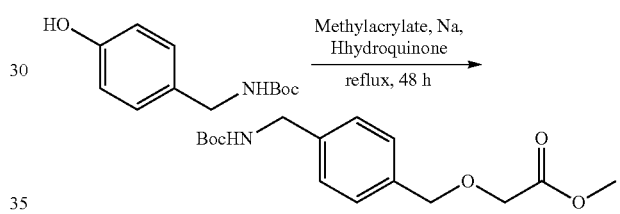

To a stirred solution of tert-butyl 4-hydroxybenzylcarbamate (5 g, 22.4 mmol) in methyl acrylate (80 mL) was added Na metal (0.15 g, 6.52 mmol) followed by hydroquinone (70 mg, 0.64 mmol) under nitrogen atmosphere and refluxed for 48 h. After completion of reaction (by TLC), the volatiles were evaporated under reduced pressure. The obtained crude material was purified by silica gel column chromatography to afford methyl 3-(4-((tert-butoxycarbonylamino)methyl)phenoxy)propionate (2 g, 29%). TLC: 30% EtOAc/Hexane (Rf: 0.4)

Step-3: Synthesis of Methyl 3-(4-(amino methyl)phenoxy)propionate

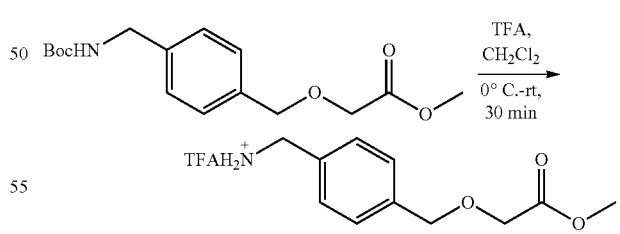

To a stirred solution of methyl 3-(4-((tert-butoxycarbonylamino)methyl)phenoxy)propionate (2.6 g) in CH₂Cl₂ (20 ml) was added TFA (2.6 mL) drop wise at 0° C. under inert atmosphere. The resulting reaction mixture was warmed up to room temperature and stirred for 20 minutes After completion of reaction (by TLC), the volatiles were evaporated under reduced pressure to afford methyl 3-(4-(amino methyl)phenoxy)propionate (2 g, crude). The crude material was taken to the next step without any further purification. TLC: 30% EtOAc/Hexane (Rf: 0.1)

Step-4: Synthesis of Methyl 3-(4-((4-((tert-butoxy-carbonylamino)methyl)benzamido) methyl)phenoxy)propionate

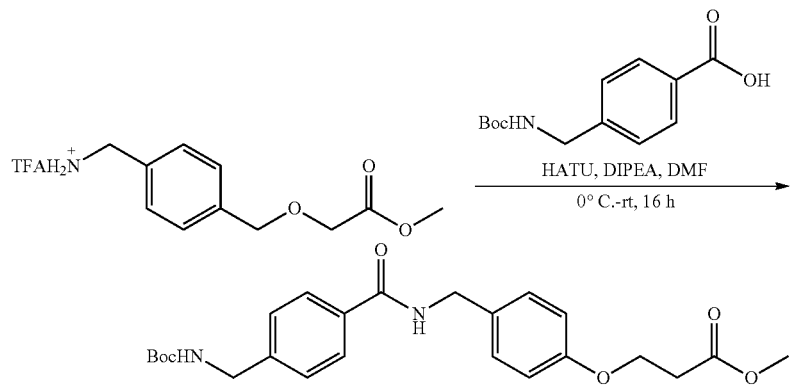

To a stirred solution of methyl 3-(4-(amino methyl)phenoxy)propionate (2 g, 6.6 mmol) in DMF (10 mL) were added DIPEA (3.23 mL, 18.0 mmol) and 4-((tert-butoxycarbonyl amino)methyl)benzoic acid (1.67 g, 6.6 mmol) followed by HATU (2.73 g, 7.2 mmol) at 0° C. under nitrogen atmosphere. The resulting reaction mixture was warmed up to room temperature and stirred for 16 h. After completion of reaction (by TLC), the reaction mixture was quenched with ice cold water and extracted with EtOAc (2×60 mL). The combined organic extracts were washed with water (2×50 mL) followed by brine solution (50 mL). The separated organic layer was dried over anhydrous $Na_2SO_4$, filtered, and concentrated under reduced pressure. The obtained crude material was purified by silica gel column chromatography to afford methyl 3-(4-((4-((tert-butoxycarbonylamino) methyl)benzamido) methyl)phenoxy)propionate (1.4 g, 72%).
TLC: 50% EtOAc/Hexane (Rf: 0.4)

Step-5: Synthesis of 3-(4-((4-((tert-butoxycarbonylamino)methyl)benzamido) methyl)phenoxy)propanoic acid

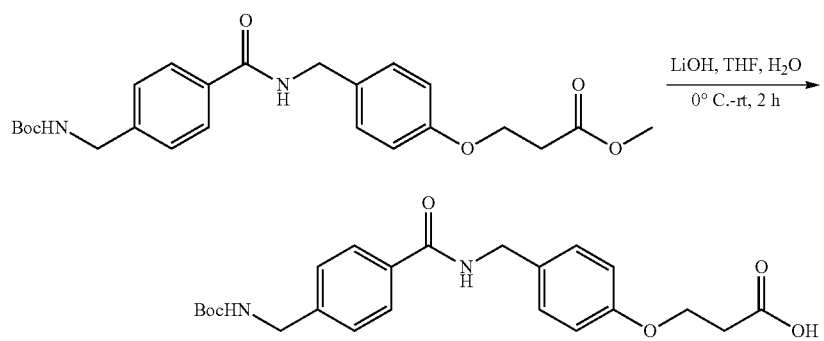

To a stirred solution of methyl 3-(4-((4-((tert-butoxycarbonylamino)methyl)benzamido) methyl)phenoxy)propionate (0.9 g, 1.97 mmol) in THF (10 mL) and $H_2O$ (5 mL) was added lithium hydroxide monohydrate (248 mg, 5.9 mmol) at 0° C. The resulting reaction mixture was warmed up to room temperature and stirred for 2 h. After completion of reaction (by TLC), the volatiles were evaporated under reduced pressure and the residue was neutralized with 1N HCl at 0° C. The precipitated solid was filtered, washed with 50% EtOAc/Hexane and dried under vacuum to afford 3-(4-((4-((tert-butoxycarbonylamino)methyl)benzamido) methyl)phenoxy)propanoic acid (0.75 g, 88%) as a white solid.
TLC: 10% MeOH/$CH_2Cl_2$ (Rf: 0.2)

Step-6: Synthesis of Tert-butyl 4-(4-(3-((3S,4S)-3-(tert-butyldimethylsilyloxy)-4-hydroxypyrrolidin-1-yl)-3-oxopropoxy)benzylcarbamoyl)benzylcarbamate

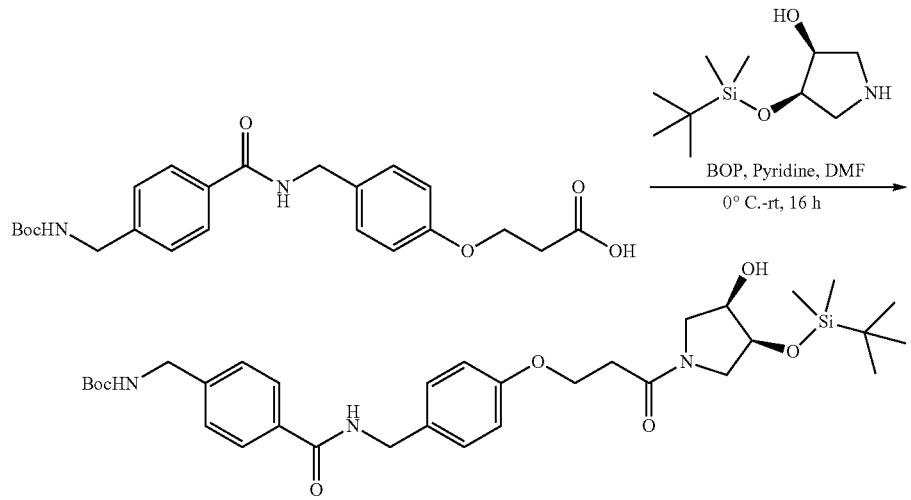

To a stirred solution of 3-(4-((4-((tert-butoxycarbonylamino)methyl)benzamido)methyl)phenoxy)propanoic acid (0.75 g, 1.7 mmol) in DMF (5 mL) was added pyridine (5 mL) and BOP (0.93 g, 2.1 mmol) at room temperature. The reaction mixture was cooled to 0° C. and stirred for 15 min. A solution of (3S,4S)-4-((tert-butyldimethylsilyl)oxy) pyrrolidin-3-ol (0.57 g, 2.6 mmol) in DMF (5 mL) was added to the reaction mixture slowly at 0° C. Then, the reaction mixture was allowed to warm to room temperature and stirred for 16 h. After completion of reaction (by TLC), the reaction mixture was quenched with saturated $CuSO_4$ solution and extracted with $Et_2O$ (2×50 mL). The combined organic phases were dried over $Na_2SO_4$. After filtration and evaporation of solvent, the crude material was purified by silica gel column chromatography to afford tert-butyl 4-(4-(3-((3S,4S)-3-(tert-butyldimethylsilyloxy)-4-hydroxypyrrolidin-1-yl)-3-oxopropoxy)benzylcarbamoyl)benzylcarbamate (0.40 g, 36%) as a white solid.

TLC: 10% $MeOH/CH_2Cl_2$ (2 runs) (Rf: 0.4)

Step-7: Synthesis of (S)-Tert-butyl 4-(4-(3-(3-(tert-butyldimethylsilyloxy)-4-oxopyrrolidin-1-yl)-3-oxopropoxy)benzylcarbamoyl)benzylcarbamate

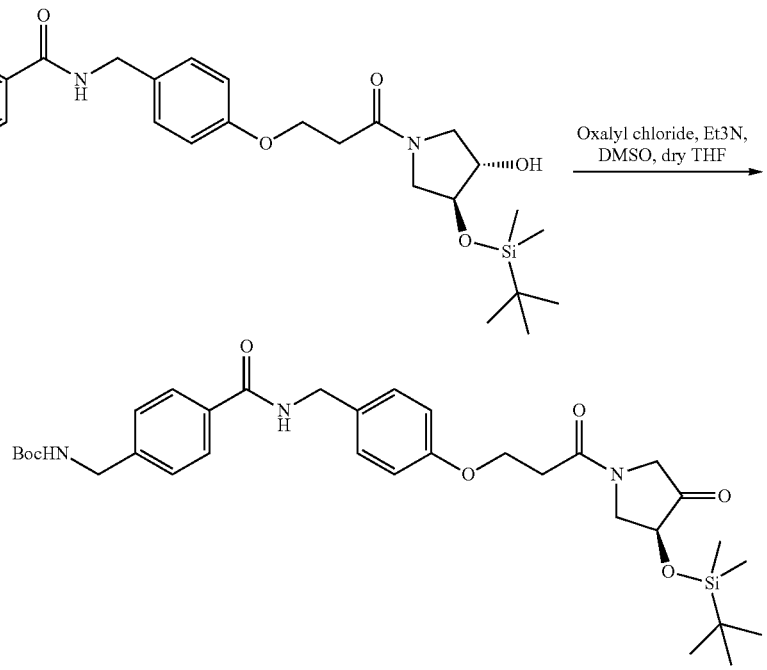

To a stirred solution of oxalyl chloride (0.06 mL, 0.56 mmol) in dry THF (4 mL) was added dimethyl sulfoxide (0.063 mL, 0.89 mmol) drop wise at −70° C. under inert atmosphere. After being stirred for 10 min at same temperature, a solution of tert-butyl 4-(4-(3-((3S,4S)-3-(tert-butyldimethylsilyloxy)-4-hydroxypyrrolidin-1-yl)-3-oxopropoxy)benzylcarbamoyl)benzylcarbamate (0.35 g, 0.56 mmol) in THF (3 mL) was added to the reaction mixture slowly at −70° C. After being stirred for 1 h at −70° C., Et$_3$N (0.34 mL, 2.7 mmol) was added to the reaction mixture at −70° C. and stirred for additional 20 min. The reaction mixture was allowed to warm to room temperature and stirred for 15 min. After completion of reaction (by TLC), the reaction mixture was diluted with water and extracted with EtOAc (2×30 mL). The combined organic phases were dried over anhydrous Na$_2$SO$_4$, filtered, and concentrated under reduced pressure. The crude material was purified by silica gel column chromatography to afford (S)-tert-butyl 4-(4-(3-(3-(tert-butyldimethylsilyloxy)-4-oxopyrrolidin-1-yl)-3-oxopropoxy)benzylcarbamoyl)benzylcarbamate (0.19 g, 54%) as an off-white solid.
TLC: 10% MeOH/CH$_2$Cl$_2$ (Rf: 0.5)

Step-8: Synthesis of (S)-4-(amino methyl)-N-(4-(3-(3-hydroxy-4-oxopyrrolidin-1-yl)-3-oxopropoxy)benzyl)benzamide hydrochloride

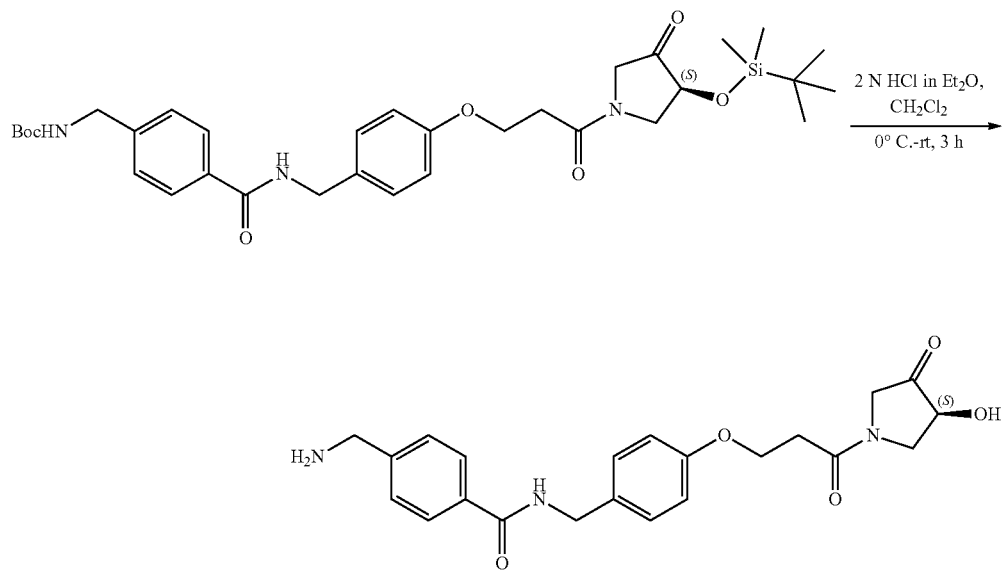

To a stirred solution of (S)-tert-butyl 4-(4-(3-(3-(tert-butyldimethylsilyloxy)-4-oxopyrrolidin-1-yl)-3-oxopropoxy)benzylcarbamoyl)benzylcarbamate (0.1 g, 0.16 mmol) in CH$_2$Cl$_2$ (3 mL) was added 4 N HCl in diethyl ether (0.5 mL) at 0° C. The resulting reaction mixture was warmed to room temperature and stirred for 3 h. After completion of reaction (by TLC), the volatiles were evaporated under reduced pressure and the residue was triturated with EtOAc (2 mL) and n-pentane (2 mL). The crude material was purified by preparative HPLC to afford (S)-4-(amino methyl)-N-(4-(3-(3-hydroxy-4-oxopyrrolidin-1-yl)-3-oxopropoxy)benzyl)benzamide hydrochloride (10 mg, 15%) as a white solid.
TLC: 10% MeOH/CH$_2$Cl$_2$ (Rf: 0.1)

$^1$H NMR (500 MHz, DMSO-d$_6$): δ 9.01 (bs, NH), 8.28 (bs, 2H), 7.92 (d, J=8.0 Hz, 2H), 7.53 (d, J=8.0 Hz, 2H), 7.23 (d, J=8.0 Hz, 2H), 6.87 (d, J=8.5 Hz, 2H), 6.07-5.92 (m, 1H), 4.41-4.13 (m, 8H), 3.73-3.62 (m, 1H), 3.46-3.23 (m, 2H), 2.73-2.20 (m, 2H).

LCMS: m/z [M+1]=412, 100% (226 nm, RT=10.48 min; purity 91.2%)

Mobile Phase A: 0.1% TFA in water, Mobile Phase B: Acetonitrile,

Flow rate: 1 ml/min; Temperature: Ambient,

Column: Primesep 200 (150×4.6 mm), 5u

Gradient: Time/% B 0.01/10, 3/10, 15/90, 25/90

Example 9—Synthesis of 4-(aminomethyl)-N-(4-(3-((3S,4S)-3,4-dihydroxypyrrolidin-1-yl)-3-oxo-propoxy)benzyl)benzamide.HCl Salt (SCN-MA9004-80)

Synthetic Scheme:

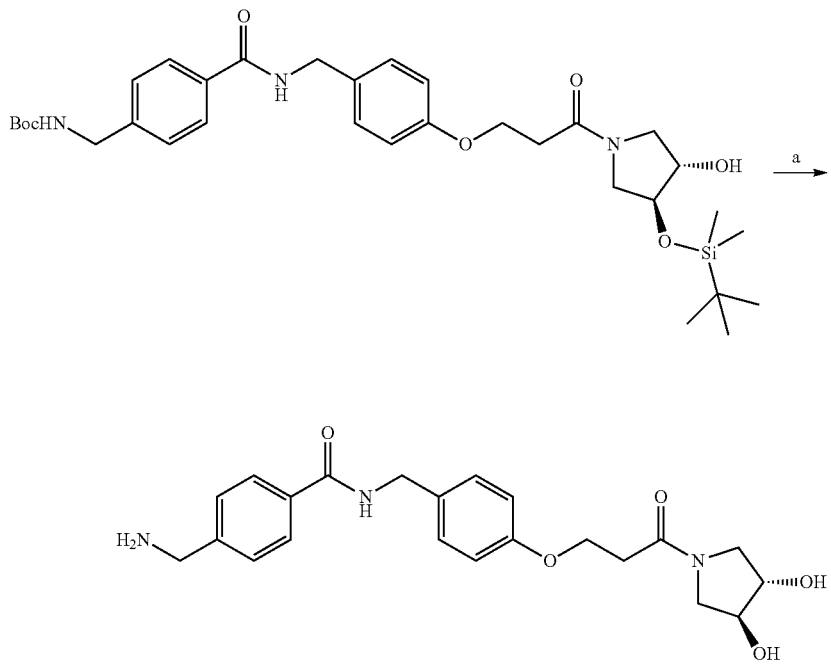

Reagents and Conditions:
a) 4 N HCl in Et$_2$O, CH$_2$Cl$_2$, 0° C.-rt, 2 h.

To a stirred solution of tert-butyl 4-(4-(3-((3S,4S)-3-(tert-butyldimethylsilyloxy)-4-hydroxypyrrolidin-1-yl)-3-oxo-propoxy)benzylcarbamoyl)benzylcarbamate (0.05 g, 0.079 mmol) in CH$_2$Cl$_2$ (2 mL) was added 2 N HCl in diethyl ether (0.3 mL) at 0° C. The resulting reaction mixture was warmed to room temperature and stirred for 2 h. After completion of reaction (by TLC), the volatiles were evaporated under reduced pressure and the residue was triturated with EtOAc (2 mL) and n-pentane (2 mL). The crude material was purified by preparative HPLC to afford 4-(aminomethyl)-N-(4-(3-((3S,4S)-3,4-dihydroxypyrrolidin-1-yl)-3-oxo-propoxy)benzyl)benzamide (15 mg) as a white solid.
TLC: 10% MeOH/CH$_2$Cl$_2$ (Rf: 0.05)
$^1$H NMR (500 MHz, DMSO-d$_6$): δ 9.03 (bs, NH), 8.17 (bs, 2H), 7.92 (d, J=8.5 Hz, 2H), 7.55 (d, J=8.5 Hz, 2H), 7.24 (d, J=8.5 Hz, 2H), 6.89 (d, J=8.5 Hz, 2H), 5.17 (s, 1H), 5.09 (s, 1H), 4.40 (d, J=3.0 Hz, 2H), 4.17 (t, J=6.0 Hz, 2H), 4.07 (s, 2H), 3.97 (s, 1H), 3.90 (s, 1H), 3.64-3.61 (m, 2H), 3.38-3.30 (m, 2H), 2.68 (t, J=6.0 Hz, 2H).
LCMS: m/z [M+1]=414, 100% [M+23]=436, 90% (226 nm, RT=10.78 min; purity 97.9%)
Mobile Phase A: 0.05% TFA in water, Mobile Phase B: Acetonitrile,
Flow rate: 1 ml/min; Temperature: Ambient,
Column: Primesep 200 (150×4.6 mm), 5u
Gradient: Time/% B 0.01/10, 3/10, 15/90, 25/90

Example 10—Synthesis of (R)-4-(amino methyl)-N-(4-(3-(3-hydroxy-4-oxopyrrolidin-1-yl)-3-oxo-propoxy)benzyl)benzamide hydrochloride (SCN-MA9004-86)

Synthetic Scheme:

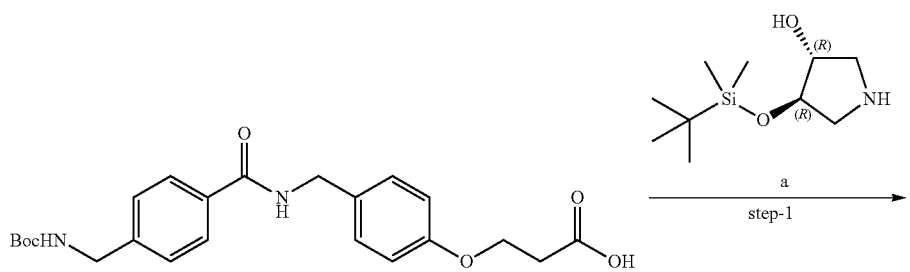

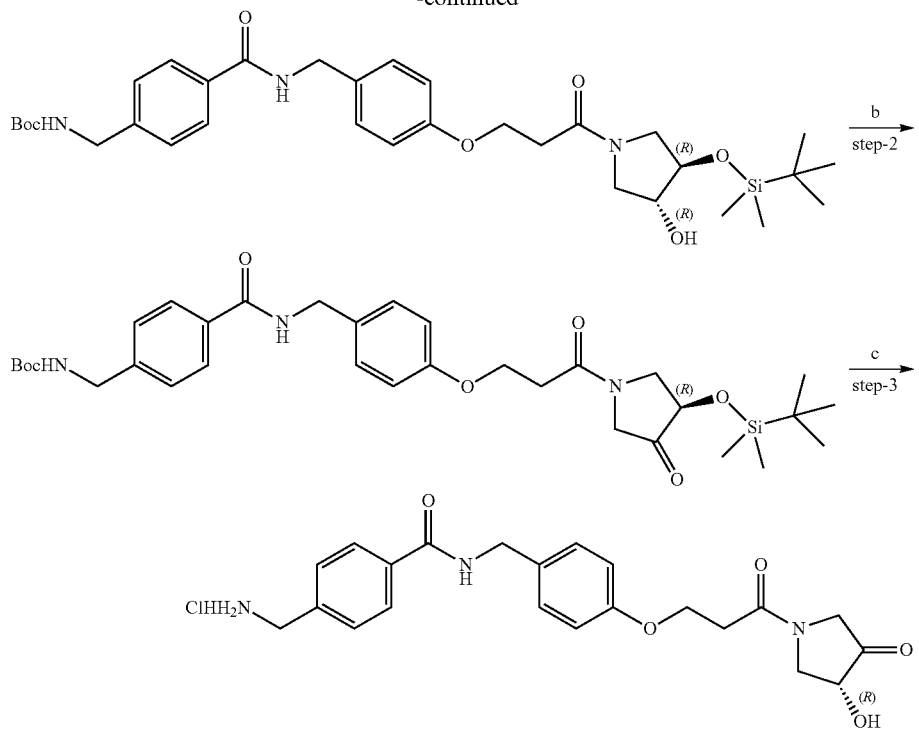

Reagents and Conditions:
a) BOP, Pyridine, DMF, 0° C.-rt, 16 h; b) Oxalyl chloride, Et₃N DMSO, dry THF, −70° C.-rt, 1.5 h; c) 4 N HCl in Et₂O, CH₂Cl₂, 0° C.-rt, 1 h.

Experimental Procedure

Step-1: Synthesis of Tert-butyl 4-(4-(3-((3R,4R)-3-(tert-butyldimethylsilyloxy)-4-hydroxypyrrolidin-1-yl)-3-oxopropoxy)benzylcarbamoyl)benzylcarbamate

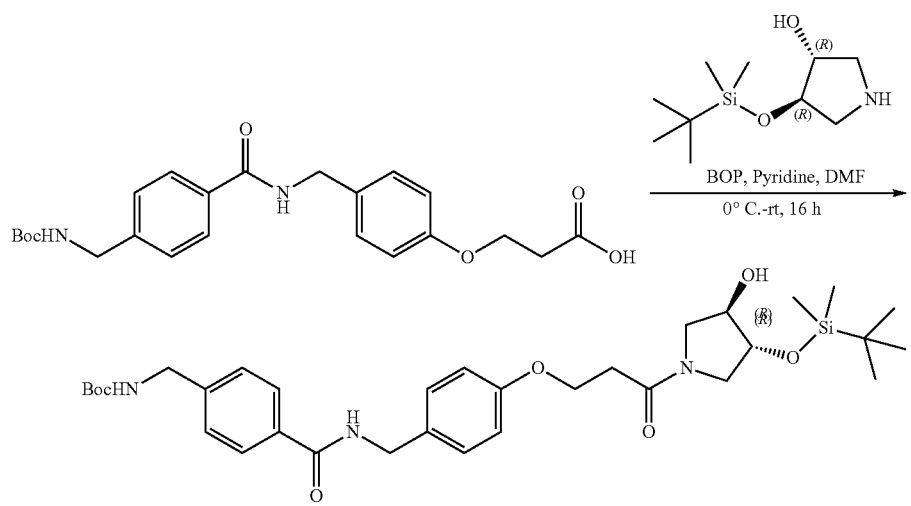

To a stirred solution of 3-(4-((4-((tert-butoxycarbonylamino)methyl)benzamido) methyl)phenoxy)propanoic acid (0.75 g, 1.7 mmol) in DMF (5 mL) was added pyridine (5 mL) and BOP (0.93 g, 2.1 mmol) at room temperature. The reaction mixture was cooled to 0° C. and stirred for 15 min. A solution of (3R,4R)-4-((tert-butyldimethylsilyl)oxy) pyrrolidin-3-ol (0.57 g, 2.6 mmol) in DMF (5 mL) was added to the reaction mixture slowly at 0° C. Then, the reaction mixture was allowed to warm to room temperature and stirred for 16 h. After completion of reaction (by TLC), the reaction mixture was quenched with saturated CuSO₄ solution and extracted with Et₂O (2×50 mL). The combined organic phases were dried over Na₂SO₄. After filtration and evaporation of solvent, the crude material was purified by silica gel column chromatography to afford tert-butyl 4-(4-(3-((3R,4R)-3-(tert-butyldimethylsilyloxy)-4-hydroxypyrrolidin-1-yl)-3-oxopropoxy)benzylcarbamoyl)benzylcarbamate (0.45 g, 40.9%) as an off-white solid.
TLC: 10% MeOH/CH₂Cl₂ (2 runs) (Rf: 0.4)

Step-2: Synthesis of (R)-Tert-butyl 4-(4-(3-(3-(tert-butyldimethylsilyloxy)-4-oxopyrrolidin-1-yl)-3-oxopropoxy)benzylcarbamoyl)benzylcarbamate

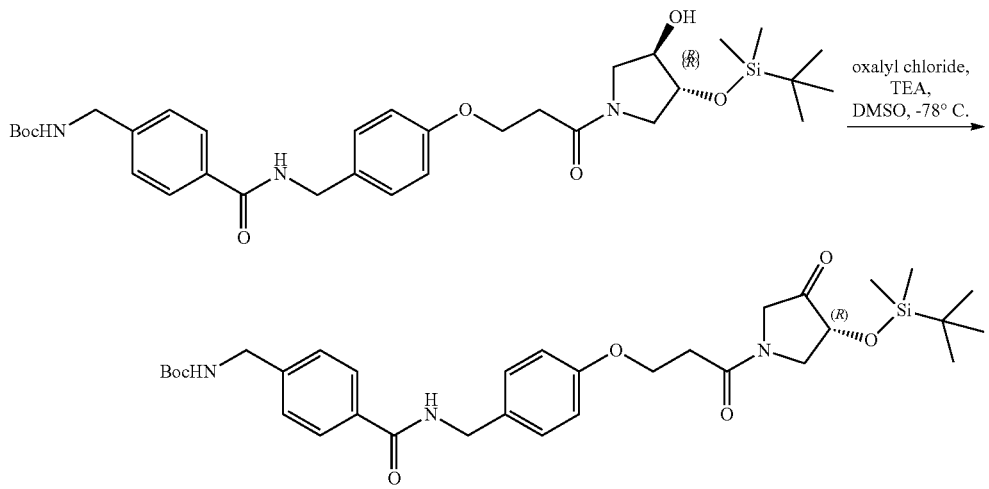

To a stirred solution of oxalyl chloride (0.06 mL, 0.56 mmol) in dry THF (4 mL) was added dimethyl sulfoxide (0.063 mL, 0.89 mmol) drop wise at −70° C. under inert atmosphere. After being stirred for 10 min at same temperature, a solution of tert-butyl 4-(4-(3-((3R,4R)-3-(tert-butyldimethylsilyloxy)-4-hydroxypyrrolidin-1-yl)-3-oxopropoxy)benzylcarbamoyl)benzylcarbamate (0.35 g, 0.56 mmol) in THF (3 mL) was added to the reaction mixture slowly at −70° C. After being stirred for 1 h at −70° C., Et₃N (0.34 mL, 2.7 mmol) was added to the reaction mixture at −70° C. and stirred for additional 20 min. The reaction mixture was allowed to warm to room temperature and stirred for 15 min. After completion of reaction (by TLC), the reaction mixture was diluted with water and extracted with EtOAc (2×30 mL). The combined organic phases were dried over anhydrous Na₂SO₄, filtered, and concentrated under reduced pressure. The crude material was purified by silica gel column chromatography to afford (R)-tert-butyl 4-(4-(3-(3-(tert-butyldimethylsilyloxy)-4-oxopyrrolidin-1-yl)-3-oxopropoxy)benzylcarbamoyl)benzylcarbamate (0.20 g, 57.3%) as an off-white solid.
TLC: 10% MeOH/CH₂Cl₂ (Rf: 0.55)

Step-3: Synthesis of (R)-4-(amino methyl)-N-(4-(3-(3-hydroxy-4-oxopyrrolidin-1-yl)-3-oxopropoxy)benzyl)benzamide hydrochloride

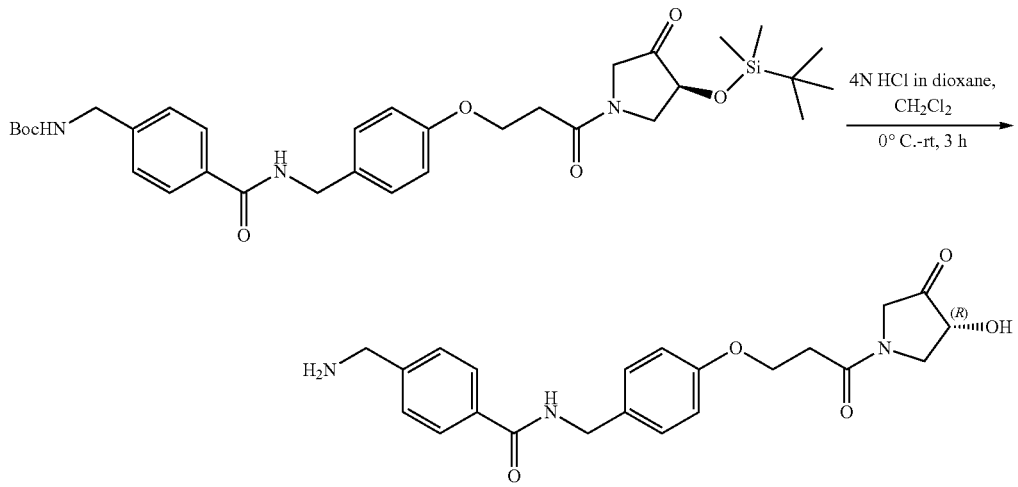

To a stirred solution of (R)-tert-butyl 4-(4-(3-(3-(tert-butyldimethylsilyloxy)-4-oxopyrrolidin-1-yl)-3-oxopropoxy)benzylcarbamoyl)benzylcarbamate (0.1 g, 0.16 mmol) in CH₂Cl₂ (3 mL) was added 4 N HCl in dioxane (0.5 mL) at 0° C. The resulting reaction mixture was warmed to room temperature and stirred for 1 h. After completion of reaction (by TLC), the volatiles were evaporated under reduced pressure and the residue was triturated with EtOAc (2 mL) and Et₂O (2 mL). The crude material was purified by preparative HPLC to afford (R)-4-(amino methyl)-N-(4-(3-

(3-hydroxy-4-oxopyrrolidin-1-yl)-3-oxopropoxy)benzyl) benzamide hydrochloride (15 mg) as a white solid.
TLC: 10% MeOH/CH$_2$Cl$_2$ (Rf: 0.05)
$^1$H NMR (500 MHz, DMSO-d$_6$): δ 9.01 (bs, NH), 8.28 (bs, 2H), 7.92 (d, J=8.0 Hz, 2H), 7.53 (d, J=8.0 Hz, 2H), 7.23 (d, J=8.0 Hz, 2H), 6.87 (d, J=8.5 Hz, 2H), 6.07-5.92 (m, 1H), 4.41-4.13 (m, 8H), 3.73-3.62 (m, 1H), 3.46-3.23 (m, 2H), 2.73-2.20 (m, 2H).
LCMS: m/z [M+1]=412, 100% [M+18]=430, 25% (226 nm, RT=10.25 min; purity 97.3%)
Mobile Phase A: 0.01% TFA in water, Mobile Phase B: Acetonitrile,
Flow rate: 1 ml/min; Temperature: Ambient,
Column: Primesep 200 (150×4.6 mm), 5u
Gradient: Time/% B 0.01/10, 3/10, 15/90, 25/90

Example 11—Synthesis of 4-(aminomethyl)-N-(4-(3-((3R,4R)-3,4-dihydroxypyrrolidin-1-yl)-3-oxo-propoxy)benzyl)benzamide (SCN-MA9004-087)

Synthetic Scheme:

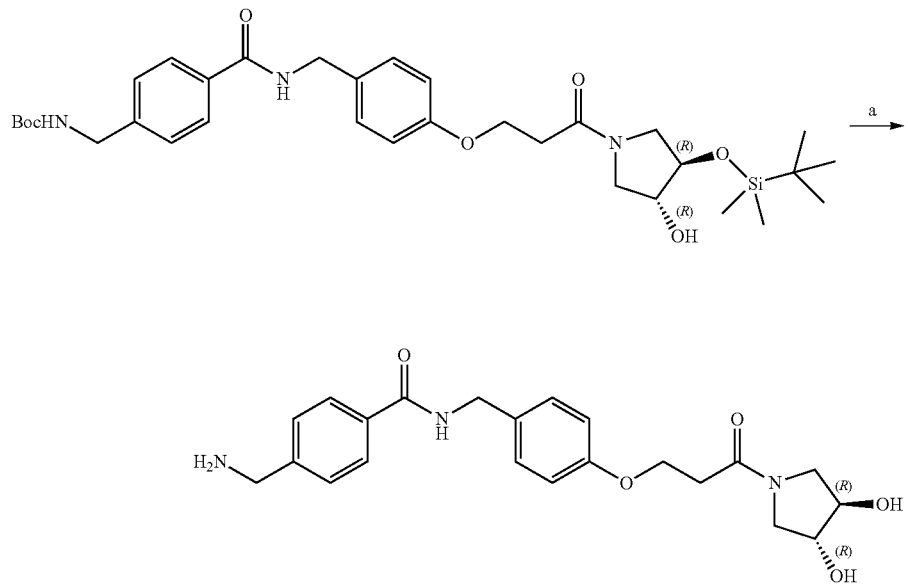

Reagents and Conditions:

a) 4 N HCl in 1,4-dioxane, 1,4-dioxane, 0° C.-rt, 1 h. To a stirred solution of tert-butyl 4-(4-(3-((3R,4R)-3-(tert-butyldimethylsilyloxy)-4-hydroxypyrrolidin-1-yl)-3-oxo-propoxy)benzylcarbamoyl)benzylcarbamate (0.08 g, 0.12 mmol) in 1,4-dioxane (3 mL) was added 4N HCl in 1,4-dioxane (0.54 mL) at 0° C. The resulting reaction mixture was warmed to room temperature and stirred for 1 h. After completion of reaction (by TLC), the volatiles were evaporated under reduced pressure and the residue was triturated with EtOAc (2 mL) and Et$_2$O (2 mL). The crude material was purified by preparative HPLC to afford 4-(aminomethyl)-N-(4-(3-((3R,4R)-3,4-dihydroxypyrrolidin-1-yl)-3-oxopropoxy)benzyl)benzamide (40 mg) as a pale-green solid.
TLC: 10% MeOH/CH$_2$Cl$_2$ (Rf: 0.05)

$^1$H NMR (500 MHz, DMSO-d$_6$): δ 9.03 (bs, NH), 8.17 (bs, 2H), 7.92 (d, J=8.5 Hz, 2H), 7.55 (d, J=8.5 Hz, 2H), 7.24 (d, J=8.5 Hz, 2H), 6.89 (d, J=8.5 Hz, 2H), 4.40 (d, J=3.0 Hz, 2H), 4.17 (t, J=6.0 Hz, 2H), 4.07 (s, 2H), 3.97 (s, 1H), 3.90 (s, 1H), 3.64-3.61 (m, 2H), 3.38-3.30 (m, 2H), 2.68 (t, J=6.0 Hz, 2H).

LCMS: m/z [M+1]=414, 100% [M+23]=436, 10% (226 nm, RT=9.57 min; purity 91.5%)

Mobile Phase A: 0.1% TFA in water, Mobile Phase B: Acetonitrile,
Flow rate: 1 ml/min; Temperature: Ambient,
Column: Primesep 200 (150×4.6 mm), 5u
Gradient: Time/% B 0.01/10, 3/10, 15/90, 25/90

Example 12—Synthesis of N-{[4-(aminomethyl)phenyl]methyl}-4-[2-(2,3-Dihydroxypropanamido)acetyl]piperazine-1-carboxamide (SCN-MA9005-083)
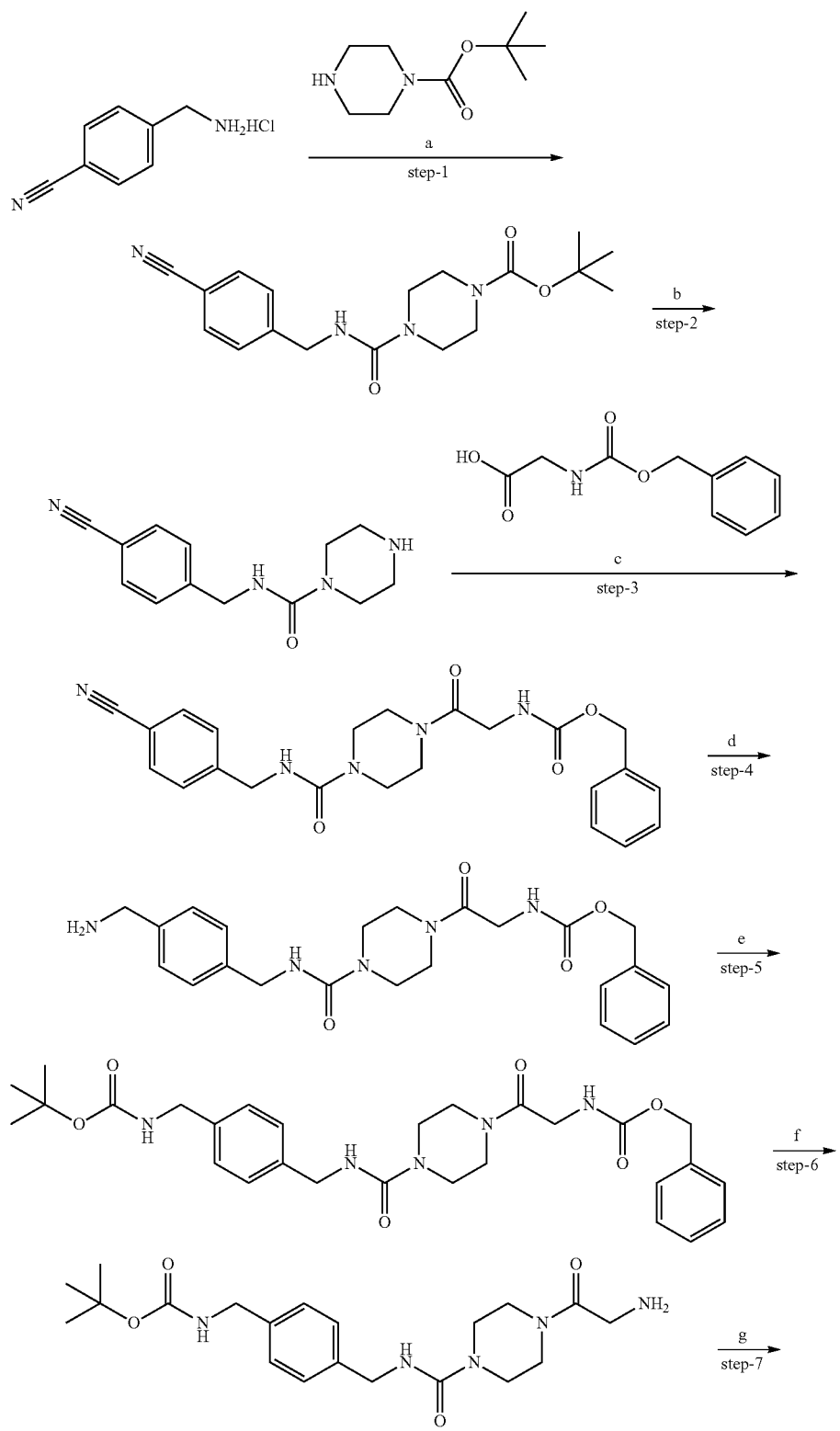

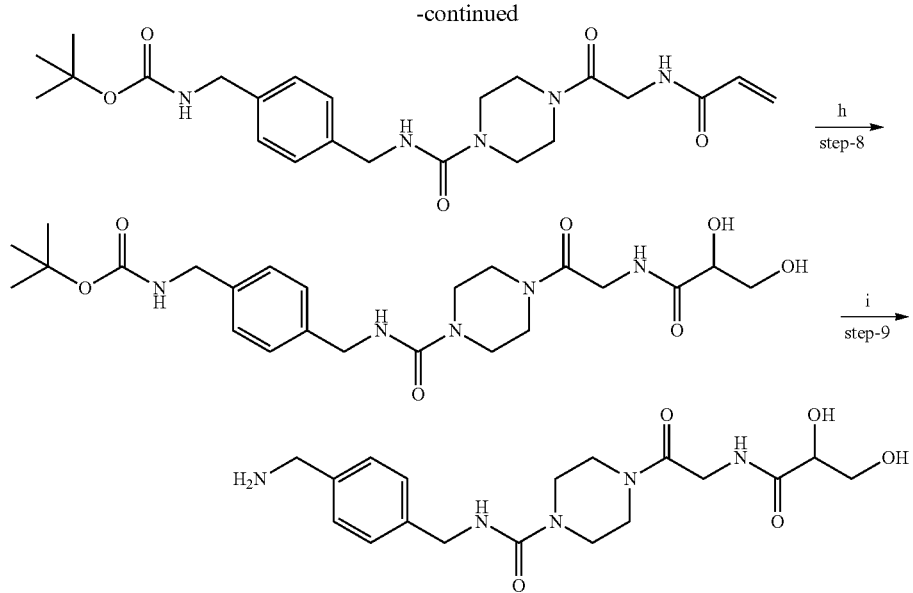

Reagents and Conditions:

a) triphosgene, Et$_3$N, CH$_3$CN, CH$_2$Cl$_2$, THF, −5° C.-rt, 13 h; b) TFA, CH$_2$Cl$_2$, 0° C.-rt, 4 h; c) BOP, pyridine, DMF, rt, 12 h; d) Raney Ni, MeOH, H$_2$ (Balloon pressure), rt, 12 h; e) (Boc)$_2$, TEA, CH$_2$Cl$_2$, 0° C.-rt, 12 h; f) Pd/C, MeOH, H$_2$ (Balloon pressure), rt, 3 h; g) Acryloyl chloride, Et$_3$N, CH$_2$Cl$_2$, 0° C.-rt, 12 h; h) OsO$_4$, NMO, Acetone, H$_2$O, rt, 3 h; i) 3N HCl-Et$_2$O, CH$_2$Cl$_2$, 0° C.-rt, 30 min.

Experimental Procedure

Step-1: Synthesis of Tert-butyl 4-(4-cyanobenzylcarbamoyl)piperazine-1-carboxylate

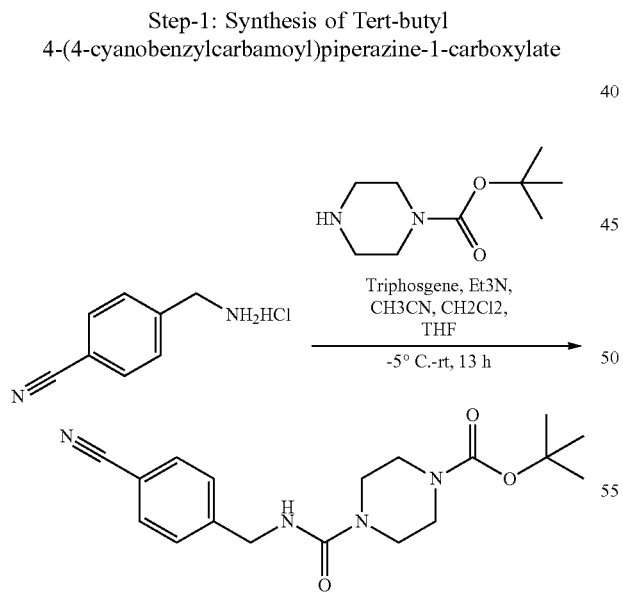

To a stirred solution of triphosgene (5.28 g, 17.8 mmol) in acetonitrile (75 mL) was added 4-(aminomethyl)benzonitrile hydrochloride (5.0 g, 29.6 mmol) in acetonitrile (200 mL) followed by Et$_3$N (8.26 mL, 59.3 mmol) at −5° C. After being stirred for 30 min, a solution of tert-butyl piperazine-1-carboxylate (5.52 g, 29.6 mmol) in CH$_2$Cl$_2$ (150 mL) was added at −5° C. and stirred for 20 min. Then TEA (8.26 mL, 59.3 mmol) was added at −5° C. and stirred for additional 20 min at −5° C. Then the reaction mixture was warmed up to room temperature and stirred for 12 h. After completion of reaction (by TLC), the volatiles were evaporated under reduced pressure and the residue was washed with 10% EtOAc/n-Hexane (50 mL) and dried to afford tert-butyl 4-{[(4-cyanophenyl)methyl]carbamoyl}piperazine-1-carboxylate (6.0 g, 58%) as a white solid.

Step-2: Synthesis of N-(4-Cyanobenzyl)piperazine-1-carboxamide

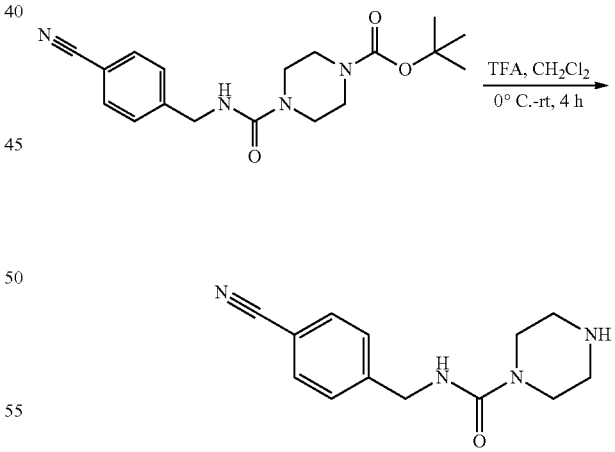

To a stirred solution of tert-butyl 4-{[(4-cyanophenyl)methyl]carbamoyl}piperazine-1-carboxylate (3.0 g, 8.72 mmol) in CH$_2$Cl$_2$ (10 mL) was added TFA (5 mL) at 0° C. The resulting reaction mixture was warmed up to room temperature and stirred for 4 h. After completion of reaction (by TLC), the volatiles were evaporated under reduced pressure and the residue was washed with Et$_2$O (2×10 mL) to afford N-(4-Cyanobenzyl)piperazine-1-carboxamide (2.0 g, 94%).

Step-3: Synthesis of Benzyl 2-(4-(4-cyanobenzyl-carbamoyl)piperazin-1-yl)-2-oxoethylcarbamate

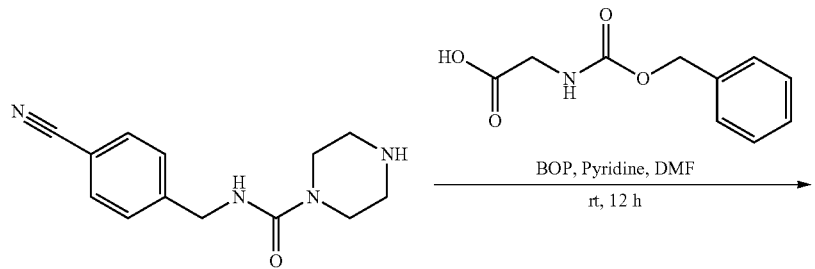

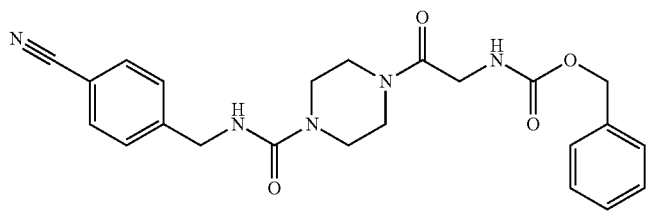

To a stirred solution of 2-{[(benzyloxy)carbonyl]amino}acetic acid (2.62 g, 12.6 mmol) and pyridine (5 mL) in DMF (10 mL) was added BOP (8.55 g, 19.3 mmol) at room temperature. After being stirred for 30 min, N-(4-cyanobenzyl)piperazine-1-carboxamide (2.36 g, 9.7 mmol) in pyridine (5 mL) was added to the reaction mixture slowly at room temperature. The resulting reaction mixture was stirred for 12 h at room temperature. After completion of reaction (by TLC), saturated CuSO₄ solution (50 mL) was added to the reaction mixture and extracted with EtOAc (2×100 mL). The organic phase was washed with water (2×50 mL), dried over anhydrous Na₂SO₄, filtered, and concentrated under reduced pressure. The crude material was purified over silica gel column chromatography to afford benzyl 2-(4-(4-cyanobenzylcarbamoyl)piperazin-1-yl)-2-oxoethylcarbamate (3.02 g, 71.9%) as a white solid.

Step-4: Synthesis of Benzyl 2-(4-(4-(aminomethyl)benzylcarbamoyl)piperazin-1-yl)-2-oxoethylcarbamate

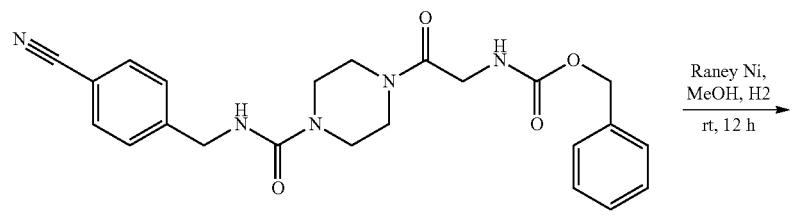

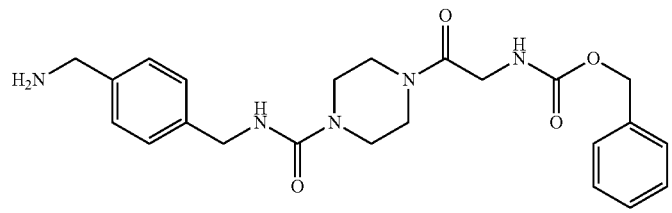

To a stirred solution of Benzyl 2-(4-(4-cyanobenzylcarbamoyl)piperazin-1-yl)-2-oxoethylcarbamate (3.0 g, 6.89 mmol) in CH₃OH (60 mL) was added Raney Ni (0.5 g) at room temperature. The resulting reaction mixture was agitated under H₂ (balloon pressure) for 12 h at room temperature. After completion of reaction (by TLC), the reaction mixture was filtered through celite pad and filtrate was concentrated under reduced pressure. The residue was washed with Et₂O (2×20 mL) to afford Benzyl 2-(4-(4-(aminomethyl)benzylcarbamoyl)piperazin-1-yl)-2-oxoethylcarbamate (2.5 g. 82.7%) as a white solid.

Step-5: Synthesis of Benzyl N-{2-[4-({[4-({[(tert-butoxy)carbonyl]amino}methyl)phenyl]methyl}carbamoyl)piperazin-1-yl]-2-oxoethyl}carbamate

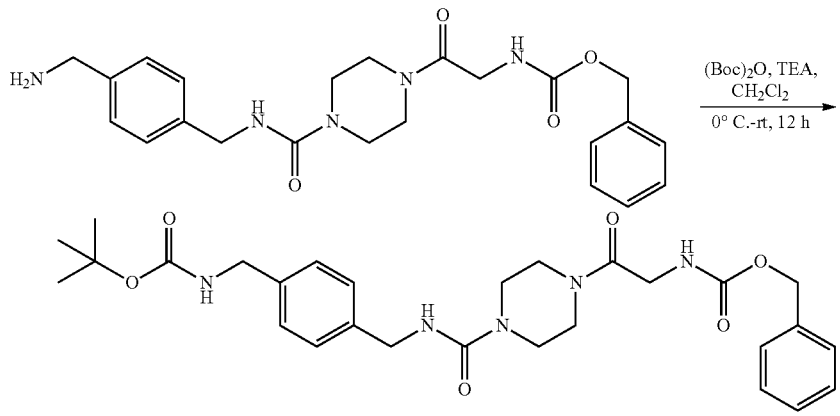

To a stirred solution of benzyl 2-(4-(4-(aminomethyl)benzylcarbamoyl)piperazin-1-yl)-2-oxoethylcarbamate (2.5 g, 5.69 mmol) in CH₂Cl₂ (25 mL) were added Et₃N (1.58 mL, 11.4 mmol) and Boc anhydride (1.56 mL, 6.83 mmol) at 0° C. The resulting reaction mixture was warmed up to room temperature and stirred for 12 h. After completion of reaction (by TLC), the reaction mixture was diluted with CH₂Cl₂ (25 mL) and washed with water (40 mL). The organic phase was separated, dried over anhydrous Na₂SO₄, filtered and concentrated under reduced pressure. The crude material was purified over silica gel column chromatography to afford Benzyl N-{2-[4-({[4-({[(tert-butoxy)carbonyl]amino}methyl)phenyl]methyl}carbamoyl)piperazin-1-yl]-2-oxoethyl}carbamate (1.05 g, 34.3%) as a white solid.

Step-6: Synthesis of Tert-butyl 4-((4-(2-aminoacetyl)piperazine-1-carboxamido) methyl)benzylcarbamate

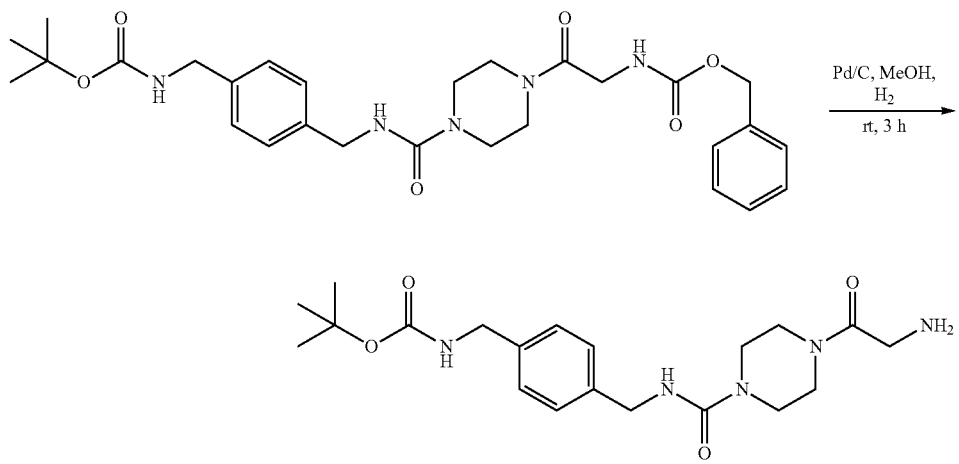

To a stirred solution of benzyl N-{2-[4-({[4-({[(tert-butoxy)carbonyl]amino}methyl)-phenyl]methyl}carbamoyl)piperazin-1-yl]-2-oxoethyl}carbamate (1.2 g, 2.85 mmol) in CH$_3$OH (20 mL) was added Pd/C (0.3 g) at room temperature under nitrogen atmosphere. The resulting reaction mixture was then stirred under H$_2$ (balloon pressure) for 3 h at room temperature. After completion of reaction (by TLC), the reaction mixture was filtered through celite pad and the filtrate was concentrated under reduced pressure to afford yellow solid residue. The crude residue was triturated with Et$_2$O (10 mL) to afford tert-butyl 4-((4-(2-aminoacetyl)piperazine-1-carboxamido) methyl)benzylcarbamate (0.77 g, 83%) as a white solid.

Step-7: Synthesis of Tert-butyl 4-((4-(2-acrylamidoacetyl)piperazine-1-carboxamido) methyl)benzylcarbamate

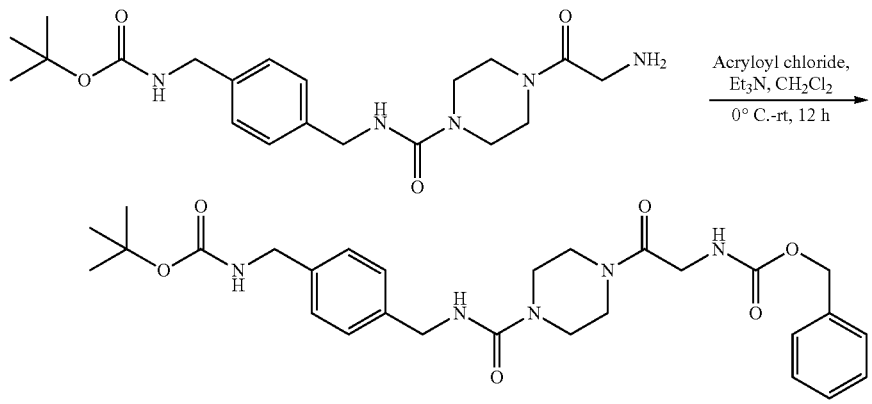

To a stirred solution of tert-butyl 4-((4-(2-aminoacetyl) piperazine-1-carboxamido) methyl)benzylcarbamate (0.77 g, 1.9 mmol) in CH$_2$Cl$_2$ (20 mL) was added Et$_3$N (0.4 mL, 2.85 mmol) followed by the drop wise addition of acryloyl chloride (0.2 mL, 2.47 mmol) at 0° C. The resulting reaction mixture was warmed up to room temperature and stirred for 12 h. After completion of reaction (by TLC), the reaction mixture was partitioned between CH$_2$Cl$_2$ (50 mL) and H$_2$O (10 mL). The organic phase was separated, dried over anhydrous Na$_2$SO$_4$, filtered, and concentrated under reduced pressure to afford tert-butyl 4-((4-(2-acrylamidoacetyl)piperazine-1-carboxamido)methyl)benzylcarbamate (0.75 g, 86%) as a white solid.

Step-8: Synthesis of Tert-butyl-4-((4-(2-(2,3-dihydroxypropanamido)acetyl)-piperazine-1-carboxamido)methyl)benzylcarbamate

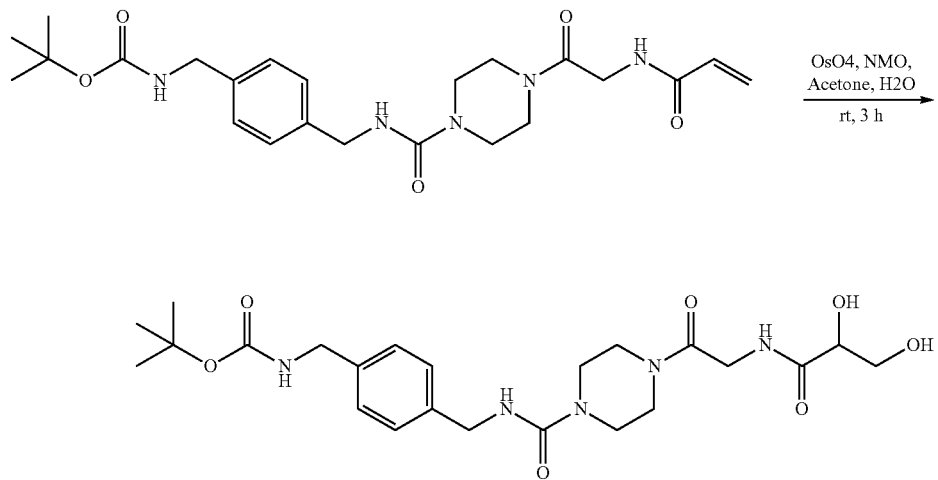

To a stirred solution of tert-butyl 4-((4-(2-acrylamido-acetyl)piperazine-1-carboxamido)methyl)benzylcarbamate (0.75 g, 1.63 mmol) in acetone (7.5 mL) and H$_2$O (4 mL) was added 0.1M OsO$_4$ solution (0.083 g in 3 mL, 0.32 mmol) drop wisely at room temperature. After being stirred for 10 min, NMO (0.67 g, 5.72 mmol) was added at room temperature and stirred for 3 h. After completion of reaction (by TLC), 10% Na$_2$SO$_3$ solution (10 mL) was added to the reaction mixture at room temperature and stirred for additional 20 min. Then, the reaction mixture was extracted with EtOAc (10 mL) and 10% CH$_3$OH/CH$_2$Cl$_2$ (10 mL). The organic phase was separated, dried over anhydrous Na$_2$SO$_4$, filtered, and concentrated under reduced pressure to afford crude as yellowish solid. The crude residue was washed with Et$_2$O (8 mL) to afford tert-butyl-4-((4-(2-(2,3-dihydroxypropanamido)acetyl)piperazine-1-carboxamido)methyl)benzylcarbamate (0.65 g, 81%) as yellowish solid.

Step-9: Synthesis of N-(4-(aminomethyl)benzyl)-4-(2-(2,3-dihydroxypropanamido)acetyl)piperazine-1-carboxamide

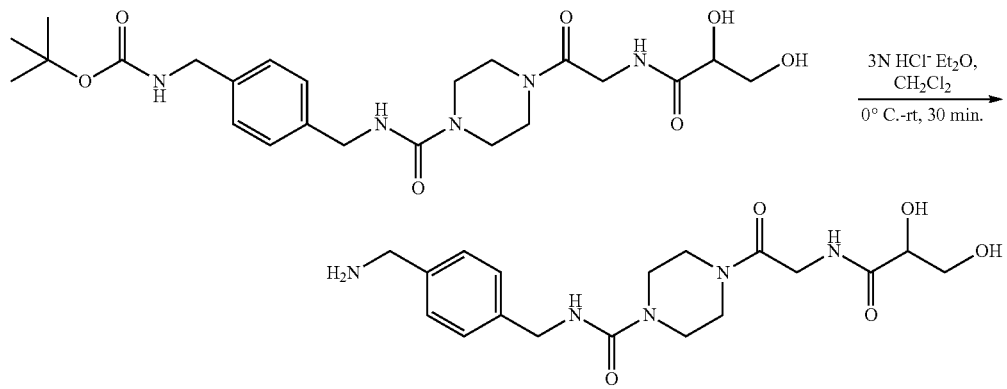

To a stirred solution of tert-butyl-4-((4-(2-(2,3-dihydroxypropanamido)acetyl)piperazine-1-carboxamido)methyl)benzylcarbamate (0.08 g, 0.16 mmol) in CH$_2$Cl$_2$ (3 mL) was added 3 N HCl in Et$_2$O (0.5 mL) at 0° C. The resulting reaction mixture was warmed up to room temperature stirred for 30 min. The precipitated solid was filtered; the crude solid was dissolved in CH$_3$OH (5 mL) and concentrated under reduced pressure. The residue was washed with Et$_2$O (3 mL) to afford crude compound as a brownish solid. The crude material was purified over preparative HPLC to afford N-(4-(aminomethyl)benzyl)-4-(2-(2,3-dihydroxypropanamido) acetyl)piperazine-1-carboxamide (0.02 g, 31.7%) as a white solid.

$^1$H NMR (500 MHz, DMSO-d$_6$): δ 8.05 (bs, 2H), 7.77 (t, J=5.0 Hz, 1H), 7.36 (d, J=8.5 Hz, 2H), 7.29 (d, J=8.5 Hz, 2H), 7.20 (t, J=6.0 Hz, 1H), 5.69 (d, J=5.5 Hz, 1H), 4.67 (t, J=6.0 Hz, 2H), 4.23 (d, J=5.5 Hz, 2H), 3.93-3.90 (m, 4H), 3.48-3.45 (m, 8H).

LCMS: m/z [M+1]=394, 100% (210 nm, RT=5.68 min; purity 90.7%)
Mobile Phase A: 0.1% TFA in water, Mobile Phase B: Acetonitrile,
Flow rate: 1 ml/min; Temperature: Ambient,
Column: Primesep 200 (150×4.6 mm), 5u
Gradient: Time/% B 0.01/10, 3/10, 15/90, 25/90

Examples 13-24

Synthesis of Sparsomycin Analogues

Synthesis of 3-(6-methyl-2,4-dioxo-1,2,3,4-tetrahydropyrimidin-5-yl)acrylic acid Synthesis of 3-(6-methyl-2,4-dioxo-1,2,3,4-tetrahydropyrimidin-5-yl)acrylic acid was carried out as shown in the scheme below. Detailed experimental procedures and analytical data are given below.

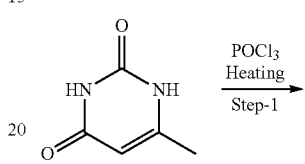

-continued

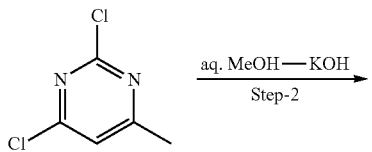

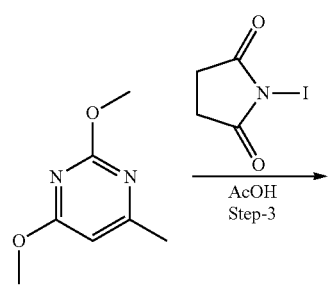

Step-2: Synthesis of 2,4-dimethoxy-6-methylpyrimidine

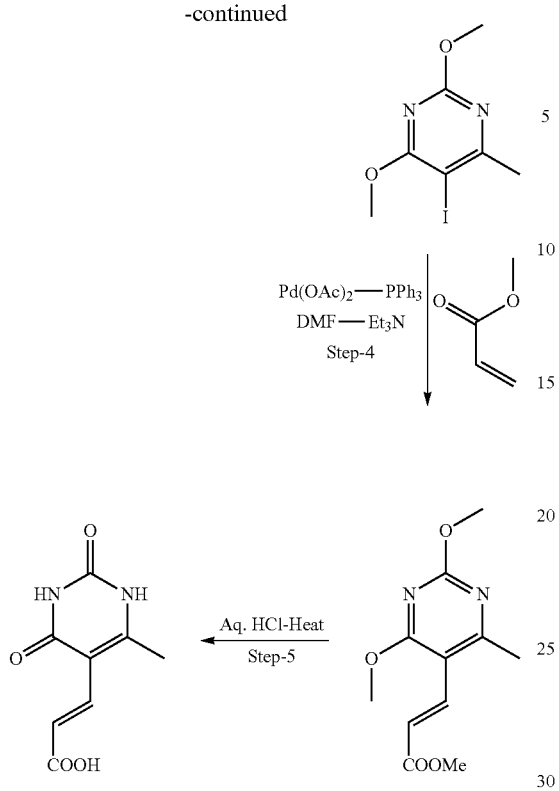

9 g of 2,4-dimethoxy-6-methylpyrimidine, methanol (100 mL), water (100 mL) and KOH (9.27 g, 2.55 eq.) were stirred at R.T. for 6 hrs when TLC (Mobile phase 20% ethyl acetate in n-hexane) indicated absence of starting material (Rf—0.5) and formation of product (Rf. 0.45). Reaction mass was then concentrated and extracted with ethyl acetate, organic layer was dried over anhydrous sodium sulfate, and concentrated to get 6 g of 2,4-dimethoxy-6-methylpyrimidine.

Yield: 6 g (70%)
Analytical Data
Mol. Wt:—154.17
  MH+ observed in LCMS:—155.05
  HPLC Purity:—99.68%
  1H NMR DMSO-d6:—2.35 (s, 3H), 3.94 (s, 3H), 3.97 (s, 3H) 6.212 (s, 1H)

Step-3: Synthesis of 5-iodo-2,4-dimethoxy-6-methylpyrimidine

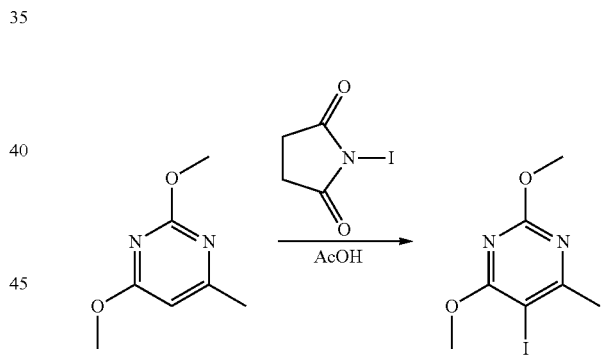

To a stirred solution of 2,4-dimethoxy-6-methylpyrimidine (18 g, 1 eq) in acetic acid (250 mL) was added N-iodo succinimide (31.55 g 1.2 eq), reaction mass stirred at 80° C. for 3 hrs when TLC (30% ethyl acetate in n-hexane) indicated absence of starting material (Rf—0.7) and formation of product (Rf. ~0.75) acetic acid was distilled in vacuum and reaction mass was quenched with water and extracted with dichloromethane. Dichloromethane extract was dried over sodium sulfate and concentrated to get 25 g 5-iodo-2,4-dimethoxy-6-methylpyrimidine which was characterized by LCMS, NMR.

Yield: 25 g (95%)
Analytical Data
Mol. Wt:—280.06
  MH+ observed in LCMS:—281.00
  HPLC Purity:—90.44%
  1H NMR DMSO-d6:—2.5 (s, 3H), 3.86 (s, 3H), 3.912 (s, 3H)

Experimental

Step-1: Synthesis of 2,4-dichloro-6-methylpyrimidine

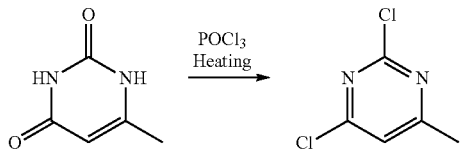

Mixture of 6-methyl uracil (10 g, 1 eq) in POCl₃ (150 mL, 20 eq.) was heated to 105° C. for three hours when TLC (Mobile phase 30% ethyl acetate in n-hexane) indicated absence of starting material (Rf 0.5) and formation of product (Rf—0.8). Excess POCl₃ was then distilled in vacuum. The residue was quenched with ice and extracted with chloroform. Chloroform extract was washed with brine till pH was neutral, dried over anhydrous sodium sulfate, and concentrated to yield 9 g 2,4-dichloro-6-methylpyrimidine as light yellow solid. This was characterized by LCMS & NMR.

Yield: 9 g (69.7%)
Analytical Data
Mol. Wt:—163.00
  MH+ observed in LCMS:—163 (M+) & 164 (MH+)
  HPLC Purity:—99.86%
  1H NMR DMSO-d6:—2.54 (s, 3H), 7.18 (s, 1H)

Step-4: Methyl 3-(2,4-dimethoxy-6-methylpyrimidin-5-yl)acrylate

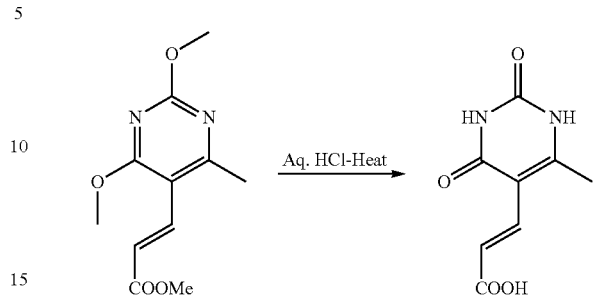

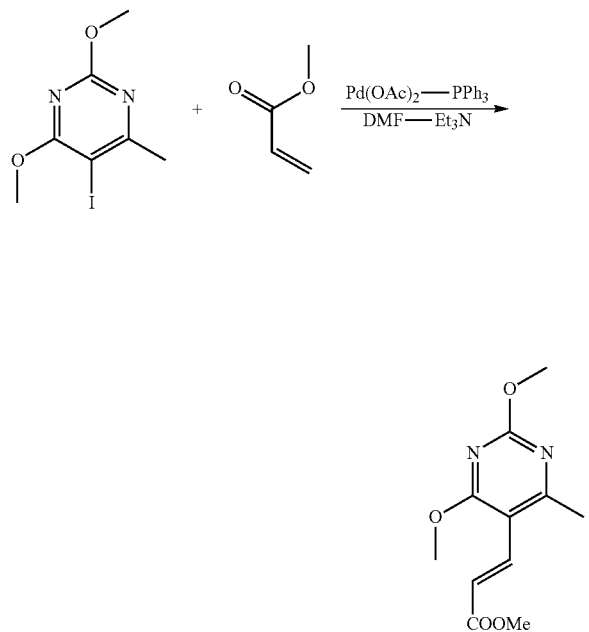

5-Iodo-2,4-dimethoxy-6-methylpyrimidine (1 g), palladium acetate (24 mg, 3 mol. %), TPP (467 mg, 0.5 eq.), TEA (721 mg, 2 eq.) and methyl acrylate (614 mg, 2 eq), were suspended in anhydrous DMF (5 mL) and heated to 140° C. in sealed tube for 2 hrs when TLC (30% ethyl acetate in hexane) indicated absence of starting material (Rf. ~0.8) and formation of the product (Rf. ~0.6). Reaction mass was then cooled to room temperature, diluted with water (25 mL) and extracted with dichloromethane. Dichloromethane extract dried over anhydrous sodium sulfate and concentrated to get 1.2 g crude product which was purified by column chromatography (Gradient, 0-5% ethyl acetate in n-Hexane) to get 300 mg pure product.

Yield: 300 mg (35%)

Analytical Data

Mol. Wt:—238.24

M.I. Peak observed:—239.15

HPLC Purity:—92.91%

1H NMR DMSO-d6:—2.58 (s, 3H), 3.8 (s, 3H), 4.00 (s, 3H), 4.06 (s, 3H), 6.64 (d, 1H, J=16 Hz), 7.78 (d, 1H, J=16.4)

Step-5: Synthesis of 3-(6-methyl-2,4-dioxo-1,2,3,4-tetrahydropyrimidin-5-yl)acrylic acid Methyl 3-(2,4-dimethoxy-6-methylpyrimidin-5-yl)acrylate (100 mg) in 2 mL 6M HCl was stirred at 80° C. for 8 h, TLC (40% ethyl acetate in n-Hexane) indicated absence of starting material (Rf—0.9). Precipitated solid product was filtered and washed with diethyl ether to get 55 mg solid product which was characterized by NMR. Ionization is not observed in LCMS.

Yield: 55 mg (58.5%)

Analytical Data

Mol. Wt:—196.16

M.I. Peak observed:—Ionization not observed

HPLC Purity:—97.31%

1H NMR DMSO-d6:—2.27 (s, 3H), 6.86 (d, 1H, J=15.6 Hz), 7.34 (d, 1H, J=15.6)

Coupling Reactions of 3-(6-methyl-2,4-dioxo-1,2,3,4-tetrahydropyrimidin-5-yl)acrylic acid

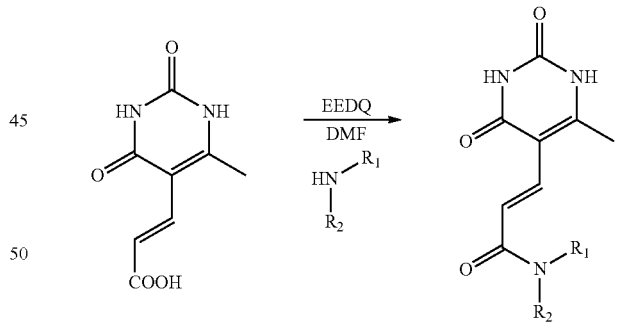

General Procedure for Coupling Reactions 100 mg (0.510 mmol) 3-(6-methyl-2,4-dioxo-1,2,3,4-tetrahydropyrimidin-5-yl)acrylic acid, desired amine (1.5 eq.), N-ethoxycarbonyl-2-ethoxy-1,2-dihydroquinoline (EEDQ 2 eq.) in dimethyl formamide (DMF, 5 mL) were heated to 100° C. and monitored by TLC & LCMS. After consumption of starting material the crude product was isolated either by diluting reaction mass by ethyl acetate followed by filtration of precipitated crude product, or concentrating the DMF in GeneVac® to obtain the crude product. Crude product was purified by preparative HPLC. Analytical data of the coupled product synthesized is tabulated below.

| Example # | Structure | Analytical data |
|---|---|---|
| Example 13 | 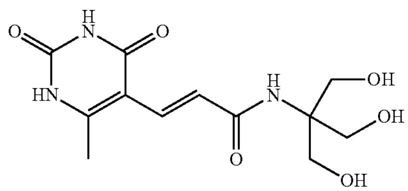 [SMILES: Cc1[nH]c(=O)[nH]c(=O)c1/C=C/C(=O)NC(CO)(CO)CO] | Mol. Wt: ~299.27<br>M.I. Peak observed 300, 322 (M + Na)<br>HPLC Purity: ~13.7 & 83.33% split peaks<br>¹H NMR DMSO-d6: ~2.25 (s, 3H), 3.56 (s, 6H), 7.11-7.22 (two d, 1H each, J = 15 Hz) |
| Example 14 | 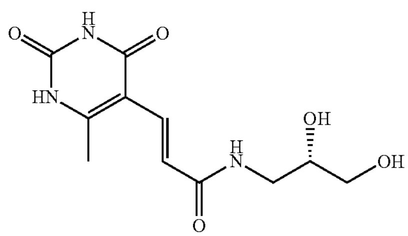 [SMILES: Cc1[nH]c(=O)[nH]c(=O)c1/C=C/C(=O)NC[C@H](O)CO] | Mol. Wt: ~269.25<br>M.I. Peak observed: ~270.00<br>HPLC Purity (Method B): ~95.00%<br>¹H NMR DMSO-d6: ~2.253 (s, 3H), 3.04-3.11 (m, 1H), 3.27-3.28 (m, 3H), 3.49-3.52 (m, 1H), 7.05-7.22 (two d, 1H each, J = 15 Hz) |
| Example 15 | 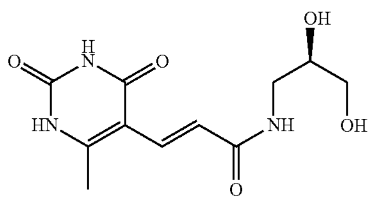 [SMILES: Cc1[nH]c(=O)[nH]c(=O)c1/C=C/C(=O)NC[C@@H](O)CO] | Mol. Wt: ~269.25<br>M.I. Peak observed: ~270.10<br>HPLC Purity (Method B): ~99.98%<br>¹H NMR DMSO-d6: ~2.251 (s, 3H), 3.05-3.11 (m, 1H), 3.21-3.32 (m, 3H), 3.48-3.52 (m, 1H), 7.05-7.22 (two d, 1H each, J = 15.6 Hz) |
| Example 16 | 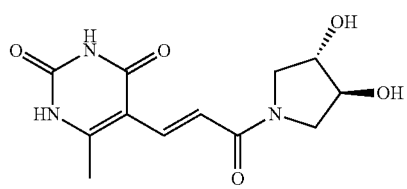 [SMILES: Cc1[nH]c(=O)[nH]c(=O)c1/C=C/C(=O)N1C[C@H](O)[C@@H](O)C1] | Mol. Wt: ~281.26<br>M.I. Peak observed: ~281.95<br>HPLC Purity (Method B) 99.98%<br>¹H NMR DMSO-d6: ~2.26 (s, 3H), 3.43-3.47 (m, 4H), 3.64-3.68 (dd, 2H), 7.1-7.20 (t, 2H) |
| Example 17 | 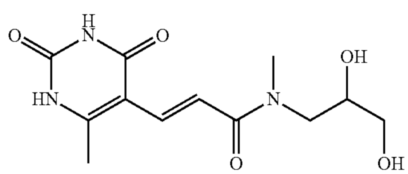 [SMILES: Cc1[nH]c(=O)[nH]c(=O)c1/C=C/C(=O)N(C)CC(O)CO] | Mol. Wt: ~283.28<br>M.I. Peak observed: ~284.25<br>HPLC Purity (Method B): ~98.93%<br>¹H NMR DMSO-d6: ~2.26 (s, 3H), 2.93 (s, 2H), 3.10 (s, 3H), 3.44-3.52 (m, 4H), 3.5-3.7 (m, 1H), 7.29 (t, 1H), 7.4-7.5 (q, 1H) |
| Example 18 | 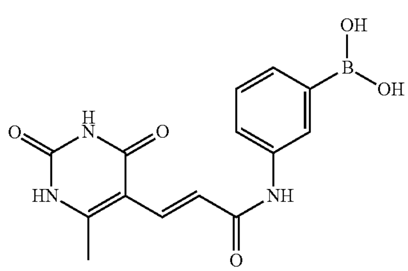 [SMILES: Cc1[nH]c(=O)[nH]c(=O)c1/C=C/C(=O)Nc1cccc(B(O)O)c1] | Mol. Wt: ~315.09<br>M.I. Peak observed: ~316.10<br>HPLC Purity (Method B): ~97.89%<br>¹H NMR DMSO-d6: ~2.25 (s, 3H), 7.25 (t, 1H), 7.32 (t, 2H), 7.46 (d, 1H, J = 8 Hz), 7.82 (d, 1H, J = 8 Hz). 7.95 (s, 1H) |
| Example 19 | 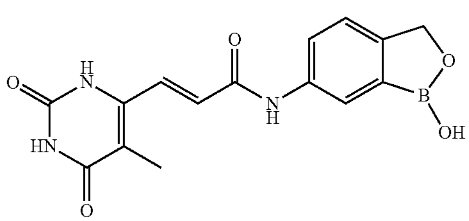 [SMILES: Cc1c(/C=C/C(=O)Nc2ccc3c(c2)B(O)OC3)[nH]c(=O)[nH]c1=O] | Mol. Wt: ~327.10<br>M.I. Peak observed: ~327.85<br>HPLC Purity (Method B): ~95.67% |

| Example # | Structure | Analytical data |
|---|---|---|
| Example 20 | 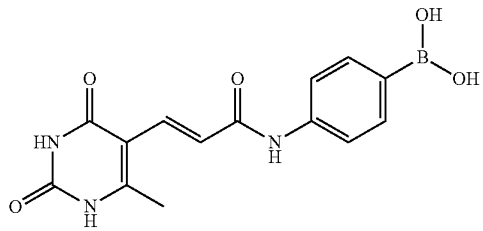 [SMILES: Cc1[nH]c(=O)[nH]c(=O)c1/C=C/C(=O)Nc1ccc(B(O)O)cc1] | Mol. Wt: ~315.09<br>M.I. Peak observed: ~316.40<br>HPLC Purity (Method B): ~99.15%<br>¹H NMR DMSO-d6: ~2.3 (s, 3H), 7.31 (d, 1H, J = 15.6 Hz), 7.37 (d, 1H, J = 15.6 Hz), 7.65 (d, 2H, J = 8.8 Hz), 7.7 (d, 2H, J = 8.4 Hz). |
| Example 21 | 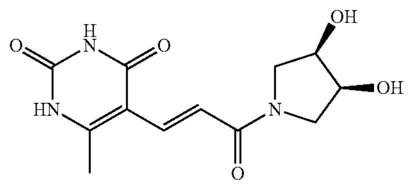 [SMILES: Cc1[nH]c(=O)[nH]c(=O)c1/C=C/C(=O)N1C[C@@H](O)[C@@H](O)C1] | Mol. Wt: ~281.26<br>M.I. Peak observed: ~282.00<br>HPLC Purity (Method B): ~95.75%<br>¹H NMR DMSO-d6: ~2.26 (s, 3H), 3.24-3.28 (m, 2H), 3.42-3.47 (m, 1H), 3.62-3.66 (m, 1H), 3.98-4.10 (m, 2H), 7.25 (d, 2H) |
| Example 22 | 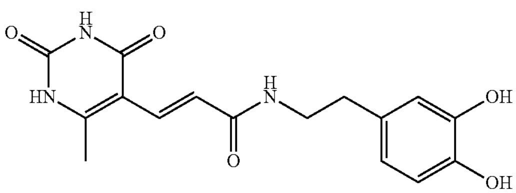 [SMILES: Cc1[nH]c(=O)[nH]c(=O)c1/C=C/C(=O)NCCc1ccc(O)c(O)c1] | Mol. Wt: ~331.32<br>M.I. Peak observed: ~332.20<br>HPLC Purity: ~99.81%<br>¹H NMR DMSO-d6: ~2.25 (s, 3H), 2.54 (t, 2H), 3.2-3.35 (m, 2H), 6.45 (d, 1H, J = 8.4 Hz), 6.55 (s, 1H), 6.61 (d, 1H, J = 8 Hz), 7.02 (d, 1H, J = 15.2 Hz), 7.17 (d, 1H, J = 15.2 Hz) |
| Example 23 | 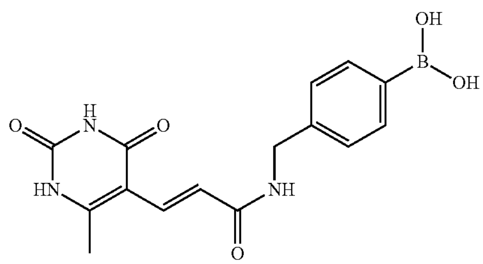 [SMILES: Cc1[nH]c(=O)[nH]c(=O)c1/C=C/C(=O)NCc1ccc(B(O)O)cc1] | Mol. Wt: ~329.12<br>M.I. Peak observed: ~330.35<br>HPLC Purity: ~99.59%<br>¹H NMR DMSO-d6: ~2.25 (s, 3H), 4.34 (d, 2H, J = 5.6 Hz), 7.12-7.26 (m, 4H), 7.71 (d, 2H J = 7.6 Hz). |
| Example 24 | 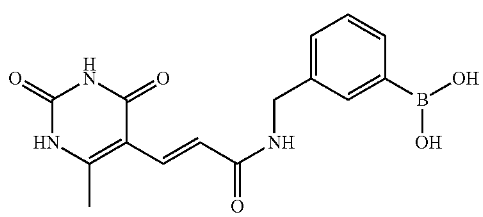 [SMILES: Cc1[nH]c(=O)[nH]c(=O)c1/C=C/C(=O)NCc1cccc(B(O)O)c1] | Mol. Wt: ~329.12<br>M.I. Peak observed: ~330.30<br>HPLC Purity: ~94.52%<br>¹H NMR DMSO-d6: ~2.25 (s, 3H), 4.34 (d, 2H, J = 5.6 Hz), 7.28 (s, 1H), 7.12 (d, 1H, J = 15.6 Hz), 7.24 (d, 1H, J = 15.6 Hz), 7.6-7.7 (m, 2H) |

Example 25—Synthesis of (S)-(4-(5-(acetamidomethyl)-2-oxooxazolidin-3-yl)-2-fluorophenyl)boronic acid (LIBOR-1)

Reaction scheme:-

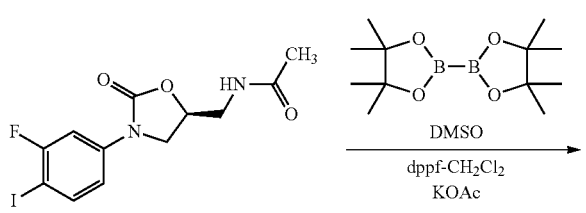

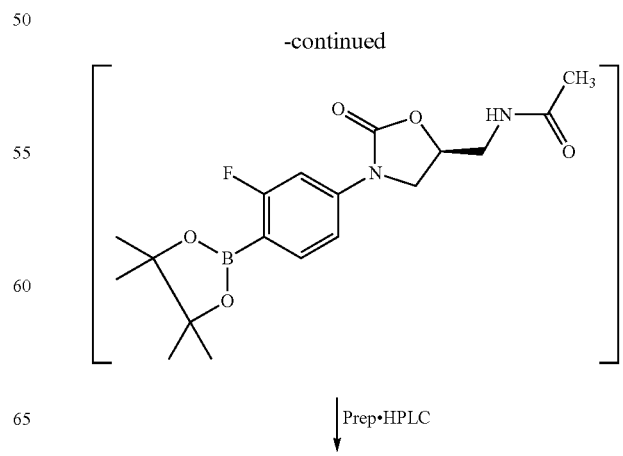

-continued

↓ Prep•HPLC

-continued

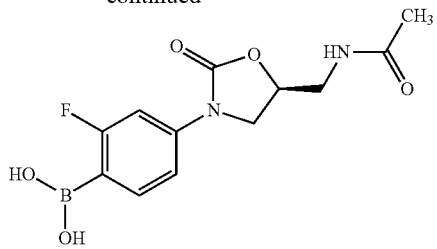

Experimental (S)—N-((3-(3-fluoro-4-iodophenyl)-2-oxooxazolidin-5-yl)methyl)acetamide was synthesized from 3-fluoro aniline as described in literature (WO2005/116017, WO2005/58886, WO2004/29066, WO2004/56817, which are hereby incorporated by reference in their entirety)

To a stirred solution of (S)—N-((3-(3-fluoro-4-iodophenyl)-2-oxooxazolidin-5-yl)methyl)acetamide (200 mg, 1 eq) in dimethyl sulfoxide (8 mL) was added bis (pinacolato)diboron (1.34 g 10 eq), and potassium acetate (155 mg, 3 eq) under argon atmosphere. Reaction mass was stirred at room temperature for 5 min and [1,1-bis (diphenylphosphino)-ferrocene]dichloro palladium (II), dichloromethane complex (43 mg, 0.1 eq) was added. Reaction mass stirred at 60° C. for 3 hrs under argon atmosphere, when TLC (5% methanol in chloroform) indicated absence of starting material (Rf—0.5) and formation of product (Rf. ~0.45) Reaction mass was then cooled to room temperature, diluted with water (25 mL) and extracted with ethyl acetate. Ethyl acetate extract dried over anhydrous sodium sulfate and concentrated residue was several times washed with n-hexane to get crude boronate ester (300 mg) this was purified by preparative HPLC* to get 25 mg pure boronic acid due to hydrolysis of pinacol ester during preparative HPLC.

*Method for prep HPLC:—Column: YMC, ODS-A, 500.0×30.0 mm. 10.0 µm, Flow rate: 30.0 ml/min, Injection Volume: 4.5 ml, Column oven temperature: Ambient, Mobile Phase: A: 0.05% (v/v) Trifluoroacetic acid in water, B: 0.05% (v/v) Trifluoroacetic acid in (Acetonitrile: MeOH::50:50), Flow mode: Isocratic Wavelength: 254 nm, Sample preparation: Water+MeOH+ACN Yield: 25 mg (12.5%)
Mol. Wt:—296.06, MH+ observed in LCMS:—297 (MH+) & 319 (M+Na)
HPLC Purity:—99.37%, 1H NMR DMSO-d6:—1.82 (s, 3H), 3.41 (t, 2H), 3.71-3.75 (q, 1H), 4.11 (t, 1H), 4.69-4.74 (m, 1H), 7.24 (dd, 1H, J=1.6 & 8.4 Hz), 7.35 (dd, 1H, J=1.6 & 12 Hz), 7.58 (t, 1H).

Example 26—Synthesis of (R)-(4-(5-(((1H-1,2,3-triazol-1-yl)methyl)-2-oxooxazolidin-3-yl)-2-fluorophenyl)boronic acid (LIBOR-3)

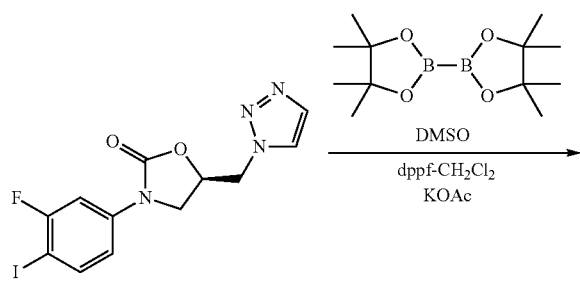

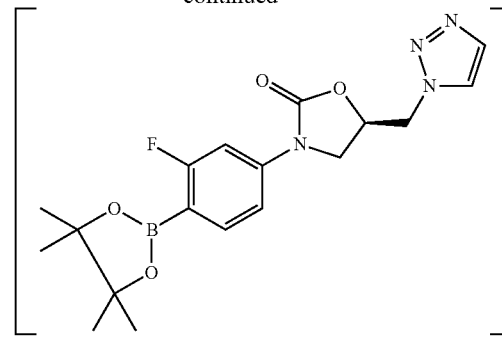

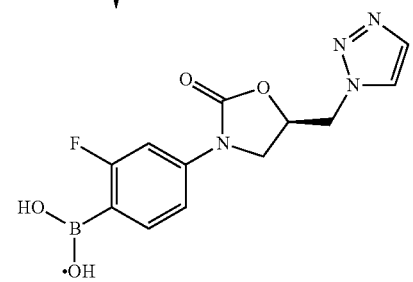

Experimental (R)-5-(((1H-1,2,3-triazol-1-yl)methyl)-3-(3-fluoro-4-iodophenyl) oxazolidin-2-one was synthesized as per procedure described in WO2006/22794, which is hereby incorporated by reference in its entirety.

To a stirred solution of (R)-5-(((1H-1,2,3-triazol-1-yl)methyl)-3-(3-fluoro-4-iodophenyl)oxazolidin-2-one (500 mg, 1 eq) in dimethyl sulfoxide (12 mL) was added bis (pinacolato)diboron (3.27 g 10 eq), and potassium acetate (378 mg, 3 eq) under argon atmosphere. Reaction mass was stirred at room temperature for 5 min and [1,1-bis(diphenylphosphino)-ferrocene]dichloro palladium(II), dichloromethane complex (104 mg, 0.1 eq) was added. Reaction mass stirred at 60° C. for 3 hrs under argon atmosphere, when TLC (5% methanol in chloroform) indicated absence of starting material (Rf—0.5) and formation of product (Rf. ~0.45) Reaction mass was then cooled to room temperature, diluted with water (25 mL) and extracted with ethyl acetate. Ethyl acetate extract dried over anhydrous sodium sulfate and concentrated residue was several times washed with n-hexane to get crude boronate ester (300 mg) this was purified by preparative HPLC to get 80 mg pure boronic acid due to hydrolysis of pinacol ester during preparative HPLC*.

*Method for prep HPLC:—Column: YMC, ODS-A, 500.0×30.0 mm. 10.0 µm, Flow rate: 30.0 ml/min, Injection Volume: 4.5 ml, Column oven temperature: Ambient, Mobile Phase: A: 0.05% (v/v) Trifluoroacetic acid in water, B: 0.05% (v/v) Trifluoroacetic acid in (Acetonitrile:MeOH::50:50), Flow mode: Isocratic Wavelength: 254 nm, Sample preparation: Water+MeOH+ACN Yield: 80 mg (16%)
Mol. Wt:—306.06, MH+ observed in LCMS:—307.20 (MH+), HPLC Purity:—99.96% 1H NMR DMSO-d6:—3.88-3.92 (q, 1H), 4.24 (t, 1H), 4.84 (d, 2H, J=5.2 Hz), 5.11-5.17 (m, 1H), 7.21 (dd, 1H, J=1.6 & 8.4 Hz), 7.32 (dd, 1H, J=1.6 & 11.6 Hz), 7.58 (t, 1H), 7.75 (s, 1H), 8.05 (s, 1H).

Example 27—Synthesis of N-(((5S)-3-(4-(1,2-dihydroxyethyl)-3-fluorophenyl)-2-oxooxazolidin-5-yl)methyl)acetamide (LZD-1) Reaction Scheme

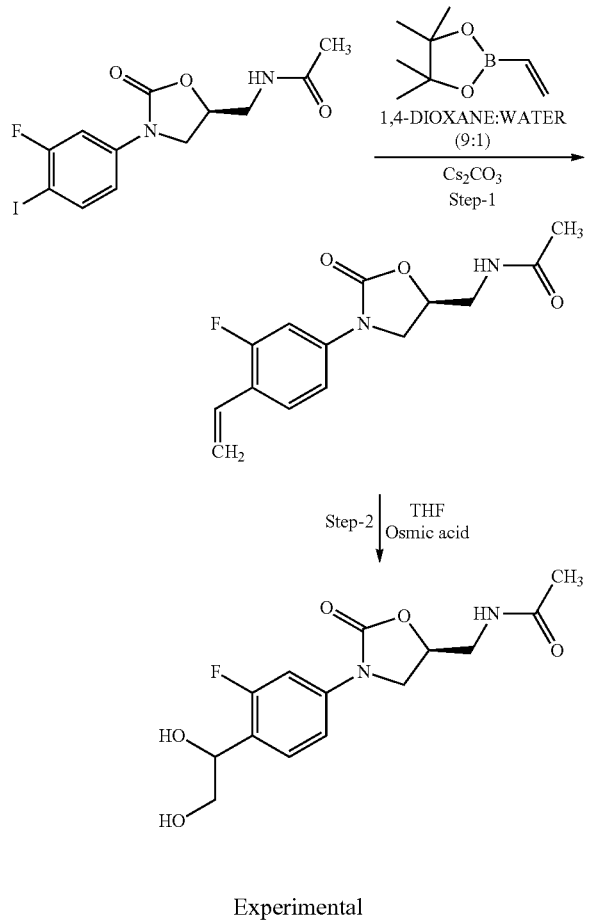

Experimental

Step-1: Synthesis of (S)—N-((3-(3-fluoro-4-vinylphenyl)-2-oxooxazolidin-5-yl)methyl)acetamide

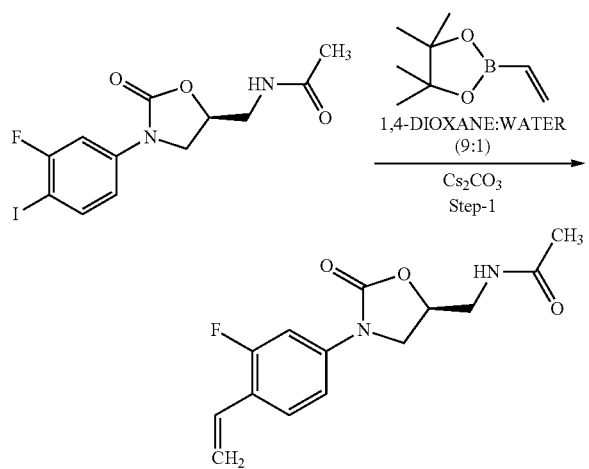

(S)—N-((3-(3-fluoro-4-iodophenyl)-2-oxooxazolidin-5-yl)methyl)acetamide was synthesized from 3-fluoro aniline as described in literature (WO2005/116017, WO2005/58886, WO2004/29066, WO2004/56817, which are hereby incorporated by reference in their entirety).

4 ml 1,4-dioxane and 0.5 ml water purged with nitrogen for 15 min. and to this solution (S)—N-((3-(3-fluoro-4-iodophenyl)-2-oxooxazolidin-5-yl)methyl)acetamide (50 mg, 1 eq), 4,4,5,5-tetramethyl-2-vinyl-1,3,2-dioxaborolane (42.7 mg 2.1 eq), cesium carbonate (172.3 mg, 4 eq), and tetrakis palladium (19.8 mg, 0.13 eq) were added. Reaction mass was stirred at 90° C. for 14 hrs under nitrogen atmosphere, when LCMS & TLC (5% methanol in chloroform) indicated absence of starting material (Rf—0.45) and formation of product (Rf. ~0.5). Reaction mass was then cooled to room temperature, concentrated in vacuum, diluted with water, (25 mL), and extracted with ethyl acetate. Ethyl acetate extract dried over anhydrous sodium sulfate and concentrated. Residue was several times washed with n-hexane to get 25 mg desired product with sufficient purity. Characterized by LCMS Yield: 25 mg (69%)

Mol. Wt:—278.05; LCMS:—Purity 92%, m/z observed 279

Step-2: Synthesis of N-(((5S)-3-(4-(1,2-dihydroxyethyl)-3-fluorophenyl)-2-oxooxazolidin-5-yl)methyl)acetamide

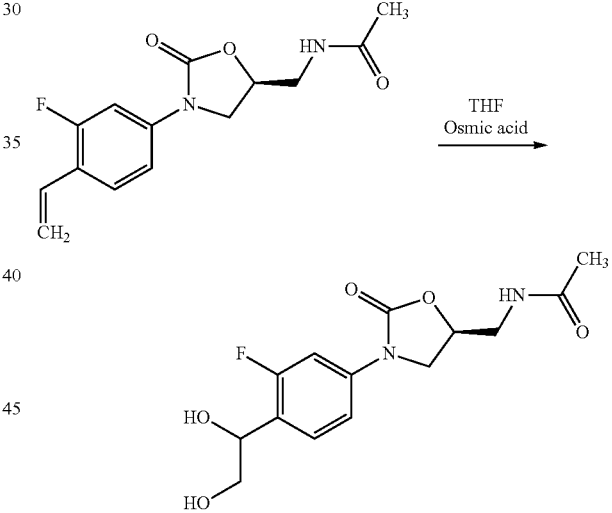

To a stirred solution of (S)—N-((3-(3-fluoro-4-vinylphenyl)-2-oxooxazolidin-5-yl)methyl)acetamide (150 mg, 1 eq) in THF (5 mL) and water (1.5 ml) was added 4-methyl morpholine N-oxide (69 mg 1.1 eq) and stirred for 5 min, then osmium tetra oxide (13.7 mg, 0.01 eq) was added and reaction mass was stirred at room temperature for 14 h, when TLC (20% methanol in chloroform) indicated absence of starting material (Rf—0.4) and formation of product (Rf. ~0.35), reaction mass was concentrated to get 160 mg crude product. Purification was carried out by column chromatography over silica gel (Gradient, 0-5% methanol in chloroform) to get 53 mg pure product.

Yield: 53 mg (31.5%)

Analytical Data

Mol. Wt:—312.29; m/z observed in LCMS:—313 (MH+) & 330 (M+18); HPLC Purity: —95.07%; $^1$H NMR DMSO-d6:—1.82 (s, 3H), 3.33-3.46 (m, 3H), 3.70-3.74 (m, 1H), 4.11 (t, 1H), 4.70-4.81 (m, 3H), 5.35 (d, 1H), 7.25 (d, 1H), 7.40-7.49 (m, 2H).

Example 28—Synthesis of 1-(4-(3-(aminomethyl)phenyl)piperidin-1-yl)-2-(3,4-dihydroxyphenyl)ethanone (Target-1)

Synthetic Scheme:

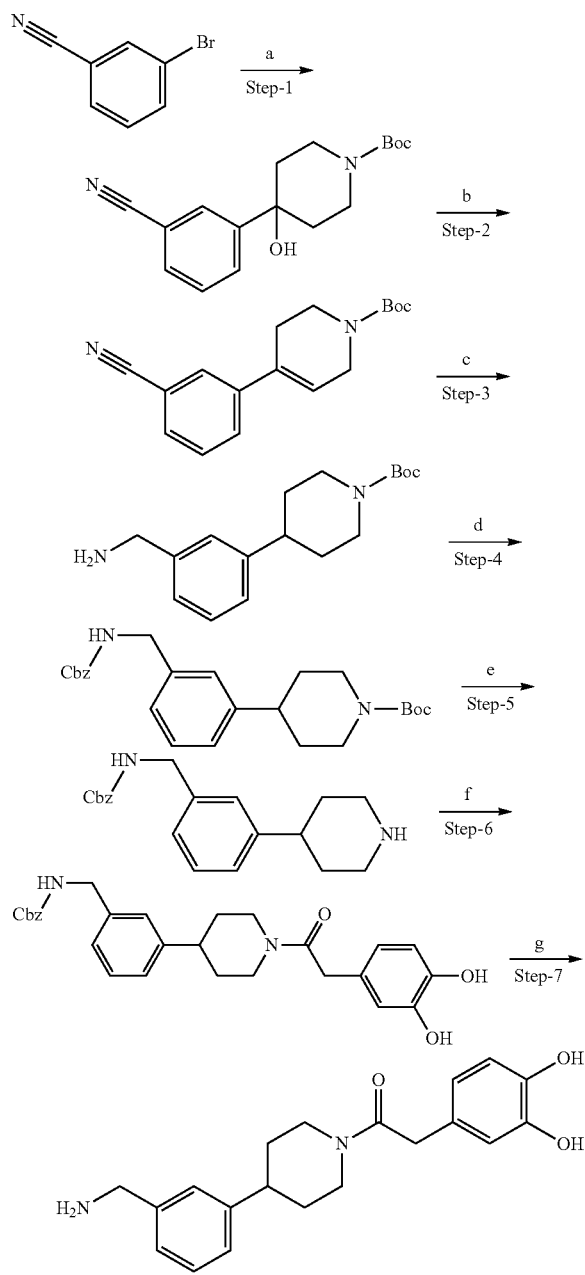

Reagents and Conditions:

a) n-BuLi, THF, −100° C., 1 h, then tert-butyl 4-oxopiperidine-1-carboxylate, THF, −100° C.-room temperature, 5 h; b) POCl₃, pyridine, 0° C.-room temperature, 72 h; c) Pd(OH)₂, EtOH, H₂ (Balloon pressure), room temperature, 2 h; d) Cbz-Cl, THF, aq. NaHCO₃, room temperature, 2 h; e) TFA, CH₂Cl₂, room temperature, 2 h; f) EDCI, HOBt, DIEA, 2-(3,4-dihydroxyphenyl)acetic acid, DMF, room temperature, 15 h; g) HBr in acetic acid, CH₂Cl₂, 1 h.

Experimental Procedure

Step-1: Synthesis of tert-butyl 4-(3-cyanophenyl)-4-hydroxypiperidine-1-carboxylate

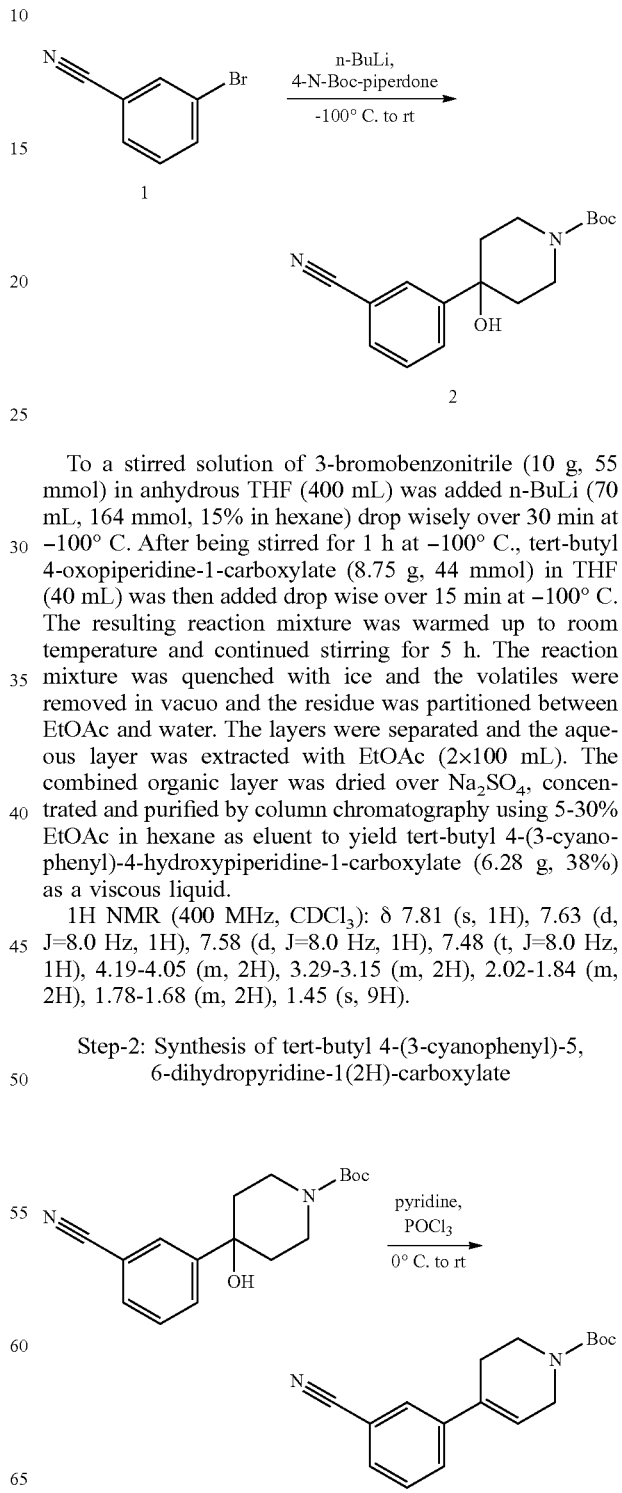

To a stirred solution of 3-bromobenzonitrile (10 g, 55 mmol) in anhydrous THF (400 mL) was added n-BuLi (70 mL, 164 mmol, 15% in hexane) drop wisely over 30 min at −100° C. After being stirred for 1 h at −100° C., tert-butyl 4-oxopiperidine-1-carboxylate (8.75 g, 44 mmol) in THF (40 mL) was then added drop wise over 15 min at −100° C. The resulting reaction mixture was warmed up to room temperature and continued stirring for 5 h. The reaction mixture was quenched with ice and the volatiles were removed in vacuo and the residue was partitioned between EtOAc and water. The layers were separated and the aqueous layer was extracted with EtOAc (2×100 mL). The combined organic layer was dried over Na₂SO₄, concentrated and purified by column chromatography using 5-30% EtOAc in hexane as eluent to yield tert-butyl 4-(3-cyanophenyl)-4-hydroxypiperidine-1-carboxylate (6.28 g, 38%) as a viscous liquid.

1H NMR (400 MHz, CDCl₃): δ 7.81 (s, 1H), 7.63 (d, J=8.0 Hz, 1H), 7.58 (d, J=8.0 Hz, 1H), 7.48 (t, J=8.0 Hz, 1H), 4.19-4.05 (m, 2H), 3.29-3.15 (m, 2H), 2.02-1.84 (m, 2H), 1.78-1.68 (m, 2H), 1.45 (s, 9H).

Step-2: Synthesis of tert-butyl 4-(3-cyanophenyl)-5,6-dihydropyridine-1(2H)-carboxylate Tert-butyl 4-(3-cyanophenyl)-4-hydroxypiperidine-1-carboxylate (6.28 g, 20.0 mmol) was dissolved in pyridine (157 mL), and cooled to 0° C. To it POCl₃ (6.28 mL) was added dropwise and the reaction mixture was stirred at room temperature for 3 days. After completion of the reaction (monitored by TLC), the volatiles were removed in vacuo and the residue was partitioned between EtOAc and water. The layers were separated and the aqueous layer was extracted with EtOAc (2×50 mL). The combined organic layer was washed with 10% aq. citric acid (25 mL), brine, dried over Na₂SO₄, concentrated and purified by column chromatography using 5-30% EtOAc in hexane as eluent to yield tert-butyl 4-(3-cyanophenyl)-5,6-dihydropyridine-1 (2H)-carboxylate (3 g, 50%) as a viscous liquid.

1H NMR (400 MHz, CDCl3): δ 7.63 (s, 1H), 7.59 (d, J=8.0 Hz, 1H), 7.53 (d, J=8.0 Hz, 1H), 7.43 (t, J=8.0 Hz, 1H), 6.12-6.08 (m, 1H), 4.09 (s, 2H), 3.64 (t, J=5.6 Hz, 2H), 2.52-2.48 (m, 2H), 1.49 (s, 9H).

Step-3: Synthesis of tert-butyl 4-(3-(aminomethyl)phenyl)piperidine-1-carboxylate

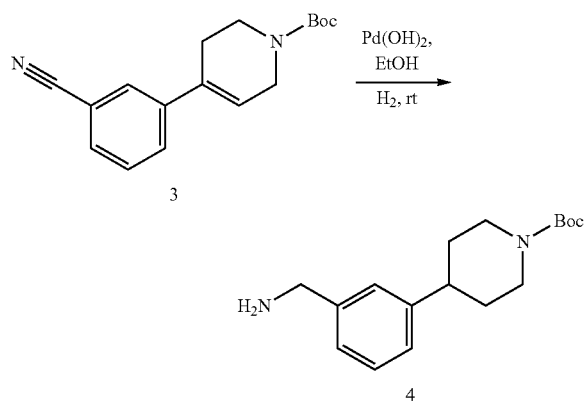

To a stirred solution of tert-butyl 4-(3-cyanophenyl)-5,6-dihydropyridine-1(2H)-carboxylate (500 mg, 1.75 mmol) in EtOH (7 mL) was added Pd (OH)₂ (250 mg) at room temperature under nitrogen atmosphere. The resulting reaction mixture was then agitated under H₂ atmosphere (balloon pressure) for 2 h. The reaction was carefully monitored by TLC and LCMS, as an over-reduced product was observed after prolonged reaction time. After completion of reaction, the reaction mixture was filtered through celite pad and filtrate was concentrated under reduced pressure to yield the crude product tert-butyl 4-(3-(aminomethyl)phenyl)piperidine-1-carboxylate (250 mg, 49%), which was used for next step without further purification.

Step-4: Synthesis of tert-butyl 4-(3-((((benzyloxy) carbonyl)amino)methyl)phenyl)piperidine-1-carboxylate

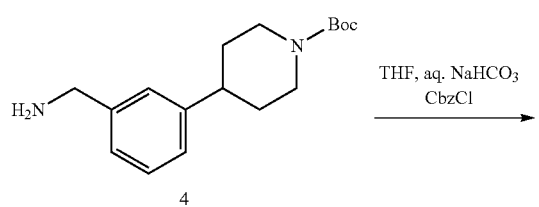

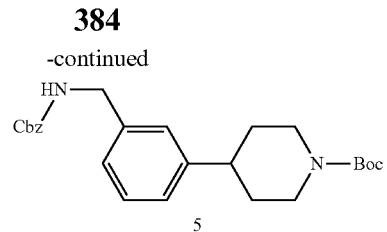

To a stirred solution of tert-butyl 4-(3-(aminomethyl) phenyl)piperidine-1-carboxylate (290 mg, 0.99 mmol) in THF (3 mL) was added aqueous NaHCO₃ (251 mg, 3 mmol) at 0° C. followed by portion wise addition of Cbz-Cl (0.21 mg, 1.5 mmol) at 0° C. The resulting mixture was stirred at 0° C. for 2 h. After completion of reaction, the reaction mixture was diluted with water and extracted with EtOAc. The organic phase was washed with water, brine solution, dried over anhydrous Na₂SO₄, filtered, and concentrated under reduced pressure. The crude material was purified over silica gel column chromatography using 5-20% EtOAc in hexane as eluent to afford tert-butyl 4-(3-((((benzyloxy) carbonyl)amino)methyl)phenyl)piperidine-1-carboxylate (194 mg, 45%).

LCMS: m/z [M+23]=447; 71.25% (254 nm)

Chromatographic Parameters

Mobile Phase A: 0.05% TFA in water, Mobile Phase B:0.05% TFA in Acetonitrile,

Flow rate: 1.2 ml/min; Temperature: Ambient,

Column: YMC ODS A, C18(50×4.6 mm) 3 uM, E-AC-2/ 08/COL/005

Gradient: Initial 20% B Conc to 95% B Conc. in 3.0 min. Hold for 0.5 min. At 3.51 min B. Conc. is 20%

Step-5: Synthesis of benzyl 3-(piperidin-4-yl)benzylcarbamate

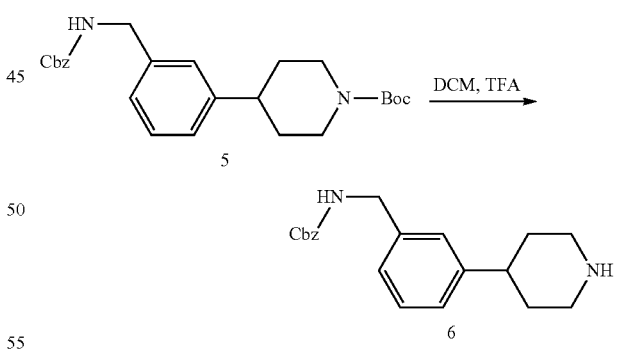

To a stirred solution of tert-butyl 4-(3-((((benzyloxy) carbonyl)amino)methyl)phenyl)piperidine-1-carboxylate (0.6 g, 1.4 mmol) in CH₂Cl₂ (6 ml) was added TFA (0.31 mL, 4.2 mmol) at 0° C. under nitrogen atmosphere and stirred for 2 h. The reaction mixture was diluted and washed with sat. aq. NaHCO₃ solution, water, brine, dried over Na₂SO₄, concentrated, and purified by column chromatography on neutral alumina using 0-5% MeOH in CHCl₃ as eluent to yield benzyl 3-(piperidin-4-yl)benzylcarbamate (260 mg, 56%).

Step-6: Synthesis of benzyl 3-(1-(2-(3,4-dihydroxy-phenyl)acetyl)piperidin-4-yl)benzylcarbamate

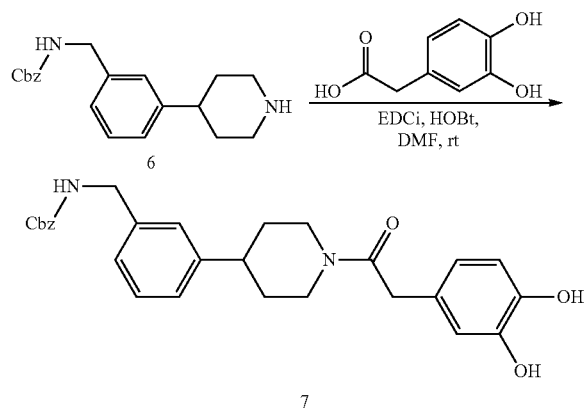

A mixture of benzyl 3-(piperidin-4-yl)benzylcarbamate (100 mg, 0.3 mmol), 3,4-dimethoxyphenylacetic acid (52 mg, 0.3 mmol), EDCI (88 mg, 0.45 mmol), HOBt (60 mg, 0.45 mmol), DIEA (0.08 mL, 0.6 mmol) in CH$_2$Cl$_2$ (5 mL) was stirred at room temperature overnight. The reaction mixture was diluted with CH$_2$Cl$_2$ and washed with water, brine, dried over Na$_2$SO$_4$, concentrated and purified by column chromatography 0-5% MeOH in CHCl$_3$ as eluent to yield benzyl 3-(1-(2-(3,4-dihydroxyphenyl)acetyl)piperidin-4-yl)benzylcarbamate (46 mg, 61%).

Step-7: Synthesis of 1-(4-(3-(aminomethyl)phenyl)piperidin-1-yl)-2-(3,4-dihydroxyphenyl)ethanone (Target-1)

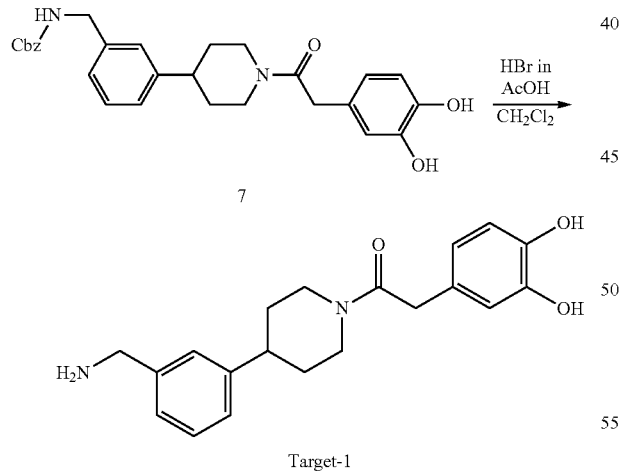

The benzyl 3-(1-(2-(3,4-dihydroxyphenyl)acetyl)piperidin-4-yl)benzylcarbamate (100 mg, 0.21 mmol) was dissolved in DCM (3 mL), and cooled to 0° C. To it HBr in acetic acid (3 mL) was added dropwise and the reaction mixture was stirred at room temperature for 1 h. After completion of reaction, the volatiles were concentrated in vacuo and the crude was purified by Prep-HPLC column using 0.5% TFA. The resultant TFA salt after lypholisation was dissolved in HPLC grade MeOH and to it conc. HCl was added and the compound was again subjected to lypholisation to yield the HCl salt of 1-(4-(3-(aminomethyl)phenyl)piperidin-1-yl)-2-(3,4-dihydroxyphenyl)ethanone (30 mg, 37%).

1H NMR (400 MHz, CD3OD): δ 7.38-7.23 (m, 4H), 6.75-6.73 (m, 2H), 6.62-6.60 (m, 1H), 4.87-4.64 (m, 2H), 4.08 (s, 2H), 3.68 (ABq, J=14.8 Hz, 2H), 3.22-3.11 (m, 2H), 2.84-2.71 (m, 2H), 1.86-1.83 (m, 1H), 1.70-1.67 (m, 1H), 1.57-1.54 (m, 1H), 1.25-1.22 (m, 1H).

LCMS: m/z [M+1]=341, [M+23]=363, 99.79% (220 nm, R.T.=1.26)
Mobile Phase A: 0.05% TFA in water, Mobile Phase B:0.05% TFA in Acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Conc to 95% B Conc. in 3.0 min. Hold for 0.5 min. At 3.51 min B. Conc. is 20%
HPLC: 98.99% (254 nm, R.T.=4.12)
Column: YMC ODS-A 150 mm×4.6 mm×5 gi, ID: E-AC-2/08/COL/006
Mobile Phase: A: 0.05% TFA in Water/B: 0.05% TFA in Acetonitrile
Inj. Vol: 10 μL, Col. Temp.: 30° C., Flow rate: 1.4 mL/min
Gradient: 5% B to 95% B in 8 min, Hold for 1.5 min, 9.51-12 min 5% B Example 29—Synthesis of (4-(3-(aminomethyl)phenyl)piperidin-1-yl)(3,4-dihydroxyphenyl)methanone hydrochloride (Target-2)

Synthetic Scheme:

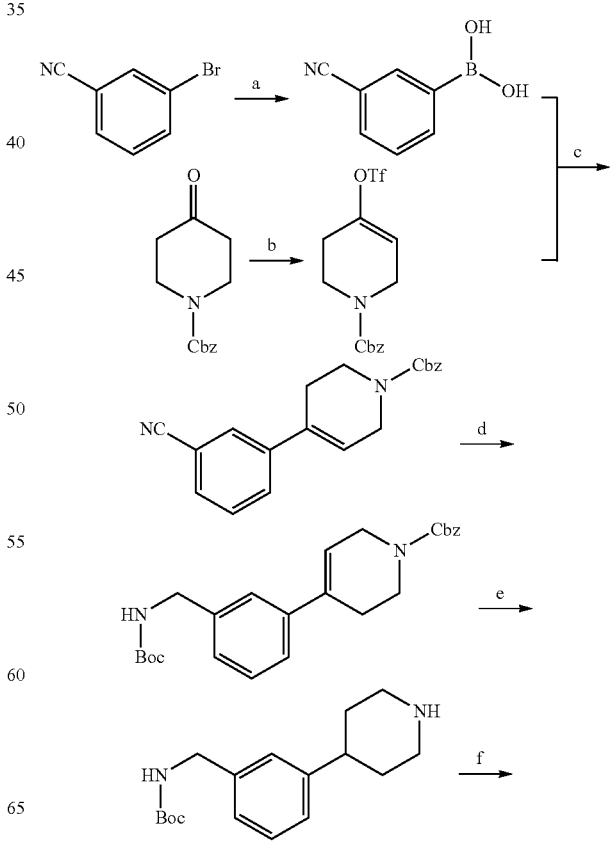

-continued

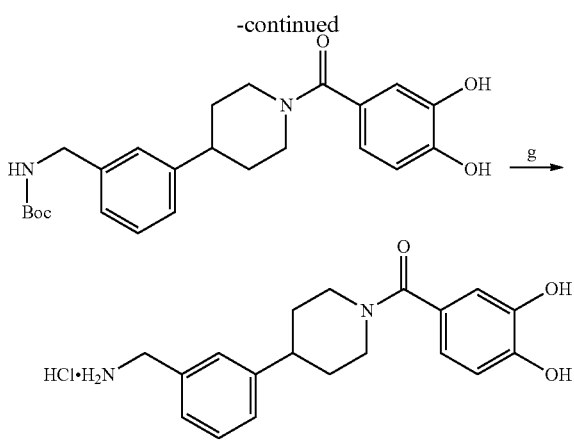

Reagents and conditions:—a) Triisopropoxyborane, n-BuLi, THF, −78° C., 30. min.; b) LDA, N-Phenyltrifluoromethanesulfonimide, THF, −78° C.-room temperature, overnight; c) Pd(PPh₃)₄, 0.4 M aq. Na₂CO₃, acetonitrile, reflux, 1 h; d) NiCl₂.6H₂O, NaBH₄, Boc₂O, MeOH, 0° C.-room temperature; e) 10% Pd/C, MeOH, room temperature, 1 h; f) (E)-3-(3,4-dihydroxyphenyl)acrylic acid, EDCi, HOBt, DIEA, DMF, room temperature, overnight; g) Conc. HCl, MeOH, room temperature, 1 h.

Experimental

Step-1: Synthesis of (3-cyanophenyl)boronic acid

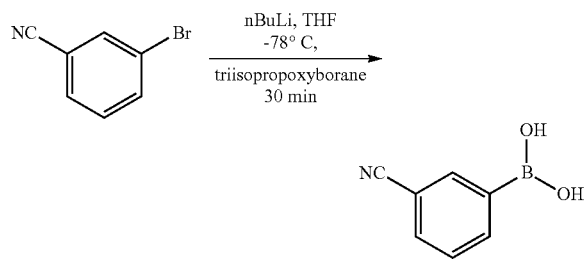

3-bromobenzonitrile (20 g, 110 mmol) was dissolved in 100 mL of dry THF, and then mixed with triisopropoxyborane (71 ml, 309 mmol) in the atmosphere of nitrogen. The solution was cooled at −78° C., and then n-butyl lithium (76 mL, 121 mmol, 1.6M in hexane) was dropwisely added to the cooled solution for about 30 minutes with stirring. The mixture was stirred at room temperature for 30 min, cooled at 0° C. and mixed with 220 mL of 4M sulfuric acid. The solution was heated and refluxed overnight, again cooled at 0° C., mixed with 340 mL of a 5M aqueous solution of sodium hydroxide, and then extracted with 200 mL of diethyl ether. The aqueous phase was separated, mixed with 6M hydrochloric acid until to give pH 2, and then twice extracted with 300 mL of with 6M hydrochloric acid until to give pH 2, and then twice extracted with 300 mL of ethyl acetate. The obtained ethyl acetate layer was dried over Na₂SO₄, and the solvent was distilled away. The obtained crude product was recrystallized from DMF-water to obtain (3-cyanophenyl)boronic acid (10.12 g, 62%) as a solid.

1H NMR (400 MHz, DMSO-d6): δ 8.39 (brs, 2H), 8.13 (s, 1H), 8.07 (d, J=7.6 Hz, 1H), 7.86 (d, J=7.6 Hz, 1H), 7.56 (t, J=7.6 Hz, 1H).

Step-2: Synthesis of benzyl 4-(((trifluoromethyl)sulfonyl)oxy)-5,6-dihydropyridine-1(2H)-carboxylate

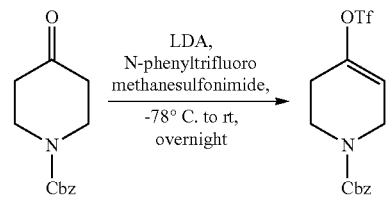 [SMILES: O=C1CCN(C(=O)OCc2ccccc2)CC1 ; O=C(OCc1ccccc1)N1CC=C(OS(=O)(=O)C(F)(F)F)CC1]

To a mixture of benzyl 4-oxopiperidine-1-carboxylate (9 g, 38 mmol) in THF (100 mL) was added 1.5M solution of LDA in hexane (30.66 mL, 46 mmol) at −78° C. dropwise. The reaction mixture was stirred for 1 h at −78° C., and then N-phenyltrifluoromethanesulfonimide (16.53 g, 46 mmol) in THF (50 mL) was added dropwise. The reaction mixture was stirred at −78° C. for 2 hours and allowed to warm up to room temperature and stirred overnight. The reaction mixture was then concentrated in vacuo and the residue dissolved in ether (100 mL). This was washed with water (500 mL), 2M sodium hydroxide solution (3×500 mL), water (500 mL) and brine (500 mL) then dried over Na₂SO₄ and concentrated, and purified by silica-gel column chromatography to give 4-(((trifluoromethyl)sulfonyl)oxy)-5,6-dihydropyridine-1(2H)-carboxylate as a pale brown oil (5.1 g, 36%).

1H NMR (400 MHz, CDCl3): δ 7.39-7.26 (m, 5H), 5.76-5.51 (m, 1H), 5.15 (s, 2H), 4.14-4.10 (m, 2H), 3.71 (t, J=3.2 Hz, 2H), 2.49-2.40 (m, 2H).

Step-3: Synthesis of benzyl 4-(3-cyanophenyl)-5,6-dihydropyridine-1(2H)-carboxylate

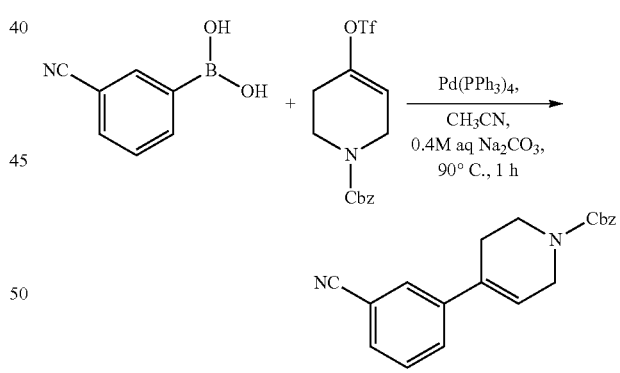

(3-cyanophenyl)boronic acid (3 g, 20 mmol) and benzyl 4-(((trifluoromethyl)sulfonyl)oxy)-5,6-dihydropyridine-1(2H)-carboxylate (8.89 g, 24 mmol) were dissolved in acetonitrile (90 mL) and 0.4M aqueous sodium carbonate (90 mL). The solution was degassed, then treated with tetrakis(triphenylphosphine)palladium (1.15 g, 1 mmol), and the reaction mixture was stirred at 90° C. for 1 h. The reaction was cooled, filtered warm, and the filtrate was concentrated to oil. The oil was extracted with methylene chloride and the solvent removed under vacuum. The residue was purified by column chromatography to yield benzyl 4-(3-cyanophenyl)-5,6-dihydropyridine-1(2H)-carboxylate yield:—3.24 g, (24%).

1H NMR (400 MHz, CDCl3): δ 7.63-7.53 (m, 3H), 7.45-7.32 (m, 6H), 6.29-6.19 (m, 1H), 5.18 (s, 2H), 4.18 (d, J=2.0 Hz, 2H), 3.73 (t, J=5.6 Hz, 2H), 2.58-2.51 (m, 2H).

Step-4: Synthesis of benzyl 4-(3-(((tert-butoxycarbonyl)amino) methyl)phenyl)-5,6-dihydropyridine-1(2H)-carboxylate

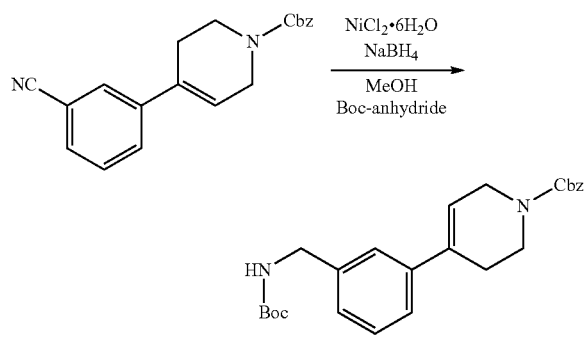

A solution of 4-(((trifluoromethyl)sulfonyl)oxy)-5,6-dihydropyridine-1(2H)-carboxylate (1.4 g, 4.39 mmol) in methanol (25 mL) was cooled in ice bath, was added Boc2O (1.9 g, 8.79 mmol) and NiCl$_2$.6H$_2$O (104 mg, 0.439 mmol) to give a green solution. To this solution was added NaBH$_4$ (1.33 g, 35.17 mmol) slowly at 0° C. The purple mixture was stirred at room temperature. The reaction mixture was concentrated and partitioned between water and EtOAc. The aqueous layer was extracted with EtOAc and the combined organic layer was dried over Na$_2$SO$_4$, concentrated, and purified by column chromatography to yield the benzyl 4-(3-(((tert-butoxycarbonyl)amino)methyl)phenyl)-5,6-dihydropyridine-1(2H)-carboxylate (900 mg, 84%).

1H NMR (400 MHz, CDCl3): δ 7.38-7.08 (m, 9H), 6.09-6.00 (m, 1H), 5.18 (s, 2H), 4.82 (bs, 1H), 4.31)d. J=5.2 Hz, 2H), 4.15 (d, J=2.8 Hz, 2H), 3.71 (t, 5.6 Hz, 2H), 2.58-2.51 (m, 2H), 1.46 (s, 9H).

Step-5: Synthesis of tert-butyl 3-(piperidin-4-yl)benzylcarbamate

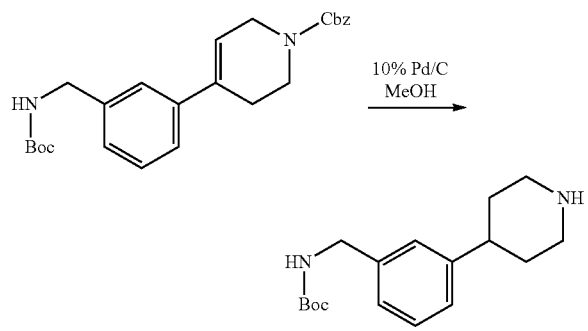

The benzyl 4-(3-(((tert-butoxycarbonyl)amino)methyl) phenyl)-5,6-dihydropyridine-1(2H)-carboxylate (2 g, 4.73 mmol) was dissolved in methanol (20 mL), 10% Pd/C (500 mg) was added and reaction mixture was stirred under hydrogen atmosphere (using a 2 L balloon pressure) for 1 h. TLC confirmed complete consumption of starting material. The reaction mixture was filtered over celite; solvent was evaporated in vacuo, and the crude was purified by column chromatography on basic alumina using 0-5% MeOH in CHCl$_3$ as eluent to yield tert-butyl 3-(piperidin-4-yl)benzylcarbamate (1.2 g, 87%).

1H NMR (400 MHz, CDCl3): δ 7.28-7.24 (m, 1H), 7.15-7.11 (m, 3H), 4.81 (bs, 1H), 4.30 (d, J=5.2 Hz, 2H), 3.18 (dt, J=2.0, 12.4 Hz, 2H), 2.73 (dt, J=2.0, 12.4 Hz, 2H), 2.61 (tt, J=3.2, 12.0 Hz, 1H), 1.83-1.59 (m, 4H), 1.46 (s, 9H).

Step-6: Synthesis of tert-butyl 3-(1-(3,4-dihydroxybenzoyl)piperidin-4-yl)benzylcarbamate

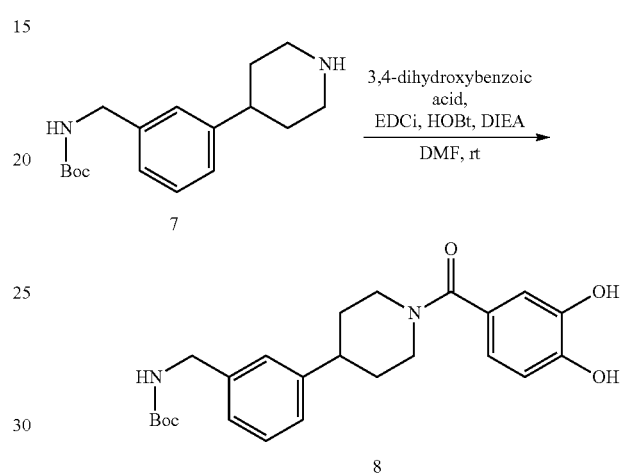

A mixture of tert-butyl 3-(piperidin-4-yl)benzylcarbamate (50 mg, 0.172 mmol), 3,4-dihydroxybenzoic acid (26 mg, 0.172 mmol), EDCI (49 mg, 0.258 mmol), HOBt (34 mg, 0.258 mmol), DIEA (0.06 mL, 0.344 mmol) in DMF (5 mL) was stirred at room temperature overnight. The reaction mixture was diluted with EtOAc and washed with water, brine, dried over Na2SO4, concentrated, and purified by silica gel column chromatography 0-5% MeOH in CHCl$_3$ as eluent to yield tert-butyl 3-(1-(3,4-dihydroxybenzoyl)piperidin-4-yl)benzylcarbamate (42 mg, 57%).

Step-7: Synthesis of tert-butyl 3-(1-(3,4-dihydroxybenzoyl)piperidin-4-yl)benzylcarbamate (Target-2)

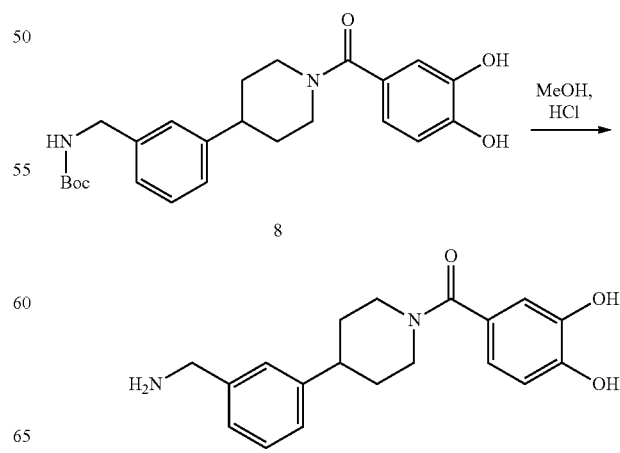

Tert-butyl 3-(1-(3,4-dihydroxybenzoyl)piperidin-4-yl)benzylcarbamate (80 mg, 0.187 mmol) in HPLC grade MeOH (2 mL) was treated with conc. HCl (0.2 mL) at room temperature. The reaction mixture was stirred at room temperature for 1 h. The solvent was evaporated in vacuo, and the residue was triturated with ether to yield tert-butyl 3-(1-(3,4-dihydroxybenzoyl)piperidin-4-yl)benzylcarbamate (30 mg, 49%) as a solid.

1H NMR (400 MHz, CD3OD): δ 7.39-7.28 (m, 4H), 6.89 (s, 1H), 6.82 (s, 2H), 4.10 (s, 2H), 3.30-3.95 (m, 4H), 1.89-1.70 (m, 4H).

LCMS: m/z [M+1]=327; 95.20% (R.T.=1.20)
Chromatographic Parameters
Mobile Phase A: 0.05% TFA in water, Mobile Phase B:0.05% TFA in Acetonitrile,
Flow rate: 1.2 ml/min; Temperature: Ambient,
Column: YMC ODS A, C18(50×4.6 mm) 3 uM, E-AC-2/08/COL/005

Gradient: Initial 20% B Conc to 95% B Conc. in 3.0 min. Hold for 0.5 min. At 3.51 min B. Conc. is 20%
HPLC: 95.63% (254 nm); 94.85% (220 nm); 96.00% (200-400 nm) (R.T.=4.28)
Column: Waters X-Bridge 150 mm×4.6 mm×5µ, ID: E-AC-3/09/COL/027
Mobile Phase: A. 10 mM Ammonium Formate in water+0.1% NH3
B. Acetonitrile+5% Solvent A+0.1% NH3
Inj. Vol: 10 µL, Col. Temp.: 40° C., Flow rate: 1.40 mL/min
Gradient:
5% B to 95% B in 8 min, Hold till 9.50 min, At 9.51 B Conc is 5% hold up to 12 min Example 30—Synthesis of (4-(3-(aminomethyl)phenyl)piperidin-1-yl)(3-(2,3-dihydroxypropoxy)phenyl)methanone (Target-3)

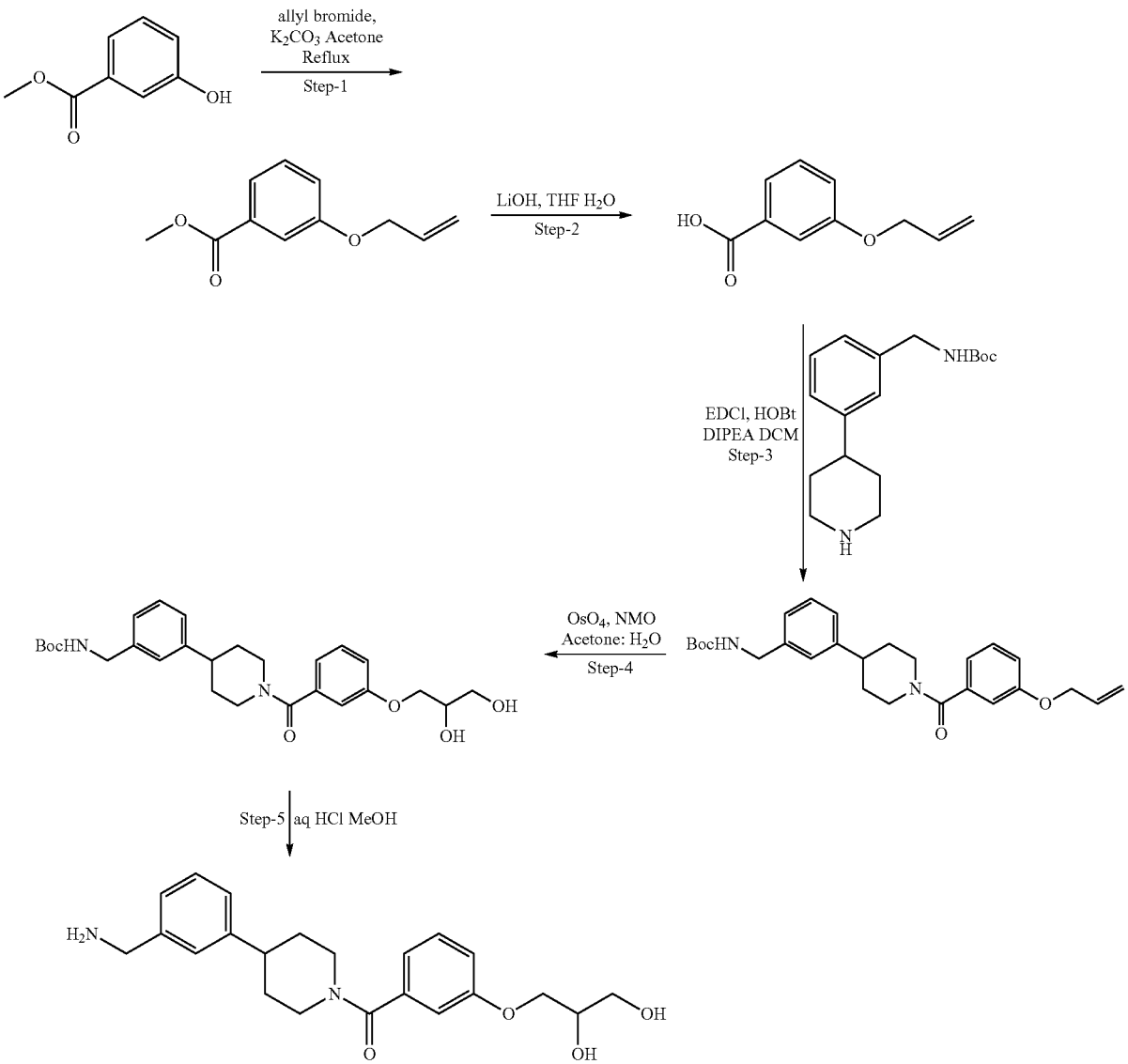

Reaction scheme

Step-1: Synthesis of methyl 3-(allyloxy)benzoate

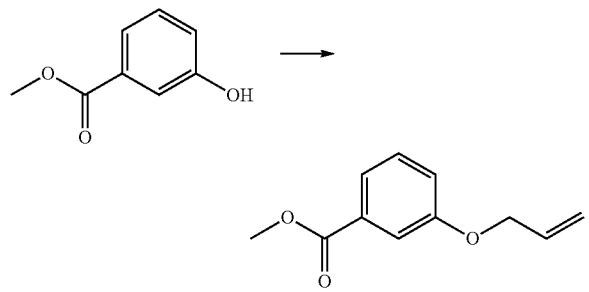

To a stirred solution of methyl-3-hydroxybenzoate (5 g, 32 mmol) in acetone (75 mL) at 0° C. anhydrous potassium carbonate (13.6 g, 98 mmol) followed by allyl bromide (3.6 mL, 42 mmol) was added. The reaction mixture was stirred for 15 min and then refluxed for 4 h. TLC (mobile phase 20% ethyl acetate in n-hexane) indicated absence of starting material (Rf 0.2) and product formation (Rf—0.5). The reaction mixture was filtered and concentrated. The compound was extracted in ethyl acetate and washed with water. The organic layer was dried over sodium sulfate, concentrated and purified by column chromatography using hexane:ethyl acetate as eluent. The product was obtained as oil. Yield: 6 g, 95.2%.

LCMS: (M+1) 192.9

$^1$H NMR (400 MHz, CDCl$_3$): δ 3.91 (s, 3H), 4.58 (d, 2H, J=5.2 Hz), 5.30 (d, 1H, J=10.4 Hz), 5.43 (d, 1H, J=17.2 Hz), 6.03-6.09 (m, 1H), 7.10-7.13 (dd, 1H, J=2 Hz, 8.4 Hz), 7.34 (t, 1H, J=7.8 Hz), 7.57 (s, 1H), 7.63 (d, 1H, J=8 Hz).

Step-2: Synthesis of 3-(allyloxy)benzoic acid

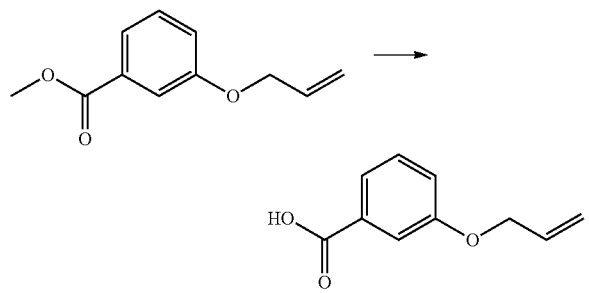

To a solution of methyl 3-(allyloxy)benzoate (2 g, 10.4 mmol) in THF: H$_2$O (15 mL: 15 mL), lithium hydroxide monohydrate (1.3 g, 31.2 mmol) was added and the reaction mixture was refluxed for 2 h. TLC (mobile phase 50% ethyl acetate in n-hexane) indicated absence of starting material (Rf 0.7) and product formation (Rf—0.5). The reaction mixture was concentrated to remove THF and the aqueous layer was acidified with 10% HCl to pH –2. Solid precipitated out, which was filtered, washed with hexane, and dried thoroughly to give the desired product as white solid. Yield: (1.46 g, 79%).

$^1$H NMR (400 MHz, CDCl$_3$): δ 4.61 (d, 2H, J=5.6 Hz), 5.32 (d, 1H, J=10 Hz), 5.44 (d, 1H, J=17.6 Hz), 6.02-6.12 (m, 1H), 7.17-7.20 (m, 1H), 7.39 (t, 1H, J=8 Hz), 7.64 (s, 1H), 7.73 (d, 1H, J=7.6 Hz).

Step-3: Synthesis of tert-butyl 3-(1-(3-(allyloxy)benzoyl)piperidin-4-yl)benzylcarbamate

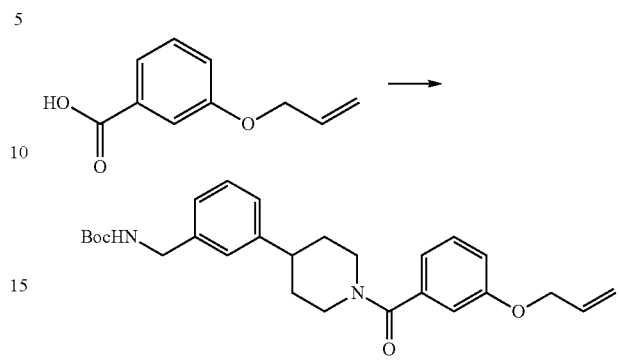

To a solution of 3-(allyloxy)benzoic acid (0.184 g, 1.03 mmol) in DCM (10 mL), tert-butyl 3-(piperidin-4-yl)benzylcarbamate (0.3 g, 1.03 mmol), EDCI (0.21 g, 1.13 mmol), HOBt (0.28 g, 2.06 mmol), DIPEA (0.45 mL, 2.58 mmol) were added and the reaction mixture was allowed to stir at room temperature overnight. TLC (mobile phase 50% ethyl acetate in n-hexane) indicated absence of starting material (Rf 0.5) and product formation (Rf—0.45). The reaction mixture was washed with water. The organic layer was separated, dried over sodium sulfate, concentrated, and purified by column chromatography using hexane ethyl acetate as eluent to give the desired product. (0.34 g, 74%).

LCMS: (M+Na) 473.4

$^1$H NMR (400 MHz, CDCl$_3$): δ 1.46 (s, 9H), 1.61-1.95 (m, 5H), 2.74-2.97 (m, 2H), 3.10 (br, 1H) 3.89 (br, 1H), 4.30 (d, 2H, J=4.8 Hz), 4.56 (d, 2H, J=5.2 Hz), 5.28-5.31 (m, 1H), 5.42 (d, 1H, J=16.8 Hz), 6.02-6.09 (m, 1H), 6.96-7.01 (m, 3H), 7.11-7.16 (m, 3H), 7.28-7.32 (m, 2H).

Step-4: Synthesis of tert-butyl 3-(1-(3-(2,3-dihydroxypropoxy)benzoyl)piperidin-4-yl)benzylcarbamate

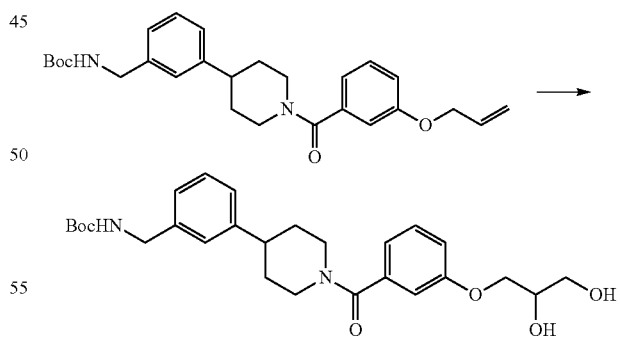

To a solution of tert-butyl 3-(1-(3-(allyloxy)benzoyl)piperidin-4-yl)benzylcarbamate (0.34 g, 0.75 mmol) in acetone (14 mL) and water (2 mL), OsO$_4$ (4% in water) (0.2 mL, 0.03 mmol), was added at room temperature. The reaction mixture was stirred for 15 min. NMO (50% aq solution) (0.2 mL, 0.9 mmol) was added drop wise and the reaction mixture was allowed to stir at room temperature overnight. TLC (mobile phase 50% ethyl acetate in n-hexane) indicated absence of starting material (Rf 0.6) and product formation (Rf—0.2). 10% sodium bisulphite solution (40 mL) was added and the reaction mixture was stirred for 10 min. The compound was extracted in ethyl acetate. The organic layer was dried over sodium sulfate and concentrated. The compound was purified by column chromatography using hexane:ethyl acetate as eluent to give the desired product as white solid. (0.3 g, 83.3%)

LCMS: (M+1) 485.4

$^1$H NMR (400 MHz, CDCl$_3$): δ 1.46 (s, 9H), 1.78-2.04 (m, 4H), 2.74-2.97 (m, 4H), 3.11 (br, 1H), 3.72-3.85 (m, 3H), 4.05-4.13 (m, 3H), 4.30 (d, 2H, J=4.8 Hz), 4.86 (br, 2H), 6.95-7.02 (m, 3H), 7.11-7.13 (m, 3H), 7.26-7.34 (m, 2H).

Step-5: Synthesis of (4-(3-(aminomethyl)phenyl)piperidin-1-yl)(3-(2,3-dihydroxypropoxy)phenyl)methanone

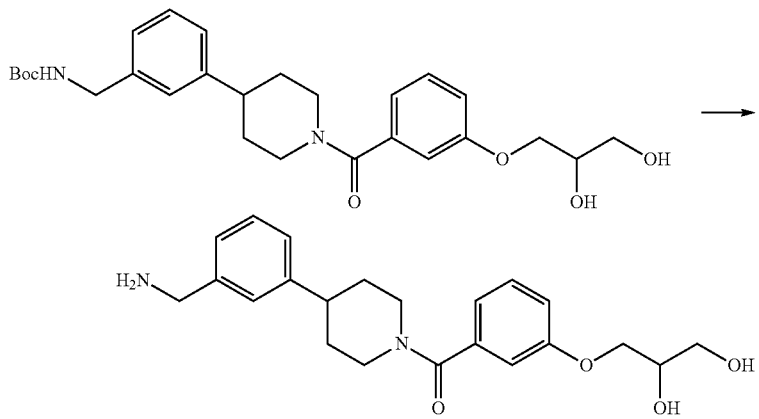

To a solution of tert-butyl 3-(1-(3-(2,3-dihydroxypropoxy)benzoyl)piperidin-4-yl)benzylcarbamate (0.02 g, 0.04 mmol) in methanol (1 mL) aqueous HCl (0.2 mL) was added drop wise. The reaction mixture was stirred at room temperature for 2 h. TLC (mobile phase 100% ethyl acetate) indicated absence of starting material (Rf 0.7). The reaction mixture was lyophilized to give desired product as HCl salt (0.012 g, 80%)

LCMS: (M+Na) 407.2

HPLC purity: 98.9% (220 nm)

$^1$H NMR (400 MHz, CD$_3$OD): δ 1.69-1.96 (m, 4H), 2.93-2.96 (m, 2H), 3.67 (br, 2H), 3.84-4.10 (m, 7H), 4.79 (br, 2H), 6.99-7.08 (m, 3H), 7.29-7.38 (m, 5H).

Example 31—Synthesis of 1-(3-(4-(3-(aminomethyl)phenyl)piperidine-1-carbonyl)phenoxy)-3-hydroxypropan-2-one (Target-4)

Reaction scheme

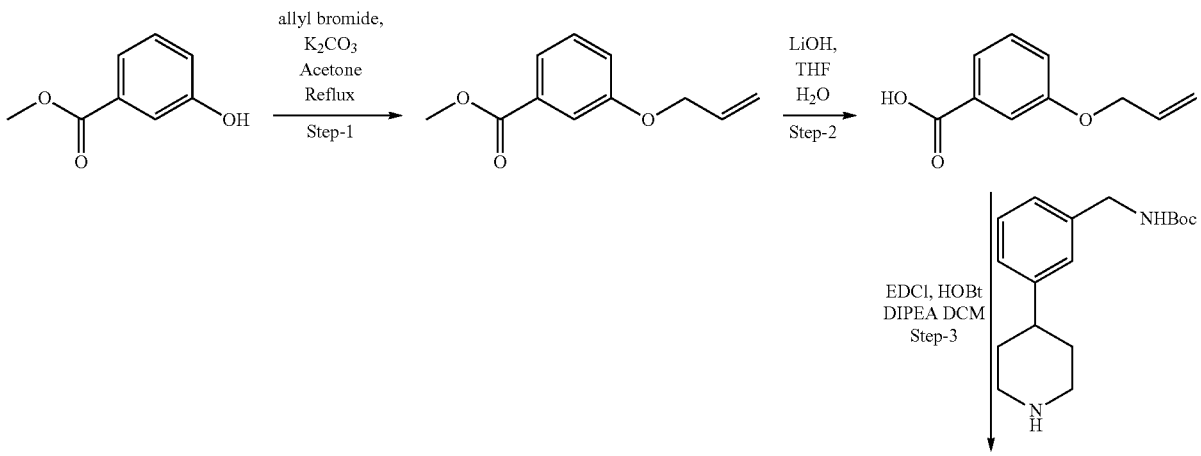

397

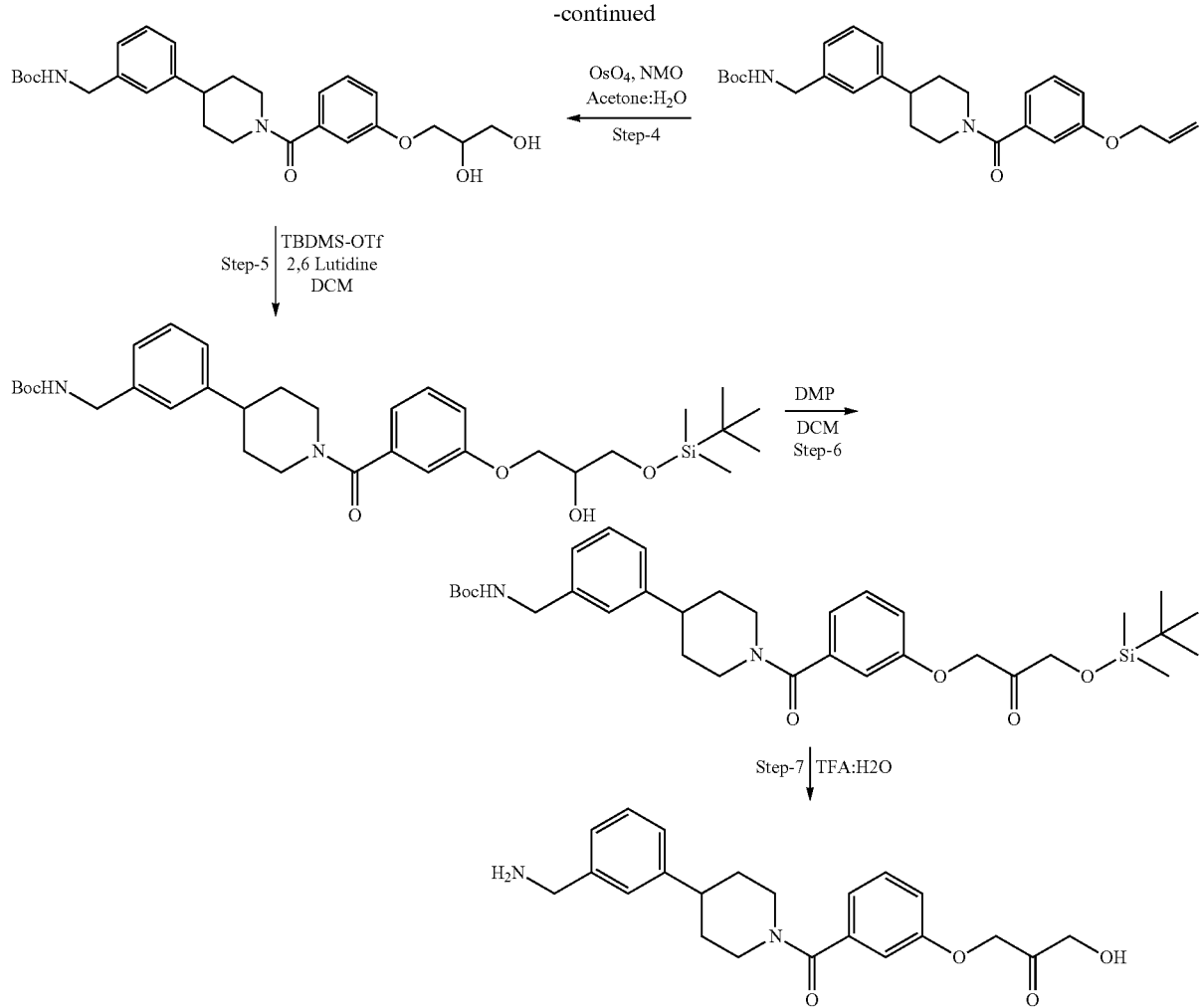

398

-continued

Experimental

Step-1: Synthesis of methyl 3-(allyloxy)benzoate

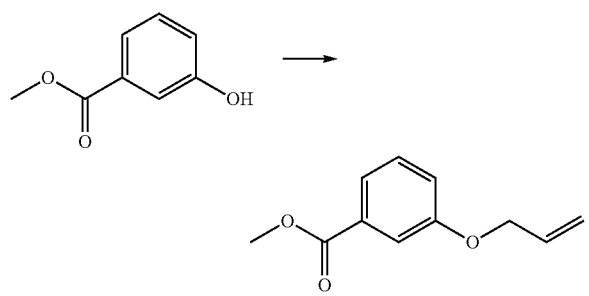

To a stirred solution of methyl-3-hydroxybenzoate (5 g, 32 mmol) in acetone (75 mL) at 0° C. anhydrous potassium carbonate (13.6 g, 98 mmol) followed by allyl bromide (3.6 mL, 42 mmol) were added. The reaction mixture was stirred for 15 min and then refluxed for 4 h. TLC (mobile phase 20% ethyl acetate in n-hexane) indicated absence of starting material (Rf 0.2) and product formation (Rf—0.5). The reaction mixture was filtered and concentrated. The compound was extracted in ethyl acetate and washed with water. The organic layer was dried over sodium sulfate, concentrated and purified by column chromatography using hexane:ethyl acetate as eluent. The product was obtained as a pale yellow oil (6 g, 95.2%)

LCMS: (M+1) 192.9

$^1$H NMR (400 MHz, CDCl$_3$): δ 3.91 (s, 3H), 4.58 (d, 2H, J=5.2 Hz), 5.30 (d, 1H, J=10.4 Hz), 5.43 (d, 1H, J=17.2 Hz), 6.03-6.09 (m, 1H), 7.10-7.13 (dd, 1H, J=2 Hz, 8.4 Hz), 7.34 (t, 1H, J=7.8 Hz), 7.57 (s, 1H), 7.63 (d, 1H, J=8 Hz).

Step-2: Synthesis of 3-(allyloxy)benzoic acid

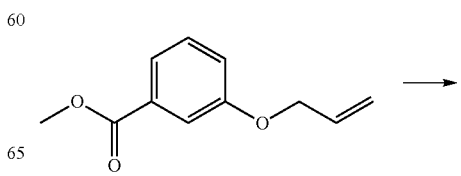

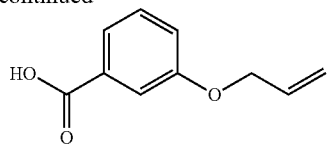

To a solution of methyl 3-(allyloxy)benzoate (2 g, 10.4 mmol) in THF: H₂O (15 mL: 15 mL), lithium hydroxide monohydrate (1.3 g, 31.2 mmol) was added, and the reaction mixture was refluxed for 2 h. TLC (mobile phase 50% ethyl acetate in n-hexane) indicated absence of starting material (Rf 0.7) and product formation (Rf—0.5). The reaction mixture was concentrated to remove THF and the aqueous layer was acidified with 10% HCl to pH 2. Solid precipitated out, which was filtered, washed with hexane, and dried thoroughly to give the desired product as white solid. (1.46 g, 79%)

¹H NMR (400 MHz, CDCl₃): δ 4.61 (d, 2H, J=5.6 Hz), 5.32 (d, 1H, J=10 Hz), 5.44 (d, 1H, J=17.6 Hz), 6.02-6.12 (m, 1H), 7.17-7.20 (m, 1H), 7.39 (t, 1H, J=8 Hz), 7.64 (s, 1H), 7.73 (d, 1H, J=7.6 Hz).

Step-3: Synthesis of tert-butyl 3-(1-(3-(allyloxy) benzoyl)piperidin-4-yl)benzylcarbamate

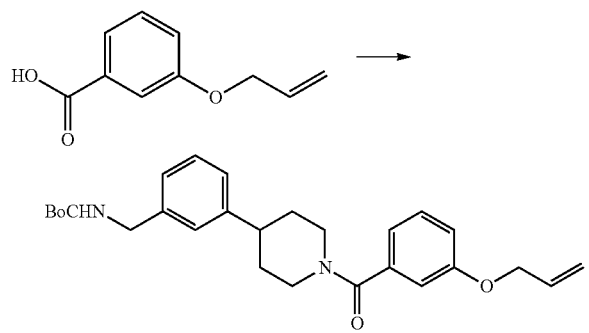

To a solution of 3-(allyloxy)benzoic acid (0.184 g, 1.03 mmol) in DCM (10 mL), tert-butyl 3-(piperidin-4-yl)benzylcarbamate (0.3 g, 1.03 mmol), EDCI (0.21 g, 1.13 mmol), HOBt (0.28 g, 2.06 mmol), DIPEA (0.45 mL, 2.58 mmol) were added and the reaction mixture was allowed to stir at room temperature overnight. TLC (Mobile phase 50% ethyl acetate in n-hexane) indicated absence of starting material (Rf 0.5) and product formation (Rf—0.45). The reaction mixture was washed with water. The organic layer was separated, dried over sodium sulfate, concentrated, and purified by column chromatography using hexane ethyl acetate as eluent to give the desired product (0.34 g, 74%)

LCMS: (M+Na) 473.4

¹H NMR (400 MHz, CDCl₃): δ 1.46 (s, 9H), 1.61-1.95 (m, 5H), 2.74-2.97 (m, 2H), 3.10 (br, 1H) 3.89 (br, 1H), 4.30 (d, 2H, J=4.8 Hz), 4.56 (d, 2H, J=5.2 Hz), 5.28-5.31 (m, 1H), 5.42 (d, 1H, J=16.8 Hz), 6.02-6.09 (m, 1H), 6.96-7.01 (m, 3H), 7.11-7.16 (m, 3H), 7.28-7.32 (m, 2H).

Step-4: Synthesis of tert-butyl 3-(1-(3-(2,3-dihydroxypropoxy)benzoyl)piperidin-4-yl)benzylcarbamate

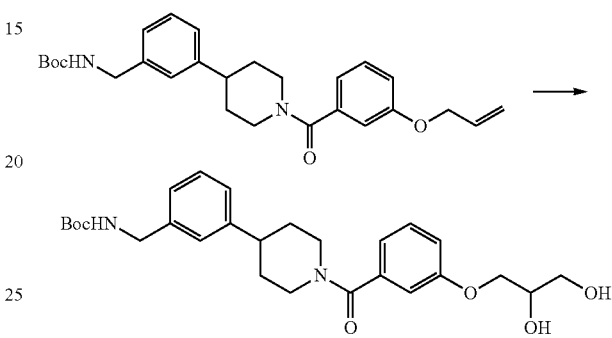

To a solution of tert-butyl 3-(1-(3-(allyloxy)benzoyl)piperidin-4-yl)benzylcarbamate (0.34 g, 0.75 mmol) in acetone (14 mL) and water (2 mL), OsO₄ (4% in water, 0.2 mL, 0.03 mmol) was added at room temperature. The reaction mixture was stirred for 15 min. NMO (50% aq solution, 0.2 mL, 0.9 mmol) was added drop wise and the reaction mixture was allowed to stir at room temperature overnight. TLC (mobile phase 50% ethyl acetate in n-hexane) indicated absence of starting material (Rf 0.6) and product formation (Rf—0.2). 10% sodium bisulphite solution (40 mL) was added and the reaction mixture was stirred for 10 min. The compound was extracted in ethyl acetate. The organic layer was dried over sodium sulfate and concentrated. The compound was purified by column chromatography using Hexane:ethyl acetate as eluent to give the desired product as white solid (0.3 g, 83.3%)

LCMS: (M+1) 485.4

¹H NMR (400 MHz, CDCl₃): δ 1.46 (s, 9H), 1.78-2.04 (m, 4H), 2.74-2.97 (m, 4H), 3.11 (br, 1H), 3.72-3.85 (m, 3H), 4.05-4.13 (m, 3H), 4.30 (d, 2H, J=4.8 Hz), 4.86 (br, 2H), 6.95-7.02 (m, 3H), 7.11-7.13 (m, 3H), 7.26-7.34 (m, 2H).

Step-5: Synthesis of tert-butyl 3-(1-(3-(3-((tert-butyldimethylsilyl)oxy)-2-hydroxypropoxy)benzoyl) piperidin-4-yl)benzylcarbamate

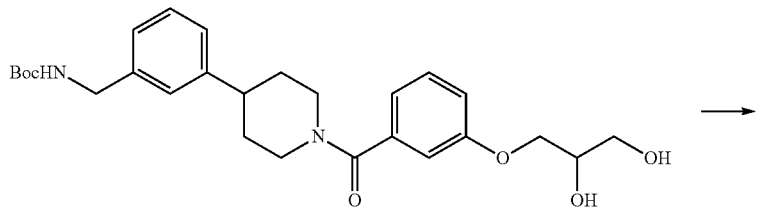

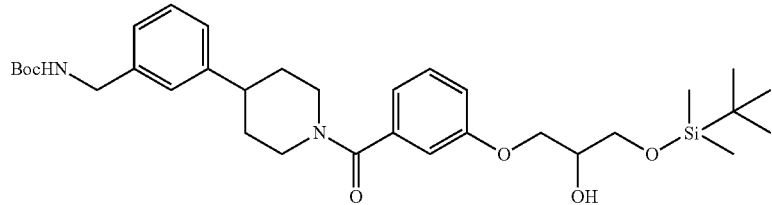

To a solution of tert-butyl 3-(1-(3-(2,3-dihydroxypropoxy)benzoyl)piperidin-4-yl)benzylcarbamate (0.2 g, 0.4 mmol) in dry DCM (8 mL), 2,6 lutidine (0.14 mL, 1.23 mmol) was added and stirred for 15 min. The reaction mixture was cooled to −78° C. TBDMS-OTf (0.18 mL, 0.82 mmol) was added and the reaction mixture was left as such 1 hr. TLC (Mobile phase 100% ethyl acetate) indicated slight presence of starting material (Rf 0.5) and product formation (Rf—0.8). The reaction mixture was washed with copper sulfate solution (4 times) till TLC showed absence of 2, 6 lutidine. The organic layer was separated, dried over sodium sulfate and concentrated. The compound was used as such for further reaction without purification (0.3 g, Crude).

LCMS: (M+Na) 621.2

Step-6: Synthesis of tert-butyl 3-(1-(3-(3-((tert-butyldimethylsilyl)oxy)-2-oxopropoxy)benzoyl)piperidin-4-yl)benzylcarbamate

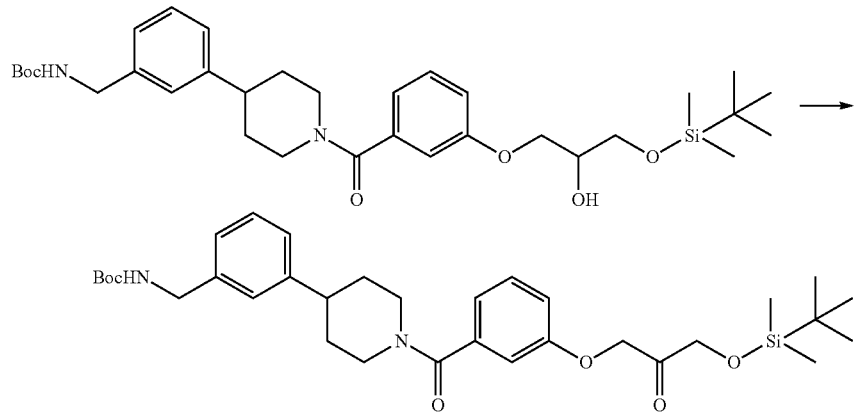

To a solution of tert-butyl 3-(1-(3-(3-((tert-butyldimethylsilyl)oxy)-2-hydroxypropoxy)benzoyl)piperidin-4-yl)benzylcarbamate (0.24 g, 0.4 mmol) in dry DCM (8 mL), Dess-Martin periodinane (0.51 g, 1.2 mmol) was added and the reaction mixture was stirred at room temperature overnight. TLC (mobile phase 50% ethyl acetate in hexane) indicated slight presence of starting material (Rf 0.4) and product formation (Rf—0.7). The reaction mixture was washed with saturated solution of sodium bicarbonate (3 times). The organic layer was dried over sodium sulfate, concentrated, and purified by column chromatography using hexane ethyl acetate as eluent to give the desired product. The product was obtained in 90% purity by LCMS. Yield: 0.15 g (63%).

LCMS: (M+Na) 618.9

$^1$H NMR (400 MHz, CDCl$_3$): δ 0.12 (s, 6H), 0.9 (s, 9H), 1.46 (s, 9H), 1.95-2.06 (m, 4H), 2.74-2.80 (m, 3H), 3.10 (br, 1H), 3.87 (br, 1H), 4.30 (d, 2H, J=4.8 Hz), 4.43 (s, 2H), 4.7-4.9 (m, 3H), 6.92-6.99 (m, 3H), 7.12-7.15 (m, 3H), 7.26-7.34 (m, 2H).

Step-7: Synthesis of 1-(3-(4-(3-(aminomethyl)phenyl)piperidine-1-carbonyl)phenoxy)-3-hydroxypropan-2-one

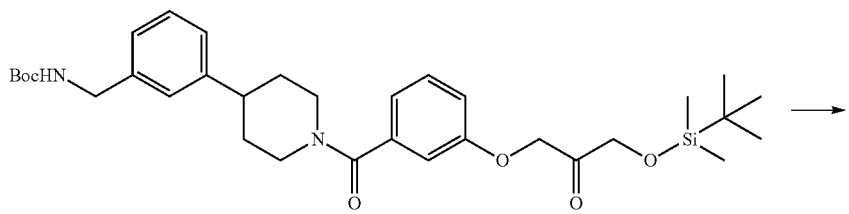

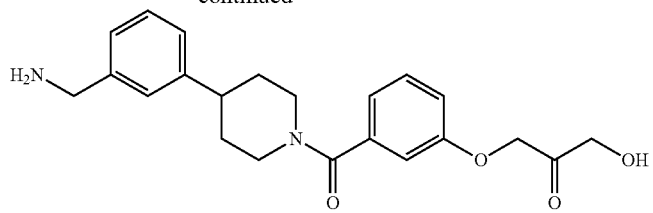

A solution of tert-butyl 3-(1-(3-(3-((tert-butyldimethylsilyl)oxy)-2-oxopropoxy)benzoyl)piperidin-4-yl)benzylcarbamate (0.09 g, 0.15 mmol) in TFA (12 mL) and water (1.3 mL) was stirred at room temperature for 1 h. TLC (mobile phase 50% ethyl acetate in hexane) indicated absence of starting material (Rf 0.7). The reaction mixture was concentrated and triturated with ether (4 times). Ether was decanted and the compound was dried under high vacuum. Yield: (0.04 g, 70%).

LCMS: (M+1) 383.3

HPLC purity: 96% (210-400 nm).

$^1$H NMR (400 MHz, CD$_3$OD): δ 1.69-1.96 (m, 5H), 2.92-2.95 (m, 2H), 3.46-3.99 (m, 4H, trace Quantity of ether present), 4.05-4.10 (m, 3H), 4.85 (m, 4H embedded in the solvent signal), 7.00-7.42 (m, 8H).

Example 32—Synthesis of N-(3-(4-(3-(aminomethyl)phenyl)piperidine-1-carbonyl)phenyl)-2,3-dihydroxypropanamide (Target-5)

Synthesis of N-(3-(4-(3-(aminomethyl)phenyl)piperidine-1-carbonyl)phenyl)-2,3-dihydroxypropanamide was carried out as shown in the scheme below. Detailed experimental procedure and analytical data is as follows.

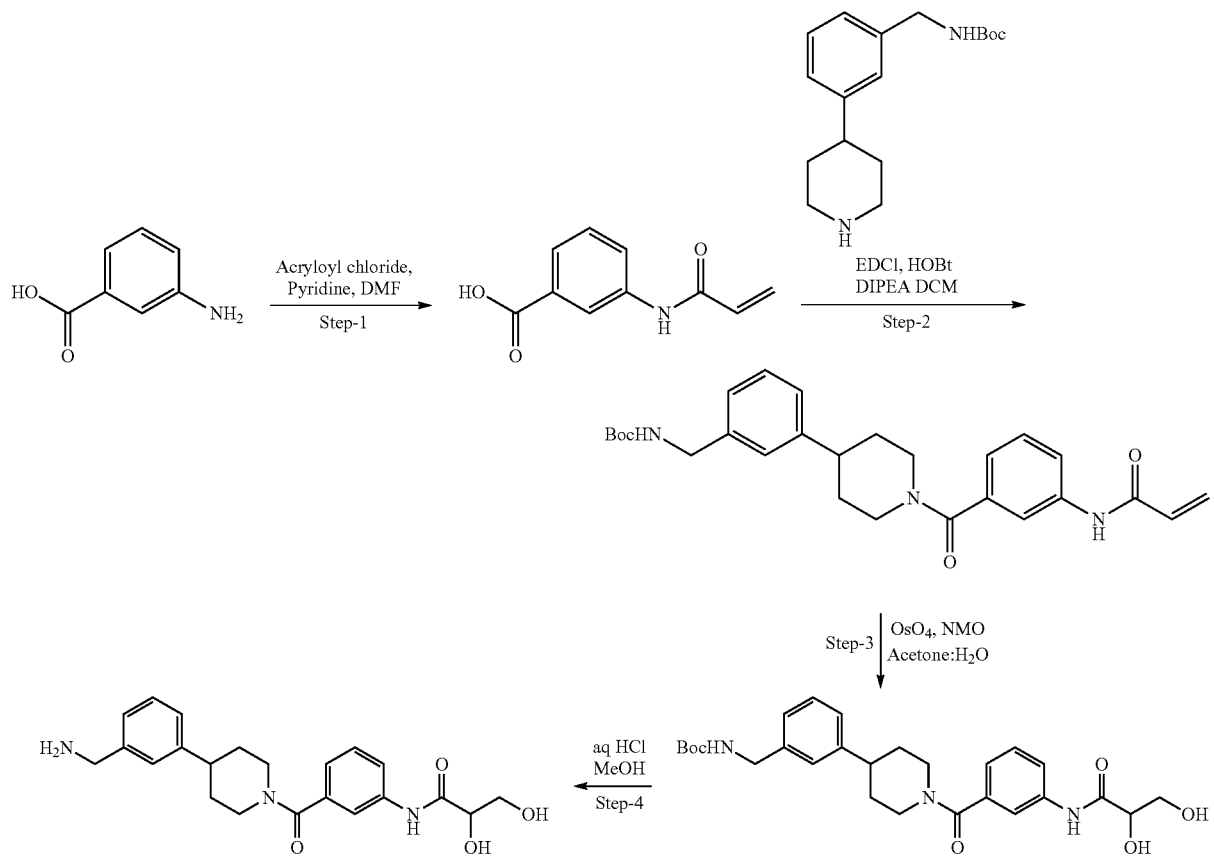

Experimental

Step-1: Synthesis of 3-acrylamidobenzoic acid

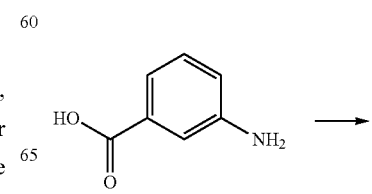

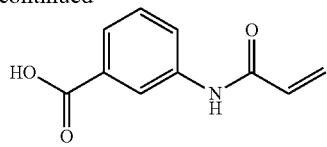

To a stirred solution of 3-amino benzoic acid (2.8 g, 20.4 mmol) in DMF (20 mL) and pyridine (1 mL) at 0° C. acryloyl chloride (1.6 mL, 20.4 mmol) was added. The reaction mixture was allowed to stir as such for 2 h. TLC (mobile phase 100% ethyl acetate) indicated absence of starting material (Rf 0.2) and product formation (Rf—0.4). The reaction mixture was poured into 200 mL of water and the off white solid obtained was filtered, washed with water, ether and dried.
Yield: 2.3 g, 59%.
LCMS: (M+1) 191.9
$^1$H NMR (400 MHz, DMSO-d$_6$): δ 5.76-5.79 (dd, 1H, J=1.6, 10 Hz), 6.26-6.30 (dd, 1H, J=1.4, 16.6 Hz), 6.40-6.47 (dd, 1H, J=10.2, 16 Hz), 7.44 (t, 1H, J=7.8 Hz), 7.64 (d, 1H, J=7.6 Hz), 7.91 (d, 1H, J=7.2 Hz), 8.29 (s, 1H), 10.33 (br, 1H).

Step-2: Synthesis of tert-butyl 3-(1-(3-acrylamido-benzoyl)piperidin-4-yl)benzylcarbamate

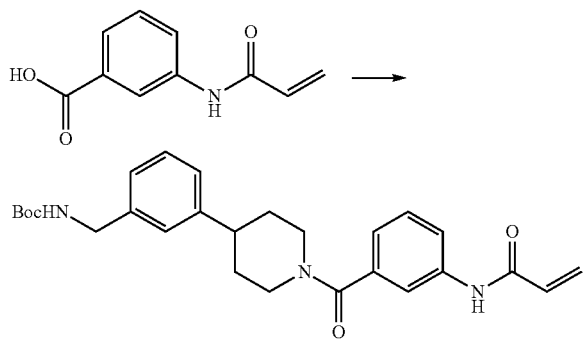

To a solution of 3-acrylamidobenzoic acid (0.5 g, 2.61 mmol) in DCM (10 mL), tert-butyl 3-(piperidin-4-yl)benzylcarbamate (0.75 g, 2.61 mmol), EDCI (0.55 g, 2.87 mmol), HOBt (0.7 g, 5.23 mmol), DIPEA (1.1 mL, 6.54 mmol) were added and the reaction mixture was allowed to stir at room temperature for 2 h. TLC (Mobile phase 100% ethyl acetate) indicated absence of starting material (Rf 0.4) and product formation (Rf—0.6). The reaction mixture was washed with water. The organic layer was separated, dried over sodium sulfate, concentrated, and purified by column chromatography using hexane ethyl acetate as eluent to give the desired product.
Yield: (0.68 g, 56%).
LCMS: (M+Na) 486.1

$^1$H NMR (400 MHz, CDCl$_3$): δ 1.46 (s, 9H), 1.61-1.95 (m, 5H), 2.74-2.85 (m, 2H), 3.11 (m, 1H), 3.85-3.90 (m, 1H), 4.3 (d, 2H, J=5.6 Hz), 4.8-4.9 (br, 2H), 5.74 (d, 1H, J=10 Hz), 6.27-6.33 (dd, 1H, J=10, 16.8 Hz), 6.43 (d, 1H, J=16.8 Hz), 7.10-7.15 (m, 4H), 7.28-7.35 (m, 2H), 7.54 (s, 1H), 7.74 (d, 1H, J=8 Hz), 8.39 (bs, 1H).

Step-3: Synthesis of tert-butyl 3-(1-(3-(2,3-dihydroxypropanamido)benzoyl)piperidin-4-yl)benzylcarbamate

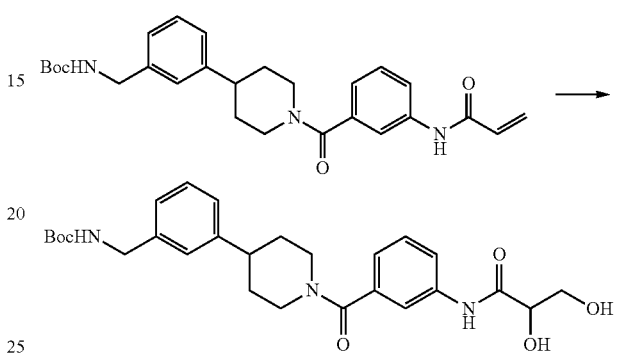

To a solution of tert-butyl 3-(1-(3-acrylamidobenzoyl)piperidin-4-yl)benzylcarbamate (0.68 g, 1.46 mmol) in acetone (21 mL) and water (3 mL), OsO$_4$ (4% in water, 0.38 mL, 0.05 mmol) was added at room temperature. The reaction mixture was stirred for 15 min. NMO (50% aq solution, 0.4 mL, 1.76 mmol) was added drop wise and the reaction mixture was allowed to stir at room temperature overnight. TLC (mobile phase 100% ethyl acetate) indicated absence of starting material (Rf 0.6) and product formation (Rf—0.3). 10% sodium bisulphite solution (80 mL) was added and the reaction mixture was stirred for 10 min. The compound was extracted in ethyl acetate. The organic layer was dried over sodium sulfate and concentrated. The compound was purified by column chromatography using hexane:ethyl acetate as eluent to give the desired product as white solid.
Yield: (0.55 g, 76.3%).
LCMS: (M+Na) 520.1
$^1$H NMR (400 MHz, CDCl$_3$): δ 1.46 (s, 9H), 1.61-1.95 (m, 5H), 2.75-2.86 (m, 3H), 3.13 (m, 1H), 3.81-3.91 (m, 2H), 4.09-4.15 (m, 1H), 4.3 (d, 2H, J=5.6 Hz), 4.88 (bs, 3H), 7.10-7.13 (m, 4H), 7.26-7.41 (m, 3H), 7.77 (s, 1H), 8.74 (br, 1H).

Step-4: Synthesis of N-(3-(4-(3-(aminomethyl)phenyl)piperidine-1-carbonyl)phenyl)-2,3-dihydroxypropanamide

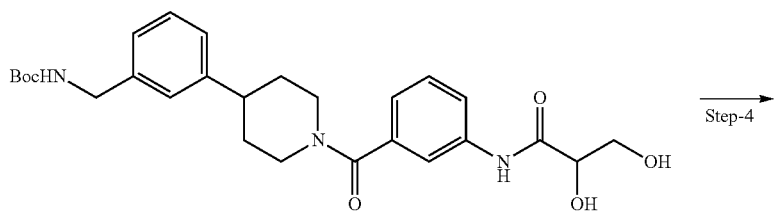

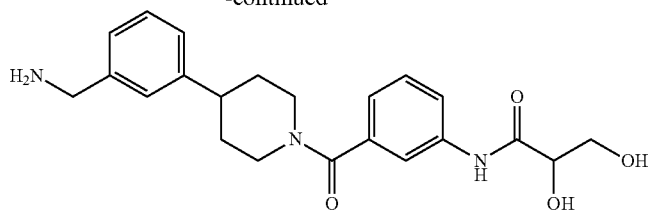

To a solution of tert-butyl 3-(1-(3-(2,3-dihydroxypropanamido)benzoyl)piperidin-4-yl)benzylcarbamate (0.05 g, 0.1 mmol) in methanol (2 mL) aqueous HCl (0.2 mL) was added drop wise. The reaction mixture was stirred at room temperature for 2 h. TLC (mobile phase 100% ethyl acetate) indicated absence of starting material (Rf 0.3). The reaction mixture was concentrated and purified by Preparative HPLC (neutral method) to give the desired product as HCl salt. Yield: (0.025 g, 64.1%).

LCMS: (M+Na) 420.1

HPLC purity: 96.2% (220 nm)

$^1$H NMR (400 MHz, CD$_3$OD): δ 1.75-1.96 (m, 4H), 2.89-2.98 (m, 3H), 3.82 (d, 2H, J=3.6 Hz), 3.87-3.90 (m, 1H), 4.19-4.21 (m, 1H), 4.71 (bs, 3H, embedded in solvent signal), 7.19 (d, 1H, J=8 Hz), 7.28-7.45 (m, 6H), 7.60 (d, 1H, J=8.4 Hz), 7.93 (bs, 1H), 8.51 (br, 1H).

Example 33—Synthesis of 4-(aminomethyl)-N-(4-(3-((3R,4R)-3,4-dihydroxypyrrolidin-1-yl)-3-oxo-propoxy)benzyl)benzamide (Target-9)

Synthetic Scheme:

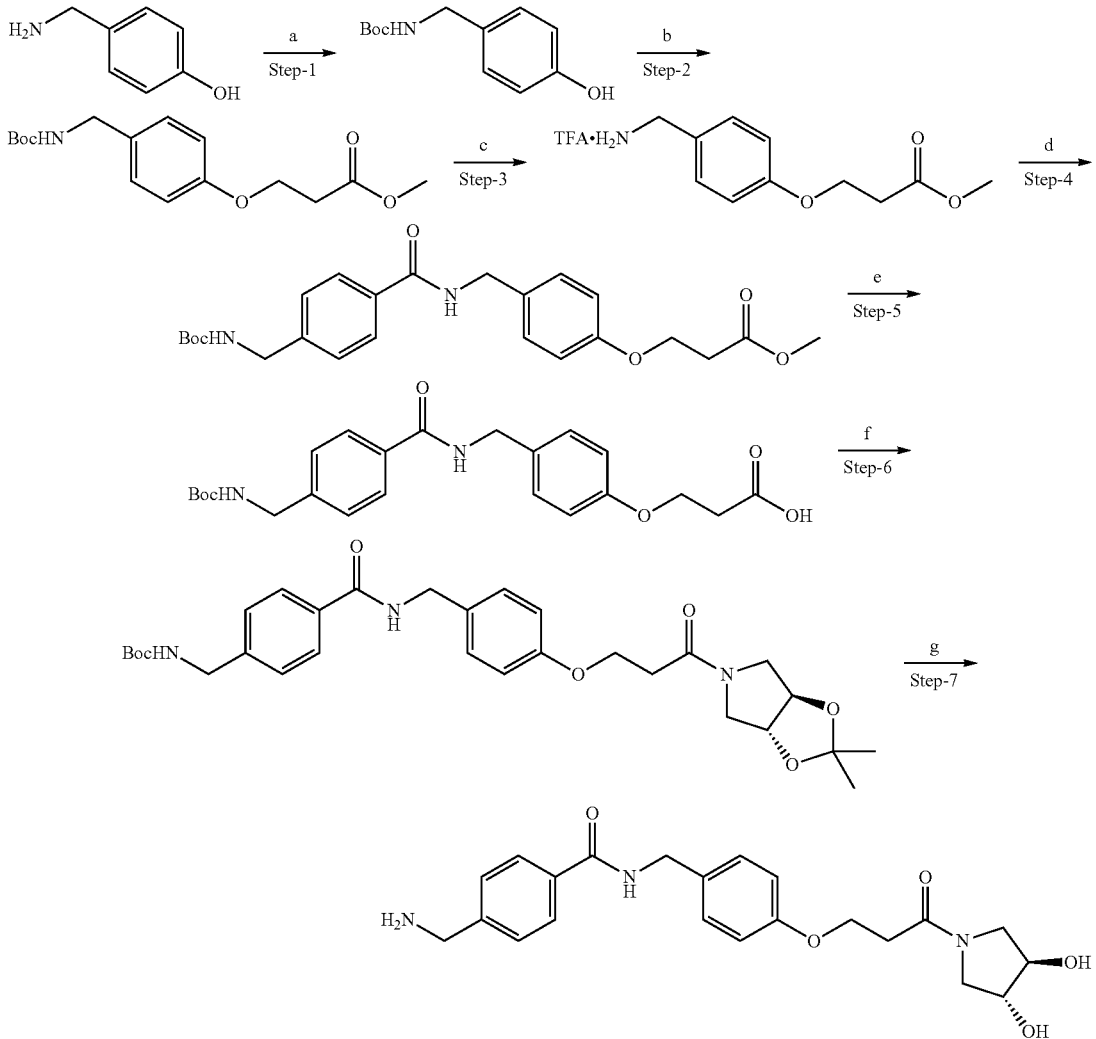

Reagents and Conditions:

a) (Boc)$_2$O, Et$_3$N, CH$_2$Cl$_2$, room temperature, 5 h; b) methyl acrylate, Na metal, hydroquinone, reflux, 48 h; c) TFA, CH$_2$Cl$_2$, 0° C.-room temperature, 3 h; d) 4-(((tert-butoxycarbonyl)amino)methyl)benzoic acid, HATU, DIEA, DMF, room temperature, 15 h; e) LiOH.H$_2$O, MeOH:H$_2$O, room temperature, 5 h; f) (3aR,6aR)-2,2-dimethyltetrahydro-3aH-[1,3]dioxolo[4,5-c]pyrrole, PyBOP, DMSO, room temperature, h; g) 2 N HCl, MeOH, room temperature, 2 h.

Experimental Procedure

Step-1: Tert-butyl 4-hydroxybenzylcarbamate

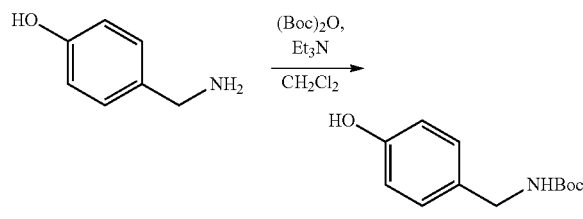

To a stirred solution of 4-(aminomethyl)phenol (5 g, 40.60 mmol) in CH$_2$Cl$_2$ (100 mL) was added Et$_3$N (17.36 mL, 121.80 mmol) followed by (Boc)$_2$O (10.85 mL, 48.72 mmol) dropwise at 0° C. under inert atmosphere. The resulting solution was allowed to stir at room temperature for 3 h. The reaction mixture was diluted with CH$_2$Cl$_2$, washed successively with saturated citric acid solution and H$_2$O, brine, dried over anhydrous sodium sulfate, concentrated under reduced pressure. The crude material was purified by silica gel column chromatography (5-10% MeOH in CHCl$_3$) to afford tert-butyl 4-hydroxybenzylcarbamate (5.2 g, 57%).

$^1$H NMR (400 MHz, CD3OD): δ 7.08 (d, J=8.4 Hz, 1H), 6.72 (d, J=8.4 Hz, 1H), 4.11 (s, 2H), 1.44 (s, 9H).

Step-2: Synthesis of methyl 3-(4-(((tert-butoxycarbonyl)amino)methyl)phenoxy)propanoate

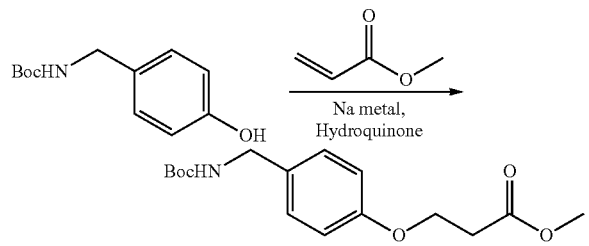

To a stirred solution of tert-butyl 4-hydroxybenzylcarbamate (5 g, 22.4 mmol) in methyl acrylate (80 mL) was added Na metal (0.103 g, 4.48 mmol) followed by hydroquinone (50 mg, 0.45 mmol) under inert atmosphere and refluxed for 48 h. The volatiles were evaporated under reduced pressure and the crude compound was purified by silica gel column chromatography (20-40% EtOAc in hexane) to afford methyl 3-(4-(((tert-butoxycarbonyl)amino)methyl)phenoxy)propanoate yield:—2.1 g (30%).

LCMS: m/z [M+Na]=332; 78.28% (R.T.=2.73 min.)
Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18 (50×4.6 mm) 3 uM, E-AC-2/08/COL/005
Gradient: Initial 20% B Conc to 95% B Conc. in 3.0 min. Hold for 0.5 min. At 3.51 min
B. Conc. is 20%

Step-3: Methyl 3-(4-(aminomethyl)phenoxy)propanoate trifluoroacetic acid salt

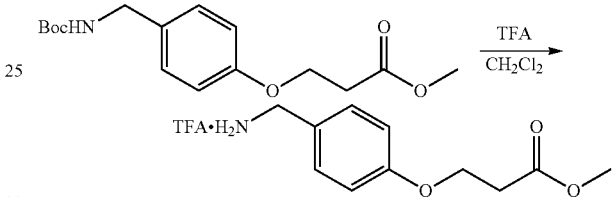

To a stirred solution of methyl 3-(4-(((tert-butoxycarbonyl)amino)methyl)phenoxy)propanoate (2.0 g, 6.47 mmol) in CH$_2$Cl$_2$ (15 ml) was added TFA (2.0 mL) dropwise at 0° C. under inert atmosphere. The resulting solution was allowed to stir at room temperature for 20 minutes. The volatiles were evaporated under reduced pressure to afford 1.6 g methyl 3-(4-(aminomethyl)phenoxy)propanoate. The crude compound was taken to the next step without any further purification.

LCMS: m/z [M+1]=210; 13.83% (R.T.=0.60 min.)
Chromatographic Parameters
Mobile Phase A: 0.05% TFA in water, Mobile Phase B: 0.05% TFA in acetonitrile,
Flow rate: 1.2 ml/min; Temperature: Ambient,
Column: YMC ODS A, C18 (50×4.6 mm) 3 uM, E-AC-2/08/COL/005
Gradient: Initial 20% B Cone to 95% B Conc. in 3.0 min. Hold for 0.5 min. At 3.51 min
B. Conc. is 20%

Step-4: Synthesis of methyl 3-(4-((4-(((tert-butoxycarbonyl)amino)methyl)benzamido)methyl)phenoxy)propanoate

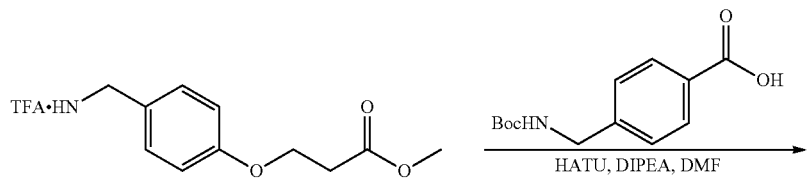

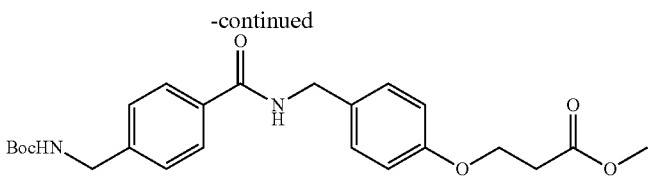

To a stirred solution of methyl 3-(4-(aminomethyl)phenoxy)propanoate (0.83 g, 2.71 mmol) in DMF (5 mL) were added DIEA (1.33 mL, 7.32 mmol) and 4-((tert-butoxycarbonylamino)methyl)benzoic acid (0.68 g, 2.71 mmol) followed by HATU (1.13 g, 2.98 mmol) at 0° C. under inert atmosphere. The resulting solution was allowed to stir at room temperature for 16 h. The reaction mixture was poured on crushed ice and extracted with EtOAc. The combined organic layer was washed with H₂O, brine, dried over anhydrous sodium sulfate and concentrated under reduced pressure. The crude compound was purified by silica gel column chromatography (2-5% MeOH in CHCl₃) to afford methyl 3-(4-((4-(((tert-butoxycarbonyl)amino)methyl)benzamido)methyl)phenoxy)propanoate (0.54 g, 46%).

LCMS: m/z [M+Na]=465; 88.52% (R.T.=2.63 min.)

Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18 (50×4.6 mm) 3 uM, E-AC-2/08/COL/005
Gradient: Initial 20% B Cone to 95% B Conc. in 3.0 min. Hold for 0.5 min. At 3.51 min
B. Conc. is 20%

Step-5: Synthesis of 3-(4-((4-(((tert-butoxycarbonyl)amino)methyl)benzamido)methyl)phenoxy)propanoic acid

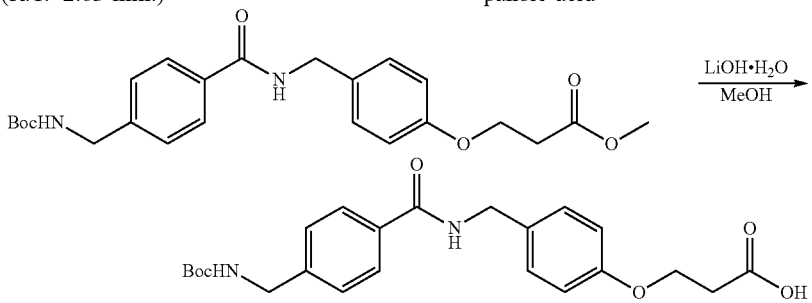

To a stirred solution of methyl 3-(4-((4-(((tert-butoxycarbonyl)amino)methyl)benzamido)methyl)phenoxy)propanoate (0.54 g, 1.22 mmol) in MeOH (5 mL) was added lithium hydroxide monohydrate (0.15 g, 3.64 mmol) at 0° C. The resulting reaction mixture was allowed to stirr at room temperature for 2 h. The volatiles were evaporated under reduced pressure and the residue was neutralized with 1N HCl at 0° C. The precipitated solid was filtered, washed with 50% EtOAc/hexane, and dried under vacuum to afford 3-(4-((4-(((tert-butoxycarbonyl)amino)methyl)benzamido)methyl)phenoxy)propanoic acid (0.52 g, 86%) as a white solid.

LCMS: m/z [M+Na]=452; 90.79% (R.T.=2.28 min.)
Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Conc to 95% B Conc. in 3.0 min. Hold for 0.5 min. At 3.51 min
B. Conc. is 20%

Step-6: Tert-butyl 4-((4-(3-((3aR,6aR)-2,2-dimethyldihydro-3aH-[1,3]dioxolo[4,5-c]pyrrol-5(4H)-yl)-3-oxopropoxy)benzyl)carbamoyl)benzylcarbamate

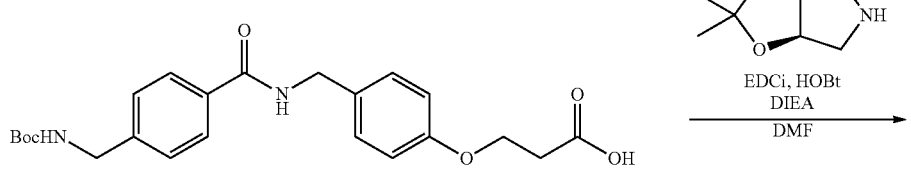

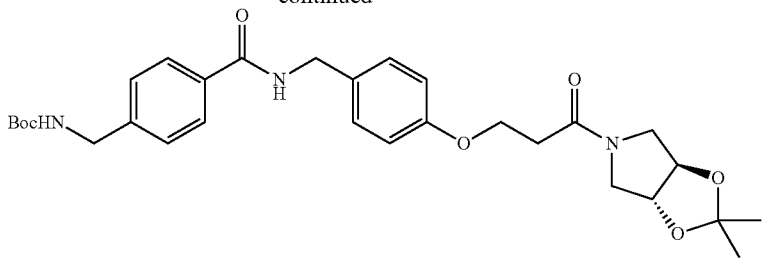

To an ice-cold solution of 3-(4-((4-((((tert-butoxycarbonyl)amino)methyl)benzamido)methyl)phenoxy)propanoic acid (0.45 g, 1.05 mmol) at 0° C. in anhydrous DMF (5 mL), was added HOBt (0.21 g, 1.57 mmol). The reaction mixture was stirred for 10 minutes and EDCI (0.30 g, 1.57 mmol), (3aR,6aR)-2,2-dimethyltetrahydro-3aH-[1,3]dioxolo[4,5-c]pyrrole (0.15 g, 1.05 mmol) and DIEA (0.38 mL, 2.10 mmol) were added. The resulting solution was allowed to stir at room temperature overnight. The reaction mixture was diluted with EtOAc and was washed with $H_2O$, dried over anhydrous sodium sulfate, and evaporated under vacuo. The crude product was purified by silica gel column chromatography (5-10% MeOH in $CHCl_3$) to afford tert-butyl 4-((4-(3-((3aR,6aR)-2,2-dimethyldihydro-3aH-[1,3]dioxolo[4,5-c]pyrrol-5(4H)-yl)-3-oxopropoxy)benzyl)carbamoyl)benzylcarbamate (0.07 g, 12%).

LCMS: m/z [M+Na]=576; 97.38% (R.T. =2.48 min.)
Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18 (50×4.6 mm) 3 uM, E-AC-2/08/COL/005
Gradient: Initial 20% B Conc to 95% B Conc. in 3.0 min. Hold for 0.5 min. At 3.51 minB.Conc.is20%

Step-7: Synthesis of 4-(aminomethyl)-N-(4-(3-((3R,4R)-3,4-dihydroxypyrrolidin-1-yl)-3-oxopropoxy)benzyl)benzamide hydrochloride To a stirred solution of tert-butyl 4-((4-(3-((3aR,6aR)-2,2-dimethyldihydro-3aH-[1,3]dioxolo[4,5-c]pyrrol-5(4H)-yl)-3-oxopropoxy)benzyl)carbamoyl)benzylcarbamate (0.07 g, 0.13 mmol) in MeOH (5 mL) was added 2 N HCl (2 mL) at 0° C. The resulting solution was stirred at 0° C. for 3 h and at room temperature for 1 h. The volatiles were evaporated under reduced pressure and the residue was triturated with diethyl ether to afford 4-(aminomethyl)-N-(4-(3-((3R,4R)-3,4-dihydroxypyrrolidin-1-yl)-3-oxopropoxy)benzyl)benzamide hydrochloride salt as a white solid yield:—0.025 g (52%).

$^1$H NMR (400 MHz, DMSO): δ 9.08-9.02 (m, 1H), 8.48-8.30 (m, 3H), 7.91 (d, J=8.4 Hz, 2H), 7.55 (d, J=8.4 Hz, 2H), 7.22 (d, J=8.0 Hz, 2H), 6.87 (d, J=8.0 Hz, 2H), 4.40 (d, J=5.6 Hz, 2H), 4.14 (t, J=6.0 Hz, 2H), 4.10-4.02 (m, 3H), 3.98 (dd, J=8.4, 4.0 Hz, 1H), 3.60 (dd, J=10.0, 6.0 Hz, 1H), 3.38 (dd, J=12.0, 5.6 Hz, 1H), 3.28 (dd, J=10.0, 5.6 Hz 1H), 3.22-3.14 (m, 1H), 2.66 (t, J=6.0 Hz, 2H)

LCMS: m/z [M+Na]=436; 16.36% (R.T.=0.62 min.), 81.66% (R.T.=0.87)
Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18(50×4.6 mm) 3 μM, E-AC-2/08/COL/005
Gradient: Initial 20% B Cone to 95% B Conc. in 3.0 min. Hold for 0.5 min. At 3.51 min
B. Conc. is 20%
HPLC: 95.72% (254 nm); (R.T.=3.62)

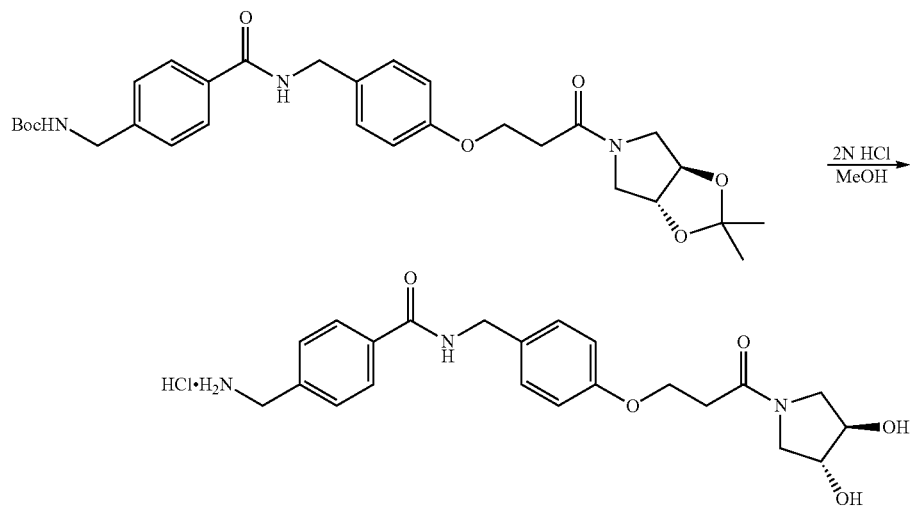

Target-9

Column: YMC ODS-A 150 mm×4.6 mm×5 g, ID: E-AC-2/08/COL/006
Mobile Phase: A: 0.05% TFA in Water/B: 0.05% TFA in Acetonitrile
Inj. Vol: 10 μL, Col. Temp.: 30° C., Flow rate: 1.4 mL/min
Gradient: 5% B to 95% B in 8 min, Hold for 1.5 min, 9.51-12 min 5% B Example 34—Synthesis of (5-(4-(3-(amino methyl)phenyl)piperidine-1-carbonyl)napthalen-2-yl)boronic acid (Target-10)

Note:—Methyl-6-(4,4,5,5-tetramethyl-1,3,2-dioxaborolan-2-yl)-1-napthoate was synthesized as per procedure described in WO2007/5668A2, which is hereby incorporated by reference in its entirety, by reaction of O-trifluoro methane sulfonate derivative of methyl ester of 6-hydroxy napthoic acid and 10 eq. excess bis(pinacolato)diboron.

To a solution of methyl 6-(4,4,5,5-tetramethyl-1,3,2-dioxaborolan-2-yl)-1-napthoate (500 mg, 1.6 mmol) in 1:1 THF:water (10 mL) was added lithium hydroxide (115 mg, 4.8 mmol). The reaction was stirred overnight at room Reaction scheme:

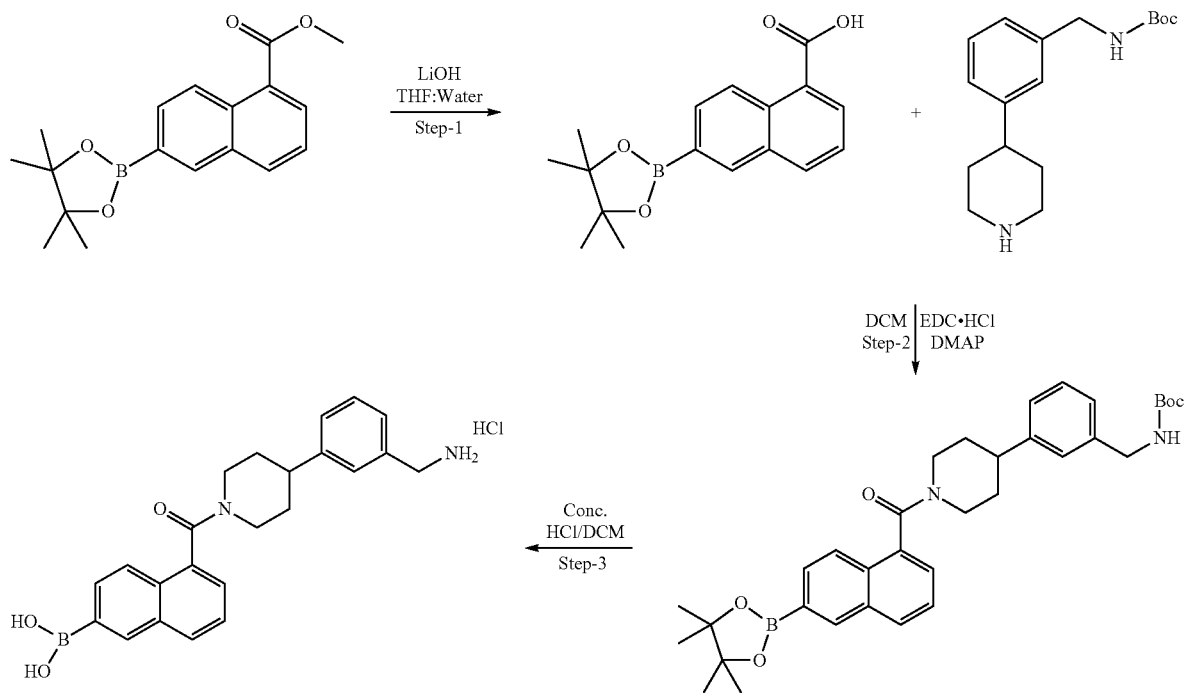

Step-1: Synthesis of 6-(4,4,5,5-tetramethyl-1,3,2-dioxaborolan-2-yl)-1-napthoic acid

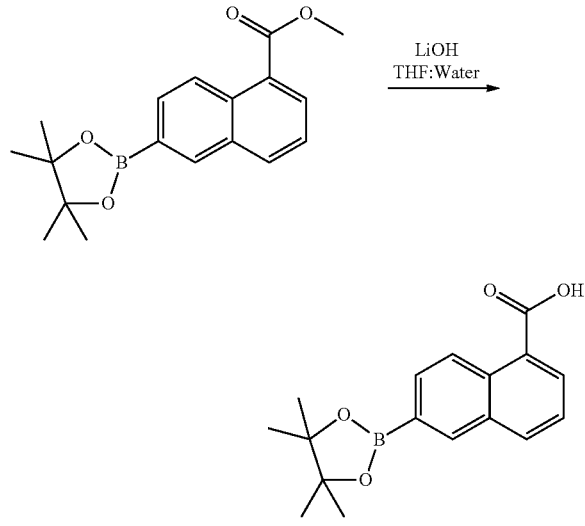

temperature, when TLC (mobile phase 30% ethyl acetate in n-hexane) indicated absence of starting material (Rf 0.6). THF was then concentrated and reaction mass was diluted with ethyl acetate (50 mL) and water. Organic layer was washed with water and combined aq. Washings were acidified with 2N HCl and extracted with ethyl acetate (2×25 mL). Ethyl acetate extract was dried over sodium sulfate and concentrated in vacuum. Oily crude product obtained was purified by column chromatography over silica gel (Gradient:—ethyl acetate 0-20% in hexane) to get 250 mg (52.4%) 6-(4,4,5,5-tetramethyl-1,3,2-dioxaborolan-2-yl)-1-napthoic acid as White solid.

Mol. wt:—298.14, Mol. Ion. peak seen in ESMS −ve mode:—297.46, Ionization not observed in LCMS, purity 93.24%

$^1$H NMR (400 MHz CDCl$_3$), 1.40 (s, 12H), 7.54 (t, 1H), 8.00 (d, 1H, J=8.8 Hz), 8.13 (d, 1H, J=8 Hz), 8.42 (m, 2H), 9.03 (d, 1H, J=8.8 Hz)

417

Step-2: Synthesis of tert-butyl 3-(1-(6-(4,4,5,5-tetramethyl-1,3,2-dioxaborolan-2-yl)-1-naphthoyl)piperidin-4-yl)benzylcarbamate

418

Step-3: Synthesis of: (5-(4-(3-(amino methyl)phenyl)piperidine-1-carbonyl)napthalen-2-yl)boronic acid (Target-10)

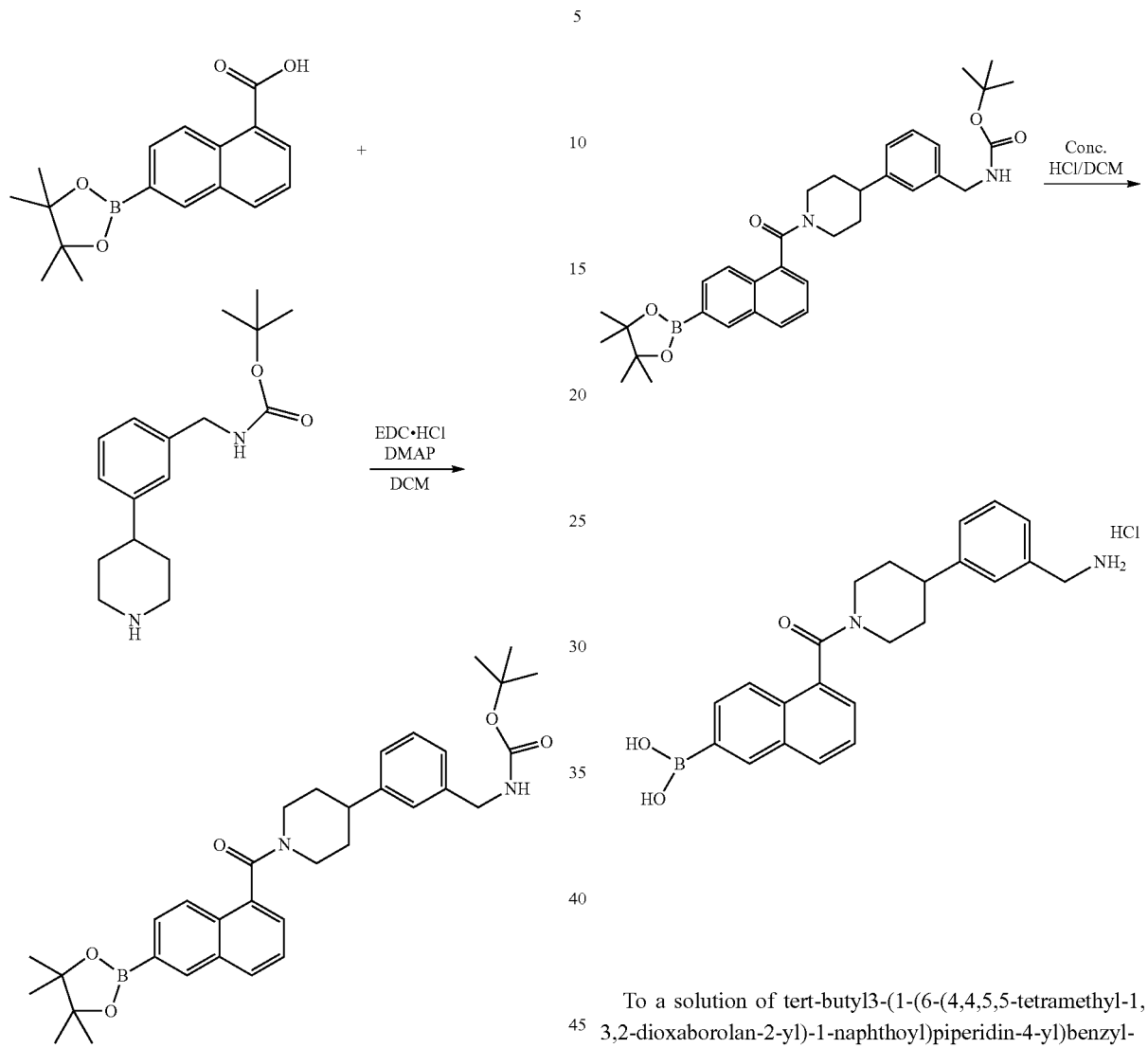

To a stirred solution of 6-(4,4,5,5-tetramethyl-1,3,2-dioxaborolan-2-yl)-1-napthoic acid (100 mg, 0.34 mmol) in 10 ml of DCM was added DMAP (49.7 mg, 0.40 mmol) and EDCI (98.1 mg, 0.51 mmol) The solution was stirred for 15 mins at 0° C. followed by addition of tert-butyl 3-(piperidin-4-yl)benzylcarbamate (107 mg, 0.0.36 mmol). Reaction mixture was then stirred at room-temperature for 4 hrs when TLC (10% methanol in chloroform) indicated consumption of starting material and formation of product. Water (10 mL) was added to the reaction mixture and organic layer was separated. Aq. layer was extracted with 2×10 ml of DCM. Combined organic layers were dried over sodium sulfate and concentrated under vacuum to give 210 mg product as colorless oil. Crude product used for next step without purification Mol. Wt.:—570.53, Molecular ion peak seen in LCMS:—571.55, Purity 48%

To a solution of tert-butyl3-(1-(6-(4,4,5,5-tetramethyl-1,3,2-dioxaborolan-2-yl)-1-naphthoyl)piperidin-4-yl)benzylcarbamate (220 mg, 0.38 mmol) in THF (10 mL), Conc. HCl (0.5 mL) was added. The reaction mixture was stirred at room temperature for 3-4 hrs temperature for 2 h. The reaction was monitored by LCMS, after completion of reaction the reaction mixture was concentrated to dryness under vacuum to give the crude product which was diluted with water (2 mL) and basified by sodium bicarbonate, solid obtained was filtered and dried to get 150 mg crude product, which was purified by preparative HPLC to yield 62 mg pure product as TFA salt. Above TFA salt was stirred in methanolic HCl for 30 min and concentrated in vacuum to get 55 mg off white solid product as HCl salt.

Mol. Wt. 388.27, M.I. peak observed in LCMS at 388.85, HPLC purity: 98.92%

$^1$H-NMR (400 MHz, DMSO) 1.61-1.94 (m, 4H), 2.82-3.16 (m, 5H), 4.0 (s, 2H), 4.85 (m, 1H), 7.06 (d, 1H), 7.18 (s, 1H),7.31-7.439 (m, 3H), 7.55 (t, 1H), 7.66 (d, 1H) 7.84 (d, 1H), 7.95 (m, 1H), 8.43 (s, 1H)

Example 35—Synthesis of (8-(4-(3-(aminomethyl)phenyl)piperidine-1-carbonyl) naphthalen-2-yl)boronic acid (Target-11)

Synthetic Scheme:

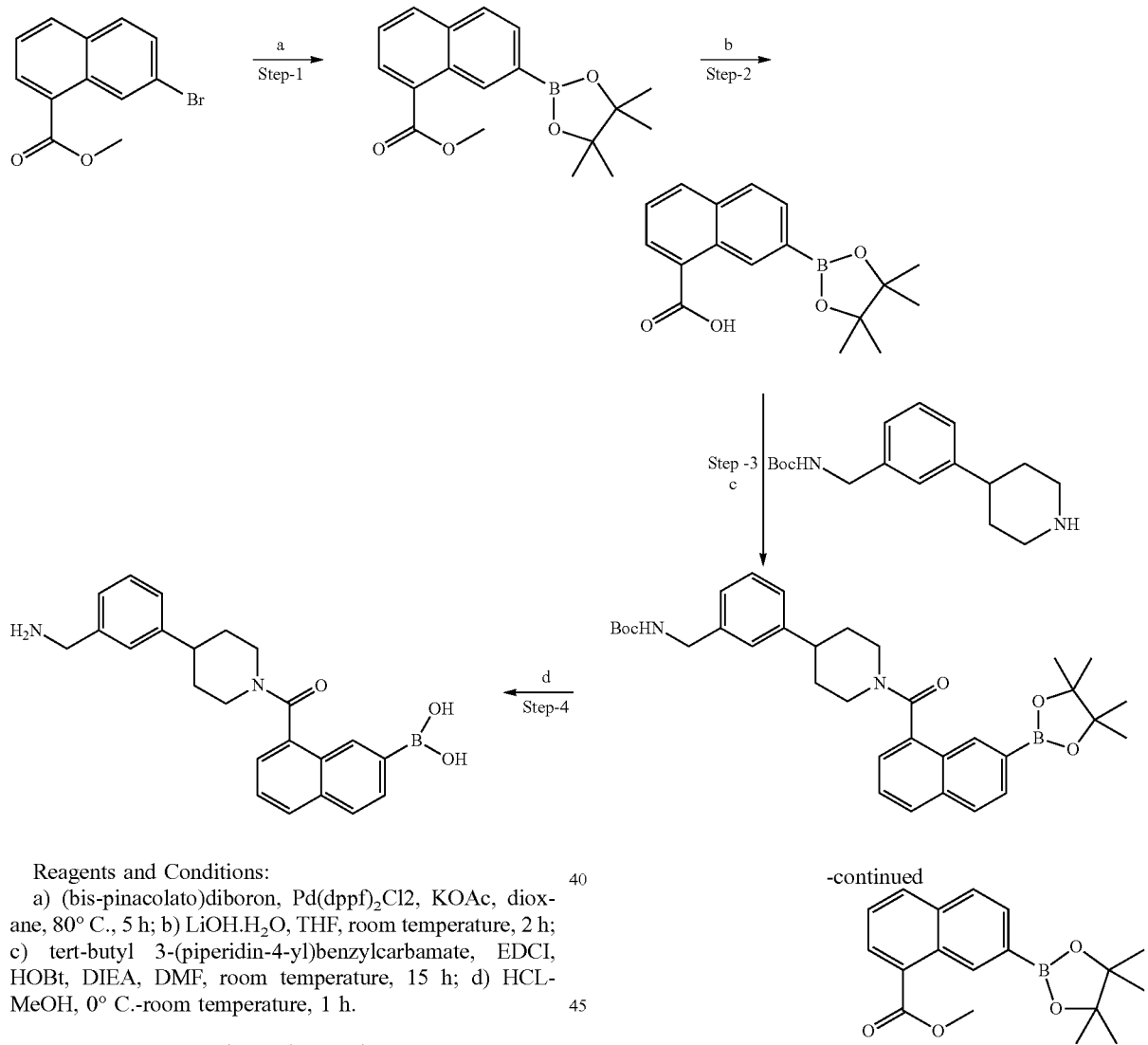

Reagents and Conditions:
a) (bis-pinacolato)diboron, Pd(dppf)$_2$Cl2, KOAc, dioxane, 80° C., 5 h; b) LiOH.H$_2$O, THF, room temperature, 2 h; c) tert-butyl 3-(piperidin-4-yl)benzylcarbamate, EDCI, HOBt, DIEA, DMF, room temperature, 15 h; d) HCL-MeOH, 0° C.-room temperature, 1 h.

Experimental Procedure

7-Bromo-1-napthoic acid and its methyl ester were synthesized from 2-Bromo napthlene by Friedel-Crafis acylation with acetyl chloride, subsequent oxidation of the ketone by sodium hypobromite & esterification using methanol-sulfuric acid as per procedures cited in the literature (*Helvetica Chimica Acta*, 21:1519-1520 (1938); U.S. Pat. No. 4,391,816, *Bull. Chem. Soc. Japan.* 48:3356-3366 (1975); WO2008/100480 A1, which are hereby incorporated by reference in their entirety)

Step-1: Synthesis of methyl 7-(4,4,5,5-tetramethyl-1,3,2-dioxaborolan-2-yl)-1-naphthoate

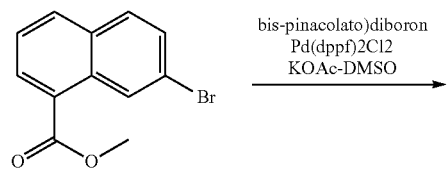

A solution of methyl 7-bromo-1-naphthoate (250 mg, 0.94 mmol) in DMSO (2.5 mL) was degassed with argon, to this solution (bis-pinacolato)diboron (2.38 g, 9.4 mmol), KOAc (277 mg, 2.8 mmol) and Pd(dppf)2Cl2 (2.3 mg, 0.0028 mmol) were added at room temperature and the mixture was heated at 80° C. for 5 h when complete consumption of the starting material (Rf. 0.35) and formation of product (Rf. 0.4) was observed in TLC (15% ethyl acetate in hexane) & LCMS. The reaction mixture was then evaporated to dryness under reduced pressure and residue obtained was diluted with EtOAc. The insoluble material was filtered off and the filtrate was evaporated under vacuum to give the crude product which was purified by column chromatography over silica gel (Gradient:—0-10% ethyl acetate in hexane) to get pure yield methyl 7-(4,4,5,5-tetramethyl-1,3,2-dioxaborolan-2-yl)-1-naphthoate yield:—170 mg (57.8%)

421

$^1$H NMR (400 MHz; CDCl3) 1.39 (s, 12H), 4.02 (s 3H, 7.52 (t, 1H), 7.85-7.93 (m, 2H), 8.00 (d, 1H J=8), 8.13-8.14 (d, 1H, J=6.8), 9.32 (s, 1H)

Step-2: Synthesis of 7-(4,4,5,5-tetramethyl-1,3,2-dioxaborolan-2-yl)-1-naphthoic acid

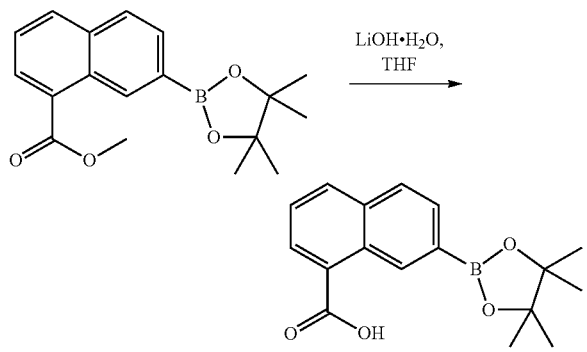

Methyl 7-(4,4,5,5-tetramethyl-1,3,2-dioxaborolan-2-yl)-1-naphthoate (150 mg, 0.48 mmol) was dissolved in THF:H2O (2.5 mL each) and LiOH (34 mg, 1.4 mmol) was added. The reaction mixture was stirred overnight at room temperature when TLC (30% ethyl acetate in hexane) complete consumption of the starting material (Rf. 0.6) and formation of product (Rf. 0.3) the solvent was evaporated in vacuum, and the residue was diluted with ethyl acetate. Organic layer was washed with water. Combined aqueous layer was acidified with 2N HCl and extracted with ethyl acetate (2×25 mL), and ethyl acetate extract was dried over Na$_2$SO$_4$ and concentrated to get crude product, which was purified by column chromatography over silica gel (gradient:—0-20% ethyl acetate in n-hexane) to get 7-(4,4,5,5-tetramethyl-1,3,2-dioxaborolan-2-yl)-1-naphthoic acid (110 mg, 76.9%) Mol. wt 298.14; Mol ion peak observed in ESMS-negative mode 297.48

Step-3: Synthesis of tert-butyl 3-(1-(7-(4,4,5,5-tetramethyl-1,3,2-dioxaborolan-2-yl)-1-naphthoyl) piperidin-4-yl)benzylcarbamate

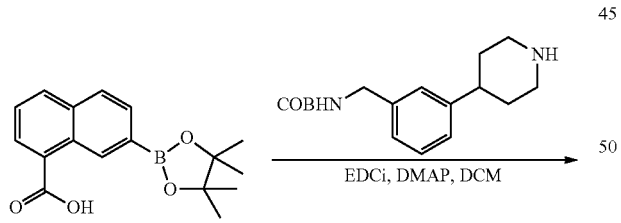

422

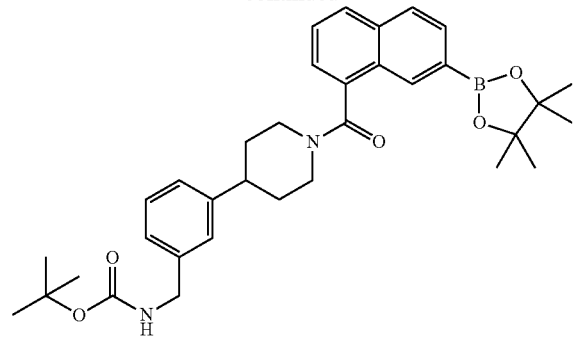

To a solution of 7-(4,4,5,5-tetramethyl-1,3,2-dioxaborolan-2-yl)-1-naphthoic acid (154 mg, 0.51 mmol) in anhydrous DMF was added DMAP (75 mg, 0.62 mmol) followed by added EDC.HCl (147 mg, 0.76 mmol) at 0° C. and stirred for 30 min. To this was added tert-butyl 3-(piperidin-4-yl) benzyl carbamate (150 mg, 0.51 mmol) at 0° C. The reaction mixture was allowed to warm to room temperature and stirred for 3 hrs when LCMS & TLC (10% MeOH in chloroform) indicated complete consumption of the carboxylic acid (Rf. 0.3) and formation of product (Rf. 0.5). The reaction mixture was diluted with DCM (25 mL) and washed with water, followed by 1N HCl. DCM layer was dried over sodium sulfate and evaporated under vacuum to yield 250 mg crude product as colorless oil which was used for next step without further purification.

Mol. Wt. 570.53, Mol. Ion. peak observed in LCMS 571.45, Purity 71.9%

Step-4: Synthesis of (8-(4-(3-(aminomethyl)phenyl) piperidine-1-carbonyl)naphthalen-2-yl)boronic acid (Target-11)

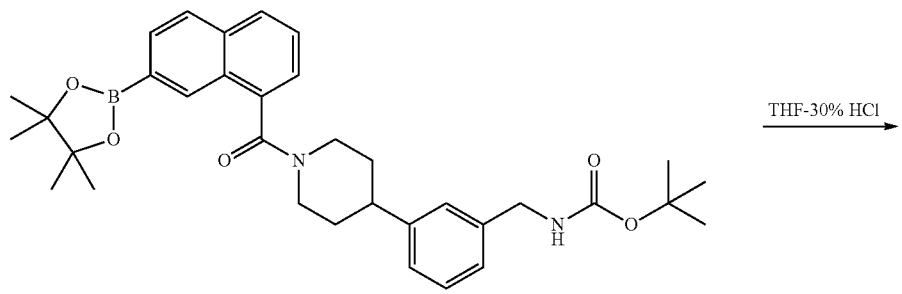

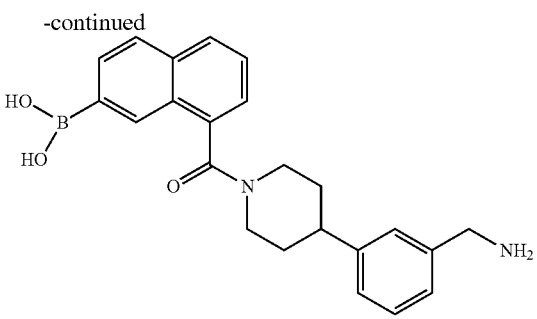

To an solution of tert-buty-13-(1-(7-(4,4,5,5-tetramethyl-1,3,2-dioxaborolan-2-yl)-1-naphthoyl)piperidin-4-yl)benzylcarbamate (200 mg, 0.35 mmol) in THF (5 mL), Conc. 1 mL HCl was added. The reaction mixture was stirred at room temperature. After 4 hrs, completion of reaction was observed by LCMS the reaction mixture was concentrated to dryness under vacuum and residue was diluted with water (2 mL) and basified by sodium bicarbonate, solid obtained was filtered and dried to get crude product (150 mg, off white solid) which was purified by preparative HPLC to yield target-11 as TFA salt, which was stirred in 10% methanolic HCl for 30 min and concentrated in vacuum to get 11 mg hydrochloride salt as off white solid.

Mol. wt:—388.27, Mol. Ion. peak observed in LCMS:—388.85, HPLC purity: 97.7%

$^1$HNMR (400 MHz, DMSO) 1.49-1.91 (m, 4H), 2.73-3.29 (m, 5H), 4.0 (s, 2H), 4.87 (m, 1H), 7.32 (s, 1H),7.32-7.58 (m, 5H), 7.93 (m, 3H), 9.47 (s, 1H)

Example 36—Synthesis of (3-(2-(4-(3-(aminomethyl)phenyl)piperidin-1-yl)-2-oxoethyl)phenyl)boronic acid (Target-12)

Reagents and Conditions:

a) SOCl$_2$, MeOH, 80° C., 15 h; b) (bis-pinacolato)diboron, Pd(dppf)$_2$Cl$_2$, KOAc, Dioxane, 80° C., 5 h; c) LiOH.H$_2$O, MeOH, room temperature, 2 h; d) benzyl 3-(piperidin-4-yl)benzylcarbamate, EDCI, HOBt, DIEA, DMF, room temperature, 15 h; e) HBr in acetic acid, 0° C.-room temperature, 1 h.

Experimental Procedure

Step-1: Synthesis of ethyl 2-(3-bromophenyl)acetate

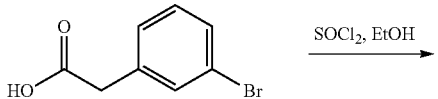

Synthetic Scheme:

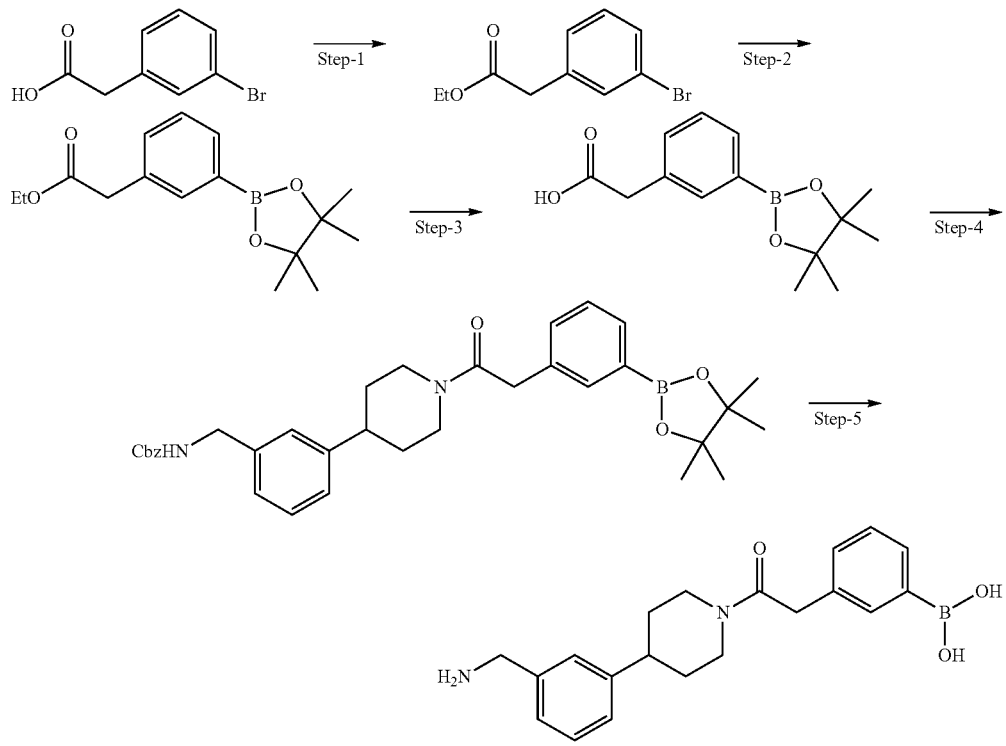

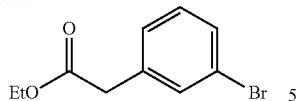

To an ice cooled solution of 2-(3-bromophenyl)acetic acid (1 g, 4.6 mmol) in EtOH (10 mL), thionyl chloride (0.67 mL, 9.3 mmol) was added dropwise. The reaction mixture was then warmed to room temperature heated at 80° C. for 15 h. The reaction was monitored by TLC and after completion of the reaction, the reaction mixture was concentrated under vacuo and water was added to the residue. A saturated aqueous solution of NaHCO3 was added to the solution until the pH of the solution was 9. Then, the aqueous solution was extracted with EtOAc, the organic layer was dried over Na$_2$SO$_4$, concentrated under vacuum, and purified by column chromatography (silica gel) to yield ethyl 2-(3-bromophenyl)acetate yield 1.13 g. (88%).

Step-2: Synthesis of ethyl 2-(3-(4,4,5,5-tetramethyl-1,3,2-dioxaborolan-2-yl)phenyl)acetate

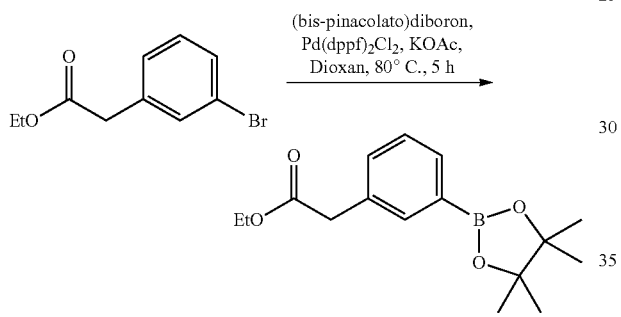

A solution of ethyl 2-(3-bromophenyl)acetate (1 g, 4.1 mmol) in dioxane (20 mL) was degassed with argon, to this solution (bis-pinacolato)diboron (1.25 g, 4.9 mmol), KOAc (1.20 g, 12.3 mmol) and Pd(dppf)$_2$Cl2 (100 mg, 0.12 mmol) were added at room temperature and the mixture was heated at 80° C. for 5 h. After complete consumption of the SM as observed by LCMS and TLC, the reaction mixture was cooled to room temperature. The reaction mixture was evaporated to dryness under reduced pressure to give residue which was dissolved in EtOAc. The un-dissolved inorganic material was filtered off and the filtrate was evaporated under vacuum to give the crude product which was purified by column chromatography (silica gel) to yield ethyl 2-(3-(4,4,5,5-tetramethyl-1,3,2-dioxaborolan-2-yl)phenyl)acetate (700 mg, 89%).

Step-3: Synthesis of 2-(3-(4,4,5,5-tetramethyl-1,3,2-dioxaborolan-2-yl)phenyl)acetic acid

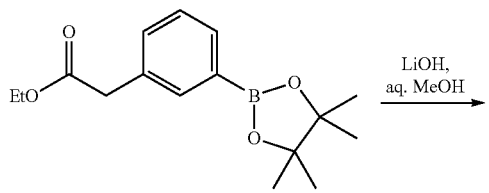

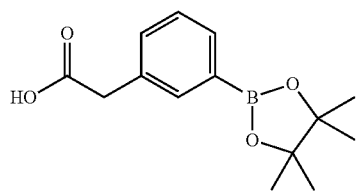

Ethyl 2-(3-(4,4,5,5-tetramethyl-1,3,2-dioxaborolan-2-yl)phenyl)acetate (100 mg, 0.34 mmol) was dissolved in MeOH:H$_2$O (4:0.4 mL) and LiOH (15 mg, 0.34 mmol) was added. The reaction mixture was stirred at room temperature overnight. After completion of the reaction, the solvent was evaporated in vacuum, and the residue was triturated with ether to give 2-(3-(4,4,5,5-tetramethyl-1,3,2-dioxaborolan-2-yl)phenyl)acetic acid yield: —50 mg (55%).

Step-4: Synthesis of benzyl 3-(1-(2-(3-(4,4,5,5-tetramethyl-1,3,2-dioxaborolan-2-yl)phenyl)acetyl)piperidin-4-yl)benzylcarbamate

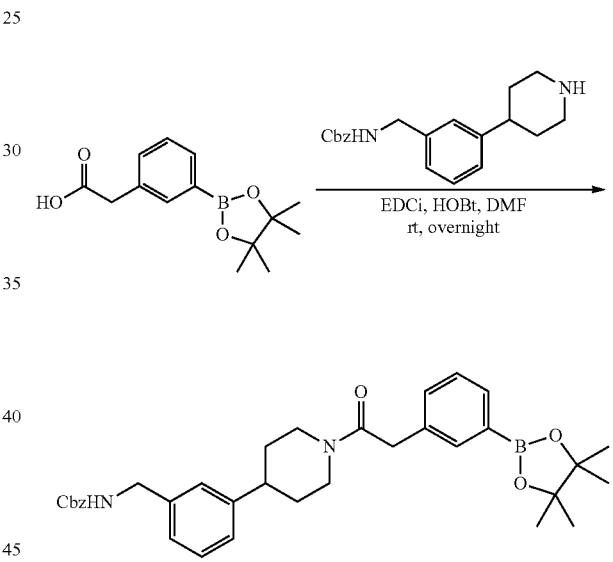

To a cooled solution of benzyl 3-(piperidin-4-yl)benzylcarbamate (100 mg, 0.38 mmol) 0° C. in anhydrous DMF (3 mL), HOBt (77 mg, 0.57 mmol) was added and the reaction mixture was stirred for 10 min. before EDCi (109 mg, 0.57 mmol), 2-(3-(4,4,5,5-tetramethyl-1,3,2-dioxaborolan-2-yl)phenyl)acetic acid (123 mg, 0.38 mmol) and DIEA (0.1 mL, 0.57 mmol) were added in succession. The reaction mixture was allowed to warm to room temperature and was stirred overnight. The reaction was monitored by LCMS (in basic medium) and TLC. The reaction mixture was then diluted with ethylacetate (25 mL) and the EtOAC solution was washed with water before it was dried over sodium sulfate and evaporated under vacuum to give the crude product. The crude product was purified by preparative HPLC to afford benzyl 3-(1-(2-(3-(4,4,5,5-tetramethyl-1,3,2-dioxaborolan-2-yl)phenyl)acetyl)piperidin-4-yl)benzylcarbamate Yield 35 mg (16%).

Step-5: Synthesis of benzyl 3-(1-(2-(3-(4,4,5,5-tetramethyl-1,3,2-dioxaborolan-2-yl)phenyl)acetyl)piperidin-4-yl)benzylcarbamate (Target-12)

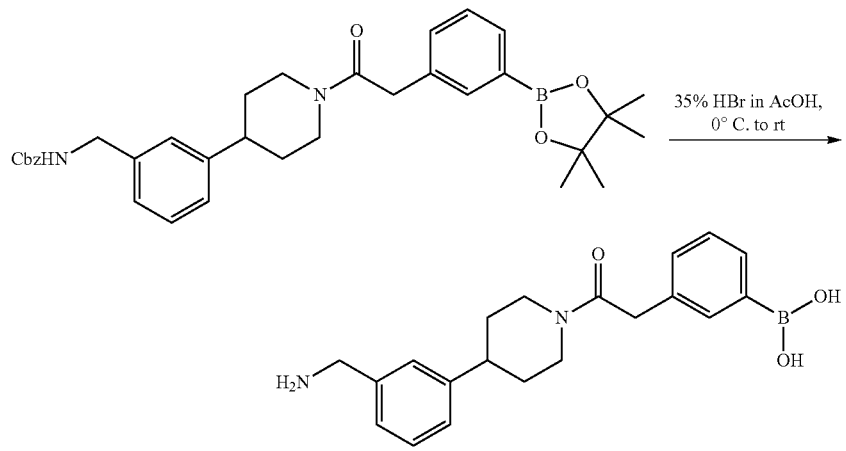

To an ice cooled solution of benzyl 3-(1-(2-(3-(4,4,5,5-tetramethyl-1,3,2-dioxaborolan-2-yl)phenyl)acetyl)piperidin-4-yl)benzylcarbamate (Int-5) (70 mg, 0.147 mmol) in $CH_2Cl_2$ (2 mL), 35% HBr in acetic acid (0.1 mL) was added. The reaction mixture was stirred at 0° C. for 30 min and warmed to room temperature. The reaction was stirred at room temperature for 2 h. The reaction was monitored by LCMS, after completion of reaction the reaction mixture was concentrated to dryness under reduced pressure to give the crude product which was isolated by preparative HPLC (C-18 column) to afford benzyl 3-(1-(2-(3-(4,4,5,5-tetramethyl-1,3,2-dioxaborolan-2-yl)phenyl)acetyl)piperidin-4-yl)benzylcarbamate (36 mg, 72%) as an acetate salt.

1H NMR (400 MHz, CD3OD): δ 7.54-7.50 (m, 2H), 7.35-7.19 (m, 6H), 4.73-4.70 (m, 1H), 4.11-4.08 (m, 1H), 4.05 (d, J=2.0 Hz, 2H), 3.83 (ABq, J=15.2 Hz, 2H), 3.15 (dt, J=2.0, 12.8 Hz, 1H), 2.80 (tt, J=3.6, 12.8 Hz, 1H), 2.73 (dt, J=2.4, 12.8 Hz, 1H), 1.93 (s, 3H), 1.85-1.82 (m, 1H), 1.66-1.58 (m, 2H), 1.32 (dq, J=2.4, 12.8 Hz, 1H).

LCMS: m/z [M+1]=353; 99.23% (R.T.=1.36)

Chromatographic Parameters

Mobile Phase A: 0.05% TFA in water, Mobile Phase B: 0.05% TFA in Acetonitrile,

Flow rate: 1.2 ml/min; Temperature: Ambient,

Column: YMC ODS A, C18(50×4.6 mm) 3 uM, E-AC-2/08/COL/005

Gradient: Initial 20% B Cone to 95% B Conc. in 3.0 min. Hold for 0.5 min. At 3.51 min B. Conc. is 20%

HPLC: 98.97% (220 nm, R.T.=4.32)

Column: YMC ODS-A 150 mm×4.6 mm×5μ, ID: E-AC-2/08/COL/006

Mobile Phase: A: 0.05% TFA in Water/B: 0.05% TFA in Acetonitrile

Inj. Vol: 10 μL, Col. Temp.: 30° C., Flow rate: 1.4 mL/min

Gradient: 5% B to 95% B in 8 min, Hold for 1.5 min, 9.51-12 min 5% B

Example 37—Synthesis of (4-(2-(4-(3-(aminomethyl)phenyl)piperidin-1-yl)-2-oxoethyl)phenyl)boronic acid (Target-13)

Synthetic Scheme:

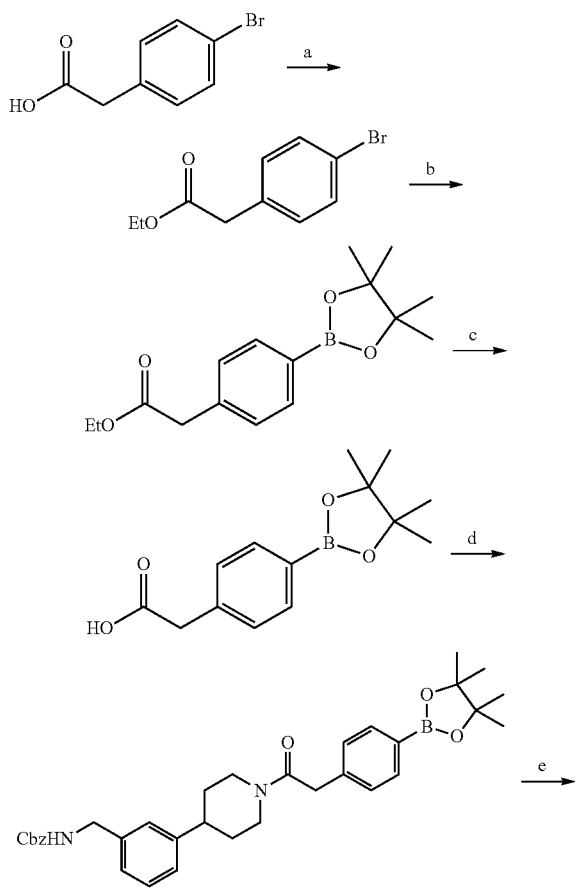

-continued

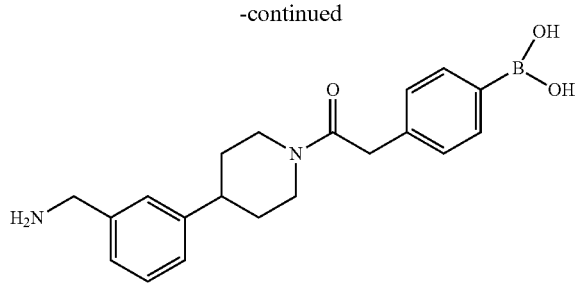

Reagents and Conditions:
a) SOCl$_2$, MeOH, 80° C., 15 h; b) (bis-pinacolato)diboron, Pd(dppf)$_2$Cl$_2$, KOAc, dioxane, 80° C., 5 h; c) LiOH.H$_2$O, MeOH, room temperature, 2 h; d) benzyl 3-(piperidin-4-yl)benzylcarbamate, EDCI, HOBt, DIEA, DMF, room temperature, 15 h; e) HBr in acetic acid, 0° C.-room temperature, 1 h.

Experimental Procedure

Step-1: Synthesis of ethyl 2-(3-bromophenyl)acetate

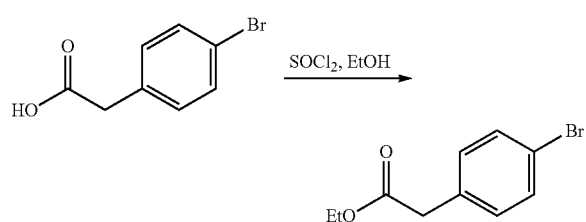

To an ice cooled solution of 2-(3-bromophenyl)acetic acid (2.5 g, 11.62 mmol) in EtOH (25 mL), thionyl chloride (1.6 mL, 23.24 mmol) was added dropwise. The reaction mixture was heated at 80° C. for 15 h. The reaction was monitored by TLC and after completion of the reaction, the reaction mixture was concentrated under vacuum and water was added to the residue. A saturated aqueous solution of NaHCO$_3$ was added to the solution until the pH of the solution was 9. Then, the aqueous solution was extracted with EtOAc, the organic layer was dried over Na$_2$SO$_4$, concentrated under vacuum, and purified by column chromatography (silica gel) to yield ethyl 2-(3-bromophenyl)acetate (2 g, 70%).

LCMS: 99.80% (254 nm, R.T.=2.99)
Mobile Phase A: 0.05% TFA in water, Mobile Phase B:0.05% TFA in acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Conc to 95% B Conc. in 3.0 min. Hold for 0.5 min. At 3.51 min B. Conc. is 20%

Step-2: Synthesis of ethyl 2-(3-(4,4,5,5-tetramethyl-1,3,2-dioxaborolan-2-yl)phenyl)acetate

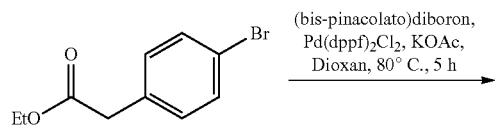

-continued

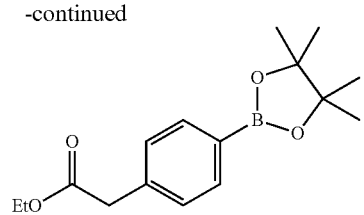

A solution of ethyl 2-(3-bromophenyl)acetate (1 g, 4.1 mmol) in dioxane (20 mL) was degassed with argon, to this solution (bis-pinacolato)diboron (1.25 g, 4.9 mmol), KOAc (1.21 g, 12 mmol) and Pd(dppf)$_2$Cl$_2$ (100 mg, 0.1 mmol) were added at room temperature and the mixture was heated at 80° C. for 5 h. After complete consumption of the starting material as observed by LCMS and TLC, the reaction mixture was cooled to room temperature. The reaction mixture was evaporated to dryness under reduced pressure to give a residue which was dissolved in EtOAc. The un-dissolved inorganic material was filtered off and the filtrate was evaporated under vacuum to give the crude product which was purified by column chromatography (silica gel) to yield ethyl 2-(3-(4,4,5,5-tetramethyl-1,3,2-dioxaborolan-2-yl)phenyl)acetate (888 mg, 80%).

LCMS: 92.13% (254 nm, R.T.=3.25)
Mobile Phase A: 0.05% TFA in water, Mobile Phase B:0.05% TFA in Acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Conc to 95% B Conc. in 3.0 min. Hold for 0.5 min. At 3.51 min B. Conc. is 20%

Step-3: Synthesis of 2-(3-(4,4,5,5-tetramethyl-1,3,2-dioxaborolan-2-yl)phenyl)acetic acid

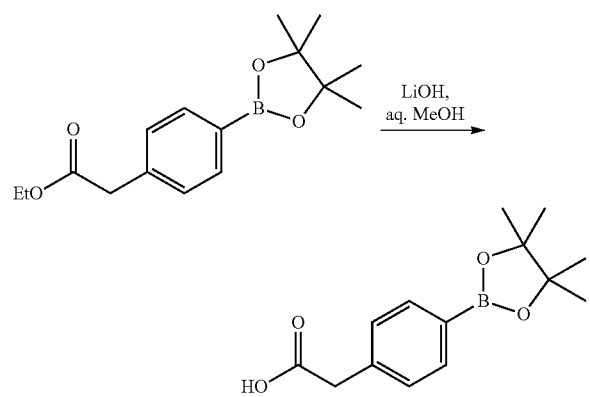

Ethyl 2-(3-(4,4,5,5-tetramethyl-1,3,2-dioxaborolan-2-yl)phenyl)acetate (350 mg, 1.2 mmol) was dissolved in MeOH:H$_2$O (5:0.5 mL) and LiOH (50 mg, 1.2 mmol) was added. The reaction mixture was stirred at room temperature overnight. After completion of the reaction, the solvent was evaporated in vacuum, and the residue was triturated with ether to give 2-(3-(4,4,5,5-tetramethyl-1,3,2-dioxaborolan-2-yl)phenyl)acetic acid (300 mg, 94%) which was used without further purification.

Step-4: Synthesis of benzyl 3-(1-(2-(3-(4,4,5,5-tetramethyl-1,3,2-dioxaborolan-2-yl)phenyl)acetyl)piperidin-4-yl)benzylcarbamate

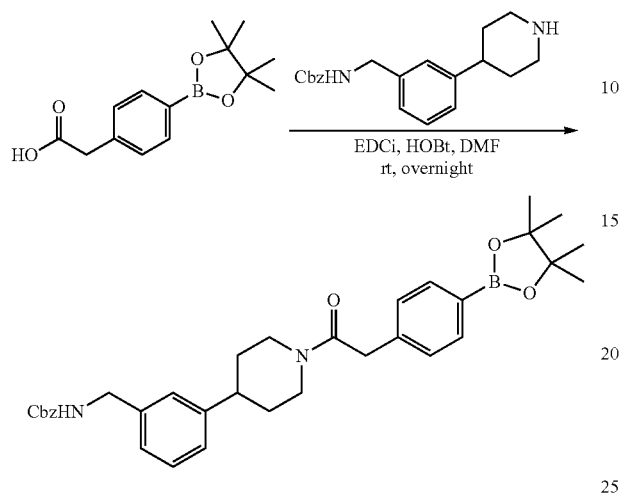

column) to afford benzyl 3-(1-(2-(3-(4,4,5,5-tetramethyl-1,3,2-dioxaborolan-2-yl)phenyl)acetyl)piperidin-4-yl)benzylcarbamate (80 mg, 10%).

LCMS: 81.31% (254 nm, R.T.=3.23)

Column: YMC, ODS, 50×4.6 mm. 3μ, Column ID: E-AC-1/07/COL/26

Mobile Phase: A. 0.05% TFA in water and B. 0.05% TFA in acetonitrile

Inj Volume; 5.0 μL, Flow Rate: 1.2 mL/minute, Gradient program: 20% B to 100% B in 3.0 minute, Hold For 0.5 min, At 3.51 min B cone is 20%

Step-5: Synthesis of benzyl 3-(1-(2-(3-(4,4,5,5-tetramethyl-1,3,2-dioxaborolan-2-yl)phenyl)acetyl)piperidin-4-yl)benzylcarbamate (Target-13)

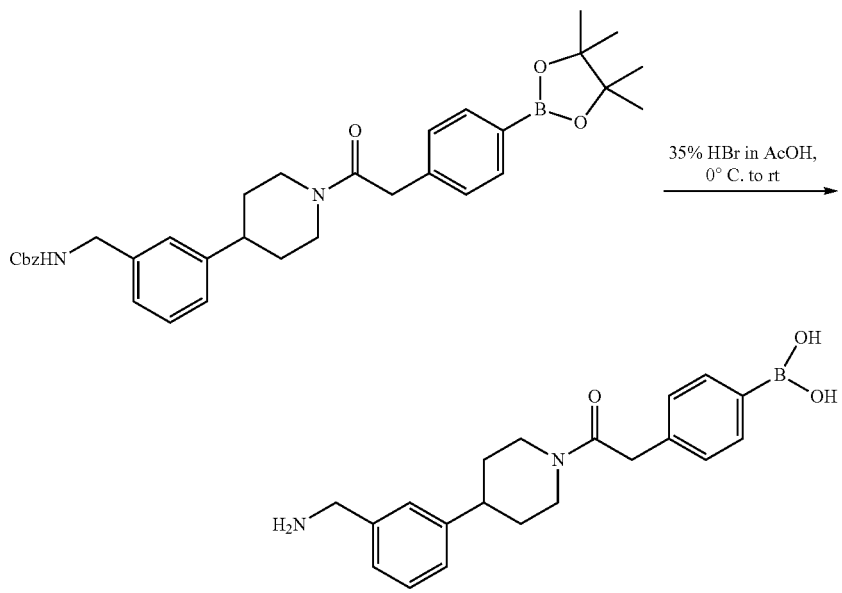

To a cooled solution of 2-(3-(4,4,5,5-tetramethyl-1,3,2-dioxaborolan-2-yl)phenyl)acetic acid of (350 mg, 1.3 mmol) at 0° C. in anhydrous DMF (5 mL), HOBt (270 mg, 2 mmol) was added and the reaction mixture was stirred for 10 min. before EDCi (384 mg, 2 mmol), benzyl 3-(piperidin-4-yl)benzylcarbamate (433 mg, 1.3 mmol) and DIEA (0.5 mL, 2.6 mmol) were added in succession. The reaction mixture was allowed to warm to room temperature and was stirred overnight. The reaction was monitored by LCMS (in basic medium) and TLC. The reaction mixture was then diluted with ethylacetate (25 mL) and the EtOAC solution was washed with water before it was dried over sodium sulfate and evaporated under vacuum to give the crude product. The crude product was purified by preparative HPLC (C-18

To an ice cooled solution of benzyl 3-(1-(2-(3-(4,4,5,5-tetramethyl-1,3,2-dioxaborolan-2-yl)phenyl)acetyl)piperidin-4-yl)benzylcarbamate (50 mg, 0.087 mmol) in $CH_2Cl_2$ (6 mL), 35% HBr in acetic acid (1.5 mL) was added. The reaction mixture was stirred at 0° C. for 30 min and warmed to room temperature. The reaction was stirred at room temperature for 2 h. The reaction was monitored by LCMS, after completion of reaction the reaction mixture was concentrated to dryness under reduced pressure to give the crude product which was isolated by preparative HPLC (C-18 column) to afford benzyl 3-(1-(2-(3-(4,4,5,5-tetramethyl-1,3,2-dioxaborolan-2-yl)phenyl)acetyl)piperidin-4-yl) benzylcarbamate (29 mg, 83%) as an acetate salt.

1H NMR (400 MHz, CD3OD): δ 7.60-7.58 (m, 1H), 7.33-7.08 (m, 6H), 4.68 (d, J=13.2 Hz, 1H), 4.09-4.003 (m,

1H), 4.04 (s, 2H), 3.82 (ABq, J=14.8 Hz, 2H), 3.11 (dt, J=2.0, 12.8 Hz, 1H), 2.75-2.67 (m, 2H), 1.93 (s, 3H), 1.78-1.75 (m, 1H), 1.53-1.46 (m, 3H).

LCMS: 99.19% (220 nm, R.T.=1.31).

Mobile Phase A: 0.05% TFA in water, Mobile Phase B:0.05% TFA in Acetonitrile,

Flow rate: 1.2 ml/min; Temperature: Ambient,

Column: YMC ODS A, C18(50×4.6 mm) 3 uM, E-AC-2/08/COL/005

Gradient: Initial 20% B Conc to 95% B Conc. in 3.0 min. Hold for 0.5 min. At 3.51 min B. Conc. is 20%

HPLC: 98.39% (220 nm, R.T.=4.21)

Example 38—Synthesis of (4-(3-(aminomethyl)phenyl)piperidin-1-yl)(3-(2-hydroxy-2-(1-hydroxycyclobutyl)ethoxy)phenyl)methanone (Target-22 diol)

Reaction scheme:-

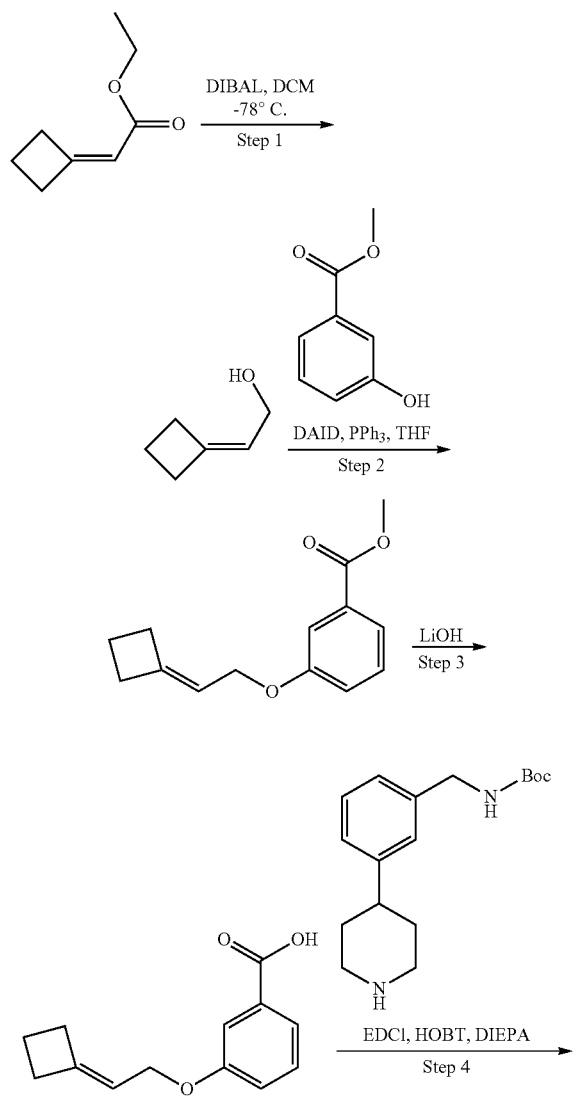

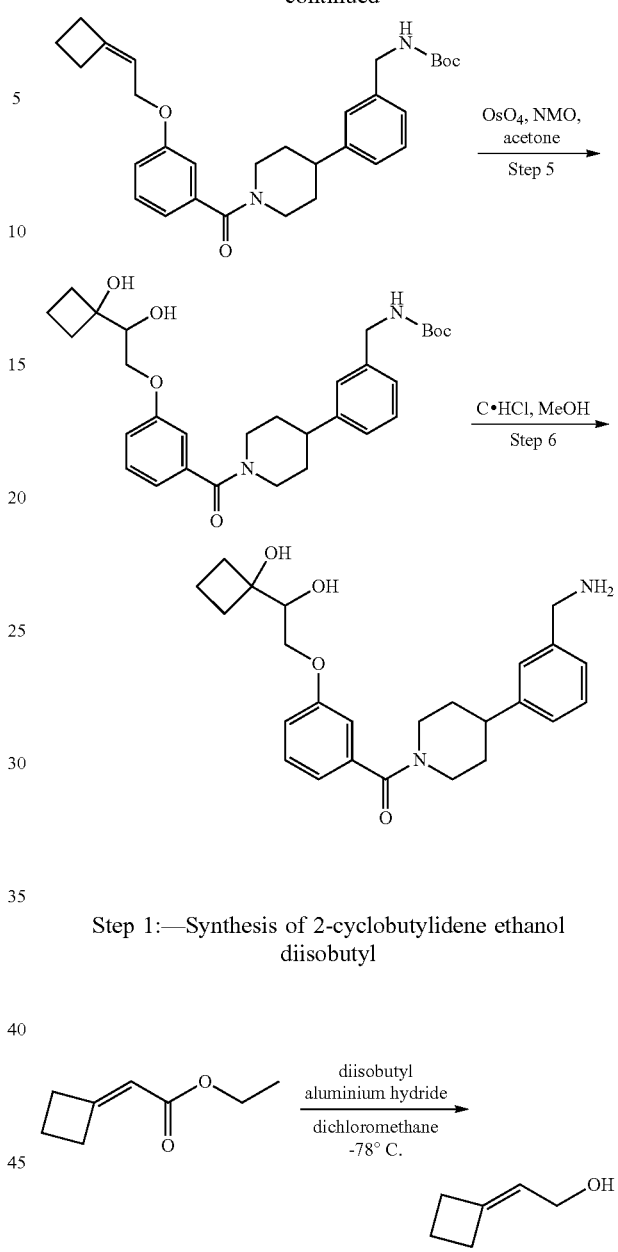

Step 1:—Synthesis of 2-cyclobutylidene ethanol diisobutyl

In 40 mL of dry DCM, ethyl 2-cyclobutylideneacetate (0.85 g, 6.07 mmol) was dissolved and mixture allowed to cool to −78° C. under nitrogen atmosphere. To this solution DIBAL-H (1M in toluene) (1.72 g, 12.1 mL, 12.1 mmol) was added dropwise. Reaction was monitored by TLC (20% ethyl acetate in n-hexane), when starting material ($R_f$=0.28) was completely consumed reaction mixture was quenched with MeOH/$H_2O$ (1:1). DCM layer was separated and dried over sodium sulfate. DCM was removed under reduced pressure. Crude product was purified by column chromatography (silica gel 60-120 mesh, 0-20% ethyl acetate in n-hexane) afforded pure product as colorless oil.

Yield: 0.5 g (84%)

$^1$H NMR (400 MHz, CDCl$_3$): δ 1.61 (br, 1H), 1.91-2.05 (m, 2H), 2.65-2.74 (m, 4H), 4.02 (d, J=7.2 Hz, 2H), 5.30-5.36 (m, 1H).

Step 2:—Synthesis of methyl 3-(2-cyclobutylideneethoxy)benzoate

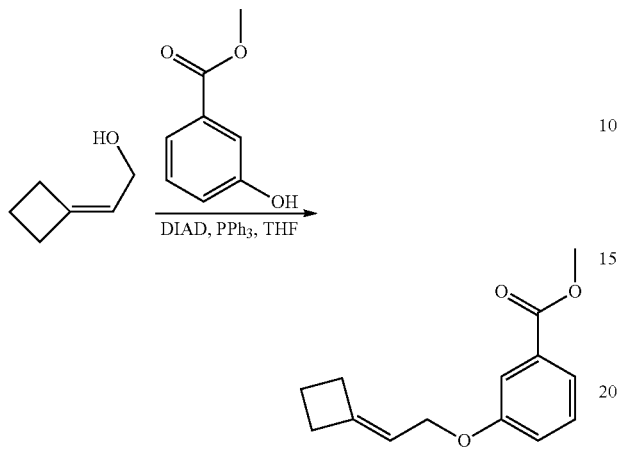

In 10 mL of dry THF and triphenyl phosphine (0.56 g, 2.25 mmol) were stirred at −20° C. To this solution DIAD (0.45 g, 0.44 mL, 2.25 mmol) was added. Yellow precipitate was observed in the reaction mixture. Methyl 3-hydroxybenzoate (0.26 g, 1.73 mmol) in 3 mL THF was added dropwise to the reaction mixture and stirred for 10-15 min. 2-cyclobutylideneethanol (0.17 g, 1.73 mmol) in 3 mL of dry THF was added dropwise (after complete addition clear yellow solution was observed) and resulting reaction mixture was stirred at room temperature overnight (product $R_f$=0.62, 20% ethyl acetate/n-Hexane). Water was added to the reaction mixture. Aqueous layer was washed with diethyl ether. Crude product was purified by column chromatography (silica gel 60-120 mesh, ethyl acetate and n-hexane) to afford light yellow oil. Yield: 0.2 g (50%)

LCMS: m/z (M+1) 233

$^1$H NMR (400 MHz, CDCl$_3$): δ 1.95-2.06 (m, 2H), 2.70-2.81 (m, 4H), 3.91 (s, 3H), 4.44 (d, J=7.2 Hz, 2H), 5.38-5.46 (m, 1H), 7.06-7.14 (dd, J=2.4 and 8.4 Hz, 1H), 7.32 (t, J=8.0 Hz, 1H), 7.57 (t, J=2.4 Hz, 1H), 7.62 (d, J=7.6 Hz, 1H).

Step 3:—Synthesis of 3-(2-cyclobutylideneethoxy)benzoic acid

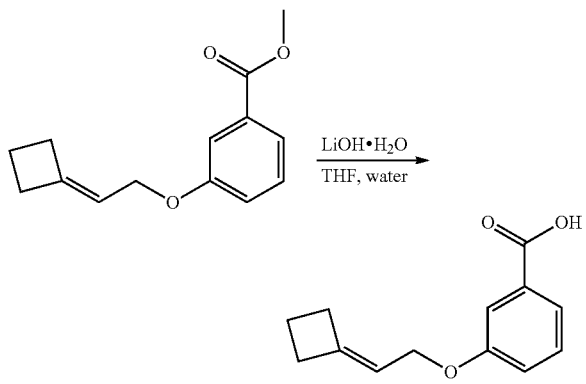

In 1:1 THF/water (5 mL each) product from step 2 (0.2 g, 0.86 mmol) and lithium hydroxide monohydrate (0.1 g, 2.58 mmol) was added and mixture stirred at room temperature. After 2 h TLC showed desired product and starting material, 3 eq. of lithium hydroxide monohydrate (0.1 g, 2.58 mmol) was added and stirred for ~2 h. TLC showed complete consumption of starting material (preduct $R_f$=0.35 in 50% ethyl acetate/n-hexane). THF was removed under reduced pressure. Aqueous layer was acidified with citric acid and extracted with ethyl acetate. Crude product was purified by column chromatography (silica gel 60-120 mesh, ethyl acetate-n-hexane as eluent) to afford colorless oil. Yield: 0.14 g (77%)

$^1$H NMR (400 MHz, CDCl$_3$): δ 1.96-2.07 (m, 2H), 2.72-2.82 (m, 4H), 4.46 (d, J=6.8 Hz, 2H), 5.38-5.47 (m, 1H), 7.12-7.18 (dd, J=2.4 and 8.0 Hz, 1H), 7.37 (t, J=8.0 Hz, 1H), 7.62 (s, 1H), 7.70 (d, J=7.6 Hz, 1H).

Step 4:—Synthesis of tert-butyl 3-(1-(3-(2-cyclobutylideneethoxy)benzoyl)piperidin-4-yl)benzyl carbamate

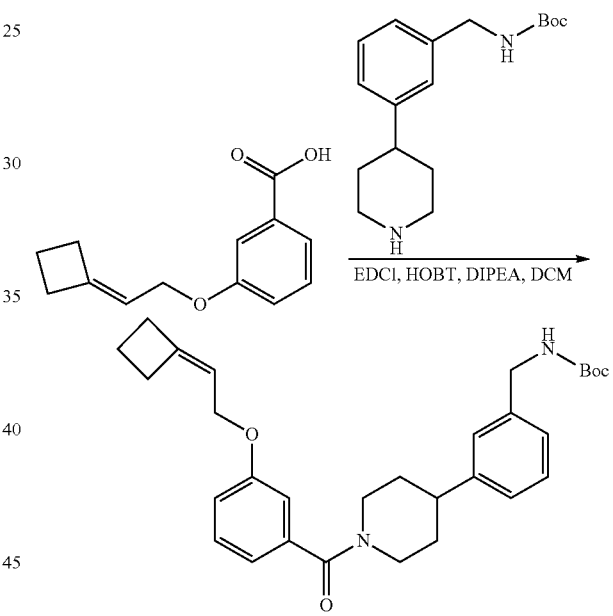

To a solution of Step 3 product (0.14 g, 0.64 mmol) in dry dichloromethane (10 mL), 3-(N-BOC-aminomethyl-phenyl)piperidine (0.18 g, 0.64 mmol), EDCI (0.14 g, 0.70 mmol), HOBt (0.17 g, 1.28 mmol), DIPEA (0.27 mL, 1.6 mmol) were added and the reaction mixture was stirred at room temperature overnight under nitrogen atmosphere. TLC showed absence of starting material (product $R_f$=0.75, 30% ethyl acetate/n-hexane). The reaction mixture was washed with saturated NaHCO$_3$ solution. The organic layer was separated, dried over sodium sulfate, concentrated, and purified by column chromatography (silica gel 60-120 mesh using 0-40% ethyl acetate in hexane as eluent) to give the desired product as colorless oil. Yield: 0.23 g (73%)

LCMS: m/z (M+1) 491

$^1$H NMR (400 MHz, CDCl$_3$): δ 1.46 (s, 11H), 1.95-2.0 (m, 2H), 2.71-2.84 (m, 7H), 3.09 (br, 1H), 3.91 (br, 1H), 4.30 (m, 2H), 4.41 (d, J=6.8 Hz, 2H), 4.82 (br, 2H), 5.40-5.45 (m, 1H), 6.90-7.00 (m, 3H), 7.10-7.20 (m, 3H), 7.26-7.33 (m, 2H).

Step 5:—Synthesis of tert-butyl 3-(1-(3-(2-cyclobutylideneethoxy)benzoyl)piperidin-4-yl)benzylcarbamate

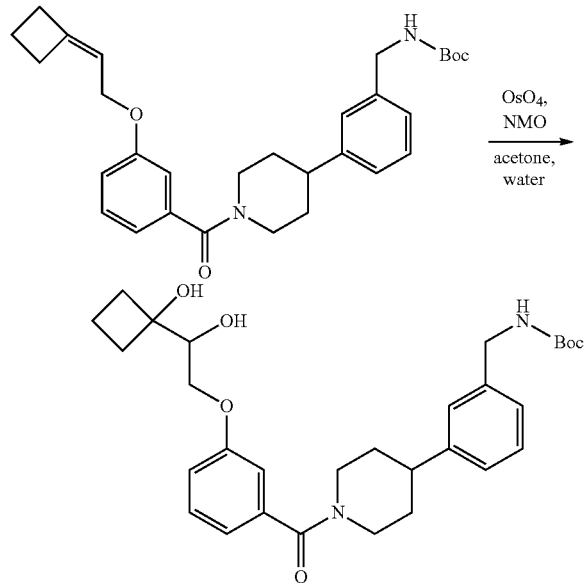

In 7 mL acetone and 1.5 mL of water, step 4 product (0.23 g, 0.47 mmol), OsO₄ (4% aqueous solution, 0.012 mL, 18.5 μmol) were added and stirred for 10 min at room temperature. Then NMO (50% aqueous solution, 0.13 mL, 0.56 mmol) was added and stirred at room temperature overnight. Reaction mixture was quenched with 10% aqueous sodium bisulphite solution and stirred for 1 h at room temperature, extracted with ethyl acetate, dried over sodium sulfate. Crude product obtained was purified by column chromatography (silica 60-120 mesh, ethyl acetate/n-hexane; $R_f$=0.14, 50% ethyl acetate/n-hexane) afforded colorless oil. Yield: 0.18 g (73%)

LCMS: m/z (M+1) 525

¹H NMR (400 MHz, CDCl₃): δ 1.47 (s, 9H), 1.61-1.76 (m, 5H), 2.05-2.16 (m, 4H), 2.35-2.40 (m, 1H), 2.70-2.90 (m, 4H), 3.11 (br, 1H), 3.38 (br, 1H), 4.05-4.20 (m, 3H), 4.30 (m, 2H), 4.85 (s, 2H), 6.93-7.06 (m, 3H), 7.11-7.17 (m, 3H), 7.26-7.35 (m, 2H).

Step 6:—Synthesis of (4-(3-(aminomethyl)phenyl)piperidin-1-yl)(3-(2-hydroxy-2-(1-hydroxycyclobutyl)ethoxy)phenyl)methanone

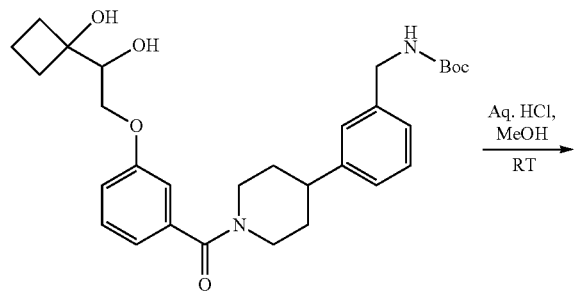

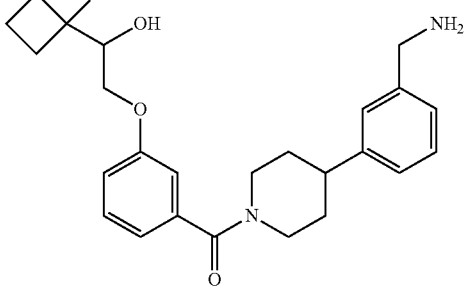

In 2 mL of methanol, product from step 5 (0.010 g, 0.019 mmol) and 0.1 mL of conc. HCl was allowed to stir at room temperature for 5 h. Starting material was not completely consumed (analyzed by TLC) again 0.1 mL of Conc. HCl was added and stirred overnight. Methanol was removed under reduced pressure. Reaction mixture was washed with diethyl ether and n-pentane and dried under vacuum. Crude reaction mixture was purified by prep. HPLC. Yield: 3.22 mg (33%, ammonium acetate salt)

LCMS: m/z (M+1) 425, HPLC purity: 99.8% (220 nm)

¹H NMR (400 MHz, CD₃OD): δ 1.60-1.70 (m, 2H), 1.79-2.05 (m, 9H), 2.24-2.36 (m, 1H), 2.38-2.48 (m, 1H), 2.86-3.02 (m, 2H), 3.89-3.94 (dd, J=2.4 and 7.6 Hz, 1H), 4.03 (t, J=8.8 Hz, 1H), 4.06 (s, 2H), 4.17-4.22 (dd, J=2.4 and 9.6 Hz, 1H), 4.59 (br, 2H), 6.99 (d, J=7.6 Hz, 2H), 7.06 (d, J=8.4 Hz, 1H), 7.27-4-7.41 (m, 5H).

Example 39—Synthesis of (E)-1-(4-(3-(aminomethyl)phenyl)piperidin-1-yl)-3-(3,4-dihydroxyphenyl)prop-2-en-1-one hydrochloride (Target-24)

Synthetic Scheme:

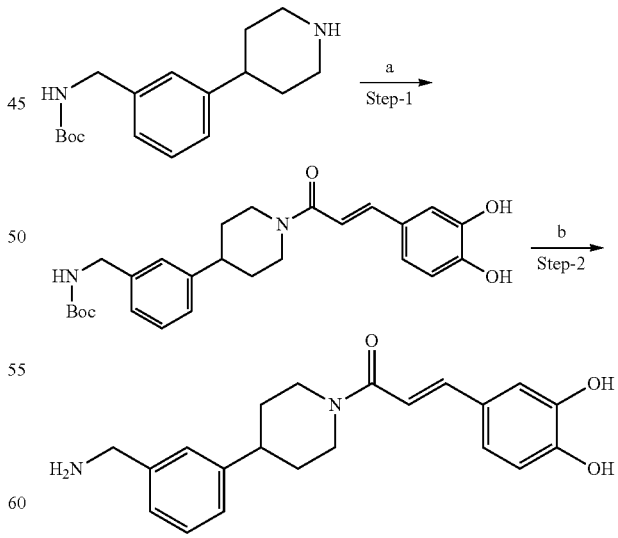

Reagents and Conditions:
a) (E)-3-(3,4-dihydroxyphenyl)acrylic acid, EDCi, HOBt, DIEA, DMF, room temperature, overnight; b) HCl, MeOH, room temperature, 1 h.

Experimental Procedure

Step-1: Synthesis of (E)-tert-butyl 3-(1-(3-(3,4-dihydroxyphenyl)acryloyl)piperidin-4-yl)benzylcarbamate

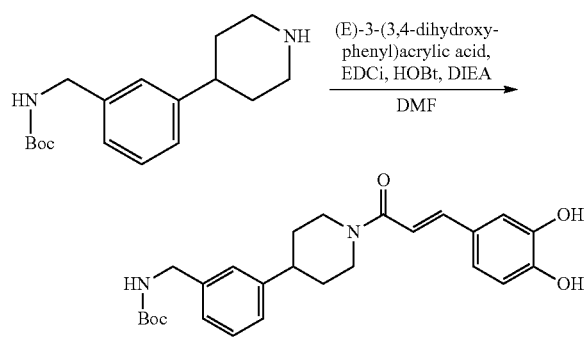

A mixture of tert-butyl 3-(piperidin-4-yl)benzyl carbamate (60 mg, 0.206 mmol), (E)-3-(3,4-dihydroxyphenyl) acrylic acid (37 mg, 0.206 mmol), EDCI (59 mg, 0.309 mmol), HOBt (42 mg, 0.309 mmol), DIEA (0.07 mL, 0.412 mmol) in DMF (4 mL) was stirred at room temperature overnight. The reaction mixture was diluted with EtOAc and washed with water, brine, dried over $Na_2SO_4$, concentrated, and purified by silica gel column chromatography (0-5% MeOH in $CHCl_3$) to yield (E)-tert-butyl 3-(1-(3-(3,4-dihydroxyphenyl)acryloyl)piperidin-4-yl)benzylcarbamate yield 90 mg (96%).

LCMS: m/z [M+1]=453; 93.24% (R.T.=2.52)
Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18 (50×4.6 mm) 3 uM, E-AC-2/08/COL/005
Gradient: Initial 20% B Conc. to 95% B Conc. in 3.0 min. Hold for 0.5 min. At 3.51 min
B. Conc. is 20%

Step-2: Synthesis of (E)-1-(4-(3-(aminomethyl)phenyl)piperidin-1-yl)-3-(3,4-dihydroxyphenyl)prop-2-en-1-one hydrochloride

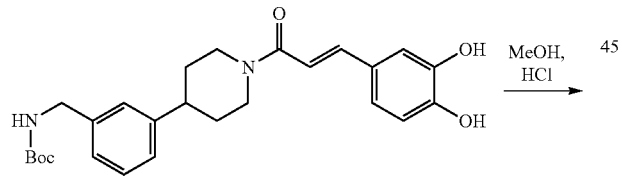

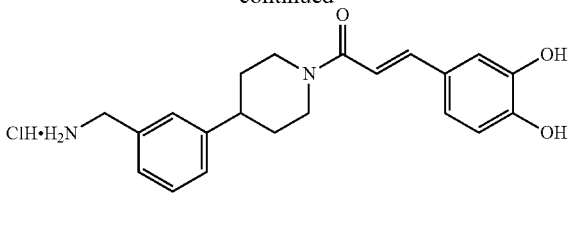

(E)-Tert-butyl 3-(1-(3-(3,4-dihydroxyphenyl)acryloyl)piperidin-4-yl)benzylcarbamate (90 mg, 0.198 mmol) dissolved in HPLC grade MeOH (2 mL) and treated with conc. HCl (0.5 mL) at room temperature. The reaction mixture was stirred at room temperature for 1 h. The solvent was evaporated in vacuo, and the residue was triturated with diethyl ether to get desired product. Yield:—40 mg (52%).

1H NMR (400 MHz, CD3OD): δ 7.49 (d, J=15.4 Hz, 1H), 7.42-7.28 (m, 4H), 7.08 (d, J=1.6 Hz, 1H), 7.00 (dd, J=8.4, 1.6 Hz, 1H), 6.94 (d, J=15.4 Hz, 1H), 6.78 (d, J=8.4 Hz, 1H), 4.85-4.75 (m, 2H), 4.45-3.60 (m, 1H), 4.10 (s, 2H), 2.98-2.87 (m, 2H), 2.05-1.90 (m, 2H), 1.80-1.65 (m, 2H)

LCMS: m/z [M+1]=353; 95.05% (R.T.=1.42)
Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18 (50×4.6 mm) 3 uM, E-AC-2/08/COL/005
Gradient: Initial 20% B Conc. to 95% B Conc. in 3.0 min. Hold for 0.5 min. At 3.51 min B. Conc. is 20%
HPLC: 97.82% (210 nm); 97.76% (254 nm); (R.T.=4.43)
Column: Waters X-Bridge 150 mm×4.6 mm×5 g, ID: E-AC-3/09/COL/027
Mobile Phase: A. 10 mM ammonium formate in water+0.1% NH3; B. acetonitrile+5% solvent A+0.1% NH3
Inj. Vol: 10 μL, Col. Temp.: 40° C., Flow rate: 1.40 mL/min
Gradient: 5% B to 95% B in 8 min, Hold till 9.50 min, At 9.51 B Conc. is 5% hold up to 12 min.

Example 40—Synthesis of (4-(3-aminomethyl)phenyl)piperidin-1-yl)(6,7-dimethoxynapthalen-1yl)methanone hydrochloride (Target-27a) & (4-(3-(aminomethyl)phenyl)piperidin-1-yl)(6,7-dihydroxynaphthalen-1-yl)methanone (Target-27)

Reaction Scheme:

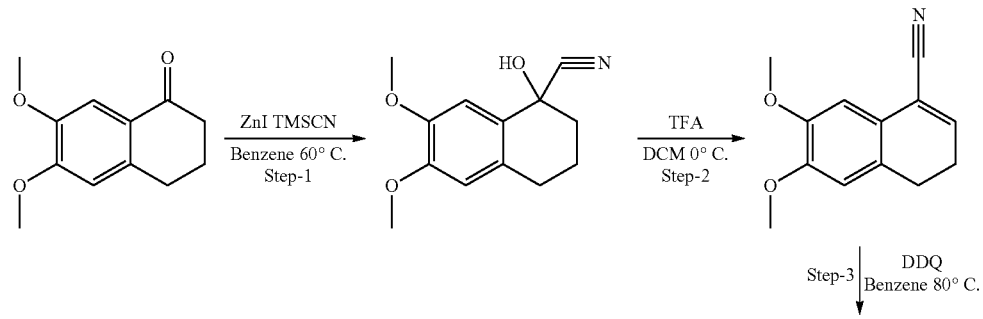

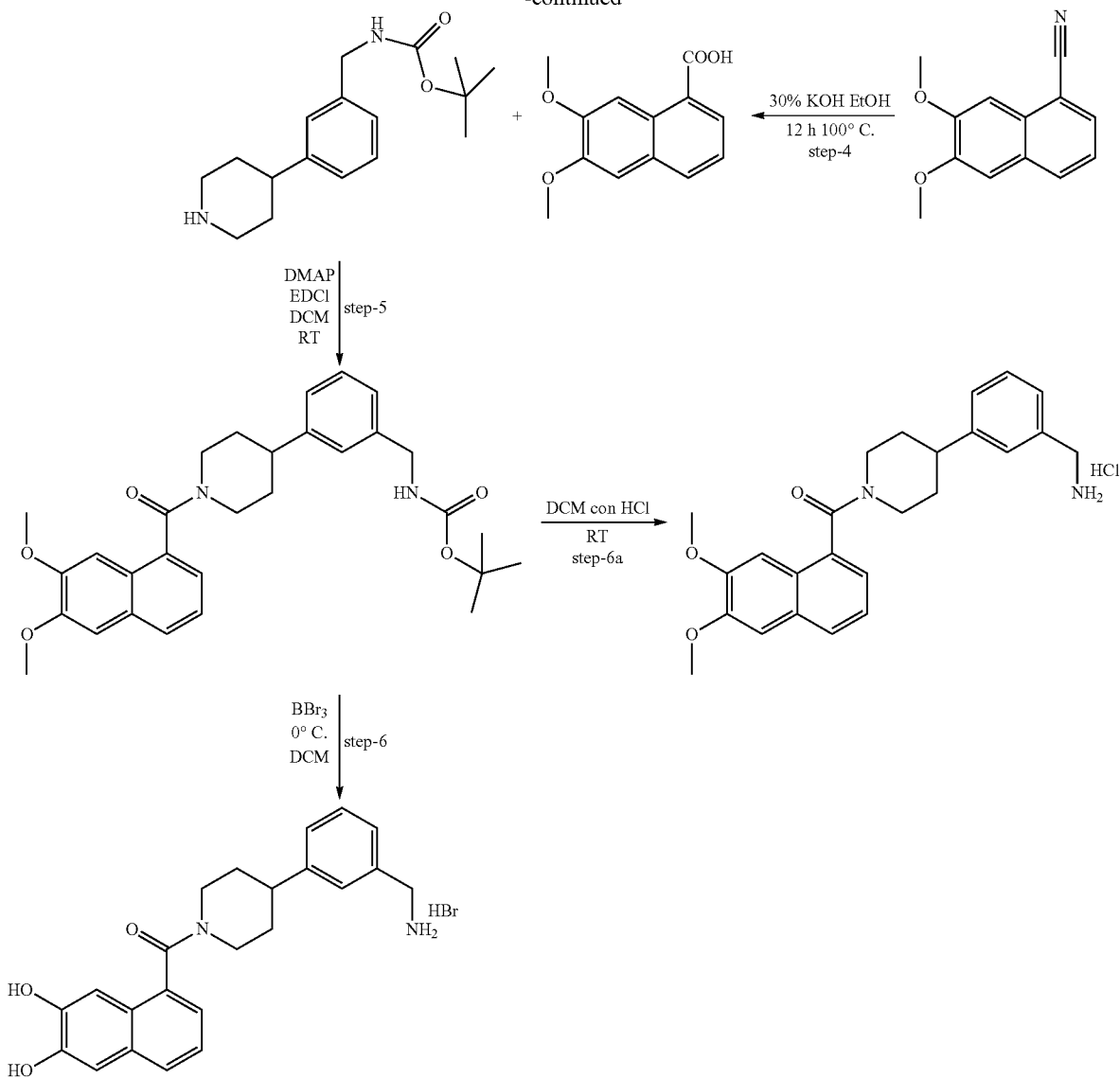

Experimental

Step-1: Synthesis of 1-hydroxy-6,7-dimethoxy-1,2,3,4 tetrahydronapthalene-1-carbonitrile

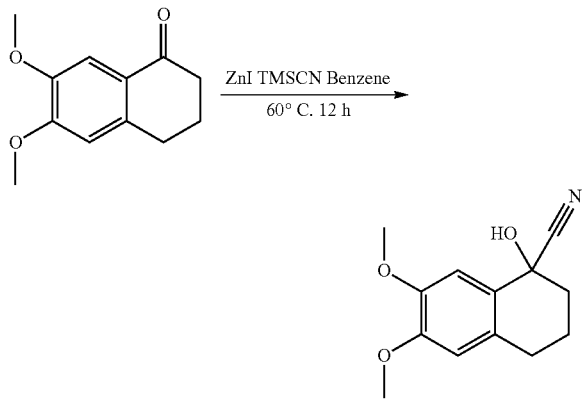

To a stirred solution of 6,7-dimethoxy tetralone (2 g, 9.70 mmol) in benzene (50 mL) under nitrogen atmosphere was added zinc iodide (154 mg, 0.485 mmol) followed by trimethylsilyl cyanide (2.88 g, 29.1 mmol) reaction was heated at 60° C. for 12 hrs when LCMS & TLC (30% ethyl acetate in hexane) indicated formation of product (Rf 0.4) and consumption of starting (Rf. 0.6). Reaction mass was cooled to room temperature and 100 ml water was added. Organic layer was separated and the aqueous layer was extracted with (50×3 ml) of ethyl acetate combined organic layers were washed with brine (50×2 ml), dried over sodium sulfate and concentrated under vacuum to get crude product which was purified by column chromatography on silica gel (gradient 10% ethyl acetate in Hexane) afforded to give 1.2 g pure product as yellow oil.

Mol. wt 233.2, LCMS indicates m/z of corresponding dehydrated product (216) Purity 94.12%, $^1$H NMR (400 MHz, CDCl$_3$) 1.96-2.04 (m, 2H), 2.1-2.17 (m, 1H), 2.3-2.33 (m, 1H), 2.73-2.76 (m, 2H), 3.86 (s 3H), 3.90 (s 3H), 6.54 (s, 1H), 7.09 (s, 1H)

Step-2: Synthesis of
6,7-dimethoxy-3,4-dihydronapthalene-1-carbonitrile

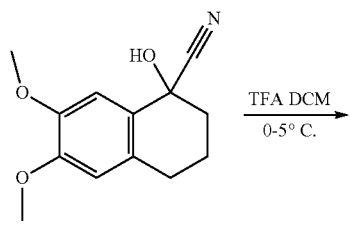

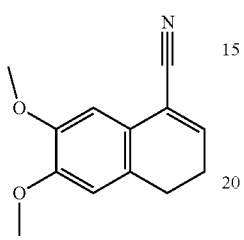

To a stirred solution of 1-hydroxy-6,7-dimethoxy-1,2,3,4 tetrahydronapthalene-1-carbonitrile (1.2 g, 5.14 mmol) in 20 ml of dichloromethane, trifluoroacetic acid (0.6 mL, 7.72 mmol) was added drop wise at 0° C. and the reaction mixture was stirred at Room temperature for 2 hrs. LCMS & TLC (20% ethyl acetate in hexane) indicated consumption of starting material (Rf. 0.2) and formation of product (Rf. 0.4) 50 ml water was added to the reaction mixture. Organic layer was separated, and the aqueous layer was extracted with (50×3 ml) of dichloromethane. Combined organic layers were washed with brine (50×2 ml), dried over sodium sulfate and concentrated under vacuum to yield crude product which was purified by column chromatography over silica gel (gradient 20% ethyl acetate in hexane) to get 700 mg pure product as white solid.
Mol. wt. 215; LCMS:—m/z 216, HPLC purity 98.55%, 1H NMR (400 MHz, CDCl3) 2.1-2.44-2.49 (m, 2H), 2.76-2.80 (m, 2H), 3.89 (s 3H), 3.91 (s 3H), 6.68 (s, 1H), 6.78 (t, 1H), 6.96 (s, 1H)

Step-3: Synthesis of 6,7-dimethoxy-1-naphthonitrile

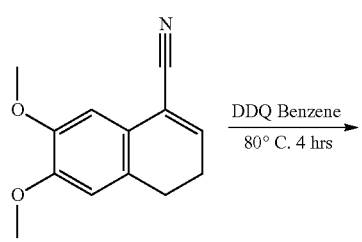

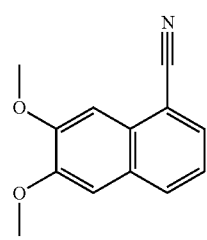

To a stirred solution of 6,7-dimethoxy-3,4-dihydronapthalene-1-carbonitrile (700 mg, 3.25 mmol) in 15 mL benzene, DDQ (739 mg, 3.25 mmol) was added under nitrogen atmosphere and reaction was refluxed at 80° C. for 4 hrs when LCMS & TLC (20% ethyl acetate in hexane) indicated formation of product (Rf. 0.6) and consumption of starting (Rf. 0.4). Reaction mass was filtered and solid washed with 20 ml benzene. Benzene layer was concentrated to give crude product which was purified by column chromatography using (10-90% ethyl acetate:hexane gradient) to get 600 mg pure product
Mol. Wt. 213, LCMS:—m/z 214, HPLC purity: 99.74%, 1H NMR (400 MHz, CDCl3) 4.028 (s 3H), 4.078 (s 3H), 7.16 (s, 1H), 7.37 (t, 1H, J=7.6), 7.44 (s, 1H), 7.74 (d, 1H, J=7.2) 7.9 (d, 1H, J=8.4)

Step-4: Synthesis of 6.7 dimethoxy-1-napthoic acid

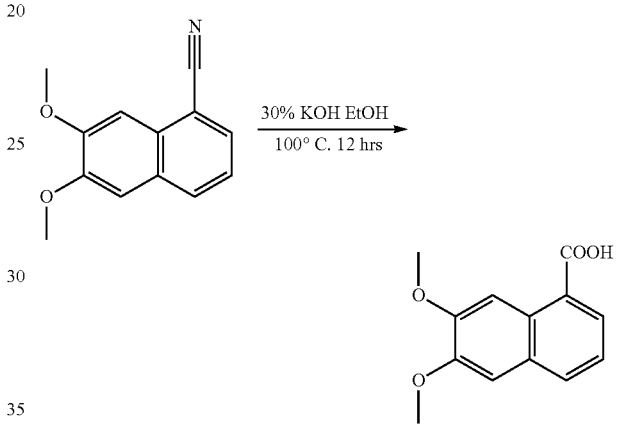

To 3 ml of 30% KOH and 3 ml ethanol was added 6,7-dimethoxy-1-naphthonitrile (600 mg, 2.81 mmol) and mixture was heated at 100° C. for 12 hrs when LCMS & TLC (10% methanol in dichloromethane) there after indicated completion of hydrolysis. Ethanol was removed from reaction mass under vacuum and residue diluted with 5 ml of water and extracted with (2×5 mL) DCM. Aqueous layer was acidified to pH-2 and was extracted with (2×20 ml) of ethyl acetate. Ethyl acetate layer was dried over sodium sulfate and concentrated in vacuum. Crude product was purified by column chromatography using (ethyl acetate:hexane 10:90) to get 400 mg pure product.
Mol. Wt. 232; LCMS:—m/z 233, HPLC purity: 99.42%, 1H NMR (400 MHz, DMSO) 3.88 (s 3H), 3.90 (s 3H), 7.37-7.39 (m, 1H), 7.40 (s, 1H), 7.98-8.03 (m, 2H), 8.40 (s, 1H), 12.89 (br. s, 1H)

Step-5: Synthesis of tert-butyl 3-(1-6,7-dimethoxy-1-napthoyl)piperidin-4-yl)benzyl carbamate

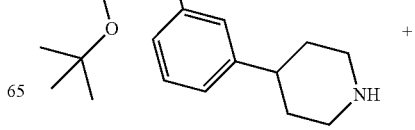

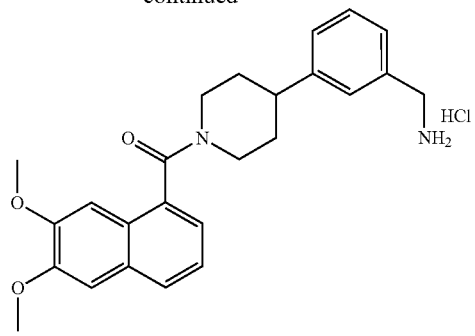

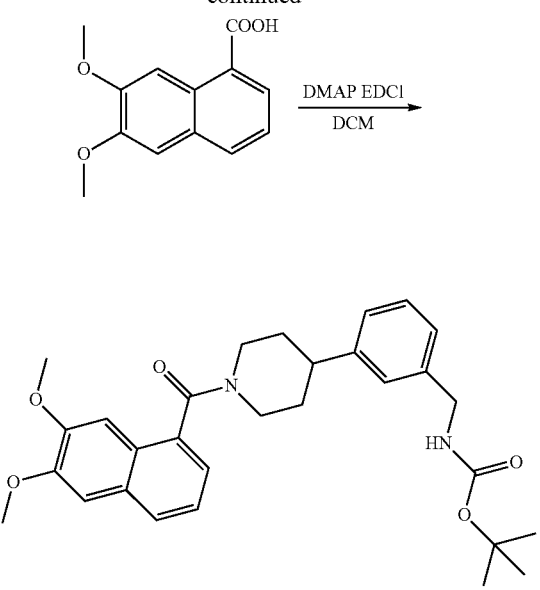

To a stirred solution of 6,7-dimethoxy napthoic acid (200 mg, 0.86 mmol) in 6 ml of DCM was added DMAP (126 mg, 1.03 mmol) and EDCI (246 mg, 1.29 mmol) The solution was stirred for 15 mins at 0° C. followed by addition of tert-butyl 3-(piperidin-4-yl)benzylcarbamate (250 mg, 0.86 mmol). Reaction mixture was then stirred at room-temperature for 4 hrs when TLC (10% methanol in dichloromethane) indicated consumption of starting materials and formation of product (Rf. 0.5). The reaction mixture was diluted with 10 ml of water, organic layer was separated and aq. layer was extracted with 2×10 ml of dichloromethane. Combined organic layers were dried over sodium sulfate and concentrated under vacuum to get crude product. Crude product was purified by column chromatography over silica gel (Gradient:—0-10% methanol in dichloro methane) to get 350 mg pure product.

Mol. Wt. 504; LCMS:—m/z 405 (corresponds to de-Boc product), HPLC purity: 92.7%

Step-6a: Synthesis of (4-(3-aminomethyl)phenyl) piperidin-1-yl)(6,7-dimethoxynapthalen-1yl)methanone hydrochloride (Target-27a)

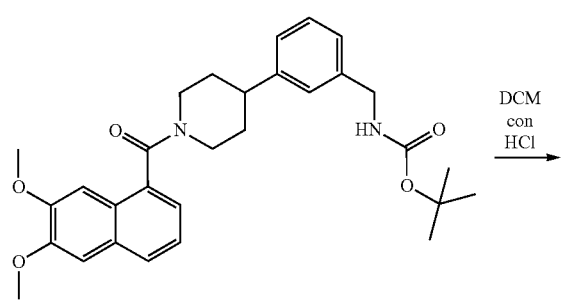

Tert-butyl3-(1-6,7-dimethoxy-1-napthoyl)piperidin-4-yl) benzyl carbamate obtained from step-5 was dissolved in DCM (5 ml) and 0.5 ml conc. HCl was added to this and stirred at room temperature for 5 hrs when TLC ((10% methanol in dichloromethane) indicated consumption of starting. Reaction mixture was then washed with 10% NaHCO₃ wash followed by water and brine, dichloromethane layer was dried over anhydrous sodium sulfate and concentrated to yield crude product. This was purified by preparative HPLC to get 8.8 mg pure product as TFA salt which was converted to hydrochloride salt (8.8 mg) by stirring with 10% methanolic HCl for 30 min and subsequent removal of volatiles in vacuum.

Mol. wt 404; LCMS:—m/z 405.3, HPLC purity: 96.03%

1H NMR (400 MHz, DMSO) 1.6-2.1 (m, 4H), 2.84 (m, 1H), 2.94-3.33 (m, 4H) 3.87 (s 3H), 3.89 S (3H), 3.98 (s, 2H), 4.84 (t, 1H) 6.95 (s, 1H), 7.09 (s, 1H) 7.22-29 (m, 1H) 7.3-7.42 (m, 5H), 7.45 (s, 1H), 8.44 (m, 2H)

Step-6: Synthesis (4-(3-(aminomethyl)phenyl)piperidin-1-yl)(6,7-dihydroxynaphthalen-1-yl)methanone (Target-27)

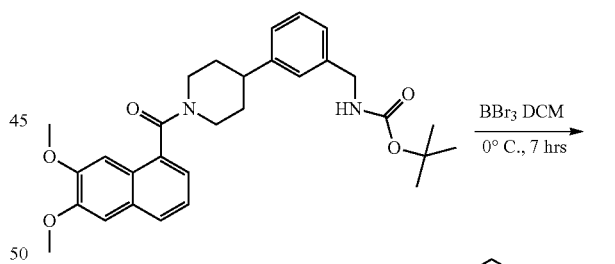

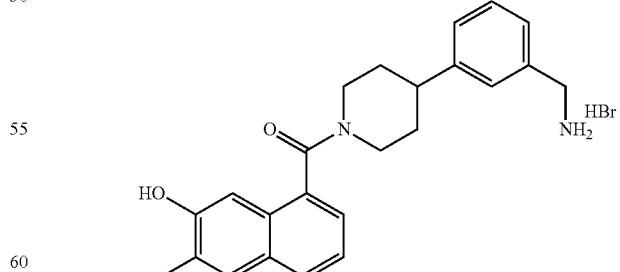

To a stirred solution of 3-(1-6,7-dimethoxy-1-napthoyl) piperidin-4-yl)benzyl carbamate (100 mg, 0.198 mmol) in 5 ml of DCM was added boron tri-bromide (14.8 mg, 0.595 mmol) at 0° C. drop wise and stirred for 1 hr at 0° C. and then 7 hrs at room-temp when TLC (10% methanol in dichloromethane) indicated completion of the reaction. To the reaction mixture was quenched with 2 g ice and the solid product obtained was filtered and washed with ethyl acetate and purified by preparative HPLC to give pure compound as TFA salt which was stirred with (10% methanolic HCl) for 30 min and concentrated in vacuum to get 8 mg product as hydrochloride salt.

Mol. Wt. 376; LCMS:—m/z 377.2, HPLC purity: 98.6%

1H NMR (400 MHz, Methanol-d3) 1.55-2.1 (m, 4H), 2.85-3.31 (m, 5H) 4.10 (s, 2H), 6.6 (s, 1H), 7.01 (s, 1H), 7.2-7.4 (m, 6H), 7.64 (d, 1H)

Example 41—Synthesis of 4-(aminomethyl)-N-(4-(2-(2,2-dimethyldihydro-3aH-[1,3]dioxolo[4,5-c]pyrrol-5(4H)-yl)-2-oxoethoxy)benzyl)benzamide Synthetic Scheme:

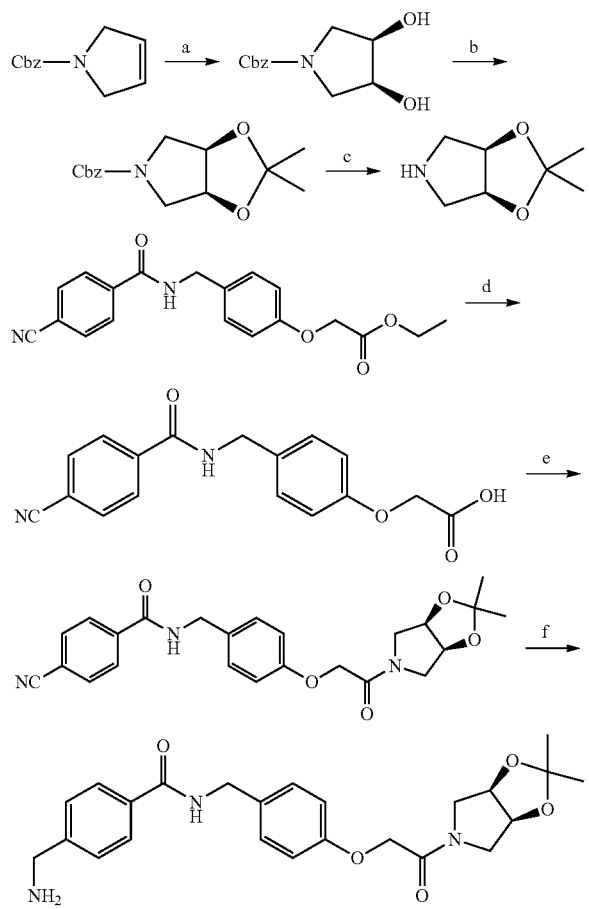

Reagents and Conditions:

a) OsO4, NMO, THF:H2O, room temperature, 15 h; b) 2,2'-dimethoxypropane, PTSA, acetone, room temperature, 5 h; c) 10% Pd/C, H2 (balloon pressure), EtOH, cat. K2CO3, room temperature, 15 h; d) LiOH.H2O, MeOH:H2O, room temperature, 1 h; e) 2,2-dimethyltetrahydro-3aH-[1,3]dioxolo[4,5-c]pyrrole, EDCI, HOBt, DIEA, DMF, room temperature, 15 h; f) Raney Nickel, MeOH, H2 (Balloon Pressure), room temperature, 5 h; Experimental Procedure Step-1: Synthesis of benzyl 3,4-dihydroxypyrrolidine-1-carboxylate

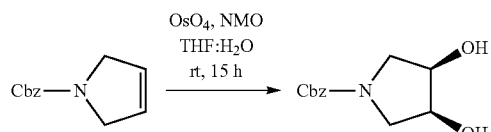

Benzyl 2,5-dihydro-1H-pyrrole-1-carboxylate (2 g, 9.84 mmol) was taken in THF (16 mL) and water (6 mL), to it OsO4 (25 mg, 0.098 mmol), NMO (1.6 g, 13 mmol) were added. The reaction mixture was stirred at room temperature for 15 h. The reaction mixture was concentrated and the crude was partitioned between EtOAc and water. Layers were separated and the aqueous layer was extracted with EtOAc. The combined organic layer was dried over Na2SO4, concentrated and purified by column chromatography to yield the pure benzyl 3,4-dihydroxypyrrolidine-1-carboxylate (2.2 g, 95%).

Step-2: Synthesis of benzyl 2,2-dimethyldihydro-3aH-[1,3]dioxolo[4,5-c]pyrrole-5(4H)-carboxylate

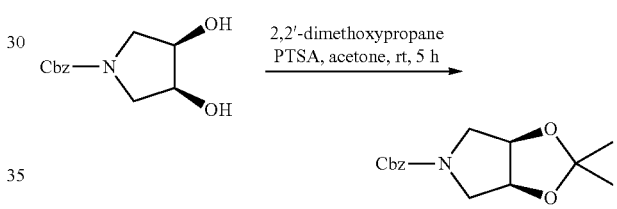

Benzyl 3,4-dihydroxypyrrolidine-1-carboxylate (2.2 g, 9.2 mmol) was dissolved in acetone (20 mL). To it 2,2'-dimethoxypropane (3.86 g, 37 mmol) was added followed by catalytic amount of PTSA (17 mg, 0.92 mmol). The reaction was stirred at room temperature for 5 h. After completion of the reaction, Et3N was added and the reaction mixture was concentrated. The crude was purified by column chromatography to yield 650 mg. benzyl 2,2-dimethyldihydro-3aH-[1,3]dioxolo[4,5-c]pyrrole-5(4H)-carboxylate (2.1 g, 85%).

LCMS: m/z [M+1]=278; 98.64% (R.T.=2.52)

Chromatographic Parameters

Mobile Phase A: 0.05% TFA in water, mobile phase B:0.05% TFA in acetonitrile,

Flow rate: 1.2 ml/min; Temperature: Ambient,

Column: YMC ODS A, C18(50×4.6 mm) 3 uM, E-AC-2/08/COL/005

Gradient: Initial 20% B Conc to 95% B Conc. in 3.0 min. Hold for 0.5 min. At 3.51 min B. Conc. is 20%

Step-3: Synthesis of 2,2-dimethyltetrahydro-3aH-[1,3]dioxolo[4,5-c]pyrrole

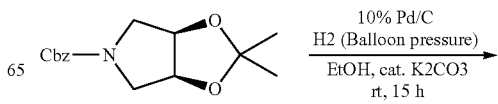

-continued

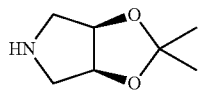

Benzyl 2,2-dimethyldihydro-3aH-[1,3]dioxolo[4,5-c]pyrrole-5(4H)-carboxylate (2 g, 7.21 mmol) was dissolved in EtOH (20 mL). To it 10% Pd/C (100 mg), anh. K$_2$CO$_3$ (100 mg) were added and the reaction mixture was stirred under H$_2$ atmosphere for 3 h. After completion of the reaction mixture, the reaction mixture was filtered through a small celite pad; the filtrate was concentrated to yield the 2,2-dimethyltetrahydro-3aH-[1,3]dioxolo[4,5-c]pyrrole (130 mg), which was used as such further (900 mg, 87%).

Step-4: Synthesis of 2-(4-((4-cyanobenzamido)methyl)phenoxy)acetic acid

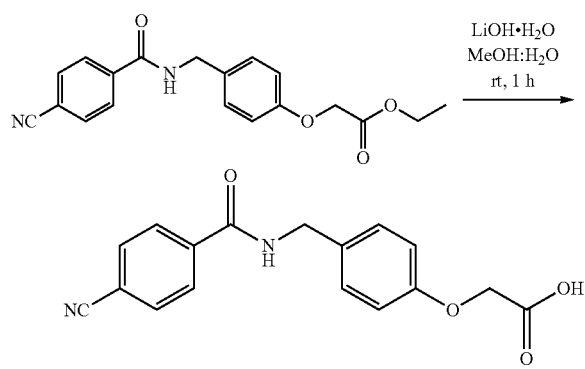

LiOH (62 mg, 1.47 mmol) was added to a MeOH (8 mL) solution of 2,2-dimethyltetrahydro-3aH-[1,3]dioxolo[4,5-c]pyrrole (500 mg, 1.47 mmol), and the reaction mixture was stirred at room temperature for 1 h. After completion of the reaction mixture, the solvent was concentrated; the crude was dissolved in water and acidified with 10% aq. Citric acid. The aqueous layer was extracted with EtOAc (3×25 mL). The combined organic layer was dried over Na$_2$SO$_4$, concentrated and triturated with ether to yield the 2-(4-((4-cyanobenzamido)methyl)phenoxy)acetic acid (400 mg, 85%).

LCMS: m/z [M+1]=311; 81.82% (R.T.=1.86)+15.02% (R.T.=1.15).
Chromatographic Parameters
Mobile Phase A: 0.05% TFA in water, Mobile Phase B:0.05% TFA in acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Conc to 95% B Conc. in 3.0 min. Hold for 0.5 min. At 3.51 min B. Conc. is 20%

Step-5: Synthesis of 4-cyano-N-(4-(2-(2,2-dimethyldihydro-3aH-[1,3]dioxolo[4,5-c]pyrrol-5(4H)-yl)-2-oxoethoxy)benzyl)benzamide

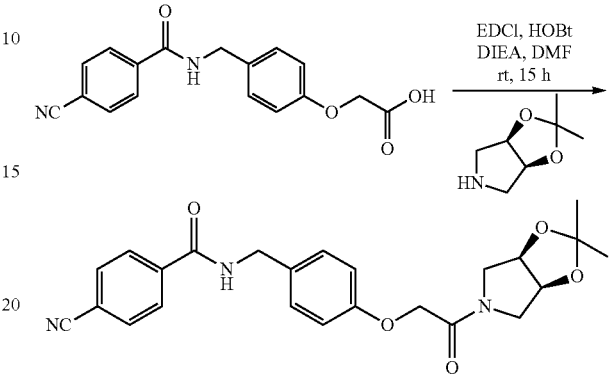

To a cooled solution of 2-(4-((4-cyanobenzamido)methyl)phenoxy)acetic acid (540 mg, 1.7 mmol) at 0° C. in anhydrous DMF (5 mL), HOBt (353 mg, 2.6) was added and the reaction mixture was stirred for 10 min. before EDCI (502 mg, 2.6 mmol), 2,2-dimethyltetrahydro-3aH-[1,3]dioxolo[4,5-c]pyrrole (250 mg, 1.7 mmol) and DIEA (0.6 mL) were added in succession. The reaction mixture was allowed to warm to room temperature and was stirred overnight. After completion of the reaction (TLC) the reaction mixture was diluted with EtOAc (20 mL) and was washed with water (3×20 mL). The EtOAc layer was they dried over Na$_2$SO$_4$ and evaporated under vacuo to give a residue that was purified by column chromatography (silica gel, gradient MeOH in CH$_2$Cl$_2$) to afford 4-cyano-N-(4-(2-(2,2-dimethyldihydro-3aH-[1,3]dioxolo[4,5-c]pyrrol-5(4H)-yl)-2-oxoethoxy)benzyl)benzamide (320 mg, 42%).

LCMS: m/z [M+11]=436; 90.31% (R.T.=2.10).
Chromatographic Parameters
Mobile Phase A: 0.05% TFA in water, Mobile Phase B:0.05% TFA in Acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Cone to 95% B Conc. in 3.0 min. Hold for 0.5 min. At 3.51 min B. Conc. is 20%

Step-6: Synthesis of 4-(aminomethyl)-N-(4-(2-((3aR,6aS)-2,2-dimethyldihydro-3aH-[1,3]dioxolo[4,5-c]pyrrol-5(4H)-yl)-2-oxoethoxy)benzyl)benzamide
(8a)

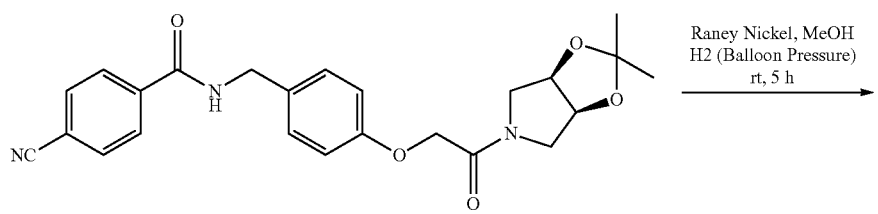

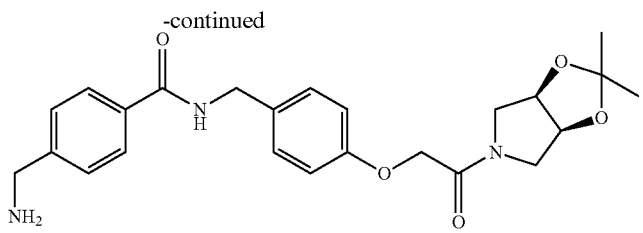

4-cyano-N-(4-(2-(2,2-dimethyldihydro-3aH-[1,3]dioxolo[4,5-c]pyrrol-5(4H)-yl)-2-oxoethoxy)benzyl)benzamide (320 mg, 0.734 mmol) was dissolved in EtOH (40 mL). To it Raney Nickel (~100 mg) was added and the reaction mixture was stirred under $H_2$ atmosphere for 5 h. After completion of the reaction mixture, the reaction mixture was filtered through a small celite pad, the filtrate was concentrated, and the residue was purified by Prep-HPLC in neutral medium to yield 4-(aminomethyl)-N-(4-(2-((3aR,6aS)-2,2-dimethyldihydro-3aH-[1,3]dioxolo[4,5-c]pyrrol-5(4H)-yl)-2-oxoethoxy)benzyl)benzamide (300 mg, 96%).

1H NMR (400 MHz, CD3OD): δ 7.86 (d, J=8.4 Hz, 2H), 7.49 (d, J=8.4 Hz, 2H), 7.26 (d, J=8.4 Hz, 2H), 6.90 (d, J=8.4 Hz, 2H), 4.85-4.73 (m, 2H), 4.69 (ABq, J=14.8 Hz, 2H), 4.48 (s, 2H), 4.07 (s, 2H), 3.94 (d, J=14.0 Hz, 1H), 3.87 (d, J=14.0 Hz, 1H), 3.50 (dd, J=4.8, 12.4 Hz, 1H), 1.88 (s, 3H), 1.33 (s, 3H), 1.27 (s, 3H).

LCMS: m/z [M+1]=440; 99.90 (R.T.=1.36)
Chromatographic Parameters
Mobile Phase A: 0.05% TFA in water, Mobile Phase B: 0.05% TFA in Acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Cone to 95% B Conc. in 3.0 min. Hold for 0.5 min. At 3.51 min B. Conc. is 20%

Example 42—Synthesis of 4-(aminomethyl)-N-(4-(2-((3R,4S)-3,4-dihydroxypyrrolidin-1-yl)-2-oxoethoxy)benzyl)benzamide hydrochloride (Target-8)

Synthetic Scheme:

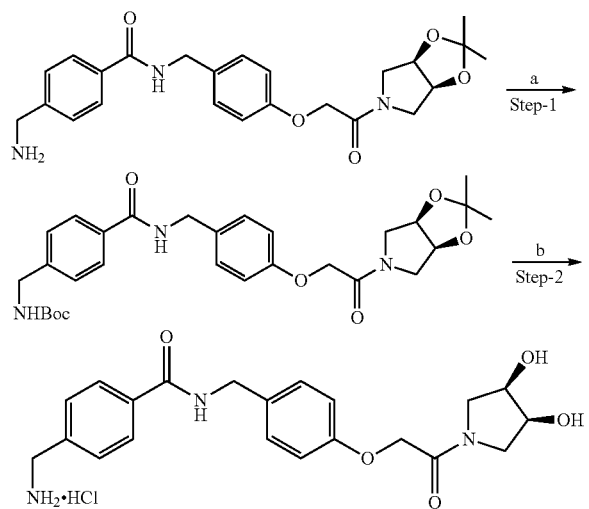

Reagents and Conditions:
a) Boc2O, THF, Et3N, 5 h; b) Conc. HCl, MeOH, room temperature, 2 h.

Experimental Procedure

Step-1: Synthesis of tert-butyl 4-((4-(2-((3aR,6aS)-2,2-dimethyldihydro-3aH-[1,3]dioxolo[4,5-c]pyrrol-5(4H)-yl)-2-oxoethoxy)benzyl)carbamoyl) benzylcarbamate

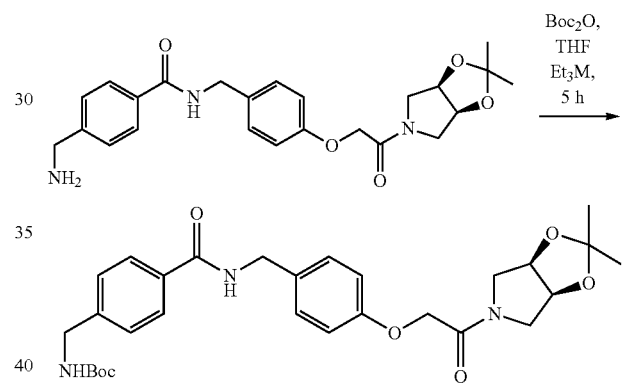

4-(aminomethyl)-N-(4-(2-(2,2-dimethyldihydro-3aH-[1,3]dioxolo[4,5-c]pyrrol-5(4H)-yl)-2-oxoethoxy)benzyl)benzamide (330 mg (crude), 0.750 mmol) was dissolved in dioxane:H2O (3.5:1.8 mL) and to it Boc2O (245 mg, 1.1 mmol), NaHCO3 (189 mg, 2.2 mmol) were added at room temperature. The reaction mixture was stirred at room temperature for 5 h. After completion of the reaction, the volatiles were evaporated in vacuo and the crude was purified by column chromatography using 0-2% MeOH:CHCl3 solvent mixture to yield tert-butyl 4-((4-(2-((3aR,6aS)-2,2-dimethyldihydro-3aH-[1,3]dioxolo[4,5-c]pyrrol-5(4H)-yl)-2-oxoethoxy)benzyl)carbamoyl)benzylcarbamate (40 mg, 13% based on crude weight).

LCMS: m/z [M+1]=562; 93.09% (R.T.=2.35)
Chromatographic Parameters
Mobile Phase A: 0.05% TFA in water, Mobile Phase B:0.05% TFA in Acetonitrile,
Flow rate: 1.2 ml/min; Temperature: Ambient,
Column: YMC ODS A, C18(50×4.6 mm) 3 uM, E-AC-2/08/COL/005
Gradient: Initial 20% B Conc to 95% B Conc. in 3.0 min. Hold for 0.5 min. At 3.51 min B. Conc. is 20%

Step-2: Synthesis of 4-(aminomethyl)-N-(4-(2-((3R,4S)-3,4-dihydroxypyrrolidin-1-yl)-2-oxoethoxy)benzyl)benzamide hydrochloride

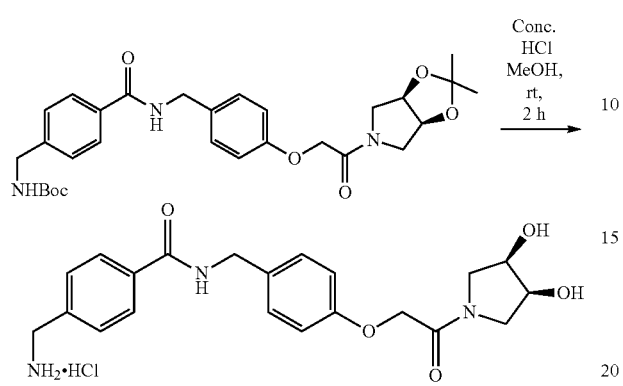

Tert-butyl 4-((4-(2-((3aR,6aS)-2,2-dimethyldihydro-3aH-[1,3]dioxolo[4,5-c]pyrrol-5(4H)-yl)-2-oxoethoxy)benzyl)carbamoyl)benzylcarbamate (35 mg, 0.064 mmol) was dissolved in MeOH (5 mL). To it conc. HCl (0.5 mL) was added at room temperature and the reaction mixture was stirred for 2 h. After completion of the reaction mixture, the volatiles were concentrated in vacuo and the residue was purified by Prep-HPLC in acidic medium to yield 4-(aminomethyl)-N-(4-(2-((3R,4S)-3,4-dihydroxypyrrolidin-1-yl)-2-oxoethoxy)benzyl)benzamide hydrochloride (0.021 g, 84%).

1H NMR (400 MHz, CD3OD): δ 7.89 (d, J=8.4 Hz, 2H), 7.52 (d, J=8.4 Hz, 2H), 7.27 (d, J=8.4 Hz, 2H), 6.90 (d, J=8.4 Hz, 2H), 4.87-4.78 (m, 1H), 4.67 (s, 2H), 4.48 (s, 2H), 4.24-4.20 (m, 1H), 4.15 (s, 2H), 3.72 (dd, J=5.6, 10.4 Hz, 1H), 3.57 (dd, J=5.6, 12.8 Hz, 1H), 3.47-3.39 (m, 2H).

LCMS: m/z [M+1]=400; 96.10% (R.T.=2.04)
Chromatographic Parameters
Mobile Phase A: 0.05% TFA in water, Mobile Phase B:0.05% TFA in acetonitrile,
Flow rate: 1.2 ml/min; Temperature: Ambient,
Column: YMC ODS A, C18(50×4.6 mm) 3 uM, E-AC-2/08/COL/005
Gradient: Initial 0% B Conc to 50% B Conc. in 3.0 min. Hold for 0.5 min. At 3.51 min B. Conc. is 0%

Example 43—Synthesis of dimethyl 3,3'-(((2,5-dihydroxy-1,4-dioxane-2,5-diyl)bis(methylene))bis(oxy))dibenzoate (Target 3&4 Step-7)

Reaction scheme

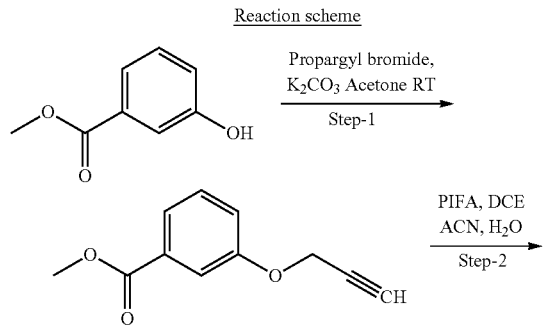

-continued

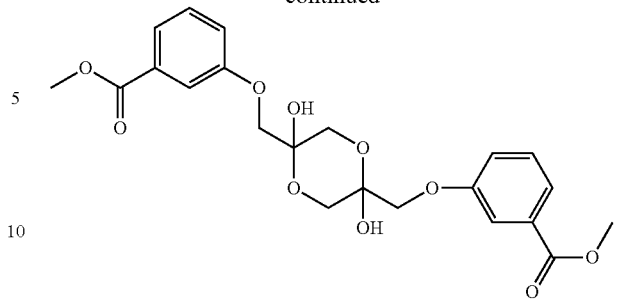

Experimentals

Step-1: Synthesis of methyl 3-(prop-2-yn-1-yloxy)benzoate

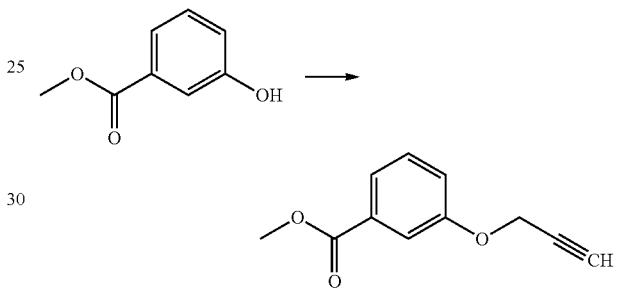

To a stirred solution of methyl-3-hydroxybenzoate (3 g, 19.7 mmol) in acetone (45 mL), propargyl bromide (3.5 mL, 23.6 mmol) was added at once. The reaction mixture was cooled to 0° C. and potassium carbonate (8.1 g, 59.2 mmol) was added. The reaction mixture was stirred at room temperature overnight. TLC (Mobile phase 20% ethyl acetate in n-hexane) indicated slight presence of starting material (Rf 0.5) and major product formation (Rf—0.7). The reaction mixture was filtered and concentrated. The compound was extracted in ethyl acetate and washed with water. The organic layer was dried over sodium sulfate, concentrated and purified by column chromatography using hexane:ethyl acetate as eluent to give the desired product as yellow oil. Yield: 3.2 g, 85.3%.

LCMS: (M+1) 190.9

$^1$H NMR (CDCl$_3$): 2.54 (t, 1H, J=2.2 Hz), 3.92 (s, 3H), 4.74 (d, 2H, J=2.4 Hz), 7.15-7.20 (dd, 1H, J=1.8, 8.2 Hz), 7.37 (t, 1H, J=8 Hz), 7.64 (s, 1H), 7.68 (d, 1H, J=7.2 Hz).

Step-2: Synthesis of dimethyl 3,3'-(((2,5-dihydroxy-1,4-dioxane-2,5-diyl)bis(methylene))bis(oxy))dibenzoate

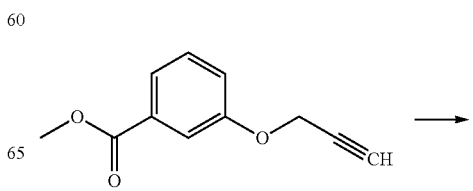

-continued

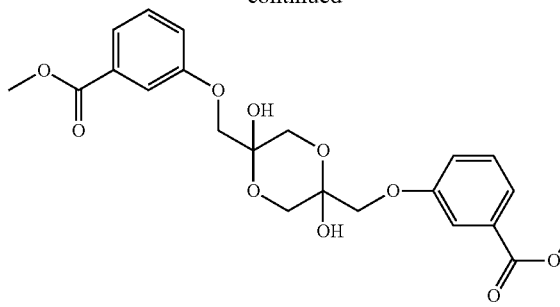

To a solution of methyl 3-(prop-2-yn-1-yloxy)benzoate (1 g, 5.26 mmol) in dichloroethane:acetonitrile:water (16:2:0.2 mL), [bis(trifluoroacetoxy)iodo]benzene (4 g, 9.47 mmol) was added and the reaction mixture was heated at 80° C. overnight. TLC (Mobile phase 50% ethyl acetate in n-hexane) indicated presence of starting material (Rf 0.6) along with product (Rf—0.3). The reaction mixture was cooled and diluted with water. The organic layer was separated, dried over sodium sulfate and concentrated. Silica gel (230-400 mesh) 2 g was added to the concentrated mass and it was allowed to stir overnight. The product was then purified by column chromatography using hexane ethyl acetate as eluent. The pale yellow solid obtained was then washed with diethyl ether to give the desired product as off-white solid.
Yield: 0.023 g, 1%.
ESMS: (M+H2O) 465.9
HPLC purity: 81.7% (200-400 nm)
$^1$H NMR (DMSO-d6): 3.55 (d, 2H, J=11.6 Hz), 3.85 (s, 6H), 3.93 (d, 2H, J=10 Hz), 3.99 (d, 2H, J=10 Hz), 4.10 (d, 2H, J=11.2 Hz), 6.31 (s, 2H), 7.25-7.28 (dd, 2H, J=2, 8 Hz), 7.45 (t, 2H, J=8 Hz), 7.47 (s, 2H), 7.56 (d, 2H, J=8 Hz).

Example 44—Synthesis of 1-(2-(benzyloxy)-1-hydroxyethyl)cyclobutanol (Target 22C)

Reaction scheme

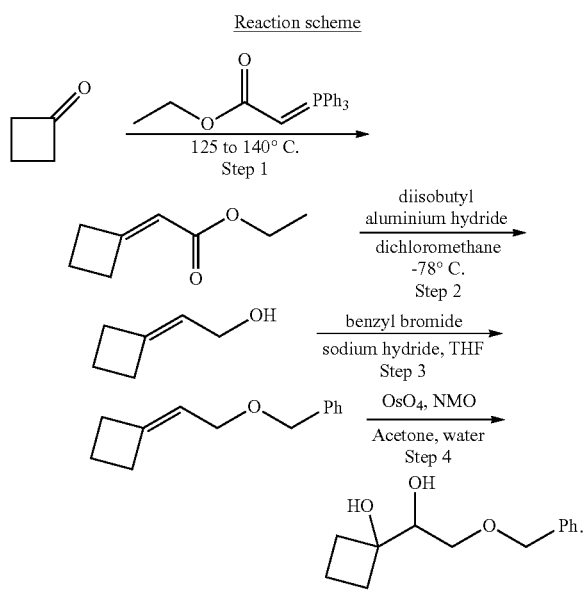

Experimental

Step-1: Synthesis of ethyl 2-cyclobutylideneacetate

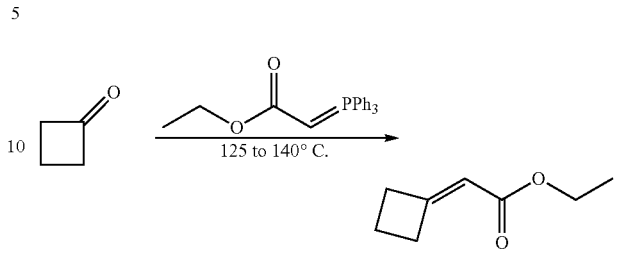

Cyclobutanone (0.5 g, 7.14 mmol) and (ethoxycarbonyl-methylen)-triphenylphosphorane (2.7 g, 7.75 mmol) were heated to 125 to 140° C. in seal tube for 24 h. Reaction mixture was cooled to room temperature; 50 mL of pentane was added and stirred for 20 min. Then reaction mixture was filtered. Pentane layer was evaporated without applying pressure. Crude product was purified by column chromatography (silica gel 60-120 mesh, diethyl ether and n-pentane was used as eluent) afforded colorless oil. Yield: 0.7 g, 70%.
$^1$H NMR (400 MHz, CDCl$_3$): δ 1.27 (t, J=7.0 Hz, 3H), 2.04-2.13 (m, 2H), 2.83 (t, J=8.0 Hz, 2H), 3.13 (t, J=8.0 Hz, 2H), 4.10-4.17 (m, 2H), 5.58 (t, J=2.2 Hz, 1H)

Step-2: Synthesis of 2-cyclobutylideneethanol

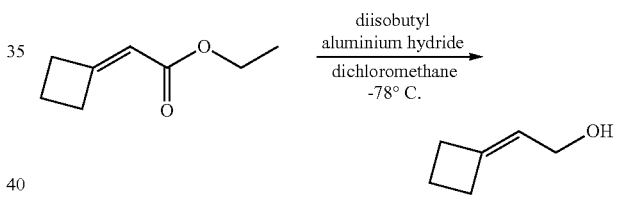

In a 47 mL of dry DCM product from step 1 (0.95 g, 6.78 mmol) was allowed to cooled to −78° C. To this solution DIBAL-H (1M in toluene) (1.92 g, 13.6 mL, 13.5 mmol) was added dropwise. Reaction monitored by TLC, as starting completely consumed reaction mixture was quenched with MeOH/H$_2$O (1:1). DCM layer was separated and dried over sodium sulfate. DCM was removed under reduced pressure. 0.5 g of crude product obtained and was used as it is for the next step.
Yield: 0.50 g. crude.
$^1$H NMR (400 MHz, CDCl$_3$): δ 1.91-2.05 (m. 2H), 2.65-2.74 (m, 4H), 4.02 (d, J=7.2 Hz, 2H), 5.3-5.36 (m, 1H).

Step 3: Synthesis of ((2-cyclobutylideneethoxy)methyl)benzene

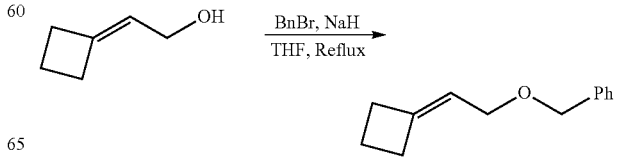

In 15 mL of dry THF, sodium hydride (0.51 g, 12.7 mmol) was allowed to stir at 0° C. To this suspension product from step 2 (0.5 g, 5.10 mmol) in 5 mL THF was added and resulting reaction mixture was allowed to stir at 0° C. for 1.5 h. Then benzyl bromide (0.87 g, 5.10 mmol) was added and resulting reaction mixture was refluxed overnight. Reaction mixture was quenched with water and extracted with ethyl acetate. Organic layer dried over sodium sulfate and concentrated under reduced pressure. Crude reaction mixture was purified by column chromatography (silica gel 60-120 mesh, ethyl acetate and n-hexane as eluent) to afford colorless oil. Yield: 0.48 g (50%)

$^1$H NMR (400 MHz, CDCl$_3$): δ 1.92-2.01 (m, 2H), 2.65-2.74 (m, 4H), 3.90 (d, J=7.2 Hz, 2H), 4.50 (s, 2H), 5.3-5.38 (m, 1H), 7.30-7.40 (m, 5H)

Step 4: Synthesis of 1-(2-(benzyloxy)-1-hydroxyethyl)cyclobutanol

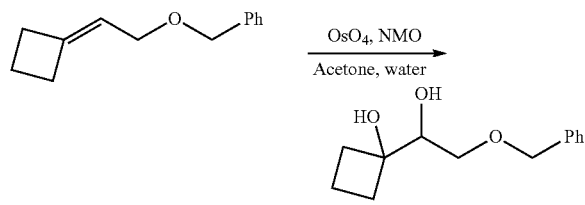

In 15 mL acetone and 3 mL of water, step-3 product (0.47 g, 2.5 mmol), and NMO (50% aq. Solution, 0.35 g, 0.7 mL, 3.0 mmol) was allowed to stir at room temperature for 15 min. OsO$_4$ (4% aqueous solution, 0.6 mL, 0.36 mmol) was added and resulting reaction mixture was allowed to stir at room temperature overnight. Reaction mixture was quenched with sodium bisulfate (10% aqueous) solution and stirred for 1 h at room temperature. Aqueous layer was extracted with ethyl acetate, dried over sodium sulfate. Crude product obtained was purified by column chromatography (silica 60-120 mesh, ethyl acetate/n-hexane) to afford colorless oil. Yield: 0.25 g, 45%

LCMS: (M+Na) 245, HPLC purity: 94.0% (220 nm)

$^1$H NMR (400 MHz, CDCl$_3$): δ 1.52-1.61 (m, 1H), 1.79-1.90 (m, 1H), 2.0-2.1 (m, 3H), 2.24-2.32 (1H), 2.62 (m, 1H), 3.0 (s, 1H), 3.70 (d, J=4.4 Hz, 2H), 3.8-3.9 (m, 1H), 4.50-4.61 (m, 2H), 7.29-7.40 (m, 5H).

Example 45—Synthesis of: 1-(tert-butoxycarbonyl)-3-hydroxyazetidine-3-carboxylic acid (Target 23, Intermediate 2 and 3)

Reaction scheme

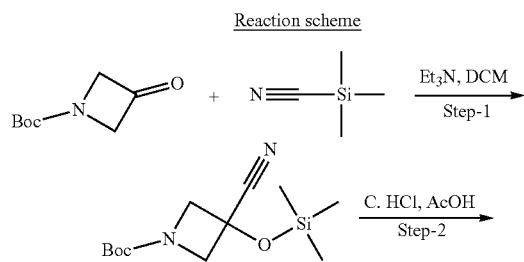

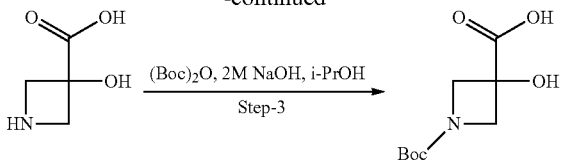

Step-1: Synthesis of 1a

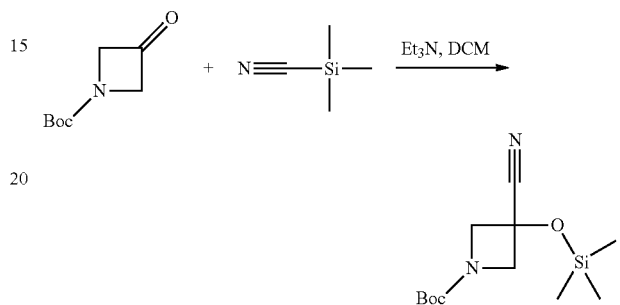

To a solution of tert-butyl 3-oxoazetidine-1-carboxylate (2.5 g, 0.015 mol) in dichloromethane (10 mL), triethyl amine (2.02 g, 0.02 mol) and trimethylsilyl cyanide (6.95 g, 0.07 mol) were added at room temperature. The reaction mixture was allowed to stir at room temperature for 16 h. Reaction was monitored by TLC and NMR. (Rf 0.37, 30% Ethyl acetate in n-Hexane as a mobile phase). The reaction mixture was quenched with 5% NaHCO$_3$ solution and extracted with dichloromethane (3×20 mL). Organic layer was washed with brine (2×20 mL) and water (2×20 mL), dried over Na$_2$SO$_4$ and concentrated under reduced pressure to afford a dark brown color oil (3.6 g, crude). The crude compound was as such taken for the next step.

Step-2: Synthesis of: 3-hydroxyazetidine-3-carboxylic acid (2a)

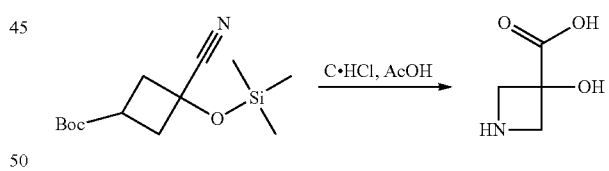

To a solution of 1:1 conc. HCl and conc. acetic acid (12 mL: 12 mL), product 1a 1.5 g (Crude) was added portion wise at room temperature. The reaction mixture was refluxed for 3 h. Reaction was monitored by TLC and ESI. (Rf 0.05, 10% methanol in a dichloromethane as a mobile phase). The reaction mixture was concentrated under reduced pressure. Further crude compound was washed with n-pentane and sonicated in methanol (6×10 mL) and dried under vacuum (0.18 g off white solid (crop-I pure compound) and 1.02 g crop-II crude). 30 mg of pure compound (crop 1, hydrochloride salt) was dispatched. The crude compound (crop 2) was used as such for the next step.

ESMS: (M+1, 118), ELSD: (M+1, 118) 99.7% purity.

$^1$H NMR (400 MHz, DMSO-d6): δ=13.5 (br, 1H), 9.71 (bs, 1H), 9.28 (bs, 1H), 6.82 (br, 1H), 4.21 (m, 2H), 3.87 (m, 2H).

$^{13}$C NMR, 400 MHz, (DMSO-d6) δ=172.3, 70.3, 55.7

Step-3: Synthesis of 1-(tert-butoxycarbonyl)-3-hydroxyazetidine-3-carboxylic acid (3a)

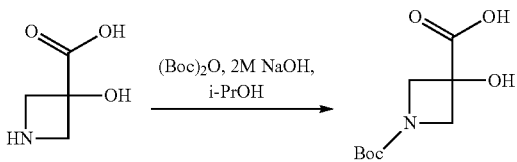 [SMILES: O=C(O)C1(O)CNC1 ; CC(C)(C)OC(=O)N1CC(O)(C(=O)O)C1]

To a solution of 3-hydroxyazetidine-3-carboxylic acid (2a) (1.02 g, 8.7 mmol) in 15 mL of 2 M NaOH solution and 15 mL of isopropyl alcohol, Boc anhydride (4.75 g, 21.8 mmol) was added at 0° C. Reaction mixture was stirred overnight at room temperature. Reaction was monitored by TLC and ESI. (Product Rf 0.1, 10% methanol in a dichloromethane). The reaction mixture was concentrated under reduced pressure. Further residue was diluted with 20 mL water and washed with diethyl ether (3×20 mL). Aqueous layer was acidified with $H_3PO_4$ (pH=3), and extracted with diethyl ether (4×10 mL). Organic layer dried over sodium sulfate and concentrated under reduced pressure. Crude compound was washed with 50% diethyl ether in n-hexane (4×15 mL) to get an off white solid.

ESMS: (M−1, 216)
$^1$H NMR (400 MHz, DMSO-d6): δ=4.08 (bs, 2H), 3.71 (bs, 2H), 1.37 (s, 9H).

Example 46—Synthesis of 2-((5-nitropyrimidin-2-yl)amino)cyclobutanone (SLnAK-04n-monomer)

Synthesis of 2-((5-nitropyrimidin-2-yl)amino)cyclobutanone was carried out as shown in the scheme below. Detailed experimental procedure and analytical data are given below.

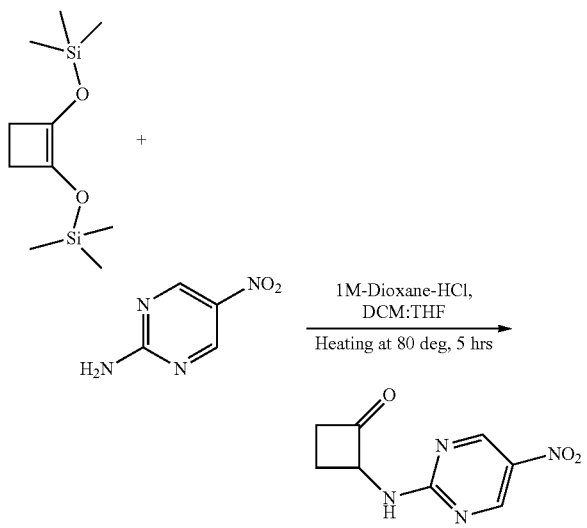

Experimental

Step-1: Synthesis of 2-((5-nitropyrimidin-2-yl)amino)cyclobutanone 1,2-bis(trimethylsilyl)oxy)cyclobut-1-ene (100 mg, 0.434 mmol) was added to a solution of-2-Amino-5-nitropyrimidine (48 mg, 0.347 mmol) in 1.0M HCl/Dioxane (1 mL), dichloromethane (4 mL), THF (4 mL) at 0° C. After 30 mins, mixture was heated at 80° C. for 5 hrs TLC (TLC System 10% methanol in chloroform) showed absence of starting material (amine) then the solvent was removed under vacuum. Product was recrystallized using solvent DCM (approx 4 mL) and 1-2 drops of methanol to give white colored solid product. Compound was characterized by LCMS, HPLC, NMR and IR. Yield=15 mg (16%)

Mol. wt 208.17, In LCMS MH+ seen at 209, HPLC purity 97.6%

NMR 1H-DMSO-d6: 2.14-2.24 (m, 1H), 2.26-2.35 (m, 1H) 2.80-2.86 (m, 1H),2.96-3.05 (m, 1H) 5.22-5.28 (q, 1H),9.08 (s, 2H)

Example 47—Synthesis of Ethyl 4-methyl-2-((2-oxocyclobutyl)amino)pyrimidine-5-carboxylate (SLnAK-04o-monomer)

Synthesis of ethyl 4-methyl-2-((2-oxocyclobutyl)amino)pyrimidine-5-carboxylate was carried out as shown in the scheme below. Detailed experimental procedures and analytical data are given below.

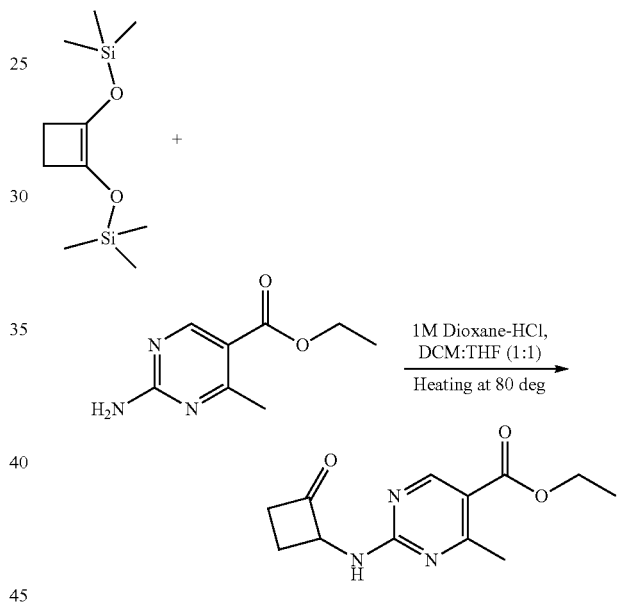

Experimental

Step-1: Synthesis of Ethyl 4-methyl-2-((2-oxocyclobutyl)amino)pyrimidine-5-carboxylate 1,2-bis(trimethylsilyl)oxy)cyclobut-1-ene (100 mg, 0.434 mmol) was added to a solution of-2-amino-5-nitropyrimidine (62.4 mg, 0.347 mmol) in 1.0M HCl/dioxane (1 mL), dichloromethane (4 mL), THF (4 mL) at 0° C. After 30 mins, mixture was heated at 80° C. for 8 hrs TLC showed presence of starting material around 5% (TLC system 10% methanol in chloroform) as no further progress was seen in reaction solvent was removed under vacuum. Chromatography on silica gel (gradient 10-40% ethyl acetate in hexane) afforded to give (off white solid) pure monomer. Compound was characterized by LCMS, NMR, HPLC and IR.

Yield=25 mg (23%)

Mol. Wt. 249.2, In LCMS MH+ was seen at 250, HPLC purity 99.2%

NMR1H-DMSO-d6:1.23-1.29 (m, 3H), 2.15-2.28 (m, 2H), 2.53 (s, 3H) 2.80-2.98 (m, 2H), 4.2-4.26 (q, 2H), 5.04-5.12 (m, 1H),8.68 (s, 1H)

Example 48—Synthesis of 2-((4-methoxy-6-methyl-pyrimidin-2-yl)amino)cyclobutanone Reaction scheme:-

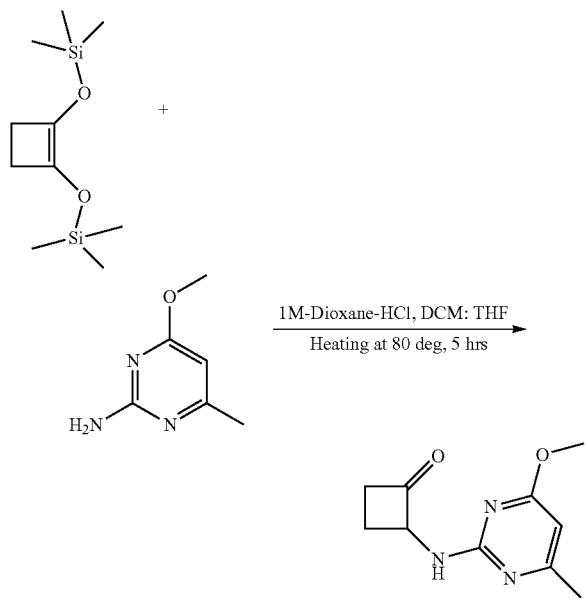

Experimental

Step-1: Synthesis of 2-((4-methoxy-6-methylpyrimidin-2-yl)amino)cyclobutanone 1,2-bis(trimethylsilyl)oxy)cyclobut-1-ene (500 mg, 2.17 mmol) was added to a solution of-4-methoxy-6methylpyrimidine (241 mg, 1.736 mmol) in 1.0M HCl/Dioxane (2 ml), dichloromethane (8 ml), THF (8 ml) at 0° C. After 30 mins, the mixture was heated at 80° C. for 28 hrs monitored by TLC (10% methanol in chloroform Product Rf:—Starting:—0.4, Product:—0.35) Indicated formation of product. LCMS indicated formation of ~10% product with desired mass peak. Solvent was removed under vacuum and residue was purified by column chromatography over silica gel (0-10% methanol in Dichloromethane) after 3 repeated chromatographic purifications, 9 mg crude compound was isolated, which was characterized by LCMS.
Yield=9 mg
Reaction Scheme:

Analytical Data
Mol. wt 207.17
In LCMS MH+ seen at 208 HPLC purity 73%

Example 49—Synthesis of 2-((1 methyl-1H-pyrazol-3-yl)amino)cyclobutanone

Reaction Scheme:

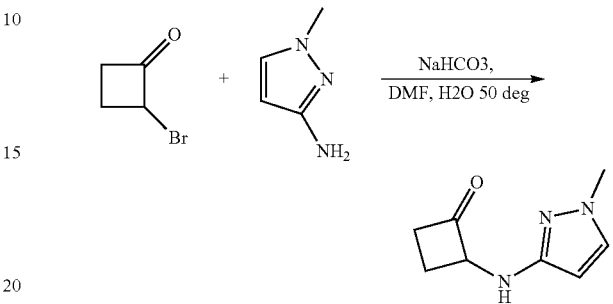

Experimental Procedure

Step-1: Synthesis of 2-((1 methyl-1H-pyrazol-3-yl)amino)cyclobutanone

To a stirred solution of 1-methyl-1H-pyrazol-3-yl amine (129 mg, 1.34 mmol) in DMF and water (0.09 ml, 5.03 mmol), NaHCO₃ (279 mg, 3.35 mmol) was added followed by addition of bromocyclobutanone (250 mg, 1.67 mmol) at Room temperature. The mixture was then heated at 50° C. for 6 hrs while monitored by LCMS & TLC (10% methanol in chloroform) which indicated formation of Product (Rf:—0.2) and consumption of the starting (Rf.:—0.15) reaction mass was diluted with water and extracted with dichloromethane. Dichloromethane layer was washed with brine, dried over sodium sulfate and concentrated to get crude product which was purified by preparative HPLC to get pure product, which was characterized by LCMS.
Yield=2.2 mg
Analytical Data
Mol. Wt. 165, MH+ observed in LCMS:—166
HPLC purity 96%

Example 50—2-(3-(4-(3-(aminomethyl)phenyl)piperidine-1-carbonyl)phenoxy)-1-((3S,4R)-3,4-dihydroxypyrrolidin-1-yl)ethanone (Target-29)

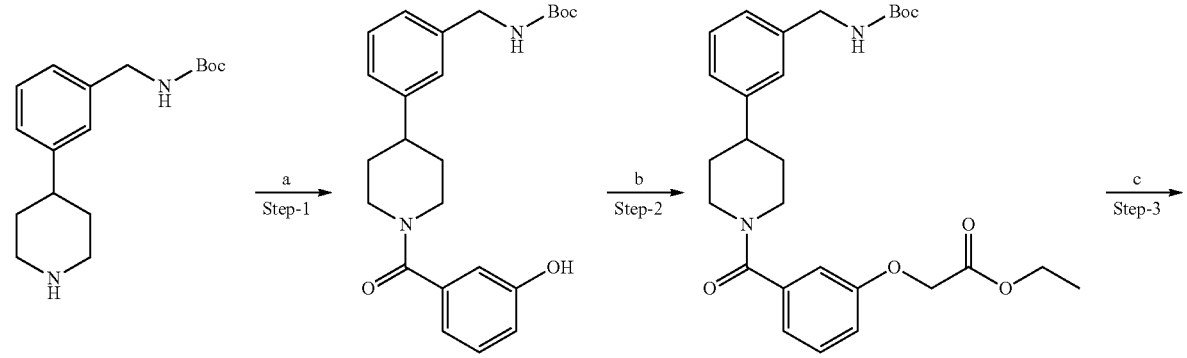

463

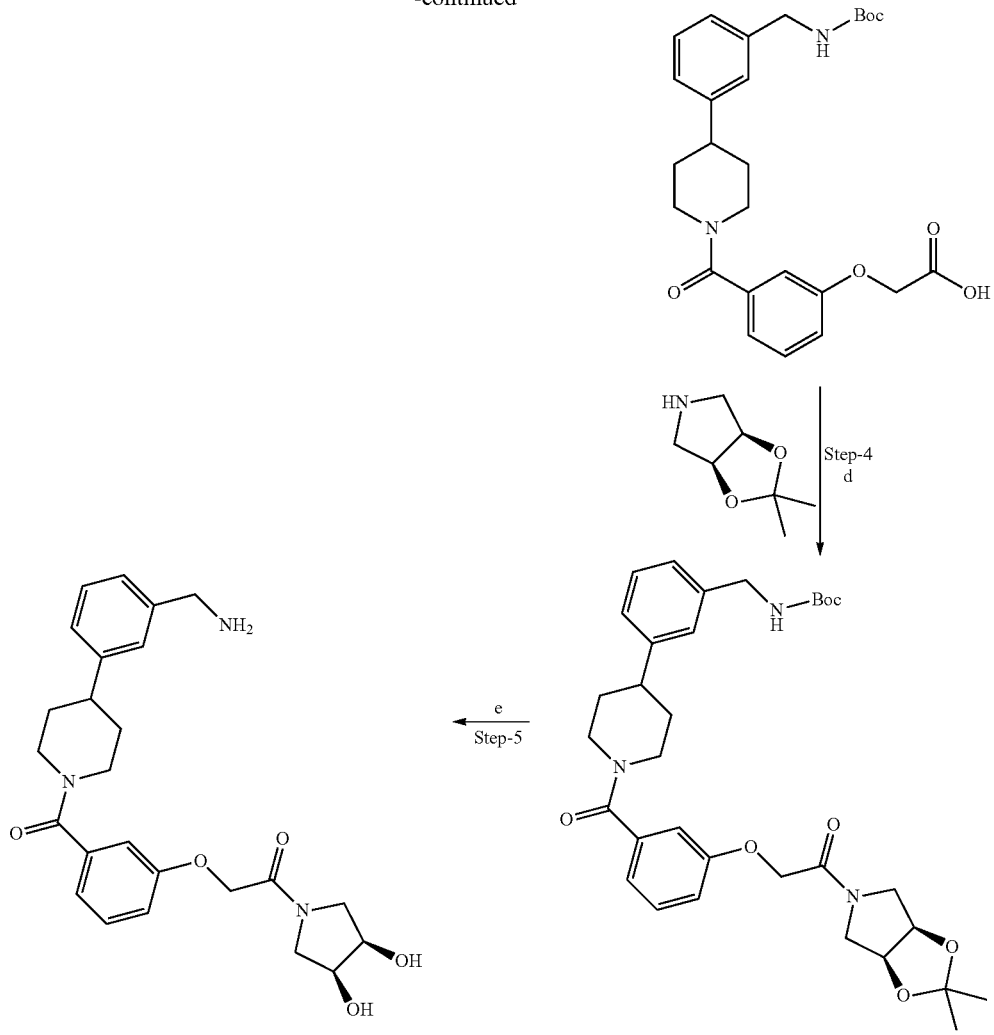

Reagents and Conditions:

a) EDC-DMAP, CH$_2$Cl$_2$-DMF, room temperature, 5 h; b) ethyl bromo acetate, K2CO3-Acetone Reflux, 5 hrs. c) NaOH.H$_2$O, THF d) EDC-DMAP, CH$_2$Cl$_2$, R.T. 5 hrs. e) TFA-dichloromethane room temperature, 2 h.

Experimental Procedure

Step-1: Tert-butyl 3-(1-(3-hydroxybenzoyl)piperidin-4-yl)benzylcarbamate

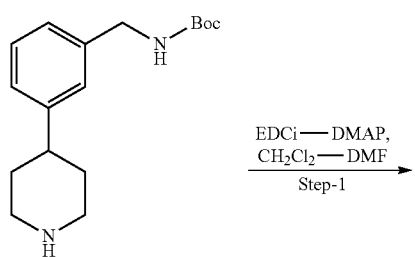

-continued

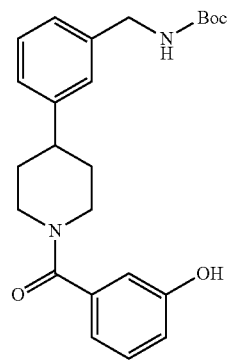

To a solution of 3-hydroxy benzoic acid (50 mg, 0.36 mmol) in anhydrous dichloromethane:DMF was added DMAP (52 mg, 0.43 mmol) & EDC.HCl (103 mg, 0.54 mmol) at 0° C. The reaction mass was stirred for 30 min. and tert-butyl 3-(piperidin-4-yl)benzylcarbamate (115 mg, 0.39 mmol) was added at 0° C. The reaction mixture was allowed to warm to room temperature and stirred for 3 hrs when LCMS & TLC (5% methanol in chloroform) indicated consumption of the 3-hydroxy benzoic acid (Rf. 0.2) and formation of product (Rf. 0.5). The reaction mixture was diluted with dichloromethane (25 mL) and washed with water followed by 1N HCl. The dichloromethane layer was dried over sodium sulphate and concentrated under vacuum to yield 90 mg crude product as colorless oil. This was characterized by LCMS and used for next step without further purification.

Mol. Wt. 410.51, Mol. Ion. peak observed in LCMS 433.20 (M+Na), Purity 65.9%

Step-2: Synthesis of ethyl 2-(3-(4-(3-(((tert-butoxy-carbonyl)amino)methyl)phenyl)piperidine-1-carbonyl)phenoxy)acetate

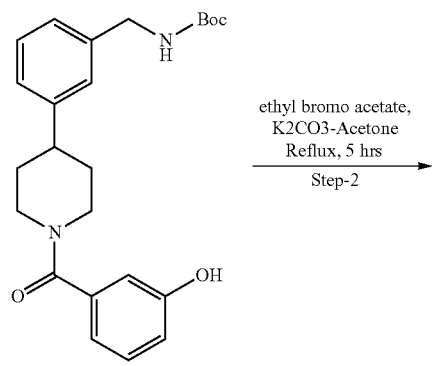

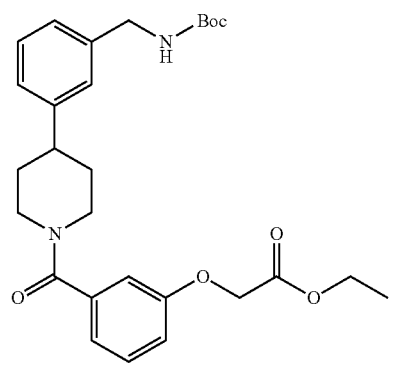

To a stirred solution of tert-butyl 3-(1-(3-hydroxybenzoyl)piperidin-4-yl)benzyl carbamate (50 mg, 0.12 mmol) and $K_2CO_3$ (49 mg, 0.36 mmol) was added ethyl bromo acetate (20 mg, 0.12 mmol) at room temperature under nitrogen atmosphere. The reaction mixture was refluxed for 5 hrs, when TLC (3% methanol in chloroform) indicated complete consumption of the starting (Rf. 0.3) and formation of product (Rf. 0.5). The reaction mixture was cooled and acetone was evaporated under vacuum. Residue was diluted with dichloromethane (25 mL) and washed with water (2×20 mL). Dichloromethane extract was dried over sodium sulphate and concentrated under vacuum to get 65 mg crude product as yellow oil. This was characterized by LCMS & used for next step without further purification.

Mol. Wt. 496.59, Mol. Ion. peak observed in LCMS 519.35 (M+Na), Purity 67.7%

Step-3: 2-(3-(4-(3-(((tert-butoxycarbonyl)amino) methyl)phenyl)piperidine-1-carbonyl)phenoxy)acetic acid

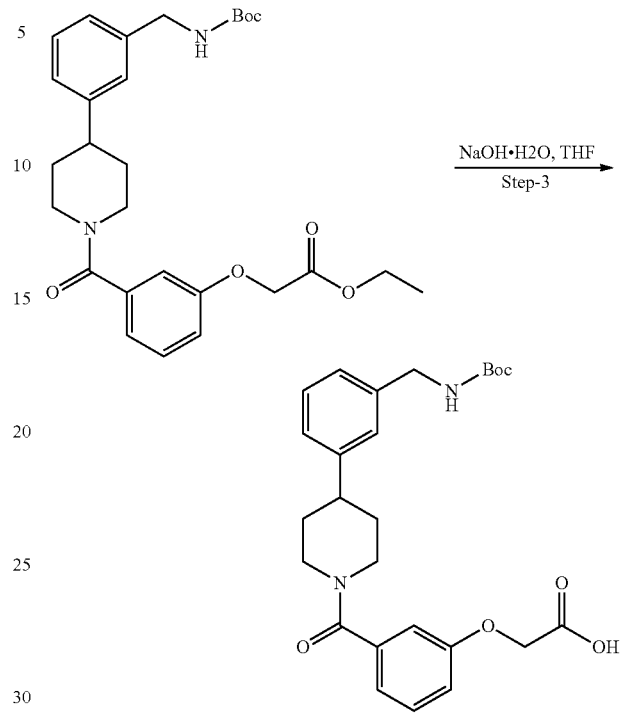

Ethyl 2-(3-(4-(3-(((tert-butoxycarbonyl)amino)methyl) phenyl)piperidine-1-carbonyl)phenoxy)acetate (50 mg, 0.1 mmol) was dissolved in THF:$H_2O$ (2.5 mL each). NaOH (12 mg, 0.3 mmol) was then added to this, and the reaction mixture was stirred for 3 hrs at room temperature when TLC (30% ethyl acetate in hexane) indicated complete consumption of the starting material (Rf. 0.4) and formation of product (Rf. 0.2). THF was evaporated in vacuum, and the residue was diluted with ethyl acetate. The organic layer was washed with water. Combined aqueous layers were acidified with 2N HCl and extracted with ethyl acetate (2×25 mL). Ethyl acetate extract was dried over $Na_2SO_4$ and concentrated in vacuum to get 2-(3-(4-(3-(((tert-butoxycarbonyl) amino)methyl)phenyl)piperidine-1-carbonyl)phenoxy)acetic acid (35 mg, 74.9%) as off white solid. This was characterized by LCMS and used for the next step without further purification. Mol. wt 468.54; Mol ion peak observed in LCMS 491.2 (M+Na), Purity 89.6%

Step-4: Tert-butyl 3-(1-(3-(2-(2,2-dimethyldihydro-3aH-[1,3]dioxolo[4,5-c]pyrrol-5(4H)-yl)-2-oxoethoxy)benzoyl)piperidin-4-yl)benzylcarbamate

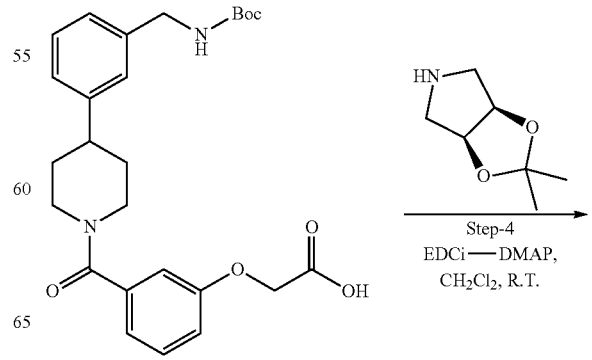

-continued

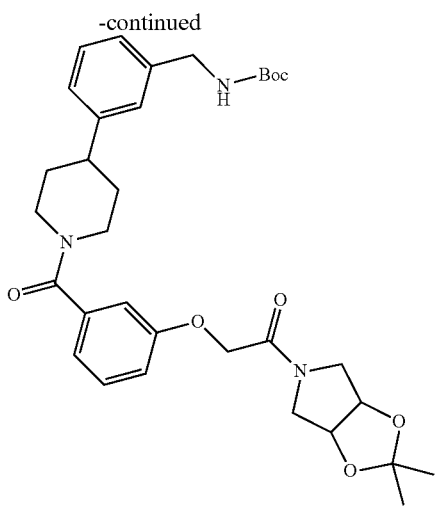

To a solution of 2-(3-(4-(3-(((tert-butoxycarbonyl)amino) methyl)phenyl)piperidine-1-carbonyl)phenoxy)acetic acid (40 mg, 0.085 mmol) in anhydrous dichloromethane, DMAP (12.4 mg, 0.1 mmol) and EDC.HCl (24.4 mg, 0.12 mmol) was added at 0° C. The reaction mass was stirred for 30 min. at the same temperature. 2,2-dimethyltetrahydro-3aH-[1,3] dioxolo[4,5-c]pyrrole (15.8 mg, 0.11 mmol) was added to this at 0° C. The reaction mixture was allowed to warm to room temperature and stirred for 3 hrs when LCMS & TLC (5% methanol in chloroform) indicated consumption of carboxylic acid (Rf. 0.3) and formation of the product (Rf. 0.5). The reaction mixture was diluted with dichloromethane (25 mL) and washed with water & 1N HCl. Dichloromethane layer was dried over sodium sulphate and concentrated under vacuum to yield 60 mg crude product as colorless oil which was purified by column chromatography over silica gel (gradient: –0-2% Methanol in chloroform) was used to get tert-butyl 3-(1-(3-(2-(2,2-dimethyldihydro-3aH-[1,3]dioxolo[4,5-c]pyrrol-5(4H)-yl)-2-oxoethoxy)benzoyl)piperidin-4-yl)benzylcarbamate (25 mg, 44.6%) as a colorless oil which was sufficient pure to use for next step.
Mol. Wt. 592.72, Mol. Ion. peak observed in LCMS 594.4, Purity 91.2%.

Step-5: 2-(3-(4-(3-(aminomethyl)phenyl)piperidine-1-carbonyl)phenoxy)-1-(3,4-dihydroxypyrrolidin-1-yl)ethanone

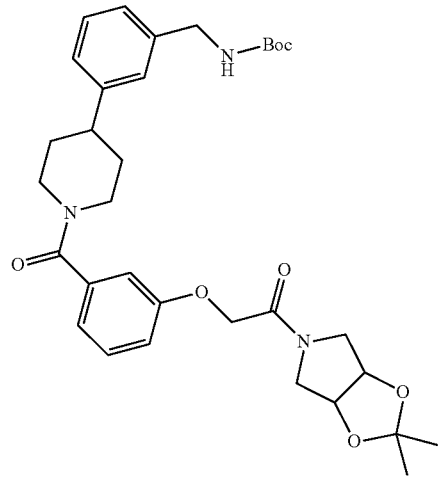 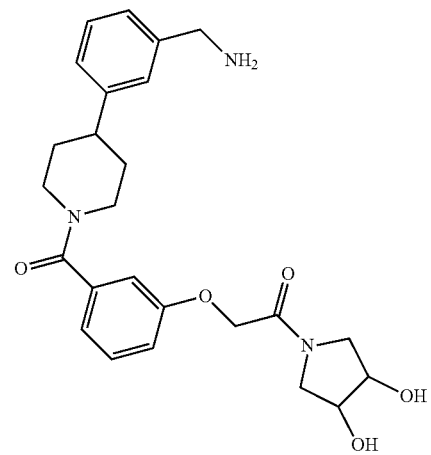

120 mg (0.2 mmol) Tert-butyl 3-(1-(3-(2-(2,2-dimethyldihydro-3aH-[1,3]dioxolo[4,5-c]pyrrol-5(4H)-yl)-2-oxoethoxy)benzoyl)piperidin-4-yl)benzyl carbamate synthesized as described in steps 1 to 4 was stirred with dichloromethane (10 mL) & TFA (138 mg, 1.2 mmol) at room temperature for 3 hrs, when completion of reaction was observed by LCMS. The reaction mixture was concentrated to dryness under vacuum to get crude product as yellow oil (100 mg) which was purified by preparative HPLC. Pure product was isolated as TFA salt was stirred in 10% methanolic HCl for 30 min and concentrated in vacuum to get 30 mg hydrochloride salt as off white solid.
Mol. wt:—453.53, Mol. Ion. peak observed in LCMS:—454.5, HPLC purity: 99.6%
$^1$HNMR (400 MHz, DMSO) 1.58-1.83 (m, 4H), 2.83 (m, 2H), 3.15-3.31 (m, 6H), 3.64 (m, 2H), 4.00 (m, 4H), 4.65 (broad s, 1H) 4.75 (s, 2H), 5.00 (Broad s, 1H) 6.92 (s, 1H), 6.98 (m, 2H), 7.27-7.4 (m, 3H), 8.13 (broad s, 2H)

Example 51—Evaluation of Inhibition of Tryptase Activity by Coferons

Stock solutions of recombinant human tryptase, beta, from lung (Promega: catalog number G5631, or Enzo Life Sciences: catalog number BML-SE418) were made at 30 μM, in solution with 50 μM heparin sulfate and 500 mM NaCl. Coferon tryptase inhibitor stock solutions were made at 50 mM in DMSO. Drug plates were made at 5× the final concentration in assay buffer (50 mM HEPES, 150 mM NaCl, 100 μM EDTA, pH 7.4, 0.02% Tween-20). A final concentration of 1 nM tryptase was used. When required, drugs were diluted in assay buffer immediately before use in 10-fold serial dilutions. After the indicated incubation time, the coferon-tryptase solution at 5× concentration, was diluted into assay buffer containing a final concentration of 200 μM N-tert-butoxycarbonyl-Gln-Ala-Arg-AMC HBr [AMC=7-amino-4-methylcoumarin](Boc-Gln-Ala-Arg-AMC; Enzo Life Sciences: catalog number BML-P237) to a final volume of 50 μl in black opaque round bottom 96 well plates (Corning, catalog number 3792). The release of fluorescent AMC was immediately measured every 60 seconds over 30-60 minutes at an excitation wavelength of 367 nm, monitoring emission at 468 nm on a Spectramax M5 (Molecular Devices) microplate reader. The Softmax Pro (Molecular Devices) and Graphpad prism software were used to determine $V_{max}$, and concentration-response curve $IC_{50}$s, respectively.

IC$_{50}$ Values of Coferon Monomers

| Monomer | IC$_{50}$ (M) |
| --- | --- |
| Example 34 | 4.80E−07 |
| Example 35 | 1.50E−05 |
| Example 36 | 8.15E−06 |
| Example 37 | 1.05E−06 |
| Example 39 | 4.30E−06 |
| Example 40 | 1.20E−06 |
| Example 50 | 7.50E−06 |

IC$_{50}$ Values of Coferon Combinations

| Monomer1 | Monomer2 | IC$_{50}$ (1:1 ratio of monomers in solution) |
| --- | --- | --- |
| Example 37 | Example 40 | 2.01E−07 |
| Example 36 | Example 40 | 1.65E−07 |
| Example 34 | Example 40 | 1.26E−07 |
| Example 35 | Example 40 | 3.15E−07 |
| Example 35 | Example 50 | 1.17E−06 |
| Example 35 | Example 39 | 3.63E−07 |

Example 52—Evaluation of Inhibition of Ribosomal Protein Synthesis by Coferons

Coferon monomers with the potential to from heterodimers were evaluated in an in vitro Transcription and Translation assay (TnT assay) using the commercially available *E. coli* S30 Extract System for Circular DNA kit (Promega Catalog #L1020) according to the manufacturers instructions with minor modifications. Coferon monomers were tested independently to determine individual IC50 values. Pairs of coferon monomers with the potential to form heterodimers were assayed at concentrations that ranged about their individual IC25 values. Each reaction uses 2 µl (250 ng/µl) of the pBESTluc™ DNA based circular luciferase plasmid (Promega Catalog #L492A), with 4 µl of complete amino acid mix (Promega Catalog #L4461), 13 µl of S30 Premix Without Amino Acids (Promega Catalog #L512A), 5 µl of S30 Extract (Promega Catalog #L464A), coferon monomers at the appropriate concentration, and nuclease free water in a total volume of 35 µl. Assays were carried out in Costar 96 well white round bottom plates. Assay plates were setup with a master mix consisting of S30 extract and water, followed by the addition of compound, with the final addition of a master mix consisting of the plasmid, amino acid mix, and the S30 Premix. Plates were incubated at 37° C. for one hour followed by addition of 35 µl of the Bright-Glo Luciferase Reagent (Promega Catalog #E2620). After removal of 35 µl of the reaction mixture, the luminescence was recorded immediately in the Spectramax M5 plate reader (Molecular Devices). The data was plotted to generate dose-response curves using GraphPad Prism.

Example 53—Evaluation of Inhibition of Bacterial Growth by Coferons

Minimum inhibitory concentrations of coferon monomers and heterodimers were determined using standard CLSI (Clinical and Laboratory Standards Institute) conditions against a panel of gram positive organisms with different resistance profiles. MIC values were determined for the coferon monomers individually using 2-fold dilutions of the compounds. Pairs of coferon monomers with the potential to form heterodimers were tested at concentrations that were lower than the individual MIC values.

Example 54—Demonstration of Dimerization of Summa linkers

For summa linkers and coferons that form dimers that are slow to hydrolyze/equilibrate under the chromatographic conditions, evidence for dimerization or oligomerization may be generated using LC-MS/MS methods in which the monomeric and dimeric species are separated by reversed-phase liquid chromatography and identified using tandem mass spectrometric methods, typically utilizing MRM transitions to maximize sensitivity. Often this approach is capable of separating and quantifying isomeric and diastereomeric dimeric states of the summa linker and coferon assemblies. For summa linkers that rapidly equilibrate following changes in pH, concentration or solvent composition, direct infusion into a MS/MS system can be employed to demonstrate evidence of the presence of dimeric species which is confirmed by its fragmentation pattern, and relative changes in abundance under various conditions can be assessed.

LC-MS/MS Determination of Dimerization:

Typically, a solution of the following homodimeric summa linker was incubated under various conditions of pH, concentration, organic cosolvent, or protein additives, etc. and aliquots were chromatographed on a Primesep 200 (150×4.6 mm, 5µ) RP-HPLC column using a flow rate of 1.0 mL/min and a linear gradient of 0.1% aqueous TFA/acetonitrile over 25-30 minutes. Preparations containing a known amount of dimeric species (as determined by NMR for example) can be employed as a standard to allow for accurate quantitation of monomeric and dimeric states. For example, using such conditions, 4 isomeric dimers of the following racemic amino-cyclobutanone summa linker moiety (RT 7.29 min; example 47; >99.7% monomeric) were quantified under various conditions. When incubated at 0.125 mg/mL at 20° C. at pH 2.0 in 0.1% TFA, dimers-1, -2 & -3 eluting at 15, 15.5 and 16 min, respectively, increased from 0.06%, 0.06% and 0.11% at time zero to 2.35, 2.3%, and 5.2% after 169 h; dimer-4 was not observed under these conditions. However, when incubated in pH7.4 HEPES buffer, the levels of dimers-1, -2, and -3 declined to below 0.01% over 169 h, and dimer-4 (RT 21.5 min) increased from <0.015 to 1.82%. Complete equilibrium between monomer and dimer-4 was not achieved within this timeframe, as dimer-4 was still increasing at 169 h.

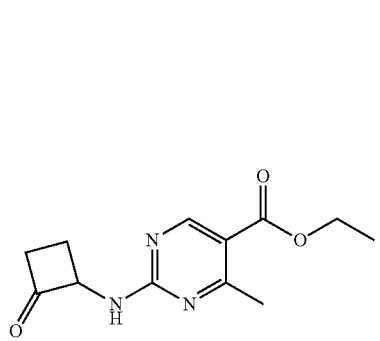

Exact Mass: 249.11
m/z: 250.11

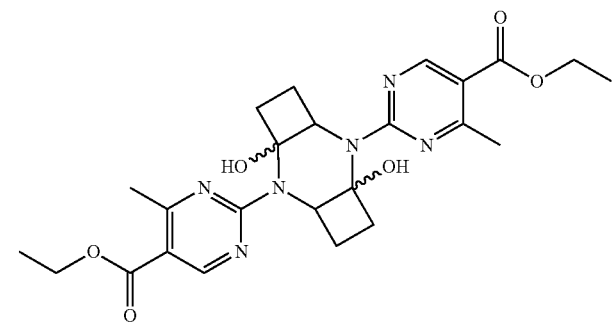

Dimer
Molecular Weight: 498.53
m/z: 499.23

OR

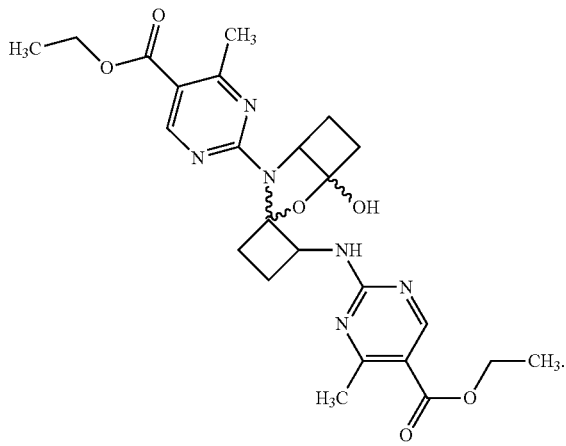

in the presence of 4% bovine serum albumin (BSA) in pH 7.4 HEPES buffer, the rate of monomer-dimer equilibration was observed to accelerate for some summa linkers. For example, Example 47 from above at 0.5 mg/mL in pH7.4 HEPES buffer with BSA showed a greatly accelerated disappearance of dimers 1,2, and 3, and an enhanced rate of formation of Dimer 4 (13.75% after 115 h in the presence of BSA, versus 4.73% in the absence). The results indicate that the rate of equilibration of monomer with dimer-4 is significantly accelerated in the presence of BSA, and that at this concentration the fraction of dimer-4 at equilibrium >14%. Equilibration of samples initially containing ~31% dimers converged on a similar fraction of dimer in pH7.4 HEPES over 72 h.

Example 55—Direct Infusion of Solutions into Mass Spectrometer for Detection of Coferon Dimers Electrospray ionization analyses were carried out on an MS such as the FinniganMAT LCQ Classic (ThermoElectron Corp, San Jose, Calif.) mass spectrometer system. For example, the electrospray needle voltage was set at 4.0 kV, the heated capillary voltage was set to 10V and the capillary temperature 207 C. Typical background source pressure was 1.2×10-5 torr as read by an ion gauge. The sample flow rate was approximately 8 microliters per minute. The drying gas was nitrogen. The LCQ was scanned to 2000 amu for these experiments. The sample was dissolved in water and/or acetonitrile.

The samples are introduced into the LCQ mass spectrometer through a capillary system that is coupled with the nozzle and skimmer array of beam defining elements. The ions then pass through a heated capillary tube into the ion optics portion of the instrument prior to being trapped in the ion trap. After the appropriate trapping interval, usually defined by the number of ions being trapped, the ions are mass analyzed and detected with an electron multiplier.

The MS/MS results were obtained by selecting the ion of interest (the precursor ion). The precursor ion was then subjected to collision-induced dissociation (CID) resulting in the formation of product ions. Helium was introduced into the system to an estimated pressure of 1 millitorr to improve trapping efficiency and also acted as the collision gas during the collisionally-induced dissociation (CID) experiments. The collision energy was set to 40% of the maximum available from the 5 volt tickle voltage, with a 2 mass unit isolation window.

(The relative collision energy varies from 0-100% for collision-induced dissociation (0-5 volt peak to peak of the resonance excitation rf voltage)

Three types of experiments were typically conducted. 1) MS analysis of coferon in acetonitrile solution. 2) MS analysis of coferon in water. 3) MS analysis of coferon mixtures in water.

The presence of covalent dimer, as opposed to MS-induced non-covalent dimer was confirmed by the MS-MS analysis and fragmentation pattern. For example, (R)-4-(amino methyl)-N-(4-(3-(3-hydroxy-4-oxopyrrolidin-1-yl)-3-oxopropoxy)benzyl)benzamide hydrochloride (Example 10) showed peaks at m/z 412 (monomer) and 823 (dimer) in a ratio of 1:2 from acetonitrile solution. The MS-MS of the dimer showed fragments with m/z 673 and 523. In aqueous solution (neutral pH) the ratio of monomer to dimer was 1:2.6 at 6 hours and 1:0.46 at 72 hours. Similarly, (S)-4-(aminomethyl)-N-(4-(2-(3-hydroxy-4-oxopyrrolidin-1-yl)-2-oxoethoxy)benzyl)benzamide (Example 4) gave peaks at m/z 398 (monomer) and 795 (dimer) with the MS-MS of the dimer showing fragments at m/z 645 and 495. The ratio of monomer to dimer in water after 6 hrs was 1:0.72 and after 72 hrs was 1:0.12. When the two coferons were combined in aqueous solution only the dimers with m/z 795 and m/z 823 were observed at t=0. Within 6 hrs both Coferon homodimers as well as the heterodimer resulting from the combination of the homologous coferon dimers were observed at m/z 795, 809 and 823 in a ratio of 1:0.35:0.54, respectively. After 72 hrs the ratio of these dimers was 1:1.3:1.1.

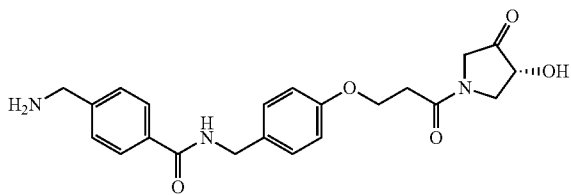 [SMILES: NCc1ccc(C(=O)NCc2ccc(OCCC(=O)N3CC(=O)[C@H](O)C3)cc2)cc1]

Example 10

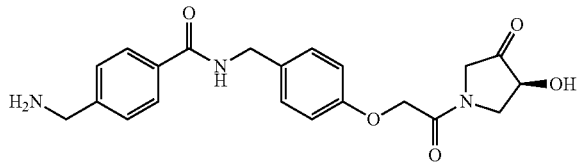 [SMILES: NCc1ccc(C(=O)NCc2ccc(OCC(=O)N3CC(=O)[C@@H](O)C3)cc2)cc1]

Example 4

Example 56—Determination of Approximate Equilibrium Constants for Boronic Acids Complexed with Dials and Other Ligands To assess the potential of boronic acid diol pairs as potential summa linkers within Coferons, the Alizarin Red S method was used essentially as described (Springsteen, G. and Wang, B, *Tetrahedron* 58: 5291-5300 (2002), which is hereby incorporated by reference in its entirety). Alizarin Red S gives a red color when free in solution, and shifts to yellow when complexed to boronic acids.

To determine equilibria between boronic acid species and Alizarin Red S (ARS), a $1.0 \times 10^{-4}$ M solution of ARS in 0.10 M phosphate buffer, pH 7.4 was prepared. Boronic acid partners, from $3 \times 10^{-2}$ M to $1.0 \times 10^{-5}$ M were serially diluted into this $1.0 \times 10^{-4}$ M solution of ARS, and absorbance spectra were determined from 350 to 750 nm. (Stock solutions were made to 100 mM in DMSO). The more boronic acid that bound to ARS, the more yellow the solution appeared. The percent complexed and percent free ARS was determined by comparing absorbance level to fully complexed and free ARS at 440 and 550 nm. The approximate equilibrium constant for a given boronic acid was estimated using the formula:

$K_{eq}$=[ARS-PBA]/[ARS]×[PBA]

(where ARS=Alizarin Red S, and PBA=phenylboronic acid as an example).

To determine equilibria between boronic acid species and diols or other ligands, a solution containing $2.0 \times 10^{-3}$ M boronic acid, $1.0 \times 10^{-4}$ M of ARS in 0.10 M phosphate buffer, pH 7.4 was prepared. Diol or other ligands from $3 \times 10^{-2}$ M to $1.0 \times 10^{-4}$ M were serially diluted into the above boronic acid-ARS mix, and absorbance spectra were determined from 350 to 750 nm. (stock solutions were made to 100 mM in DMSO). The higher concentrations of diol would displace the boronic acid from complexation with ARS, liberating free ARS and turning the solution pink. The percent complexed and percent free ARS was determined by comparing absorbance level to fully complexed and free ARS at 440 and 550 nm. The approximate equilibrium constant Keq2 for a given boronic acid-diol complexation was estimated using the formula:

$K_{eq}$=[ARS-PBA]/[ARS]×[PBA]

[PBA]=[ARS-PBA]/[ARS]×$K$eq

[Sorb-PBA]=0.002-[PBA]-[ARS-PBA]

[Sorb]=Total Sorb-[Sorb-PBA]

$K_{eq2}$=[Sorb PBA]/[Sorb]×[PBA]

(where ARS=Alizarin Red S; Sorb=sorbitol; and PBA=Phenylboronic acid as an example).

The boronic acids with the highest affinity for ligands in aqueous solution (i.e. those most suitable for use as summa linkers) exhibited approximate equilibrium constants $K_{eq}$ within a three-fold range of about $2 \times 10^3$ M$^{-1}$ to about $2 \times 10^5$ M$^{-1}$. These are listed below: (5-amino-2-hydroxymethylphenyl)boronic acid; 2-(hydroxymethyl)phenylboronic acid; 2-(N,N-dimethylamino)pyridine-5-boronic acid hydrate; 2-(trifluoromethyl)pyridine-5-boronic acid; 2-chloroquinoline-3-boronic acid; 2-fluorophenylboronic acid; 2-fluoropyridine-3-boronic acid; 2-fluoropyridine-5-boronic acid; 2-methoxypyridine-5-boronic acid; 2-methoxypyrimidine-5-boronic acid; 2,3-difluorophenylboronic acid; 2,4-bis(trifluoromethyl)phenylboronic acid; 2,4-bis(trifluoromethyl)phenylboronic acid; 2,4-difluorophenylboronic acid; 2,5-difluorophenylboronic acid; 2,6-difluorophenylboronic acid; 2,6-difluorophenylboronic acid; 2,6-difluoropyridine-3-boronic acid hydrate; 3-(trifluoromethyl)phenylboronic acid; 3-fluorophenylboronic acid; 3-nitrophenylboronic acid; 3,4-difluorophenylboronic acid; 3,5-bis(trifluoromethyl)phenylboronic acid; 3,5-difluorophenylboronic acid; 4-fluorophenylboronic acid; 4-nitrophenylboronic acid; 5-quinolinylboronic acid; benzofuran-2-boronic acid; benzothiophene-2-boronic acid; furan-2-boronic acid; phenylboronic acid; pyridine-3-boronic acid; pyrimidine-5-boronic acid; and thiophene-2-boronic acid.

Boronic acids moieties with lower affinities for ARS that, are still suitable for use as summa linkers, exhibited approximate equilibrium constants $K_{eq}$ within three-fold range of about $2 \times 10^2$ M$^{-1}$ to about $2 \times 10^3$ M$^{-1}$. These are listed below: 2-hydroxymethyl-5-nitrophenylboronic acid; 2-hydroxyphenylboronic acid; 2,4-dimethoxyphenylboronic acid; 2,6-dimethoxypyridine-3-boronic acid; 4-(N,N-dimethylamino)phenylboronic acid; 6-indolylboronic acid; and trans-2-phenylvinylboronic acid.

The diol moieties with the highest affinities for boronic acids or other ligands in aqueous solution (i.e., those most suitable for use as summa linkers) often exhibited approximate equilibrium constants $K_{eq}$ in a three-fold range of about $1 \times 10^3$ M$^{-1}$ to about $1 \times 10^5$ M$^{-1}$. These are listed below:

(±)-exo,exo-2,3-Camphanediol; (−)-epigallocatechin gallate; (1R,2R,3S,5R)-(−)-pinanediol; 2-hydroxy-3-naphthalenecarboxamide; 2-hydroxy-4-methoxybenzoic acid; 2-hydroxybenzyl alcohol; 2,2,6,6-tetrakis(hydroxymethyl)cyclohexanol; 2,3,4-trihydroxybenzophenone; 2,6-bis(hydroxymethyl)-p-cresol; 2,6-dihydroxybenzamide; 3-fluorocatechol; 3-methyl-1,3,5-pentanetriol; 3,4-dihydroxybenzonitrile; 3,4,5-trihydroxybenzamide; 4-methoxysalicylamide; 4-methylcatechol; 6,7-dihydroxy-4-methylcoumarin; 7,8-dihydroxy-4-methylcoumarin; adenosine; Alizarin Red S; benzilic acid; cis-1,2-cyclooctanediol; cis-1,2-cyclopentanediol; D-(−)-fructose; D-(−)-quinic acid; D-sorbitol; DL-atrolactic acid hemihydrate; gallic acid; gallic acid ethanolamide; labetalol hydrochloride; meso-erythritol; methyl 3,4,5-trihydroxybenzoate; propyl gallate; pyrocatechol; pyrogallol; salicylamide; tricine; triisopropanolamine; α-cyclohexylmandelic acid; α-cyclopentylmandelic acid; and α-hydroxyisobutyric acid.

Diols and other ligands with lower affinities for boronic acids in aqueous solution, which are still suitable for use as summa linkers, exhibited approximate equilibrium constants $K_{eq}$ within a three-fold range. These are listed below: 1,1,1-tris(hydroxymethyl)ethane; 1,3-dihydroxyacetone; 2-(methylamino)phenol; 2-acetamidophenol; 2-amino-3-methyl-1,3-propanediol; 2-amino-4-methylphenol; 2-fluoromandelic acid; 2-hydroxy-3-methoxybenzyl alcohol; 2,2-bis(hydroxymethyl)propionic acid; 2,3-difluoromandelic acid; 2,4-difluoromandelic acid; 2,5-difluoromandelic acid; 2,6-difluoromandelic acid; 2,6-dihydroxybenzoic acid; 3-methylamino-1,2-propanediol; 3,3,3-trifluoro-2-hydroxy-2-(trifluoromethyl)propionic acid; 3,3,3-trifluoro-2-hydroxy-2-methylpropionic acid; 3,5-difluoromandelic acid; 4-(trifluoromethyl)mandelic acid; cis-1,2-cyclohexanediol; D-(+)-glucose; DL-mandelic acid; hydroxypyruvic acid, lithium salt; 3-hydroxyazetidine-3-carboxylic acid; (3S,4R)-pyrrolidine-3,4-diol; lactic acid (solution); N-(2-hydroxyethyl)salicylamide; pentaerythritol; phenylpyruvic acid; pinacol; salicylic acid; trans-1,2-cyclohexanediol; and tris base (TRIZMA Base).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:
1. A therapeutic dimer comprising:
covalently or non-covalently linked monomers, each monomer comprising either a boronic acid linker element or a binding partner linker element,
wherein the monomer comprising the boronic acid linker element is selected from the group consisting of:
[2-({4-[3-(aminomethyl)phenyl]piperidin-1-yl}carbonyl)-1H-indol-4-yl]boronic acid; (2-{[5-(aminomethyl)-2H-spiro[1-benzofuran-3,4'-piperidine]-1'-yl]carbonyl}-1H-indol-4-yl)boronic acid; (5-{[5-(aminomethyl)-2H-spiro[1-benzofuran-3,4'-piperidine]-1'-yl]carbonyl}naphthalen-2-yl)boronic acid; [5-({4-[3-(aminomethyl)phenyl]piperidin-1-yl}carbonyl)naphthalen-2-yl]boronic acid; [2-({4-[3-(aminomethyl)phenyl]piperidin-1-yl}carbonyl)-1H-indol-5-yl]boronic acid; [5-({4-[3-(aminomethyl)phenyl]piperidin-1-yl}carbonyl)-1H-indol-2-yl]boronic acid; [2-({4-[3-(aminomethyl)phenyl]piperidin-1-yl}carbonyl)-1H-indol-6-yl]boronic acid; [8-({4-[3-(aminomethyl)phenyl]piperidin-1-yl}carbonyl)naphthalen-2-yl]boronic acid; (2-{[5-(aminomethyl)-2H-spiro[1-benzofuran-3,4'-piperidine]-1'-yl]carbonyl}-1H-indol-6-yl)boronic acid; (2-{[5-(aminomethyl)-2H-spiro[1-benzofuran-3,4'-piperidine]-1'-yl]carbonyl}-1H-indol-5-yl)boronic acid; (2-{[5-(aminomethyl)-2H-spiro[1-benzofuran-3,4'-piperidine]-1'-yl]carbonyl}-1H-indol-5-yl)boronic acid; (5-{[5-(aminomethyl)-2H-spiro[1-benzofuran-3,4'-piperidine]-1'-yl]carbonyl}-1H-indol-3-yl)boronic acid; [4-({4-[3-(aminomethyl)phenyl]piperidin-1-yl}carbonyl)-1-benzofuran-2-yl]boronic acid; (3-{[5-(aminomethyl)-2H-spiro[1-benzofuran-3,4'-piperidine]-1'-yl]carbonyl}-1H-indol-6-yl)boronic acid; and
wherein the monomer comprising the binding partner linker element is selected from the group consisting of:
4-(2-{4-[3-(aminomethyl)phenyl]piperidin-1-yl}-2-oxoethyl)-2-hydroxybenzamide; 4-[(1E)-3-{4-[3-(aminomethyl)phenyl]piperidin-1-yl}-3-oxoprop-1-en-1-yl]-2-hydroxybenzamide; 5-[(1E)-3-{4-[3-(aminomethyl)phenyl]piperidin-1-yl}-3-oxoprop-1-en-1-yl]-2-hydroxybenzamide; 8-({4-[3-(aminomethyl)phenyl]piperidin-1-yl}carbonyl)-1,3-dihydroxynaphthalene-2-carboxamide; 3-[(1E)-3-{4-[3-(aminomethyl)phenyl]piperidin-1-yl}-3-oxoprop-1-en-1-yl]-2,6-dihydroxybenzamide; (2R)-2-[3-({4-[3-(aminomethyl)phenyl]piperidin-1-yl}carbonyl)phenyl]-2-hydroxy-2-phenylacetic acid; (2R)-2-[3-({4-[3-(aminomethyl)phenyl]piperidin-1-yl}carbonyl)phenyl]-2-cyclopentyl-2-hydroxyacetic acid; (2R)-2-[3-({4-[3-(aminomethyl)phenyl]piperidin-1-yl}carbonyl)phenyl]-2-cyclopropyl-2-hydroxyacetic acid; 4-({4-[3-(aminomethyl)phenyl]piperidin-1-yl}carbonyl)-7,8-dihydroxy-2H-chromen-2-one; 3-({4-[3-(aminomethyl)phenyl]piperidin-1-yl}carbonyl)-6,7-dihydroxy-2H-chromen-2-one; 4-(2-{4-[3-(aminomethyl)phenyl]piperidin-1-yl}-2-oxoethyl)-6,7-dihydroxy-2H-chromen-2-one; 3-({4-[3-(aminomethyl)phenyl]piperidin-1-yl}carbonyl)-7,8-dihydroxy-2H-chromen-2-one; 3-(2-{4-[3-(aminomethyl)phenyl]piperidin-1-yl}-2-oxoethyl)-6,7-dihydroxy-4-methyl-2H-chromen-2-one; 3-(2-{4-[3-(aminomethyl)phenyl]piperidin-1-yl}-2-oxoethyl)-7,8-dihydroxy-4-methyl-2H-chromen-2-one; 4-(2-{4-[3-(aminomethyl)phenyl]piperidin-1-yl}-2-oxoethyl)-7,8-dihydroxy-2H-chromen-2-one; (1S,2S,3R,5S)-2-{2-[4-({4-[3-(aminomethyl)phenyl]piperidin-1-yl}carbonyl)phenoxy]ethyl}-6,6-dimethylbicyclo[3.1.1]heptane-2,3-diol; (1R,2R,4S,5R,6S)—N-[3-({4-[3-(aminomethyl)phenyl]piperidin-1-yl}carbonyl)phenyl]-5,6-dihydroxybicyclo[2.2.2]octane-2-carboxamide; (1R,2R,3R,4R,5S)-4-[3-({4-[3-(aminomethyl)phenyl]piperidin-1-yl}carbonyl)phenoxy]-2,6,6-trimethylbicyclo[3.1.1]heptane-2,3-diol; (1R,2R,4S,5S,6R)—N-[3-({4-[3-(aminomethyl)phenyl]piperidin-1-yl}carbonyl)phenyl]-5,6-dihydroxybicyclo[2.2.2]octane-2-carboxamide; (1S,2R,3R,4R,5R)-4-[3-({4-[3-(aminomethyl)phenyl]piperidin-1-yl}carbonyl)phenoxy]-2,6,6-trimethylbicyclo[3.1.1]heptane-2,3-diol; (1R,2R,4S,5R,6S)—N-[3-({4-[3-(aminomethyl)phenyl]piperidin-1-yl}carbonyl)phenyl]-5,6-dihydroxybicyclo[2.2.1]heptane-2-carboxamide; (1S,2R,3S,4S,5R)-5-[4-({4-[3-(aminomethyl)phenyl]piperidin-1-yl}carbonyl)phenoxy]-5-methylbicyclo[2.2.1]heptane-2,3-diol; (1S,2R,4R,5S,6R)—N-[3-({4-[3-(aminomethyl)phenyl]piperidin-1-yl}carbonyl)phenyl]-5,6-dihydroxybicyclo[2.2.2]octane-2-carboxamide; (1R,2R,3S,4R,5S)-

5-[3-({4-[3-(aminomethyl)phenyl]piperidin-1-yl}carbonyl)phenoxy]bicyclo[2.2.2]octane-2,3-diol; (1R,2S,3R,4R,5S)-5-[3-({4-[3-(aminomethyl)phenyl]piperidin-1-yl}carbonyl)phenoxy]-5-methylbicyclo[2.2.1]heptane-2,3-diol; (2R)-3-{[3-({4-[3-(aminomethyl)phenyl]piperidin-1-yl}carbonyl)phenyl]carbamoyl}-2-hydroxy-2-phenylpropanoic acid; (2S)-3-{[3-({4-[3-(aminomethyl)phenyl]piperidin-1-yl}carbonyl)phenyl]carbamoyl}-2-hydroxy-2-phenylpropanoic acid; (2R)-2-[4-({4-[3-(aminomethyl)phenyl]piperidin-1-yl}carbonyl)-]H-indol-2-yl]-2-hydroxypropanoic acid; (2S)-3-{[3-({4-[3-(aminomethyl)phenyl]piperidin-1-yl}carbonyl)phenyl]carbamoyl}-2-hydroxy-2-methylpropanoic acid; (2S)-3-[3-({4-[3-(aminomethyl)phenyl]piperidin-1-yl}carbonyl)phenoxy]-2-hydroxy-2-phenylpropanoic acid; (2R)-3-[3-({4-[3-(aminomethyl)phenyl]piperidin-1-yl}carbonyl)phenoxy]-2-hydroxy-2-phenylpropanoic acid; (2S)-3-[3-({4-[3-(aminomethyl)phenyl]piperidin-1-yl}carbonyl)phenoxy]-2-hydroxy-2-methylpropanoic acid; (2R)-3-[3-({4-[3-(aminomethyl)phenyl]piperidin-1-yl}carbonyl)phenoxy]-2-hydroxy-2-methylpropanoic acid; (2S)-2-[2-({4-[3-(aminomethyl)phenyl]piperidin-1-yl}carbonyl)-1H-indol-4-yl]-2-hydroxypropanoic acid; (2R)-2-[2-({4-[3-(aminomethyl)phenyl]piperidin-1-yl}carbonyl)-]H-indol-4-yl]-2-hydroxy-2-phenylacetic acid; (2R)-2-[2-({4-[3-(aminomethyl)phenyl]piperidin-1-yl}carbonyl)-1H-indol-4-yl]-2-hydroxypropanoic acid; (2R)-2-[2-({4-[3-(aminomethyl)phenyl]piperidin-1-yl}carbonyl)-1H-indol-6-yl]-2-hydroxypropanoic acid; 2-[3-({4-[3-(aminomethyl)phenyl]piperidin-1-yl}carbonyl)phenoxy]-1-[(3R,4S)-3,4-dihydroxypyrrolidin-1-yl]ethan-1-one; (2R)-3-[3-({4-[3-(aminomethyl)phenyl]piperidin-1-yl}carbonyl)phenoxy]propane-1,2-diol; 2-[(1E)-3-{4-[3-(aminomethyl)phenyl]piperidin-1-yl}-3-oxoprop-1-en-1-yl]-6-hydroxybenzamide; 8-({4-[3-(aminomethyl)phenyl]piperidin-1-yl}carbonyl)-3-hydroxynaphthalene-2-carboxamide; (1R,2S,3R,4R,5S)-5-[3-({4-[3-(aminomethyl)phenyl]piperidin-1-yl}carbonyl)phenoxy]bicyclo[2.2.2]octane-2,3-diol; (1R,2S,4S,5S,6R)—N-[3-({4-[3-(aminomethyl)phenyl]piperidin-1-yl}carbonyl)phenyl]-5,6-dihydroxybicyclo[2.2.2]octane-2-carboxamide; (2S)-3-[3-({4-[3-(aminomethyl)phenyl]piperidin-1-yl}carbonyl)phenoxy]-2-cyclopentyl-2-hydroxypropanoic acid; (2S)-3-{[4-({4-[3-(aminomethyl)phenyl]piperidin-1-yl}carbonyl)phenyl]carbamoyl}-2-hydroxy-2-phenylpropanoic acid; (2R)-2-[2-({4-[3-(aminomethyl)phenyl]piperidin-1-yl}carbonyl)-]H-indol-6-yl]-2-hydroxy-2-phenylacetic acid; (2R)—S-[3-({4-[3-(aminomethyl)phenyl]piperidin-1-yl}carbonyl)phenyl]-3,3,3-trifluoro-2-hydroxypropane-1-sulfonamido; 1-{4-[3-(aminomethyl)phenyl]piperidin-1-yl}-2-(3,4-dihydroxyphenyl)ethan-1-one; (2R)-2-[3-(2-{4-[3-(aminomethyl)phenyl]piperidin-1-yl}-2-oxoethyl)phenyl]-2-hydroxy-2-phenylacetic acid; (2S)-2-[5-({4-[3-(aminomethyl)phenyl]piperidin-1-yl}carbonyl)naphthalen-2-yl]-2-hydroxypropanoic acid; (2S)-2-[2-({4-[3-(aminomethyl)phenyl]piperidin-1-yl}carbonyl)-]H-indol-6-yl]-2-hydroxypropanoic acid; (2S)-2-[2-({4-[3-(aminomethyl)phenyl]piperidin-1-yl}carbonyl)-1H-indol-6-yl]-2-hydroxy-2-phenylacetic acid; (4-(3-(aminomethyl)phenyl)piperidin-1-yl)(3-(2-hydroxy-2-(1-hydroxycyclobutyl)ethoxy)phenyl)methanone; (E)-1-(4-(3-(aminomethyl)phenyl)piperidin-1-yl)-3-(3,4-dihydroxyphenyl)prop-2-en-1-one; (4-(3-(aminomethyl)phenyl)piperidin-1-yl)(6,7-dihydroxynaphthalen-1-yl)methanone; and 4-(aminomethyl)-N-(4-(2-((3R,4S)-3,4-dihydroxypyrrolidin-1-yl)-2-oxoethoxy)benzyl)benzamide.

2. The therapeutic dimer of claim 1, wherein the therapeutic dimer is selected from the group consisting of:
7-[(1E)-3-{4-[3-(aminomethyl)phenyl]piperidin-1-yl}-3-oxoprop-1-en-1-yl]-2-[2-({4-[3-(aminomethyl)phenyl]piperidin-1-yl}carbonyl)-1H-indol-4-yl]-3,4-dihydro-2H-1,3,2-benzoxazaborinin-4-one; 2-(2-{[5-(aminomethyl)-2H-spiro[1-benzofuran-3,4'-piperidine]-1'-yl]carbonyl}-1H-indol-4-yl)-6-[(1E)-3-{4-[3-(aminomethyl)phenyl]piperidin-1-yl}-3-oxoprop-1-en-1-yl]-3,4-dihydro-2H-1,3,2-benzoxazaborinin-4-one; 6-({4-[3-(aminomethyl)phenyl]piperidin-1-yl}carbonyl)-2-[2-({4-[3-(aminomethyl)phenyl]piperidin-1-yl}carbonyl)-1H-indol-4-yl]-5-hydroxy-2H,3H,4H-naphtho[2,3-e][1,3,2]oxazaborinin-4-one; 2-(2-{[5-(aminomethyl)-2H-spiro[1-benzofuran-3,4'-piperidine]-1'-yl]carbonyl}-1H-indol-4-yl)-6-[(1E)-3-{4-[3-(aminomethyl)phenyl]piperidin-1-yl}-3-oxoprop-1-en-1-yl]-5-hydroxy-3,4-dihydro-2H-1,3,2-benzoxazaborinin-4-one; (5R)-2-(5-{[5-(aminomethyl)-2H-spiro[1-benzofuran-3,4'-piperidine]-1'-yl]carbonyl}naphthalen-2-yl)-5-[3-({4-[3-(aminomethyl)phenyl]piperidin-1-yl}carbonyl)phenyl]-5-phenyl-1,3,2-dioxaborolan-4-one; (5R)-2-(2-{[5-(aminomethyl)-2H-spiro[1-benzofuran-3,4'-piperidine]-1'-yl]carbonyl}-1H-indol-4-yl)-5-[3-({4-[3-(aminomethyl)phenyl]piperidin-1-yl}carbonyl)phenyl]-5-cyclopentyl-1,3,2-dioxaborolan-4-one; (5R)-2-[2-({4-[3-(aminomethyl)phenyl]piperidin-1-yl}carbonyl)-1H-indol-4-yl]-5-[3-({4-[3-(aminomethyl)phenyl]piperidin-1-yl}carbonyl)phenyl]-5-cyclopropyl-1,3,2-dioxaborolan-4-one; (5R)-2-[5-({4-[3-(aminomethyl)phenyl]piperidin-1-yl}carbonyl)naphthalen-2-yl]-5-[3-({4-[3-(aminomethyl)phenyl]piperidin-1-yl}carbonyl)phenyl]-5-phenyl-1,3,2-dioxaborolan-4-one; 2-(2-{[5-(aminomethyl)-2H-spiro[1-benzofuran-3,4'-piperidine]-1'-yl]carbonyl}-1H-indol-4-yl)-7-({4-[3-(aminomethyl)phenyl]piperidin-1-yl}carbonyl)-2H,6H-[1,3,2]dioxaborolo[4,5-g]chromen-6-one; 8-(2-{4-[3-(aminomethyl)phenyl]piperidin-1-yl}-2-oxoethyl)-2-[2-({4-[3-(aminomethyl)phenyl]piperidin-1-yl}carbonyl)-1H-indol-5-yl]-2H,6H-[1,3,2]dioxaborolo[4,5-g]chromen-6-one; 7-({4-[3-(aminomethyl)phenyl]piperidin-1-yl}carbonyl)-2-[2-({4-[3-(aminomethyl)phenyl]piperidin-1-yl}carbonyl)-1H-indol-4-yl]-2H,6H-[1,3,2]dioxaborolo[4,5-g]chromen-6-one; 2-(2-{[5-(aminomethyl)-2H-spiro[1-benzofuran-3,4'-piperidine]-1'-yl]carbonyl}-1H-indol-4-yl)-7-({4-[3-(aminomethyl)phenyl]piperidin-1-yl}carbonyl)-2H,8H-[1,3,2]dioxaborolo[4,5-h]chromen-8-one; 6-(2-{4-[3-(aminomethyl)phenyl]piperidin-1-yl}-2-oxoethyl)-2-[2-({4-[3-(aminomethyl)phenyl]piperidin-1-yl}carbonyl)-1H-indol-4-yl]-2H,8H-[1,3,2]dioxaborolo[4,5-h]chromen-8-one; 7-(2-{4-[3-(aminomethyl)phenyl]piperidin-1-yl}-2-oxoethyl)-2-[2-({4-[3-(aminomethyl)phenyl]piperidin-1-yl}carbonyl)-1H-indol-4-yl]-6-methyl-2H,8H-[1,3,2]dioxaborolo[4,5-h]chromen-8-one; (3-{1-[(4-{2-[(1S,2S,6R,8S)-4-[2-({4-[3-(aminomethyl)phenyl]piperidin-1-yl}carbonyl)-1H-indol-4-yl]-9,9-dimethyl-3,5-dioxa-4-boratricyclo[6.1.1.0$^{2,6}$]decan-2-yl]ethoxy}phenyl)carbonyl]piperidin-4-yl}phenyl)methanamine; (1S,2R,6S,7R,8R)-4-(2-{[5-

(aminomethyl)-2H-spiro[1-benzofuran-3,4'-piperidine]-1'-yl]carbonyl}-1H-indol-4-yl)-N-[3-({4-[3-(aminomethyl)phenyl]piperidin-1-yl}carbonyl)phenyl]-3,5-dioxa-4-boratricyclo[5.2.2.0²,⁶]undecane-8-carboxamide; 1'-({4-[(1R,2R,6R,7R,8S)-7-[3-({4-[3-(aminomethyl)phenyl]piperidin-1-yl}carbonyl)phenoxy]-2,9,9-trimethyl-3,5-dioxa-4-boratricyclo[6.1.1.0²,⁶]decan-4-yl]-1H-indol-2-yl}carbonyl)-2H-spiro[1-benzofuran-3,4'-piperidine]-5-ylmethanamine; (1S,2S,6R,7R,8R)-4-(2-{[5-(aminomethyl)-2H-spiro[1-benzofuran-3,4'-piperidine]-1'-yl]carbonyl}-1H-indol-4-yl)-N-[3-({4-[3-(aminomethyl)phenyl]piperidin-1-yl}carbonyl)phenyl]-3,5-dioxa-4-boratricyclo[5.2.2.0²,⁶]undecane-8-carboxamide; (3-{1-[(3-{[(1S,2R,6R,7R,8R)-4-[2-({4-[3-(aminomethyl)phenyl]piperidin-1-yl}carbonyl)-1H-indol-4-yl]-2,9,9-trimethyl-3,5-dioxa-4-boratricyclo[6.1.1.0²,⁶]decan-7-yl]oxy}phenyl)carbonyl]piperidin-4-yl}phenyl)methanamine; (1S,2R,6S,7R,8R)-4-(2-{[5-(aminomethyl)-2H-spiro[1-benzofuran-3,4'-piperidine]-1'-yl]carbonyl}-1H-indol-4-yl)-N-[3-({4-[3-(aminomethyl)phenyl]piperidin-1-yl}carbonyl)phenyl]-3,5-dioxa-4-boratricyclo[5.2.1.0²,⁶]decane-8-carboxamide; {3-[1-({4-[(1S,2R,6S,7S,8R)-8-[4-({4-[3-(aminomethyl)phenyl]piperidin-1-yl}carbonyl)phenoxy]-8-methyl-3,5-dioxa-4-boratricyclo[5.2.1.0²,⁶]decan-4-yl]-1H-indol-2-yl}carbonyl)piperidin-4-yl]phenyl}methanamine; (1R,2S,6R,7R,8R)-4-[2-({4-[3-(aminomethyl)phenyl]piperidin-1-yl}carbon 1)-1H-indol-4-yl]-N-[3-({4-[3-(aminomethyl)phenyl]piperidin-1-yl}carbonyl)phenyl]-3,5-dioxa-4-boratricyclo[5.2.2.0²,⁶]undecane-8-carboxamide; (3-{1-[(3-{[(1R,2R,6S,7R,8S)-4-[2-({4-[3-(aminomethyl)phenyl]piperidin-1-yl}carbonyl)-1H-indol-4-yl]-3,5-dioxa-4-boratricyclo[5.2.2.0²,⁶]undecan-8-yl]oxy}phenyl)carbonyl]piperidin-4-yl}phenyl)methanamine; {3-[1-({4-[(1R,2S,6R,7R,8S)-8-[3-({4-[3-(aminomethyl)phenyl]piperidin-1-yl}carbonyl)phenoxy]-8-methyl-3,5-dioxa-4-boratricyclo[5.2.1.0²,⁶]decan-4-yl]-1H-indol-2-yl}carbonyl)piperidin-4-yl]phenyl}methanamine; 2-[(4R)-2-[5-({4-[3-(aminomethyl)phenyl]piperidin-1-yl}carbonyl)-1H-indol-2-yl]-5-oxo-4-phenyl-1,3,2-dioxaborolan-4-yl]-N-[3-({4-[3-(aminomethyl)phenyl]piperidin-1-yl}carbonyl)phenyl]acetamide; 2-[(4S)-2-[2-({4-[3-(aminomethyl)phenyl]piperidin-1-yl}carbonyl)-1H-indol-4-yl]-5-oxo-4-phenyl-1,3,2-dioxaborolan-4-yl]-N-[3-({4-[3-(aminomethyl)phenyl]piperidin-1-yl}carbonyl)phenyl]acetamide; (5R)-5-[4-({4-[3-(aminomethyl)phenyl]piperidin-1-yl}carbonyl)-1H-indol-2-yl]-2-[2-({4-[3-(aminomethyl)phenyl]piperidin-1-yl}carbonyl)-1H-indol-4-yl]-5-methyl-1,3,2-dioxaborolan-4-one; 2-[(4R)-2-(2-{[5-(aminomethyl)-2H-spiro[1-benzofuran-3,4'-piperidine]-1'-yl]carbonyl}-1H-indol-4-yl)-5-oxo-4-phenyl-1,3,2-dioxaborolan-4-yl]-N-[3-({4-[3-(aminomethyl)phenyl]piperidin-1-yl}carbonyl)phenyl]acetamide; 2-[(4S)-2-[2-({4-[3-(aminomethyl)phenyl]piperidin-1-yl}carbonyl)-1H-indol-4-yl]-4-methyl-5-oxo-1,3,2-dioxaborolan-4-yl]-N-[3-({4-[3-(aminomethyl)phenyl]piperidin-1-yl}carbonyl)phenyl]acetamide; (5S)-2-[2-({4-[3-(aminomethyl)phenyl]piperidin-1-yl}carbonyl)-1H-indol-6-yl]-5-[3-({4-[3-(aminomethyl)phenyl]piperidin-1-yl}carbonyl)phenoxymethyl]-5-phenyl-1,3,2-dioxaborolan-4-one; (5R)-2-[2-({4-[3-(aminomethyl)phenyl]piperidin-1-yl}carbonyl)-1H-indol-6-yl]-5-[3-({4-[3-(aminomethyl)phenyl]piperidin-1-yl}carbonyl)phenoxymethyl]-5-phenyl-1,3,2-dioxaborolan-4-one; (5S)-2-[2-({4-[3-(aminomethyl)phenyl]piperidin-1-yl}carbonyl)-1H-indol-4-yl]-5-[3-({4-[3-(aminomethyl)phenyl]piperidin-1-yl}carbonyl)phenoxymethyl]-5-methyl-1,3,2-dioxaborolan-4-one; (5R)-2-[2-({4-[3-(aminomethyl)phenyl]piperidin-1-yl}carbonyl)-1H-indol-4-yl]-5-[3-({4-[3-(aminomethyl)phenyl]piperidin-1-yl}carbonyl)phenoxymethyl]-5-methyl-1,3,2-dioxaborolan-4-one; (5R)-2-[8-({4-[3-(aminomethyl)phenyl]piperidin-1-yl}carbonyl)naphthalen-2-yl]-5-[3-({4-[3-(aminomethyl)phenyl]piperidin-1-yl}carbonyl)phenoxymethyl]-5-phenyl-1,3,2-dioxaborolan-4-one; (5S)-5-[2-({4-[3-(aminomethyl)phenyl]piperidin-1-yl}carbonyl)-1H-indol-4-yl]-2-[5-({4-[3-(aminomethyl)phenyl]piperidin-1-yl}carbonyl)naphthalen-2-yl]-5-methyl-1,3,2-dioxaborolan-4-one; (5S)-2-(2-{[5-(aminomethyl)-2H-spiro[1-benzofuran-3,4'-piperidine]-1'-yl]carbonyl}-1H-indol-6-yl)-5-[2-({4-[3-(aminomethyl)phenyl]piperidin-1-yl}carbonyl)-1H-indol-4-yl]-5-methyl-1,3,2-dioxaborolan-4-one; (5R)-2-(2-{[5-(aminomethyl)-2H-spiro[1-benzofuran-3,4'-piperidine]-1'-yl]carbonyl}-1H-indol-5-yl)-5-[2-({4-[3-(aminomethyl)phenyl]piperidin-1-yl}carbonyl)-1H-indol-4-yl]-5-phenyl-1,3,2-dioxaborolan-4-one; (5R)-2,5-bis[2-({4-[3-(aminomethyl)phenyl]piperidin-1-yl}carbonyl)-1H-indol-4-yl]-5-methyl-1,3,2-dioxaborolan-4-one; (5R)-2,5-bis[2-({4-[3-(aminomethyl)phenyl]piperidin-1-yl}carbonyl)-1H-indol-4-yl]-5-phenyl-1,3,2-dioxaborolan-4-one; (5R)-2-[2-({4-[3-(aminomethyl)phenyl]piperidin-1-yl}carbonyl)-1H-indol-4-yl]-5-[2-({4-[3-(aminomethyl)phenyl]piperidin-1-yl}carbonyl)-1H-indol-6-yl]-5-methyl-1,3,2-dioxaborolan-4-one; 1-[(3aR,6aS)-2-(2-{[5-(aminomethyl)-2H-spiro[1-benzofuran-3,4'-piperidine]-1'-yl]carbonyl}-1H-indol-4-yl)-hexahydro-[1,3,2]dioxaborolo[4,5-c]pyrrol-5-yl]-2-[3-({4-[3-(aminomethyl)phenyl]piperidin-1-yl}carbonyl)phenoxy]ethan-1-one; (3-{1-[(3-{[(4R)-2-[2-({4-[3-(aminomethyl)phenyl]piperidin-1-yl}carbonyl)-1H-indol-4-yl]-1,3,2-dioxaborolan-4-yl]methoxy}phenyl)carbonyl]piperidin-4-yl}phenyl)methanamine; 1-[(3aR,6aS)-2-[2-({4-[3-(aminomethyl)phenyl]piperidin-1-yl}carbonyl)-1H-indol-6-yl]-hexahydro-[1,3,2]dioxaborolo[4,5-c]pyrrol-5-yl]-2-[3-({4-[3-(aminomethyl)phenyl]piperidin-1-yl}carbonyl)phenoxy]ethan-1-one; 5-[(1E)-3-{4-[3-(aminomethyl)phenyl]piperidin-1-yl}-3-oxoprop-1-en-1-yl]-2-[2-({4-[3-(aminomethyl)phenyl]piperidin-1-yl}carbonyl)-1H-indol-6-yl]-3,4-dihydro-2H-1,3,2-benzoxazaborinin-4-one; 6-({4-[3-(aminomethyl)phenyl]piperidin-1-yl}carbonyl)-2-[2-({4-[3-(aminomethyl)phenyl]piperidin-1-yl}carbonyl)-1H-indol-6-yl]-2H,3H,4H-naphtho[2,3-e][1,3,2]oxazaborinin-4-one; 2-(2-{[5-(aminomethyl)-2H-spiro[1-benzofuran-3,4'-piperidine]-1'-yl]carbonyl}-1H-indol-5-yl)-5-[(1E)-3-{4-[3-(aminomethyl)phenyl]piperidin-1-yl}-3-oxoprop-1-en-1-yl]-3,4-dihydro-2H-1,3,2-benzoxazaborinin-4-one; (5R)-2-(2-{[5-(aminomethyl)-2H-spiro[1-benzofuran-3,4'-piperidine]-1'-yl]carbonyl}-1H-indol-4-yl)-5-[3-({4-[3-(aminomethyl)phenyl]piperidin-1-yl}carbonyl)phenyl]-5-cyclopropyl-1,3,2-dioxaborolan-4-one; (5R)-2-(2-{[5-(aminomethyl)-2H-spiro[1-benzofuran-3,4'-piperidine]-1'-yl]carbonyl}-1H-indol-5-yl)-5-[3-({4-[3-(aminomethyl)phenyl]piperidin-1-yl}carbonyl)phenyl]-5-phenyl-1,3,2-dioxaborolan-4-one; (5R)-2-(2-{[5-(aminomethyl)-2H-spiro[1-benzofuran-3,4'-piperidine]-1'-yl]carbonyl}-1H-indol-6-yl)-5-[3-({4-[3-(aminomethyl)phenyl]piperidin-1-yl}carbonyl)phenyl]-5-cyclopropyl-1,3,2-dioxaborolan-4-one; (5R)-2-(2-{[5-(aminomethyl)-2H-spiro[1-benzofuran-3,4'-piperidine]-1'-yl]carbonyl}-1H-indol-5-yl)-5-[3-({4-[3-(aminomethyl)phenyl]piperidin-1-yl}carbonyl)

phenyl]-5-cyclopentyl-1,3,2-dioxaborolan-4-one; (5R)-2-(2-{[5-(aminomethyl)-2H-spiro[1-benzofuran-3,4'-piperidine]-1'-yl]carbonyl}-1H-indol-5-yl)-5-[3-({4-[3-(aminomethyl)phenyl]piperidin-1-yl}carbonyl)phenyl]-5-cyclopropyl-1,3,2-dioxaborolan-4-one; (5R)-2-[2-({4-[3-(aminomethyl)phenyl]piperidin-1-yl}carbonyl)-1H-indol-6-yl]-5-[3-({4-[3-(aminomethyl)phenyl]piperidin-1-yl}carbonyl)phenyl]-5-phenyl-1,3,2-dioxaborolan-4-one; 2-(5-{[5-(aminomethyl)-2H-spiro[1-benzofuran-3,4'-piperidine]-1'-yl]carbonyl}naphthalen-2-yl)-7-({4-[3-(aminomethyl)phenyl]piperidin-1-yl}carbonyl)-2H,6H-[1,3,2]dioxaborolo[4,5-g]chromen-6-one; 1'-({5-[(1R,2S,6R,7R,8S)-8-[3-({4-[3-(aminomethyl)phenyl]piperidin-1-yl}carbonyl)phenoxy]-3,5-dioxa-4-boratricyclo[5.2.2.0$^{2,6}$]undecan-4-yl]-1H-indol-2-yl}carbonyl)-2H-spiro[1-benzofuran-3,4'-piperidine]-5-ylmethanamine; (1S,2S,6R,7R,8S)-4-[2-({4-[3-(aminomethyl)phenyl]piperidin-1-yl}carbonyl)-1H-indol-6-yl]-N-[3-({4-[3-(aminomethyl)phenyl]piperidin-1-yl}carbonyl)phenyl]-3,5-dioxa-4-boratricyclo[5.2.2.0$^{2,6}$]undecane-8-carboxamide; 2-[(4S)-2-(2-{[5-(aminomethyl)-2H-spiro[1-benzofuran-3,4'-piperidine]-1'-yl]carbonyl}-1H-indol-4-yl)-4-methyl-5-oxo-1,3,2-dioxaborolan-4-yl]-N-[3-({4-[3-(aminomethyl)phenyl]piperidin-1-yl}carbonyl)phenyl]acetamide; 2-[(4R)-2-(5-{[5-(aminomethyl)-2H-spiro[1-benzofuran-3,4'-piperidine]-1'-yl]carbonyl})-1H-indol-3-yl)-5-oxo-4-phenyl-1,3,2-dioxaborolan-4-yl]-N-[3-({4-[3-(aminomethyl)phenyl]piperidin-1-yl}carbonyl)phenyl]acetamide; (5S)-2-(2-{[5-(aminomethyl)-2H-spiro[1-benzofuran-3,4'-piperidine]-1'-yl]carbonyl})-1H-indol-4-yl)-5-[3-({4-[3-(aminomethyl)phenyl]piperidin-1-yl}carbonyl)phenoxymethyl]-5-phenyl-1,3,2-dioxaborolan-4-one; 2-[(4S)-2-[4-({4-[3-(aminomethyl)phenyl]piperidin-1-yl}carbonyl)-1-benzofuran-2-yl]-5-oxo-4-phenyl-1,3,2-dioxaborolan-4-yl]-N-[4-({4-[3-(aminomethyl)phenyl]piperidin-1-yl}carbonyl)phenyl]acetamide; (5R)-2-[2-({4-[3-(aminomethyl)phenyl]piperidin-1-yl}carbonyl)-1H-indol-4-yl]-5-[2-({4-[3-(aminomethyl)phenyl]piperidin-1-yl}carbonyl)-1H-indol-6-yl]-5-phenyl-1,3,2-dioxaborolan-4-one; {3-[1-({6-[(5R)-3-{[3-({4-[3-(aminomethyl)phenyl]piperidin-1-yl}carbonyl)benzene]sulfonyl}-5-(trifluoromethyl)-1,3,2-oxazaborolidin-2-yl]-1H-indol-2-yl}carbonyl)piperidin-4-yl]phenyl}methanamine; 1-{4-[3-(aminomethyl)phenyl]piperidin-1-yl}-2-{2-[2-({4-[3-(aminomethyl)phenyl]piperidin-1-yl}carbonyl)-1H-indol-6-yl]-2H-1,3,2-benzodioxaborol-5-yl}ethan-1-one; (5R)-5-[3-(2-{4-[3-(aminomethyl)phenyl]piperidin-1-yl}-2-oxoethyl)phenyl]-2-[2-({4-[3-(aminomethyl)phenyl]piperidin-1-yl}carbonyl)-1H-indol-6-yl]-5-phenyl-1,3,2-dioxaborolan-4-one; (5S)-2-(2-{[5-(aminomethyl)-2H-spiro[1-benzofuran-3,4'-piperidine]-1'-yl]carbonyl}-1H-indol-6-yl)-5-[5-({4-[3-(aminomethyl)phenyl]piperidin-1-yl}carbonyl)naphthalen-2-yl]-5-methyl-1,3,2-dioxaborolan-4-one; (5S)-2-(3-{[5-(aminomethyl)-2H-spiro[1-benzofuran-3,4'-piperidine]-1'-yl]carbonyl})-1H-indol-6-yl)-5-[2-({4-[3-(aminomethyl)phenyl]piperidin-1-yl}carbonyl)-1H-indol-6-yl]-5-methyl-1,3,2-dioxaborolan-4-one; (2E)-1-{4-[3-(aminomethyl)phenyl]piperidin-1-yl}-3-{2-[8-({4-[3-(aminomethyl)phenyl]piperidin-1-yl}carbonyl)naphthalen-2-yl]-2H-1,3,2-benzodioxaborol-5-yl}prop-2-en-1-one; {3-[1-({2-[5-({4-[3-(aminomethyl)phenyl]piperidin-1-yl}carbonyl)naphthalen-2-yl]-2H-naphtho[2,3-d][1,3,2]dioxaborol-5-yl}carbonyl)piperidin-4-yl]phenyl}methanamine; {3-[1-({2-[8-({4-[3-(aminomethyl)phenyl]piperidin-1-yl}carbonyl)naphthalen-2-yl]-2H-naphtho[2,3-d][1,3,2]dioxaborol-5-yl}carbonyl)piperidin-4-yl]phenyl}methanamine; 1-{4-[3-(aminomethyl)phenyl]piperidin-1-yl}-2-{3-[5-({4-[3-(aminomethyl)phenyl]piperidin-1-yl}carbonyl)-2H-naphtho[2,3-d][1,3,2]dioxaborol-2-yl]phenyl}ethan-1-one; 1-{4-[3-(aminomethyl)phenyl]piperidin-1-yl}-2-{4-[5-({4-[3-(aminomethyl)phenyl]piperidin-1-yl}carbonyl)-2H-naphtho[2,3-d][1,3,2]dioxaborol-2-yl]phenyl}ethan-1-one; 2-{[5-({4-[3-(aminomethyl)phenyl]piperidin-1-yl}carbonyl)cyclohexa-2,4-dien-1-yl]oxy}-1-{2-[8-({4-[3-(aminomethyl)phenyl]piperidin-1-yl}carbonyl)naphthalen-2-yl]-hexahydro-[1,3,2]dioxaborolo[4,5-c]pyrrol-5-yl}ethan-1-one; or both enantiomers of any tetrahedral boronate diesters of the dimers listed above.

* * * * *

UNITED STATES PATENT AND TRADEMARK OFFICE
CERTIFICATE OF CORRECTION

| | | |
|---|---|---|
| PATENT NO. | : 9,771,345 B2 | Page 1 of 1 |
| APPLICATION NO. | : 13/500857 | |
| DATED | : September 26, 2017 | |
| INVENTOR(S) | : Barany et al. | |

It is certified that error appears in the above-identified patent and that said Letters Patent is hereby corrected as shown below:

In the Specification

Column 1 at Lines 10-14, delete "This invention was made with government support under Public Health Service grant AI062579-03 from the National Institute of Allergy and Infectious Diseases and Grant No. CA65930-08 from the National Cancer Institute. The government has certain rights in this invention." and insert -- This invention was made with government support under Grant Numbers AI062570 & CA065030 awarded by the National Institutes of Health. The Government has certain rights in the invention. --

In the Claims

Column 476 at Lines 65, insert -- - -- between "(1S,2R,4R,5S,6R)" and "N-[3-({4-[3-(aminomethyl)phe-".

Column 477 at Line 11, delete "carbonyl)-]H" and insert -- carbonyl)-1H --.

Column 477 at Line 27, delete "carbonyl)-]H-indol" and insert -- carbonyl)-1H --.

Column 477 at Line 51, delete "carbonyl)-]H" and insert -- carbonyl)-1H --.

Column 477 at Line 62, delete "carbonyl)-]H" and insert -- carbonyl)-1H --.

Signed and Sealed this
Third Day of April, 2018

Andrei Iancu
*Director of the United States Patent and Trademark Office*